US009433228B2

(12) United States Patent
Zank et al.

(10) Patent No.: US 9,433,228 B2
(45) Date of Patent: *Sep. 6, 2016

(54) METHOD FOR THE PRODUCTION OF MULTIPLE-UNSATURATED FATTY ACIDS IN TRANSGENIC ORGANISMS

(75) Inventors: Thorsten Zank, Mannheim (DE); Jörg Bauer, Ludwigshafen (DE); Petra Cirpus, Mannheim (DE); Amine Abbadi, Ebergötzen (DE); Ernst Heinz, Hamburg (DE); Xiao Qiu, Saskatoon (CA); Patricia Vrinten, Saskatoon (CA); Petra Sperling, Hamburg (DE); Frederic Domergue, Hamburg (DE); Astrid Meyer, Hamburg (DE); Jelena Kirsch, Hamburg (DE)

(73) Assignee: BASF Plant Science GmbH, Ludwigshafen (DE)

( * ) Notice: Subject to any disclaimer, the term of this patent is extended or adjusted under 35 U.S.C. 154(b) by 1408 days.

This patent is subject to a terminal disclaimer.

(21) Appl. No.: 10/566,944

(22) PCT Filed: Jul. 16, 2004

(86) PCT No.: PCT/EP2004/007957
§ 371 (c)(1),
(2), (4) Date: Feb. 22, 2006

(87) PCT Pub. No.: WO2005/012316
PCT Pub. Date: Feb. 10, 2005

(65) Prior Publication Data
US 2008/0155705 A1 Jun. 26, 2008

(30) Foreign Application Priority Data

| Aug. 1, 2003 | (DE) | 103 35 992 |
| Sep. 24, 2003 | (DE) | 103 44 557 |
| Oct. 10, 2003 | (DE) | 103 47 869 |
| Dec. 18, 2003 | (DE) | 103 59 593 |
| Feb. 27, 2004 | (DE) | 10 2004 009 457 |
| Mar. 13, 2004 | (DE) | 10 2004 012 370 |
| May 14, 2004 | (DE) | 10 2004 024 014 |

(51) Int. Cl.
*C12N 15/82* (2006.01)
*A23D 9/00* (2006.01)
(Continued)

(52) U.S. Cl.
CPC .............. *A23D 9/00* (2013.01); *C12N 9/0083* (2013.01); *C12N 9/0093* (2013.01);
(Continued)

(58) Field of Classification Search
None
See application file for complete search history.

(56) References Cited

U.S. PATENT DOCUMENTS

| 5,614,393 A | 3/1997 | Thomas et al. |
| 6,043,411 A | 3/2000 | Nishizawa et al. |

(Continued)

FOREIGN PATENT DOCUMENTS

| CA | 2485060 | 11/2003 |
| DE | 101 02 337 A1 | 7/2002 |

(Continued)

OTHER PUBLICATIONS

GenSeq Accession ABV74260, Lerchl et al, Mar. 28, 2003.*
(Continued)

*Primary Examiner* — Elizabeth McElwain
(74) *Attorney, Agent, or Firm* — Drinker Biddle & Reath LLP

(57) ABSTRACT

The invention relates to a method for the production of multiply-unsaturated fatty acids in an organism, into which nucleic acids have been introduced, which code for polypeptides with Δ-5 elongase activity. Said nucleic acid sequences, optionally with further nucleic acid sequences, coding for polypeptides for the biosynthesis of fatty acids and lipid metabolism, are advantageously expressed in the organism. Nucleic acid sequences coding for a Δ-6 desaturase, a Δ-5 desaturase, Δ-4 desaturase and/or Δ-6 elongase activity are particularly advantageous and, advantageously, said saturases and elongases are derived from *Thalassiosira, Euglena* or *Ostreococcus*. The invention further relates to a method for the production of oils and/or triacylglycerides with an increased content of long-chain, multiply-unsaturated fatty acids. A particular embodiment of the invention is a method for the production of unsaturated ω-3 fatty acids and a method for the production of triglycerides with an increased content of unsaturated fatty acids, in particular, of Δ-3 fatty acids with more than three double bonds. Also disclosed is the production of a transgenic organism, preferably a transgenic plant, or a transgenic microorganism with increased content of ω-3 fatty acids, oils or lipids with ω-3 double bonds as a result of the expression of the elongases and desaturases employed in the above method, preferably in combination with ω-3 desaturases, for example a ω-3 desaturase from fungi of the family Pythiaceae such as the genus *Phytophtora*, for example, the genus and species *Phytophtora infestans*, or a ω-3 desaturase from algae such as the family Prasinophyceae, for example, the genus *Ostreococcus* and, particularly, the genus and species *Ostreococcus tauri* or diatomaceæ such as the genus *Thalassiosira* and, particularly, the genus and species *Thalassiosira pseudonana*. The invention also relates to the nucleic acid sequences, nucleic acid constructs, vectors and organisms containing the nucleic acid sequences and/or the nucleic acid constructs and transgenic organisms containing said nucleic acid sequences, nucleic acid constructs and/or vectors. A further part of the invention relates to oils, lipids and/or fatty acids produced according to the above method and use thereof and, furthermore, unsaturated fatty acids and triglycerides with an increased content of unsaturated fatty acids and use thereof.

27 Claims, 30 Drawing Sheets

(51) Int. Cl.
  *C12N 9/02* (2006.01)
  *C12N 9/10* (2006.01)
  *C12P 7/64* (2006.01)

(52) U.S. Cl.
  CPC ....... *C12N 9/1029* (2013.01); *C12N 15/8247* (2013.01); *C12P 7/6409* (2013.01); *C12P 7/6427* (2013.01); *C12P 7/6463* (2013.01); *C12P 7/6472* (2013.01); *Y02P 20/52* (2015.11)

(56) References Cited

U.S. PATENT DOCUMENTS

| | | | |
|---|---|---|---|
| 6,459,018 | B1 | 10/2002 | Knutzon |
| 6,884,921 | B2 | 4/2005 | Browse et al. |
| 7,777,098 | B2 | 8/2010 | Cirpus et al. |
| 2004/0049805 | A1 | 3/2004 | Lerchl et al. |
| 2004/0053379 | A1 | 3/2004 | Lerchl et al. |
| 2004/0111763 | A1 | 6/2004 | Heinz et al. |
| 2004/0172682 | A1 | 9/2004 | Kinney et al. |
| 2008/0155705 | A1 | 6/2008 | Zank et al. |
| 2009/0222951 | A1 | 9/2009 | Cirpus et al. |
| 2010/0021976 | A1 | 1/2010 | Lerchl et al. |

FOREIGN PATENT DOCUMENTS

| | | |
|---|---|---|
| DE | 10219203 | 11/2003 |
| EP | 0550162 | 7/1993 |
| EP | 0794250 | 9/1997 |
| WO | WO-91/13972 | 9/1991 |
| WO | WO-93/06712 | 4/1993 |
| WO | WO-93/11245 | 6/1993 |
| WO | WO-94/11516 | 5/1994 |
| WO | WO-94/18337 | 8/1994 |
| WO | WO-95/18222 | 7/1995 |
| WO | WO-96/21022 | 7/1996 |
| WO | WO-97/21340 | 6/1997 |
| WO | WO-97/30582 | 8/1997 |
| WO | WO-98/46763 | 10/1998 |
| WO | WO-98/46764 | 10/1998 |
| WO | WO-98/46765 | 10/1998 |
| WO | WO-98/46776 | 10/1998 |
| WO | WO-99/27111 | 6/1999 |
| WO | WO-99/64616 | 12/1999 |
| WO | WO-00/12720 | 3/2000 |
| WO | WO-00/21557 | 4/2000 |
| WO | WO-01/59128 | 8/2001 |
| WO | WO-02/08401 | 1/2002 |
| WO | WO-02/44320 | 6/2002 |
| WO | WO-02/057464 A2 | 7/2002 |
| WO | WO-02/077213 | 10/2002 |
| WO | WO-02/081668 A2 | 10/2002 |
| WO | WO-02/092540 A1 | 11/2002 |
| WO | WO-03/064596 A2 | 8/2003 |
| WO | WO-2004/071467 A2 | 8/2004 |
| WO | WO-2005/083093 A2 | 9/2005 |

OTHER PUBLICATIONS

GenSeq Accession ABV74262, Lerchl et al, Mar. 28, 2003.*
EST Accession BE777235, Kamoun et al, Sep. 20, 2000.*
Broun et al, Science 282: 1315-1317, Nov. 13, 1998.*
Van de Loo et al, PNAS, USA 92: 6743-6747, Jul. 1995.*
Doerks et al, TIG 14(6): 248-250, Jun. 1998.*
Bork et al, TIG 12(10): 425-427, Oct. 1996.*
Poulos, A. "Very Long Chain Fatty Acids in Higher Animals—A Review", Lipids, 1995, vol. 30, No. 1, pp. 1-14.
Horrocks, L. A., et al., "Health Benefits of Docosahexaenoic Acid (DHA)." Pharmacological Research, 1999, vol. 40, No. 3, pp. 211-225.
Stukey, J. E., et al. "The *OLE1* Gene of *Saccharomyces cerevisiae* Encodes the Δ9 Fatty Acid Desaturase and Can be Functionally Replaced by the Rat Stearoyl-CoA Desatuase Gene." The Journal of Biological Chemistry, 1990, vol. 265, No. 33, pp. 20144-20149.

Wada, H., et al. "Enhancement of Chilling Tolerance of a Cyanobacterium by Genetic Manipulation of Fatty Acid Desaturation". Nature, 1990, vol. 347, pp. 200-203.
McKeon T., et al. "Stearoyl-Acyl Carrier Protein Desaturase from Safflower Seeds", from Methods in Enzymology, Lowenstein J. M. ed., 1981, vol. 71(C), Lipids, pp. 275-281, Academic Press.
Wang, X. M., et al. "Synthesis and Regulation of Linolenic Acid in Higher Plants", Plant Physiol. Biochem., 1988, vol. 26, No. 6, pp. 777-792.
Vazhappilly, R., et al., "Heterotrophic Production Potential of Omega-3 Polyunsaturated Fatty Acids by Microalgae and Algae-like Microorganisms", Botanica Marina, 1998, vol. 41, pp. 553-558.
Totani, N., et al. "The Filamentous Fungus *Mortierella alpina*, High in Arachidonic Acid." Lipids, 1987, vol. 22, No. 12, pp. 1060-1062.
Akimoto, M., et al. "Carbon Dioxide Fixation and Polyunsaturated Fatty Acid Production by the Red Alga *Porphyridium cruentum*", Applied Biochemistry and Biotechology, 1998, vol. 73, pp. 269-278.
Takeyama, H., et al. "Expression of the Eicosapentaenoic Acid Synthesis Gene Cluster from *Shewanella* sp. In a Transgenic Marine Cyanobacterium, *Synechococcus* sp.", Microbiology, 1997, vol. 143, pp. 2725-2731.
Zank, T. K., et al. "Cloning and Functional Characterisation of an Enzyme Involved in the Elongation of Δ6-polyunsaturated Fatty Acids from the Moss *Physcomitrella patens*", The Plant Journal, 2002, vol. 31, No. 3, pp. 255-268.
Sakuradani, E., et al. "Δ6-Fatty Acid Desaturase from an Arachidonic Acid-Producing *Mortierella* Fungus—Gene Cloning and its Heterologous Expression in a Fungus, *Aspergillus*", Gene, 1999, vol. 238, pp. 445-453.
Sprecher, H. "Metabolism of Highly Unsaturated n-3 and n-6 Fatty Acids", Biochimica et Biophysica Acta, 2000, vol. 1486, pp. 219-231.
Tocher, D. R., et al., "Recent Advances in the Biochemistry and Molecular Biology of Fatty Acyl Desaturases", Prog. Lipid Res., 1998, vol. 37. No. 2/3, pp. 73-117.
Domergue, F., et al. "Cloning and Functional Characterization of *Phaeodactylum tricornutum* Front-End Desaturases Involved in Eicosapentaenoic Acid Biosynthesis", Eur. J. Biochem., 2002, vol. 269, pp. 4105-4113.
Shimokawa, H., "Beneficial Effects of Eicosapentaenoic Acid on Endothelial Vasodilator Functions in Animals and Humans", World Rev. Nutr. Diet., 2001, vol. 88, pp. 100-108.
Calder, P. C., "Dietary Modification of Inflammation with Lipids", Proceedings of the Nutrition Society, 2002, vol. 61, pp. 345-358.
Cleland, L. G., et al., "Fish Oil and Rheumatoid Arthritis: Antiinflammatory and Collateral Health Benefits", The Journal of Rheumatology, 2000, vol. 27, pp. 2305-2307.
Pereira, S. L. et al., "A Novel ω3-Fatty Acid Desaturase Involved in the Biosynthesis of Eicosapentaenoic Acid", Biochem. J., 2004, vol. 378, pp. 665-671.
Millar, A. A., et al., "CUT1, An Arabidopsis Gene Required for Cuticular Wax Biosynthesis and Pollen Fertility, Encodes a Very-Long-Chain Fatty Acid Condensing Enzyme", The Plant Cell, 1999, vol. 11, pp. 825-838.
Tvrdik, P., et al., "Role of a New Mammalian Gene Family in the Biosynthesis of Very Long Chain Fatty Acids and Sphingolipids", The Journal of Cell Biology, 2000, vol. 149, pp. 707-717.
Drexler, H., et al. "Metabolic Engineering of Fatty Acids for Breeding of New Oilseed Crops: Strategies, Problems and First Results", Journal of Plant Physiology, 2003, vol. 160, pp. 779-802.
Beaudoin, F., et al., "Heterologous Reconstitution in Yeast of the Polyunsaturated Fatty Acid Biosynthetic Pathway", Proc. Natl. Acad. Sci. U. S. A., 2000, vol. 97, No. 12, pp. 6421-6426.
Meyer, A., et al., "Novel Fatty Acid Elongases and Their Use for the Reconstitution of Docosahexaenoic Acid Biosynthesis", Journal of Lipid Research, 2004, vol. 45, pp. 1899-1909.
Yu, R., et al., "Production of Eicosapentaenoic Acid by a Recombinant Marine Cyanobacterium, *Synechococcus* sp.", Lipids, 2000, vol. 35, No. 10, pp. 1061-1064.

(56) References Cited

OTHER PUBLICATIONS

Huang, Y-S., et al. "Cloning of β12- and Δ6-Desaturases from *Mortierella alpina* and Recombinant Production of γ-Linolenic Acid in *Saccharomyces cerevisiae*", Lipids, 1999, vol. 34, No. 7, pp. 649-659.

Millar, A. A., et al. "Very-Long-Chain Fatty Acid Biosynthesis is Controlled Through the Expression and Specificity of the Condensing Enzyme", The Plant Journal, 1997, vol. 12, No. 1, pp. 121-131.

Zank, T. K., et al., "Cloning and Functional Expression of the First Plant Fatty Acid Elongase Specific for $\Delta^6$-polyunsaturated Fatty Acids", Biochemical Society Transactions, 2000, vol. 28, part 6, pp. 654-658.

"Nouveau Dictionnaire des Huiles Végétales: Compositions en Acides; Gras", Ucciani E., Ed. Technique & Documentation—Lavoisler, 1995 ISBN: 2-7430-0009-0, pp. 577, 578 and 582.

Kajikawa, M., et al., "Isolation and Functional Characterization of Fatty Acid Δ5-Elongase Gene from the Liverwort *Marchantia polymorpha* L.", FEBS Letters, 2006, vol. 580, pp. 149-154.

Robert, S. S., et al., "Isolation and Characterisation of a Δ5-Fatty Acid Elongase from the Marine Microalga *Pavlova salina*", Mar. Biotechnol., 2009, vol. 11, pp. 410-418.

Pereira, S. L., et al., "Identification of Two Novel Microalgal Enzymes Involved in the Conversion of the ω3-Fatty Acid, Eicosapentaenoic Acid, into Docosahexaenoic Acid", Biochem. J., 2004, vol. 384, pp. 357-366.

Leonard, A. E., et al., "Elongation of Long-Chain Fatty Acids", Progress in Lipid Research, 2004, vol. 43, pp. 36-54.

Sperling, P., et al., "The Evolution of Desaturases", Prostaglandins, Leukotrienes and Essential Fatty Acids, 2003, vol. 68, pp. 73-95.

Domergue, F., et al., "New Insight into *Phaeodactylum tricornutum* Fatty Acid Metabolism. Cloning and Functional Characterization of Plastidial and Microsomal Δ12-Fatty Acid Desaturases", Plant Physiology, 2003, vol. 131, pp. 1648-1660.

Wu, G., et al., "Stepwise Engineering to Produce High Yields of Very Long-Chain Polyunsaturated Fatty Acids in Plants", Nature Biotechnology, 2005, vol. 23, No. 8, pp. 1013-1017.

Nakamura, M. T., et al., "Structure, Function, and Dietary Regulation of Δ6, Δ5, and Δ9 Desaturases", Annu. Rev. Nutr., 2004, vol. 24, pp. 345-376.

"P. patens Delta6 Elongase SEQ ID 29", GeneSeq Database Accession No. ABG73608, Mar. 25, 2003.

"Subname: Full = Polyunsaturated Fatty Acid Elongase elvol5a", UniProt Database Accession No. Q8AWE7, Oct. 25, 2005.

"Polyunsaturated Fatty Acid Elongase (ELOVL Family Member 5, Elongation of Long Chain Fatty Acids) (YEAST)", UniProt Database Accession No. Q8AX86, Mar. 1, 2003.

"633167 NCCCWA 1RT Oncorhynchus Mykiss cDNA Clone 1RT126D03_B_B02 5', mRNA Sequence", EMBL Database Accession No. CA360014, Nov. 7, 2002.

"LOC398440 Protein", UniProt Database Accession No. Q7ZXJ4, Jun. 1, 2003.

Huang, Y.-S., et al., "Enzymes for Transgenic Biosynthesis of Long-Chain Polyunsaturated Fatty Acids", Biochimie, 2004, vol. 86, No. 11, pp. 793-798.

Cronan, J.E. et al., "Biosynthesis of Membrane Lipids", in "*E. coli und Salmonella*", Section B2, Neidhardt, F.C. et al. eds., ASM Press, Washington, DC, (1996), pp. 612-636.

Gerhardt, B., "Fatty Acid Degradation in Plants", Prog. Lipid Res. 31:4 (1992), pp. 417-446.

Magnuson, K. et al., "Regulation of Fatty Acid Biosynthesis in *Escherichia coli*", Microbiological Reviews, 57:3 (1993), pp. 522-542.

Stymne, S., "Biosynthesis of 'Uncommon' Fatty Acids and Their Incorporation into Triacylglycerols", Biochemistry and Molecular Biology of Membrane and Storage Lipids of Plants, N. Murata et al., Editors, The American Society of Plant Physiologists (1993), pp. 150-158.

Kunau, W.-H., et al., "β-oxidation of Fatty Acids in Mitochondria, Peroxisomes, and Bacteria: A Century of Continued Progress", Prog. Lipid Res. 34:4 (1995), pp. 267-342.

Ohlrogge, J. et al., "Lipid Biosynthesis", The Plant Cell 7 (1995), pp. 957-970.

Chalova, L. I., et al. "The Composition of Lipids of Phytophthora infestans and Their Ability to Induce Potato Phytoalexin Accumulation". Biokhimiya, 1987, vol. 52, No. 9, pp. 1445-1453; also see Database BIOSIS, Abstract No. PREV198885045135.

Kamoun, S. et al., "Initial Assessment of Gene Diversity for the Oomycete Pathogen *Phytophthora infestans* Based on Expressed Sequences", Fungal Genetics and Biology 28 (1999), pp. 94-106.

Pereira, S.L. et al., "Recent Advances in the Study of Fatty Acid Desaturases from Animals and Lower Eukaryotes", Prostaglandins, Leukotrienes and Essential Fatty Acids 68 (2003), pp. 97-106.

Spychalla, J.P. et al., "Identification of an Animal ω-3 Fatty Acid Desaturase by Heterologous Expression in *Arabidopsis*", Proc. Natl. Acad. Sci. USA 94 (1997), pp. 1142-1147.

Brenner, S. E., "Errors in Genome Annotation", TIG, 15:4 (1999), pp. 132-133.

"Phaeodactylum tricornutum Elongase Encoding cDNA Seq ID No. 9",GeneSeq Database Accession No. ABV74261, Mar. 28, 2003.

Stymne, S., "Biosynthesis of 'Uncommon' Fatty Acids and Their Incorporation into Triacylglycerols", Biochemistry and Molecular Biology of Memebrane and Storage Lipids of Plants, N. Murata et al., Editors, The American Society of Plant Physiologists (19993), pp. 150-158.

Frentzen, M., "Acyltransferases from Basic Science to Modified Seed Oils", Fett/Lipid, 100:4-5, S. (1998), pp. 161-166.

Shanklin, J. et al., "Desaturation and Related Modifications of Fatty Acids", Annu. Rev. Plant Physiol. Plant Mol. Biol. 49 (1998), pp. 611-641.

Domergue, F. et al., "Cloning and Functional Characterization of Phaeodactylum tricornutum Front-End Desaturases Involved in Eicosapentaenoic Acid Biosynthesis", Eur. J. Biochem. 269 (2002), pp. 4105-4113.

Guehnemann-Schaefer, K. et al., "Fatty Acid β-oxidation in Glyoxysomes. Characterization of a New Tetrafunctional Protein (MFPIII)", Biochimica et Biophysica Acta 1256 (1995), pp. 181-186.

Kinney, A.J., "Genetic Engineering of Oilseeds for Desired Traits", in "Genetic Emgineering, Principles and Methods"1997, vol. 19, Editor: J. Setlow, pp. 149-166.

Voelker, T., "Plant Acyl-ACP Thioesterases: Chain-Length Determining Enzymes in Plant Fatty Acid Biosynthesis", in "Genetic Engineering, Principles and Methods", vol. 18, Editor: J. Setlow, pp. 111-113 (1996).

Murphy, D.J. et al., "Biosynthesis, Targeting and Processing of Oleosin-like Proteins, Which are Major Pollen Coat Components in Brassica napus", The Plant Journal 13:1 (1998), pp. 1-16.

Kunau, W.H., et al., "β-oxidation of Fatty Acids in Mitochondria, Peroxisomes, and Bacteria: A Centruy of Continued Progress", Prog. Lipid Res. 34:4 (1995), pp. 267-342.

Ohlrogge, J. et al., "Lipid Biosynthesis". The Plant Cell 7 (1995), pp. 957-970.

Chalova, L. I., et al. "The Composition of Lipids of Phytophthora infestans and Their Ability to Induce Potato Phytoalexin Accumlation". Biokhimiya, 1987, vol. 52, No. 9, pp. 1445-1453; also see Database BIOSIS, Abstract No. PREV198885045135.

Abbadi, A. et al., "Biosynthesis of Very-Long-Chain Polyunsaturated Fatty Acids in Transgenic Oilseeds: Constraints on Their Accumulation", The Plant Cell 16 (2004), pp. 2734-2748.

Kamoun, S. et al., "Intial Assessment of Gene Diversity for the Oomycete Pathogen *Phytophtora infestans*Based on Expressed Sequences", Fungal Genetics and Biology 28 (1999), pp. 94-106.

Khozin, I. et al., "Elucidation of the Biosynthesis of Eicosapentaenoic Acid in the Microalga *Porphyridium cruentum*", Plant Physiol. 114 (1997), pp. 223-230.

* cited by examiner

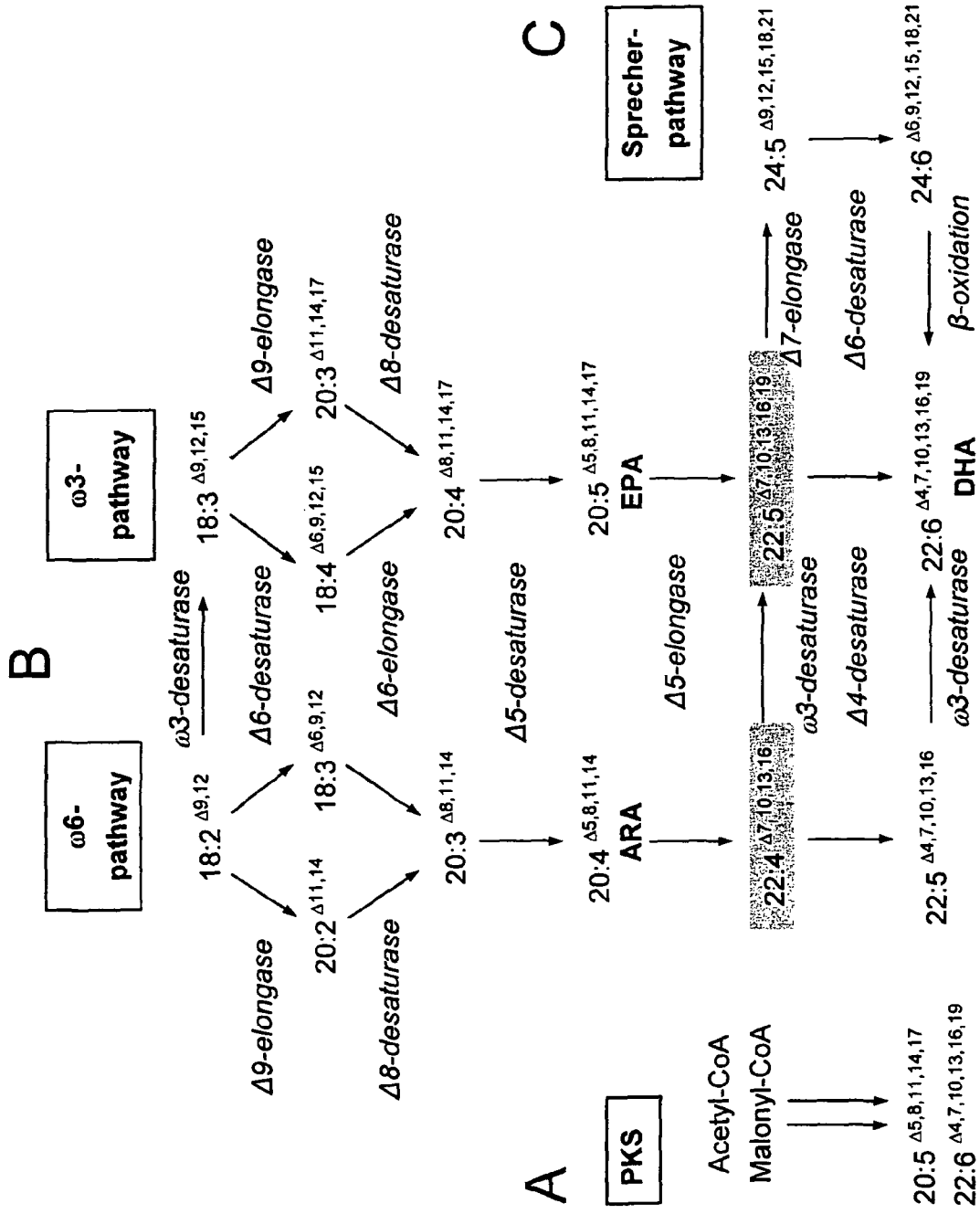
Figure 1: Various synthetic pathways for the biosynthesis of DHA (docosahexaenoic acid)

Figure 2: Substrate specificity of the Δ5-elongase (SEQ ID NO: 53) for various fatty acids
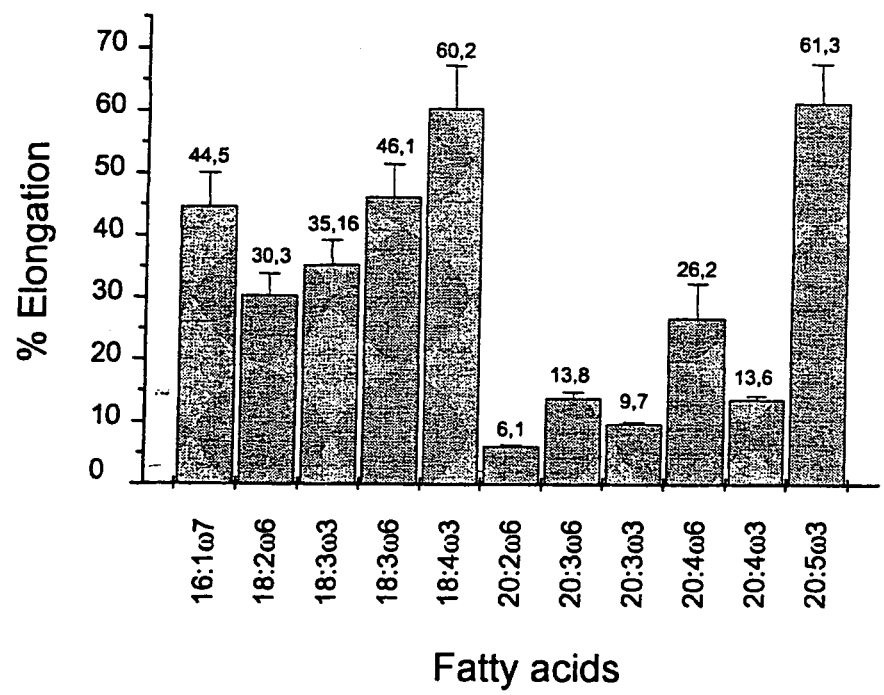

Figure 3: Reconstitution of DHA biosynthesis in yeast starting from 20:5ω3.
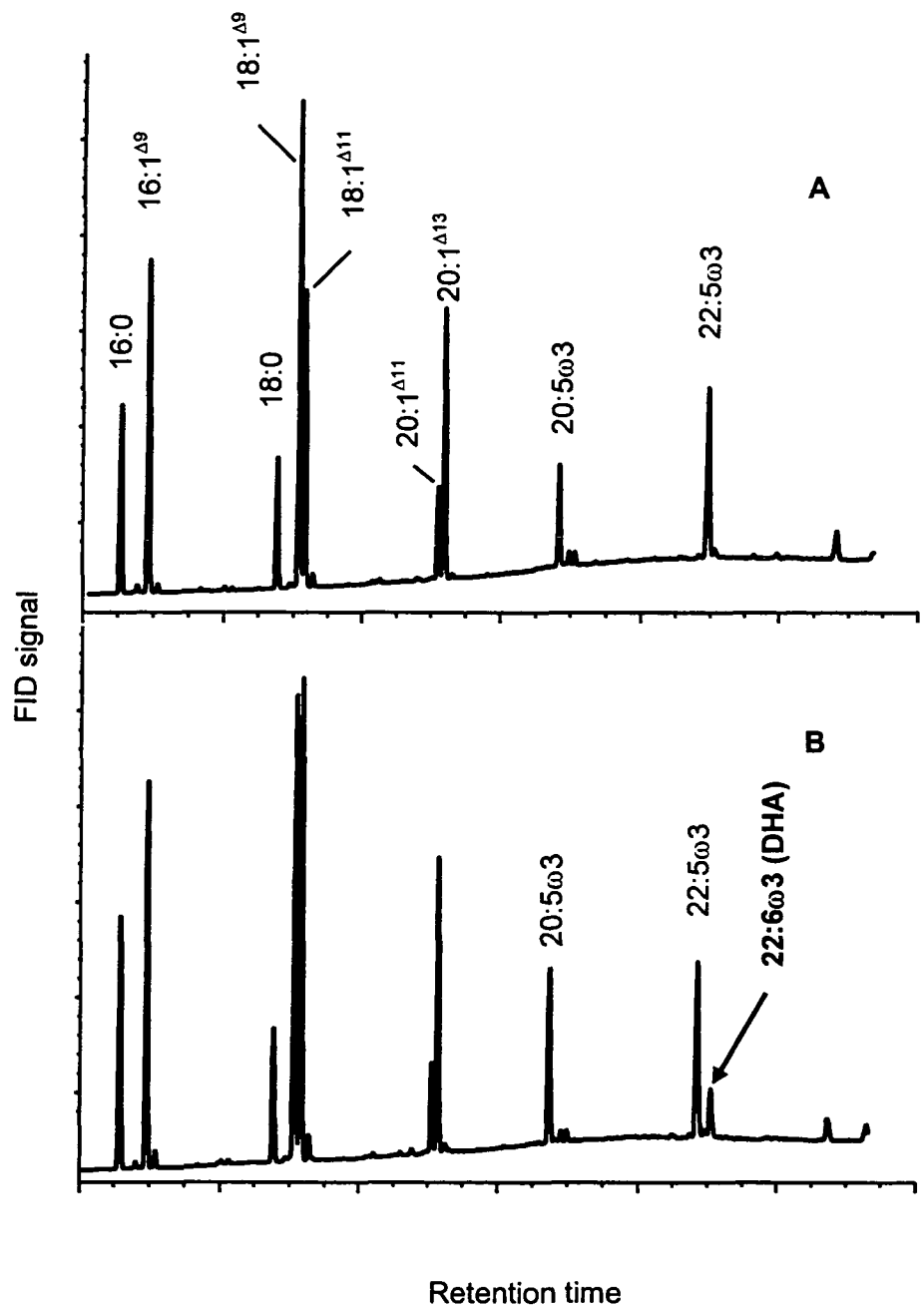

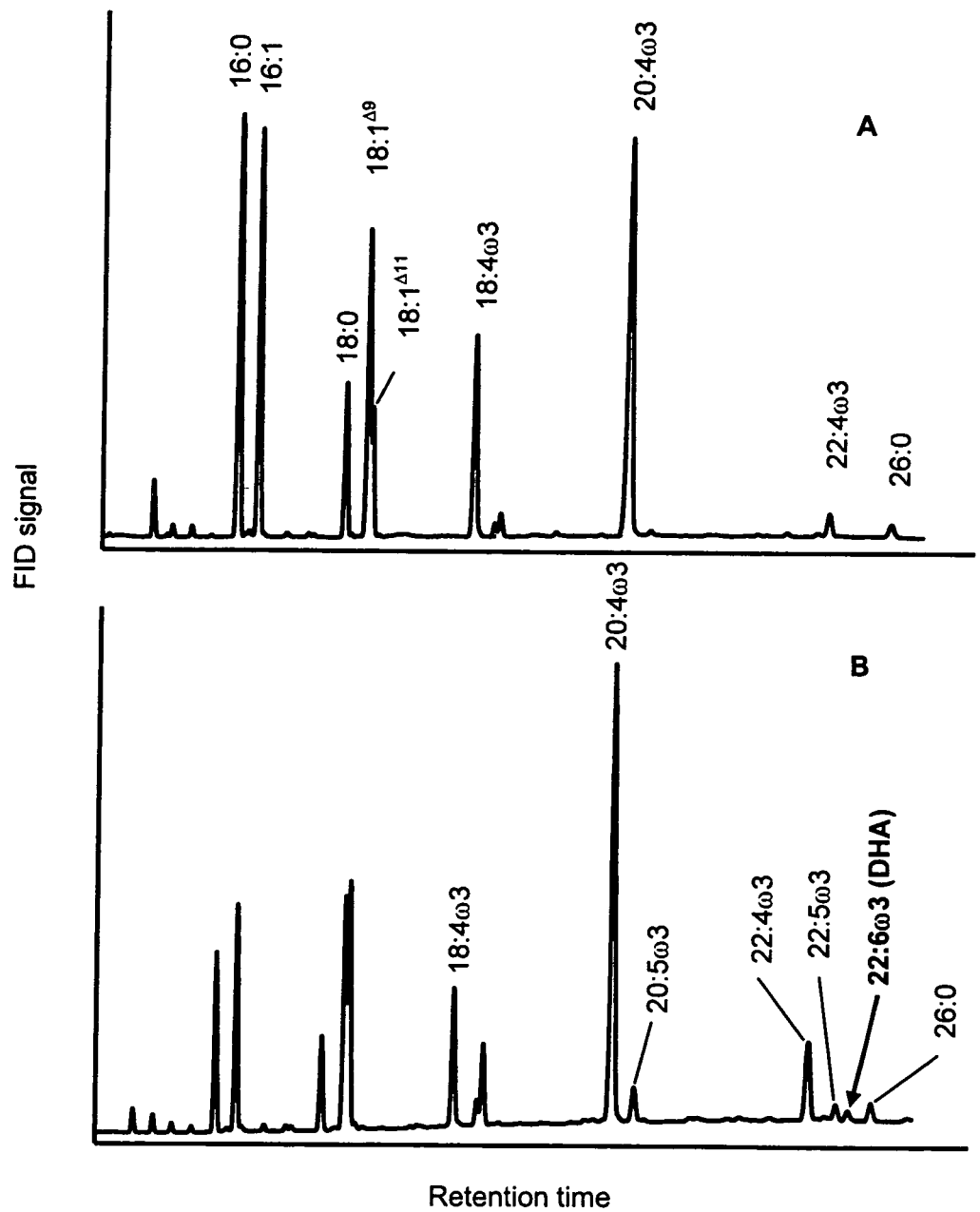
Figure 4: Reconstitution of DHA biosynthesis in yeast starting from 18:4ω3.

Figure 5: Fatty acid composition (in mol%) transgenic yeasts which had been transformed with the vectors pYes3-OmELO3/pYes2-EgD4 or pYes3-OmELO3/pYes2-EgD4+pESCLeu-PtD5. The yeast cells were grown in minimal medium with tryptophan and uracil / and leucin in the presence of 250 µM 20:5$^{\Delta5,8,11,14,17}$ and 18:4$^{\Delta6,9,12,15}$, respectively. The fatty acid methyl esters were obtained from cell sediments by acid methanolysis and analyzed via GLC. Each value represents the mean value (n=4) ± standard deviation.

| Fatty acids | pYes3-OmELO/pYes2-EgD4<br>Feeding with 20:5$^{\Delta5,8,11,14,17}$ | pYes3-OmELO/pYes2-EgD4<br>EgD4 + pESCLeu-PtD5<br>Feeding with 18:4$^{\Delta6,9,12,15}$ |
|---|---|---|
| 16:0 | 9.35 ± 1.61 | 7.35 ± 1.37 |
| 16:1 $^{\Delta9}$ | 14.70 ± 2.72 | 10.02 ± 1.81 |
| 18:0 | 5.11 ± 1.09 | 4.27 ± 1.21 |
| 18:1 $^{\Delta9}$ | 19.49 ± 3.01 | 10.81 ± 1.95 |
| 18:1 $^{\Delta11}$ | 18.93 ± 2.71 | 11.61 ± 1.48 |
| 18:4 $^{\Delta6,9,12,15}$ | - | 7.79 ± 1.29 |
| 20:1 $^{\Delta11}$ | 3.24 ± 0.41 | 1.56 ± 0.23 |
| 20:1 $^{\Delta13}$ | 11.13 ± 2.07 | 4.40 ± 0.78 |
| 20:4 $^{\Delta8,11,14,17}$ | - | 30.05 ± 3.16 |
| 20:5 $^{\Delta5,8,11,14,17}$ | 6.91 ± 1.10 | 3.72 ± 0.59 |
| 22:4 $^{\Delta10,13,16,17}$ | - | 5.71 ± 1.30 |
| 22:5 $^{\Delta7,10,13,16,19}$ | 8.77 ± 1.32 | 1.10 ± 0.27 |
| 22:6 $^{\Delta4,7,10,13,16,19}$ | 2.73 ± 0.39 | 0.58 ± 0.10 |

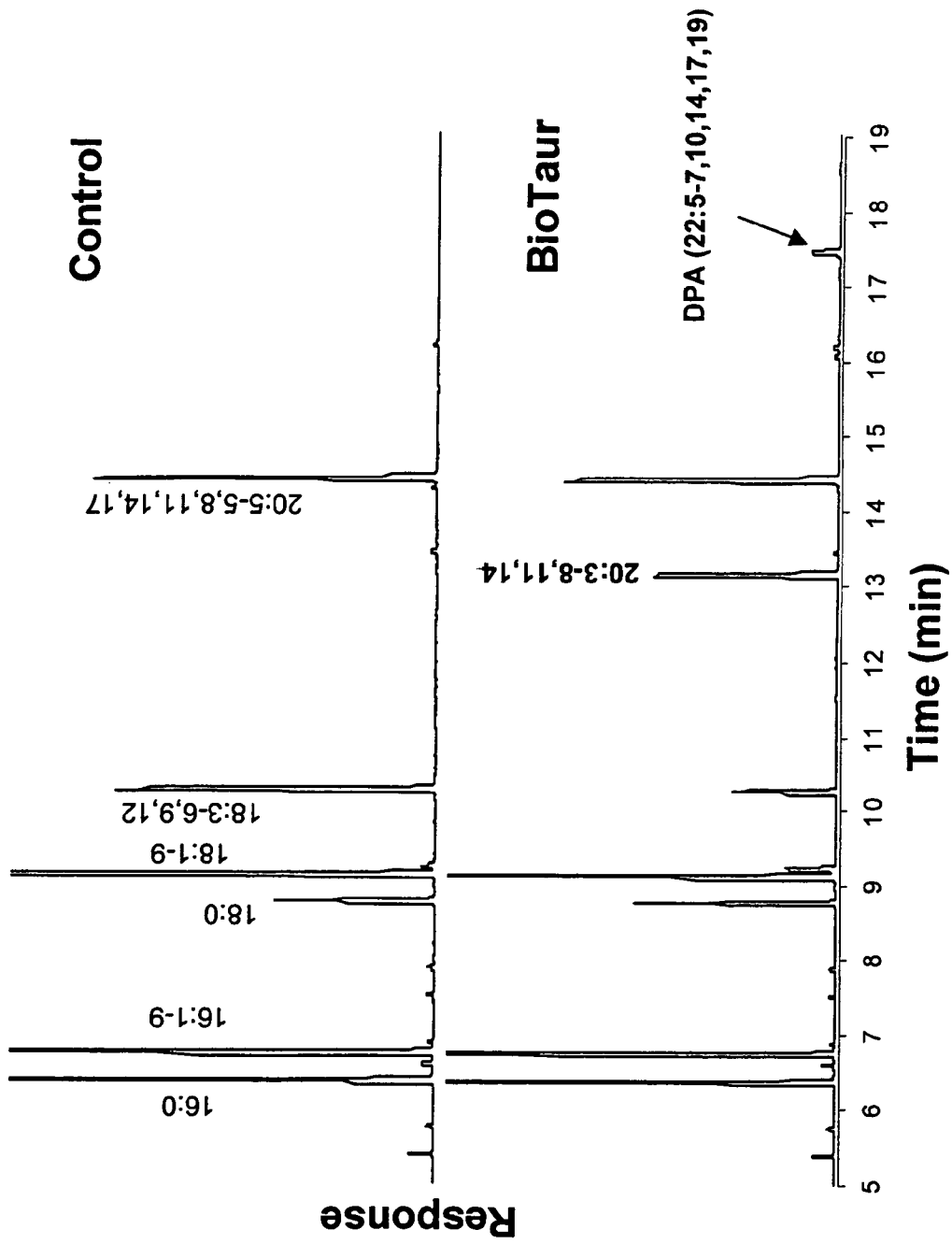
Figure 6: Feeding experiment for determining the functionality and substrate specificity with yeast strains

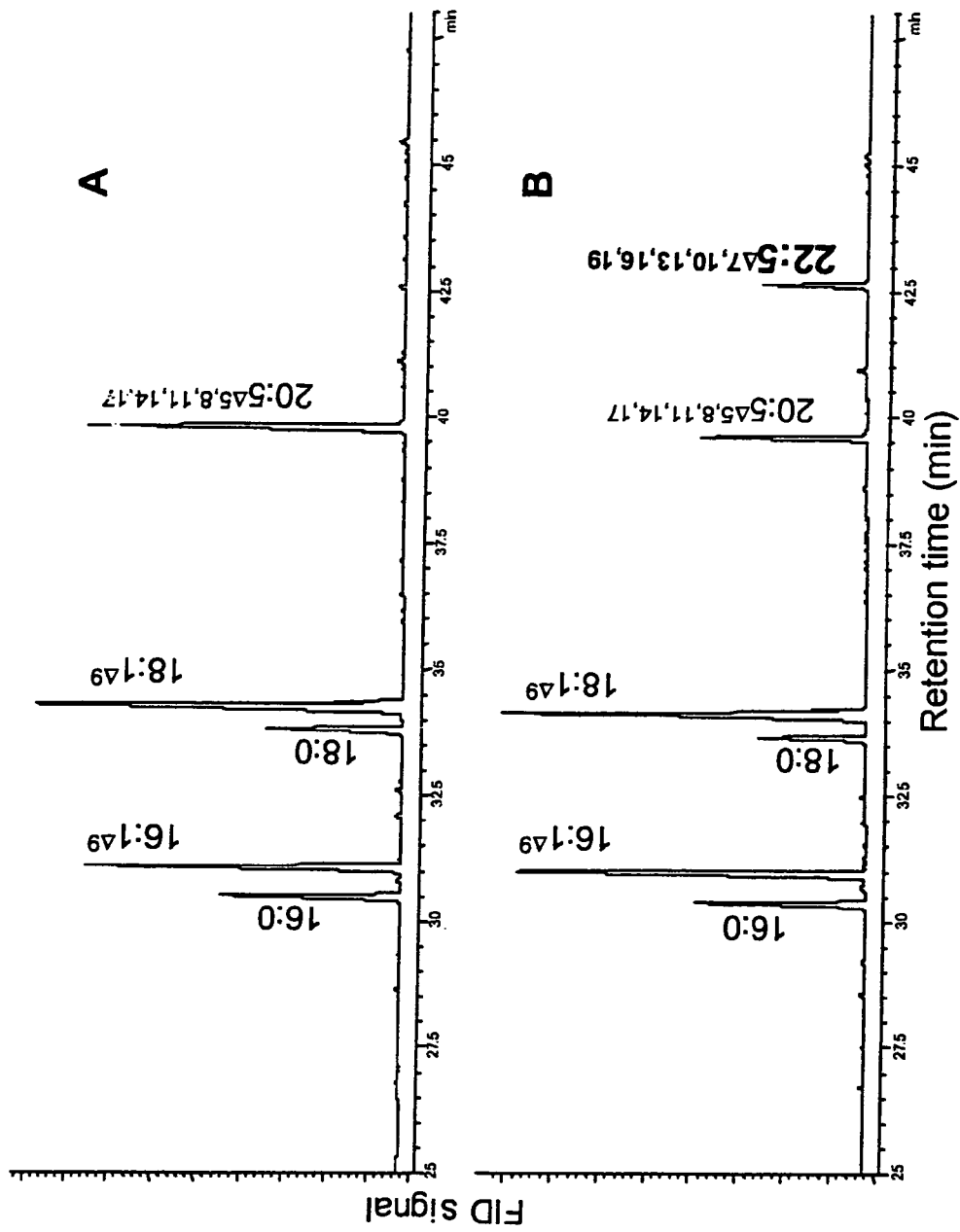
Figure 7: Elongation of eicosapentaenoic acid by OtElo1

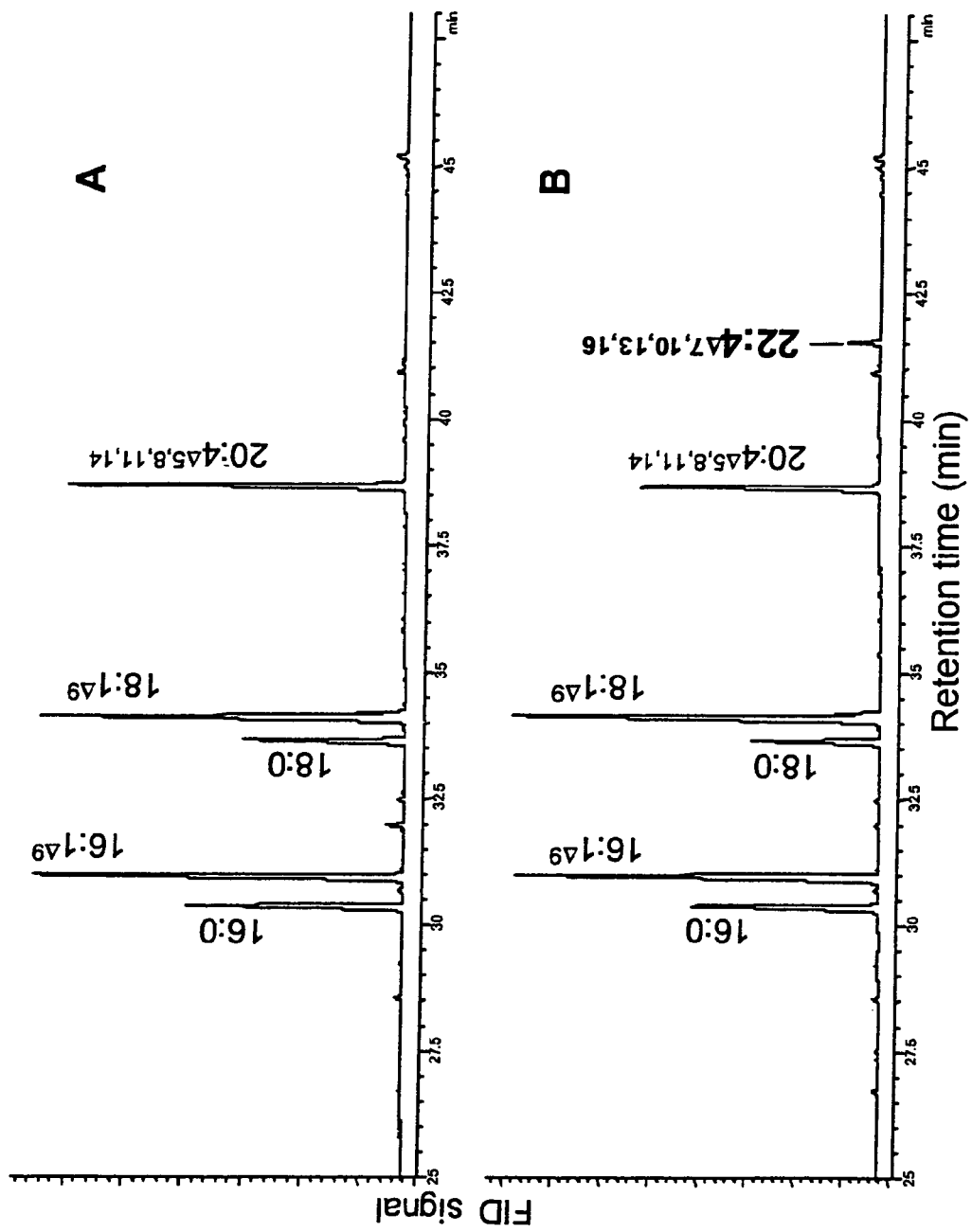
Figure 8: Elongation of arachidonic acid by OtElo1

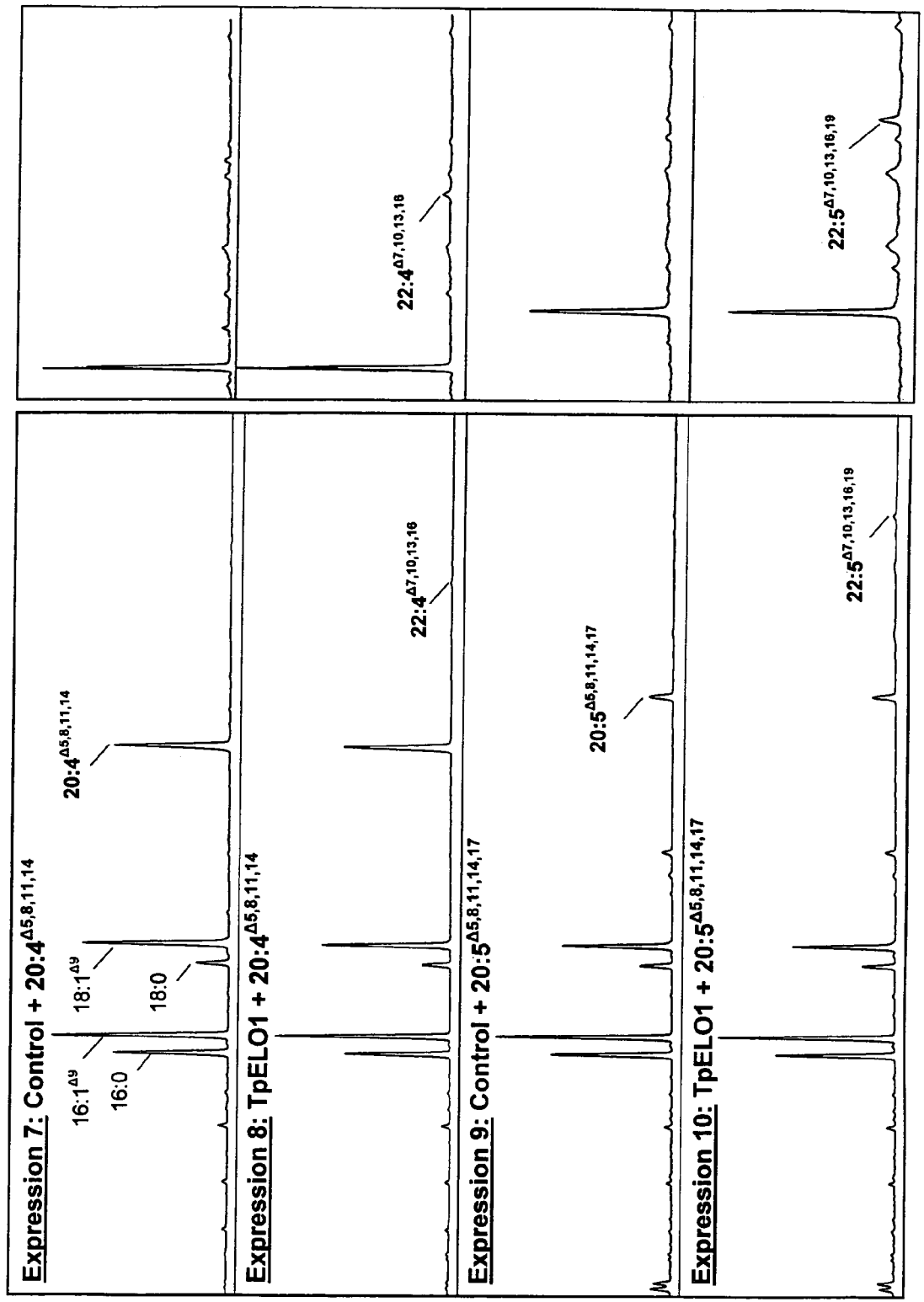
Figure 9: Expression of TpELO1 in yeast

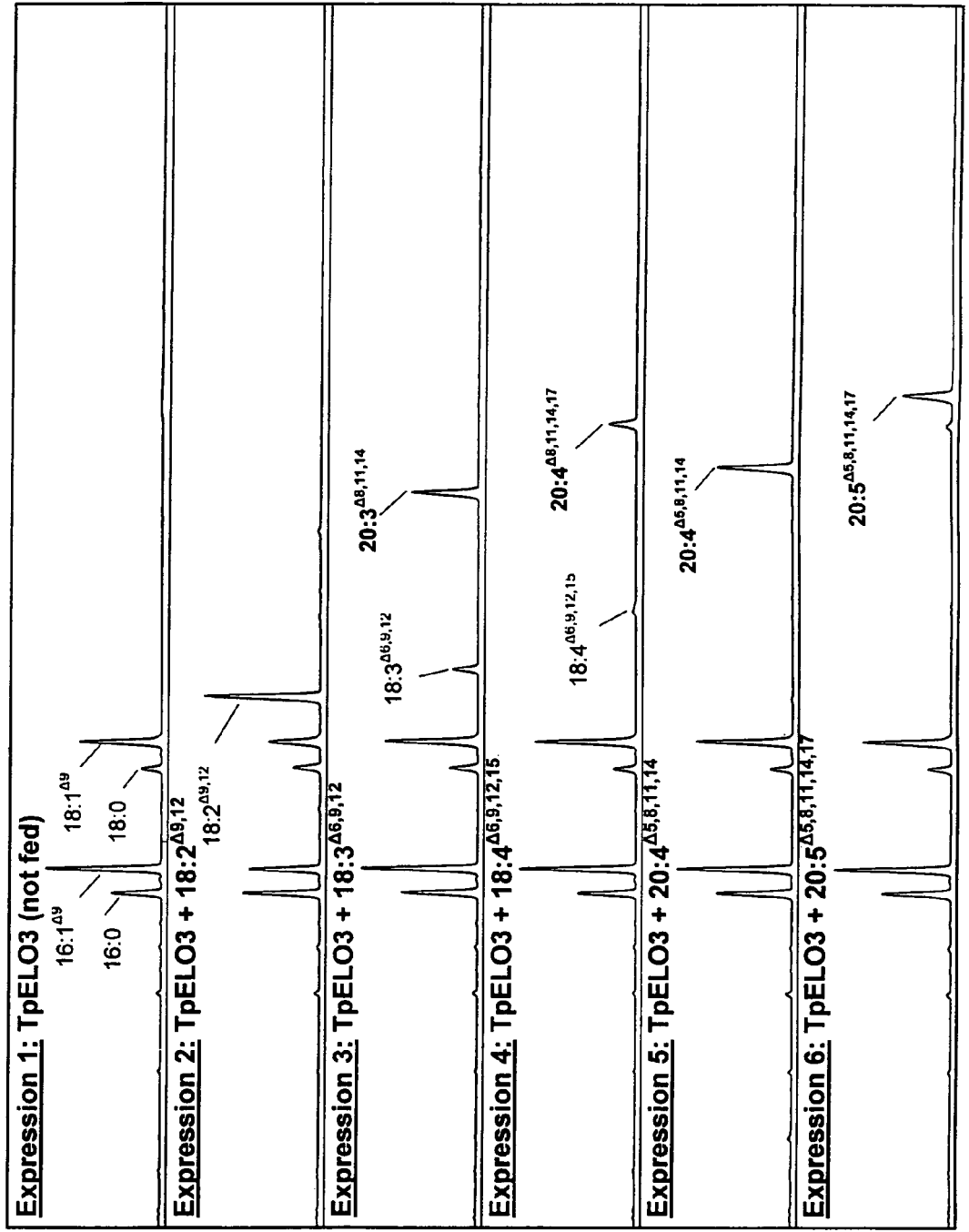
Figure 10: Expression of TpELO3 in yeast

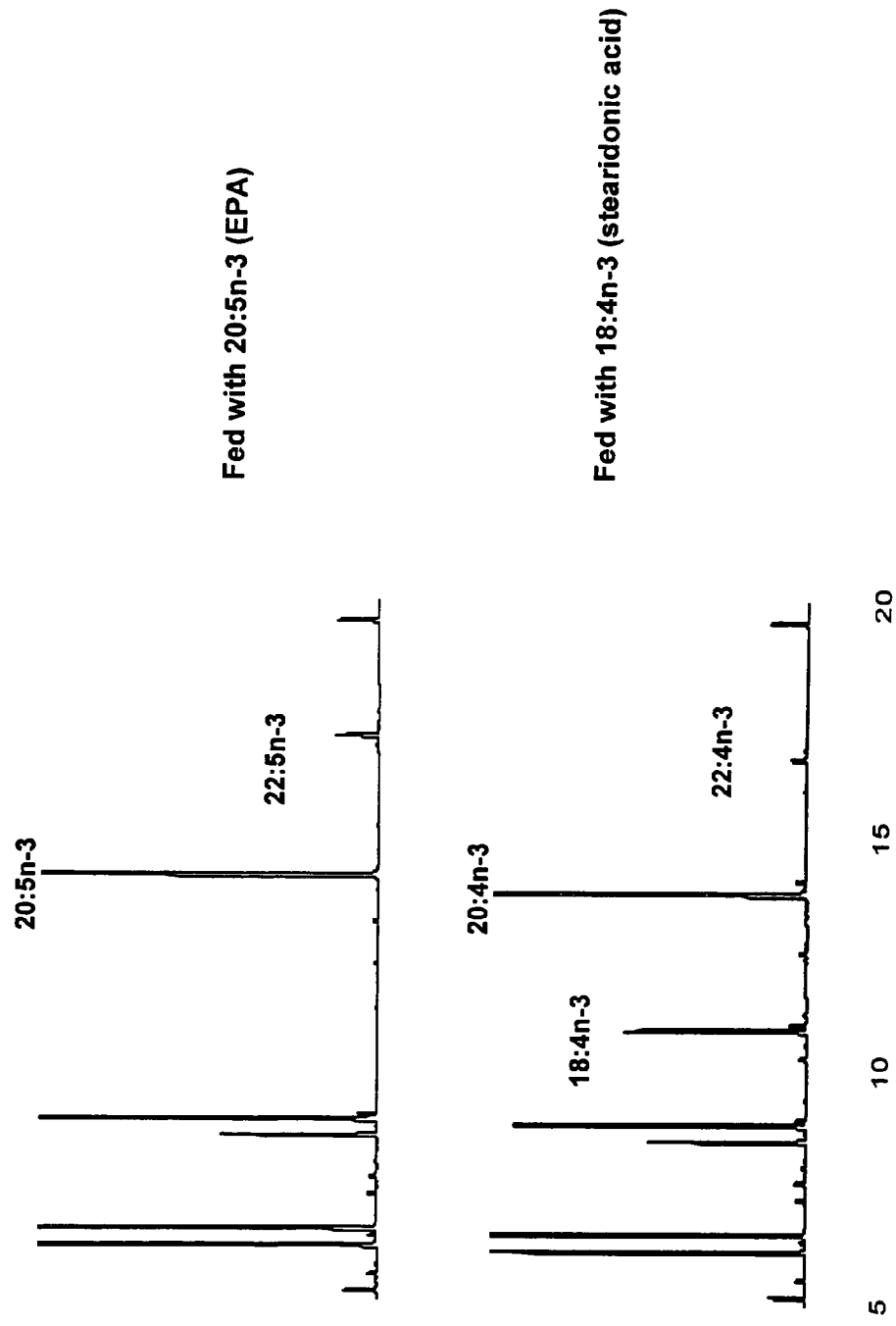
Figure 11: Expression of Thraustochytrium Δ5-elongase TL16/pYES2.1 in yeast Figure 12: Desaturation of linoleic acid (18:2 ω6-fatty acid) to give α-linolenic acid (18:3 ω3-fatty acid) by Pi-omega3Des.
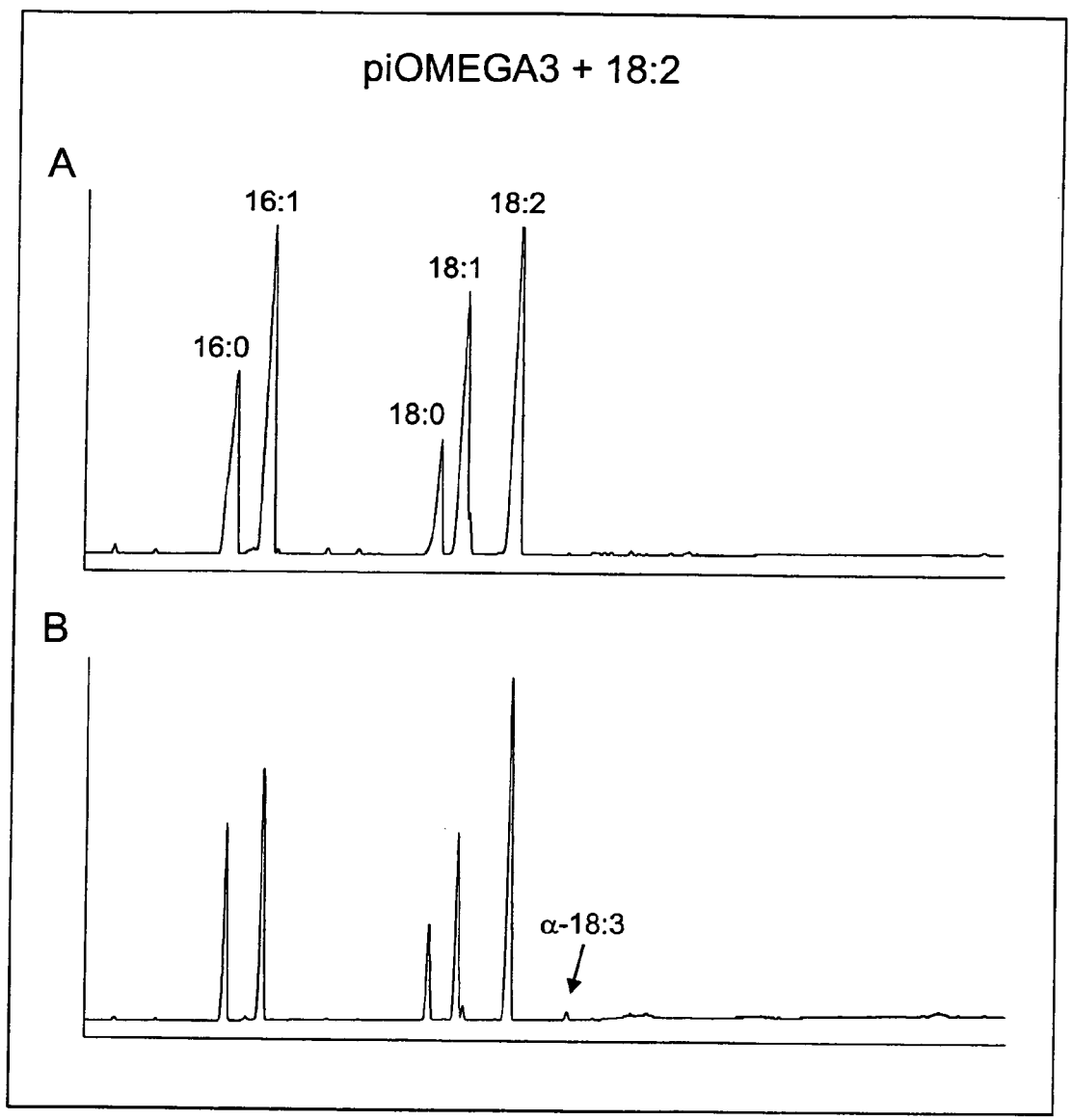

Figure 13: Desaturation of γ-linolenic acid (18:3 ω6-fatty acid) to give stearidonic acid (18:4 ω3 fatty acid) by Pi-omega3Des.
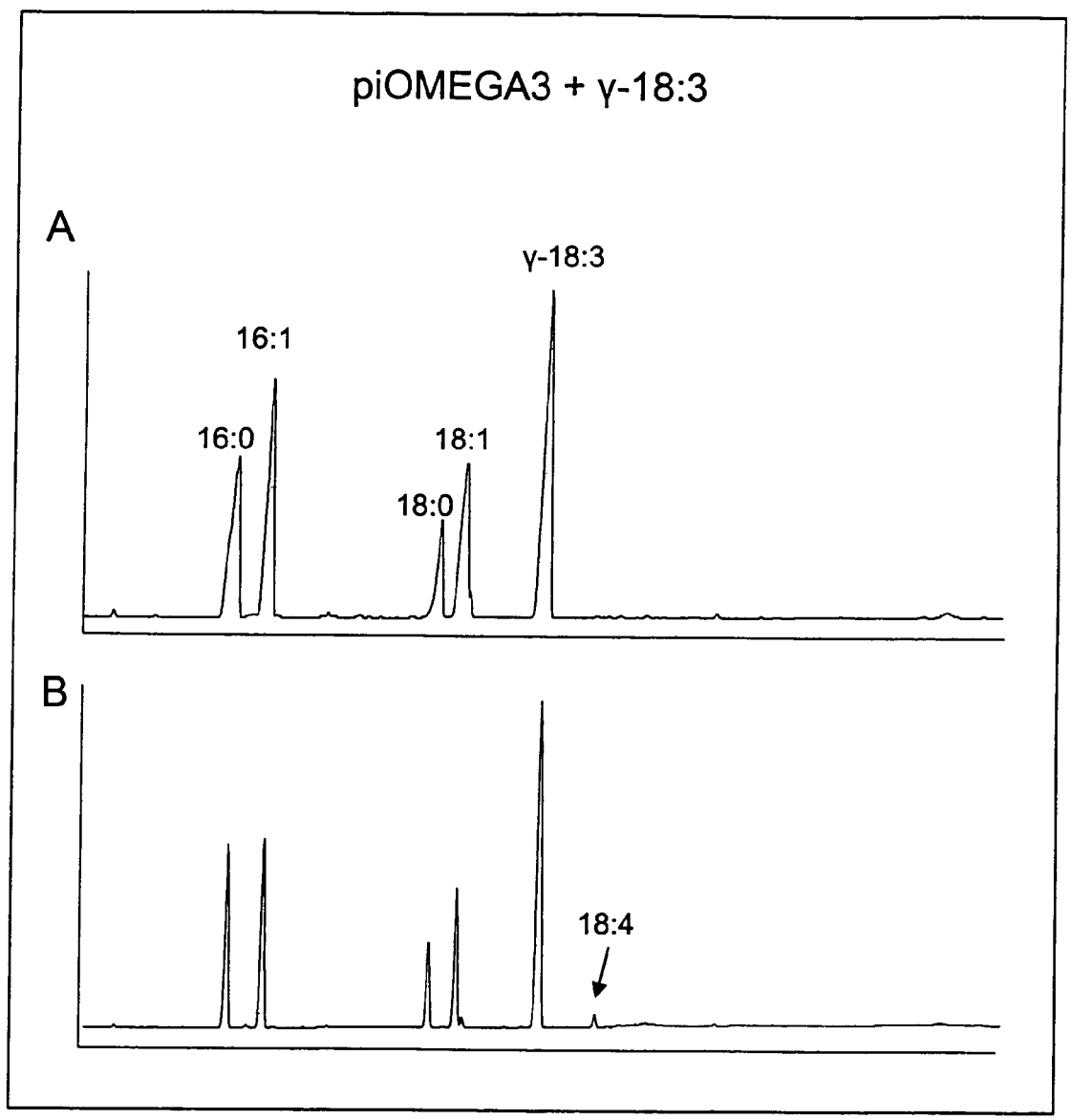

Figure 14: Desaturation of C20:2 ω6-fatty acid to give C20:3 ω3-fatty acid by Pi-omega3Des.
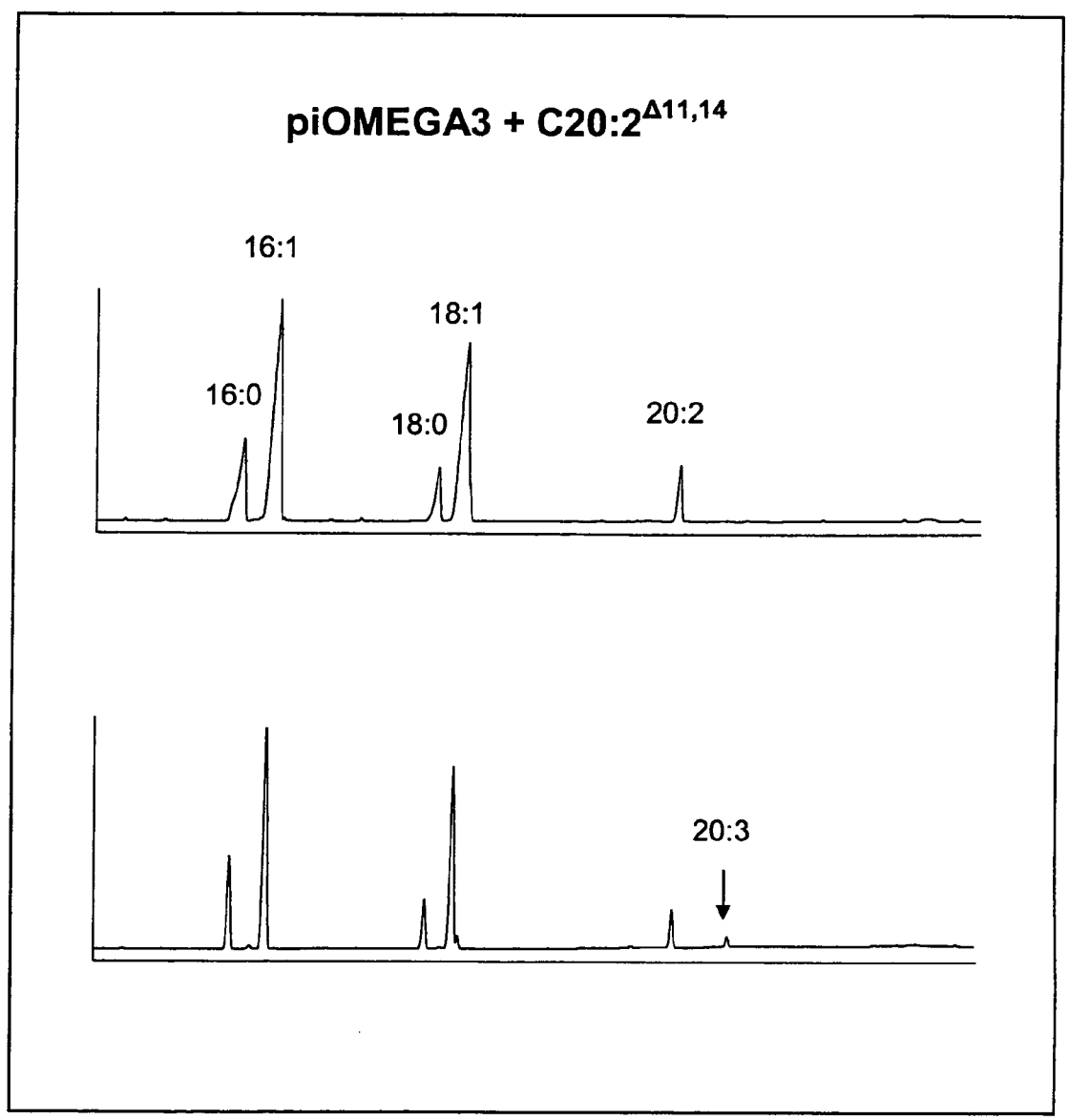

Figure 15: Desaturation of C20:3 ω6-fatty acid to give C20:4 ω3-fatty acid by Pi-omega3Des.
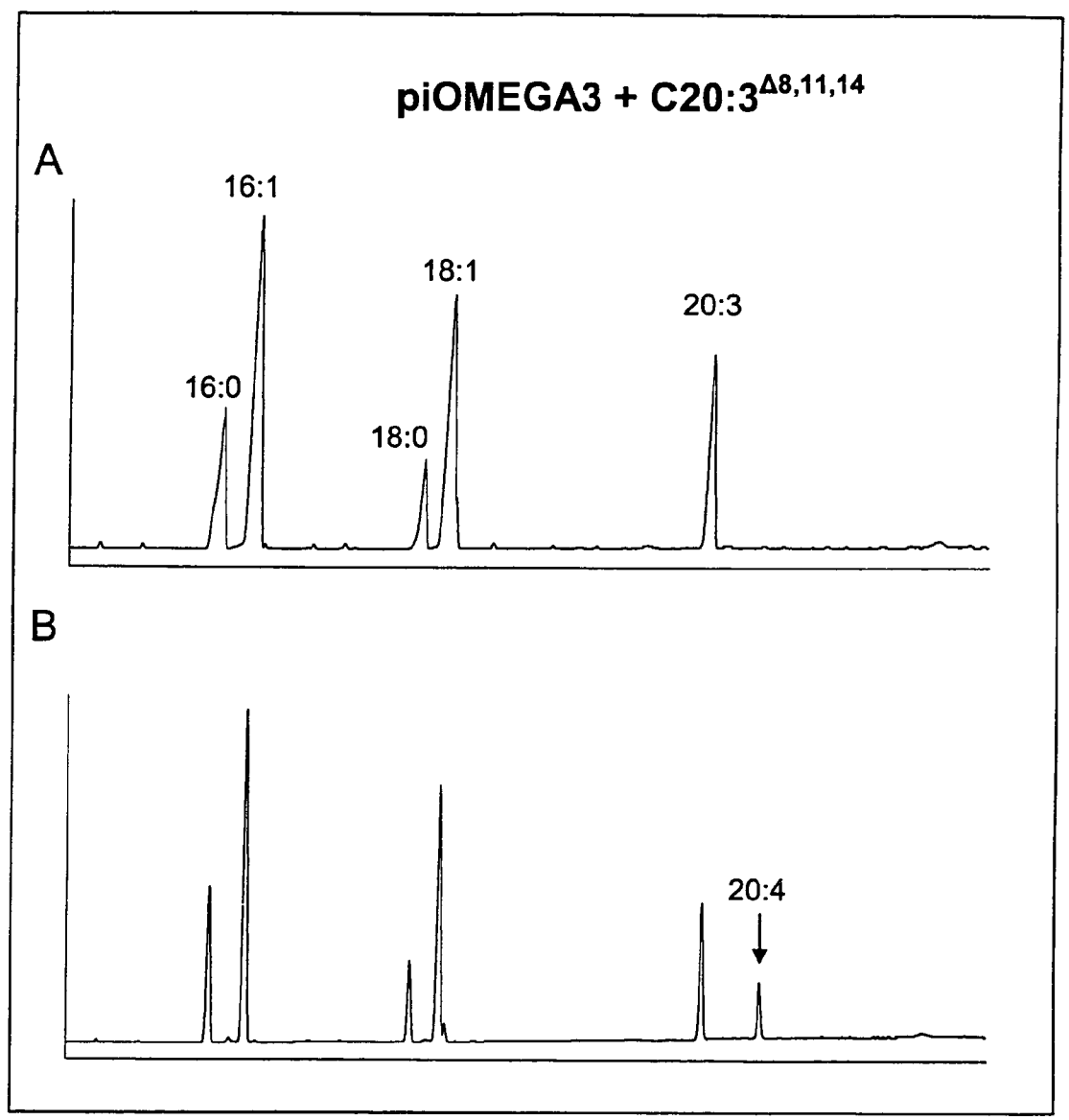

Figure 16: Desaturation of arachidonic acid (C20:4 ω6-fatty acid) to give eicosapentaenoic acid (C20:5 ω3-fatty acid) by Pi-omega3Des.
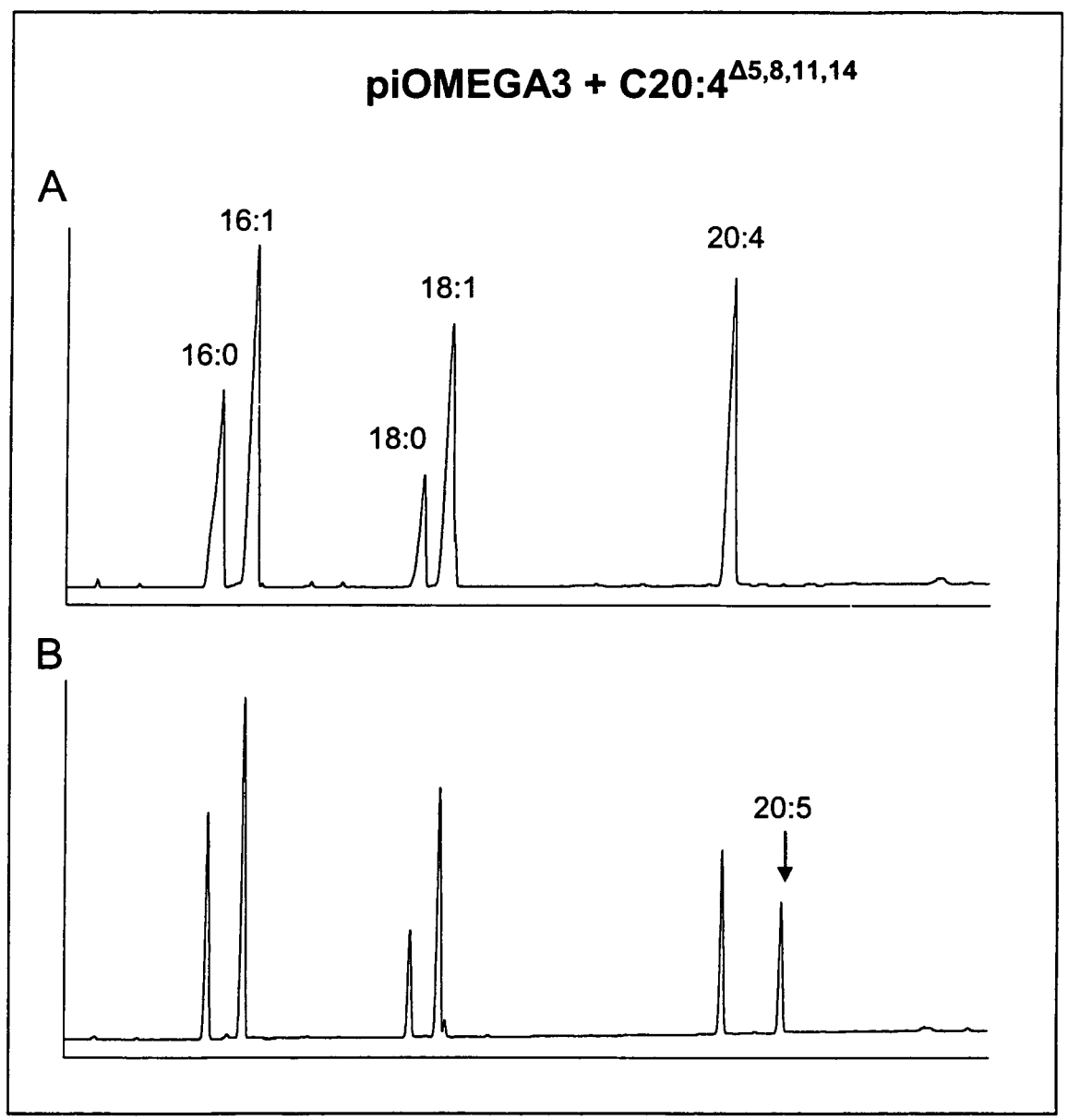

Figure 17: Desaturation of docosatetraenoic acid (C22:4 ω6-fatty acid) to give docosapentaenoic acid (C22:5 ω3-fatty acid) by Pi-omega3Des.
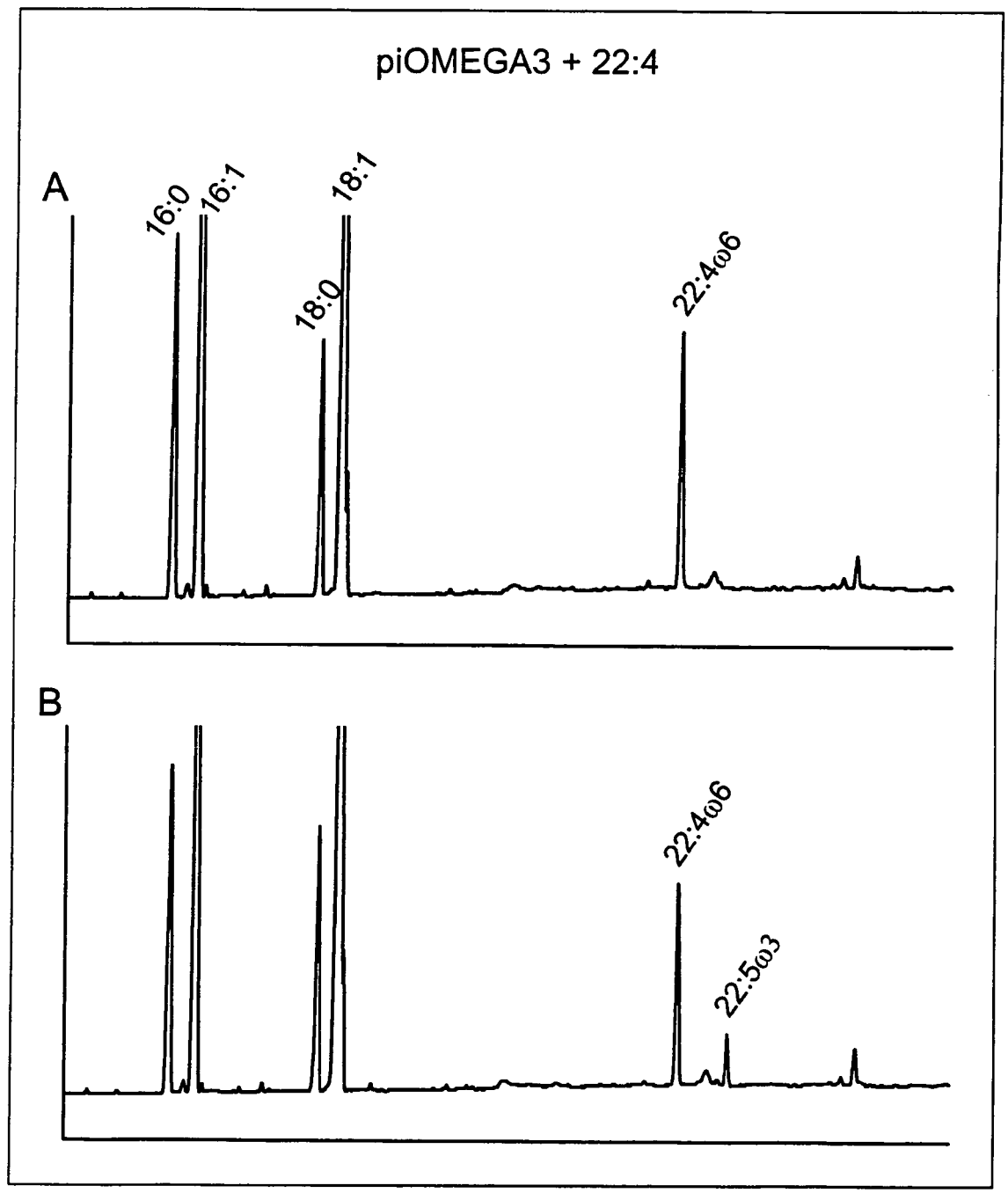

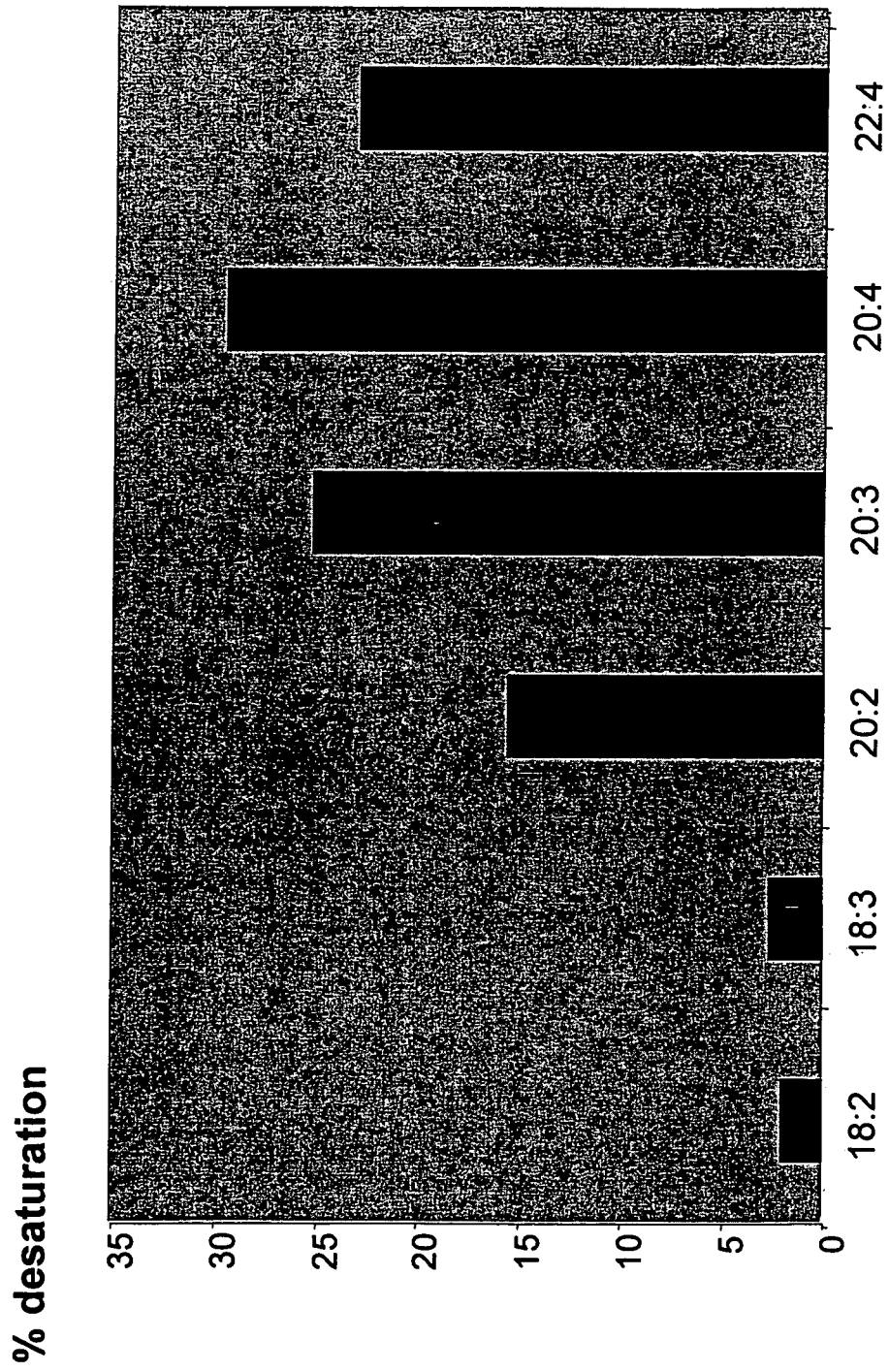
Figure 18: Substrate specificity of Pi-omega3Des for various fatty acids

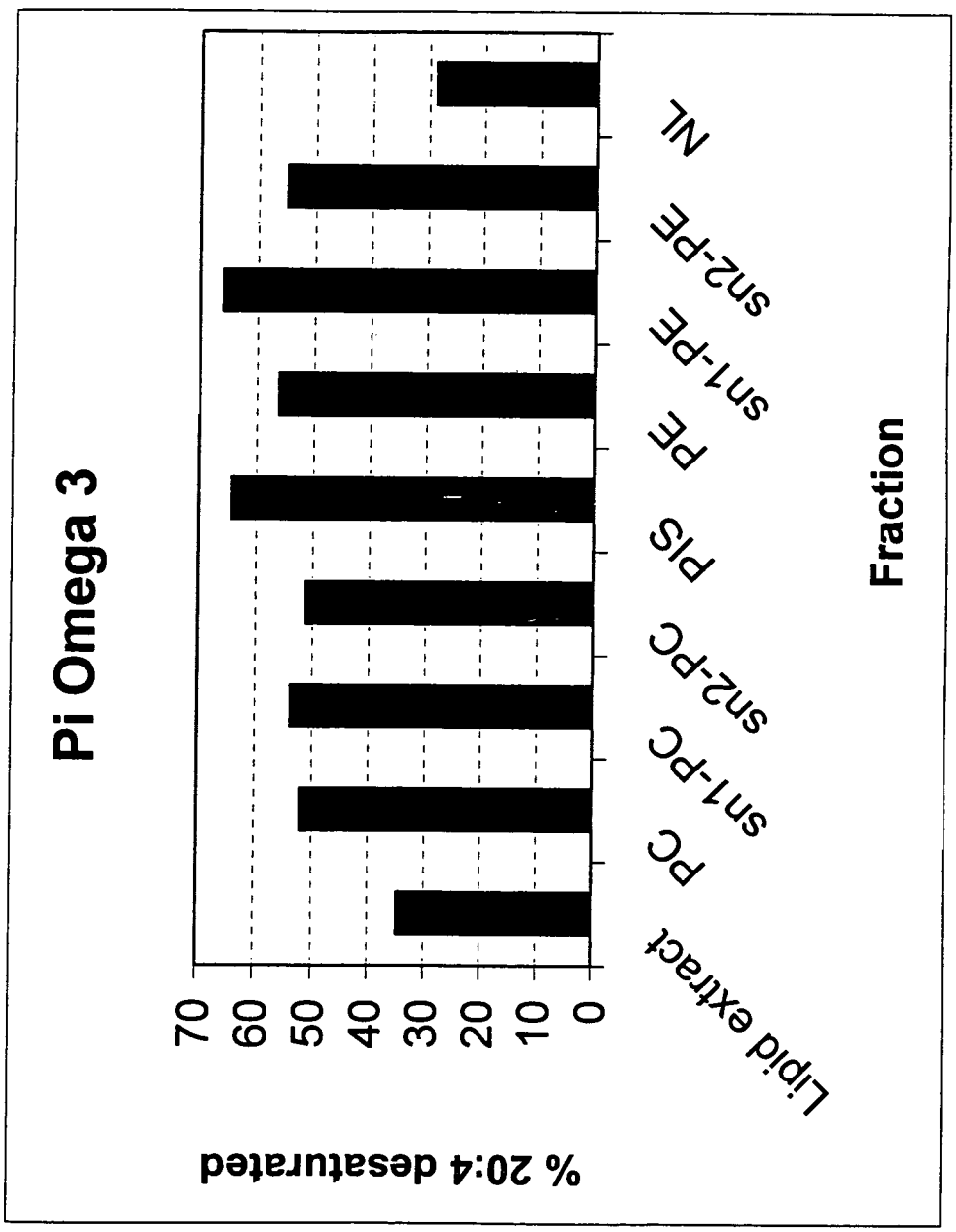
Figure 19: Desaturaturation of phospholipid-bound arachidonic acid to EPA by Pi-Omega3Des Figure 20: Conversion by OtDes6.1 of linoleic acid (arrow) into γ-linolenic acid (γ-18:3).
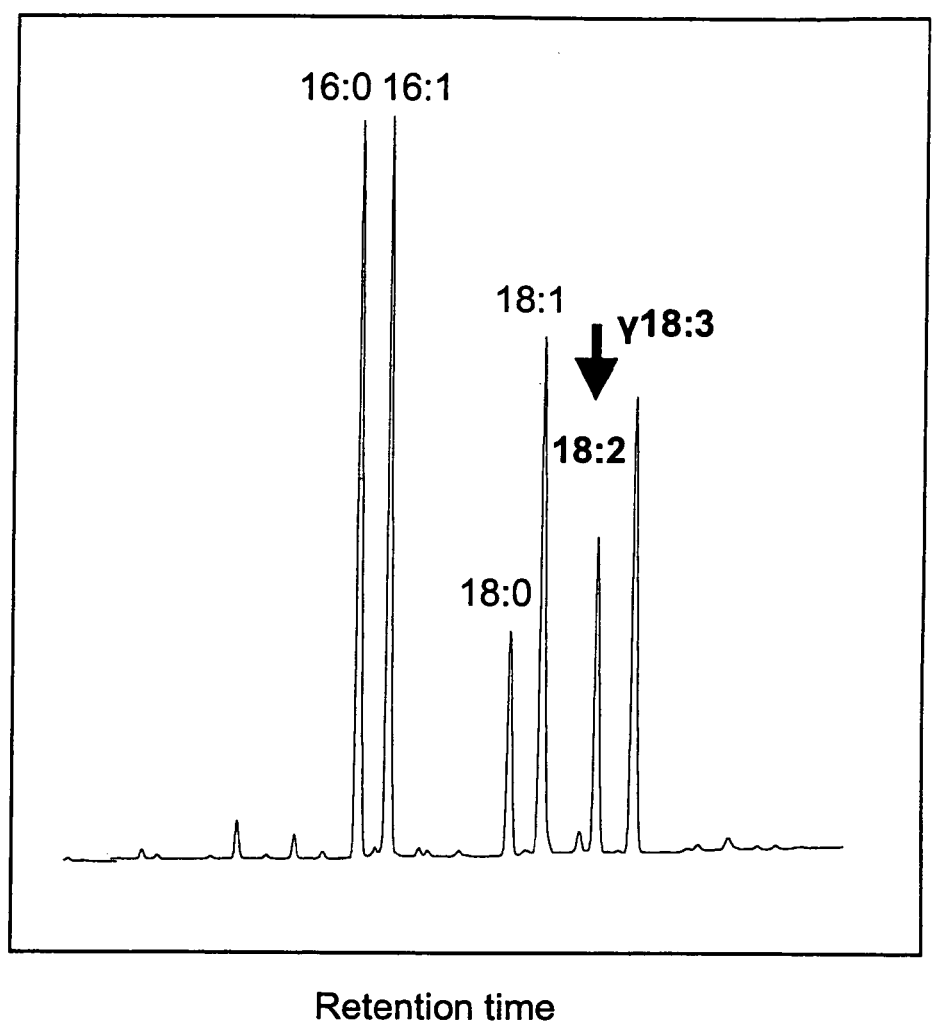

Figure 21: Conversion of linoleic acid and Umsetzung von Linolsäure und α-lLinolenic acidsäure (A aund C), and sowie rReconstitution of the ARA and EPA synthetic pathways, respectively, in yeast (B and D) in the presence of OtD6.1.
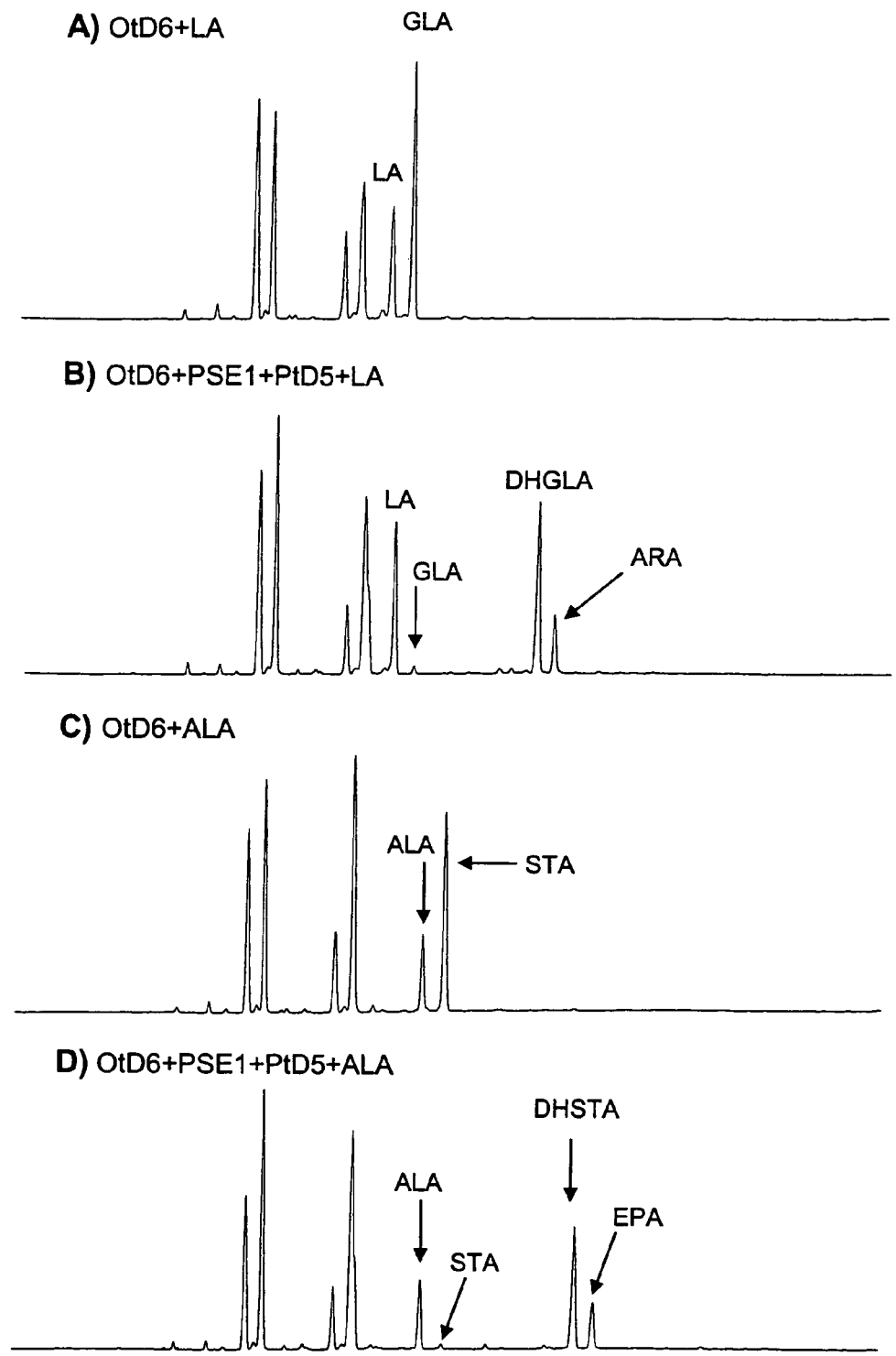

Figure 22: Expression of ELO(XI) in yeast
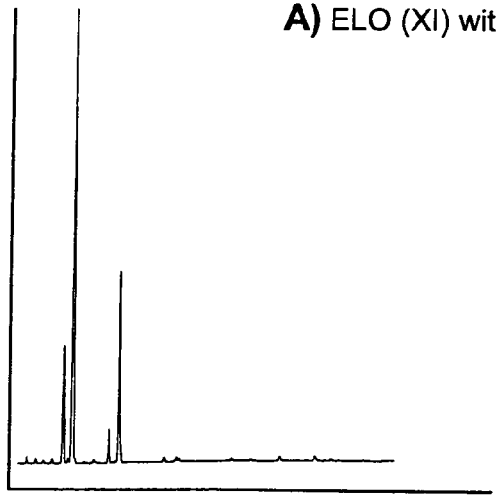
A) ELO (XI) without fatty acid feeding
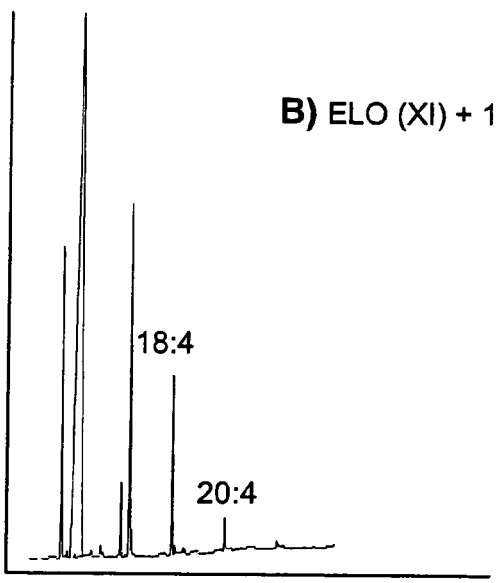
B) ELO (XI) + 18:4Δ6,9,12,15 (250 µM)
18:4
20:4
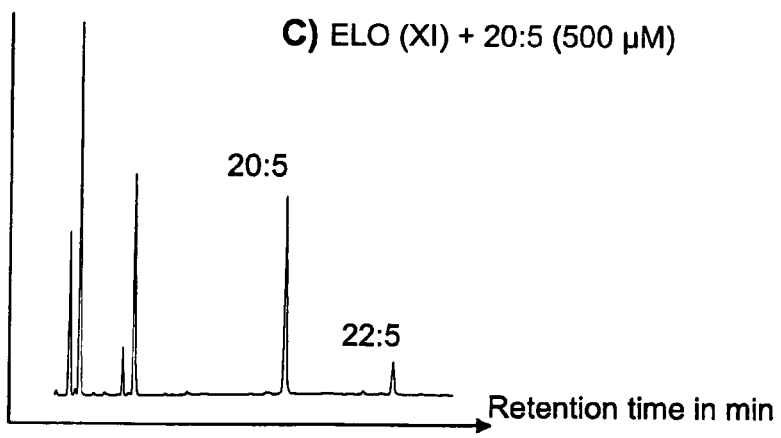
C) ELO (XI) + 20:5 (500 µM)
20:5
22:5
Retention time in min Figure 24: Elongation of eicosapentaenoic acid by OtElo1 (B) and OtElo1.2 (D), respectively. The controls (A, C) do not show the elongation product (22:5ω3).
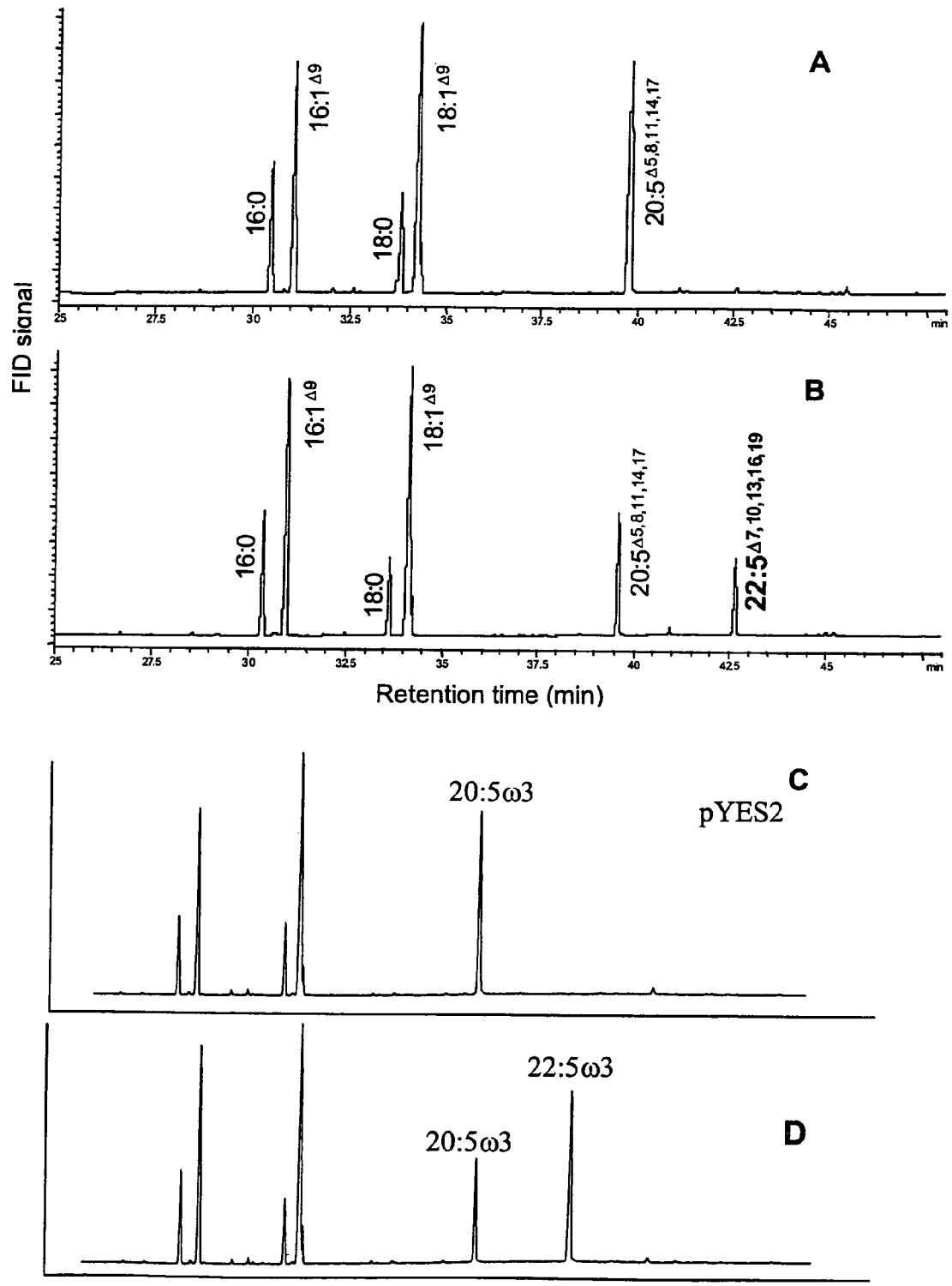

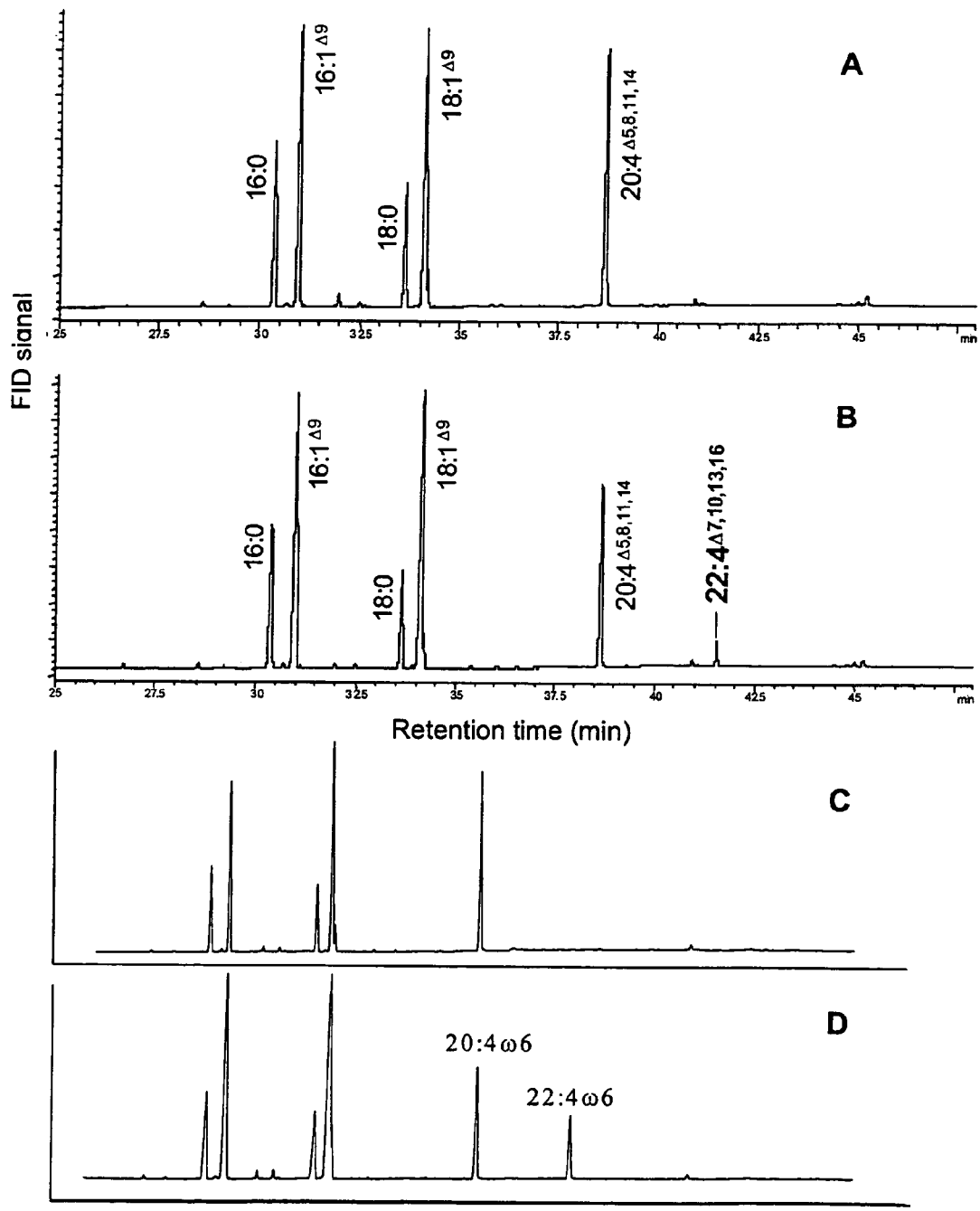
Figure 25: Elongation of arachidonic acid by OtElo1 (B) and OtElo1.2 (D), respectively. The controls (A, C) do not show the elongation product (22:4ω6).

Figure 26: Elongation of 20:5n-3 by the elongases At3g06470.
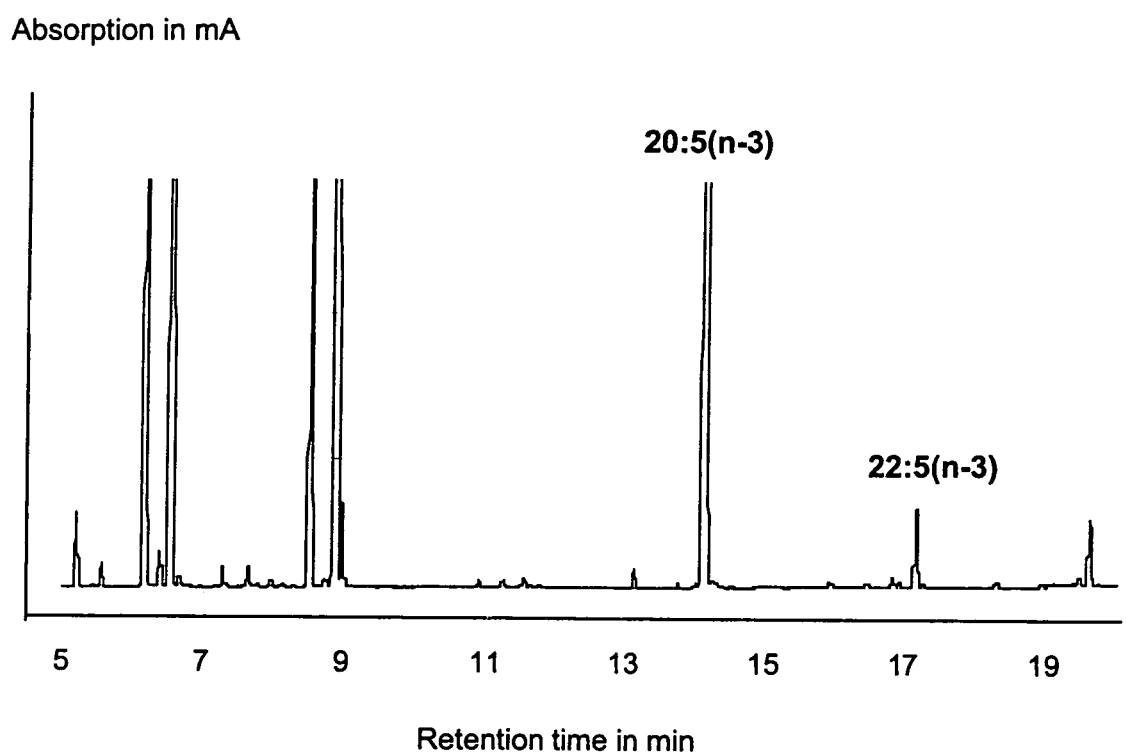

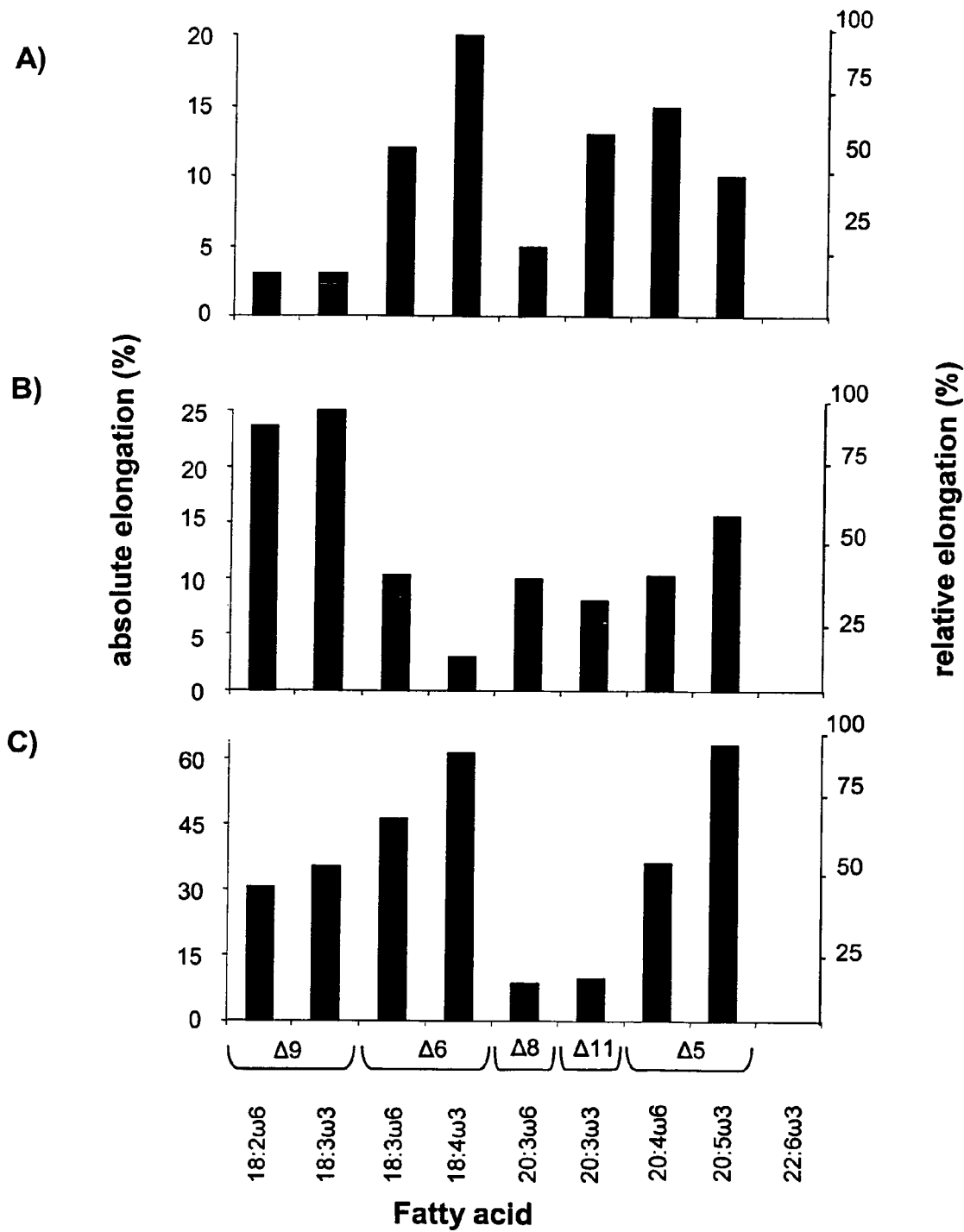
Figure 27: Substrate specificity of the Xenopus Elongase (A), the Ciona Elongase (B) and the Oncorhynchus Elongase (C)

Figure 28: Substrate specificity of the Ostreococcus Δ5-elongase (A), the Ostreococcus Δ6-elongase (B), the Thalassiosira Δ5-elongase (C) and Thalassiosira Ostreococcus Δ6-elongase (D)
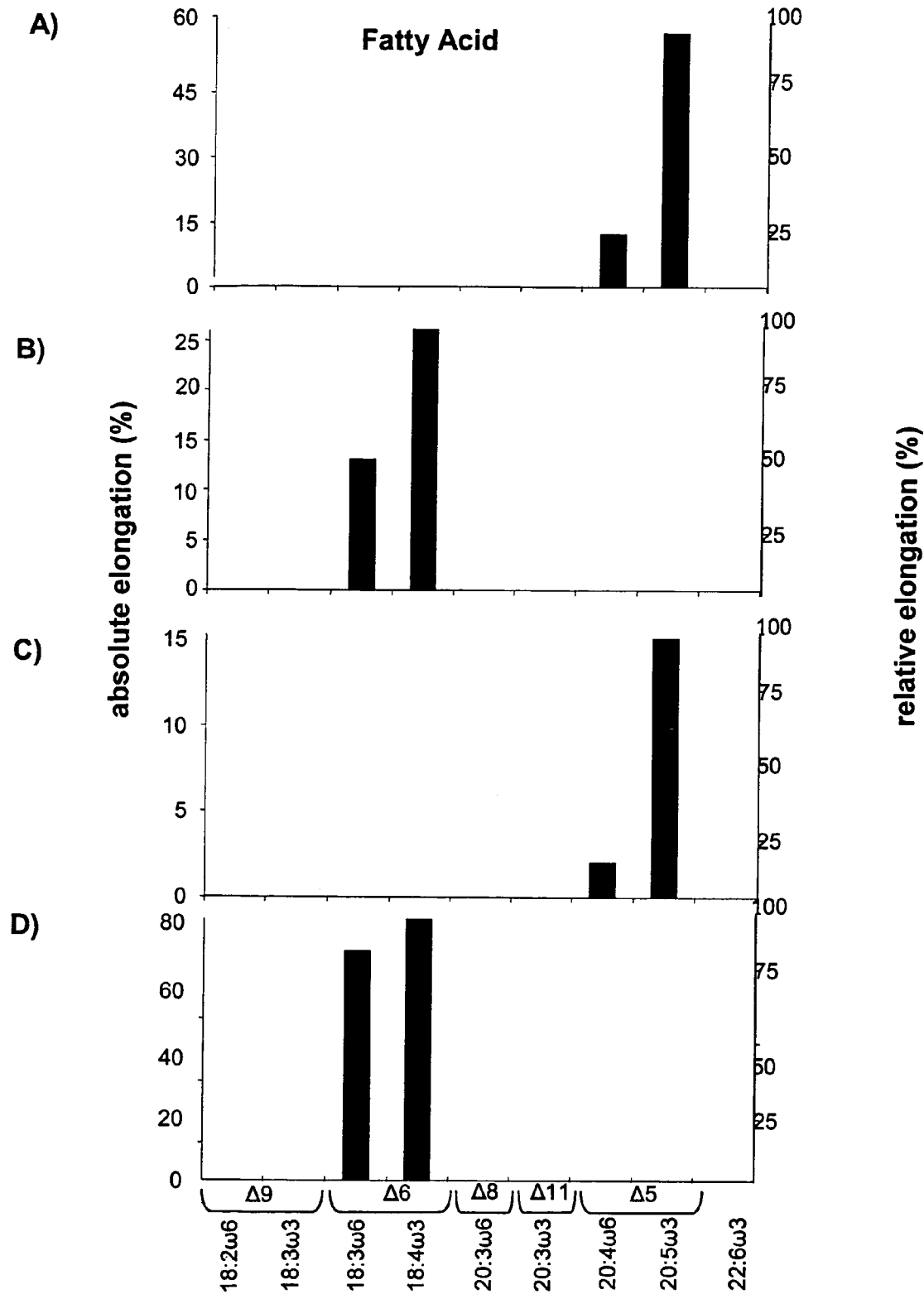

Figure 29: Expression of the Phaeodactylum tricornutum Δ6-elongase (PtELO6) in yeast. A) shows the elongation of the $C18:3^{\Delta 6,9,12}$-fatty acid and B) the elongation of the $C18:4^{\Delta 6,9,12,15}$-fatty acid
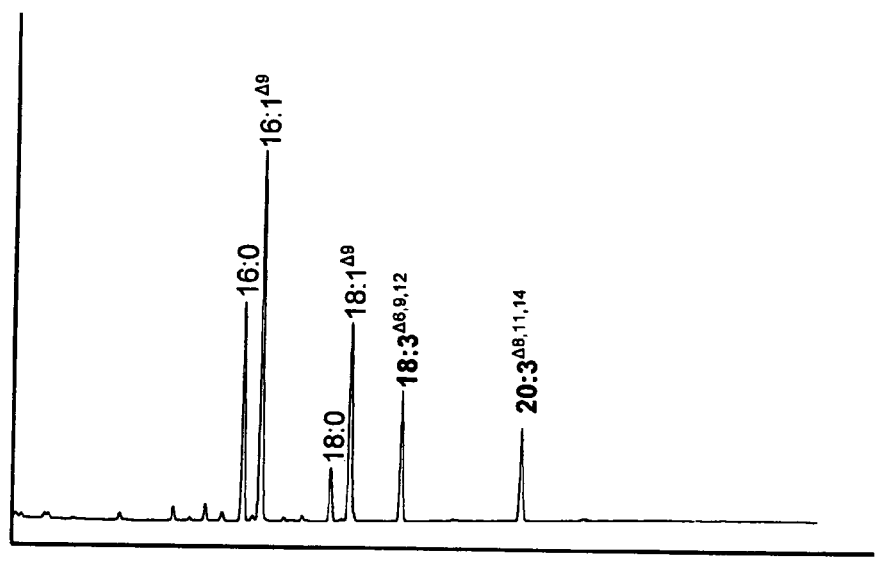
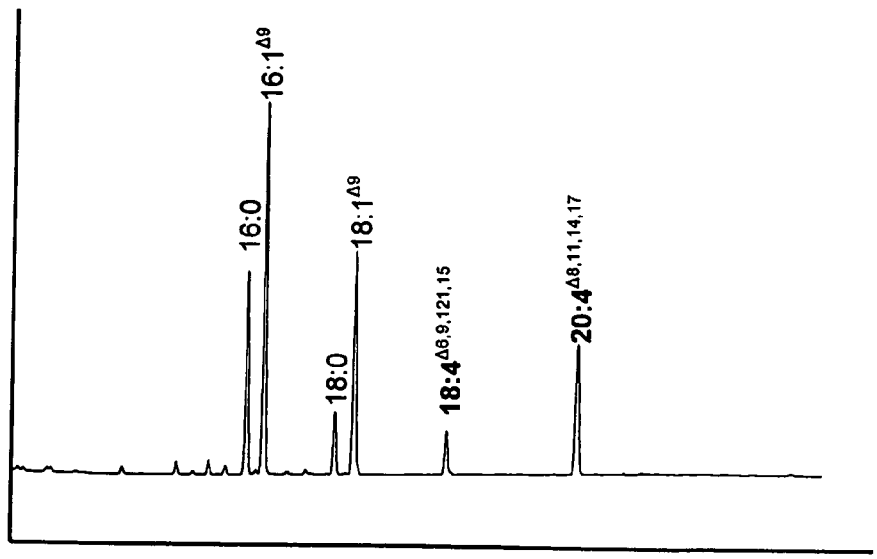

Figure 30: Figure 30 shows the substrate specificity of PtELO6 with regard to the substrates fed
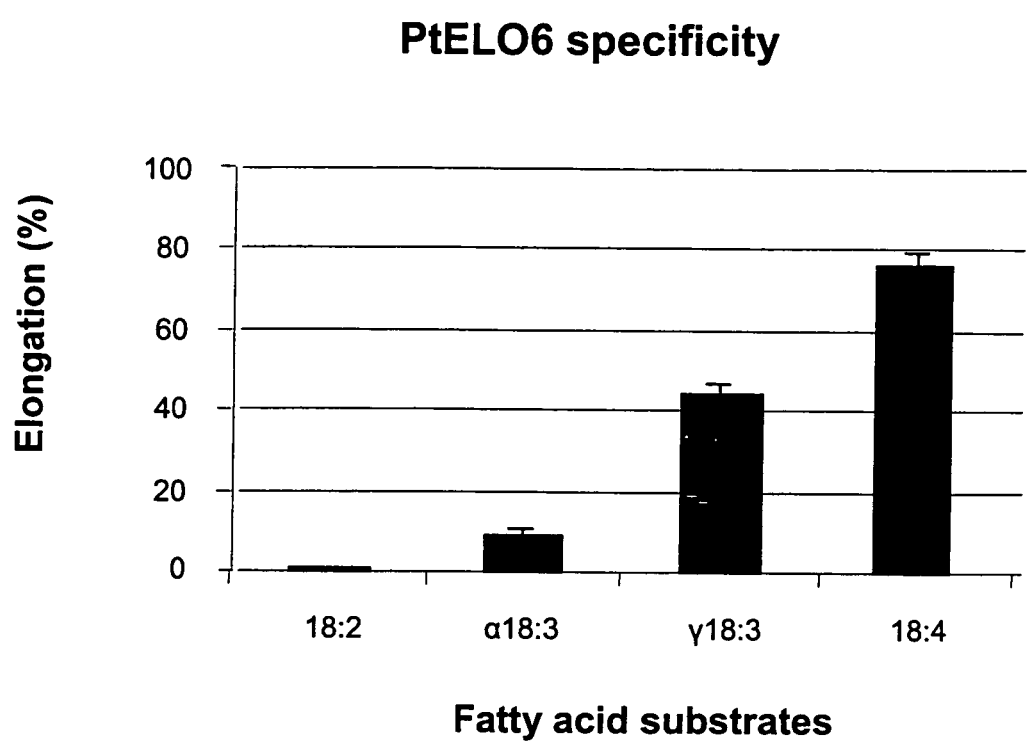

SEQUENCE LISTING

<160> NUMBER OF SEQ ID NOS: 192

<210> SEQ ID NO 1
<211> LENGTH: 1266
<212> TYPE: DNA
<213> ORGANISM: Euglena gracilis
<220> FEATURE:
<221> NAME/KEY: CDS
<222> LOCATION: (1)..(1266)
<223> OTHER INFORMATION: delta8-desaturase

<400> SEQUENCE: 1

```
atg aag tca aag cgc caa gcg ctt ccc ctt aca att gat gga aca aca      48
Met Lys Ser Lys Arg Gln Ala Leu Pro Leu Thr Ile Asp Gly Thr Thr
1               5                   10                  15 tat gat gtg tct gcc tgg gtc aat ttc cac cct ggt ggt gcg gaa att      96
Tyr Asp Val Ser Ala Trp Val Asn Phe His Pro Gly Gly Ala Glu Ile
            20                  25                  30 ata gag aat tac caa gga agg gat gcc act gat gcc ttc atg gtt atg     144
Ile Glu Asn Tyr Gln Gly Arg Asp Ala Thr Asp Ala Phe Met Val Met
        35                  40                  45 cac tct caa gaa gcc ttc gac aag ctc aag cgc atg ccc aaa atc aat     192
His Ser Gln Glu Ala Phe Asp Lys Leu Lys Arg Met Pro Lys Ile Asn
    50                  55                  60 ccc agt tct gag ttg cca ccc cag gct gca gtg aat gaa gct caa gag     240
Pro Ser Ser Glu Leu Pro Pro Gln Ala Ala Val Asn Glu Ala Gln Glu
65                  70                  75                  80 gat ttc cgg aag ctc cga gaa gag ttg atc gca act ggc atg ttt gat     288
Asp Phe Arg Lys Leu Arg Glu Glu Leu Ile Ala Thr Gly Met Phe Asp
                85                  90                  95
```

```
gcc tcc ccc ctc tgg tac tca tac aaa atc agc acc aca ctg ggc ctt    336
Ala Ser Pro Leu Trp Tyr Ser Tyr Lys Ile Ser Thr Thr Leu Gly Leu
            100                 105                 110 gga gtg ctg ggt tat ttc ctg atg gtt cag tat cag atg tat ttc att    384
Gly Val Leu Gly Tyr Phe Leu Met Val Gln Tyr Gln Met Tyr Phe Ile
        115                 120                 125 ggg gca gtg ttg ctt ggg atg cac tat caa cag atg ggc tgg ctt tct    432
Gly Ala Val Leu Leu Gly Met His Tyr Gln Gln Met Gly Trp Leu Ser
130                 135                 140 cat gac att tgc cac cac cag act ttc aag aac cgg aac tgg aac aac    480
His Asp Ile Cys His His Gln Thr Phe Lys Asn Arg Asn Trp Asn Asn
145                 150                 155                 160 ctc gtg gga ctg gta ttt ggc aat ggt ctg caa ggt ttt tcc gtg aca    528
Leu Val Gly Leu Val Phe Gly Asn Gly Leu Gln Gly Phe Ser Val Thr
                165                 170                 175 tgc tgg aag gac aga cac aat gca cat cat tcg gca acc aat gtt caa    576
Cys Trp Lys Asp Arg His Asn Ala His His Ser Ala Thr Asn Val Gln
            180                 185                 190 ggg cac gac cct gat att gac aac ctc ccc ctc tta gcc tgg tct gag    624
Gly His Asp Pro Asp Ile Asp Asn Leu Pro Leu Leu Ala Trp Ser Glu
        195                 200                 205 gat gac gtc aca cgg gcg tca ccg att tcc cgc aag ctc att cag ttc    672
Asp Asp Val Thr Arg Ala Ser Pro Ile Ser Arg Lys Leu Ile Gln Phe
210                 215                 220 cag cag tat tat ttc ttg gtc atc tgt atc ttg ttg cgg ttc att tgg    720
Gln Gln Tyr Tyr Phe Leu Val Ile Cys Ile Leu Leu Arg Phe Ile Trp
225                 230                 235                 240 tgt ttc cag agc gtg ttg acc gtg cgc agt ctg aag gac aga gat aac    768
Cys Phe Gln Ser Val Leu Thr Val Arg Ser Leu Lys Asp Arg Asp Asn
                245                 250                 255 caa ttc tat cgc tct cag tat aag aag gag gcc att ggc ctc gcc ctg    816
Gln Phe Tyr Arg Ser Gln Tyr Lys Lys Glu Ala Ile Gly Leu Ala Leu
            260                 265                 270 cat tgg aca ttg aag gcc ctg ttc cac tta ttc ttt atg ccc agc atc    864
His Trp Thr Leu Lys Ala Leu Phe His Leu Phe Phe Met Pro Ser Ile
        275                 280                 285 ctc aca tcg ctg ttg gta ttt ttc gtt tcg gag ctg gtt ggc ggc ttc    912
Leu Thr Ser Leu Leu Val Phe Phe Val Ser Glu Leu Val Gly Gly Phe
290                 295                 300 ggc att gcg atc gtg gtg ttc atg aac cac tac cca ctg gag aag atc    960
Gly Ile Ala Ile Val Val Phe Met Asn His Tyr Pro Leu Glu Lys Ile
305                 310                 315                 320 ggg gac tcg gtc tgg gat ggc cat gga ttc tcg gtt ggc cag atc cat   1008
Gly Asp Ser Val Trp Asp Gly His Gly Phe Ser Val Gly Gln Ile His
                325                 330                 335 gag acc atg aac att cgg cga ggg att atc aca gat tgg ttt ttc gga   1056
Glu Thr Met Asn Ile Arg Arg Gly Ile Ile Thr Asp Trp Phe Phe Gly
            340                 345                 350 ggc ttg aac tac cag atc gag cac cat ttg tgg ccg acc ctc cct cgc   1104
Gly Leu Asn Tyr Gln Ile Glu His His Leu Trp Pro Thr Leu Pro Arg
        355                 360                 365 cac aac ctg aca gcg gtt agc tac cag gtg gaa cag ctg tgc cag aag   1152
His Asn Leu Thr Ala Val Ser Tyr Gln Val Glu Gln Leu Cys Gln Lys
370                 375                 380 cac aac ctg ccg tat cgg aac ccg ctg ccc cat gaa ggg ttg gtc atc   1200
His Asn Leu Pro Tyr Arg Asn Pro Leu Pro His Glu Gly Leu Val Ile
385                 390                 395                 400 ctg ctg cgc tat ctg gcg gtg ttc gcc cgg atg gcg gag aag caa ccc   1248
Leu Leu Arg Tyr Leu Ala Val Phe Ala Arg Met Ala Glu Lys Gln Pro
```

```
                         405                 410                 415
gcg ggg aag gct cta taa                                                      1266
Ala Gly Lys Ala Leu
                420

<210> SEQ ID NO 2
<211> LENGTH: 421
<212> TYPE: PRT
<213> ORGANISM: Euglena gracilis

<400> SEQUENCE: 2

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Glu Leu Pro Pro Gln Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Cys Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Ala Leu Phe His Leu Phe Phe Met Pro Ser Ile
        275                 280                 285

Leu Thr Ser Leu Leu Val Phe Phe Val Ser Glu Leu Val Gly Gly Phe
    290                 295                 300

Gly Ile Ala Ile Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350
```

```
Gly Leu Asn Tyr Gln Ile Glu His His Leu Trp Pro Thr Leu Pro Arg
            355                 360                 365

His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
            405                 410                 415

Ala Gly Lys Ala Leu
            420

<210> SEQ ID NO 3
<211> LENGTH: 777
<212> TYPE: DNA
<213> ORGANISM: Isochrysis galbana
<220> FEATURE:
<221> NAME/KEY: CDS
<222> LOCATION: (1)..(777)
<223> OTHER INFORMATION: delta9-elongase

<400> SEQUENCE: 3
```

| | | | | | | | | | | | | | | | | |
|---|---|---|---|---|---|---|---|---|---|---|---|---|---|---|---|---|
| atg | gcc | ctc | gca | aac | gac | gcg | gga | gag | cgc | atc | tgg | gcg | gct | gtg | acc | 48 |
| Met | Ala | Leu | Ala | Asn | Asp | Ala | Gly | Glu | Arg | Ile | Trp | Ala | Ala | Val | Thr | |
| 1 | | | | 5 | | | | | 10 | | | | | 15 | | |
| gac | ccg | gaa | atc | ctc | att | ggc | acc | ttc | tcg | tac | ttg | cta | ctc | aaa | ccg | 96 |
| Asp | Pro | Glu | Ile | Leu | Ile | Gly | Thr | Phe | Ser | Tyr | Leu | Leu | Leu | Lys | Pro | |
| | | | | 20 | | | | | 25 | | | | | 30 | | |
| ctg | ctc | cgc | aat | tcc | ggg | ctg | gtg | gat | gag | aag | aag | ggc | gca | tac | agg | 144 |
| Leu | Leu | Arg | Asn | Ser | Gly | Leu | Val | Asp | Glu | Lys | Lys | Gly | Ala | Tyr | Arg | |
| | | | 35 | | | | | 40 | | | | | 45 | | | |
| acg | tcc | atg | atc | tgg | tac | aac | gtt | ctg | ctg | gcg | ctc | ttc | tct | gcg | ctg | 192 |
| Thr | Ser | Met | Ile | Trp | Tyr | Asn | Val | Leu | Leu | Ala | Leu | Phe | Ser | Ala | Leu | |
| | | | 50 | | | | | 55 | | | | | 60 | | | |
| agc | ttc | tac | gtg | acg | gcg | acc | gcc | ctc | ggc | tgg | gac | tat | ggt | acg | ggc | 240 |
| Ser | Phe | Tyr | Val | Thr | Ala | Thr | Ala | Leu | Gly | Trp | Asp | Tyr | Gly | Thr | Gly | |
| 65 | | | | | 70 | | | | | 75 | | | | | 80 | |
| gcg | tgg | ctg | cgc | agg | caa | acc | ggc | gac | aca | ccg | cag | ccg | ctc | ttc | cag | 288 |
| Ala | Trp | Leu | Arg | Arg | Gln | Thr | Gly | Asp | Thr | Pro | Gln | Pro | Leu | Phe | Gln | |
| | | | | 85 | | | | | 90 | | | | | 95 | | |
| tgc | ccg | tcc | ccg | gtt | tgg | gac | tcg | aag | ctc | ttc | aca | tgg | acc | gcc | aag | 336 |
| Cys | Pro | Ser | Pro | Val | Trp | Asp | Ser | Lys | Leu | Phe | Thr | Trp | Thr | Ala | Lys | |
| | | | | 100 | | | | | 105 | | | | | 110 | | |
| gca | ttc | tat | tac | tcc | aag | tac | gtg | gag | tac | ctc | gac | acg | gcc | tgg | ctg | 384 |
| Ala | Phe | Tyr | Tyr | Ser | Lys | Tyr | Val | Glu | Tyr | Leu | Asp | Thr | Ala | Trp | Leu | |
| | | | 115 | | | | | 120 | | | | | 125 | | | |
| agg | gtc | tcc | ttt | ctc | cag | gcc | ttc | cac | cac | ttt | ggc | gcg | ccg | tgg | gat | 432 |
| Arg | Val | Ser | Phe | Leu | Gln | Ala | Phe | His | His | Phe | Gly | Ala | Pro | Trp | Asp | |
| | | | 130 | | | | | 135 | | | | | 140 | | | |
| gtg | tac | ctc | ggc | att | cgg | ctg | cac | aac | gag | ggc | gta | tgg | atc | ttc | atg | 480 |
| Val | Tyr | Leu | Gly | Ile | Arg | Leu | His | Asn | Glu | Gly | Val | Trp | Ile | Phe | Met | |
| 145 | | | | | 150 | | | | | 155 | | | | | 160 | |
| ttt | ttc | aac | tcg | ttc | att | cac | acc | atc | atg | tac | acc | tac | tac | ggc | ctc | 528 |
| Phe | Phe | Asn | Ser | Phe | Ile | His | Thr | Ile | Met | Tyr | Thr | Tyr | Tyr | Gly | Leu | |
| | | | | 165 | | | | | 170 | | | | | 175 | | |
| acc | gcc | gcc | ggg | tat | aag | ttc | aag | gcc | aag | ccg | ctc | atc | acc | gcg | atg | 576 |
| Thr | Ala | Ala | Gly | Tyr | Lys | Phe | Lys | Ala | Lys | Pro | Leu | Ile | Thr | Ala | Met | |
| | | | | 180 | | | | | 185 | | | | | 190 | | |
| cag | atc | tgc | cag | ttc | gtg | ggc | ggc | ttc | ctg | ttg | gtc | tgg | gac | tac | atc | 624 |
| Gln | Ile | Cys | Gln | Phe | Val | Gly | Gly | Phe | Leu | Leu | Val | Trp | Asp | Tyr | Ile | |
| | | | 195 | | | | | 200 | | | | | 205 | | | |

```
aac gtc ccc tgc ttc aac tcg gac aaa ggg aag ttg ttc agc tgg gct    672
Asn Val Pro Cys Phe Asn Ser Asp Lys Gly Lys Leu Phe Ser Trp Ala
    210                 215                 220 ttc aac tat gca tac gtc ggc tcg gtc ttg ctc ttc tgc cac ttt        720
Phe Asn Tyr Ala Tyr Val Gly Ser Val Phe Leu Leu Phe Cys His Phe
225                 230                 235                 240 ttc tac cag gac aac ttg gca acg aag aaa tcg gcc aag gcg ggc aag    768
Phe Tyr Gln Asp Asn Leu Ala Thr Lys Lys Ser Ala Lys Ala Gly Lys
                245                 250                 255 cag ctc tag                                                        777
Gln Leu

<210> SEQ ID NO 4
<211> LENGTH: 258
<212> TYPE: PRT
<213> ORGANISM: Isochrysis galbana

<400> SEQUENCE: 4

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Arg Val Ser Phe Leu Gln Ala Phe His His Phe Gly Ala Pro Trp Asp
    130                 135                 140

Val Tyr Leu Gly Ile Arg Leu His Asn Glu Gly Val Trp Ile Phe Met
145                 150                 155                 160

Phe Phe Asn Ser Phe Ile His Thr Ile Met Tyr Thr Tyr Tyr Gly Leu
                165                 170                 175

Thr Ala Ala Gly Tyr Lys Phe Lys Ala Lys Pro Leu Ile Thr Ala Met
            180                 185                 190

Gln Ile Cys Gln Phe Val Gly Gly Phe Leu Leu Val Trp Asp Tyr Ile
        195                 200                 205

Asn Val Pro Cys Phe Asn Ser Asp Lys Gly Lys Leu Phe Ser Trp Ala
    210                 215                 220

Phe Asn Tyr Ala Tyr Val Gly Ser Val Phe Leu Leu Phe Cys His Phe
225                 230                 235                 240

Phe Tyr Gln Asp Asn Leu Ala Thr Lys Lys Ser Ala Lys Ala Gly Lys
                245                 250                 255

Gln Leu

<210> SEQ ID NO 5
<211> LENGTH: 1410
<212> TYPE: DNA
<213> ORGANISM: Phaeodactylum tricornutum
```

```
<220> FEATURE:
<221> NAME/KEY: CDS
<222> LOCATION: (1)..(1410)
<223> OTHER INFORMATION: delta5-desaturase

<400> SEQUENCE: 5
```

| | | | | | | | | | | | | | | | | |
|---|---|---|---|---|---|---|---|---|---|---|---|---|---|---|---|---|
| atg | gct | ccg | gat | gcg | gat | aag | ctt | cga | caa | cgc | cag | acg | act | gcg | gta | 48 |
| Met | Ala | Pro | Asp | Ala | Asp | Lys | Leu | Arg | Gln | Arg | Gln | Thr | Thr | Ala | Val | |
| 1 | | | | 5 | | | | | 10 | | | | | 15 | | |
| gcg | aag | cac | aat | gct | gct | acc | ata | tcg | acg | cag | gaa | cgc | ctt | tgc | agt | 96 |
| Ala | Lys | His | Asn | Ala | Ala | Thr | Ile | Ser | Thr | Gln | Glu | Arg | Leu | Cys | Ser | |
| | | | 20 | | | | | 25 | | | | | 30 | | | |
| ctg | tct | tcg | ctc | aaa | ggc | gaa | gaa | gtc | tgc | atc | gac | gga | atc | atc | tat | 144 |
| Leu | Ser | Ser | Leu | Lys | Gly | Glu | Glu | Val | Cys | Ile | Asp | Gly | Ile | Ile | Tyr | |
| | | 35 | | | | | 40 | | | | | 45 | | | | |
| gac | ctc | caa | tca | ttc | gat | cat | ccc | ggg | ggt | gaa | acg | atc | aaa | atg | ttt | 192 |
| Asp | Leu | Gln | Ser | Phe | Asp | His | Pro | Gly | Gly | Glu | Thr | Ile | Lys | Met | Phe | |
| | 50 | | | | | 55 | | | | | 60 | | | | | |
| ggt | ggc | aac | gat | gtc | act | gta | cag | tac | aag | atg | att | cac | ccg | tac | cat | 240 |
| Gly | Gly | Asn | Asp | Val | Thr | Val | Gln | Tyr | Lys | Met | Ile | His | Pro | Tyr | His | |
| 65 | | | | | 70 | | | | | 75 | | | | | 80 | |
| acc | gag | aag | cat | ttg | gaa | aag | atg | aag | cgt | gtc | ggc | aag | gtg | acg | gat | 288 |
| Thr | Glu | Lys | His | Leu | Glu | Lys | Met | Lys | Arg | Val | Gly | Lys | Val | Thr | Asp | |
| | | | | 85 | | | | | 90 | | | | | 95 | | |
| ttc | gtc | tgc | gag | tac | aag | ttc | gat | acc | gaa | ttt | gaa | cgc | gaa | atc | aaa | 336 |
| Phe | Val | Cys | Glu | Tyr | Lys | Phe | Asp | Thr | Glu | Phe | Glu | Arg | Glu | Ile | Lys | |
| | | | 100 | | | | | 105 | | | | | 110 | | | |
| cga | gaa | gtc | ttc | aag | att | gtg | cga | cga | ggc | aag | gat | ttc | ggt | act | ttg | 384 |
| Arg | Glu | Val | Phe | Lys | Ile | Val | Arg | Arg | Gly | Lys | Asp | Phe | Gly | Thr | Leu | |
| | | 115 | | | | | 120 | | | | | 125 | | | | |
| gga | tgg | ttc | ttc | cgt | gcg | ttt | tgc | tac | att | gcc | att | ttc | ttc | tac | ctg | 432 |
| Gly | Trp | Phe | Phe | Arg | Ala | Phe | Cys | Tyr | Ile | Ala | Ile | Phe | Phe | Tyr | Leu | |
| | 130 | | | | | 135 | | | | | 140 | | | | | |
| cag | tac | cat | tgg | gtc | acc | acg | gga | acc | tct | tgg | ctg | ctg | gcc | gtg | gcc | 480 |
| Gln | Tyr | His | Trp | Val | Thr | Thr | Gly | Thr | Ser | Trp | Leu | Leu | Ala | Val | Ala | |
| 145 | | | | | 150 | | | | | 155 | | | | | 160 | |
| tac | gga | atc | tcc | caa | gcg | atg | att | ggc | atg | aat | gtc | cag | cac | gat | gcc | 528 |
| Tyr | Gly | Ile | Ser | Gln | Ala | Met | Ile | Gly | Met | Asn | Val | Gln | His | Asp | Ala | |
| | | | | 165 | | | | | 170 | | | | | 175 | | |
| aac | cac | ggg | gcc | acc | tcc | aag | cgt | ccc | tgg | gtc | aac | gac | atg | cta | ggc | 576 |
| Asn | His | Gly | Ala | Thr | Ser | Lys | Arg | Pro | Trp | Val | Asn | Asp | Met | Leu | Gly | |
| | | | 180 | | | | | 185 | | | | | 190 | | | |
| ctc | ggt | gcg | gat | ttt | att | ggt | ggt | tcc | aag | tgg | ctc | tgg | cag | gaa | caa | 624 |
| Leu | Gly | Ala | Asp | Phe | Ile | Gly | Gly | Ser | Lys | Trp | Leu | Trp | Gln | Glu | Gln | |
| | | 195 | | | | | 200 | | | | | 205 | | | | |
| cac | tgg | acc | cac | cac | gct | tac | acc | aat | cac | gcc | gag | atg | gat | ccc | gat | 672 |
| His | Trp | Thr | His | His | Ala | Tyr | Thr | Asn | His | Ala | Glu | Met | Asp | Pro | Asp | |
| | 210 | | | | | 215 | | | | | 220 | | | | | |
| agc | ttt | ggt | gcc | gaa | cca | atg | ctc | cta | ttc | aac | gac | tat | ccc | ttg | gat | 720 |
| Ser | Phe | Gly | Ala | Glu | Pro | Met | Leu | Leu | Phe | Asn | Asp | Tyr | Pro | Leu | Asp | |
| 225 | | | | | 230 | | | | | 235 | | | | | 240 | |
| cat | ccc | gct | cgt | acc | tgg | cta | cat | cgc | ttt | caa | gca | ttc | ttt | tac | atg | 768 |
| His | Pro | Ala | Arg | Thr | Trp | Leu | His | Arg | Phe | Gln | Ala | Phe | Phe | Tyr | Met | |
| | | | | 245 | | | | | 250 | | | | | 255 | | |
| ccc | gtc | ttg | gct | gga | tac | tgg | ttg | tcc | gct | gtc | ttc | aat | cca | caa | att | 816 |
| Pro | Val | Leu | Ala | Gly | Tyr | Trp | Leu | Ser | Ala | Val | Phe | Asn | Pro | Gln | Ile | |
| | | | 260 | | | | | 265 | | | | | 270 | | | |
| ctt | gac | ctc | cag | caa | cgc | ggc | gca | ctt | tcc | gtc | ggt | atc | cgt | ctc | gac | 864 |
| Leu | Asp | Leu | Gln | Gln | Arg | Gly | Ala | Leu | Ser | Val | Gly | Ile | Arg | Leu | Asp | |
| | | 275 | | | | | 280 | | | | | 285 | | | | |

```
aac gct ttc att cac tcg cga cgc aag tat gcg gtt ttc tgg cgg gct         912
Asn Ala Phe Ile His Ser Arg Arg Lys Tyr Ala Val Phe Trp Arg Ala
290                 295                 300 gtg tac att gcg gtg aac gtg att gct ccg ttt tac aca aac tcc ggc         960
Val Tyr Ile Ala Val Asn Val Ile Ala Pro Phe Tyr Thr Asn Ser Gly
305                 310                 315                 320 ctc gaa tgg tcc tgg cgt gtc ttt gga aac atc atg ctc atg ggt gtg        1008
Leu Glu Trp Ser Trp Arg Val Phe Gly Asn Ile Met Leu Met Gly Val
                325                 330                 335 gcg gaa tcg ctc gcg ctg gcg gtc ctg ttt tcg ttg tcg cac aat ttc        1056
Ala Glu Ser Leu Ala Leu Ala Val Leu Phe Ser Leu Ser His Asn Phe
        340                 345                 350 gaa tcc gcg gat cgc gat ccg acc gcc cca ctg aaa aag acg gga gaa        1104
Glu Ser Ala Asp Arg Asp Pro Thr Ala Pro Leu Lys Lys Thr Gly Glu
    355                 360                 365 cca gtc gac tgg ttc aag aca cag gtc gaa act tcc tgc act tac ggt        1152
Pro Val Asp Trp Phe Lys Thr Gln Val Glu Thr Ser Cys Thr Tyr Gly
370                 375                 380 gga ttc ctt tcc ggt tgc ttc acg gga ggt ctc aac ttt cag gtt gaa        1200
Gly Phe Leu Ser Gly Cys Phe Thr Gly Gly Leu Asn Phe Gln Val Glu
385                 390                 395                 400 cac cac ttg ttc cca cgc atg agc agc gct tgg tat ccc tac att gcc        1248
His His Leu Phe Pro Arg Met Ser Ser Ala Trp Tyr Pro Tyr Ile Ala
                405                 410                 415 ccc aag gtc cgc gaa att tgc gcc aaa cac ggc gtc cac tac gcc tac        1296
Pro Lys Val Arg Glu Ile Cys Ala Lys His Gly Val His Tyr Ala Tyr
        420                 425                 430 tac ccg tgg atc cac caa aac ttt ctc tcc acc gtc cgc tac atg cac        1344
Tyr Pro Trp Ile His Gln Asn Phe Leu Ser Thr Val Arg Tyr Met His
    435                 440                 445 gcg gcc ggg acc ggt gcc aac tgg cgc cag atg gcc aga gaa aat ccc        1392
Ala Ala Gly Thr Gly Ala Asn Trp Arg Gln Met Ala Arg Glu Asn Pro
450                 455                 460 ttg acc gga cgg gcg taa                                                 1410
Leu Thr Gly Arg Ala
465

<210> SEQ ID NO 6
<211> LENGTH: 469
<212> TYPE: PRT
<213> ORGANISM: Phaeodactylum tricornutum

<400> SEQUENCE: 6

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
                20                  25                  30

Leu Ser Ser Leu Lys Gly Glu Glu Val Cys Ile Asp Gly Ile Ile Tyr
            35                  40                  45

Asp Leu Gln Ser Phe Asp His Pro Gly Gly Glu Thr Ile Lys Met Phe
        50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Gly Lys Asp Phe Gly Thr Leu
        115                 120                 125
```

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
    290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 7
<211> LENGTH: 1344
<212> TYPE: DNA
<213> ORGANISM: Ceratodon purpureus
<220> FEATURE:
<221> NAME/KEY: CDS
<222> LOCATION: (1)..(1344)
<223> OTHER INFORMATION: delta5-desaturase

<400> SEQUENCE: 7

-continued

| | |
|---|---|
| atg gta tta cga gag caa gag cat gag cca ttc ttc att aaa att gat<br>Met Val Leu Arg Glu Gln Glu His Glu Pro Phe Phe Ile Lys Ile Asp<br>1                        5                            10                        15 | 48 |
| gga aaa tgg tgt caa att gac gat gct gtc ctg aga tca cat cca ggt<br>Gly Lys Trp Cys Gln Ile Asp Asp Ala Val Leu Arg Ser His Pro Gly<br>                20                          25                          30 | 96 |
| ggt agt gca att act acc tat aaa aat atg gat gcc act acc gta ttc<br>Gly Ser Ala Ile Thr Thr Tyr Lys Asn Met Asp Ala Thr Thr Val Phe<br>                35                          40                          45 | 144 |
| cac aca ttc cat act ggt tct aaa gaa gcg tat caa tgg ctg aca gaa<br>His Thr Phe His Thr Gly Ser Lys Glu Ala Tyr Gln Trp Leu Thr Glu<br>     50                        55                          60 | 192 |
| ttg aaa aaa gag tgc cct aca caa gaa cca gag atc cca gat att aag<br>Leu Lys Lys Glu Cys Pro Thr Gln Glu Pro Glu Ile Pro Asp Ile Lys<br>65                        70                            75                        80 | 240 |
| gat gac cca atc aaa gga att gat gat gtg aac atg gga act ttc aat<br>Asp Asp Pro Ile Lys Gly Ile Asp Asp Val Asn Met Gly Thr Phe Asn<br>                        85                          90                          95 | 288 |
| att tct gag aaa cga tct gcc caa ata aat aaa agt ttc act gat cta<br>Ile Ser Glu Lys Arg Ser Ala Gln Ile Asn Lys Ser Phe Thr Asp Leu<br>                100                        105                        110 | 336 |
| cgt atg cga gtt cgt gca gaa gga ctt atg gat gga tct cct ttg ttc<br>Arg Met Arg Val Arg Ala Glu Gly Leu Met Asp Gly Ser Pro Leu Phe<br>                115                        120                        125 | 384 |
| tac att aga aaa att ctt gaa aca atc ttc aca att ctt ttt gca ttc<br>Tyr Ile Arg Lys Ile Leu Glu Thr Ile Phe Thr Ile Leu Phe Ala Phe<br>     130                        135                        140 | 432 |
| tac ctt caa tac cac aca tat tat ctt cca tca gct att cta atg gga<br>Tyr Leu Gln Tyr His Thr Tyr Tyr Leu Pro Ser Ala Ile Leu Met Gly<br>145                        150                        155                        160 | 480 |
| gtt gcg tgg caa caa ttg gga tgg tta atc cat gaa ttc gca cat cat<br>Val Ala Trp Gln Gln Leu Gly Trp Leu Ile His Glu Phe Ala His His<br>                165                        170                        175 | 528 |
| cag ttg ttc aaa aac aga tac tac aat gat ttg gcc agc tat ttc gtt<br>Gln Leu Phe Lys Asn Arg Tyr Tyr Asn Asp Leu Ala Ser Tyr Phe Val<br>     180                        185                          190 | 576 |
| gga aac ttt tta caa gga ttc tca tct ggt ggt tgg aaa gag cag cac<br>Gly Asn Phe Leu Gln Gly Phe Ser Ser Gly Gly Trp Lys Glu Gln His<br>                195                        200                        205 | 624 |
| aat gtg cat cac gca gcc aca aat gtt gtt gga cga gac gga gat ctt<br>Asn Val His His Ala Ala Thr Asn Val Val Gly Arg Asp Gly Asp Leu<br>     210                        215                        220 | 672 |
| gat tta gtc cca ttc tat gct aca gtg gca gaa cat ctc aac aat tat<br>Asp Leu Val Pro Phe Tyr Ala Thr Val Ala Glu His Leu Asn Asn Tyr<br>225                        230                        235                        240 | 720 |
| tct cag gat tca tgg gtt atg act cta ttc aga tgg caa cat gtt cat<br>Ser Gln Asp Ser Trp Val Met Thr Leu Phe Arg Trp Gln His Val His<br>                245                        250                        255 | 768 |
| tgg aca ttc atg tta cca ttc ctc cgt ctc tcg tgg ctt ctt cag tca<br>Trp Thr Phe Met Leu Pro Phe Leu Arg Leu Ser Trp Leu Leu Gln Ser<br>                260                        265                        270 | 816 |
| atc att ttt gtt agt cag atg cca act cat tat tat gac tat tac aga<br>Ile Ile Phe Val Ser Gln Met Pro Thr His Tyr Tyr Asp Tyr Tyr Arg<br>     275                        280                        285 | 864 |
| aat act gcg att tat gaa cag gtt ggt ctc tct ttg cac tgg gct tgg<br>Asn Thr Ala Ile Tyr Glu Gln Val Gly Leu Ser Leu His Trp Ala Trp<br>     290                        295                        300 | 912 |
| tca ttg ggt caa ttg tat ttc cta ccc gat tgg tca act aga ata atg<br>Ser Leu Gly Gln Leu Tyr Phe Leu Pro Asp Trp Ser Thr Arg Ile Met<br>305                        310                        315                        320 | 960 |

```
ttc ttc ctt gtt tct cat ctt gtt gga ggt ttc ctg ctc tct cat gta      1008
Phe Phe Leu Val Ser His Leu Val Gly Gly Phe Leu Leu Ser His Val
                325                 330                 335 gtt act ttc aat cat tat tca gtg gag aag ttt gca ttg agc tcg aac      1056
Val Thr Phe Asn His Tyr Ser Val Glu Lys Phe Ala Leu Ser Ser Asn
            340                 345                 350 atc atg tca aat tac gct tgt ctt caa atc atg acc aca aga aat atg      1104
Ile Met Ser Asn Tyr Ala Cys Leu Gln Ile Met Thr Thr Arg Asn Met
        355                 360                 365 aga cct gga aga ttc att gac tgg ctt tgg gga ggt ctt aac tat cag      1152
Arg Pro Gly Arg Phe Ile Asp Trp Leu Trp Gly Gly Leu Asn Tyr Gln
    370                 375                 380 att gag cac cat ctt ttc cca acg atg cca cga cac aac ttg aac act      1200
Ile Glu His His Leu Phe Pro Thr Met Pro Arg His Asn Leu Asn Thr
385                 390                 395                 400 gtt atg cca ctt gtt aag gag ttt gca gca gca aat ggt tta cca tac      1248
Val Met Pro Leu Val Lys Glu Phe Ala Ala Ala Asn Gly Leu Pro Tyr
                405                 410                 415 atg gtc gac gat tat ttc aca gga ttc tgg ctt gaa att gag caa ttc      1296
Met Val Asp Asp Tyr Phe Thr Gly Phe Trp Leu Glu Ile Glu Gln Phe
            420                 425                 430 cga aat att gca aat gtt gct gct aaa ttg act aaa aag att gcc tag      1344
Arg Asn Ile Ala Asn Val Ala Ala Lys Leu Thr Lys Lys Ile Ala
        435                 440                 445

<210> SEQ ID NO 8
<211> LENGTH: 447
<212> TYPE: PRT
<213> ORGANISM: Ceratodon purpureus

<400> SEQUENCE: 8

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Glu Ile Pro Asp Ile Lys
65                  70                  75                  80

Asp Asp Pro Ile Lys Gly Ile Asp Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125

Tyr Ile Arg Lys Ile Leu Glu Thr Ile Phe Thr Ile Leu Phe Ala Phe
    130                 135                 140

Tyr Leu Gln Tyr His Thr Tyr Leu Pro Ser Ala Ile Leu Met Gly
145                 150                 155                 160

Val Ala Trp Gln Gln Leu Gly Trp Leu Ile His Glu Phe Ala His
                165                 170                 175

Gln Leu Phe Lys Asn Arg Tyr Tyr Asn Asp Leu Ala Ser Tyr Phe Val
            180                 185                 190

Gly Asn Phe Leu Gln Gly Phe Ser Ser Gly Gly Trp Lys Glu Gln His
        195                 200                 205
```

```
Asn Val His His Ala Ala Thr Asn Val Val Gly Arg Asp Gly Asp Leu
        210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
            245                 250                 255

Trp Thr Phe Met Leu Pro Phe Leu Arg Leu Ser Trp Leu Leu Gln Ser
        260                 265                 270

Ile Ile Phe Val Ser Gln Met Pro Thr His Tyr Tyr Asp Tyr Tyr Arg
        275                 280                 285

Asn Thr Ala Ile Tyr Glu Gln Val Gly Leu Ser Leu His Trp Ala Trp
        290                 295                 300

Ser Leu Gly Gln Leu Tyr Phe Leu Pro Asp Trp Ser Thr Arg Ile Met
305                 310                 315                 320

Phe Phe Leu Val Ser His Leu Val Gly Gly Phe Leu Leu Ser His Val
                325                 330                 335

Val Thr Phe Asn His Tyr Ser Val Glu Lys Phe Ala Leu Ser Ser Asn
        340                 345                 350

Ile Met Ser Asn Tyr Ala Cys Leu Gln Ile Met Thr Thr Arg Asn Met
        355                 360                 365

Arg Pro Gly Arg Phe Ile Asp Trp Leu Trp Gly Leu Asn Tyr Gln
        370                 375                 380

Ile Glu His His Leu Phe Pro Thr Met Pro Arg His Asn Leu Asn Thr
385                 390                 395                 400

Val Met Pro Leu Val Lys Glu Phe Ala Ala Asn Gly Leu Pro Tyr
                405                 410                 415

Met Val Asp Asp Tyr Phe Thr Gly Phe Trp Leu Glu Ile Glu Gln Phe
                420                 425                 430

Arg Asn Ile Ala Asn Val Ala Ala Lys Leu Thr Lys Lys Ile Ala
        435                 440                 445

<210> SEQ ID NO 9
<211> LENGTH: 1443
<212> TYPE: DNA
<213> ORGANISM: Physcomitrella patens
<220> FEATURE:
<221> NAME/KEY: CDS
<222> LOCATION: (1)..(1443)
<223> OTHER INFORMATION: delta5-desaturase

<400> SEQUENCE: 9 atg gcg ccc cac tct gcg gat act gct ggg ctc gtg cct tct gac gaa    48
Met Ala Pro His Ser Ala Asp Thr Ala Gly Leu Val Pro Ser Asp Glu
1               5                   10                  15 ttg agg cta cga acg tcg aat tca aag ggt ccc gaa caa gag caa act    96
Leu Arg Leu Arg Thr Ser Asn Ser Lys Gly Pro Glu Gln Glu Gln Thr
            20                  25                  30 ttg aag aag tac acc ctt gaa gat gtc agc cgc cac aac acc cca gca   144
Leu Lys Lys Tyr Thr Leu Glu Asp Val Ser Arg His Asn Thr Pro Ala
        35                  40                  45 gat tgt tgg ttg gtg ata tgg ggc aaa gtc tac gat gtc aca agc tgg   192
Asp Cys Trp Leu Val Ile Trp Gly Lys Val Tyr Asp Val Thr Ser Trp
50                  55                  60 att ccc aat cat ccg ggg ggc agt ctc atc cac gta aaa gca ggg cag   240
Ile Pro Asn His Pro Gly Gly Ser Leu Ile His Val Lys Ala Gly Gln
65                  70                  75                  80 gat tcc act cag ctt ttc gat tcc tat cac ccc ctt tat gtc agg aaa   288
```

```
                Asp Ser Thr Gln Leu Phe Asp Ser Tyr His Pro Leu Tyr Val Arg Lys
                                85                  90                  95 atg ctc gcg aag tac tgt att ggg gaa tta gta ccg tct gct ggt gat        336
Met Leu Ala Lys Tyr Cys Ile Gly Glu Leu Val Pro Ser Ala Gly Asp
            100                 105                 110 gac aag ttt aag aaa gca act ctg gag tat gca gat gcc gaa aat gaa        384
Asp Lys Phe Lys Lys Ala Thr Leu Glu Tyr Ala Asp Ala Glu Asn Glu
        115                 120                 125 gat ttc tat ttg gtt gtg aag caa cga gtt gaa tct tat ttc aag agt        432
Asp Phe Tyr Leu Val Val Lys Gln Arg Val Glu Ser Tyr Phe Lys Ser
    130                 135                 140 aac aag ata aac ccc caa att cat cca cat atg atc ctg aag tca ttg        480
Asn Lys Ile Asn Pro Gln Ile His Pro His Met Ile Leu Lys Ser Leu
145                 150                 155                 160 ttc att ctt ggg gga tat ttc gcc agt tac tat tta gcg ttc ttc tgg        528
Phe Ile Leu Gly Gly Tyr Phe Ala Ser Tyr Tyr Leu Ala Phe Phe Trp
                165                 170                 175 tct tca agt gtc ctt gtt tct ttg ttt ttc gca ttg tgg atg ggg ttc        576
Ser Ser Ser Val Leu Val Ser Leu Phe Phe Ala Leu Trp Met Gly Phe
            180                 185                 190 ttc gca gcg gaa gtc ggc gtg tcg att caa cat gat gga aat cat ggt        624
Phe Ala Ala Glu Val Gly Val Ser Ile Gln His Asp Gly Asn His Gly
        195                 200                 205 tca tac act aaa tgg cgt ggc ttt gga tat atc atg gga gcc tcc cta        672
Ser Tyr Thr Lys Trp Arg Gly Phe Gly Tyr Ile Met Gly Ala Ser Leu
    210                 215                 220 gat cta gtc gga gcc agt agc ttc atg tgg aga cag caa cac gtt gtg        720
Asp Leu Val Gly Ala Ser Ser Phe Met Trp Arg Gln Gln His Val Val
225                 230                 235                 240 gga cat cac tcg ttt aca aat gtg gac aac tac gat cct gat att cgt        768
Gly His His Ser Phe Thr Asn Val Asp Asn Tyr Asp Pro Asp Ile Arg
                245                 250                 255 gtg aaa gat cca gat gtc agg agg gtt gcg acc aca caa cca aga caa        816
Val Lys Asp Pro Asp Val Arg Arg Val Ala Thr Thr Gln Pro Arg Gln
            260                 265                 270 tgg tat cat gcg tat cag cat atc tac ctg gca gta tta tat gga act        864
Trp Tyr His Ala Tyr Gln His Ile Tyr Leu Ala Val Leu Tyr Gly Thr
        275                 280                 285 cta gct ctt aag agt att ttt cta gat gat ttc ctt gcg tac ttc aca        912
Leu Ala Leu Lys Ser Ile Phe Leu Asp Asp Phe Leu Ala Tyr Phe Thr
    290                 295                 300 gga tca att ggc cct gtc aag gtg gcg aaa atg acc ccc ctg gag ttc        960
Gly Ser Ile Gly Pro Val Lys Val Ala Lys Met Thr Pro Leu Glu Phe
305                 310                 315                 320 aac atc ttc ttt cag gga aag ctg cta tat gcg ttc tac atg ttc gtg       1008
Asn Ile Phe Phe Gln Gly Lys Leu Leu Tyr Ala Phe Tyr Met Phe Val
                325                 330                 335 ttg cca tct gtg tac ggt gtt cac tcc gga gga act ttc ttg gca cta       1056
Leu Pro Ser Val Tyr Gly Val His Ser Gly Gly Thr Phe Leu Ala Leu
            340                 345                 350 tat gtg gct tct cag ctc att aca ggt tgg atg tta gct ttt ctt ttt       1104
Tyr Val Ala Ser Gln Leu Ile Thr Gly Trp Met Leu Ala Phe Leu Phe
        355                 360                 365 caa gta gca cat gtc gtg gat gat gtt gca ttt cct aca cca gaa ggt       1152
Gln Val Ala His Val Val Asp Asp Val Ala Phe Pro Thr Pro Glu Gly
    370                 375                 380 ggg aag gtg aag gga gga tgg gct gca atg cag gtt gca aca act acg       1200
Gly Lys Val Lys Gly Gly Trp Ala Ala Met Gln Val Ala Thr Thr Thr
385                 390                 395                 400
```

```
gat ttc agt cca cgc tca tgg ttc tgg ggt cat gtc tct gga gga tta      1248
Asp Phe Ser Pro Arg Ser Trp Phe Trp Gly His Val Ser Gly Gly Leu
            405                 410                 415 aac aac caa att gag cat cat ctg ttt cca gga gtg tgc cat gtt cat      1296
Asn Asn Gln Ile Glu His His Leu Phe Pro Gly Val Cys His Val His
        420                 425                 430 tat cca gcc att cag cct att gtc gag aag acg tgc aag gaa ttc gat      1344
Tyr Pro Ala Ile Gln Pro Ile Val Glu Lys Thr Cys Lys Glu Phe Asp
    435                 440                 445 gtg cct tat gta gcc tac cca act ttt tgg act gcg ttg aga gcc cac      1392
Val Pro Tyr Val Ala Tyr Pro Thr Phe Trp Thr Ala Leu Arg Ala His
450                 455                 460 ttt gcg cat ttg aaa aag gtt gga ttg aca gag ttt cgg ctc gat ggc      1440
Phe Ala His Leu Lys Lys Val Gly Leu Thr Glu Phe Arg Leu Asp Gly
465                 470                 475                 480 tga                                                                   1443

<210> SEQ ID NO 10
<211> LENGTH: 480
<212> TYPE: PRT
<213> ORGANISM: Physcomitrella patens

<400> SEQUENCE: 10

Met Ala Pro His Ser Ala Asp Thr Ala Gly Leu Val Pro Ser Asp Glu
1               5                   10                  15

Leu Arg Leu Arg Thr Ser Asn Ser Lys Gly Pro Glu Gln Glu Gln Thr
            20                  25                  30

Leu Lys Lys Tyr Thr Leu Glu Asp Val Ser Arg His Asn Thr Pro Ala
        35                  40                  45

Asp Cys Trp Leu Val Ile Trp Gly Lys Val Tyr Asp Val Thr Ser Trp
    50                  55                  60

Ile Pro Asn His Pro Gly Gly Ser Leu Ile His Val Lys Ala Gly Gln
65                  70                  75                  80

Asp Ser Thr Gln Leu Phe Asp Ser Tyr His Pro Leu Tyr Val Arg Lys
                85                  90                  95

Met Leu Ala Lys Tyr Cys Ile Gly Glu Leu Val Pro Ser Ala Gly Asp
            100                 105                 110

Asp Lys Phe Lys Lys Ala Thr Leu Glu Tyr Ala Asp Ala Glu Asn Glu
        115                 120                 125

Asp Phe Tyr Leu Val Val Lys Gln Arg Val Glu Ser Tyr Phe Lys Ser
    130                 135                 140

Asn Lys Ile Asn Pro Gln Ile His Pro His Met Ile Leu Lys Ser Leu
145                 150                 155                 160

Phe Ile Leu Gly Gly Tyr Phe Ala Ser Tyr Tyr Leu Ala Phe Phe Trp
                165                 170                 175

Ser Ser Ser Val Leu Val Ser Leu Phe Phe Ala Leu Trp Met Gly Phe
            180                 185                 190

Phe Ala Ala Glu Val Gly Val Ser Ile Gln His Asp Gly Asn His Gly
        195                 200                 205

Ser Tyr Thr Lys Trp Arg Gly Phe Gly Tyr Ile Met Gly Ala Ser Leu
    210                 215                 220

Asp Leu Val Gly Ala Ser Ser Phe Met Trp Arg Gln His Val Val
225                 230                 235                 240

Gly His His Ser Phe Thr Asn Val Asp Asn Tyr Asp Pro Asp Ile Arg
                245                 250                 255

Val Lys Asp Pro Asp Val Arg Arg Val Ala Thr Thr Gln Pro Arg Gln
```

```
              260                 265                 270
Trp Tyr His Ala Tyr Gln His Ile Tyr Leu Ala Val Leu Tyr Gly Thr
        275                 280                 285
Leu Ala Leu Lys Ser Ile Phe Leu Asp Asp Phe Leu Ala Tyr Phe Thr
290                 295                 300
Gly Ser Ile Gly Pro Val Lys Val Ala Lys Met Thr Pro Leu Glu Phe
305                 310                 315                 320
Asn Ile Phe Phe Gln Gly Lys Leu Leu Tyr Ala Phe Tyr Met Phe Val
                325                 330                 335
Leu Pro Ser Val Tyr Gly Val His Ser Gly Gly Thr Phe Leu Ala Leu
            340                 345                 350
Tyr Val Ala Ser Gln Leu Ile Thr Gly Trp Met Leu Ala Phe Leu Phe
        355                 360                 365
Gln Val Ala His Val Val Asp Asp Val Ala Phe Pro Thr Pro Glu Gly
    370                 375                 380
Gly Lys Val Lys Gly Gly Trp Ala Ala Met Gln Val Ala Thr Thr Thr
385                 390                 395                 400
Asp Phe Ser Pro Arg Ser Trp Phe Trp Gly His Val Ser Gly Gly Leu
                405                 410                 415
Asn Asn Gln Ile Glu His His Leu Phe Pro Gly Val Cys His Val His
            420                 425                 430
Tyr Pro Ala Ile Gln Pro Ile Val Glu Lys Thr Cys Lys Glu Phe Asp
        435                 440                 445
Val Pro Tyr Val Ala Tyr Pro Thr Phe Trp Thr Ala Leu Arg Ala His
    450                 455                 460
Phe Ala His Leu Lys Lys Val Gly Leu Thr Glu Phe Arg Leu Asp Gly
465                 470                 475                 480

<210> SEQ ID NO 11
<211> LENGTH: 1320
<212> TYPE: DNA
<213> ORGANISM: Thraustrochytrium
<220> FEATURE:
<221> NAME/KEY: CDS
<222> LOCATION: (1)..(1320)

<400> SEQUENCE: 11 atg ggc aag ggc agc gag ggc cgc agc gcg gcg cgc gag atg acg gcc      48
Met Gly Lys Gly Ser Glu Gly Arg Ser Ala Ala Arg Glu Met Thr Ala
1               5                   10                  15 gag gcg aac ggc gac aag cgg aaa acg att ctg atc gag ggc gtc ctg      96
Glu Ala Asn Gly Asp Lys Arg Lys Thr Ile Leu Ile Glu Gly Val Leu
            20                  25                  30 tac gac gcg acg aac ttt aag cac ccg ggc ggt tcg atc atc aac ttc     144
Tyr Asp Ala Thr Asn Phe Lys His Pro Gly Gly Ser Ile Ile Asn Phe
        35                  40                  45 ttg acc gag ggc gag gcc ggc gtg gac gcg acg cag gcg tac cgc gag     192
Leu Thr Glu Gly Glu Ala Gly Val Asp Ala Thr Gln Ala Tyr Arg Glu
    50                  55                  60 ttt cat cag cgg tcc ggc aag gcc gac aag tac ctc aag tcg ctg ccg     240
Phe His Gln Arg Ser Gly Lys Ala Asp Lys Tyr Leu Lys Ser Leu Pro
65                  70                  75                  80 aag ctg gat gcg tcc aag gtg gag tcg cgg ttc tcg gcc aaa gag cag     288
Lys Leu Asp Ala Ser Lys Val Glu Ser Arg Phe Ser Ala Lys Glu Gln
                85                  90                  95 gcg cgg cgc gac gcc atg acg cgc gac tac gcg gcc ttt cgc gag gag     336
Ala Arg Arg Asp Ala Met Thr Arg Asp Tyr Ala Ala Phe Arg Glu Glu
            100                 105                 110
```

-continued

| | |
|---|---|
| ctc gtc gcc gag ggg tac ttt gac ccg tcg atc ccg cac atg att tac<br>Leu Val Ala Glu Gly Tyr Phe Asp Pro Ser Ile Pro His Met Ile Tyr<br>115                         120                         125 | 384 |
| cgc gtc gtg gag atc gtg gcg ctc ttc gcg ctc tcg ttc tgg ctc atg<br>Arg Val Val Glu Ile Val Ala Leu Phe Ala Leu Ser Phe Trp Leu Met<br>    130                       135                       140 | 432 |
| tcc aag gcc tcg ccc acc tcg ctc gtg ctg ggc gtg gtg atg aac ggc<br>Ser Lys Ala Ser Pro Thr Ser Leu Val Leu Gly Val Val Met Asn Gly<br>145                         150                       155                   160 | 480 |
| att gcg cag ggc cgc tgc ggc tgg gtc atg cac gag atg ggc cac ggg<br>Ile Ala Gln Gly Arg Cys Gly Trp Val Met His Glu Met Gly His Gly<br>                 165                       170                       175 | 528 |
| tcg ttc acg ggc gtc atc tgg ctc gac gac cgg atg tgc gag ttc ttc<br>Ser Phe Thr Gly Val Ile Trp Leu Asp Asp Arg Met Cys Glu Phe Phe<br>    180                       185                       190 | 576 |
| tac ggc gtc ggc tgc ggc atg agc ggg cac tac tgg aag aac cag cac<br>Tyr Gly Val Gly Cys Gly Met Ser Gly His Tyr Trp Lys Asn Gln His<br>         195                       200                       205 | 624 |
| agc aag cac cac gcc gcg ccc aac cgc ctc gag cac gat gtc gat ctc<br>Ser Lys His His Ala Ala Pro Asn Arg Leu Glu His Asp Val Asp Leu<br>210                         215                       220 | 672 |
| aac acg ctg ccc ctg gtc gcc ttt aac gag cgc gtg gtg cgc aag gtc<br>Asn Thr Leu Pro Leu Val Ala Phe Asn Glu Arg Val Val Arg Lys Val<br>225                         230                       235                   240 | 720 |
| aag ccg gga tcg ctg ctg gcg ctc tgg ctg cgc gtg cag gcg tac ctc<br>Lys Pro Gly Ser Leu Leu Ala Leu Trp Leu Arg Val Gln Ala Tyr Leu<br>                 245                       250                       255 | 768 |
| ttt gcg ccc gtc tcg tgc ctc ctc atc ggc ctt ggc tgg acg ctc tac<br>Phe Ala Pro Val Ser Cys Leu Leu Ile Gly Leu Gly Trp Thr Leu Tyr<br>    260                       265                       270 | 816 |
| ctg cac ccg cgc tac atg ctg cgc acc aag cgg cac atg gag ttc gtc<br>Leu His Pro Arg Tyr Met Leu Arg Thr Lys Arg His Met Glu Phe Val<br>         275                       280                       285 | 864 |
| tgg atc ttc gcg cgc tac att ggc tgg ttc tcg ctc atg ggc gct ctc<br>Trp Ile Phe Ala Arg Tyr Ile Gly Trp Phe Ser Leu Met Gly Ala Leu<br>290                         295                       300 | 912 |
| ggc tac tcg ccg ggc acc tcg gtc ggg atg tac ctg tgc tcg ttc ggc<br>Gly Tyr Ser Pro Gly Thr Ser Val Gly Met Tyr Leu Cys Ser Phe Gly<br>305                         310                       315                   320 | 960 |
| ctc ggc tgc att tac att ttc ctg cag ttc gcc gtc agc cac acg cac<br>Leu Gly Cys Ile Tyr Ile Phe Leu Gln Phe Ala Val Ser His Thr His<br>                 325                       330                       335 | 1008 |
| ctg ccg gtg acc aac ccg gag gac cag ctg cac tgg ctc gag tac gcg<br>Leu Pro Val Thr Asn Pro Glu Asp Gln Leu His Trp Leu Glu Tyr Ala<br>    340                       345                       350 | 1056 |
| gcc gac cac acg gtg aac att agc acc aag tcc tgg ctc gtc acg tgg<br>Ala Asp His Thr Val Asn Ile Ser Thr Lys Ser Trp Leu Val Thr Trp<br>         355                       360                       365 | 1104 |
| tgg atg tcg aac ctg aac ttt cag atc gag cac cac ctc ttc ccc acg<br>Trp Met Ser Asn Leu Asn Phe Gln Ile Glu His His Leu Phe Pro Thr<br>370                         375                       380 | 1152 |
| gcg ccg cag ttc cgc ttc aag gaa atc agt cct cgc gtc gag gcc ctc<br>Ala Pro Gln Phe Arg Phe Lys Glu Ile Ser Pro Arg Val Glu Ala Leu<br>385                         390                       395                   400 | 1200 |
| ttc aag cgc cac aac ctc ccg tac tac gac ctg ccc tac acg agc gcg<br>Phe Lys Arg His Asn Leu Pro Tyr Tyr Asp Leu Pro Tyr Thr Ser Ala<br>                 405                       410                       415 | 1248 |
| gtc tcg acc acc ttt gcc aat ctt tat tcc gtc ggc cac tcg gtc ggc<br>Val Ser Thr Thr Phe Ala Asn Leu Tyr Ser Val Gly His Ser Val Gly | 1296 |

```
                      420           425           430
gcc gac acc aag aag cag gac tga                                    1320
Ala Asp Thr Lys Lys Gln Asp
        435
```

<210> SEQ ID NO 12
<211> LENGTH: 439
<212> TYPE: PRT
<213> ORGANISM: Thraustochytrium

<400> SEQUENCE: 12

```
Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350
```

```
Ala Asp His Thr Val Asn Ile Ser Thr Lys Ser Trp Leu Val Thr Trp
            355                 360                 365

Trp Met Ser Asn Leu Asn Phe Gln Ile Glu His His Leu Phe Pro Thr
        370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
                420                 425                 430

Ala Asp Thr Lys Lys Gln Asp
            435

<210> SEQ ID NO 13
<211> LENGTH: 1341
<212> TYPE: DNA
<213> ORGANISM: Mortierella alpina
<220> FEATURE:
<221> NAME/KEY: CDS
<222> LOCATION: (1)..(1341)
<223> OTHER INFORMATION: delta5-desaturase

<400> SEQUENCE: 13 atg gga acg gac caa gga aaa acc ttc acc tgg gaa gag ctg gcg gcc      48
Met Gly Thr Asp Gln Gly Lys Thr Phe Thr Trp Glu Glu Leu Ala Ala
1               5                   10                  15 cat aac acc aag gac gac cta ctc ttg gcc atc cgc ggc agg gtg tac      96
His Asn Thr Lys Asp Asp Leu Leu Leu Ala Ile Arg Gly Arg Val Tyr
                20                  25                  30 gat gtc aca aag ttc ttg agc cgc cat cct ggt gga gtg gac act ctc     144
Asp Val Thr Lys Phe Leu Ser Arg His Pro Gly Gly Val Asp Thr Leu
            35                  40                  45 ctg ctc gga gct ggc cga gat gtt act ccg gtc ttt gag atg tat cac     192
Leu Leu Gly Ala Gly Arg Asp Val Thr Pro Val Phe Glu Met Tyr His
    50                  55                  60 gcg ttt ggg gct gca gat gcc att atg aag aag tac tat gtc ggt aca     240
Ala Phe Gly Ala Ala Asp Ala Ile Met Lys Lys Tyr Tyr Val Gly Thr
65                  70                  75                  80 ctg gtc tcg aat gag ctg ccc atc ttc ccg gag cca acg gtg ttc cac     288
Leu Val Ser Asn Glu Leu Pro Ile Phe Pro Glu Pro Thr Val Phe His
                85                  90                  95 aaa acc atc aag acg aga gtc gag ggc tac ttt acg gat cgg aac att     336
Lys Thr Ile Lys Thr Arg Val Glu Gly Tyr Phe Thr Asp Arg Asn Ile
                100                 105                 110 gat ccc aag aat aga cca gag atc tgg gga cga tac gct ctt atc ttt     384
Asp Pro Lys Asn Arg Pro Glu Ile Trp Gly Arg Tyr Ala Leu Ile Phe
            115                 120                 125 gga tcc ttg atc gct tcc tac tac gcg cag ctc ttt gtg cct ttc gtt     432
Gly Ser Leu Ile Ala Ser Tyr Tyr Ala Gln Leu Phe Val Pro Phe Val
    130                 135                 140 gtc gaa cgc aca tgg ctt cag gtg gtg ttt gca atc atc atg gga ttt     480
Val Glu Arg Thr Trp Leu Gln Val Val Phe Ala Ile Ile Met Gly Phe
145                 150                 155                 160 gcg tgc gca caa gtc gga ctc aac cct ctt cat gat gcg tct cac ttt     528
Ala Cys Ala Gln Val Gly Leu Asn Pro Leu His Asp Ala Ser His Phe
                165                 170                 175 tca gtg acc cac aac ccc act gtc tgg aag att ctg gga gcc acg cac     576
Ser Val Thr His Asn Pro Thr Val Trp Lys Ile Leu Gly Ala Thr His
                180                 185                 190
```

```
gac ttt ttc aac gga gca tcg tac ctg gtg tgg atg tac caa cat atg        624
Asp Phe Phe Asn Gly Ala Ser Tyr Leu Val Trp Met Tyr Gln His Met
        195                 200                 205 ctc ggc cat cac ccc tac acc aac att gct gga gca gat ccc gac gtg        672
Leu Gly His His Pro Tyr Thr Asn Ile Ala Gly Ala Asp Pro Asp Val
210                 215                 220 tcg acg tct gag ccc gat gtt cgt cgt atc aag ccc aac caa aag tgg        720
Ser Thr Ser Glu Pro Asp Val Arg Arg Ile Lys Pro Asn Gln Lys Trp
225                 230                 235                 240 ttt gtc aac cac atc aac cag cac atg ttt gtt cct ttc ctg tac gga        768
Phe Val Asn His Ile Asn Gln His Met Phe Val Pro Phe Leu Tyr Gly
            245                 250                 255 ctg ctg gcg ttc aag gtg cgc att cag gac atc aac att ttg tac ttt        816
Leu Leu Ala Phe Lys Val Arg Ile Gln Asp Ile Asn Ile Leu Tyr Phe
        260                 265                 270 gtc aag acc aat gac gct att cgt gtc aat ccc atc tcg aca tgg cac        864
Val Lys Thr Asn Asp Ala Ile Arg Val Asn Pro Ile Ser Thr Trp His
        275                 280                 285 act gtg atg ttc tgg ggc ggc aag gct ttc ttt gtc tgg tat cgc ctg        912
Thr Val Met Phe Trp Gly Gly Lys Ala Phe Phe Val Trp Tyr Arg Leu
290                 295                 300 att gtt ccc ctg cag tat ctg ccc ctg ggc aag gtg ctg ctc ttg ttc        960
Ile Val Pro Leu Gln Tyr Leu Pro Leu Gly Lys Val Leu Leu Leu Phe
305                 310                 315                 320 acg gtc gcg gac atg gtg tcg tct tac tgg ctg gcg ctg acc ttc cag       1008
Thr Val Ala Asp Met Val Ser Ser Tyr Trp Leu Ala Leu Thr Phe Gln
            325                 330                 335 gcg aac cac gtt gtt gag gaa gtt cag tgg ccg ttg cct gac gag aac       1056
Ala Asn His Val Val Glu Glu Val Gln Trp Pro Leu Pro Asp Glu Asn
        340                 345                 350 ggg atc atc caa aag gac tgg gca gct atg cag gtc gag act acg cag       1104
Gly Ile Ile Gln Lys Asp Trp Ala Ala Met Gln Val Glu Thr Thr Gln
        355                 360                 365 gat tac gca cac gat tcg cac ctc tgg acc agc atc act ggc agc ttg       1152
Asp Tyr Ala His Asp Ser His Leu Trp Thr Ser Ile Thr Gly Ser Leu
370                 375                 380 aac tac cag gct gtg cac cat ctg ttc ccc aac gtg tcg cag cac cat       1200
Asn Tyr Gln Ala Val His His Leu Phe Pro Asn Val Ser Gln His His
385                 390                 395                 400 tat ccc gat att ctg gcc atc atc aag aac acc tgc agc gag tac aag       1248
Tyr Pro Asp Ile Leu Ala Ile Ile Lys Asn Thr Cys Ser Glu Tyr Lys
            405                 410                 415 gtt cca tac ctt gtc aag gat acg ttt tgg caa gca ttt gct tca cat       1296
Val Pro Tyr Leu Val Lys Asp Thr Phe Trp Gln Ala Phe Ala Ser His
        420                 425                 430 ttg gag cac ttg cgt gtt ctt gga ctc cgt ccc aag gaa gag tag           1341
Leu Glu His Leu Arg Val Leu Gly Leu Arg Pro Lys Glu Glu
        435                 440                 445

<210> SEQ ID NO 14
<211> LENGTH: 446
<212> TYPE: PRT
<213> ORGANISM: Mortierella alpina

<400> SEQUENCE: 14

Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
```

35                  40                  45

Leu Leu Gly Ala Gly Arg Asp Val Thr Pro Val Phe Glu Met Tyr His
 50                  55                  60

Ala Phe Gly Ala Ala Asp Ala Ile Met Lys Lys Tyr Tyr Val Gly Thr
 65                  70                  75                  80

Leu Val Ser Asn Glu Leu Pro Ile Phe Pro Glu Pro Thr Val Phe His
                 85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445

<210> SEQ ID NO 15

```
<211> LENGTH: 1344
<212> TYPE: DNA
<213> ORGANISM: Caenorhabditis elegans
<220> FEATURE:
<221> NAME/KEY: CDS
<222> LOCATION: (1)..(1344)
<223> OTHER INFORMATION: delta5-desaturase

<400> SEQUENCE: 15
```

| | | | | | | | | | | | | | | | | |
|---|---|---|---|---|---|---|---|---|---|---|---|---|---|---|---|---|
| atg | gta | tta | cga | gag | caa | gag | cat | gag | cca | ttc | ttc | att | aaa | att | gat | 48 |
| Met | Val | Leu | Arg | Glu | Gln | Glu | His | Glu | Pro | Phe | Phe | Ile | Lys | Ile | Asp | |
| 1 | | | | 5 | | | | | 10 | | | | | 15 | | |
| gga | aaa | tgg | tgt | caa | att | gac | gat | gct | gtc | ctg | aga | tca | cat | cca | ggt | 96 |
| Gly | Lys | Trp | Cys | Gln | Ile | Asp | Asp | Ala | Val | Leu | Arg | Ser | His | Pro | Gly | |
| | | | 20 | | | | | 25 | | | | | 30 | | | |
| ggt | agt | gca | att | act | acc | tat | aaa | aat | atg | gat | gcc | act | acc | gta | ttc | 144 |
| Gly | Ser | Ala | Ile | Thr | Thr | Tyr | Lys | Asn | Met | Asp | Ala | Thr | Thr | Val | Phe | |
| | | 35 | | | | | 40 | | | | | 45 | | | | |
| cac | aca | ttc | cat | act | ggt | tct | aaa | gaa | gcg | tat | caa | tgg | ctg | aca | gaa | 192 |
| His | Thr | Phe | His | Thr | Gly | Ser | Lys | Glu | Ala | Tyr | Gln | Trp | Leu | Thr | Glu | |
| | 50 | | | | | 55 | | | | | 60 | | | | | |
| ttg | aaa | aaa | gag | tgc | cct | aca | caa | gaa | cca | gag | atc | cca | gat | att | aag | 240 |
| Leu | Lys | Lys | Glu | Cys | Pro | Thr | Gln | Glu | Pro | Glu | Ile | Pro | Asp | Ile | Lys | |
| 65 | | | | | 70 | | | | | 75 | | | | | 80 | |
| gat | gac | cca | atc | aaa | gga | att | gat | gat | gtg | aac | atg | gga | act | ttc | aat | 288 |
| Asp | Asp | Pro | Ile | Lys | Gly | Ile | Asp | Asp | Val | Asn | Met | Gly | Thr | Phe | Asn | |
| | | | | 85 | | | | | 90 | | | | | 95 | | |
| att | tct | gag | aaa | cga | tct | gcc | caa | ata | aat | aaa | agt | ttc | act | gat | cta | 336 |
| Ile | Ser | Glu | Lys | Arg | Ser | Ala | Gln | Ile | Asn | Lys | Ser | Phe | Thr | Asp | Leu | |
| | | | 100 | | | | | 105 | | | | | 110 | | | |
| cgt | atg | cga | gtt | cgt | gca | gaa | gga | ctt | atg | gat | gga | tct | cct | ttg | ttc | 384 |
| Arg | Met | Arg | Val | Arg | Ala | Glu | Gly | Leu | Met | Asp | Gly | Ser | Pro | Leu | Phe | |
| | | 115 | | | | | 120 | | | | | 125 | | | | |
| tac | att | aga | aaa | att | ctt | gaa | aca | atc | ttc | aca | att | ctt | ttt | gca | ttc | 432 |
| Tyr | Ile | Arg | Lys | Ile | Leu | Glu | Thr | Ile | Phe | Thr | Ile | Leu | Phe | Ala | Phe | |
| | 130 | | | | | 135 | | | | | 140 | | | | | |
| tac | ctt | caa | tac | cac | aca | tat | tat | ctt | cca | tca | gct | att | cta | atg | gga | 480 |
| Tyr | Leu | Gln | Tyr | His | Thr | Tyr | Tyr | Leu | Pro | Ser | Ala | Ile | Leu | Met | Gly | |
| 145 | | | | | 150 | | | | | 155 | | | | | 160 | |
| gtt | gcg | tgg | caa | caa | ttg | gga | tgg | tta | atc | cat | gaa | ttc | gca | cat | cat | 528 |
| Val | Ala | Trp | Gln | Gln | Leu | Gly | Trp | Leu | Ile | His | Glu | Phe | Ala | His | His | |
| | | | | 165 | | | | | 170 | | | | | 175 | | |
| cag | ttg | ttc | aaa | aac | aga | tac | tac | aat | gat | ttg | gcc | agc | tat | ttc | gtt | 576 |
| Gln | Leu | Phe | Lys | Asn | Arg | Tyr | Tyr | Asn | Asp | Leu | Ala | Ser | Tyr | Phe | Val | |
| | | | 180 | | | | | 185 | | | | | 190 | | | |
| gga | aac | ttt | tta | caa | gga | ttc | tca | tct | ggt | ggt | tgg | aaa | gag | cag | cac | 624 |
| Gly | Asn | Phe | Leu | Gln | Gly | Phe | Ser | Ser | Gly | Gly | Trp | Lys | Glu | Gln | His | |
| | | 195 | | | | | 200 | | | | | 205 | | | | |
| aat | gtg | cat | cac | gca | gcc | aca | aat | gtt | gtt | gga | cga | gac | gga | gat | ctt | 672 |
| Asn | Val | His | His | Ala | Ala | Thr | Asn | Val | Val | Gly | Arg | Asp | Gly | Asp | Leu | |
| | 210 | | | | | 215 | | | | | 220 | | | | | |
| gat | tta | gtc | cca | ttc | tat | gct | aca | gtg | gca | gaa | cat | ctc | aac | aat | tat | 720 |
| Asp | Leu | Val | Pro | Phe | Tyr | Ala | Thr | Val | Ala | Glu | His | Leu | Asn | Asn | Tyr | |
| 225 | | | | | 230 | | | | | 235 | | | | | 240 | |
| tct | cag | gat | tca | tgg | gtt | atg | act | cta | ttc | aga | tgg | caa | cat | gtt | cat | 768 |
| Ser | Gln | Asp | Ser | Trp | Val | Met | Thr | Leu | Phe | Arg | Trp | Gln | His | Val | His | |
| | | | | 245 | | | | | 250 | | | | | 255 | | |
| tgg | aca | ttc | atg | tta | cca | ttc | ctc | cgt | ctc | tcg | tgg | ctt | ctt | cag | tca | 816 |
| Trp | Thr | Phe | Met | Leu | Pro | Phe | Leu | Arg | Leu | Ser | Trp | Leu | Leu | Gln | Ser | |
| | | | 260 | | | | | 265 | | | | | 270 | | | |
| atc | att | ttt | gtt | agt | cag | atg | cca | act | cat | tat | tat | gac | tat | tac | aga | 864 |

```
Ile Ile Phe Val Ser Gln Met Pro Thr His Tyr Tyr Asp Tyr Tyr Arg
            275                 280                 285 aat act gcg att tat gaa cag gtt ggt ctc tct ttg cac tgg gct tgg      912
Asn Thr Ala Ile Tyr Glu Gln Val Gly Leu Ser Leu His Trp Ala Trp
        290                 295                 300 tca ttg ggt caa ttg tat ttc cta ccc gat tgg tca act aga ata atg      960
Ser Leu Gly Gln Leu Tyr Phe Leu Pro Asp Trp Ser Thr Arg Ile Met
305                 310                 315                 320 ttc ttc ctt gtt tct cat ctt gtt gga ggt ttc ctg ctc tct cat gta     1008
Phe Phe Leu Val Ser His Leu Val Gly Gly Phe Leu Leu Ser His Val
                325                 330                 335 gtt act ttc aat cat tat tca gtg gag aag ttt gca ttg agc tcg aac     1056
Val Thr Phe Asn His Tyr Ser Val Glu Lys Phe Ala Leu Ser Ser Asn
            340                 345                 350 atc atg tca aat tac gct tgt ctt caa atc atg acc aca aga aat atg     1104
Ile Met Ser Asn Tyr Ala Cys Leu Gln Ile Met Thr Thr Arg Asn Met
        355                 360                 365 aga cct gga aga ttc att gac tgg ctt tgg gga ggt ctt aac tat cag     1152
Arg Pro Gly Arg Phe Ile Asp Trp Leu Trp Gly Gly Leu Asn Tyr Gln
370                 375                 380 att gag cac cat ctt ttc cca acg atg cca cga cac aac ttg aac act     1200
Ile Glu His His Leu Phe Pro Thr Met Pro Arg His Asn Leu Asn Thr
385                 390                 395                 400 gtt atg cca ctt gtt aag gag ttt gca gca gca aat ggt tta cca tac     1248
Val Met Pro Leu Val Lys Glu Phe Ala Ala Ala Asn Gly Leu Pro Tyr
                405                 410                 415 atg gtc gac gat tat ttc aca gga ttc tgg ctt gaa att gag caa ttc     1296
Met Val Asp Asp Tyr Phe Thr Gly Phe Trp Leu Glu Ile Glu Gln Phe
            420                 425                 430 cga aat att gca aat gtt gct gct aaa ttg act aaa aag att gcc tag     1344
Arg Asn Ile Ala Asn Val Ala Ala Lys Leu Thr Lys Lys Ile Ala
        435                 440                 445

<210> SEQ ID NO 16
<211> LENGTH: 447
<212> TYPE: PRT
<213> ORGANISM: Caenorhabditis elegans

<400> SEQUENCE: 16

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Glu Ile Pro Asp Ile Lys
65                  70                  75                  80

Asp Asp Pro Ile Lys Gly Ile Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125

Tyr Ile Arg Lys Ile Leu Glu Thr Ile Phe Thr Ile Leu Phe Ala Phe
    130                 135                 140

Tyr Leu Gln Tyr His Thr Tyr Tyr Leu Pro Ser Ala Ile Leu Met Gly
```

-continued

```
            145                 150                 155                 160
        Val Ala Trp Gln Gln Leu Gly Trp Leu Ile His Glu Phe Ala His His
                        165                 170                 175

Gln Leu Phe Lys Asn Arg Tyr Tyr Asn Asp Leu Ala Ser Tyr Phe Val
                        180                 185                 190

Gly Asn Phe Leu Gln Gly Phe Ser Gly Gly Trp Lys Glu Gln His
                        195                 200                 205

Asn Val His His Ala Ala Thr Asn Val Val Gly Arg Asp Gly Asp Leu
                        210                 215                 220

Asp Leu Val Pro Phe Tyr Ala Thr Val Ala Glu His Leu Asn Asn Tyr
        225                 230                 235                 240

Ser Gln Asp Ser Trp Val Met Thr Leu Phe Arg Trp Gln His Val His
                        245                 250                 255

Trp Thr Phe Met Leu Pro Phe Leu Arg Leu Ser Trp Leu Leu Gln Ser
                        260                 265                 270

Ile Ile Phe Val Ser Gln Met Pro Thr His Tyr Tyr Asp Tyr Tyr Arg
                        275                 280                 285

Asn Thr Ala Ile Tyr Glu Gln Val Gly Leu Ser Leu His Trp Ala Trp
                        290                 295                 300

Ser Leu Gly Gln Leu Tyr Phe Leu Pro Asp Trp Ser Thr Arg Ile Met
        305                 310                 315                 320

Phe Phe Leu Val Ser His Leu Val Gly Gly Phe Leu Leu Ser His Val
                        325                 330                 335

Val Thr Phe Asn His Tyr Ser Val Glu Lys Phe Ala Leu Ser Ser Asn
                        340                 345                 350

Ile Met Ser Asn Tyr Ala Cys Leu Gln Ile Met Thr Thr Arg Asn Met
                        355                 360                 365

Arg Pro Gly Arg Phe Ile Asp Trp Leu Trp Gly Gly Leu Asn Tyr Gln
                        370                 375                 380

Ile Glu His His Leu Phe Pro Thr Met Pro Arg His Asn Leu Asn Thr
        385                 390                 395                 400

Val Met Pro Leu Val Lys Glu Phe Ala Ala Ala Asn Gly Leu Pro Tyr
                        405                 410                 415

Met Val Asp Asp Tyr Phe Thr Gly Phe Trp Leu Glu Ile Glu Gln Phe
                        420                 425                 430

Arg Asn Ile Ala Asn Val Ala Ala Lys Leu Thr Lys Lys Ile Ala
                        435                 440                 445

<210> SEQ ID NO 17
<211> LENGTH: 1683
<212> TYPE: DNA
<213> ORGANISM: Borago officinalis
<220> FEATURE:
<221> NAME/KEY: CDS
<222> LOCATION: (42)..(1388)
<223> OTHER INFORMATION: delta6-desaturase

<400> SEQUENCE: 17
tatctgccta ccctcccaaa gagagtagtc atttttcatc a atg gct gct caa atc      56
                                             Met Ala Ala Gln Ile
                                               1               5 aag aaa tac att acc tca gat gaa ctc aag aac cac gat aaa ccc gga     104
Lys Lys Tyr Ile Thr Ser Asp Glu Leu Lys Asn His Asp Lys Pro Gly
                10                  15                  20 gat cta tgg atc tcg att caa ggg aaa gcc tat gat gtt tcg gat tgg     152
Asp Leu Trp Ile Ser Ile Gln Gly Lys Ala Tyr Asp Val Ser Asp Trp
        25                  30                  35
```

-continued

```
gtg aaa gac cat cca ggt ggc agc ttt ccc ttg aag agt ctt gct ggt    200
Val Lys Asp His Pro Gly Gly Ser Phe Pro Leu Lys Ser Leu Ala Gly
        40                  45                  50 caa gag gta act gat gca ttt gtt gca ttc cat cct gcc tct aca tgg    248
Gln Glu Val Thr Asp Ala Phe Val Ala Phe His Pro Ala Ser Thr Trp
55                  60                  65 aag aat ctt gat aag ttt ttc act ggg tat tat ctt aaa gat tac tct    296
Lys Asn Leu Asp Lys Phe Phe Thr Gly Tyr Tyr Leu Lys Asp Tyr Ser
70                  75                  80                  85 gtt tct gag gtt tct aaa gat tat agg aag ctt gtt ttt gag ttt tct    344
Val Ser Glu Val Ser Lys Asp Tyr Arg Lys Leu Val Phe Glu Phe Ser
                90                  95                  100 aaa atg ggt ttg tat gac aaa aaa ggt cat att atg ttt gca act ttg    392
Lys Met Gly Leu Tyr Asp Lys Lys Gly His Ile Met Phe Ala Thr Leu
        105                 110                 115 tgc ttt ata gca atg ctg ttt gct atg agt gtt tat ggg gtt ttg ttt    440
Cys Phe Ile Ala Met Leu Phe Ala Met Ser Val Tyr Gly Val Leu Phe
                120                 125                 130 tgt gag ggt gtt ttg gta cat ttg ttt tct ggg tgt ttg atg ggg ttt    488
Cys Glu Gly Val Leu Val His Leu Phe Ser Gly Cys Leu Met Gly Phe
135                 140                 145 ctt tgg att cag agt ggt tgg att gga cat gat gct ggg cat tat atg    536
Leu Trp Ile Gln Ser Gly Trp Ile Gly His Asp Ala Gly His Tyr Met
150                 155                 160                 165 gta gtg tct gat tca agg ctt aat aag ttt atg ggt att ttt gct gca    584
Val Val Ser Asp Ser Arg Leu Asn Lys Phe Met Gly Ile Phe Ala Ala
                170                 175                 180 aat tgt ctt tca gga ata agt att ggt tgg tgg aaa tgg aac cat aat    632
Asn Cys Leu Ser Gly Ile Ser Ile Gly Trp Trp Lys Trp Asn His Asn
        185                 190                 195 gca cat cac att gcc tgt aat agc ctt gaa tat gac cct gat tta caa    680
Ala His His Ile Ala Cys Asn Ser Leu Glu Tyr Asp Pro Asp Leu Gln
        200                 205                 210 tat ata cca ttc ctt gtt gtg tct tcc aag ttt ttt ggt tca ctc acc    728
Tyr Ile Pro Phe Leu Val Val Ser Ser Lys Phe Phe Gly Ser Leu Thr
        215                 220                 225 tct cat ttc tat gag aaa agg ttg act ttt gac tct tta tca aga ttc    776
Ser His Phe Tyr Glu Lys Arg Leu Thr Phe Asp Ser Leu Ser Arg Phe
230                 235                 240                 245 ttt gta agt tat caa cat tgg aca ttt tac cct att atg tgt gct gct    824
Phe Val Ser Tyr Gln His Trp Thr Phe Tyr Pro Ile Met Cys Ala Ala
                250                 255                 260 agg ctc aat atg tat gta caa tct ctc ata atg ttg ttg acc aag aga    872
Arg Leu Asn Met Tyr Val Gln Ser Leu Ile Met Leu Leu Thr Lys Arg
        265                 270                 275 aat gtg tcc tat cga gct cag gaa ctc ttg gga tgc cta gtg ttc tcg    920
Asn Val Ser Tyr Arg Ala Gln Glu Leu Leu Gly Cys Leu Val Phe Ser
        280                 285                 290 att tgg tac ccg ttg ctt gtt tct tgt ttg cct aat tgg ggt gaa aga    968
Ile Trp Tyr Pro Leu Leu Val Ser Cys Leu Pro Asn Trp Gly Glu Arg
        295                 300                 305 att atg ttt gtt att gca agt tta tca gtg act gga atg caa caa gtt    1016
Ile Met Phe Val Ile Ala Ser Leu Ser Val Thr Gly Met Gln Gln Val
310                 315                 320                 325 cag ttc tcc ttg aac cac ttc tct tca gtt tat gtt gga aag cct    1064
Gln Phe Ser Leu Asn His Phe Ser Ser Val Tyr Val Gly Lys Pro
                330                 335                 340 aaa ggg aat aat tgg ttt gag aaa caa acg gat ggg aca ctt gac att    1112
Lys Gly Asn Asn Trp Phe Glu Lys Gln Thr Asp Gly Thr Leu Asp Ile
```

-continued

```
                    345                 350                 355
tct tgt cct cct tgg atg gat tgg ttt cat ggt gga ttg caa ttc caa      1160
Ser Cys Pro Pro Trp Met Asp Trp Phe His Gly Gly Leu Gln Phe Gln
        360                 365                 370 att gag cat cat ttg ttt ccc aag atg cct aga tgc aac ctt agg aaa      1208
Ile Glu His His Leu Phe Pro Lys Met Pro Arg Cys Asn Leu Arg Lys
375                 380                 385 atc tcg ccc tac gtg atc gag tta tgc aag aaa cat aat ttg cct tac      1256
Ile Ser Pro Tyr Val Ile Glu Leu Cys Lys Lys His Asn Leu Pro Tyr
390                 395                 400                 405 aat tat gca tct ttc tcc aag gcc aat gaa atg aca ctc aga aca ttg      1304
Asn Tyr Ala Ser Phe Ser Lys Ala Asn Glu Met Thr Leu Arg Thr Leu
            410                 415                 420 agg aac aca gca ttg cag gct agg gat ata acc aag ccg ctc ccg aag      1352
Arg Asn Thr Ala Leu Gln Ala Arg Asp Ile Thr Lys Pro Leu Pro Lys
            425                 430                 435 aat ttg gta tgg gaa gct ctt cac act cat ggt taa aattccctt            1398
Asn Leu Val Trp Glu Ala Leu His Thr His Gly
            440                 445 agttcatgta ataatttgag attatgtatc tcctatgttt gtgtcttgtc ttggttctac    1458
ttgttggagt cattgcaact tgtcttttat ggtttattag atgttttta atatatttta    1518 gaggttttgc tttcatctcc attattgatg aataaggagt tgcatattgt caattgttgt   1578
gctcaatatc tgatattttg gaatgtactt tgtaccactg tgttttcagt tgaagctcat   1638
gtgtacttct atagactttg tttaaatggt tatgtcatgt tattt                   1683
```

<210> SEQ ID NO 18
<211> LENGTH: 448
<212> TYPE: PRT
<213> ORGANISM: Borago officinalis

<400> SEQUENCE: 18

```
Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
                20                  25                  30

Asp Val Ser Asp Trp Val Lys Asp His Pro Gly Gly Ser Phe Pro Leu
            35                  40                  45

Lys Ser Leu Ala Gly Gln Glu Val Thr Asp Ala Phe Val Ala Phe His
        50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
                100                 105                 110

Met Phe Ala Thr Leu Cys Phe Ile Ala Met Leu Phe Ala Met Ser Val
            115                 120                 125

Tyr Gly Val Leu Phe Cys Glu Gly Val Leu Val His Leu Phe Ser Gly
        130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190
```

```
Lys Trp Asn His Asn Ala His His Ile Ala Cys Asn Ser Leu Glu Tyr
        195                 200                 205

Asp Pro Asp Leu Gln Tyr Ile Pro Phe Leu Val Val Ser Ser Lys Phe
210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
                260                 265                 270

Leu Leu Thr Lys Arg Asn Val Ser Tyr Arg Ala Gln Glu Leu Leu Gly
            275                 280                 285

Cys Leu Val Phe Ser Ile Trp Tyr Pro Leu Leu Val Ser Cys Leu Pro
        290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
                340                 345                 350

Gly Thr Leu Asp Ile Ser Cys Pro Pro Trp Met Asp Trp Phe His Gly
            355                 360                 365

Gly Leu Gln Phe Gln Ile Glu His His Leu Phe Pro Lys Met Pro Arg
        370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
            420                 425                 430

Lys Pro Leu Pro Lys Asn Leu Val Trp Glu Ala Leu His Thr His Gly
        435                 440                 445
```

<210> SEQ ID NO 19
<211> LENGTH: 1563
<212> TYPE: DNA
<213> ORGANISM: Ceratodon purpureus
<220> FEATURE:
<221> NAME/KEY: CDS
<222> LOCATION: (1)..(1563)
<223> OTHER INFORMATION: delta6-desaturase

<400> SEQUENCE: 19

```
atg gtg tcc cag ggc ggc ggt ctc tcg cag ggt tcc att gaa gaa aac     48
Met Val Ser Gln Gly Gly Gly Leu Ser Gln Gly Ser Ile Glu Glu Asn
1               5                   10                  15 att gac gtt gag cac ttg gca acg atg ccc ctc gtc agt gac ttc cta     96
Ile Asp Val Glu His Leu Ala Thr Met Pro Leu Val Ser Asp Phe Leu
            20                  25                  30 aat gtc ctg gga acg act ttg ggc cag tgg agt ctt tcc act aca ttc    144
Asn Val Leu Gly Thr Thr Leu Gly Gln Trp Ser Leu Ser Thr Thr Phe
        35                  40                  45 gct ttc aag agg ctc acg act aag aaa cac agt tcg gac atc tcg gtg    192
Ala Phe Lys Arg Leu Thr Thr Lys Lys His Ser Ser Asp Ile Ser Val
    50                  55                  60 gag gca caa aaa gaa tcg gtt gcg cgg ggg cca gtt gag aat att tct    240
Glu Ala Gln Lys Glu Ser Val Ala Arg Gly Pro Val Glu Asn Ile Ser
65                  70                  75                  80
```

```
                65                  70                  75                  80
caa tcg gtt gcg cag ccc atc agg cgg agg tgg gtg cag gat aaa aag          288
Gln Ser Val Ala Gln Pro Ile Arg Arg Arg Trp Val Gln Asp Lys Lys
                    85                  90                  95 ccg gtt act tac agc ctg aag gat gta gct tcg cac gat atg ccc cag          336
Pro Val Thr Tyr Ser Leu Lys Asp Val Ala Ser His Asp Met Pro Gln
            100                 105                 110 gac tgc tgg att ata atc aaa gag aag gtg tat gat gtg agc acc ttc          384
Asp Cys Trp Ile Ile Ile Lys Glu Lys Val Tyr Asp Val Ser Thr Phe
        115                 120                 125 gct gag cag cac cct gga ggc acg gtt atc aac acc tac ttc gga cga          432
Ala Glu Gln His Pro Gly Gly Thr Val Ile Asn Thr Tyr Phe Gly Arg
    130                 135                 140 gac gcc aca gat gtt ttc tct act ttc cac gca tcc acc tca tgg aag          480
Asp Ala Thr Asp Val Phe Ser Thr Phe His Ala Ser Thr Ser Trp Lys
145                 150                 155                 160 att ctt cag aat ttc tac atc ggg aac ctt gtt agg gag gag ccg act          528
Ile Leu Gln Asn Phe Tyr Ile Gly Asn Leu Val Arg Glu Glu Pro Thr
                    165                 170                 175 ttg gag ctg ctg aag gag tac aga gag ttg aga gcc ctt ttc ttg aga          576
Leu Glu Leu Leu Lys Glu Tyr Arg Glu Leu Arg Ala Leu Phe Leu Arg
                180                 185                 190 gaa cag ctt ttc aag agt tcc aaa tcc tac tac ctt ttc aag act ctc          624
Glu Gln Leu Phe Lys Ser Ser Lys Ser Tyr Tyr Leu Phe Lys Thr Leu
            195                 200                 205 ata aat gtt tcc att gtt gcc aca agc att gcg ata atc agt ctg tac          672
Ile Asn Val Ser Ile Val Ala Thr Ser Ile Ala Ile Ile Ser Leu Tyr
        210                 215                 220 aag tct tac cgg gcg gtt ctg tta tca gcc agt ttg atg ggc ttg ttt          720
Lys Ser Tyr Arg Ala Val Leu Leu Ser Ala Ser Leu Met Gly Leu Phe
225                 230                 235                 240 att caa cag tgc gga tgg ttg tct cac gat ttt cta cac cat cag gta          768
Ile Gln Gln Cys Gly Trp Leu Ser His Asp Phe Leu His His Gln Val
                    245                 250                 255 ttt gag aca cgc tgg ctc aat gac gtt gtt ggc tat gtg gtc ggc aac          816
Phe Glu Thr Arg Trp Leu Asn Asp Val Val Gly Tyr Val Val Gly Asn
                260                 265                 270 gtt gtt ctg gga ttc agt gtc tcg tgg tgg aag acc aag cac aac ctg          864
Val Val Leu Gly Phe Ser Val Ser Trp Trp Lys Thr Lys His Asn Leu
            275                 280                 285 cat cat gct gct ccg aat gaa tgc gac caa aag tac aca ccg att gat          912
His His Ala Ala Pro Asn Glu Cys Asp Gln Lys Tyr Thr Pro Ile Asp
        290                 295                 300 gag gat att gat act ctc ccc atc att gct tgg agt aaa gat ctc ttg          960
Glu Asp Ile Asp Thr Leu Pro Ile Ile Ala Trp Ser Lys Asp Leu Leu
305                 310                 315                 320 gcc act gtt gag agc aag acc atg ttg cga gtt ctt cag tac cag cac         1008
Ala Thr Val Glu Ser Lys Thr Met Leu Arg Val Leu Gln Tyr Gln His
                    325                 330                 335 cta ttc ttt ttg gtt ctt ttg acg ttt gcc cgg gcg agt tgg cta ttt         1056
Leu Phe Phe Leu Val Leu Leu Thr Phe Ala Arg Ala Ser Trp Leu Phe
                340                 345                 350 tgg agc gcg gcc ttc act ctc agg ccc gag ttg acc ctt ggc gag aag         1104
Trp Ser Ala Ala Phe Thr Leu Arg Pro Glu Leu Thr Leu Gly Glu Lys
            355                 360                 365 ctt ttg gag agg gga acg atg gct ttg cac tac att tgg ttt aat agt         1152
Leu Leu Glu Arg Gly Thr Met Ala Leu His Tyr Ile Trp Phe Asn Ser
        370                 375                 380 gtt gcg ttt tat ctg ctc ccc gga tgg aaa cca gtt gta tgg atg gtg         1200
```

```
Val Ala Phe Tyr Leu Leu Pro Gly Trp Lys Pro Val Val Trp Met Val
385                 390                 395                 400 gtc agc gag ctc atg tct ggt ttc ctg ctg gga tac gta ttt gta ctc   1248
Val Ser Glu Leu Met Ser Gly Phe Leu Leu Gly Tyr Val Phe Val Leu
                405                 410                 415 agt cac aat gga atg gag gtg tac aat acg tca aag gac ttc gtg aat   1296
Ser His Asn Gly Met Glu Val Tyr Asn Thr Ser Lys Asp Phe Val Asn
            420                 425                 430 gcc cag att gca tcg act cgc gac atc aaa gca ggg gtg ttt aat gat   1344
Ala Gln Ile Ala Ser Thr Arg Asp Ile Lys Ala Gly Val Phe Asn Asp
                435                 440                 445 tgg ttc acc gga ggt ctc aac aga cag att gag cat cat cta ttt cca   1392
Trp Phe Thr Gly Gly Leu Asn Arg Gln Ile Glu His His Leu Phe Pro
        450                 455                 460 acg atg ccc agg cac aac ctt aat aaa att tct cct cac gtg gag act   1440
Thr Met Pro Arg His Asn Leu Asn Lys Ile Ser Pro His Val Glu Thr
465                 470                 475                 480 ttg tgc aag aag cat gga ctg gtc tac gaa gac gtg agc atg gct tcg   1488
Leu Cys Lys Lys His Gly Leu Val Tyr Glu Asp Val Ser Met Ala Ser
                485                 490                 495 ggc act tac cgg gtt ttg aaa aca ctt aag gac gtt gcc gat gct gct   1536
Gly Thr Tyr Arg Val Leu Lys Thr Leu Lys Asp Val Ala Asp Ala Ala
            500                 505                 510 tca cac cag cag ctt gct gcg agt tga                               1563
Ser His Gln Gln Leu Ala Ala Ser
                515                 520

<210> SEQ ID NO 20
<211> LENGTH: 520
<212> TYPE: PRT
<213> ORGANISM: Ceratodon purpureus

<400> SEQUENCE: 20

Met Val Ser Gln Gly Gly Leu Ser Gln Gly Ser Ile Glu Glu Asn
1                   5                   10                  15

Ile Asp Val Glu His Leu Ala Thr Met Pro Leu Val Ser Asp Phe Leu
                20                  25                  30

Asn Val Leu Gly Thr Thr Leu Gly Gln Trp Ser Leu Ser Thr Thr Phe
            35                  40                  45

Ala Phe Lys Arg Leu Thr Thr Lys Lys His Ser Ser Asp Ile Ser Val
        50                  55                  60

Glu Ala Gln Lys Glu Ser Val Ala Arg Gly Pro Val Glu Asn Ile Ser
65                  70                  75                  80

Gln Ser Val Ala Gln Pro Ile Arg Arg Arg Trp Val Gln Asp Lys Lys
                85                  90                  95

Pro Val Thr Tyr Ser Leu Lys Asp Val Ala Ser His Asp Met Pro Gln
                100                 105                 110

Asp Cys Trp Ile Ile Ile Lys Glu Lys Val Tyr Asp Val Ser Thr Phe
            115                 120                 125

Ala Glu Gln His Pro Gly Gly Thr Val Ile Asn Thr Tyr Phe Gly Arg
        130                 135                 140

Asp Ala Thr Asp Val Phe Ser Thr Phe His Ala Ser Thr Ser Trp Lys
145                 150                 155                 160

Ile Leu Gln Asn Phe Tyr Ile Gly Asn Leu Val Arg Glu Glu Pro Thr
                165                 170                 175

Leu Glu Leu Leu Lys Glu Tyr Arg Glu Leu Arg Ala Leu Phe Leu Arg
            180                 185                 190
```

```
Glu Gln Leu Phe Lys Ser Ser Lys Ser Tyr Tyr Leu Phe Lys Thr Leu
            195                 200                 205
Ile Asn Val Ser Ile Val Ala Thr Ser Ile Ala Ile Ser Leu Tyr
    210                 215                 220
Lys Ser Tyr Arg Ala Val Leu Leu Ser Ala Ser Leu Met Gly Leu Phe
225                 230                 235                 240
Ile Gln Gln Cys Gly Trp Leu Ser His Asp Phe Leu His His Gln Val
                245                 250                 255
Phe Glu Thr Arg Trp Leu Asn Asp Val Val Gly Tyr Val Val Gly Asn
            260                 265                 270
Val Val Leu Gly Phe Ser Val Ser Trp Trp Lys Thr Lys His Asn Leu
    275                 280                 285
His His Ala Ala Pro Asn Glu Cys Asp Gln Lys Tyr Thr Pro Ile Asp
290                 295                 300
Glu Asp Ile Asp Thr Leu Pro Ile Ile Ala Trp Ser Lys Asp Leu Leu
305                 310                 315                 320
Ala Thr Val Glu Ser Lys Thr Met Leu Arg Val Leu Gln Tyr Gln His
                325                 330                 335
Leu Phe Phe Leu Val Leu Leu Thr Phe Ala Arg Ala Ser Trp Leu Phe
            340                 345                 350
Trp Ser Ala Ala Phe Thr Leu Arg Pro Glu Leu Thr Leu Gly Glu Lys
        355                 360                 365
Leu Leu Glu Arg Gly Thr Met Ala Leu His Tyr Ile Trp Phe Asn Ser
    370                 375                 380
Val Ala Phe Tyr Leu Leu Pro Gly Trp Lys Pro Val Val Trp Met Val
385                 390                 395                 400
Val Ser Glu Leu Met Ser Gly Phe Leu Leu Gly Tyr Val Phe Val Leu
                405                 410                 415
Ser His Asn Gly Met Glu Val Tyr Asn Thr Ser Lys Asp Phe Val Asn
            420                 425                 430
Ala Gln Ile Ala Ser Thr Arg Asp Ile Lys Ala Gly Val Phe Asn Asp
        435                 440                 445
Trp Phe Thr Gly Gly Leu Asn Arg Gln Ile Glu His His Leu Phe Pro
    450                 455                 460
Thr Met Pro Arg His Asn Leu Asn Lys Ile Ser Pro His Val Glu Thr
465                 470                 475                 480
Leu Cys Lys Lys His Gly Leu Val Tyr Glu Asp Val Ser Met Ala Ser
                485                 490                 495
Gly Thr Tyr Arg Val Leu Lys Thr Leu Lys Asp Val Ala Asp Ala Ala
            500                 505                 510
Ser His Gln Gln Leu Ala Ala Ser
        515                 520

<210> SEQ ID NO 21
<211> LENGTH: 1434
<212> TYPE: DNA
<213> ORGANISM: Phaeodactylum tricornutum
<220> FEATURE:
<221> NAME/KEY: CDS
<222> LOCATION: (1)..(1434)
<223> OTHER INFORMATION: delta6-desaturase

<400> SEQUENCE: 21 atg ggc aaa gga ggg gac gct cgg gcc tcg aag ggc tca acg gcg gct    48
Met Gly Lys Gly Gly Asp Ala Arg Ala Ser Lys Gly Ser Thr Ala Ala
1               5                   10                  15
```

| | |
|---|---|
| cgc aag atc agt tgg cag gaa gtc aag acc cac gcg tct ccg gag gac<br>Arg Lys Ile Ser Trp Gln Glu Val Lys Thr His Ala Ser Pro Glu Asp<br>20                       25                  30 | 96 |
| gcc tgg atc att cac tcc aat aag gtc tac gac gtg tcc aac tgg cac<br>Ala Trp Ile Ile His Ser Asn Lys Val Tyr Asp Val Ser Asn Trp His<br>35                 40                 45 | 144 |
| gaa cat ccc gga ggc gcc gtc att ttc acg cac gcc ggt gac gac atg<br>Glu His Pro Gly Gly Ala Val Ile Phe Thr His Ala Gly Asp Asp Met<br>50                   55                 60 | 192 |
| acg gac att ttc gct gcc ttt cac gca ccc gga tcg cag tcg ctc atg<br>Thr Asp Ile Phe Ala Ala Phe His Ala Pro Gly Ser Gln Ser Leu Met<br>65                   70               75              80 | 240 |
| aag aag ttc tac att ggc gaa ttg ctc ccg gaa acc acc ggc aag gag<br>Lys Lys Phe Tyr Ile Gly Glu Leu Leu Pro Glu Thr Thr Gly Lys Glu<br>85                 90                 95 | 288 |
| ccg cag caa atc gcc ttt gaa aag ggc tac cgc gat ctg cgc tcc aaa<br>Pro Gln Gln Ile Ala Phe Glu Lys Gly Tyr Arg Asp Leu Arg Ser Lys<br>100                 105               110 | 336 |
| ctc atc atg atg ggc atg ttc aag tcc aac aag tgg ttc tac gtc tac<br>Leu Ile Met Met Gly Met Phe Lys Ser Asn Lys Trp Phe Tyr Val Tyr<br>115                 120               125 | 384 |
| aag tgc ctc agc aac atg gcc att tgg gcc gcc gcc tgt gct ctc gtc<br>Lys Cys Leu Ser Asn Met Ala Ile Trp Ala Ala Ala Cys Ala Leu Val<br>130                 135               140 | 432 |
| ttt tac tcg gac cgc ttc tgg gta cac ctg gcc agc gcc gtc atg ctg<br>Phe Tyr Ser Asp Arg Phe Trp Val His Leu Ala Ser Ala Val Met Leu<br>145                 150               155             160 | 480 |
| gga aca ttc ttt cag cag tcg gga tgg ttg gca cac gac ttt ctg cac<br>Gly Thr Phe Phe Gln Gln Ser Gly Trp Leu Ala His Asp Phe Leu His<br>                    165               170               175 | 528 |
| cac cag gtc ttc acc aag cgc aag cac ggg gat ctc gga gga ctc ttt<br>His Gln Val Phe Thr Lys Arg Lys His Gly Asp Leu Gly Gly Leu Phe<br>180                 185               190 | 576 |
| tgg ggg aac ctc atg cag ggt tac tcc gta cag tgg tgg aaa aac aag<br>Trp Gly Asn Leu Met Gln Gly Tyr Ser Val Gln Trp Trp Lys Asn Lys<br>195                 200               205 | 624 |
| cac aac gga cac cac gcc gtc ccc aac ctc cac tgc tcc tcc gca gtc<br>His Asn Gly His His Ala Val Pro Asn Leu His Cys Ser Ser Ala Val<br>210                 215               220 | 672 |
| gcg caa gat ggg gac ccg gac atc gat acc atg ccc ctt ctc gcc tgg<br>Ala Gln Asp Gly Asp Pro Asp Ile Asp Thr Met Pro Leu Leu Ala Trp<br>225                 230               235             240 | 720 |
| tcc gtc cag caa gcc cag tct tac cgg gaa ctc caa gcc gac gga aag<br>Ser Val Gln Gln Ala Gln Ser Tyr Arg Glu Leu Gln Ala Asp Gly Lys<br>                    245               250               255 | 768 |
| gat tcg ggt ttg gtc aag ttc atg atc cgt aac caa tcc tac ttt tac<br>Asp Ser Gly Leu Val Lys Phe Met Ile Arg Asn Gln Ser Tyr Phe Tyr<br>260                 265               270 | 816 |
| ttt ccc atc ttg ttg ctc gcc cgc ctg tcg tgg ttg aac gag tcc ttc<br>Phe Pro Ile Leu Leu Leu Ala Arg Leu Ser Trp Leu Asn Glu Ser Phe<br>275                 280               285 | 864 |
| aag tgc gcc ttt ggg ctt gga gct gcg tcg gag aac gct gct ctc gaa<br>Lys Cys Ala Phe Gly Leu Gly Ala Ala Ser Glu Asn Ala Ala Leu Glu<br>290                 295               300 | 912 |
| ctc aag gcc aag ggt ctt cag tac ccc ctt ttg gaa aag gct ggc atc<br>Leu Lys Ala Lys Gly Leu Gln Tyr Pro Leu Leu Glu Lys Ala Gly Ile<br>305                 310               315             320 | 960 |
| ctg ctg cac tac gct tgg atg ctt aca gtt tcg tcc ggc ttt gga cgc<br>Leu Leu His Tyr Ala Trp Met Leu Thr Val Ser Ser Gly Phe Gly Arg<br>                    325               330               335 | 1008 |

```
ttc tcg ttc gcg tac acc gca ttt tac ttt cta acc gcg acc gcg tcc      1056
Phe Ser Phe Ala Tyr Thr Ala Phe Tyr Phe Leu Thr Ala Thr Ala Ser
        340                 345                 350 tgt gga ttc ttg ctc gcc att gtc ttt ggc ctc ggc cac aac ggc atg      1104
Cys Gly Phe Leu Leu Ala Ile Val Phe Gly Leu Gly His Asn Gly Met
    355                 360                 365 gcc acc tac aat gcc gac gcc cgt ccg gac ttc tgg aag ctc caa gtc      1152
Ala Thr Tyr Asn Ala Asp Ala Arg Pro Asp Phe Trp Lys Leu Gln Val
370                 375                 380 acc acg act cgc aac gtc acg ggc gga cac ggt ttc ccc caa gcc ttt      1200
Thr Thr Thr Arg Asn Val Thr Gly Gly His Gly Phe Pro Gln Ala Phe
385                 390                 395                 400 gtc gac tgg ttc tgt ggt ggc ctc cag tac caa gtc gac cac cac tta      1248
Val Asp Trp Phe Cys Gly Gly Leu Gln Tyr Gln Val Asp His His Leu
                405                 410                 415 ttc ccc agc ctg ccc cga cac aat ctg gcc aag aca cac gca ctg gtc      1296
Phe Pro Ser Leu Pro Arg His Asn Leu Ala Lys Thr His Ala Leu Val
                420                 425                 430 gaa tcg ttc tgc aag gag tgg ggt gtc cag tac cac gaa gcc gac ctt      1344
Glu Ser Phe Cys Lys Glu Trp Gly Val Gln Tyr His Glu Ala Asp Leu
            435                 440                 445 gtg gac ggg acc atg gaa gtc ttg cac cat ttg ggc agc gtg gcc ggc      1392
Val Asp Gly Thr Met Glu Val Leu His His Leu Gly Ser Val Ala Gly
450                 455                 460 gaa ttc gtc gtg gat ttt gta cgc gat gga ccc gcc atg taa              1434
Glu Phe Val Val Asp Phe Val Arg Asp Gly Pro Ala Met
465                 470                 475
```

<210> SEQ ID NO 22
<211> LENGTH: 477
<212> TYPE: PRT
<213> ORGANISM: Phaeodactylum tricornutum

<400> SEQUENCE: 22

```
Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
        35                  40                  45

Glu His Pro Gly Gly Ala Val Ile Phe Thr His Ala Gly Asp Asp Met
    50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125

Lys Cys Leu Ser Asn Met Ala Ile Trp Ala Ala Cys Ala Leu Val
    130                 135                 140

Phe Tyr Ser Asp Arg Phe Trp Val His Leu Ala Ser Ala Val Met Leu
145                 150                 155                 160

Gly Thr Phe Phe Gln Gln Ser Gly Trp Leu Ala His Asp Phe Leu His
                165                 170                 175

His Gln Val Phe Thr Lys Arg Lys His Gly Asp Leu Gly Gly Leu Phe
```

```
                180                 185                 190
Trp Gly Asn Leu Met Gln Gly Tyr Ser Val Gln Trp Trp Lys Asn Lys
            195                 200                 205

His Asn Gly His His Ala Val Pro Asn Leu His Cys Ser Ser Ala Val
        210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
            245                 250                 255

Asp Ser Gly Leu Val Lys Phe Met Ile Arg Asn Gln Ser Tyr Phe Tyr
        260                 265                 270

Phe Pro Ile Leu Leu Leu Ala Arg Leu Ser Trp Leu Asn Glu Ser Phe
    275                 280                 285

Lys Cys Ala Phe Gly Leu Gly Ala Ala Ser Glu Asn Ala Ala Leu Glu
290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
            325                 330                 335

Phe Ser Phe Ala Tyr Thr Ala Phe Tyr Phe Leu Thr Ala Thr Ala Ser
        340                 345                 350

Cys Gly Phe Leu Leu Ala Ile Val Phe Gly Leu Gly His Asn Gly Met
    355                 360                 365

Ala Thr Tyr Asn Ala Asp Ala Arg Pro Asp Phe Trp Lys Leu Gln Val
370                 375                 380

Thr Thr Thr Arg Asn Val Thr Gly Gly His Gly Phe Pro Gln Ala Phe
385                 390                 395                 400

Val Asp Trp Phe Cys Gly Gly Leu Gln Tyr Gln Val Asp His His Leu
            405                 410                 415

Phe Pro Ser Leu Pro Arg His Asn Leu Ala Lys Thr His Ala Leu Val
        420                 425                 430

Glu Ser Phe Cys Lys Glu Trp Gly Val Gln Tyr His Glu Ala Asp Leu
    435                 440                 445

Val Asp Gly Thr Met Glu Val Leu His His Leu Gly Ser Val Ala Gly
450                 455                 460

Glu Phe Val Val Asp Phe Val Arg Asp Gly Pro Ala Met
465                 470                 475

<210> SEQ ID NO 23
<211> LENGTH: 1578
<212> TYPE: DNA
<213> ORGANISM: Physcomitrella patens
<220> FEATURE:
<221> NAME/KEY: CDS
<222> LOCATION: (1)..(1578)
<223> OTHER INFORMATION: delta6-desaturase

<400> SEQUENCE: 23 atg gta ttc gcg ggc ggt gga ctt cag cag ggc tct ctc gaa gaa aac      48
Met Val Phe Ala Gly Gly Gly Leu Gln Gln Gly Ser Leu Glu Glu Asn
1               5                   10                  15 atc gac gtc gag cac att gcc agt atg tct ctc ttc agc gac ttc ttc      96
Ile Asp Val Glu His Ile Ala Ser Met Ser Leu Phe Ser Asp Phe Phe
            20                  25                  30 agt tat gtg tct tca act gtt ggt tcg tgg agc gta cac agt ata caa     144
Ser Tyr Val Ser Ser Thr Val Gly Ser Trp Ser Val His Ser Ile Gln
        35                  40                  45
```

| | | | | | | | | | | | | | | | | |
|---|---|---|---|---|---|---|---|---|---|---|---|---|---|---|---|---|
| cct | ttg | aag | cgc | ctg | acg | agt | aag | aag | cgt | gtt | tcg | gaa | agc | gct | gcc | 192 |
| Pro | Leu | Lys | Arg | Leu | Thr | Ser | Lys | Lys | Arg | Val | Ser | Glu | Ser | Ala | Ala | |
| | 50 | | | | 55 | | | | | 60 | | | | | | |

| | | | | | | | | | | | | | | | | |
|---|---|---|---|---|---|---|---|---|---|---|---|---|---|---|---|---|
| gtg | caa | tgt | ata | tca | gct | gaa | gtt | cag | aga | aat | tcg | agt | acc | cag | gga | 240 |
| Val | Gln | Cys | Ile | Ser | Ala | Glu | Val | Gln | Arg | Asn | Ser | Ser | Thr | Gln | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| act | gcg | gag | gca | ctc | gca | gaa | tca | gtc | gtg | aag | ccc | acg | aga | cga | agg | 288 |
| Thr | Ala | Glu | Ala | Leu | Ala | Glu | Ser | Val | Val | Lys | Pro | Thr | Arg | Arg | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| tca | tct | cag | tgg | aag | aag | tcg | aca | cac | ccc | cta | tca | gaa | gta | gca | gta | 336 |
| Ser | Ser | Gln | Trp | Lys | Lys | Ser | Thr | His | Pro | Leu | Ser | Glu | Val | Ala | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| cac | aac | aag | cca | agc | gat | tgc | tgg | att | gtt | gta | aaa | aac | aag | gtg | tat | 384 |
| His | Asn | Lys | Pro | Ser | Asp | Cys | Trp | Ile | Val | Val | Lys | Asn | Lys | Val | Tyr | |
| | | 115 | | | | | 120 | | | | | 125 | | | | |

| | | | | | | | | | | | | | | | | |
|---|---|---|---|---|---|---|---|---|---|---|---|---|---|---|---|---|
| gat | gtt | tcc | aat | ttt | gcg | gac | gag | cat | ccc | gga | gga | tca | gtt | att | agt | 432 |
| Asp | Val | Ser | Asn | Phe | Ala | Asp | Glu | His | Pro | Gly | Gly | Ser | Val | Ile | Ser | |
| 130 | | | | | 135 | | | | | 140 | | | | | | |

| | | | | | | | | | | | | | | | | |
|---|---|---|---|---|---|---|---|---|---|---|---|---|---|---|---|---|
| act | tat | ttt | gga | cga | gac | ggc | aca | gat | gtt | ttc | tct | agt | ttt | cat | gca | 480 |
| Thr | Tyr | Phe | Gly | Arg | Asp | Gly | Thr | Asp | Val | Phe | Ser | Ser | Phe | His | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gct | tct | aca | tgg | aaa | att | ctt | caa | gac | ttt | tac | att | ggt | gac | gtg | gag | 528 |
| Ala | Ser | Thr | Trp | Lys | Ile | Leu | Gln | Asp | Phe | Tyr | Ile | Gly | Asp | Val | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| agg | gtg | gag | ccg | act | cca | gag | ctg | ctg | aaa | gat | ttc | cga | gaa | atg | aga | 576 |
| Arg | Val | Glu | Pro | Thr | Pro | Glu | Leu | Leu | Lys | Asp | Phe | Arg | Glu | Met | Arg | |
| | | | 180 | | | | | 185 | | | | | 190 | | | |

| | | | | | | | | | | | | | | | | |
|---|---|---|---|---|---|---|---|---|---|---|---|---|---|---|---|---|
| gct | ctt | ttc | ctg | agg | gag | caa | ctt | ttc | aaa | agt | tcg | aaa | ttg | tac | tat | 624 |
| Ala | Leu | Phe | Leu | Arg | Glu | Gln | Leu | Phe | Lys | Ser | Ser | Lys | Leu | Tyr | Tyr | |
| | | 195 | | | | | 200 | | | | | 205 | | | | |

| | | | | | | | | | | | | | | | | |
|---|---|---|---|---|---|---|---|---|---|---|---|---|---|---|---|---|
| gtt | atg | aag | ctg | ctc | acg | aat | gtt | gct | att | ttt | gct | gcg | agc | att | gca | 672 |
| Val | Met | Lys | Leu | Leu | Thr | Asn | Val | Ala | Ile | Phe | Ala | Ala | Ser | Ile | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| ata | ata | tgt | tgg | agc | aag | act | att | tca | gcg | gtt | ttg | gct | tca | gct | tgt | 720 |
| Ile | Ile | Cys | Trp | Ser | Lys | Thr | Ile | Ser | Ala | Val | Leu | Ala | Ser | Ala | Cys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| atg | atg | gct | ctg | tgt | ttc | caa | cag | tgc | gga | tgg | cta | tcc | cat | gat | ttt | 768 |
| Met | Met | Ala | Leu | Cys | Phe | Gln | Gln | Cys | Gly | Trp | Leu | Ser | His | Asp | Phe | |
| | | | | 245 | | | | | 250 | | | | | 255 | | |

| | | | | | | | | | | | | | | | | |
|---|---|---|---|---|---|---|---|---|---|---|---|---|---|---|---|---|
| ctc | cac | aat | cag | gtg | ttt | gag | aca | cgc | tgg | ctt | aat | gaa | gtt | gtc | ggg | 816 |
| Leu | His | Asn | Gln | Val | Phe | Glu | Thr | Arg | Trp | Leu | Asn | Glu | Val | Val | Gly | |
| | | | 260 | | | | | 265 | | | | | 270 | | | |

| | | | | | | | | | | | | | | | | |
|---|---|---|---|---|---|---|---|---|---|---|---|---|---|---|---|---|
| tat | gtg | atc | ggc | aac | gcc | gtt | ctg | ggg | ttt | agt | aca | ggg | tgg | tgg | aag | 864 |
| Tyr | Val | Ile | Gly | Asn | Ala | Val | Leu | Gly | Phe | Ser | Thr | Gly | Trp | Trp | Lys | |
| | | 275 | | | | | 280 | | | | | 285 | | | | |

| | | | | | | | | | | | | | | | | |
|---|---|---|---|---|---|---|---|---|---|---|---|---|---|---|---|---|
| gag | aag | cat | aac | ctt | cat | cat | gct | gct | cca | aat | gaa | tgc | gat | cag | act | 912 |
| Glu | Lys | His | Asn | Leu | His | His | Ala | Ala | Pro | Asn | Glu | Cys | Asp | Gln | Thr | |
| | 290 | | | | | 295 | | | | | 300 | | | | | |

| | | | | | | | | | | | | | | | | |
|---|---|---|---|---|---|---|---|---|---|---|---|---|---|---|---|---|
| tac | caa | cca | att | gat | gaa | gat | att | gat | act | ctc | ccc | ctc | att | gcc | tgg | 960 |
| Tyr | Gln | Pro | Ile | Asp | Glu | Asp | Ile | Asp | Thr | Leu | Pro | Leu | Ile | Ala | Trp | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| agc | aag | gac | ata | ctg | gcc | aca | gtt | gag | aat | aag | aca | ttc | ttg | cga | atc | 1008 |
| Ser | Lys | Asp | Ile | Leu | Ala | Thr | Val | Glu | Asn | Lys | Thr | Phe | Leu | Arg | Ile | |
| | | | | 325 | | | | | 330 | | | | | 335 | | |

| | | | | | | | | | | | | | | | | |
|---|---|---|---|---|---|---|---|---|---|---|---|---|---|---|---|---|
| ctc | caa | tac | cag | cat | ctg | ttc | ttc | atg | ggt | ctg | tta | ttt | ttc | gcc | cgt | 1056 |
| Leu | Gln | Tyr | Gln | His | Leu | Phe | Phe | Met | Gly | Leu | Leu | Phe | Phe | Ala | Arg | |
| | | | 340 | | | | | 345 | | | | | 350 | | | |

| | | | | | | | | | | | | | | | | |
|---|---|---|---|---|---|---|---|---|---|---|---|---|---|---|---|---|
| ggt | agt | tgg | ctc | ttt | tgg | agc | tgg | aga | tat | acc | tct | aca | gca | gtg | ctc | 1104 |
| Gly | Ser | Trp | Leu | Phe | Trp | Ser | Trp | Arg | Tyr | Thr | Ser | Thr | Ala | Val | Leu | |

```
tca cct gtc gac agg ttg ttg gag aag gga act gtt ctg ttt cac tac    1152
Ser Pro Val Asp Arg Leu Leu Glu Lys Gly Thr Val Leu Phe His Tyr
    370                 375                 380 ttt tgg ttc gtc ggg aca gcg tgc tat ctt ctc cct ggt tgg aag cca    1200
Phe Trp Phe Val Gly Thr Ala Cys Tyr Leu Leu Pro Gly Trp Lys Pro
385                 390                 395                 400 tta gta tgg atg gcg gtg act gag ctc atg tcc ggc atg ctg ctg ggc    1248
Leu Val Trp Met Ala Val Thr Glu Leu Met Ser Gly Met Leu Leu Gly
                405                 410                 415 ttt gta ttt gta ctt agc cac aat ggg atg gag gtt tat aat tcg tct    1296
Phe Val Phe Val Leu Ser His Asn Gly Met Glu Val Tyr Asn Ser Ser
            420                 425                 430 aaa gaa ttc gtg agt gca cag atc gta tcc aca cgg gat atc aaa gga    1344
Lys Glu Phe Val Ser Ala Gln Ile Val Ser Thr Arg Asp Ile Lys Gly
        435                 440                 445 aac ata ttc aac gac tgg ttc act ggt ggc ctt aac agg caa ata gag    1392
Asn Ile Phe Asn Asp Trp Phe Thr Gly Gly Leu Asn Arg Gln Ile Glu
    450                 455                 460 cat cat ctt ttc cca aca atg ccc agg cat aat tta aac aaa ata gca    1440
His His Leu Phe Pro Thr Met Pro Arg His Asn Leu Asn Lys Ile Ala
465                 470                 475                 480 cct aga gtg gag gtg ttc tgt aag aaa cac ggt ctg gtg tac gaa gac    1488
Pro Arg Val Glu Val Phe Cys Lys Lys His Gly Leu Val Tyr Glu Asp
                485                 490                 495 gta tct att gct acc ggc act tgc aag gtt ttg aaa gca ttg aag gaa    1536
Val Ser Ile Ala Thr Gly Thr Cys Lys Val Leu Lys Ala Leu Lys Glu
            500                 505                 510 gtc gcg gag gct gcg gca gag cag cat gct acc acc agt taa            1578
Val Ala Glu Ala Ala Ala Glu Gln His Ala Thr Thr Ser
        515                 520                 525

<210> SEQ ID NO 24
<211> LENGTH: 525
<212> TYPE: PRT
<213> ORGANISM: Physcomitrella patens

<400> SEQUENCE: 24

Met Val Phe Ala Gly Gly Gly Leu Gln Gln Gly Ser Leu Glu Glu Asn
1               5                   10                  15

Ile Asp Val Glu His Ile Ala Ser Met Ser Leu Phe Ser Asp Phe Phe
            20                  25                  30

Ser Tyr Val Ser Ser Thr Val Gly Ser Trp Ser Val His Ser Ile Gln
        35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Lys Asn Lys Val Tyr
        115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160
```

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
        275                 280                 285

Glu Lys His Asn Leu His His Ala Ala Pro Asn Glu Cys Asp Gln Thr
    290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
            340                 345                 350

Gly Ser Trp Leu Phe Trp Ser Trp Arg Tyr Thr Ser Thr Ala Val Leu
        355                 360                 365

Ser Pro Val Asp Arg Leu Leu Glu Lys Gly Thr Val Leu Phe His Tyr
    370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
            420                 425                 430

Lys Glu Phe Val Ser Ala Gln Ile Val Ser Thr Arg Asp Ile Lys Gly
        435                 440                 445

Asn Ile Phe Asn Asp Trp Phe Thr Gly Gly Leu Asn Arg Gln Ile Glu
    450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Ala Glu Gln His Ala Thr Thr Ser
        515                 520                 525

<210> SEQ ID NO 25
<211> LENGTH: 1332
<212> TYPE: DNA
<213> ORGANISM: Caenorhabditis elegans
<220> FEATURE:
<221> NAME/KEY: CDS
<222> LOCATION: (1)..(1332)
<223> OTHER INFORMATION: delta6-desaturase

<400> SEQUENCE: 25

```
atg gtc gtc gac aag aat gcc tcc ggg ctt cga atg aag gtc gat ggc      48
Met Val Val Asp Lys Asn Ala Ser Gly Leu Arg Met Lys Val Asp Gly
1               5                   10                  15 aaa tgg ctc tac ctt agc gag gaa ttg gtg aag aaa cat cca gga gga      96
Lys Trp Leu Tyr Leu Ser Glu Glu Leu Val Lys Lys His Pro Gly Gly
            20                  25                  30 gct gtt att gaa caa tat aga aat tcg gat gct act cat att ttc cac     144
Ala Val Ile Glu Gln Tyr Arg Asn Ser Asp Ala Thr His Ile Phe His
        35                  40                  45 gct ttc cac gaa gga tct tct cag gct tat aag caa ctt gac ctt ctg     192
Ala Phe His Glu Gly Ser Ser Gln Ala Tyr Lys Gln Leu Asp Leu Leu
    50                  55                  60 aaa aag cac gga gag cac gat gaa ttc ctt gag aaa caa ttg gaa aag     240
Lys Lys His Gly Glu His Asp Glu Phe Leu Glu Lys Gln Leu Glu Lys
65                  70                  75                  80 aga ctt gac aaa gtt gat atc aat gta tca gca tat gat gtc agt gtt     288
Arg Leu Asp Lys Val Asp Ile Asn Val Ser Ala Tyr Asp Val Ser Val
                85                  90                  95 gca caa gaa aag aaa atg gtt gaa tca ttc gaa aaa cta cga cag aag     336
Ala Gln Glu Lys Lys Met Val Glu Ser Phe Glu Lys Leu Arg Gln Lys
            100                 105                 110 ctt cat gat gat gga tta atg aaa gca aat gaa aca tat ttc ctg ttt     384
Leu His Asp Asp Gly Leu Met Lys Ala Asn Glu Thr Tyr Phe Leu Phe
        115                 120                 125 aaa gcg att tca aca ctt tca att atg gca ttt gca ttt tat ctt cag     432
Lys Ala Ile Ser Thr Leu Ser Ile Met Ala Phe Ala Phe Tyr Leu Gln
    130                 135                 140 tat ctt gga tgg tat att act tct gca tgt tta tta gca ctt gca tgg     480
Tyr Leu Gly Trp Tyr Ile Thr Ser Ala Cys Leu Leu Ala Leu Ala Trp
145                 150                 155                 160 caa caa ttc gga tgg tta aca cat gag ttc tgc cat caa cag cca aca     528
Gln Gln Phe Gly Trp Leu Thr His Glu Phe Cys His Gln Gln Pro Thr
                165                 170                 175 aag aac aga cct ttg aat gat act att tct ttg ttc ttt ggt aat ttc     576
Lys Asn Arg Pro Leu Asn Asp Thr Ile Ser Leu Phe Phe Gly Asn Phe
            180                 185                 190 tta caa gga ttt tca aga gat tgg tgg aag gac aag cat aac act cat     624
Leu Gln Gly Phe Ser Arg Asp Trp Trp Lys Asp Lys His Asn Thr His
        195                 200                 205 cac gct gcc aca aat gta att gat cat gac ggt gat atc gac ttg gca     672
His Ala Ala Thr Asn Val Ile Asp His Asp Gly Asp Ile Asp Leu Ala
    210                 215                 220 cca ctt ttc gca ttt att cca gga gat ttg tgc aag tat aag gcc agc     720
Pro Leu Phe Ala Phe Ile Pro Gly Asp Leu Cys Lys Tyr Lys Ala Ser
225                 230                 235                 240 ttt gaa aaa gca att ctc aag att gta cca tat caa cat ctc tat ttc     768
Phe Glu Lys Ala Ile Leu Lys Ile Val Pro Tyr Gln His Leu Tyr Phe
                245                 250                 255 acc gca atg ctt cca atg ctc cgt ttc tca tgg act ggt cag tca gtt     816
Thr Ala Met Leu Pro Met Leu Arg Phe Ser Trp Thr Gly Gln Ser Val
            260                 265                 270 caa tgg gta ttc aaa gag aat caa atg gag tac aag gtc tat caa aga     864
Gln Trp Val Phe Lys Glu Asn Gln Met Glu Tyr Lys Val Tyr Gln Arg
        275                 280                 285 aat gca ttc tgg gag caa gca aca att gtt gga cat tgg gct tgg gta     912
Asn Ala Phe Trp Glu Gln Ala Thr Ile Val Gly His Trp Ala Trp Val
    290                 295                 300
```

```
ttc tat caa ttg ttc tta tta cca aca tgg cca ctt cgg gtt gct tat    960
Phe Tyr Gln Leu Phe Leu Leu Pro Thr Trp Pro Leu Arg Val Ala Tyr
305                 310                 315                 320 ttc att att tca caa atg gga gga ggc ctt ttg att gct cac gta gtc   1008
Phe Ile Ile Ser Gln Met Gly Gly Gly Leu Leu Ile Ala His Val Val
                325                 330                 335 act ttc aac cat aac tct gtt gat aag tat cca gcc aat tct cga att   1056
Thr Phe Asn His Asn Ser Val Asp Lys Tyr Pro Ala Asn Ser Arg Ile
                340                 345                 350 tta aac aac ttc gcc gct ctt caa att ttg acc aca cgc aac atg act   1104
Leu Asn Asn Phe Ala Ala Leu Gln Ile Leu Thr Thr Arg Asn Met Thr
                355                 360                 365 cca tct cca ttc att gat tgg ctt tgg ggt gga ctc aat tat cag atc   1152
Pro Ser Pro Phe Ile Asp Trp Leu Trp Gly Gly Leu Asn Tyr Gln Ile
370                 375                 380 gag cac cac ttg ttc cca aca atg cca cgt tgc aat ctg aat gct tgc   1200
Glu His His Leu Phe Pro Thr Met Pro Arg Cys Asn Leu Asn Ala Cys
385                 390                 395                 400 gtg aaa tat gtg aaa gaa tgg tgc aaa gag aat aat ctt cct tac ctc   1248
Val Lys Tyr Val Lys Glu Trp Cys Lys Glu Asn Asn Leu Pro Tyr Leu
                405                 410                 415 gtc gat gac tac ttt gac gga tat gca atg aat ttg caa caa ttg aaa   1296
Val Asp Asp Tyr Phe Asp Gly Tyr Ala Met Asn Leu Gln Gln Leu Lys
                420                 425                 430 aat atg gct gag cac att caa gct aaa gct gcc taa                   1332
Asn Met Ala Glu His Ile Gln Ala Lys Ala Ala
                435                 440
```

<210> SEQ ID NO 26
<211> LENGTH: 443
<212> TYPE: PRT
<213> ORGANISM: Caenorhabditis elegans

<400> SEQUENCE: 26

```
Met Val Val Asp Lys Asn Ala Ser Gly Leu Arg Met Lys Val Asp Gly
1               5                   10                  15

Lys Trp Leu Tyr Leu Ser Glu Glu Leu Val Lys Lys His Pro Gly Gly
                20                  25                  30

Ala Val Ile Glu Gln Tyr Arg Asn Ser Asp Ala Thr His Ile Phe His
            35                  40                  45

Ala Phe His Glu Gly Ser Gln Ala Tyr Lys Gln Leu Asp Leu Leu
        50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95

Ala Gln Glu Lys Lys Met Val Glu Ser Phe Glu Lys Leu Arg Gln Lys
            100                 105                 110

Leu His Asp Asp Gly Leu Met Lys Ala Asn Glu Thr Tyr Phe Leu Phe
        115                 120                 125

Lys Ala Ile Ser Thr Leu Ser Ile Met Ala Phe Ala Phe Tyr Leu Gln
    130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175

Lys Asn Arg Pro Leu Asn Asp Thr Ile Ser Leu Phe Phe Gly Asn Phe
            180                 185                 190
```

```
Leu Gln Gly Phe Ser Arg Asp Trp Trp Lys Asp Lys His Asn Thr His
        195                 200                 205

His Ala Ala Thr Asn Val Ile Asp His Asp Gly Ile Asp Leu Ala
    210                 215                 220

Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
            260                 265                 270

Gln Trp Val Phe Lys Glu Asn Gln Met Glu Tyr Lys Val Tyr Gln Arg
        275                 280                 285

Asn Ala Phe Trp Glu Gln Ala Thr Ile Val Gly His Trp Ala Trp Val
    290                 295                 300

Phe Tyr Gln Leu Phe Leu Pro Thr Trp Pro Leu Arg Val Ala Tyr
305                 310                 315                 320

Phe Ile Ile Ser Gln Met Gly Gly Gly Leu Leu Ile Ala His Val Val
                325                 330                 335

Thr Phe Asn His Asn Ser Val Asp Lys Tyr Pro Ala Asn Ser Arg Ile
            340                 345                 350

Leu Asn Asn Phe Ala Ala Leu Gln Ile Leu Thr Thr Arg Asn Met Thr
        355                 360                 365

Pro Ser Pro Phe Ile Asp Trp Leu Trp Gly Gly Leu Asn Tyr Gln Ile
    370                 375                 380

Glu His His Leu Phe Pro Thr Met Pro Arg Cys Asn Leu Asn Ala Cys
385                 390                 395                 400

Val Lys Tyr Val Lys Glu Trp Cys Lys Glu Asn Asn Leu Pro Tyr Leu
                405                 410                 415

Val Asp Asp Tyr Phe Asp Gly Tyr Ala Met Asn Leu Gln Gln Leu Lys
            420                 425                 430

Asn Met Ala Glu His Ile Gln Ala Lys Ala Ala
        435                 440

<210> SEQ ID NO 27
<211> LENGTH: 873
<212> TYPE: DNA
<213> ORGANISM: Physcomitrella patens
<220> FEATURE:
<221> NAME/KEY: CDS
<222> LOCATION: (1)..(873)
<223> OTHER INFORMATION: delta6-elongase

<400> SEQUENCE: 27 atg gag gtc gtg gag aga ttc tac ggt gag ttg gat ggg aag gtc tcg    48
Met Glu Val Val Glu Arg Phe Tyr Gly Glu Leu Asp Gly Lys Val Ser
1               5                  10                  15 cag ggc gtg aat gca ttg ctg ggt agt ttt ggg gtg gag ttg acg gat    96
Gln Gly Val Asn Ala Leu Leu Gly Ser Phe Gly Val Glu Leu Thr Asp
            20                  25                  30 acg ccc act acc aaa ggc ttg ccc ctc gtt gac agt ccc aca ccc atc   144
Thr Pro Thr Thr Lys Gly Leu Pro Leu Val Asp Ser Pro Thr Pro Ile
        35                  40                  45 gtc ctc ggt gtt tct gta tac ttg act att gtc att gga ggg ctt ttg   192
Val Leu Gly Val Ser Val Tyr Leu Thr Ile Val Ile Gly Gly Leu Leu
    50                  55                  60 tgg ata aag gcc agg gat ctg aaa ccg cgc gcc tcg gag cca ttt ttg   240
Trp Ile Lys Ala Arg Asp Leu Lys Pro Arg Ala Ser Glu Pro Phe Leu
```

```
                        65                  70                  75                  80
ctc caa gct ttg gtg ctt gtg cac aac ctg ttc tgt ttt gcg ctc agt       288
Leu Gln Ala Leu Val Leu Val His Asn Leu Phe Cys Phe Ala Leu Ser
                    85                  90                  95 ctg tat atg tgc gtg ggc atc gct tat cag gct att acc tgg cgg tac       336
Leu Tyr Met Cys Val Gly Ile Ala Tyr Gln Ala Ile Thr Trp Arg Tyr
                100                 105                 110 tct ctc tgg ggc aat gca tac aat cct aaa cat aaa gag atg gcg att       384
Ser Leu Trp Gly Asn Ala Tyr Asn Pro Lys His Lys Glu Met Ala Ile
            115                 120                 125 ctg gta tac ttg ttc tac atg tct aag tac gtg gaa ttc atg gat acc       432
Leu Val Tyr Leu Phe Tyr Met Ser Lys Tyr Val Glu Phe Met Asp Thr
        130                 135                 140 gtt atc atg ata ctg aag cgc agc acc agg caa ata agc ttc ctc cac       480
Val Ile Met Ile Leu Lys Arg Ser Thr Arg Gln Ile Ser Phe Leu His
145                 150                 155                 160 gtt tat cat cat tct tca att tcc ctc att tgg tgg gct att gct cat       528
Val Tyr His His Ser Ser Ile Ser Leu Ile Trp Trp Ala Ile Ala His
                165                 170                 175 cac gct cct ggc ggt gaa gca tat tgg tct gcg gct ctg aac tca gga       576
His Ala Pro Gly Gly Glu Ala Tyr Trp Ser Ala Ala Leu Asn Ser Gly
                180                 185                 190 gtg cat gtt ctc atg tat gcg tat tac ttc ttg gct gcc tgc ctt cga       624
Val His Val Leu Met Tyr Ala Tyr Tyr Phe Leu Ala Ala Cys Leu Arg
            195                 200                 205 agt agc cca aag tta aaa aat aag tac ctt ttt tgg ggc agg tac ttg       672
Ser Ser Pro Lys Leu Lys Asn Lys Tyr Leu Phe Trp Gly Arg Tyr Leu
        210                 215                 220 aca caa ttc caa atg ttc cag ttt atg ctg aac tta gtg cag gct tac       720
Thr Gln Phe Gln Met Phe Gln Phe Met Leu Asn Leu Val Gln Ala Tyr
225                 230                 235                 240 tac gac atg aaa acg aat gcg cca tat cca caa tgg ctg atc aag att       768
Tyr Asp Met Lys Thr Asn Ala Pro Tyr Pro Gln Trp Leu Ile Lys Ile
                245                 250                 255 ttg ttc tac tac atg atc tcg ttg ctg ttt ctt ttc ggc aat ttt tac       816
Leu Phe Tyr Tyr Met Ile Ser Leu Leu Phe Leu Phe Gly Asn Phe Tyr
                260                 265                 270 gta caa aaa tac atc aaa ccc tct gac gga aag caa aag gga gct aaa       864
Val Gln Lys Tyr Ile Lys Pro Ser Asp Gly Lys Gln Lys Gly Ala Lys
            275                 280                 285 act gag tga                                                           873
Thr Glu
    290

<210> SEQ ID NO 28
<211> LENGTH: 290
<212> TYPE: PRT
<213> ORGANISM: Physcomitrella patens

<400> SEQUENCE: 28

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
                20                  25                  30

Thr Pro Thr Thr Lys Gly Leu Pro Leu Val Asp Ser Pro Thr Pro Ile
            35                  40                  45

Val Leu Gly Val Ser Val Tyr Leu Thr Ile Val Ile Gly Gly Leu Leu
        50                  55                  60

Trp Ile Lys Ala Arg Asp Leu Lys Pro Arg Ala Ser Glu Pro Phe Leu
```

```
             65                  70                  75                  80
Leu Gln Ala Leu Val Leu Val His Asn Leu Phe Cys Phe Ala Leu Ser
                 85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 29
<211> LENGTH: 1049
<212> TYPE: DNA
<213> ORGANISM: Thraustochytrium
<220> FEATURE:
<221> NAME/KEY: CDS
<222> LOCATION: (43)..(858)
<223> OTHER INFORMATION: delta6-elongase

<400> SEQUENCE: 29
gaattcggca cgagagcgcg cggagcggag acctcggccg cg atg atg gag ccg        54
                                            Met Met Glu Pro
                                             1 ctc gac agg tac agg gcg ctg gcg gag ctc gcc gcg agg tac gcc agc      102
Leu Asp Arg Tyr Arg Ala Leu Ala Glu Leu Ala Ala Arg Tyr Ala Ser
 5              10                  15                  20 tcg gcg gcc ttc aag tgg caa gtc acg tac gac gcc aag gac agc ttc      150
Ser Ala Ala Phe Lys Trp Gln Val Thr Tyr Asp Ala Lys Asp Ser Phe
             25                  30                  35 gtc ggg ccc ctg gga atc cgg gag ccg ctc ggg ctc ctg gtg ggc tcc      198
Val Gly Pro Leu Gly Ile Arg Glu Pro Leu Gly Leu Leu Val Gly Ser
         40                  45                  50 gtg gtc ctc tac ctg agc ctg ctg gcc gtg gtc tac gcg ctg cgg aac      246
Val Val Leu Tyr Leu Ser Leu Leu Ala Val Val Tyr Ala Leu Arg Asn
     55                  60                  65 tac ctt ggc ggc ctc atg gcg ctc cgc agc gtg cat aac ctc ggg ctc      294
Tyr Leu Gly Gly Leu Met Ala Leu Arg Ser Val His Asn Leu Gly Leu
 70                  75                  80
```

```
tgc ctc ttc tcg ggc gcc gtg tgg atc tac acg agc tac ctc atg atc      342
Cys Leu Phe Ser Gly Ala Val Trp Ile Tyr Thr Ser Tyr Leu Met Ile
 85                  90                  95                 100 cag gat ggg cac ttt cgc agc ctc gag gcg gca acg tgc gag ccg ctc      390
Gln Asp Gly His Phe Arg Ser Leu Glu Ala Ala Thr Cys Glu Pro Leu
                105                 110                 115 aag cat ccg cac ttc cag ctc atc agc ttg ctc ttt gcg ctg tcc aag      438
Lys His Pro His Phe Gln Leu Ile Ser Leu Leu Phe Ala Leu Ser Lys
            120                 125                 130 atc tgg gag tgg ttc gac acg gtg ctc ctc atc gtc aag ggc aac aag      486
Ile Trp Glu Trp Phe Asp Thr Val Leu Leu Ile Val Lys Gly Asn Lys
        135                 140                 145 ctc cgc ttc ctg cac gtc ttg cac cac gcc acg acc ttt tgg ctc tac      534
Leu Arg Phe Leu His Val Leu His His Ala Thr Thr Phe Trp Leu Tyr
    150                 155                 160 gcc atc gac cac atc ttt ctc tcg tcc atc aag tac ggc gtc gcg gtc      582
Ala Ile Asp His Ile Phe Leu Ser Ser Ile Lys Tyr Gly Val Ala Val
165                 170                 175                 180 aat gct ttc atc cac acc gtc atg tac gcg cac tac ttc cgc cca ttc      630
Asn Ala Phe Ile His Thr Val Met Tyr Ala His Tyr Phe Arg Pro Phe
                185                 190                 195 ccg aag ggc ttg cgc ccg ctt att acg cag ttg cag atc gtc cag ttc      678
Pro Lys Gly Leu Arg Pro Leu Ile Thr Gln Leu Gln Ile Val Gln Phe
                200                 205                 210 att ttc agc atc ggc atc cat acc gcc att tac tgg cac tac gac tgc      726
Ile Phe Ser Ile Gly Ile His Thr Ala Ile Tyr Trp His Tyr Asp Cys
            215                 220                 225 gag ccg ctc gtg cat acc cac ttt tgg gaa tac gtc acg ccc tac ctt      774
Glu Pro Leu Val His Thr His Phe Trp Glu Tyr Val Thr Pro Tyr Leu
        230                 235                 240 ttc gtc gtg ccc ttc ctc atc ctc ttt ttc aat ttt tac ctg cag cag      822
Phe Val Val Pro Phe Leu Ile Leu Phe Phe Asn Phe Tyr Leu Gln Gln
245                 250                 255                 260 tac gtc ctc gcg ccc gca aaa acc aag aag gca tag ccacgtaaca           868
Tyr Val Leu Ala Pro Ala Lys Thr Lys Lys Ala
                265                 270 gtagaccagc agcgccgagg acgcgtgccg cgttatcgcg aagcacgaaa taaagaagat    928
catttgattc aacgaggcta cttgcggcca cgagaaaaaa aaaaaaaaaa aaaaaaaaaa    988
aaaaaaaaaa aaaaaaaaaa aaaaaaaaaa aaaaaaaaaa aaaaaaaaaa aaaaaaaaaa   1048
c                                                                  1049

<210> SEQ ID NO 30
<211> LENGTH: 271
<212> TYPE: PRT
<213> ORGANISM: Thraustochytrium

<400> SEQUENCE: 30

Met Met Glu Pro Leu Asp Arg Tyr Arg Ala Leu Ala Glu Leu Ala Ala
1               5                   10                  15

Arg Tyr Ala Ser Ser Ala Ala Phe Lys Trp Gln Val Thr Tyr Asp Ala
            20                  25                  30

Lys Asp Ser Phe Val Gly Pro Leu Gly Ile Arg Glu Pro Leu Gly Leu
        35                  40                  45

Leu Val Gly Ser Val Val Leu Tyr Leu Ser Leu Leu Ala Val Val Tyr
    50                  55                  60

Ala Leu Arg Asn Tyr Leu Gly Gly Leu Met Ala Leu Arg Ser Val His
65                  70                  75                  80
```

```
Asn Leu Gly Leu Cys Leu Phe Ser Gly Ala Val Trp Ile Tyr Thr Ser
                85                  90                  95
Tyr Leu Met Ile Gln Asp Gly His Phe Arg Ser Leu Glu Ala Ala Thr
            100                 105                 110
Cys Glu Pro Leu Lys His Pro His Phe Gln Leu Ile Ser Leu Leu Phe
        115                 120                 125
Ala Leu Ser Lys Ile Trp Glu Trp Phe Asp Thr Val Leu Leu Ile Val
    130                 135                 140
Lys Gly Asn Lys Leu Arg Phe Leu His Val Leu His His Ala Thr Thr
145                 150                 155                 160
Phe Trp Leu Tyr Ala Ile Asp His Ile Phe Leu Ser Ser Ile Lys Tyr
                165                 170                 175
Gly Val Ala Val Asn Ala Phe Ile His Thr Val Met Tyr Ala His Tyr
            180                 185                 190
Phe Arg Pro Phe Pro Lys Gly Leu Arg Pro Leu Ile Thr Gln Leu Gln
        195                 200                 205
Ile Val Gln Phe Ile Phe Ser Ile Gly Ile His Thr Ala Ile Tyr Trp
    210                 215                 220
His Tyr Asp Cys Glu Pro Leu Val His Thr His Phe Trp Glu Tyr Val
225                 230                 235                 240
Thr Pro Tyr Leu Phe Val Val Pro Phe Leu Ile Leu Phe Phe Asn Phe
                245                 250                 255
Tyr Leu Gln Gln Tyr Val Leu Ala Pro Ala Lys Thr Lys Lys Ala
            260                 265                 270

<210> SEQ ID NO 31
<211> LENGTH: 837
<212> TYPE: DNA
<213> ORGANISM: Phytophthora infestans
<220> FEATURE:
<221> NAME/KEY: CDS
<222> LOCATION: (1)..(837)
<223> OTHER INFORMATION: delta6-elongase

<400> SEQUENCE: 31 atg tcg act gag cta ctg cag agc tac tac gcg tgg gcc aac gcc acg     48
Met Ser Thr Glu Leu Leu Gln Ser Tyr Tyr Ala Trp Ala Asn Ala Thr
1               5                   10                  15 gag gcc aag ctg ctg gac tgg gtc gac cct gag ggc ggc tgg aag gtg     96
Glu Ala Lys Leu Leu Asp Trp Val Asp Pro Glu Gly Gly Trp Lys Val
            20                  25                  30 cat cct atg gca gac tac ccc cta gcc aac ttc tcc agc gtc tac gcc    144
His Pro Met Ala Asp Tyr Pro Leu Ala Asn Phe Ser Ser Val Tyr Ala
        35                  40                  45 atc tgc gtc gga tac ttg ctc ttc gta atc ttc ggc acg gcc ctg atg    192
Ile Cys Val Gly Tyr Leu Leu Phe Val Ile Phe Gly Thr Ala Leu Met
    50                  55                  60 aaa atg gga gtc ccc gcc atc aag acc agt cca tta cag ttt gtg tac    240
Lys Met Gly Val Pro Ala Ile Lys Thr Ser Pro Leu Gln Phe Val Tyr
65                  70                  75                  80 aac ccc atc caa gtc att gcc tgc tct tat atg tgc gtg gag gcc gcc    288
Asn Pro Ile Gln Val Ile Ala Cys Ser Tyr Met Cys Val Glu Ala Ala
                85                  90                  95 atc cag gcc tac cgc aac ggc tac acc gcc gcc ccg tgc aac gcc ttt    336
Ile Gln Ala Tyr Arg Asn Gly Tyr Thr Ala Ala Pro Cys Asn Ala Phe
            100                 105                 110 aag tcc gac gac ccc gtc atg ggc aac gtt ctg tac ctc ttc tat ctc    384
Lys Ser Asp Asp Pro Val Met Gly Asn Val Leu Tyr Leu Phe Tyr Leu
```

```
                    115                 120                 125
tcc aag atg ctc gac ctg tgc gac aca gtc ttc att atc cta gga aag      432
Ser Lys Met Leu Asp Leu Cys Asp Thr Val Phe Ile Ile Leu Gly Lys
    130                 135                 140 aag tgg aaa cag ctt tcc atc ttg cac gtg tac cac cac ctt acc gtg      480
Lys Trp Lys Gln Leu Ser Ile Leu His Val Tyr His His Leu Thr Val
145                 150                 155                 160 ctt ttc gtc tac tat gtg acg ttc cgc gcc gct cag gac ggg gac tca      528
Leu Phe Val Tyr Tyr Val Thr Phe Arg Ala Ala Gln Asp Gly Asp Ser
                165                 170                 175 tat gct acc atc gtg ctc aac ggc ttc gtg cac acc atc atg tac act      576
Tyr Ala Thr Ile Val Leu Asn Gly Phe Val His Thr Ile Met Tyr Thr
            180                 185                 190 tac tac ttc gtc agc gcc cac acg cgc aac att tgg tgg aag aag tac      624
Tyr Tyr Phe Val Ser Ala His Thr Arg Asn Ile Trp Trp Lys Lys Tyr
        195                 200                 205 ctc acg cgc att cag ctt atc cag ttc gtg acc atg aac gtg cag ggc      672
Leu Thr Arg Ile Gln Leu Ile Gln Phe Val Thr Met Asn Val Gln Gly
    210                 215                 220 tac ctg acc tac tct cga cag tgc cca ggc atg cct cct aag gtg ccg      720
Tyr Leu Thr Tyr Ser Arg Gln Cys Pro Gly Met Pro Pro Lys Val Pro
225                 230                 235                 240 ctc atg tac ctt gtg tac gtg cag tca ctc ttc tgg ctc ttc atg aat      768
Leu Met Tyr Leu Val Tyr Val Gln Ser Leu Phe Trp Leu Phe Met Asn
                245                 250                 255 ttc tac att cgc gcg tac gtg ttc ggc ccc aag aaa ccg gcc gtg gag      816
Phe Tyr Ile Arg Ala Tyr Val Phe Gly Pro Lys Lys Pro Ala Val Glu
            260                 265                 270 gaa tcg aag aag aag ttg taa                                          837
Glu Ser Lys Lys Lys Leu
        275

<210> SEQ ID NO 32
<211> LENGTH: 278
<212> TYPE: PRT
<213> ORGANISM: Phytophthora infestans

<400> SEQUENCE:

-continued

```
Leu Phe Val Tyr Tyr Val Thr Phe Arg Ala Ala Gln Asp Gly Asp Ser
                165                 170                 175

Tyr Ala Thr Ile Val Leu Asn Gly Phe Val His Thr Ile Met Tyr Thr
            180                 185                 190

Tyr Tyr Phe Val Ser Ala His Thr Arg Asn Ile Trp Trp Lys Lys Tyr
        195                 200                 205

Leu Thr Arg Ile Gln Leu Ile Gln Phe Val Thr Met Asn Val Gln Gly
    210                 215                 220

Tyr Leu Thr Tyr Ser Arg Gln Cys Pro Gly Met Pro Pro Lys Val Pro
225                 230                 235                 240

Leu Met Tyr Leu Val Tyr Val Gln Ser Leu Phe Trp Leu Phe Met Asn
                245                 250                 255

Phe Tyr Ile Arg Ala Tyr Val Phe Gly Pro Lys Lys Pro Ala Val Glu
            260                 265                 270

Glu Ser Lys Lys Lys Leu
        275
```

<210> SEQ ID NO 33
<211> LENGTH: 954
<212> TYPE: DNA
<213> ORGANISM: Mortierella alpina
<220> FEATURE:
<221> NAME/KEY: CDS
<222> LOCATION: (1)..(954)
<223> OTHER INFORMATION: delta6-elongase

<400> SEQUENCE: 33

```
atg gcc gcc gca atc ttg gac aag gtc aac ttc ggc att gat cag ccc      48
Met Ala Ala Ala Ile Leu Asp Lys Val Asn Phe Gly Ile Asp Gln Pro
1               5                   10                  15 ttc gga atc aag ctc gac acc tac ttt gct cag gcc tat gaa ctc gtc      96
Phe Gly Ile Lys Leu Asp Thr Tyr Phe Ala Gln Ala Tyr Glu Leu Val
            20                  25                  30 acc gga aag tcc atc gac tcc ttc gtc ttc cag gag ggc gtc acg cct     144
Thr Gly Lys Ser Ile Asp Ser Phe Val Phe Gln Glu Gly Val Thr Pro
        35                  40                  45 ctc tcg acc cag aga gag gtc gcc atg tgg act atc act tac ttc gtc     192
Leu Ser Thr Gln Arg Glu Val Ala Met Trp Thr Ile Thr Tyr Phe Val
    50                  55                  60 gtc atc ttt ggt ggt cgc cag atc atg aag agc cag gac gcc ttc aag     240
Val Ile Phe Gly Gly Arg Gln Ile Met Lys Ser Gln Asp Ala Phe Lys
65                  70                  75                  80 ctc aag ccc ctc ttc atc ctc cac aac ttc ctc ctg acg atc gcg tcc     288
Leu Lys Pro Leu Phe Ile Leu His Asn Phe Leu Leu Thr Ile Ala Ser
                85                  90                  95 gga tcg ctg ttg ctc ctg ttc atc gag aac ctg gtc ccc atc ctc gcc     336
Gly Ser Leu Leu Leu Leu Phe Ile Glu Asn Leu Val Pro Ile Leu Ala
            100                 105                 110 aga aac gga ctt ttc tac gcc atc tgc gac gac ggt gcc tgg acc cag     384
Arg Asn Gly Leu Phe Tyr Ala Ile Cys Asp Asp Gly Ala Trp Thr Gln
        115                 120                 125 cgc ctc gag ctc ctc tac tac ctc aac tac ctg gtc aag tac tgg gag     432
Arg Leu Glu Leu Leu Tyr Tyr Leu Asn Tyr Leu Val Lys Tyr Trp Glu
    130                 135                 140 ttg gcc gac acc gtc ttt ttg gtc ctc aag aag aag cct ctt gag ttc     480
Leu Ala Asp Thr Val Phe Leu Val Leu Lys Lys Lys Pro Leu Glu Phe
145                 150                 155                 160 ctg cac tac ttc cac cac tcg atg acc atg gtt ctc tgc ttt gtc cag     528
Leu His Tyr Phe His His Ser Met Thr Met Val Leu Cys Phe Val Gln
```

```
                              165                 170                 175
ctt gga gga tac act tca gtg tcc tgg gtc cct att acc ctc aac ttg       576
Leu Gly Gly Tyr Thr Ser Val Ser Trp Val Pro Ile Thr Leu Asn Leu
            180                 185                 190 act gtc cac gtc ttc atg tac tac tac atg cgc tcc gct gcc ggt           624
Thr Val His Val Phe Met Tyr Tyr Tyr Met Arg Ser Ala Ala Gly
        195                 200                 205 gtt cgc atc tgg tgg aag cag tac ttg acc act ctc cag atc gtc cag       672
Val Arg Ile Trp Trp Lys Gln Tyr Leu Thr Thr Leu Gln Ile Val Gln
    210                 215                 220 ttc gtt ctt gac ctc gga ttc atc tac ttc tgc gcc tac acc tac ttc       720
Phe Val Leu Asp Leu Gly Phe Ile Tyr Phe Cys Ala Tyr Thr Tyr Phe
225                 230                 235                 240 gcc ttc acc tac ttc ccc tgg gct ccc aac gtc ggc aag tgc gcc ggt       768
Ala Phe Thr Tyr Phe Pro Trp Ala Pro Asn Val Gly Lys Cys Ala Gly
                245                 250                 255 acc gag ggt gct gct ctc ttt ggc tgc gga ctc ctc tcc agc tat ctc       816
Thr Glu Gly Ala Ala Leu Phe Gly Cys Gly Leu Leu Ser Ser Tyr Leu
            260                 265                 270 ttg ctc ttt atc aac ttc tac cgc att acc tac aat gcc aag gcc aag       864
Leu Leu Phe Ile Asn Phe Tyr Arg Ile Thr Tyr Asn Ala Lys Ala Lys
        275                 280                 285 gca gcc aag gag cgt gga agc aac ttt acc ccc aag act gtc aag tcc       912
Ala Ala Lys Glu Arg Gly Ser Asn Phe Thr Pro Lys Thr Val Lys Ser
    290                 295                 300 ggc gga tcg ccc aag aag ccc tcc aag agc aag cac atc taa               954
Gly Gly Ser Pro Lys Lys Pro Ser Lys Ser Lys His Ile
305                 310                 315

<210> SEQ ID NO 34
<211> LENGTH: 317
<212> TYPE: PRT
<213> ORGANISM: Mortierella alpina

<400> SEQUENCE: 34

Met Ala Ala Ala Ile Leu Asp Lys Val Asn Phe Gly Ile Asp Gln Pro
1               5                   10                  15

Phe Gly Ile Lys Leu Asp Thr Tyr Phe Ala Gln Ala Tyr Glu Leu Val
            20                  25                  30

Thr Gly Lys Ser Ile Asp Ser Phe Val Phe Gln Glu Gly Val Thr Pro
        35                  40                  45

Leu Ser Thr Gln Arg Glu Val Ala Met Trp Thr Ile Thr Tyr Phe Val
    50                  55                  60

Val Ile Phe Gly Gly Arg Gln Ile Met Lys Ser Gln Asp Ala Phe Lys
65                  70                  75                  80

Leu Lys Pro Leu Phe Ile Leu His Asn Phe Leu Leu Thr Ile Ala Ser
                85                  90                  95

Gly Ser Leu Leu Leu Leu Phe Ile Glu Asn Leu Val Pro Ile Leu Ala
            100                 105                 110

Arg Asn Gly Leu Phe Tyr Ala Ile Cys Asp Asp Gly Ala Trp Thr Gln
        115                 120                 125

Arg Leu Glu Leu Tyr Tyr Leu Asn Tyr Leu Val Lys Tyr Trp Glu
    130                 135                 140

Leu Ala Asp Thr Val Phe Leu Val Leu Lys Lys Pro Leu Glu Phe
145                 150                 155                 160

Leu His Tyr Phe His His Ser Met Thr Met Val Leu Cys Phe Val Gln
                165                 170                 175
```

```
Leu Gly Gly Tyr Thr Ser Val Ser Trp Val Pro Ile Thr Leu Asn Leu
            180                 185                 190

Thr Val His Val Phe Met Tyr Tyr Tyr Met Arg Ser Ala Ala Gly
        195                 200                 205

Val Arg Ile Trp Trp Lys Gln Tyr Leu Thr Thr Leu Gln Ile Val Gln
        210                 215                 220

Phe Val Leu Asp Leu Gly Phe Ile Tyr Phe Cys Ala Tyr Thr Tyr Phe
225                 230                 235                 240

Ala Phe Thr Tyr Phe Pro Trp Ala Pro Asn Val Gly Lys Cys Ala Gly
                245                 250                 255

Thr Glu Gly Ala Ala Leu Phe Gly Cys Gly Leu Leu Ser Ser Tyr Leu
                260                 265                 270

Leu Leu Phe Ile Asn Phe Tyr Arg Ile Thr Tyr Asn Ala Lys Ala Lys
            275                 280                 285

Ala Ala Lys Glu Arg Gly Ser Asn Phe Thr Pro Lys Thr Val Lys Ser
        290                 295                 300

Gly Gly Ser Pro Lys Lys Pro Ser Lys Ser Lys His Ile
305                 310                 315

<210> SEQ ID NO 35
<211> LENGTH: 957
<212> TYPE: DNA
<213> ORGANISM: Mortierella alpina
<220> FEATURE:
<221> NAME/KEY: CDS
<222> LOCATION: (1)..(957)
<223> OTHER INFORMATION: delta6-elongase

<400> SEQUENCE: 35 atg gag tcg att gcg cca ttc ctc cca tca aag atg ccg caa gat ctg      48
Met Glu Ser Ile Ala Pro Phe Leu Pro Ser Lys Met Pro Gln Asp Leu
1               5                   10                  15 ttt atg gac ctt gcc acc gct atc ggt gtc cgg gcc gcg ccc tat gtc      96
Phe Met Asp Leu Ala Thr Ala Ile Gly Val Arg Ala Ala Pro Tyr Val
            20                  25                  30 gat cct ctc gag gcc gcg ctg gtg gcc cag gcc gag aag tac atc ccc     144
Asp Pro Leu Glu Ala Ala Leu Val Ala Gln Ala Glu Lys Tyr Ile Pro
        35                  40                  45 acg att gtc cat cac acg cgt ggg ttc ctg gtc gcg gtg gag tcg cct     192
Thr Ile Val His His Thr Arg Gly Phe Leu Val Ala Val Glu Ser Pro
    50                  55                  60 ttg gcc cgt gag ctg ccg ttg atg aac ccg ttc cac gtg ctg ttg atc     240
Leu Ala Arg Glu Leu Pro Leu Met Asn Pro Phe His Val Leu Leu Ile
65                  70                  75                  80 gtg ctc gct tat ttg gtc acg gtc ttt gtg ggc atg cag atc atg aag     288
Val Leu Ala Tyr Leu Val Thr Val Phe Val Gly Met Gln Ile Met Lys
                85                  90                  95 aac ttt gag cgg ttc gag gtc aag acg ttt tcg ctc ctg cac aac ttt     336
Asn Phe Glu Arg Phe Glu Val Lys Thr Phe Ser Leu Leu His Asn Phe
            100                 105                 110 tgt ctg gtc tcg atc agc gcc tac atg tgc ggt ggg atc ctg tac gag     384
Cys Leu Val Ser Ile Ser Ala Tyr Met Cys Gly Gly Ile Leu Tyr Glu
        115                 120                 125 gct tat cag gcc aac tat gga ctg ttt gag aac gct gct gat cat acc     432
Ala Tyr Gln Ala Asn Tyr Gly Leu Phe Glu Asn Ala Ala Asp His Thr
    130                 135                 140 ttc aag ggt ctt cct atg gcc aag atg atc tgg ctc ttc tac ttc tcc     480
Phe Lys Gly Leu Pro Met Ala Lys Met Ile Trp Leu Phe Tyr Phe Ser
145                 150                 155                 160
```

```
aag atc atg gag ttt gtc gac acc atg atc atg gtc ctc aag aag aac    528
Lys Ile Met Glu Phe Val Asp Thr Met Ile Met Val Leu Lys Lys Asn
            165                 170                 175 aac cgc cag atc tcc ttc ttg cac gtt tac cac cac agc tcc atc ttc    576
Asn Arg Gln Ile Ser Phe Leu His Val Tyr His His Ser Ser Ile Phe
            180                 185                 190 acc atc tgg tgg ttg gtc acc ttt gtt gca ccc aac ggt gaa gcc tac    624
Thr Ile Trp Trp Leu Val Thr Phe Val Ala Pro Asn Gly Glu Ala Tyr
            195                 200                 205 ttc tct gct gcg ttg aac tcg ttc atc cat gtg atc atg tac ggc tac    672
Phe Ser Ala Ala Leu Asn Ser Phe Ile His Val Ile Met Tyr Gly Tyr
            210                 215                 220 tac ttc ttg tcg gcc ttg ggc ttc aag cag gtg tcg ttc atc aag ttc    720
Tyr Phe Leu Ser Ala Leu Gly Phe Lys Gln Val Ser Phe Ile Lys Phe
225                 230                 235                 240 tac atc acg cgc tcg cag atg aca cag ttc tgc atg atg tcg gtc cag    768
Tyr Ile Thr Arg Ser Gln Met Thr Gln Phe Cys Met Met Ser Val Gln
                245                 250                 255 tct tcc tgg gac atg tac gcc atg aag gtc ctt ggc cgc ccc gga tac    816
Ser Ser Trp Asp Met Tyr Ala Met Lys Val Leu Gly Arg Pro Gly Tyr
            260                 265                 270 ccc ttc ttc atc acg gct ctg ctt tgg ttc tac atg tgg acc atg ctc    864
Pro Phe Phe Ile Thr Ala Leu Leu Trp Phe Tyr Met Trp Thr Met Leu
            275                 280                 285 ggt ctc ttc tac aac ttt tac aga aag aac gcc aag ttg gcc aag cag    912
Gly Leu Phe Tyr Asn Phe Tyr Arg Lys Asn Ala Lys Leu Ala Lys Gln
            290                 295                 300 gcc aag gcc gac gct gcc aag gag aag gca agg aag ttg cag taa        957
Ala Lys Ala Asp Ala Ala Lys Glu Lys Ala Arg Lys Leu Gln
305                 310                 315

<210> SEQ ID NO 36
<211> LENGTH: 318
<212> TYPE: PRT
<213> ORGANISM: Mortierella alpina

<400> SEQUENCE: 36

Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
```

```
                165                 170                 175
Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
            195                 200                 205

Phe Ser Ala Ala Leu Asn Ser Phe Ile His Val Ile Met Tyr Gly Tyr
        210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
            245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
            275                 280                 285

Gly Leu Phe Tyr Asn Phe Tyr Arg Lys Asn Ala Lys Leu Ala Lys Gln
            290                 295                 300

Ala Lys Ala Asp Ala Ala Lys Glu Lys Ala Arg Lys Leu Gln
305                 310                 315

<210> SEQ ID NO 37
<211> LENGTH: 867
<212> TYPE: DNA
<213> ORGANISM: Caenorhabditis elegans
<220> FEATURE:
<221> NAME/KEY: CDS
<222> LOCATION: (1)..(867)
<223> OTHER INFORMATION: delta6-elongase

<400> SEQUENCE: 37 atg gct cag cat ccg ctc gtt caa cgg ctt ctc gat gtc aaa ttc gac     48
Met Ala Gln His Pro Leu Val Gln Arg Leu Leu Asp Val Lys Phe Asp
1               5                  10                  15 acg aaa cga ttt gtg gct att gct act cat ggg cca aag aat ttc cct     96
Thr Lys Arg Phe Val Ala Ile Ala Thr His Gly Pro Lys Asn Phe Pro
            20                  25                  30 gac gca gaa ggt cgc aag ttc ttt gct gat cac ttt gat gtt act att    144
Asp Ala Glu Gly Arg Lys Phe Phe Ala Asp His Phe Asp Val Thr Ile
        35                  40                  45 cag gct tca atc ctg tac atg gtc gtt gtg ttc gga aca aaa tgg ttc    192
Gln Ala Ser Ile Leu Tyr Met Val Val Val Phe Gly Thr Lys Trp Phe
    50                  55                  60 atg cgt aat cgt caa cca ttc caa ttg act att cca ctc aac atc tgg    240
Met Arg Asn Arg Gln Pro Phe Gln Leu Thr Ile Pro Leu Asn Ile Trp
65                  70                  75                  80 aat ttc atc ctc gcc gca ttt tcc atc gca gga gct gtc aaa atg acc    288
Asn Phe Ile Leu Ala Ala Phe Ser Ile Ala Gly Ala Val Lys Met Thr
                85                  90                  95 cca gag ttc ttt gga acc att gcc aac aaa gga att gtc gca tcc tac    336
Pro Glu Phe Phe Gly Thr Ile Ala Asn Lys Gly Ile Val Ala Ser Tyr
            100                 105                 110 tgc aaa gtg ttt gat ttc acg aaa gga gag aat gga tac tgg gtg tgg    384
Cys Lys Val Phe Asp Phe Thr Lys Gly Glu Asn Gly Tyr Trp Val Trp
        115                 120                 125 ctc ttc atg gct tcc aaa ctt ttc gaa ctt gtt gac acc atc ttc ttg    432
Leu Phe Met Ala Ser Lys Leu Phe Glu Leu Val Asp Thr Ile Phe Leu
    130                 135                 140 gtt ctc cgt aaa cgt cca ctc atg ttc ctt cac tgg tat cac cat att    480
Val Leu Arg Lys Arg Pro Leu Met Phe Leu His Trp Tyr His His Ile
145                 150                 155                 160
```

```
                        145                 150                 155                 160
ctc acc atg atc tac gcc tgg tac tct cat cca ttg acc cca gga ttc      528
Leu Thr Met Ile Tyr Ala Trp Tyr Ser His Pro Leu Thr Pro Gly Phe
                165                 170                 175 aac aga tac gga att tat ctt aac ttt gtc gtc cac gcc ttc atg tac      576
Asn Arg Tyr Gly Ile Tyr Leu Asn Phe Val Val His Ala Phe Met Tyr
            180                 185                 190 tct tac tac ttc ctt cgc tcg atg aag att cgc gtg cca gga ttc atc      624
Ser Tyr Tyr Phe Leu Arg Ser Met Lys Ile Arg Val Pro Gly Phe Ile
        195                 200                 205 gcc caa gct atc aca tct ctt caa atc gtt caa ttc atc atc tct tgc      672
Ala Gln Ala Ile Thr Ser Leu Gln Ile Val Gln Phe Ile Ile Ser Cys
    210                 215                 220 gcc gtt ctt gct cat ctt ggt tat ctc atg cac ttc acc aat gcc aac      720
Ala Val Leu Ala His Leu Gly Tyr Leu Met His Phe Thr Asn Ala Asn
225                 230                 235                 240 tgt gat ttc gag cca tca gta ttc aag ctc gca gtt ttc atg gac aca      768
Cys Asp Phe Glu Pro Ser Val Phe Lys Leu Ala Val Phe Met Asp Thr
                245                 250                 255 aca tac ttg gct ctt ttc gtc aac ttc ttc ctc caa tca tat gtt ctc      816
Thr Tyr Leu Ala Leu Phe Val Asn Phe Phe Leu Gln Ser Tyr Val Leu
            260                 265                 270 cgc gga gga aaa gac aag tac aag gca gtg cca aag aag aag aac aac      864
Arg Gly Gly Lys Asp Lys Tyr Lys Ala Val Pro Lys Lys Lys Asn Asn
        275                 280                 285 taa                                                                  867
```

<210> SEQ ID NO 38
<211> LENGTH: 288
<212> TYPE: PRT
<213> ORGANISM: Caenorhabditis elegans

<400> SEQUENCE: 38

```
Met Ala Gln His Pro Leu Val Gln Arg Leu Leu Asp Val Lys Phe Asp
1               5                   10                  15

Thr Lys Arg Phe Val Ala Ile Ala Thr His Gly Pro Lys Asn Phe Pro
            20                  25                  30

Asp Ala Glu Gly Arg Lys Phe Phe Ala Asp His Phe Asp Val Thr Ile
        35                  40                  45

Gln Ala Ser Ile Leu Tyr Met Val Val Phe Gly Thr Lys Trp Phe
    50                  55                  60

Met Arg Asn Arg Gln Pro Phe Gln Leu Thr Ile Pro Leu Asn Ile Trp
65                  70                  75                  80

Asn Phe Ile Leu Ala Ala Phe Ser Ile Ala Gly Ala Val Lys Met Thr
                85                  90                  95

Pro Glu Phe Phe Gly Thr Ile Ala Asn Lys Gly Ile Val Ala Ser Tyr
            100                 105                 110

Cys Lys Val Phe Asp Phe Thr Lys Gly Glu Asn Gly Tyr Trp Val Trp
        115                 120                 125

Leu Phe Met Ala Ser Lys Leu Phe Glu Leu Val Asp Thr Ile Phe Leu
    130                 135                 140

Val Leu Arg Lys Arg Pro Leu Met Phe Leu His Trp Tyr His Ile
145                 150                 155                 160

Leu Thr Met Ile Tyr Ala Trp Tyr Ser His Pro Leu Thr Pro Gly Phe
                165                 170                 175

Asn Arg Tyr Gly Ile Tyr Leu Asn Phe Val Val His Ala Phe Met Tyr
            180                 185                 190
```

```
Ser Tyr Tyr Phe Leu Arg Ser Met Lys Ile Arg Val Pro Gly Phe Ile
        195                 200                 205

Ala Gln Ala Ile Thr Ser Leu Gln Ile Val Gln Phe Ile Ile Ser Cys
    210                 215                 220

Ala Val Leu Ala His Leu Gly Tyr Leu Met His Phe Thr Asn Ala Asn
225                 230                 235                 240

Cys Asp Phe Glu Pro Ser Val Phe Lys Leu Ala Val Phe Met Asp Thr
                245                 250                 255

Thr Tyr Leu Ala Leu Phe Val Asn Phe Phe Leu Gln Ser Tyr Val Leu
            260                 265                 270

Arg Gly Gly Lys Asp Lys Tyr Lys Ala Val Pro Lys Lys Lys Asn Asn
                275                 280                 285

<210> SEQ ID NO 39
<211> LENGTH: 1626
<212> TYPE: DNA
<213> ORGANISM: Euglena gracilis
<220> FEATURE:
<221> NAME/KEY: CDS
<222> LOCATION: (1)..(1626)
<223> OTHER INFORMATION: delta4-desaturase

<400> SEQUENCE: 39
```

| | |
|---|---|
| atg ttg gtg ctg ttt ggc aat ttc tat gtc aag caa tac tcc caa aag<br>Met Leu Val Leu Phe Gly Asn Phe Tyr Val Lys Gln Tyr Ser Gln Lys<br>1                     5                   10                 15 | 48 |
| aac ggc aag ccg gag aac gga gcc acc cct gag aac gga gcg aag ccg<br>Asn Gly Lys Pro Glu Asn Gly Ala Thr Pro Glu Asn Gly Ala Lys Pro<br>            20                   25                   30 | 96 |
| caa cct tgc gag aac ggc acg gtg gaa aag cga gag aat gac acc gcc<br>Gln Pro Cys Glu Asn Gly Thr Val Glu Lys Arg Glu Asn Asp Thr Ala<br>              35                   40               45 | 144 |
| aac gtt cgg ccc acc cgt cca gct gga ccc ccg ccg gcc acg tac tac<br>Asn Val Arg Pro Thr Arg Pro Ala Gly Pro Pro Pro Ala Thr Tyr Tyr<br>50                   55                   60 | 192 |
| gac tcc ctg gca gtg tcg ggg cag ggc aag gag cgg ctg ttc acc acc<br>Asp Ser Leu Ala Val Ser Gly Gln Gly Lys Glu Arg Leu Phe Thr Thr<br>65                   70                   75               80 | 240 |
| gat gag gtg agg cgg cac atc ctc ccc acc gat ggc tgg ctg acg tgc<br>Asp Glu Val Arg Arg His Ile Leu Pro Thr Asp Gly Trp Leu Thr Cys<br>                 85                   90                  95 | 288 |
| cac gaa gga gtc tac gat gtc act gat ttc ctt gcc aag cac cct ggt<br>His Glu Gly Val Tyr Asp Val Thr Asp Phe Leu Ala Lys His Pro Gly<br>                  100                 105               110 | 336 |
| ggc ggt gtc atc acg ctg ggc ctt gga agg gac tgc aca atc ctc atc<br>Gly Gly Val Ile Thr Leu Gly Leu Gly Arg Asp Cys Thr Ile Leu Ile<br>             115                   120               125 | 384 |
| gag tca tac cac cct gct ggg cgc ccg gac aag gtg atg gag aag tac<br>Glu Ser Tyr His Pro Ala Gly Arg Pro Asp Lys Val Met Glu Lys Tyr<br>130                  135                 140 | 432 |
| cgc att ggt acg ctg cag gac ccc aag acg ttc tat gct tgg gga gag<br>Arg Ile Gly Thr Leu Gln Asp Pro Lys Thr Phe Tyr Ala Trp Gly Glu<br>145                   150                 155               160 | 480 |
| tcc gat ttc tac cct gag ttg aag cgc cgg gcc ctt gca agg ctg aag<br>Ser Asp Phe Tyr Pro Glu Leu Lys Arg Arg Ala Leu Ala Arg Leu Lys<br>                  165                170               175 | 528 |
| gag gct ggt cag gcg cgg cgc ggc ggc ctt ggg gtg aag gcc ctc ctg<br>Glu Ala Gly Gln Ala Arg Arg Gly Gly Leu Gly Val Lys Ala Leu Leu<br>             180                   185               190 | 576 |

```
gtg ctc acc ctc ttc ttc gtg tcg tgg tac atg tgg gtg gcc cac aag    624
Val Leu Thr Leu Phe Phe Val Ser Trp Tyr Met Trp Val Ala His Lys
    195                 200                 205 tcc ttc ctc tgg gcc gcc gtc tgg ggc ttc gcc ggc tcc cac gtc ggg    672
Ser Phe Leu Trp Ala Ala Val Trp Gly Phe Ala Gly Ser His Val Gly
210                 215                 220 ctg agc atc cag cac gat ggc aac cac ggc gcg ttc agc cgc aac aca    720
Leu Ser Ile Gln His Asp Gly Asn His Gly Ala Phe Ser Arg Asn Thr
225                 230                 235                 240 ctg gtg aac cgc ctg gcg ggg tgg ggc atg gac ttg atc ggc gcg tcg    768
Leu Val Asn Arg Leu Ala Gly Trp Gly Met Asp Leu Ile Gly Ala Ser
            245                 250                 255 tcc acg gtg tgg gag tac cag cac gtc atc ggc cac cac cag tac acc    816
Ser Thr Val Trp Glu Tyr Gln His Val Ile Gly His His Gln Tyr Thr
        260                 265                 270 aac ctc gtg tcg gac acg cta ttc agt ctg cct gag aac gat ccg gac    864
Asn Leu Val Ser Asp Thr Leu Phe Ser Leu Pro Glu Asn Asp Pro Asp
    275                 280                 285 gtc ttc tcc agc tac ccg ctg atg cgc atg cac ccg gat acg gcg tgg    912
Val Phe Ser Ser Tyr Pro Leu Met Arg Met His Pro Asp Thr Ala Trp
290                 295                 300 cag ccg cac cac cgc ttc cag cac ctg ttc gcg ttc cca ctg ttc gcc    960
Gln Pro His His Arg Phe Gln His Leu Phe Ala Phe Pro Leu Phe Ala
305                 310                 315                 320 ctg atg aca atc agc aag gtg ctg acc agc gat ttc gct gtc tgc ctc   1008
Leu Met Thr Ile Ser Lys Val Leu Thr Ser Asp Phe Ala Val Cys Leu
            325                 330                 335 agc atg aag aag ggg tcc atc gac tgc tcc tcc agg ctc gtc cca ctg   1056
Ser Met Lys Lys Gly Ser Ile Asp Cys Ser Ser Arg Leu Val Pro Leu
        340                 345                 350 gag ggg cag ctg ctg ttc tgg ggg gcc aag ctg gcg aac ttc ctg ttg   1104
Glu Gly Gln Leu Leu Phe Trp Gly Ala Lys Leu Ala Asn Phe Leu Leu
    355                 360                 365 cag att gtg ttg cca tgc tac ctc cac ggg aca gct atg ggc ctg gcc   1152
Gln Ile Val Leu Pro Cys Tyr Leu His Gly Thr Ala Met Gly Leu Ala
370                 375                 380 ctc ttc tct gtt gct cac ctt gtg tcg ggg gag tac ctc gcg atc tgc   1200
Leu Phe Ser Val Ala His Leu Val Ser Gly Glu Tyr Leu Ala Ile Cys
385                 390                 395                 400 ttc atc atc aac cac atc agc gag tct tgt gag ttt atg aat aca agc   1248
Phe Ile Ile Asn His Ile Ser Glu Ser Cys Glu Phe Met Asn Thr Ser
            405                 410                 415 ttt caa acc gcc gcc cgg agg aca gag atg ctt cag gca gca cat cag   1296
Phe Gln Thr Ala Ala Arg Arg Thr Glu Met Leu Gln Ala Ala His Gln
        420                 425                 430 gca gcg gag gcc aag aag gtg aag ccc acc cct cca ccg aac gat tgg   1344
Ala Ala Glu Ala Lys Lys Val Lys Pro Thr Pro Pro Pro Asn Asp Trp
    435                 440                 445 gct gtg aca cag gtc caa tgc tgc gtg aat tgg aga tca ggt ggc gtg   1392
Ala Val Thr Gln Val Gln Cys Cys Val Asn Trp Arg Ser Gly Gly Val
450                 455                 460 ttg gcc aat cac ctc tct gga ggc ttg aac cac cag atc gag cat cat   1440
Leu Ala Asn His Leu Ser Gly Gly Leu Asn His Gln Ile Glu His His
465                 470                 475                 480 ctg ttc ccc agc atc tcg cat gcc aac tac ccc acc atc gcc cct gtt   1488
Leu Phe Pro Ser Ile Ser His Ala Asn Tyr Pro Thr Ile Ala Pro Val
            485                 490                 495 gtg aag gag gtg tgc gag gag tac ggg ttg ccg tac aag aat tac gtc   1536
Val Lys Glu Val Cys Glu Glu Tyr Gly Leu Pro Tyr Lys Asn Tyr Val
        500                 505                 510
```

```
acg ttc tgg gat gca gtc tgt ggc atg gtt cag cac ctc cgg ttg atg         1584
Thr Phe Trp Asp Ala Val Cys Gly Met Val Gln His Leu Arg Leu Met
        515                 520                 525 ggt gct cca ccg gtg cca acg aac ggg gac aaa aag tca taa                 1626
Gly Ala Pro Pro Val Pro Thr Asn Gly Asp Lys Lys Ser
530                 535                 540
```

<210> SEQ ID NO 40
<211> LENGTH: 541
<212> TYPE: PRT
<213> ORGANISM: Euglena gracilis

<400> SEQUENCE: 40

```
Met Leu Val Leu Phe Gly Asn Phe Tyr Val Lys Gln Tyr Ser Gln Lys
1               5                   10                  15

Asn Gly Lys Pro Glu Asn Gly Ala Thr Pro Glu Asn Gly Ala Lys Pro
            20                  25                  30

Gln Pro Cys Glu Asn Gly Thr Val Glu Lys Arg Glu Asn Asp Thr Ala
        35                  40                  45

Asn Val Arg Pro Thr Arg Pro Ala Gly Pro Pro Ala Thr Tyr Tyr
    50                  55                  60

Asp Ser Leu Ala Val Ser Gly Gln Gly Lys Glu Arg Leu Phe Thr Thr
65                  70                  75                  80

Asp Glu Val Arg Arg His Ile Leu Pro Thr Asp Gly Trp Leu Thr Cys
                85                  90                  95

His Glu Gly Val Tyr Asp Val Thr Asp Phe Leu Ala Lys His Pro Gly
            100                 105                 110

Gly Gly Val Ile Thr Leu Gly Leu Gly Arg Asp Cys Thr Ile Leu Ile
        115                 120                 125

Glu Ser Tyr His Pro Ala Gly Arg Pro Asp Lys Val Met Glu Lys Tyr
    130                 135                 140

Arg Ile Gly Thr Leu Gln Asp Pro Lys Thr Phe Tyr Ala Trp Gly Glu
145                 150                 155                 160

Ser Asp Phe Tyr Pro Glu Leu Lys Arg Arg Ala Leu Ala Arg Leu Lys
                165                 170                 175

Glu Ala Gly Gln Ala Arg Arg Gly Gly Leu Gly Val Lys Ala Leu Leu
            180                 185                 190

Val Leu Thr Leu Phe Phe Val Ser Trp Tyr Met Trp Val Ala His Lys
        195                 200                 205

Ser Phe Leu Trp Ala Ala Val Trp Gly Phe Ala Gly Ser His Val Gly
    210                 215                 220

Leu Ser Ile Gln His Asp Gly Asn His Gly Ala Phe Ser Arg Asn Thr
225                 230                 235                 240

Leu Val Asn Arg Leu Ala Gly Trp Gly Met Asp Leu Ile Gly Ala Ser
                245                 250                 255

Ser Thr Val Trp Glu Tyr Gln His Val Ile Gly His His Gln Tyr Thr
            260                 265                 270

Asn Leu Val Ser Asp Thr Leu Phe Ser Leu Pro Glu Asn Asp Pro Asp
        275                 280                 285

Val Phe Ser Ser Tyr Pro Leu Met Arg Met His Pro Asp Thr Ala Trp
    290                 295                 300

Gln Pro His His Arg Phe Gln His Leu Phe Ala Phe Pro Leu Phe Ala
305                 310                 315                 320

Leu Met Thr Ile Ser Lys Val Leu Thr Ser Asp Phe Ala Val Cys Leu
                325                 330                 335
```

```
Ser Met Lys Lys Gly Ser Ile Asp Cys Ser Ser Arg Leu Val Pro Leu
         340                 345                 350

Glu Gly Gln Leu Leu Phe Trp Gly Ala Lys Leu Ala Asn Phe Leu Leu
         355                 360                 365

Gln Ile Val Leu Pro Cys Tyr Leu His Gly Thr Ala Met Gly Leu Ala
370                 375                 380

Leu Phe Ser Val Ala His Leu Val Ser Gly Glu Tyr Leu Ala Ile Cys
385                 390                 395                 400

Phe Ile Ile Asn His Ile Ser Glu Ser Cys Glu Phe Met Asn Thr Ser
                405                 410                 415

Phe Gln Thr Ala Ala Arg Arg Thr Glu Met Leu Gln Ala Ala His Gln
             420                 425                 430

Ala Ala Glu Ala Lys Lys Val Lys Pro Thr Pro Pro Asn Asp Trp
         435                 440                 445

Ala Val Thr Gln Val Gln Cys Cys Val Asn Trp Arg Ser Gly Gly Val
         450                 455                 460

Leu Ala Asn His Leu Ser Gly Gly Leu Asn His Gln Ile Glu His His
465                 470                 475                 480

Leu Phe Pro Ser Ile Ser His Ala Asn Tyr Pro Thr Ile Ala Pro Val
                485                 490                 495

Val Lys Glu Val Cys Glu Glu Tyr Gly Leu Pro Tyr Lys Asn Tyr Val
             500                 505                 510

Thr Phe Trp Asp Ala Val Cys Gly Met Val Gln His Leu Arg Leu Met
             515                 520                 525

Gly Ala Pro Pro Val Pro Thr Asn Gly Asp Lys Lys Ser
         530                 535                 540

<210> SEQ ID NO 41
<211> LENGTH: 1548
<212> TYPE: DNA
<213> ORGANISM: Thraustochytrium
<220> FEATURE:
<221> NAME/KEY: CDS
<222> LOCATION: (1)..(1548)
<223> OTHER INFORMATION: delta4-desaturase

<400> SEQUENCE: 41 atg acg gtc ggg ttt gac gaa acg gtg act atg gac acg gtc cgc aac       48
Met Thr Val Gly Phe Asp Glu Thr Val Thr Met Asp Thr Val Arg Asn
1               5                   10                  15 cac aac atg ccg gac gac gcc tgg tgc gcg atc cac ggc acc gtg tac       96
His Asn Met Pro Asp Asp Ala Trp Cys Ala Ile His Gly Thr Val Tyr
            20                  25                  30 gac atc acc aag ttc agc aag gtg cac ccc ggc ggg gac atc atc atg      144
Asp Ile Thr Lys Phe Ser Lys Val His Pro Gly Gly Asp Ile Ile Met
        35                  40                  45 ctg gcc gct ggc aag gag gcc acc atc ctg ttc gag acc tac cac atc      192
Leu Ala Ala Gly Lys Glu Ala Thr Ile Leu Phe Glu Thr Tyr His Ile
    50                  55                  60 aag ggc gtc ccg gac gcg gtg ctg cgc aag tac aag gtc ggc aag ctc      240
Lys Gly Val Pro Asp Ala Val Leu Arg Lys Tyr Lys Val Gly Lys Leu
65                  70                  75                  80 ccc cag ggc aag aag ggc gaa acg agc cac atg ccc acc ggg ctc gac      288
Pro Gln Gly Lys Lys Gly Glu Thr Ser His Met Pro Thr Gly Leu Asp
                85                  90                  95 tcg gcc tcc tac tac tcg tgg gac agc gag ttt tac agg gtg ctc cgc      336
Ser Ala Ser Tyr Tyr Ser Trp Asp Ser Glu Phe Tyr Arg Val Leu Arg
            100                 105                 110
```

```
gag cgc gtc gcc aag aag ctg gcc gag ccc ggc ctc atg cag cgc gcg      384
Glu Arg Val Ala Lys Lys Leu Ala Glu Pro Gly Leu Met Gln Arg Ala
        115                 120                 125 cgc atg gag ctc tgg gcc aag gcg atc ttc ctc ctg gca ggt ttc tgg      432
Arg Met Glu Leu Trp Ala Lys Ala Ile Phe Leu Leu Ala Gly Phe Trp
130                 135                 140 ggc tcc ctt tac gcc atg tgc gtg cta gac ccg cac ggc ggt gcc atg      480
Gly Ser Leu Tyr Ala Met Cys Val Leu Asp Pro His Gly Gly Ala Met
145                 150                 155                 160 gta gcc gcc gtt acg ctc ggc gtg ttc gct gcc ttt gtc gga act tgc      528
Val Ala Ala Val Thr Leu Gly Val Phe Ala Ala Phe Val Gly Thr Cys
                165                 170                 175 atc cag cac gac ggc agc cac ggc gcc ttc tcc aag tcg cga ttc atg      576
Ile Gln His Asp Gly Ser His Gly Ala Phe Ser Lys Ser Arg Phe Met
                180                 185                 190 aac aag gcg gcg ggc tgg acc ctc gac atg atc ggc gcg agt gcg atg      624
Asn Lys Ala Ala Gly Trp Thr Leu Asp Met Ile Gly Ala Ser Ala Met
                195                 200                 205 acc tgg gag atg cag cac gtt ctt ggc cac cac ccg tac acc aac ctc      672
Thr Trp Glu Met Gln His Val Leu Gly His His Pro Tyr Thr Asn Leu
        210                 215                 220 atc gag atg gag aac ggt ttg gcc aag gtc aag ggc gcc gac gtc gac      720
Ile Glu Met Glu Asn Gly Leu Ala Lys Val Lys Gly Ala Asp Val Asp
225                 230                 235                 240 ccg aag aag gtc gac cag gag agc gac ccg gac gtc ttc agt acg tac      768
Pro Lys Lys Val Asp Gln Glu Ser Asp Pro Asp Val Phe Ser Thr Tyr
                245                 250                 255 ccg atg ctt cgc ctg cac ccg tgg cac cgc cag cgg ttt tac cac aag      816
Pro Met Leu Arg Leu His Pro Trp His Arg Gln Arg Phe Tyr His Lys
                260                 265                 270 ttc cag cac ctg tac gcc ccg ttt atc ttt ggg tct atg acg att aac      864
Phe Gln His Leu Tyr Ala Pro Phe Ile Phe Gly Ser Met Thr Ile Asn
        275                 280                 285 aag gtg att tcc cag gat gtc ggg gtt gtg ctg cgc aag cgc ctg ttc      912
Lys Val Ile Ser Gln Asp Val Gly Val Val Leu Arg Lys Arg Leu Phe
        290                 295                 300 cag atc gac gcc aac tgc cgg tat ggc agc ccc tgg tac gtg gcc cgc      960
Gln Ile Asp Ala Asn Cys Arg Tyr Gly Ser Pro Trp Tyr Val Ala Arg
305                 310                 315                 320 ttc tgg atc atg aag ctc ctc acc acg ctc tac atg gtg gcg ctt ccc     1008
Phe Trp Ile Met Lys Leu Leu Thr Thr Leu Tyr Met Val Ala Leu Pro
                325                 330                 335 atg tac atg cag ggg cct gct cag ggc ttg aag ctt ttc ttc atg gcc     1056
Met Tyr Met Gln Gly Pro Ala Gln Gly Leu Lys Leu Phe Phe Met Ala
                340                 345                 350 cac ttc acc tgc gga gag gtc ctc gcc acc atg ttt att gtc aac cac     1104
His Phe Thr Cys Gly Glu Val Leu Ala Thr Met Phe Ile Val Asn His
        355                 360                 365 atc atc gag ggc gtc agc tac gct tcc aag gac gcg gtc aag ggc gtc     1152
Ile Ile Glu Gly Val Ser Tyr Ala Ser Lys Asp Ala Val Lys Gly Val
        370                 375                 380 atg gct ccg ccg cgc act gtg cac ggt gtc acc ccg atg cag gtg acg     1200
Met Ala Pro Pro Arg Thr Val His Gly Val Thr Pro Met Gln Val Thr
385                 390                 395                 400 caa aag gcg ctc agt gcg gcc gag tcg gcc aag tcg gac gcc gac aag     1248
Gln Lys Ala Leu Ser Ala Ala Glu Ser Ala Lys Ser Asp Ala Asp Lys
                405                 410                 415 acg acc atg atc ccc ctc aac gac tgg gcc gct gtg cag tgc cag acc     1296
Thr Thr Met Ile Pro Leu Asn Asp Trp Ala Ala Val Gln Cys Gln Thr
```

-continued

```
                420             425             430
tct gtg aac tgg gct gtc ggg tcg tgg ttt tgg aac cac ttt tcg ggc    1344
Ser Val Asn Trp Ala Val Gly Ser Trp Phe Trp Asn His Phe Ser Gly
        435                 440                 445 ggc ctc aac cac cag att gag cac cac tgc ttc ccc caa aac ccc cac    1392
Gly Leu Asn His Gln Ile Glu His His Cys Phe Pro Gln Asn Pro His
    450                 455                 460 acg gtc aac gtc tac atc tcg ggc atc gtc aag gag acc tgc gaa gaa    1440
Thr Val Asn Val Tyr Ile Ser Gly Ile Val Lys Glu Thr Cys Glu Glu
465                 470                 475                 480 tac ggc gtg ccg tac cag gct gag atc agc ctc ttc tct gcc tat ttc    1488
Tyr Gly Val Pro Tyr Gln Ala Glu Ile Ser Leu Phe Ser Ala Tyr Phe
                485                 490                 495 aag atg ctg tcg cac ctc cgc acg ctc ggc aac gag gac ctc acg gcc    1536
Lys Met Leu Ser His Leu Arg Thr Leu Gly Asn Glu Asp Leu Thr Ala
            500                 505                 510 tgg tcc acg tga                                                    1548
Trp Ser Thr
        515

<210> SEQ ID NO 42
<211> LENGTH: 515
<212> TYPE: PRT
<213> ORGANISM: Thraustochytrium

<400> SEQUENCE: 42

Met Thr Val Gly Phe Asp Glu Thr Val Thr Met Asp Thr Val Arg Asn
1               5                   10                  15

His Asn Met Pro Asp Asp Ala Trp Cys Ala Ile His Gly Thr Val Tyr
            20                  25                  30

Asp Ile Thr Lys Phe Ser Lys Val His Pro Gly Gly Asp Ile Ile Met
        35                  40                  45

Leu Ala Ala Gly Lys Glu Ala Thr Ile Leu Phe Glu Thr Tyr His Ile
    50                  55                  60

Lys Gly Val Pro Asp Ala Val Leu Arg Lys Tyr Lys Val Gly Lys Leu
65                  70                  75                  80

Pro Gln Gly Lys Lys Gly Glu Thr Ser His Met Pro Thr Gly Leu Asp
                85                  90                  95

Ser Ala Ser Tyr Tyr Ser Trp Asp Ser Glu Phe Tyr Arg Val Leu Arg
            100                 105                 110

Glu Arg Val Ala Lys Lys Leu Ala Glu Pro Gly Leu Met Gln Arg Ala
        115                 120                 125

Arg Met Glu Leu Trp Ala Lys Ala Ile Phe Leu Leu Ala Gly Phe Trp
    130                 135                 140

Gly Ser Leu Tyr Ala Met Cys Val Leu Asp Pro His Gly Gly Ala Met
145                 150                 155                 160

Val Ala Ala Val Thr Leu Gly Val Phe Ala Ala Phe Val Gly Thr Cys
                165                 170                 175

Ile Gln His Asp Gly Ser His Gly Ala Phe Ser Lys Ser Arg Phe Met
            180                 185                 190

Asn Lys Ala Ala Gly Trp Thr Leu Asp Met Ile Gly Ala Ser Ala Met
        195                 200                 205

Thr Trp Glu Met Gln His Val Leu Gly His His Pro Tyr Thr Asn Leu
    210                 215                 220

Ile Glu Met Glu Asn Gly Leu Ala Lys Val Lys Gly Ala Asp Val Asp
225                 230                 235                 240
```

```
Pro Lys Lys Val Asp Gln Glu Ser Asp Pro Asp Val Phe Ser Thr Tyr
                245                 250                 255
Pro Met Leu Arg Leu His Pro Trp His Arg Gln Arg Phe Tyr His Lys
            260                 265                 270
Phe Gln His Leu Tyr Ala Pro Phe Ile Phe Gly Ser Met Thr Ile Asn
        275                 280                 285
Lys Val Ile Ser Gln Asp Val Gly Val Leu Arg Lys Arg Leu Phe
    290                 295                 300
Gln Ile Asp Ala Asn Cys Arg Tyr Gly Ser Pro Trp Tyr Val Ala Arg
305                 310                 315                 320
Phe Trp Ile Met Lys Leu Leu Thr Thr Leu Tyr Met Val Ala Leu Pro
                325                 330                 335
Met Tyr Met Gln Gly Pro Ala Gln Gly Leu Lys Leu Phe Phe Met Ala
            340                 345                 350
His Phe Thr Cys Gly Glu Val Leu Ala Thr Met Phe Ile Val Asn His
        355                 360                 365
Ile Ile Glu Gly Val Ser Tyr Ala Ser Lys Asp Ala Val Lys Gly Val
    370                 375                 380
Met Ala Pro Pro Arg Thr Val His Gly Val Thr Pro Met Gln Val Thr
385                 390                 395                 400
Gln Lys Ala Leu Ser Ala Ala Glu Ser Ala Lys Ser Asp Ala Asp Lys
                405                 410                 415
Thr Thr Met Ile Pro Leu Asn Asp Trp Ala Ala Val Gln Cys Gln Thr
            420                 425                 430
Ser Val Asn Trp Ala Val Gly Ser Trp Phe Trp Asn His Phe Ser Gly
        435                 440                 445
Gly Leu Asn His Gln Ile Glu His His Cys Phe Pro Gln Asn Pro His
    450                 455                 460
Thr Val Asn Val Tyr Ile Ser Gly Ile Val Lys Glu Thr Cys Glu Glu
465                 470                 475                 480
Tyr Gly Val Pro Tyr Gln Ala Glu Ile Ser Leu Phe Ser Ala Tyr Phe
                485                 490                 495
Lys Met Leu Ser His Leu Arg Thr Leu Gly Asn Glu Asp Leu Thr Ala
            500                 505                 510
Trp Ser Thr
        515

<210> SEQ ID NO 43
<211> LENGTH: 960
<212> TYPE: DNA
<213> ORGANISM: Thalassiosira pseudonana
<220> FEATURE:
<221> NAME/KEY: CDS
<222> LOCATION: (1)..(960)
<223> OTHER INFORMATION: delta5-elongase

<400> SEQUENCE: 43 atg gtg ttg tac aat gtg gcg caa gtg ctg ctc aat ggg tgg acg gtg      48
Met Val Leu Tyr Asn Val Ala Gln Val Leu Leu Asn Gly Trp Thr Val
1               5                   10                  15 tat gcg att gtg gat gcg gtg atg aat aga gac cat ccg ttt att gga      96
Tyr Ala Ile Val Asp Ala Val Met Asn Arg Asp His Pro Phe Ile Gly
            20                  25                  30 agt aga agt ttg gtt ggg gcg gcg ttg cat agt ggg agc tcg tat gcg     144
Ser Arg Ser Leu Val Gly Ala Ala Leu His Ser Gly Ser Ser Tyr Ala
        35                  40                  45 gtg tgg gtt cat tat tgt gat aag tat ttg gag ttc ttt gat acg tat     192
```

```
Val Trp Val His Tyr Cys Asp Lys Tyr Leu Glu Phe Phe Asp Thr Tyr
     50                  55                  60 ttt atg gtg ttg agg ggg aaa atg gac cag atg gta ctt ggt gaa gtt        240
Phe Met Val Leu Arg Gly Lys Met Asp Gln Met Val Leu Gly Glu Val
 65                  70                  75                  80 ggt ggc agt gtg tgg tgt ggc gtt gga tat atg gat atg gag aag atg        288
Gly Gly Ser Val Trp Cys Gly Val Gly Tyr Met Asp Met Glu Lys Met
                 85                  90                  95 ata cta ctc agc ttt gga gtg cat cgg tct gct cag gga acg ggg aag        336
Ile Leu Leu Ser Phe Gly Val His Arg Ser Ala Gln Gly Thr Gly Lys
            100                 105                 110 gct ttc acc aac aac gtt acc aat cca cat ctc acg ctt cca cct cat        384
Ala Phe Thr Asn Asn Val Thr Asn Pro His Leu Thr Leu Pro Pro His
        115                 120                 125 tct aca aaa aca aaa aaa cag gtc tcc ttc ctc cac atc tac cac cac        432
Ser Thr Lys Thr Lys Lys Gln Val Ser Phe Leu His Ile Tyr His His
    130                 135                 140 acg acc ata gcg tgg gca tgg tgg atc gcc ctc cgc ttc tcc ccc ggt        480
Thr Thr Ile Ala Trp Ala Trp Trp Ile Ala Leu Arg Phe Ser Pro Gly
145                 150                 155                 160 gga gac att tac ttc ggg gca ctc ctc aac tcc atc atc cac gtc ctc        528
Gly Asp Ile Tyr Phe Gly Ala Leu Leu Asn Ser Ile Ile His Val Leu
                165                 170                 175 atg tat tcc tac tac gcc ctt gcc cta ctc aag gtc agt tgt cca tgg        576
Met Tyr Ser Tyr Tyr Ala Leu Ala Leu Leu Lys Val Ser Cys Pro Trp
            180                 185                 190 aaa cga tac ctg act caa gct caa tta ttg caa ttc aca agt gtg gtg        624
Lys Arg Tyr Leu Thr Gln Ala Gln Leu Leu Gln Phe Thr Ser Val Val
        195                 200                 205 gtt tat acg ggg tgt acg ggt tat act cat tac tat cat acg aag cat        672
Val Tyr Thr Gly Cys Thr Gly Tyr Thr His Tyr Tyr His Thr Lys His
    210                 215                 220 gga gcg gat gag aca cag cct agt tta gga acg tat tat ttc tgt tgt        720
Gly Ala Asp Glu Thr Gln Pro Ser Leu Gly Thr Tyr Tyr Phe Cys Cys
225                 230                 235                 240 gga gtg cag gtg ttt gag atg gtt agt ttg ttt gta ctc ttt tcc atc        768
Gly Val Gln Val Phe Glu Met Val Ser Leu Phe Val Leu Phe Ser Ile
                245                 250                 255 ttt tat aaa cga tcc tat tcg aag aag aac aag tca gga gga aag gat        816
Phe Tyr Lys Arg Ser Tyr Ser Lys Lys Asn Lys Ser Gly Gly Lys Asp
            260                 265                 270 agc aag aag aat gat gat ggg aat aat gag gat caa tgt cac aag gct        864
Ser Lys Lys Asn Asp Asp Gly Asn Asn Glu Asp Gln Cys His Lys Ala
        275                 280                 285 atg aag gat ata tcg gag ggt gcg aag gag gtt gtg ggg cat gca gcg        912
Met Lys Asp Ile Ser Glu Gly Ala Lys Glu Val Val Gly His Ala Ala
    290                 295                 300 aag gat gct gga aag ttg gtg gct acg aga gta agg tgt aag gtg taa        960
Lys Asp Ala Gly Lys Leu Val Ala Thr Arg Val Arg Cys Lys Val
305                 310                 315

<210> SEQ ID NO 44
<211> LENGTH: 319
<212> TYPE: PRT
<213> ORGANISM: Thalassiosira pseudonana

<400> SEQUENCE: 44

Met Val Leu Tyr Asn Val Ala Gln Val Leu Leu Asn Gly Trp Thr Val
1               5                   10                  15

Tyr Ala Ile Val Asp Ala Val Met Asn Arg Asp His Pro Phe Ile Gly
```

```
                    20                  25                  30
Ser Arg Ser Leu Val Gly Ala Ala Leu His Ser Gly Ser Ser Tyr Ala
            35                  40                  45

Val Trp Val His Tyr Cys Asp Lys Tyr Leu Glu Phe Phe Asp Thr Tyr
 50                  55                  60

Phe Met Val Leu Arg Gly Lys Met Asp Gln Met Val Leu Gly Glu Val
 65                  70                  75                  80

Gly Gly Ser Val Trp Cys Gly Val Gly Tyr Met Asp Met Glu Lys Met
                85                  90                  95

Ile Leu Leu Ser Phe Gly Val His Arg Ser Ala Gln Gly Thr Gly Lys
            100                 105                 110

Ala Phe Thr Asn Asn Val Thr Asn Pro His Leu Thr Leu Pro Pro His
        115                 120                 125

Ser Thr Lys Thr Lys Gln Val Ser Phe Leu His Ile Tyr His His
        130                 135                 140

Thr Thr Ile Ala Trp Ala Trp Trp Ile Ala Leu Arg Phe Ser Pro Gly
145                 150                 155                 160

Gly Asp Ile Tyr Phe Gly Ala Leu Leu Asn Ser Ile Ile His Val Leu
                165                 170                 175

Met Tyr Ser Tyr Tyr Ala Leu Ala Leu Leu Lys Val Ser Cys Pro Trp
            180                 185                 190

Lys Arg Tyr Leu Thr Gln Ala Gln Leu Leu Gln Phe Thr Ser Val Val
        195                 200                 205

Val Tyr Thr Gly Cys Thr Gly Tyr Thr His Tyr Tyr His Thr Lys His
    210                 215                 220

Gly Ala Asp Glu Thr Gln Pro Ser Leu Gly Thr Tyr Tyr Phe Cys Cys
225                 230                 235                 240

Gly Val Gln Val Phe Glu Met Val Ser Leu Phe Val Leu Phe Ser Ile
                245                 250                 255

Phe Tyr Lys Arg Ser Tyr Ser Lys Lys Asn Lys Ser Gly Gly Lys Asp
            260                 265                 270

Ser Lys Lys Asn Asp Asp Gly Asn Asn Glu Asp Gln Cys His Lys Ala
        275                 280                 285

Met Lys Asp Ile Ser Glu Gly Ala Lys Glu Val Val Gly His Ala Ala
    290                 295                 300

Lys Asp Ala Gly Lys Leu Val Ala Thr Arg Val Arg Cys Lys Val
305                 310                 315
```

<210> SEQ ID NO 45
<211> LENGTH: 819
<212> TYPE: DNA
<213> ORGANISM: Thalassiosira pseudonana
<220> FEATURE:
<221> NAME/KEY: CDS
<222> LOCATION: (1)..(819)
<223> OTHER INFORMATION: delta5-elongase

<400> SEQUENCE: 45

```
atg gac gcc tac aac gct gca atg gat aag atc ggt gcc gcc atc atc    48
Met Asp Ala Tyr Asn Ala Ala Met Asp Lys Ile Gly Ala Ala Ile Ile
 1               5                  10                  15 gat tgg tct gat ccc gat gga aag ttc cgt gcc gat aga gag gac tgg    96
Asp Trp Ser Asp Pro Asp Gly Lys Phe Arg Ala Asp Arg Glu Asp Trp
                20                  25                  30 tgg ctc tgc gac ttc cgt agc gcc atc acc atc gcc ctc atc tac atc   144
Trp Leu Cys Asp Phe Arg Ser Ala Ile Thr Ile Ala Leu Ile Tyr Ile
            35                  40                  45
```

```
gcc ttc gtc atc ctc ggt tcc gcc gtc atg caa tcc ctc ccc gca atg      192
Ala Phe Val Ile Leu Gly Ser Ala Val Met Gln Ser Leu Pro Ala Met
     50                  55                  60 gat ccc tac ccc atc aaa ttc ctc tac aac gtc tcc caa atc ttc ctt      240
Asp Pro Tyr Pro Ile Lys Phe Leu Tyr Asn Val Ser Gln Ile Phe Leu
 65                  70                  75                  80 tgt gcc tac atg act gtc gag gcg gga ttt ttg gcc tac cgc aat gga      288
Cys Ala Tyr Met Thr Val Glu Ala Gly Phe Leu Ala Tyr Arg Asn Gly
             85                  90                  95 tat acc gtc atg cct tgc aat cat ttc aat gtg aat gat cct ccc gtg      336
Tyr Thr Val Met Pro Cys Asn His Phe Asn Val Asn Asp Pro Pro Val
            100                 105                 110 gcg aat ctt ctt tgg ttg ttt tat att tcc aag gtg tgg gac ttt tgg      384
Ala Asn Leu Leu Trp Leu Phe Tyr Ile Ser Lys Val Trp Asp Phe Trp
        115                 120                 125 gat acc att ttc att gtg ttg ggg aag aag tgg cgt caa tta tct ttc      432
Asp Thr Ile Phe Ile Val Leu Gly Lys Lys Trp Arg Gln Leu Ser Phe
130                 135                 140 ttg cat gta tac cat cac acc acc atc ttt cta ttc tat tgg ctg aat      480
Leu His Val Tyr His His Thr Thr Ile Phe Leu Phe Tyr Trp Leu Asn
145                 150                 155                 160 gcc aat gtc ttg tac gat ggt gac atc ttc ctt acc atc ttg ctc aat      528
Ala Asn Val Leu Tyr Asp Gly Asp Ile Phe Leu Thr Ile Leu Leu Asn
                165                 170                 175 gga ttc atc cac acg gtg atg tac acg tat tac ttc atc tgt atg cat      576
Gly Phe Ile His Thr Val Met Tyr Thr Tyr Tyr Phe Ile Cys Met His
            180                 185                 190 acc aaa gat tcc aag acg ggc aag agt ctt cct ata tgg tgg aag tcg      624
Thr Lys Asp Ser Lys Thr Gly Lys Ser Leu Pro Ile Trp Trp Lys Ser
        195                 200                 205 agt ttg acg gcg ttt cag ttg ttg caa ttc act atc atg atg agt cag      672
Ser Leu Thr Ala Phe Gln Leu Leu Gln Phe Thr Ile Met Met Ser Gln
210                 215                 220 gct acc tac ctt gtc ttc cac ggg tgt gat aag gtg tcg ctt cgt atc      720
Ala Thr Tyr Leu Val Phe His Gly Cys Asp Lys Val Ser Leu Arg Ile
225                 230                 235                 240 acg att gtg tac ttt gtg tcc ctt ttg agt ttg ttc ttc ctt ttt gct      768
Thr Ile Val Tyr Phe Val Ser Leu Leu Ser Leu Phe Phe Leu Phe Ala
                245                 250                 255 cag ttc ttt gtg caa tca tac atg gca ccc aaa aag aag aag agt gct      816
Gln Phe Phe Val Gln Ser Tyr Met Ala Pro Lys Lys Lys Lys Ser Ala
            260                 265                 270 tag                                                                  819

<210> SEQ ID NO 46
<211> LENGTH: 272
<212> TYPE: PRT
<213> ORGANISM: Thalassiosira pseudonana

<400> SEQUENCE: 46

Met Asp Ala Tyr Asn Ala Ala Met Asp Lys Ile Gly Ala Ala Ile Ile
 1               5                  10                  15

Asp Trp Ser Asp Pro Asp Gly Lys Phe Arg Ala Asp Arg Glu Asp Trp
             20                  25                  30

Trp Leu Cys Asp Phe Arg Ser Ala Ile Thr Ile Ala Leu Ile Tyr Ile
         35                  40                  45

Ala Phe Val Ile Leu Gly Ser Ala Val Met Gln Ser Leu Pro Ala Met
     50                  55                  60
```

```
Asp Pro Tyr Pro Ile Lys Phe Leu Tyr Asn Val Ser Gln Ile Phe Leu
 65                  70                  75                  80

Cys Ala Tyr Met Thr Val Glu Ala Gly Phe Leu Ala Tyr Arg Asn Gly
                 85                  90                  95

Tyr Thr Val Met Pro Cys Asn His Phe Asn Val Asn Asp Pro Pro Val
            100                 105                 110

Ala Asn Leu Leu Trp Leu Phe Tyr Ile Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Ser Leu Leu Ser Leu Phe Phe Leu Phe Ala
                245                 250                 255

Gln Phe Phe Val Gln Ser Tyr Met Ala Pro Lys Lys Lys Ser Ala
            260                 265                 270

<210> SEQ ID NO 47
<211> LENGTH: 936
<212> TYPE: DNA
<213> ORGANISM: Crypthecodinium cohnii
<220> FEATURE:
<221> NAME/KEY: CDS
<222> LOCATION: (1)..(936)
<223> OTHER INFORMATION: delta5-elongase

<400> SEQUENCE: 47 atg tct gcc ttc atg act ctc cca cag gct ctc tcc gat gtg acc tcg      48
Met Ser Ala Phe Met Thr Leu Pro Gln Ala Leu Ser Asp Val Thr Ser
  1               5                  10                  15 gcc ttg gtc acg ctg gga aag gat gtc tcc agc cct tca gct ttt caa      96
Ala Leu Val Thr Leu Gly Lys Asp Val Ser Ser Pro Ser Ala Phe Gln
             20                  25                  30 gct gtc act ggc ttc tgc agg gag cag tgg ggg att ccg aca gta ttc     144
Ala Val Thr Gly Phe Cys Arg Glu Gln Trp Gly Ile Pro Thr Val Phe
         35                  40                  45 tgc ctg ggc tac ttg gcc atg gtc tac gcg gcc aga aga ccc ctc ccg     192
Cys Leu Gly Tyr Leu Ala Met Val Tyr Ala Ala Arg Arg Pro Leu Pro
     50                  55                  60 cag cac ggc tac atg gtt gcg gtg gac cgt tgc ttc gct gct tgg aac     240
Gln His Gly Tyr Met Val Ala Val Asp Arg Cys Phe Ala Ala Trp Asn
 65                  70                  75                  80 ttg gct ctc tct gtc ttc agc act tgg ggc ttc tac cac atg gct gtc     288
Leu Ala Leu Ser Val Phe Ser Thr Trp Gly Phe Tyr His Met Ala Val
                 85                  90                  95 ggg ctc tac aac atg aca gag acg agg ggc ttg caa ttc acc atc tgc     336
Gly Leu Tyr Asn Met Thr Glu Thr Arg Gly Leu Gln Phe Thr Ile Cys
            100                 105                 110
```

```
ggt tcg act ggg gag ctc gtg cag aac ctt cag act ggc cca acc gct    384
Gly Ser Thr Gly Glu Leu Val Gln Asn Leu Gln Thr Gly Pro Thr Ala
        115                 120                 125 ctg gcg ctc tgc ctc ttc tgc ttc agc aag atc ccc gag ttg atg gac    432
Leu Ala Leu Cys Leu Phe Cys Phe Ser Lys Ile Pro Glu Leu Met Asp
130                 135                 140 acg gtg ttt ctc atc ctg aag gcc aag aag gtc cgc ttc ttg cag tgg    480
Thr Val Phe Leu Ile Leu Lys Ala Lys Lys Val Arg Phe Leu Gln Trp
145                 150                 155                 160 tac cac cat gcc aca gtc atg ctc ttc tgt tgg ctc gcc ctc gcg acg    528
Tyr His His Ala Thr Val Met Leu Phe Cys Trp Leu Ala Leu Ala Thr
                165                 170                 175 gag tac act cct ggc ttg tgg ttt gcg gcg acg aac tac ttc gtg cac    576
Glu Tyr Thr Pro Gly Leu Trp Phe Ala Ala Thr Asn Tyr Phe Val His
            180                 185                 190 tcc atc atg tac atg tac ttc ttc ctc atg acc ttc aag tcg gcc gcg    624
Ser Ile Met Tyr Met Tyr Phe Phe Leu Met Thr Phe Lys Ser Ala Ala
        195                 200                 205 aag gtg gtg aag ccc atc gcc cct ctc atc aca gtt atc cag att gct    672
Lys Val Val Lys Pro Ile Ala Pro Leu Ile Thr Val Ile Gln Ile Ala
210                 215                 220 cag atg gtc tgg ggc ctc atc gtc aac ggc atc gcc atc acc acc ttc    720
Gln Met Val Trp Gly Leu Ile Val Asn Gly Ile Ala Ile Thr Thr Phe
225                 230                 235                 240 ttc acg act ggt gcc tgc cag atc cag tct gtg act gtg tat tcg gcc    768
Phe Thr Thr Gly Ala Cys Gln Ile Gln Ser Val Thr Val Tyr Ser Ala
                245                 250                 255 atc atc atg tac gct tcg tac ttc tac ctg ttc tcc cag ctc ttc ttc    816
Ile Ile Met Tyr Ala Ser Tyr Phe Tyr Leu Phe Ser Gln Leu Phe Phe
            260                 265                 270 gag gcc cat ggt gcc gct ggc aag aac aag aag aag ttg acc cgc gag    864
Glu Ala His Gly Ala Ala Gly Lys Asn Lys Lys Lys Leu Thr Arg Glu
        275                 280                 285 ctc tct cga aaa atc tcg gag gct ctc ctg aac acc ggt gac gag gtt    912
Leu Ser Arg Lys Ile Ser Glu Ala Leu Leu Asn Thr Gly Asp Glu Val
    290                 295                 300 tcc aag cac ctg aag gtg aat tga                                    936
Ser Lys His Leu Lys Val Asn
305                 310
```

<210> SEQ ID NO 48
<211> LENGTH: 311
<212> TYPE: PRT
<213> ORGANISM: Crypthecodinium cohnii

<400> SEQUENCE: 48

```
Met Ser Ala Phe Met Thr Leu Pro Gln Ala Leu Ser Asp Val Thr Ser
1               5                   10                  15

Ala Leu Val Thr Leu Gly Lys Asp Val Ser Ser Pro Ser Ala Phe Gln
            20                  25                  30

Ala Val Thr Gly Phe Cys Arg Glu Gln Trp Gly Ile Pro Thr Val Phe
        35                  40                  45

Cys Leu Gly Tyr Leu Ala Met Val Tyr Ala Ala Arg Arg Pro Leu Pro
    50                  55                  60

Gln His Gly Tyr Met Val Ala Val Asp Arg Cys Phe Ala Ala Trp Asn
65                  70                  75                  80

Leu Ala Leu Ser Val Phe Ser Thr Trp Gly Phe Tyr His Met Ala Val
                85                  90                  95

Gly Leu Tyr Asn Met Thr Glu Thr Arg Gly Leu Gln Phe Thr Ile Cys
```

```
                100             105             110
Gly Ser Thr Gly Glu Leu Val Gln Asn Leu Gln Thr Gly Pro Thr Ala
        115                 120                 125

Leu Ala Leu Cys Leu Phe Cys Phe Ser Lys Ile Pro Glu Leu Met Asp
    130                 135                 140

Thr Val Phe Leu Ile Leu Lys Ala Lys Lys Val Arg Phe Leu Gln Trp
145                 150                 155                 160

Tyr His His Ala Thr Val Met Leu Phe Cys Trp Leu Ala Leu Ala Thr
                165                 170                 175

Glu Tyr Thr Pro Gly Leu Trp Phe Ala Ala Thr Asn Tyr Phe Val His
                180                 185                 190

Ser Ile Met Tyr Met Tyr Phe Phe Leu Met Thr Phe Lys Ser Ala Ala
                195                 200                 205

Lys Val Val Lys Pro Ile Ala Pro Leu Ile Thr Val Ile Gln Ile Ala
        210                 215                 220

Gln Met Val Trp Gly Leu Ile Val Asn Gly Ile Ala Ile Thr Thr Phe
225                 230                 235                 240

Phe Thr Thr Gly Ala Cys Gln Ile Gln Ser Val Thr Val Tyr Ser Ala
                245                 250                 255

Ile Ile Met Tyr Ala Ser Tyr Phe Tyr Leu Phe Ser Gln Leu Phe Phe
                260                 265                 270

Glu Ala His Gly Ala Ala Gly Lys Asn Lys Lys Lys Leu Thr Arg Glu
        275                 280                 285

Leu Ser Arg Lys Ile Ser Glu Ala Leu Leu Asn Thr Gly Asp Glu Val
        290                 295                 300

Ser Lys His Leu Lys Val Asn
305                 310

<210> SEQ ID NO 49
<211> LENGTH: 927
<212> TYPE: DNA
<213> ORGANISM: Crypthecodinium cohnii
<220> FEATURE:
<221> NAME/KEY: CDS
<222> LOCATION: (1)..(927)
<223> OTHER INFORMATION: delta5-elongase

<400> SEQUENCE: 49 atg gct tcc tac caa caa gca ttc tcc gaa ttg gct aga gct ttg tcc    48
Met Ala Ser Tyr Gln Gln Ala Phe Ser Glu Leu Ala Arg Ala Leu Ser
1               5                   10                  15 act ttg aac cac gac ttc tcc agc gtc gag cca ttc aaa gtc gtg acg    96
Thr Leu Asn His Asp Phe Ser Ser Val Glu Pro Phe Lys Val Val Thr
            20                  25                  30 cag ttc tgc agg gac cag tgg gcg atc ccg aca gtc ttt tgc atc ggt   144
Gln Phe Cys Arg Asp Gln Trp Ala Ile Pro Thr Val Phe Cys Ile Gly
        35                  40                  45 tac ttg gca atg gtc tac gcc acg cga aga cct atc gcg aag cac ccc   192
Tyr Leu Ala Met Val Tyr Ala Thr Arg Arg Pro Ile Ala Lys His Pro
    50                  55                  60 tac atg tct ctc gtg gat cgc tgc ttt gcg gcc tgg aac ttg ggc ctc   240
Tyr Met Ser Leu Val Asp Arg Cys Phe Ala Ala Trp Asn Leu Gly Leu
65                  70                  75                  80 tcg ctc ttc agt tgc tgg ggc ttc tac cac atg gca gtg gga ctc tcc   288
Ser Leu Phe Ser Cys Trp Gly Phe Tyr His Met Ala Val Gly Leu Ser
                85                  90                  95 cac acc act tgg aat ttc ggg ctc cag ttc acc atc tgc ggc agc acc   336
His Thr Thr Trp Asn Phe Gly Leu Gln Phe Thr Ile Cys Gly Ser Thr
```

```
acg gag ctt gtg aat ggc ttc cag aag ggc ccg gcg gcc ctc gcc ctc      384
Thr Glu Leu Val Asn Gly Phe Gln Lys Gly Pro Ala Ala Leu Ala Leu
        115                 120                 125 atc ctg ttc tgc ttc tcc aag atc ccg gag ttg ggc gac acc gtc ttc      432
Ile Leu Phe Cys Phe Ser Lys Ile Pro Glu Leu Gly Asp Thr Val Phe
130                 135                 140 ttg atc ttg aag gga aag aag gtc cgc ttc ttg cag tgg tac cac cac      480
Leu Ile Leu Lys Gly Lys Lys Val Arg Phe Leu Gln Trp Tyr His His
145                 150                 155                 160 acg acc gtg atg ctc ttc tgt tgg atg gcc ttg gcg act gag tac act      528
Thr Thr Val Met Leu Phe Cys Trp Met Ala Leu Ala Thr Glu Tyr Thr
                165                 170                 175 cct gga ttg tgg ttc gcg gcc acg aac tac ttc gtg cac tcc atc atg      576
Pro Gly Leu Trp Phe Ala Ala Thr Asn Tyr Phe Val His Ser Ile Met
            180                 185                 190 tac atg tac ttc ttc ctc atg acc ttc aag acg gcc gcc ggc atc atc      624
Tyr Met Tyr Phe Phe Leu Met Thr Phe Lys Thr Ala Ala Gly Ile Ile
        195                 200                 205 aag ccc atc gcg cct ctc atc acc atc atc cag atc tcc cag atg gtc      672
Lys Pro Ile Ala Pro Leu Ile Thr Ile Ile Gln Ile Ser Gln Met Val
210                 215                 220 tgg ggc ttg gtc gtg aac gcc atc gcc gtc ggc acc ttc ttc acc aca      720
Trp Gly Leu Val Val Asn Ala Ile Ala Val Gly Thr Phe Phe Thr Thr
225                 230                 235                 240 ggc aac tgc cag atc cag gca gtg aca gtc tac tcc gcc atc gtg atg      768
Gly Asn Cys Gln Ile Gln Ala Val Thr Val Tyr Ser Ala Ile Val Met
                245                 250                 255 tac gcc tcc tac ttc tac ctc ttc ggc cag ctc ttc ttc gag gcc cag      816
Tyr Ala Ser Tyr Phe Tyr Leu Phe Gly Gln Leu Phe Phe Glu Ala Gln
            260                 265                 270 ggt tcg gct gga aag gac aag aag aag ttg gcc cga gag ctg agc cga      864
Gly Ser Ala Gly Lys Asp Lys Lys Lys Leu Ala Arg Glu Leu Ser Arg
        275                 280                 285 aag gtc tcg cgg gct ctc aca gca acg ggc gaa gag gtg tcg aag cac      912
Lys Val Ser Arg Ala Leu Thr Ala Thr Gly Glu Glu Val Ser Lys His
290                 295                 300 atg aag gtg aat tga                                                   927
Met Lys Val Asn
305
```

<210> SEQ ID NO 50
<211> LENGTH: 308
<212> TYPE: PRT
<213> ORGANISM: Crypthecodinium cohnii

<400> SEQUENCE: 50

```
Met Ala Ser Tyr Gln Gln Ala Phe Ser Glu Leu Ala Arg Ala Leu Ser
1               5                   10                  15

Thr Leu Asn His Asp Phe Ser Ser Val Glu Pro Phe Lys Val Val Thr
            20                  25                  30

Gln Phe Cys Arg Asp Gln Trp Ala Ile Pro Thr Val Phe Cys Ile Gly
        35                  40                  45

Tyr Leu Ala Met Val Tyr Ala Thr Arg Arg Pro Ile Ala Lys His Pro
    50                  55                  60

Tyr Met Ser Leu Val Asp Arg Cys Phe Ala Ala Trp Asn Leu Gly Leu
65                  70                  75                  80

Ser Leu Phe Ser Cys Trp Gly Phe Tyr His Met Ala Val Gly Leu Ser
                85                  90                  95
```

```
His Thr Thr Trp Asn Phe Gly Leu Gln Phe Thr Ile Cys Gly Ser Thr
            100                 105                 110

Thr Glu Leu Val Asn Gly Phe Gln Lys Gly Pro Ala Ala Leu Ala Leu
        115                 120                 125

Ile Leu Phe Cys Phe Ser Lys Ile Pro Glu Leu Gly Asp Thr Val Phe
    130                 135                 140

Leu Ile Leu Lys Gly Lys Lys Val Arg Phe Leu Gln Trp Tyr His His
145                 150                 155                 160

Thr Thr Val Met Leu Phe Cys Trp Met Ala Leu Ala Thr Glu Tyr Thr
                165                 170                 175

Pro Gly Leu Trp Phe Ala Ala Thr Asn Tyr Phe Val His Ser Ile Met
            180                 185                 190

Tyr Met Tyr Phe Phe Leu Met Thr Phe Lys Thr Ala Ala Gly Ile Ile
        195                 200                 205

Lys Pro Ile Ala Pro Leu Ile Thr Ile Ile Gln Ile Ser Gln Met Val
    210                 215                 220

Trp Gly Leu Val Val Asn Ala Ile Ala Val Gly Thr Phe Phe Thr Thr
225                 230                 235                 240

Gly Asn Cys Gln Ile Gln Ala Val Thr Val Tyr Ser Ala Ile Val Met
                245                 250                 255

Tyr Ala Ser Tyr Phe Tyr Leu Phe Gly Gln Leu Phe Phe Glu Ala Gln
            260                 265                 270

Gly Ser Ala Gly Lys Asp Lys Lys Leu Ala Arg Glu Leu Ser Arg
        275                 280                 285

Lys Val Ser Arg Ala Leu Thr Ala Thr Gly Glu Glu Val Ser Lys His
    290                 295                 300

Met Lys Val Asn
305

<210> SEQ ID NO 51
<211> LENGTH: 795
<212> TYPE: DNA
<213> ORGANISM: Oncorhynchus mykiss
<220> FEATURE:
<221> NAME/KEY: CDS
<222> LOCATION: (1)..(795)
<223> OTHER INFORMATION: delta5-elongase

<400> SEQUENCE: 51 atg gct tca aca tgg caa agc gtt cag tcc atg cgc cag tgg att tta      48
Met Ala Ser Thr Trp Gln Ser Val Gln Ser Met Arg Gln Trp Ile Leu
1               5                   10                  15 gag aat gga gat aaa agg aca gac cca tgg cta ctg gtc tac tcc cct      96
Glu Asn Gly Asp Lys Arg Thr Asp Pro Trp Leu Leu Val Tyr Ser Pro
                20                  25                  30 atg cca gtg gcc att ata ttc ctc ctc tat ctt ggt gtg gtc tgg gct     144
Met Pro Val Ala Ile Ile Phe Leu Leu Tyr Leu Gly Val Val Trp Ala
            35                  40                  45 ggg ccc aag ctg atg aaa cgc agg gaa cca gtt gat ctc aag gct gta     192
Gly Pro Lys Leu Met Lys Arg Arg Glu Pro Val Asp Leu Lys Ala Val
        50                  55                  60 ctc att gtc tac aac ttc gcc atg gtc tgc ctg tct gtc tac atg ttc     240
Leu Ile Val Tyr Asn Phe Ala Met Val Cys Leu Ser Val Tyr Met Phe
65                  70                  75                  80 cat gag ttc ttg gtc acg tcc ttg ctg tct aac tac agt tac ctg tgt     288
His Glu Phe Leu Val Thr Ser Leu Leu Ser Asn Tyr Ser Tyr Leu Cys
                85                  90                  95
```

| | | |
|---|---|---|
| caa cct gtg gat tac agc act agt cca ctg gcg atg agg atg gcc aaa<br>Gln Pro Val Asp Tyr Ser Thr Ser Pro Leu Ala Met Arg Met Ala Lys<br>100                105               110 | | 336 |
| gta tgc tgg tgg ttt ttc ttc tcc aag gtc ata gaa ttg gct gac acg<br>Val Cys Trp Trp Phe Phe Phe Ser Lys Val Ile Glu Leu Ala Asp Thr<br>      115               120               125 | | 384 |
| gtg ttc ttc atc ctg agg aag aag aac agt cag ctg act ttc ctg cat<br>Val Phe Phe Ile Leu Arg Lys Lys Asn Ser Gln Leu Thr Phe Leu His<br>130                135               140 | | 432 |
| gtc tat cac cat ggc acc atg atc ttc aac tgg tgg gca ggg gtc aag<br>Val Tyr His His Gly Thr Met Ile Phe Asn Trp Trp Ala Gly Val Lys<br>145                150               155               160 | | 480 |
| tat ctg gct gga ggc caa tcg ttc ttc atc ggc ctg ctc aat acc ttt<br>Tyr Leu Ala Gly Gly Gln Ser Phe Phe Ile Gly Leu Leu Asn Thr Phe<br>                    165               170               175 | | 528 |
| gtg cac atc gtg atg tac tct tac tac gga ctg gct gcc ctg ggg cct<br>Val His Ile Val Met Tyr Ser Tyr Tyr Gly Leu Ala Ala Leu Gly Pro<br>                  180               185               190 | | 576 |
| cac acg cag aag tac tta tgg tgg aag cgc tat ctg acc tca ctg cag<br>His Thr Gln Lys Tyr Leu Trp Trp Lys Arg Tyr Leu Thr Ser Leu Gln<br>              195               200               205 | | 624 |
| ctg ctc cag ttt gtc ctg ttg acc act cac act ggc tac aac ctc ttc<br>Leu Leu Gln Phe Val Leu Leu Thr Thr His Thr Gly Tyr Asn Leu Phe<br>210                215               220 | | 672 |
| act gag tgt gac ttc ccg gac tcc atg aac gct gtg gtg ttt gcc tac<br>Thr Glu Cys Asp Phe Pro Asp Ser Met Asn Ala Val Val Phe Ala Tyr<br>225                230               235               240 | | 720 |
| tgt gtc agt ctc att gct ctc ttc agc aac ttc tac tat cag agc tac<br>Cys Val Ser Leu Ile Ala Leu Phe Ser Asn Phe Tyr Tyr Gln Ser Tyr<br>                    245               250               255 | | 768 |
| ctc aac agg aag agc aag aag aca taa<br>Leu Asn Arg Lys Ser Lys Lys Thr<br>              260 | | 795 |

```
<210> SEQ ID NO 52
<211> LENGTH: 264
<212> TYPE: PRT
<213> ORGANISM: Oncorhynchus mykiss

<400> SEQUENCE: 52
```

Met Ala Ser Thr Trp Gln Ser Val Gln Ser Met Arg Gln Trp Ile Leu
1                 5                      10                   15

Glu Asn Gly Asp Lys Arg Thr Asp Pro Trp Leu Leu Val Tyr Ser Pro
                    20                   25                   30

Met Pro Val Ala Ile Ile Phe Leu Leu Tyr Leu Gly Val Val Trp Ala
                    35                   40                   45

Gly Pro Lys Leu Met Lys Arg Arg Glu Pro Val Asp Leu Lys Ala Val
    50                55                   60

Leu Ile Val Tyr Asn Phe Ala Met Val Cys Leu Ser Val Tyr Met Phe
65                70                     75                     80

His Glu Phe Leu Val Thr Ser Leu Leu Ser Asn Tyr Ser Tyr Leu Cys
                    85                   90                   95

Gln Pro Val Asp Tyr Ser Thr Ser Pro Leu Ala Met Arg Met Ala Lys
                 100              105              110

Val Cys Trp Trp Phe Phe Phe Ser Lys Val Ile Glu Leu Ala Asp Thr
      115               120               125

Val Phe Phe Ile Leu Arg Lys Lys Asn Ser Gln Leu Thr Phe Leu His
130                135               140

```
Val Tyr His His Gly Thr Met Ile Phe Asn Trp Trp Ala Gly Val Lys
145                 150                 155                 160

Tyr Leu Ala Gly Gly Gln Ser Phe Phe Ile Gly Leu Leu Asn Thr Phe
            165                 170                 175

Val His Ile Val Met Tyr Ser Tyr Tyr Gly Leu Ala Ala Leu Gly Pro
            180                 185                 190

His Thr Gln Lys Tyr Leu Trp Trp Lys Arg Tyr Leu Thr Ser Leu Gln
            195                 200                 205

Leu Leu Gln Phe Val Leu Leu Thr Thr His Thr Gly Tyr Asn Leu Phe
    210                 215                 220

Thr Glu Cys Asp Phe Pro Asp Ser Met Asn Ala Val Val Phe Ala Tyr
225                 230                 235                 240

Cys Val Ser Leu Ile Ala Leu Phe Ser Asn Phe Tyr Tyr Gln Ser Tyr
                245                 250                 255

Leu Asn Arg Lys Ser Lys Lys Thr
            260

<210> SEQ ID NO 53
<211> LENGTH: 885
<212> TYPE: DNA
<213> ORGANISM: Oncorhynchus mykiss
<220> FEATURE:
<221> NAME/KEY: CDS
<222> LOCATION: (1)..(885)
<223> OTHER INFORMATION: delta5-elongase

<400> SEQUENCE: 53 atg gag act ttt aat tat aaa cta aac atg tac ata gac tca tgg atg       48
Met Glu Thr Phe Asn Tyr Lys Leu Asn Met Tyr Ile Asp Ser Trp Met
1               5                   10                  15 ggt ccc aga gat gag cgg gta cag gga tgg ctg ctt ctg gac aac tac       96
Gly Pro Arg Asp Glu Arg Val Gln Gly Trp Leu Leu Leu Asp Asn Tyr
                20                  25                  30 cct cca acc ttt gca cta aca gtc atg tac ctg ctg atc gta tgg atg      144
Pro Pro Thr Phe Ala Leu Thr Val Met Tyr Leu Leu Ile Val Trp Met
            35                  40                  45 ggg ccc aag tac atg aga cac aga cag ccg gtg tct tgc cgg ggt ctc      192
Gly Pro Lys Tyr Met Arg His Arg Gln Pro Val Ser Cys Arg Gly Leu
        50                  55                  60 ctc ttg gtc tac aat ctg ggc ctc acg atc ttg tcc ttc tat atg ttc      240
Leu Leu Val Tyr Asn Leu Gly Leu Thr Ile Leu Ser Phe Tyr Met Phe
65                  70                  75                  80 tat gag atg gtg tct gct gtg tgg cac ggg gat tat aac ttc ttt tgc      288
Tyr Glu Met Val Ser Ala Val Trp His Gly Asp Tyr Asn Phe Phe Cys
                85                  90                  95 caa gac aca cac agt gca gga gaa acc gat acc aag atc ata aat gtg      336
Gln Asp Thr His Ser Ala Gly Glu Thr Asp Thr Lys Ile Ile Asn Val
            100                 105                 110 ctg tgg tac tac ttc tcc aag ctc ata gag ttt atg gat acc ttc          384
Leu Trp Trp Tyr Tyr Phe Ser Lys Leu Ile Glu Phe Met Asp Thr Phe
        115                 120                 125 ttc ttc atc ctg cgg aag aac aac cat caa atc acg ttt ctg cac atc      432
Phe Phe Ile Leu Arg Lys Asn Asn His Gln Ile Thr Phe Leu His Ile
    130                 135                 140 tac cac cat gct agc atg ctc aac atc tgg tgg ttc gtc atg aac tgg      480
Tyr His His Ala Ser Met Leu Asn Ile Trp Trp Phe Val Met Asn Trp
145                 150                 155                 160 gtg ccc tgt ggt cac tcc tac ttt ggt gcc tcc ctg aac agc ttc atc      528
Val Pro Cys Gly His Ser Tyr Phe Gly Ala Ser Leu Asn Ser Phe Ile
                165                 170                 175
```

```
cat gtc ctg atg tac tct tac tat ggg ctc tct gct gtc ccg gcc ttg      576
His Val Leu Met Tyr Ser Tyr Tyr Gly Leu Ser Ala Val Pro Ala Leu
        180                 185                 190 cgg ccc tat cta tgg tgg aag aaa tac atc aca caa gta cag ctg att      624
Arg Pro Tyr Leu Trp Trp Lys Lys Tyr Ile Thr Gln Val Gln Leu Ile
        195                 200                 205 cag ttc ttt ttg acc atg tcc cag acg ata tgt gca gtc att tgg cca      672
Gln Phe Phe Leu Thr Met Ser Gln Thr Ile Cys Ala Val Ile Trp Pro
    210                 215                 220 tgt gat ttc ccc aga ggg tgg ctg tat ttc cag ata ttc tat gtc atc      720
Cys Asp Phe Pro Arg Gly Trp Leu Tyr Phe Gln Ile Phe Tyr Val Ile
225                 230                 235                 240 aca ctt att gcc ctt ttc tca aac ttc tac att cag act tac aag aaa      768
Thr Leu Ile Ala Leu Phe Ser Asn Phe Tyr Ile Gln Thr Tyr Lys Lys
                245                 250                 255 cac ctt gtt tca caa aag aag gag tat cat cag aat ggc tct gtt gct      816
His Leu Val Ser Gln Lys Lys Glu Tyr His Gln Asn Gly Ser Val Ala
            260                 265                 270 tca ttg aat ggc cat gtg aat ggg gtg aca ccc acg gaa acc att aca      864
Ser Leu Asn Gly His Val Asn Gly Val Thr Pro Thr Glu Thr Ile Thr
        275                 280                 285 cac agg aaa gtg agg ggg gac                                          885
His Arg Lys Val Arg Gly Asp
        290                 295

<210> SEQ ID NO 54
<211> LENGTH: 295
<212> TYPE: PRT
<213> ORGANISM: Oncorhynchus mykiss

<400> SEQUENCE: 54

Met Glu Thr Phe Asn Tyr Lys Leu Asn Met Tyr Ile Asp Ser Trp Met
1               5                   10                  15

Gly Pro Arg Asp Glu Arg Val Gln Gly Trp Leu Leu Leu Asp Asn Tyr
            20                  25                  30

Pro Pro Thr Phe Ala Leu Thr Val Met Tyr Leu Leu Ile Val Trp Met
        35                  40                  45

Gly Pro Lys Tyr Met Arg His Arg Gln Pro Val Ser Cys Arg Gly Leu
    50                  55                  60

Leu Leu Val Tyr Asn Leu Gly Leu Thr Ile Leu Ser Phe Tyr Met Phe
65                  70                  75                  80

Tyr Glu Met Val Ser Ala Val Trp His Gly Asp Tyr Asn Phe Phe Cys
                85                  90                  95

Gln Asp Thr His Ser Ala Gly Glu Thr Asp Thr Lys Ile Ile Asn Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Phe Leu His Ile
    130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Ser Leu Asn Ser Phe Ile
                165                 170                 175

His Val Leu Met Tyr Ser Tyr Tyr Gly Leu Ser Ala Val Pro Ala Leu
            180                 185                 190

Arg Pro Tyr Leu Trp Trp Lys Lys Tyr Ile Thr Gln Val Gln Leu Ile
        195                 200                 205
```

```
Gln Phe Phe Leu Thr Met Ser Gln Thr Ile Cys Ala Val Ile Trp Pro
    210                 215                 220
Cys Asp Phe Pro Arg Gly Trp Leu Tyr Phe Gln Ile Phe Tyr Val Ile
225                 230                 235                 240
Thr Leu Ile Ala Leu Phe Ser Asn Phe Tyr Ile Gln Thr Tyr Lys Lys
                245                 250                 255
His Leu Val Ser Gln Lys Lys Glu Tyr His Gln Asn Gly Ser Val Ala
            260                 265                 270
Ser Leu Asn Gly His Val Asn Gly Val Thr Pro Thr Glu Thr Ile Thr
        275                 280                 285
His Arg Lys Val Arg Gly Asp
    290                 295

<210> SEQ ID NO 55
<211> LENGTH: 6753
<212> TYPE: DNA
<213> ORGANISM: Oncorhynchus mykiss
<220> FEATURE:
<221> NAME/KEY: CDS
<222> LOCATION: (513)..(1397)
<223> OTHER INFORMATION: delta5-elongase

<400> SEQUENCE: 55
acggattaga agccgccgag cgggtgacag ccctccgaag gaagactctc ctccgtgcgt      60
cctcgtcctc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcatt aaccactttta actaatactt tcaacatttt    360
cggtttgtat tacttcttat tcaaatgtaa taaaagtatc aacaaaaaat tgttaatata     420
cctctatact ttaacgtcaa ggagaaaaaa ccccggatcg gactactagc agctgtaata     480
cgactcacta tagggaatat taagcttaca ta atg gag act ttt aat tat aaa      533
                                    Met Glu Thr Phe Asn Tyr Lys
                                    1               5 cta aac atg tac ata gac tca tgg atg ggt ccc aga gat gag cgg gta      581
Leu Asn Met Tyr Ile Asp Ser Trp Met Gly Pro Arg Asp Glu Arg Val
        10                  15                  20 cag gga tgg ctg ctt ctg gac aac tac cct cca acc ttt gca cta aca      629
Gln Gly Trp Leu Leu Leu Asp Asn Tyr Pro Pro Thr Phe Ala Leu Thr
    25                  30                  35 gtc atg tac ctg ctg atc gta tgg atg ggg ccc aag tac atg aga cac      677
Val Met Tyr Leu Leu Ile Val Trp Met Gly Pro Lys Tyr Met Arg His
40                  45                  50                  55 aga cag ccg gtg tct tgc cgg ggt ctc ctc ttg gtc tac aat ctg ggc      725
Arg Gln Pro Val Ser Cys Arg Gly Leu Leu Leu Val Tyr Asn Leu Gly
                60                  65                  70 ctc acg atc ttg tcc ttc tat atg ttc tat gag atg gtg tct gct gtg      773
Leu Thr Ile Leu Ser Phe Tyr Met Phe Tyr Glu Met Val Ser Ala Val
            75                  80                  85 tgg cac ggg gat tat aac ttc ttt tgc caa gac aca cac agt gca gga      821
Trp His Gly Asp Tyr Asn Phe Phe Cys Gln Asp Thr His Ser Ala Gly
        90                  95                  100 gaa acc gat acc aag atc ata aat gtg ctg tgg tgg tac tac ttc tcc      869
Glu Thr Asp Thr Lys Ile Ile Asn Val Leu Trp Trp Tyr Tyr Phe Ser
    105                 110                 115
```

| | | |
|---|---|---|
| aag ctc ata gag ttt atg gat acc ttc ttc ttc atc ctg cgg aag aac<br>Lys Leu Ile Glu Phe Met Asp Thr Phe Phe Phe Ile Leu Arg Lys Asn<br>120                        125                        130                       135 | 917 |
| aac cat caa atc acg ttt ctg cac atc tac cac cat gct agc atg ctc<br>Asn His Gln Ile Thr Phe Leu His Ile Tyr His His Ala Ser Met Leu<br>140                       145                      150 | 965 |
| aac atc tgg tgg ttc gtc atg aac tgg gtg ccc tgt ggt cac tcc tac<br>Asn Ile Trp Trp Phe Val Met Asn Trp Val Pro Cys Gly His Ser Tyr<br>                 155                       160                      165 | 1013 |
| ttt ggt gcc tcc ctg aac agc ttc atc cat gtc ctg atg tac tct tac<br>Phe Gly Ala Ser Leu Asn Ser Phe Ile His Val Leu Met Tyr Ser Tyr<br>       170                       175                       180 | 1061 |
| tat ggg ctc tct gct gtc ccg gcc ttg cgg ccc tat cta tgg tgg aag<br>Tyr Gly Leu Ser Ala Val Pro Ala Leu Arg Pro Tyr Leu Trp Trp Lys<br>185                       190                       195 | 1109 |
| aaa tac atc aca caa gta cag ctg att cag ttc ttt ttg acc atg tcc<br>Lys Tyr Ile Thr Gln Val Gln Leu Ile Gln Phe Phe Leu Thr Met Ser<br>200                       205                      210                      215 | 1157 |
| cag acg ata tgt gca gtc att tgg cca tgt gat ttc ccc aga ggg tgg<br>Gln Thr Ile Cys Ala Val Ile Trp Pro Cys Asp Phe Pro Arg Gly Trp<br>                220                       225                      230 | 1205 |
| ctg tat ttc cag ata ttc tat gtc atc aca ctt att gcc ctt ttc tca<br>Leu Tyr Phe Gln Ile Phe Tyr Val Ile Thr Leu Ile Ala Leu Phe Ser<br>     235                     240                      245 | 1253 |
| aac ttc tac att cag act tac aag aaa cac ctt gtt tca caa aag aag<br>Asn Phe Tyr Ile Gln Thr Tyr Lys Lys His Leu Val Ser Gln Lys Lys<br>250                       255                      260 | 1301 |
| gag tat cat cag aat ggc tct gtt gct tca ttg aat ggc cat gtg aat<br>Glu Tyr His Gln Asn Gly Ser Val Ala Ser Leu Asn Gly His Val Asn<br>     265                     270                      275 | 1349 |
| ggg gtg aca ccc acg gaa acc att aca cac agg aaa gtg agg ggg gac<br>Gly Val Thr Pro Thr Glu Thr Ile Thr His Arg Lys Val Arg Gly Asp<br>280                       285                      290                      295 | 1397 |
| tgaaggatcc actagtaacg gccgccagtg tgctggaatt ctgcagatat ccagcacagt | 1457 |
| ggcggccgct cgagtctaga gggcccttcg aaggtaagcc tatccctaac cctctcctcg | 1517 |
| gtctcgattc tacgcgtacc ggtcatcatc accatcacca ttgagtttaa accgctgatc | 1577 |
| cctagagggc cgcatcatgt aattagttat gtcacgctta cattcacgcc ctcccccac | 1637 |
| atccgctcta accgaaaagg aaggagttag acaacctgaa gtctaggtcc ctatttattt | 1697 |
| ttttatagtt atgttagtat taagaacgtt atttatattt caaatttttc ttttttttct | 1757 |
| gtacagacgc gtgtacgcat gtaacattat actgaaaacc ttgcttgaga aggttttggg | 1817 |
| acgctcgaag gctttaattt gcaagctgcg gccctgcatt aatgaatcgg ccaacgcgcg | 1877 |
| gggagaggcg gtttgcgtat tgggcgctct tccgcttcct cgctcactga ctcgctgcgc | 1937 |
| tcggtcgttc ggctgcggcg agcggtatca gctcactcaa aggcggtaat acggttatcc | 1997 |
| acagaatcag gggataacgc aggaaagaac atgtgagcaa aaggccagca aaagcccagg | 2057 |
| aaccgtaaaa aggccgcgtt gctggcgttt ttccataggc tccgccccc tgacgagcat | 2117 |
| cacaaaaatc gacgctcaag tcagaggtgg cgaaacccga caggactata aagataccag | 2177 |
| gcgtttcccc ctggaagctc cctcgtgcgc tctcctgttc cgaccctgcc gcttaccgga | 2237 |
| tacctgtccg cctttctccc ttcgggaagc gtggcgcttt ctcatagctc acgctgtagg | 2297 |
| tatctcagtt cggtgtaggt cgttcgctcc aagctgggct gtgtgcacga acccccgtt | 2357 |
| cagcccgacc gctgcgcctt atccggtaac tatcgtcttg agtccaaccc ggtaagacac | 2417 |
| gacttatcgc cactggcagc agccactggt aacaggatta gcagagcgag gtatgtaggc | 2477 |

```
ggtgctacag agttcttgaa gtggtggcct aactacggct acactagaag gacagtattt    2537
ggtatctgcg ctctgctgaa gccagttacc ttcggaaaaa gagttggtag ctcttgatcc    2597
ggcaaacaaa ccaccgctgg tagcggtggt tttttgttt gcaagcagca gattacgcgc    2657
agaaaaaaag gatctcaaga agatcctttg atcttttcta cggggtctga cgctcagtgg    2717
aacgaaaact cacgttaagg gattttggtc atgagattat caaaaaggat cttcacctag    2777
atccttttaa attaaaaatg aagttttaaa tcaatctaaa gtatatatga gtaaacttgg    2837
tctgacagtt accaatgctt aatcagtgag gcacctatct cagcgatctg tctatttcgt    2897
tcatccatag ttgcctgact ccccgtcgtg tagataacta cgatacggga gcgcttacca    2957
tctggcccca gtgctgcaat gataccgcga gcccacgct caccggctcc agatttatca    3017
gcaataaacc agccagccgg aagggccgag cgcagaagtg gtcctgcaac tttatccgcc    3077
tccatccagt ctattaattg ttgccgggaa gctagagtaa gtagttcgcc agttaatagt    3137
ttgcgcaacg ttgttgccat tgctacaggc atcgtggtgt cacgctcgtc gtttggtatg    3197
gcttcattca gctccggttc ccaacgatca aggcgagtta catgatcccc catgttgtgc    3257
aaaaaagcgg ttagctcctt cggtcctccg atcgttgtca gaagtaagtt ggccgcagtg    3317
ttatcactca tggttatggc agcactgcat aattctctta ctgtcatgcc atccgtaaga    3377
tgcttttctg tgactggtga gtactcaacc aagtcattct gagaatagtg tatgcggcga    3437
ccgagttgct cttgcccggc gtcaacacgg gataataccg cgccacatag cagaacttta    3497
aaagtgctca tcattggaaa acgttcttcg gggcgaaaac tctcaaggat cttaccgctg    3557
ttgagatcca gttcgatgta acccactcgt gcacccaact gatcttcagc atcttttact    3617
ttcaccagcg tttctgggtg agcaaaaaca ggaaggcaaa atgccgcaaa aaagggaata    3677
agggcgacac ggaaatgttg aatactcata ctcttccttt ttcaatatta ttgaagcatt    3737
tatcagggtt attgtctcat gagcggatac atatttgaat gtatttagaa aaataaacaa    3797
ataggggttc cgcgcacatt tccccgaaaa gtgccacctg acgtctaaga aaccattatt    3857
atcatgacat taacctataa aaataggcgt atcacgaggc cctttcgtct tcaagaaatt    3917
cggtcgaaaa aagaaaagga gagggccaag agggagggca ttggtgacta ttgagcacgt    3977
gagtatacgt gattaagcac acaaaggcag cttggagtat gtctgttatt aatttcacag    4037
gtagttctgg tccattggtg aaagtttgcg gcttgcagag cacagaggcc gcagaatgtg    4097
ctctagattc cgatgctgac ttgctgggta ttatatgtgt gcccaataga aagagaacaa    4157
ttgacccggt tattgcaagg aaaatttcaa gtcttgtaaa agcatataaa aatagttcag    4217
gcactccgaa atacttggtt ggcgtgtttc gtaatcaacc taaggaggat gttttggctc    4277
tggtcaatga ttacggcatt gatatcgtcc aactgcacgg agatgagtcg tggcaagaat    4337
accaagagtt cctcggtttg ccagttatta aaagactcgt atttccaaaa gactgcaaca    4397
tactactcag tgcagcttca cagaaacctc attcgtttat tcccttgttt gattcagaag    4457
caggtgggac aggtgaactt ttggattgga actcgatttc tgactgggtt ggaaggcaag    4517
agagccccga gagcttacat tttatgttag ctggtggact gacgccagaa atgttggtg    4577
atgcgcttag attaaatggc gttattggtg ttgatgtaag cggaggtgtg gagacaaatg    4637
gtgtaaaaga ctctaacaaa atagcaaatt tcgtcaaaaa tgctaagaaa taggttatta    4697
ctgagtagta tttatttaag tattgtttgt gcacttgccc tagcttatcg atgataagct    4757
gtcaaagatg agaattaatt ccacggacta tagactatac tagatactcc gtctactgta    4817
```

-continued

```
cgatacactt ccgctcaggt ccttgtcctt taacgaggcc ttaccactct tttgttactc    4877
tattgatcca gctcagcaaa ggcagtgtga tctaagattc tatcttcgcg atgtagtaaa    4937
actagctaga ccgagaaaga gactagaaat gcaaaggca cttctacaat ggctgccatc     4997
attattatcc gatgtgacgc tgcagcttct caatgatatt cgaatacgct ttgaggagat    5057
acagcctaat atccgacaaa ctgttttaca gatttacgat cgtacttgtt acccatcatt    5117
gaattttgaa catccgaacc tgggagtttt ccctgaaaca gatagtatat ttgaacctgt    5177
ataataatat atagtctagc gctttacgga agacaatgta tgtatttcgg ttcctggaga    5237
aactattgca tctattgcat aggtaatctt gcacgtcgca tccccggttc attttctgcg    5297
tttccatctt gcacttcaat agcatatctt tgttaacgaa gcatctgtgc ttcattttgt    5357
agaacaaaaa tgcaacgcga gagcgctaat ttttcaaaca aagaatctga gctgcatttt    5417
tacagaacag aaatgcaacg cgaaagcgct attttaccaa cgaagaatct gtgcttcatt    5477
tttgtaaaac aaaaatgcaa cgcgacgaga gcgctaattt ttcaaacaaa gaatctgagc    5537 tgcatttta cagaacagaa atgcaacgcg agagcgctat tttaccaaca aagaatctat     5597
acttcttttt tgttctacaa aaatgcatcc cgagagcgct attttttctaa caaagcatct    5657 tagattactt tttttctcct ttgtgcgctc tataatgcag tctcttgata acttttttgca   5717 ctgtaggtcc gttaaggtta gaagaaggct actttggtgt ctattttctc ttccataaaa    5777
aaagcctgac tccacttccc gcgtttactg attactagcg aagctgcggg tgcattttt     5837 caagataaag gcatccccga ttatattcta taccgatgtg gattgcgcat actttgtgaa    5897
cagaaagtga tagcgttgat gattcttcat tggtcagaaa attatgaacg gtttcttcta    5957
ttttgtctct atatactacg tataggaaat gtttacattt tcgtattgtt ttcgattcac    6017
tctatgaata gttcttacta caatttttt gtctaaagag taatactaga gataaacata    6077
aaaaatgtag aggtcgagtt tagatgcaag ttcaaggagc gaaaggtgga tgggtaggtt    6137
atatagggat atagcacaga gatatatagc aaagagatac ttttgagcaa tgtttgtgga    6197
agcggtattc gcaatgggaa gctccacccc ggttgataat cagaaaagcc ccaaaaacag    6257
gaagattgta taagcaaata tttaaattgt aaacgttaat attttgttaa aattcgcgtt    6317 aaattttgt taaatcagct catttttttaa cgaatagccc gaaatcggca aaatcccttaa   6377 taaatcaaaa gaatagaccg agataggggtt gagtgttgtt ccagtttcca acaagagtcc    6437
actattaaag aacgtggact ccaacgtcaa agggcgaaaa agggtctatc agggcgatgg    6497
cccactacgt gaaccatcac cctaatcaag ttttttgggg tcgaggtgcc gtaaagcagt    6557
aaatcggaag ggtaaacgga tgcccccatt tagagcttga cggggaaagc cggcgaacgt    6617
ggcgagaaag gaagggaaga aagcgaaagg agcgggggct agggcggtgg gaagtgtagg    6677
ggtcacgctg ggcgtaacca ccacacccgc cgcgcttaat ggggcgctac agggcgcgtg    6737
gggatgatcc actagt                                                   6753
```

<210> SEQ ID NO 56
<211> LENGTH: 295
<212> TYPE: PRT
<213> ORGANISM: Oncorhynchus mykiss

<400> SEQUENCE: 56

Met Glu Thr Phe Asn Tyr Lys Leu Asn Met Tyr Ile Asp Ser Trp Met
1               5                   10                  15

Gly Pro Arg Asp Glu Arg Val Gln Gly Trp Leu Leu Leu Asp Asn Tyr
            20                  25                  30

Pro Pro Thr Phe Ala Leu Thr Val Met Tyr Leu Leu Ile Val Trp Met
            35                  40                  45
Gly Pro Lys Tyr Met Arg His Arg Gln Pro Val Ser Cys Arg Gly Leu
        50                  55                  60
Leu Leu Val Tyr Asn Leu Gly Leu Thr Ile Leu Ser Phe Tyr Met Phe
 65                  70                  75                  80
Tyr Glu Met Val Ser Ala Val Trp His Gly Asp Tyr Asn Phe Phe Cys
                85                  90                  95
Gln Asp Thr His Ser Ala Gly Glu Thr Asp Thr Lys Ile Ile Asn Val
            100                 105                 110
Leu Trp Trp Tyr Tyr Phe Ser Lys Leu Ile Glu Phe Met Asp Thr Phe
            115                 120                 125
Phe Phe Ile Leu Arg Lys Asn Asn His Gln Ile Thr Phe Leu His Ile
        130                 135                 140
Tyr His His Ala Ser Met Leu Asn Ile Trp Trp Phe Val Met Asn Trp
145                 150                 155                 160
Val Pro Cys Gly His Ser Tyr Phe Gly Ala Ser Leu Asn Ser Phe Ile
                165                 170                 175
His Val Leu Met Tyr Ser Tyr Tyr Gly Leu Ser Ala Val Pro Ala Leu
            180                 185                 190
Arg Pro Tyr Leu Trp Trp Lys Lys Tyr Ile Thr Gln Val Gln Leu Ile
        195                 200                 205
Gln Phe Phe Leu Thr Met Ser Gln Thr Ile Cys Ala Val Ile Trp Pro
    210                 215                 220
Cys Asp Phe Pro Arg Gly Trp Leu Tyr Phe Gln Ile Phe Tyr Val Ile
225                 230                 235                 240
Thr Leu Ile Ala Leu Phe Ser Asn Phe Tyr Ile Gln Thr Tyr Lys Lys
                245                 250                 255
His Leu Val Ser Gln Lys Lys Glu Tyr His Gln Asn Gly Ser Val Ala
            260                 265                 270
Ser Leu Asn Gly His Val Asn Gly Val Thr Pro Thr Glu Thr Ile Thr
        275                 280                 285
His Arg Lys Val Arg Gly Asp
    290                 295

<210> SEQ ID NO 57
<211> LENGTH: 6645
<212> TYPE: DNA
<213> ORGANISM: Oncorhynchus mykiss
<220> FEATURE:
<221> NAME/KEY: CDS
<222> LOCATION: (513)..(1304)
<223> OTHER INFORMATION: delta5-elongase

<400> SEQUENCE: 57
acggattaga agccgccgag cgggtgacag ccctccgaag gaagactctc ctccgtgcgt    60
cctcgtcctc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagtttttt agccttattt ctggggtaat taatcagcga agcgatgatt tttgatctat   300
taacagatat ataaatgcaa aaactgcatt aaccacttta actaatactt tcaacatttt   360
cggtttgtat tacttcttat tcaaatgtaa taaagtatc aacaaaaaat tgttaatata    420
cctctatact ttaacgtcaa ggagaaaaaa ccccggatcg gactactagc agctgtaata   480

```
cgactcacta tagggaatat taagcttaca ta atg gct tca aca tgg caa agc            533
                                    Met Ala Ser Thr Trp Gln Ser
                                     1               5 gtt cag tcc atg cgc cag tgg att tta gag aat gga gat aaa agg aca            581
Val Gln Ser Met Arg Gln Trp Ile Leu Glu Asn Gly Asp Lys Arg Thr
         10              15                  20 gac cca tgg cta ctg gtc tac tcc cct atg cca gtg gcc att ata ttc            629
Asp Pro Trp Leu Leu Val Tyr Ser Pro Met Pro Val Ala Ile Ile Phe
     25                  30                  35 ctc ctc tat ctt ggt gtg gtc tgg gct ggg ccc aag ctg atg aaa cgc            677
Leu Leu Tyr Leu Gly Val Val Trp Ala Gly Pro Lys Leu Met Lys Arg
 40              45                  50                  55 agg gaa cca gtt gat ctc aag gct gta ctc att gtc tac aac ttc gcc            725
Arg Glu Pro Val Asp Leu Lys Ala Val Leu Ile Val Tyr Asn Phe Ala
                 60                  65                  70 atg gtc tgc ctg tct gtc tac atg ttc cat gag ttc ttg gtc acg tcc            773
Met Val Cys Leu Ser Val Tyr Met Phe His Glu Phe Leu Val Thr Ser
             75                  80                  85 ttg ctg tct aac tac agt tac ctg tgt caa cct gtg gat tac agc act            821
Leu Leu Ser Asn Tyr Ser Tyr Leu Cys Gln Pro Val Asp Tyr Ser Thr
         90                  95                 100 agt cca ctg gcg atg agg atg gcc aaa gta tgc tgg tgg ttt ttc ttc            869
Ser Pro Leu Ala Met Arg Met Ala Lys Val Cys Trp Trp Phe Phe Phe
    105                 110                 115 tcc aag gtc ata gaa ttg gct gac acg gtg ttc ttc atc ctg agg aag            917
Ser Lys Val Ile Glu Leu Ala Asp Thr Val Phe Phe Ile Leu Arg Lys
120                 125                 130                 135 aag aac agt cag ctg act ttc ctg cat gtc tat cac cat ggc acc atg            965
Lys Asn Ser Gln Leu Thr Phe Leu His Val Tyr His His Gly Thr Met
                140                 145                 150 atc ttc aac tgg tgg gca ggg gtc aag tat ctg gct gga ggc caa tcg           1013
Ile Phe Asn Trp Trp Ala Gly Val Lys Tyr Leu Ala Gly Gly Gln Ser
            155                 160                 165 ttc ttc atc ggc ctg ctc aat acc ttt gtg cac atc gtg atg tac tct           1061
Phe Phe Ile Gly Leu Leu Asn Thr Phe Val His Ile Val Met Tyr Ser
        170                 175                 180 tac tac gga ctg gct gcc ctg ggg cct cac acg cag aag tac tta tgg           1109
Tyr Tyr Gly Leu Ala Ala Leu Gly Pro His Thr Gln Lys Tyr Leu Trp
    185                 190                 195 tgg aag cgc tat ctg acc tca ctg cag ctg ctc cag ttt gtc ctg ttg           1157
Trp Lys Arg Tyr Leu Thr Ser Leu Gln Leu Leu Gln Phe Val Leu Leu
200                 205                 210                 215 acc act cac act ggc tac aac ctc ttc act gag tgt gac ttc ccg gac           1205
Thr Thr His Thr Gly Tyr Asn Leu Phe Thr Glu Cys Asp Phe Pro Asp
                220                 225                 230 tcc atg aac gct gtg gtg ttt gcc tac tgt gtc agt ctc att gct ctc           1253
Ser Met Asn Ala Val Val Phe Ala Tyr Cys Val Ser Leu Ile Ala Leu
            235                 240                 245 ttc agc aac ttc tac tat cag agc tac ctc aac agg aag agc aag aag           1301
Phe Ser Asn Phe Tyr Tyr Gln Ser Tyr Leu Asn Arg Lys Ser Lys Lys
        250                 255                 260 aca taaggatcca ctagtaacgg ccgccagtgt gctggaattc tgcagatatc                1354
Thr catcacactg gcggccgctc gagcatgcat ctagagggcc gcatcatgta attagttatg         1414
tcacgcttac attcacgccc tccccccaca tccgctctaa ccgaaaagga aggagttaga         1474
caacctgaag tctaggtccc tatttatttt tttatagtta tgttagtatt aagaacgtta         1534
tttatatttc aaattttcct ttttttctg tacagacgcg tgtacgcatg taacattata          1594
```

```
ctgaaaacct tgcttgagaa ggttttggga cgctcgaagg ctttaatttg cggccctgca    1654
ttaatgaatc ggccaacgcg cggggagagg cggtttgcgt attgggcgct cttccgcttc    1714
ctcgctcact gactcgctgc gctcggtcgt tcggctgcgg cgagcggtat cagctcactc    1774
aaaggcggta atacggttat ccacagaatc aggggataac gcaggaaaga acatgtgagc    1834
aaaaggccag caaaagccca ggaaccgtaa aaaggccgcg ttgctggcgt ttttccatag    1894
gctccgcccc cctgacgagc atcacaaaaa tcgacgctca agtcagaggt ggcgaaaccc    1954
gacaggacta taaagatacc aggcgtttcc ccctggaagc tccctcgtgc gctctcctgt    2014
tccgaccctg ccgcttaccg gatacctgtc cgcctttctc ccttcgggaa gcgtggcgct    2074
ttctcatagc tcacgctgta ggtatctcag ttcggtgtag gtcgttcgct ccaagctggg    2134
ctgtgtgcac gaaccccccg ttcagcccga ccgctgcgcc ttatccggta actatcgtct    2194
tgagtccaac ccggtaagac acgacttatc gccactggca gcagccactg gtaacaggat    2254
tagcagagcg aggtatgtag gcggtgctac agagttcttg aagtggtggc ctaactacgg    2314
ctacactaga aggacagtat ttggtatctg cgctctgctg aagccagtta ccttcggaaa    2374
aagagttggt agctcttgat ccggcaaaca aaccaccgct ggtagcggtg gtttttttgt    2434
ttgcaagcag cagattacgc gcagaaaaaa aggatctcaa gaagatcctt tgatcttttc    2494
tacgggtct gacgctcagt ggaacgaaaa ctcacgttaa gggattttgg tcatgagatt    2554
atcaaaaagg atcttcacct agatcctttt aaattaaaaa tgaagtttta atcaatcta    2614
aagtatatat gagtaaactt ggtctgacag ttaccaatgc ttaatcagtg aggcacctat    2674
ctcagcgatc tgtctatttc gttcatccat agttgcctga ctccccgtcg tgtagataac    2734
tacgatacgg gagcgcttac catctggccc cagtgctgca atgataccgc gagacccacg    2794
ctcaccggct ccagatttat cagcaataaa ccagccagcc ggaagggccg agcgcagaag    2854
tggtcctgca actttatccg cctccattca gtctattaat tgttgccggg aagctagagt    2914
aagtagttcg ccagttaata gtttgcgcaa cgttgttggc attgctacag gcatcgtggt    2974
gtcactctcg tcgtttggta tggcttcatt cagctccggt tcccaacgat caaggcgagt    3034
tacatgatcc cccatgttgt gcaaaaaagc ggttagctcc ttcggtcctc cgatcgttgt    3094
cagaagtaag ttggccgcag tgttatcact catggttatg gcagcactgc ataattctct    3154
tactgtcatg ccatccgtaa gatgcttttc tgtgactggt gagtactcaa ccaagtcatt    3214
ctgagaatag tgtatgcggc gaccgagttg ctcttgcccg gcgtcaatac gggataatag    3274
tgtatcacat agcagaactt taaaagtgct catcattgga aaacgttctt cggggcgaaa    3334
actctcaagg atcttaccgc tgttgagatc cagttcgatg taacccactc gtgcacccaa    3394
ctgatcttca gcatctttta ctttcaccag cgtttctggg tgagcaaaaa caggaaggca    3454
aaatgccgca aaaaagggaa taagggcgac acggaaatgt tgaatactca tactcttcct    3514
ttttcaatgg gtaataactg atataattaa attgaagctc taatttgtga gtttagtata    3574
catgcatttta cttataatac agttttttag ttttgctggc cgcatcttct caaatatgct    3634
tcccagcctg ctttttctgta acgttcaccc tctaccttag catcccttcc ctttgcaaat    3694
agtcctcttc aacaataat aatgtcagat cctgtagaga ccacatcatc cacgttcta    3754
tactgttgac ccaatgcgtc tcccttgtca tctaaaccca caccgggtgt cataatcaac    3814
caatcgtaac cttcatctct tccacccatg tctctttgag caataaagcc gataacaaaa    3874
tctttgtcgc tcttcgcaat gtcaacagta cccttagtat attctccagt agataggag    3934
```

```
cccttgcatg acaattctgc taacatcaaa aggcctctag gttcctttgt tacttcttct    3994
gccgcctgct tcaaaccgct aacaatacct gggcccacca caccgtgtgc attcgtaatg    4054
tctgcccatt ctgctattct gtatacaccc gcagagtact gcaatttgac tgtattacca    4114
atgtcagcaa attttctgtc ttcgaagagt aaaaaattgt acttggcgga taatgccttt    4174
agcggcttaa ctgtgccctc catggaaaaa tcagtcaaga tatccacatg tgttttagt     4234
aaacaaattt tgggacctaa tgcttcaact aactccagta attccttggt ggtacgaaca    4294
tccaatgaag cacacaagtt tgtttgcttt tcgtgcatga tattaaatag cttggcagca    4354
acaggactag gatgagtagc agcacgttcc ttatatgtag ctttcgacat gatttatctt    4414
cgtttcctgc aggttttgt tctgtgcagt tgggttaaga atactgggca atttcatgtt     4474
tcttcaacac tacatatgcg tatatatacc aatctaagtc tgtgctcctt ccttcgttct    4534
tccttctgtt cggagattac cgaatcaaaa aaatttcaaa gaaaccgaaa tcaaaaaaaa    4594
gaataaaaaa aaaatgatga attgaattga aaagctagct tatcgatgat aagctgtcaa    4654
agatgagaat taattccacg gactatagac tatactagat actccgtcta ctgtacgata    4714
cacttccgct caggtccttg tcctttaacg aggccttacc actcttttgt tactctattg    4774
atccagctca gcaaaggcag tgtgatctaa gattctatct tcgcgatgta gtaaaactag    4834
ctagaccgag aaagagacta gaaatgcaaa aggcacttct acaatggctg ccatcattat    4894
tatccgatgt gacgctgcag cttctcaatg atattcgaat acgctttgag gagatacagc    4954
ctaatatccg acaaactgtt ttacagattt acgatcgtac ttgttaccca tcattgaatt    5014
ttgaacatcc gaacctggga gttttccctg aaacagatag tatatttgaa cctgtataat    5074
aatatatagt ctagcgcttt acggaagaca atgtatgtat ttcggttcct ggagaaacta    5134
ttgcatctat tgcataggta atcttgcacg tcgcatcccc ggttcatttt ctgcgtttcc    5194
atcttgcact tcaatagcat atctttgtta acgaagcatc tgtgcttcat tttgtagaac    5254
aaaaatgcaa cgcgagagcg ctaattttc aaacaaagaa tctgagctgc atttttacag     5314
aacagaaatg caacgcgaaa gcgctatttt accaacgaag aatctgtgct tcattttgt     5374
aaaacaaaaa tgcaacgcga cgagagcgct aattttcaa acaaagaatc tgagctgcat     5434
ttttacagaa cagaaatgca acgcgagagc gctatttac caacaaagaa tctatacttc     5494
ttttttgttc tacaaaaatg catcccgaga gcgctatttt tctaacaaag catcttagat    5554
tacttttttt ctcctttgtg cgctctataa tgcagtctct tgataacttt ttgcactgta    5614
ggtccgttaa ggttagaaga aggctacttt ggtgtctatt ttctcttcca taaaaaaagc    5674
ctgactccac ttcccgcgtt tactgattac tagcgaagct gcgggtgcat tttttcaaga    5734
taaaggcatc cccgattata ttctataccg atgtggattg cgcatacttt gtgaacagaa    5794
agtgatagcg ttgatgattc ttcattggtc agaaaattat gaacggtttc ttctattttg    5854
tctctatata ctacgtatag gaaatgttta cattttcgta ttgttttcga ttcactctat    5914
gaatagttct tactacaatt ttttgtcta aagagtaata ctagagataa acataaaaaa     5974
tgtagaggtc gagtttagat gcaagttcaa ggagcgaaag gtggatgggt aggttatata    6034
gggatatagc acagagatat atagcaaaga gatactttg agcaatgttt gtggaagcgg     6094
tattcgcaat gggaagctcc accccggttg ataatcagaa aagccccaaa acaggaaga    6154
ttgtataagc aaatatttaa attgtaaacg ttaatatttt gttaaaattc gcgttaaatt    6214
tttgttaaat cagctcattt tttaacgaat agcccgaaat cggcaaaatc ccttataaat    6274
caaaagaata gaccgagata gggttgagtg ttgttccagt ttccaacaag agtccactat    6334
```

```
taaagaacgt ggactccaac gtcaaagggc gaaaaagggt ctatcagggc gatggcccac   6394
tacgtgaacc atcaccctaa tcaagttttt tggggtcgag gtgccgtaaa gcagtaaatc   6454
ggaagggtaa acggatgccc ccatttagag cttgacgggg aaagccggcg aacgtggcga   6514
gaaaggaagg gaagaaagcg aaaggagcgg gggctagggc ggtgggaagt gtaggggtca   6574
cgctgggcgt aaccaccaca cccgccgcgc ttaatggggc gctacagggc gcgtggggat   6634
gatccactag t                                                        6645
```

<210> SEQ ID NO 58
<211> LENGTH: 264
<212> TYPE: PRT
<213> ORGANISM: Oncorhynchus mykiss

<400> SEQUENCE: 58

```
Met Ala Ser Thr Trp Gln Ser Val Gln Ser Met Arg Gln Trp Ile Leu
1               5                   10                  15

Glu Asn Gly Asp Lys Arg Thr Asp Pro Trp Leu Leu Val Tyr Ser Pro
            20                  25                  30

Met Pro Val Ala Ile Ile Phe Leu Leu Tyr Leu Gly Val Val Trp Ala
        35                  40                  45

Gly Pro Lys Leu Met Lys Arg Arg Glu Pro Val Asp Leu Lys Ala Val
    50                  55                  60

Leu Ile Val Tyr Asn Phe Ala Met Val Cys Leu Ser Val Tyr Met Phe
65                  70                  75                  80

His Glu Phe Leu Val Thr Ser Leu Leu Ser Asn Tyr Ser Tyr Leu Cys
                85                  90                  95

Gln Pro Val Asp Tyr Ser Thr Ser Pro Leu Ala Met Arg Met Ala Lys
            100                 105                 110

Val Cys Trp Trp Phe Phe Ser Lys Val Ile Glu Leu Ala Asp Thr
        115                 120                 125

Val Phe Phe Ile Leu Arg Lys Lys Asn Ser Gln Leu Thr Phe Leu His
    130                 135                 140

Val Tyr His His Gly Thr Met Ile Phe Asn Trp Trp Ala Gly Val Lys
145                 150                 155                 160

Tyr Leu Ala Gly Gly Gln Ser Phe Phe Ile Gly Leu Leu Asn Thr Phe
                165                 170                 175

Val His Ile Val Met Tyr Ser Tyr Tyr Gly Leu Ala Ala Leu Gly Pro
            180                 185                 190

His Thr Gln Lys Tyr Leu Trp Trp Lys Arg Tyr Leu Thr Ser Leu Gln
        195                 200                 205

Leu Leu Gln Phe Val Leu Leu Thr Thr His Thr Gly Tyr Asn Leu Phe
    210                 215                 220

Thr Glu Cys Asp Phe Pro Asp Ser Met Asn Ala Val Val Phe Ala Tyr
225                 230                 235                 240

Cys Val Ser Leu Ile Ala Leu Phe Ser Asn Phe Tyr Tyr Gln Ser Tyr
                245                 250                 255

Leu Asn Arg Lys Ser Lys Lys Thr
            260
```

<210> SEQ ID NO 59
<211> LENGTH: 1077
<212> TYPE: DNA
<213> ORGANISM: Thalassiosira pseudonana
<220> FEATURE:
<221> NAME/KEY: CDS
<222> LOCATION: (1)..(1077)
<223> OTHER INFORMATION: delta5-elongase

<400> SEQUENCE: 59

| | | | | | | | | | | | | | | | | |
|---|---|---|---|---|---|---|---|---|---|---|---|---|---|---|---|---|
| atg | tgc | tca | tca | ccg | ccg | tca | caa | tcc | aaa | aca | aca | tcc | ctc | cta | gca | 48 |
| Met | Cys | Ser | Ser | Pro | Pro | Ser | Gln | Ser | Lys | Thr | Thr | Ser | Leu | Leu | Ala | |
| 1 | | | | 5 | | | | | 10 | | | | | 15 | | |
| cgg | tac | acc | acc | gcc | gcc | ctc | ctc | ctc | acc | ctc | aca | aca | tgg | tgc | | 96 |
| Arg | Tyr | Thr | Thr | Ala | Ala | Leu | Leu | Leu | Thr | Leu | Thr | Thr | Trp | Cys | | |
| | | | 20 | | | | | 25 | | | | | 30 | | | |
| cac | ttc | gcc | ttc | cca | gcc | gcc | acc | gcc | aca | ccc | ggc | ctc | acc | gcc | gaa | 144 |
| His | Phe | Ala | Phe | Pro | Ala | Ala | Thr | Ala | Thr | Pro | Gly | Leu | Thr | Ala | Glu | |
| | | 35 | | | | | 40 | | | | | 45 | | | | |
| atg | cac | tcc | tac | aaa | gtc | cca | ctc | ggt | ctc | acc | gta | ttc | tac | ctg | ctg | 192 |
| Met | His | Ser | Tyr | Lys | Val | Pro | Leu | Gly | Leu | Thr | Val | Phe | Tyr | Leu | Leu | |
| | 50 | | | | | 55 | | | | | 60 | | | | | |
| agt | cta | ccg | tca | cta | aag | tac | gtt | acg | gac | aac | tac | ctt | gcc | aaa | aag | 240 |
| Ser | Leu | Pro | Ser | Leu | Lys | Tyr | Val | Thr | Asp | Asn | Tyr | Leu | Ala | Lys | Lys | |
| 65 | | | | | 70 | | | | | 75 | | | | | 80 | |
| tat | gat | atg | aag | tca | ctc | cta | acg | gaa | tca | atg | gtg | ttg | tac | aat | gtg | 288 |
| Tyr | Asp | Met | Lys | Ser | Leu | Leu | Thr | Glu | Ser | Met | Val | Leu | Tyr | Asn | Val | |
| | | | | 85 | | | | | 90 | | | | | 95 | | |
| gcg | caa | gtg | ctg | ctc | aat | ggg | tgg | acg | gtg | tat | gcg | att | gtg | gat | gcg | 336 |
| Ala | Gln | Val | Leu | Leu | Asn | Gly | Trp | Thr | Val | Tyr | Ala | Ile | Val | Asp | Ala | |
| | | | 100 | | | | | 105 | | | | | 110 | | | |
| gtg | atg | aat | aga | gac | cat | ccg | ttt | att | gga | agt | aga | agt | ttg | gtt | ggg | 384 |
| Val | Met | Asn | Arg | Asp | His | Pro | Phe | Ile | Gly | Ser | Arg | Ser | Leu | Val | Gly | |
| | | 115 | | | | | 120 | | | | | 125 | | | | |
| gcg | gcg | ttg | cat | agt | ggg | agc | tcg | tat | gcg | gtg | tgg | gtt | cat | tat | tgt | 432 |
| Ala | Ala | Leu | His | Ser | Gly | Ser | Ser | Tyr | Ala | Val | Trp | Val | His | Tyr | Cys | |
| | 130 | | | | | 135 | | | | | 140 | | | | | |
| gat | aag | tat | ttg | gag | ttc | ttt | gat | acg | tat | ttt | atg | gtg | ttg | agg | ggg | 480 |
| Asp | Lys | Tyr | Leu | Glu | Phe | Phe | Asp | Thr | Tyr | Phe | Met | Val | Leu | Arg | Gly | |
| 145 | | | | | 150 | | | | | 155 | | | | | 160 | |
| aaa | atg | gac | cag | gtc | tcc | ttc | ctc | cac | atc | tac | cac | cac | acg | acc | ata | 528 |
| Lys | Met | Asp | Gln | Val | Ser | Phe | Leu | His | Ile | Tyr | His | His | Thr | Thr | Ile | |
| | | | | 165 | | | | | 170 | | | | | 175 | | |
| gcg | tgg | gca | tgg | tgg | atc | gcc | ctc | cgc | ttc | tcc | ccc | ggt | gga | gac | att | 576 |
| Ala | Trp | Ala | Trp | Trp | Ile | Ala | Leu | Arg | Phe | Ser | Pro | Gly | Gly | Asp | Ile | |
| | | | 180 | | | | | 185 | | | | | 190 | | | |
| tac | ttc | ggg | gca | ctc | ctc | aac | tcc | atc | atc | cac | gtc | ctc | atg | tat | tcc | 624 |
| Tyr | Phe | Gly | Ala | Leu | Leu | Asn | Ser | Ile | Ile | His | Val | Leu | Met | Tyr | Ser | |
| | | 195 | | | | | 200 | | | | | 205 | | | | |
| tac | tac | gcc | ctt | gcc | cta | ctc | aag | gtc | agt | tgt | cca | tgg | aaa | cga | tac | 672 |
| Tyr | Tyr | Ala | Leu | Ala | Leu | Leu | Lys | Val | Ser | Cys | Pro | Trp | Lys | Arg | Tyr | |
| | 210 | | | | | 215 | | | | | 220 | | | | | |
| ctg | act | caa | gct | caa | tta | ttg | caa | ttc | aca | agt | gtg | gtg | gtt | tat | acg | 720 |
| Leu | Thr | Gln | Ala | Gln | Leu | Leu | Gln | Phe | Thr | Ser | Val | Val | Val | Tyr | Thr | |
| 225 | | | | | 230 | | | | | 235 | | | | | 240 | |
| ggg | tgt | acg | ggt | tat | act | cat | tac | tat | cat | acg | aag | cat | gga | gcg | gat | 768 |
| Gly | Cys | Thr | Gly | Tyr | Thr | His | Tyr | Tyr | His | Thr | Lys | His | Gly | Ala | Asp | |
| | | | | 245 | | | | | 250 | | | | | 255 | | |
| gag | aca | cag | cct | agt | tta | gga | acg | tat | tat | ttc | tgt | tgt | gga | gtg | cag | 816 |
| Glu | Thr | Gln | Pro | Ser | Leu | Gly | Thr | Tyr | Tyr | Phe | Cys | Cys | Gly | Val | Gln | |
| | | | 260 | | | | | 265 | | | | | 270 | | | |
| gtg | ttt | gag | atg | gtt | agt | ttg | ttt | gta | ctc | ttt | tcc | atc | ttt | tat | aaa | 864 |
| Val | Phe | Glu | Met | Val | Ser | Leu | Phe | Val | Leu | Phe | Ser | Ile | Phe | Tyr | Lys | |
| | | 275 | | | | | 280 | | | | | 285 | | | | |
| cga | tcc | tat | tcg | aag | aag | aac | aag | tca | gga | gga | aag | gat | agc | aag | aag | 912 |
| Arg | Ser | Tyr | Ser | Lys | Lys | Asn | Lys | Ser | Gly | Gly | Lys | Asp | Ser | Lys | Lys | |

```
                     290                 295                 300
aat gat gat ggg aat aat gag gat caa tgt cac aag gct atg aag gat        960
Asn Asp Asp Gly Asn Asn Glu Asp Gln Cys His Lys Ala Met Lys Asp
305                 310                 315                 320 ata tcg gag ggt gcg aag gag gtt gtg ggg cat gca gcg aag gat gct       1008
Ile Ser Glu Gly Ala Lys Glu Val Val Gly His Ala Ala Lys Asp Ala
                325                 330                 335 gga aag ttg gtg gct acg gcg agt aag gct gta aag agg aag gga act       1056
Gly Lys Leu Val Ala Thr Ala Ser Lys Ala Val Lys Arg Lys Gly Thr
                340                 345                 350 cgt gtt act ggt gcc atg tag                                           1077
Arg Val Thr Gly Ala Met
                355

<210> SEQ ID NO 60
<211> LENGTH: 358
<212> TYPE: PRT
<213> ORGANISM: Thalassiosira pseudonana

<400> SEQUENCE: 60
```

Met Cys Ser Ser Pro Ser Gln Ser Lys Thr Thr Ser Leu Leu Ala
1               5                   10                  15

Arg Tyr Thr Thr Ala Ala Leu Leu Leu Thr Leu Thr Thr Trp Cys
                20                  25                  30

His Phe Ala Phe Pro Ala Ala Thr Ala Thr Pro Gly Leu Thr Ala Glu
                35                  40                  45

Met His Ser Tyr Lys Val Pro Leu Gly Leu Thr Val Phe Tyr Leu Leu
                50                  55                  60

Ser Leu Pro Ser Leu Lys Tyr Val Thr Asp Asn Tyr Leu Ala Lys Lys
65                  70                  75                  80

Tyr Asp Met Lys Ser Leu Leu Thr Glu Ser Met Val Leu Tyr Asn Val
                85                  90                  95

Ala Gln Val Leu Leu Asn Gly Trp Thr Val Tyr Ala Ile Val Asp Ala
                100                 105                 110

Val Met Asn Arg Asp His Pro Phe Ile Gly Ser Arg Ser Leu Val Gly
                115                 120                 125

Ala Ala Leu His Ser Gly Ser Ser Tyr Ala Val Trp Val His Tyr Cys
                130                 135                 140

Asp Lys Tyr Leu Glu Phe Phe Asp Thr Tyr Phe Met Val Leu Arg Gly
145                 150                 155                 160

Lys Met Asp Gln Val Ser Phe Leu His Ile Tyr His His Thr Thr Ile
                165                 170                 175

Ala Trp Ala Trp Trp Ile Ala Leu Arg Phe Ser Pro Gly Gly Asp Ile
                180                 185                 190

Tyr Phe Gly Ala Leu Leu Asn Ser Ile Ile His Val Leu Met Tyr Ser
                195                 200                 205

Tyr Tyr Ala Leu Ala Leu Leu Lys Val Ser Cys Pro Trp Lys Arg Tyr
                210                 215                 220

Leu Thr Gln Ala Gln Leu Leu Gln Phe Thr Ser Val Val Tyr Thr
225                 230                 235                 240

Gly Cys Thr Gly Tyr Thr His Tyr Tyr His Thr Lys His Gly Ala Asp
                245                 250                 255

Glu Thr Gln Pro Ser Leu Gly Thr Tyr Tyr Phe Cys Cys Gly Val Gln
                260                 265                 270

Val Phe Glu Met Val Ser Leu Phe Val Leu Phe Ser Ile Phe Tyr Lys
                275                 280                 285

```
Arg Ser Tyr Ser Lys Lys Asn Lys Ser Gly Gly Lys Asp Ser Lys Lys
    290                 295                 300

Asn Asp Asp Gly Asn Asn Glu Asp Gln Cys His Lys Ala Met Lys Asp
305                 310                 315                 320

Ile Ser Glu Gly Ala Lys Glu Val Val Gly His Ala Ala Lys Asp Ala
                325                 330                 335

Gly Lys Leu Val Ala Thr Ala Ser Lys Ala Val Lys Arg Lys Gly Thr
            340                 345                 350

Arg Val Thr Gly Ala Met
        355

<210> SEQ ID NO 61
<211> LENGTH: 933
<212> TYPE: DNA
<213> ORGANISM: Thalassiosira pseudonana
<220> FEATURE:
<221> NAME/KEY: CDS
<222> LOCATION: (1)..(933)
<223> OTHER INFORMATION: delta5-elongase

<400> SEQUENCE: 61
```

| | | | | | | | | | | | | | | | | |
|---|---|---|---|---|---|---|---|---|---|---|---|---|---|---|---|---|
| atg | cac | tcc | tac | aaa | gtc | cca | ctc | ggt | ctc | acc | gta | ttc | tac | ctg | ctg | 48 |
| Met | His | Ser | Tyr | Lys | Val | Pro | Leu | Gly | Leu | Thr | Val | Phe | Tyr | Leu | Leu | |
| 1 | | | | 5 | | | | | 10 | | | | | 15 | | |
| agt | cta | ccg | tca | cta | aag | tac | gtt | acg | gac | aac | tac | ctt | gcc | aaa | aag | 96 |
| Ser | Leu | Pro | Ser | Leu | Lys | Tyr | Val | Thr | Asp | Asn | Tyr | Leu | Ala | Lys | Lys | |
| | | | 20 | | | | | 25 | | | | | 30 | | | |
| tat | gat | atg | aag | tca | ctc | cta | acg | gaa | tca | atg | gtg | ttg | tac | aat | gtg | 144 |
| Tyr | Asp | Met | Lys | Ser | Leu | Leu | Thr | Glu | Ser | Met | Val | Leu | Tyr | Asn | Val | |
| | | 35 | | | | | 40 | | | | | 45 | | | | |
| gcg | caa | gtg | ctg | ctc | aat | ggg | tgg | acg | gtg | tat | gcg | att | gtg | gat | gcg | 192 |
| Ala | Gln | Val | Leu | Leu | Asn | Gly | Trp | Thr | Val | Tyr | Ala | Ile | Val | Asp | Ala | |
| 50 | | | | | 55 | | | | | 60 | | | | | | |
| gtg | atg | aat | aga | gac | cat | ccg | ttt | att | gga | agt | aga | agt | ttg | gtt | ggg | 240 |
| Val | Met | Asn | Arg | Asp | His | Pro | Phe | Ile | Gly | Ser | Arg | Ser | Leu | Val | Gly | |
| 65 | | | | | 70 | | | | | 75 | | | | | 80 | |
| gcg | gcg | ttg | cat | agt | ggg | agc | tcg | tat | gcg | gtg | tgg | gtt | cat | tat | tgt | 288 |
| Ala | Ala | Leu | His | Ser | Gly | Ser | Ser | Tyr | Ala | Val | Trp | Val | His | Tyr | Cys | |
| | | | | 85 | | | | | 90 | | | | | 95 | | |
| gat | aag | tat | ttg | gag | ttc | ttt | gat | acg | tat | ttt | atg | gtg | ttg | agg | ggg | 336 |
| Asp | Lys | Tyr | Leu | Glu | Phe | Phe | Asp | Thr | Tyr | Phe | Met | Val | Leu | Arg | Gly | |
| | | | | 100 | | | | | 105 | | | | | 110 | | |
| aaa | atg | gac | cag | gtc | tcc | ttc | ctc | cac | atc | tac | cac | cac | acg | acc | ata | 384 |
| Lys | Met | Asp | Gln | Val | Ser | Phe | Leu | His | Ile | Tyr | His | His | Thr | Thr | Ile | |
| | | | 115 | | | | | 120 | | | | | 125 | | | |
| gcg | tgg | gca | tgg | tgg | atc | gcc | ctc | cgc | ttc | tcc | ccc | ggt | gga | gac | att | 432 |
| Ala | Trp | Ala | Trp | Trp | Ile | Ala | Leu | Arg | Phe | Ser | Pro | Gly | Gly | Asp | Ile | |
| | | 130 | | | | | 135 | | | | | 140 | | | | |
| tac | ttc | ggg | gca | ctc | ctc | aac | tcc | atc | atc | cac | gtc | ctc | atg | tat | tcc | 480 |
| Tyr | Phe | Gly | Ala | Leu | Leu | Asn | Ser | Ile | Ile | His | Val | Leu | Met | Tyr | Ser | |
| 145 | | | | | 150 | | | | | 155 | | | | | 160 | |
| tac | tac | gcc | ctt | gcc | cta | ctc | aag | gtc | agt | tgt | cca | tgg | aaa | cga | tac | 528 |
| Tyr | Tyr | Ala | Leu | Ala | Leu | Leu | Lys | Val | Ser | Cys | Pro | Trp | Lys | Arg | Tyr | |
| | | | | 165 | | | | | 170 | | | | | 175 | | |
| ctg | act | caa | gct | caa | tta | ttg | caa | ttc | aca | agt | gtg | gtg | gtt | tat | acg | 576 |
| Leu | Thr | Gln | Ala | Gln | Leu | Leu | Gln | Phe | Thr | Ser | Val | Val | Val | Tyr | Thr | |
| | | | 180 | | | | | 185 | | | | | 190 | | | |
| ggg | tgt | acg | ggt | tat | act | cat | tac | tat | cat | acg | aag | cat | gga | gcg | gat | 624 |
| Gly | Cys | Thr | Gly | Tyr | Thr | His | Tyr | Tyr | His | Thr | Lys | His | Gly | Ala | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| gag | aca | cag | cct | agt | tta | gga | acg | tat | tat | ttc | tgt | tgt | gga | gtg | cag | 672 |
| Glu | Thr | Gln | Pro | Ser | Leu | Gly | Thr | Tyr | Tyr | Phe | Cys | Cys | Gly | Val | Gln | |
| 210 | | | | | 215 | | | | | 220 | | | | | | |
| gtg | ttt | gag | atg | gtt | agt | ttg | ttt | gta | ctc | ttt | tcc | atc | ttt | tat | aaa | 720 |
| Val | Phe | Glu | Met | Val | Ser | Leu | Phe | Val | Leu | Phe | Ser | Ile | Phe | Tyr | Lys | |
| 225 | | | | | 230 | | | | | 235 | | | | | 240 | |
| cga | tcc | tat | tcg | aag | aag | aac | aag | tca | gga | gga | aag | gat | agc | aag | aag | 768 |
| Arg | Ser | Tyr | Ser | Lys | Lys | Asn | Lys | Ser | Gly | Gly | Lys | Asp | Ser | Lys | Lys | |
| | | | | 245 | | | | | 250 | | | | | 255 | | |
| aat | gat | gat | ggg | aat | aat | gag | gat | caa | tgt | cac | aag | gct | atg | aag | gat | 816 |
| Asn | Asp | Asp | Gly | Asn | Asn | Glu | Asp | Gln | Cys | His | Lys | Ala | Met | Lys | Asp | |
| | | | 260 | | | | | 265 | | | | | 270 | | | |
| ata | tcg | gag | ggt | gcg | aag | gag | gtt | gtg | ggg | cat | gca | gcg | aag | gat | gct | 864 |
| Ile | Ser | Glu | Gly | Ala | Lys | Glu | Val | Val | Gly | His | Ala | Ala | Lys | Asp | Ala | |
| | | 275 | | | | | 280 | | | | | 285 | | | | |
| gga | aag | ttg | gtg | gct | acg | gcg | agt | aag | gct | gta | aag | agg | aag | gga | act | 912 |
| Gly | Lys | Leu | Val | Ala | Thr | Ala | Ser | Lys | Ala | Val | Lys | Arg | Lys | Gly | Thr | |
| 290 | | | | | 295 | | | | | 300 | | | | | | |
| cgt | gtt | act | ggt | gcc | atg | tag | | | | | | | | | | 933 |
| Arg | Val | Thr | Gly | Ala | Met | | | | | | | | | | | |
| 305 | | | | | 310 | | | | | | | | | | | |

<210> SEQ ID NO 62
<211> LENGTH: 310
<212> TYPE: PRT
<213> ORGANISM: Thalassiosira pseudonana

<400> SEQUENCE: 62

Met His Ser Tyr Lys Val Pro Leu Gly Leu Thr Val Phe Tyr Leu Leu
1               5                   10                  15

Ser Leu Pro Ser Leu Lys Tyr Val Thr Asp Asn Tyr Leu Ala Lys Lys
            20                  25                  30

Tyr Asp Met Lys Ser Leu Leu Thr Glu Ser Met Val Leu Tyr Asn Val
        35                  40                  45

Ala Gln Val Leu Leu Asn Gly Trp Thr Val Tyr Ala Ile Val Asp Ala
    50                  55                  60

Val Met Asn Arg Asp His Pro Phe Ile Gly Ser Arg Ser Leu Val Gly
65                  70                  75                  80

Ala Ala Leu His Ser Gly Ser Ser Tyr Ala Val Trp Val His Tyr Cys
                85                  90                  95

Asp Lys Tyr Leu Glu Phe Phe Asp Thr Tyr Phe Met Val Leu Arg Gly
            100                 105                 110

Lys Met Asp Gln Val Ser Phe Leu His Ile Tyr His His Thr Thr Ile
        115                 120                 125

Ala Trp Ala Trp Trp Ile Ala Leu Arg Phe Ser Pro Gly Gly Asp Ile
    130                 135                 140

Tyr Phe Gly Ala Leu Leu Asn Ser Ile Ile His Val Leu Met Tyr Ser
145                 150                 155                 160

Tyr Tyr Ala Leu Ala Leu Leu Lys Val Ser Cys Pro Trp Lys Arg Tyr
                165                 170                 175

Leu Thr Gln Ala Gln Leu Leu Gln Phe Thr Ser Val Val Tyr Thr
            180                 185                 190

Gly Cys Thr Gly Tyr Thr His Tyr Tyr His Thr Lys His Gly Ala Asp
        195                 200                 205

Glu Thr Gln Pro Ser Leu Gly Tyr Tyr Phe Cys Cys Gly Val Gln
    210                 215                 220

```
Val Phe Glu Met Val Ser Leu Phe Val Leu Phe Ser Ile Phe Tyr Lys
225                 230                 235                 240

Arg Ser Tyr Ser Lys Lys Asn Lys Ser Gly Gly Lys Asp Ser Lys Lys
            245                 250                 255

Asn Asp Asp Gly Asn Asn Glu Asp Gln Cys His Lys Ala Met Lys Asp
        260                 265                 270

Ile Ser Glu Gly Ala Lys Glu Val Val Gly His Ala Ala Lys Asp Ala
        275                 280                 285

Gly Lys Leu Val Ala Thr Ala Ser Lys Ala Val Lys Arg Lys Gly Thr
        290                 295                 300

Arg Val Thr Gly Ala Met
305                 310

<210> SEQ ID NO 63
<211> LENGTH: 933
<212> TYPE: DNA
<213> ORGANISM: Thalassiosira pseudonana
<220> FEATURE:
<221> NAME/KEY: CDS
<222> LOCATION: (1)..(933)
<223> OTHER INFORMATION: delta5-elongase

<400> SEQUENCE: 63 atg cac tcc tac aaa gtc cca ctc ggt ctc acc gta ttc tac ctg ctg      48
Met His Ser Tyr Lys Val Pro Leu Gly Leu Thr Val Phe Tyr Leu Leu
1               5                   10                  15 agt cta ccg tca cta aag tac gtt acg gac aac tac ctt gcc aaa aag      96
Ser Leu Pro Ser Leu Lys Tyr Val Thr Asp Asn Tyr Leu Ala Lys Lys
            20                  25                  30 tat gat atg aag tca ctc cta acg gaa tca atg gtg ttg tac aat gtg     144
Tyr Asp Met Lys Ser Leu Leu Thr Glu Ser Met Val Leu Tyr Asn Val
        35                  40                  45 gcg caa gtg ctg ctc aat ggg tgg acg gtg tat gcg att gtg gat gcg     192
Ala Gln Val Leu Leu Asn Gly Trp Thr Val Tyr Ala Ile Val Asp Ala
    50                  55                  60 gtg atg aat aga gac cat ccg ttt att gga agt aga agt ttg gtt ggg     240
Val Met Asn Arg Asp His Pro Phe Ile Gly Ser Arg Ser Leu Val Gly
65                  70                  75                  80 gcg gcg ttg cat agt ggg agc tcg tat gcg gtg tgg gtt cat tat tgt     288
Ala Ala Leu His Ser Gly Ser Ser Tyr Ala Val Trp Val His Tyr Cys
                85                  90                  95 gat aag tat ttg gag ttc ttt gat acg tat ttt atg gtg ttg agg ggg     336
Asp Lys Tyr Leu Glu Phe Phe Asp Thr Tyr Phe Met Val Leu Arg Gly
            100                 105                 110 aaa atg gac cag gtc tcc ttc ctc cac atc tac cac cac acg acc ata     384
Lys Met Asp Gln Val Ser Phe Leu His Ile Tyr His His Thr Thr Ile
        115                 120                 125 gcg tgg gca tgg tgg atc gcc ctc cgc ttc tcc ccc ggt gga gac att     432
Ala Trp Ala Trp Trp Ile Ala Leu Arg Phe Ser Pro Gly Gly Asp Ile
    130                 135                 140 tac ttc ggg gca ctc ctc aac tcc atc atc cac gtc ctc atg tat tcc     480
Tyr Phe Gly Ala Leu Leu Asn Ser Ile Ile His Val Leu Met Tyr Ser
145                 150                 155                 160 tac tac gcc ctt gcc cta ctc aag gtc agt tgt cca tgg aaa cga tac     528
Tyr Tyr Ala Leu Ala Leu Leu Lys Val Ser Cys Pro Trp Lys Arg Tyr
                165                 170                 175 ctg act caa gct caa tta ttg caa ttc aca agt gtg gtg gtt tat acg     576
Leu Thr Gln Ala Gln Leu Leu Gln Phe Thr Ser Val Val Val Tyr Thr
            180                 185                 190 ggg tgt acg ggt tat act cat tac tat cat acg aag cat gga gcg gat     624
```

```
Gly Cys Thr Gly Tyr Thr His Tyr His Thr Lys His Gly Ala Asp
        195                 200                 205 gag aca cag cct agt tta gga acg tat tat ttc tgt tgt gga gtg cag      672
Glu Thr Gln Pro Ser Leu Gly Thr Tyr Tyr Phe Cys Cys Gly Val Gln
210                 215                 220 gtg ttt gag atg gtt agt ttg ttt gta ctc ttt tcc atc ttt tat aaa      720
Val Phe Glu Met Val Ser Leu Phe Val Leu Phe Ser Ile Phe Tyr Lys
225                 230                 235                 240 cga tcc tat tcg aag aag aac aag tca gga gga aag gat agc aag aag      768
Arg Ser Tyr Ser Lys Lys Asn Lys Ser Gly Gly Lys Asp Ser Lys Lys
            245                 250                 255 aat gat gat ggg aat aat gag gat caa tgt cac aag gct atg aag gat      816
Asn Asp Asp Gly Asn Asn Glu Asp Gln Cys His Lys Ala Met Lys Asp
        260                 265                 270 ata tcg gag ggt gcg aag gag gtt gtg ggg cat gca gcg aag gat gct      864
Ile Ser Glu Gly Ala Lys Glu Val Val Gly His Ala Ala Lys Asp Ala
    275                 280                 285 gga aag ttg gtg gct acg gcg agt aag gct gta aag agg aag gga act      912
Gly Lys Leu Val Ala Thr Ala Ser Lys Ala Val Lys Arg Lys Gly Thr
290                 295                 300 cgt gtt act ggt gcc atg tag                                          933
Arg Val Thr Gly Ala Met
305                 310

<210> SEQ ID NO 64
<211> LENGTH: 310
<212> TYPE: PRT
<213> ORGANISM: Thalassiosira pseudonana

<400> SEQUENCE: 64

Met His Ser Tyr Lys Val Pro Leu Gly Leu Thr Val Phe Tyr Leu Leu
1               5                   10                  15

Ser Leu Pro Ser Leu Lys Tyr Val Thr Asp Asn Tyr Leu Ala Lys Lys
            20                  25                  30

Tyr Asp Met Lys Ser Leu Leu Thr Glu Ser Met Val Leu Tyr Asn Val
        35                  40                  45

Ala Gln Val Leu Leu Asn Gly Trp Thr Val Tyr Ala Ile Val Asp Ala
    50                  55                  60

Val Met Asn Arg Asp His Pro Phe Ile Gly Ser Arg Ser Leu Val Gly
65                  70                  75                  80

Ala Ala Leu His Ser Gly Ser Ser Tyr Ala Val Trp Val His Tyr Cys
                85                  90                  95

Asp Lys Tyr Leu Glu Phe Phe Asp Thr Tyr Phe Met Val Leu Arg Gly
            100                 105                 110

Lys Met Asp Gln Val Ser Phe Leu His Ile Tyr His His Thr Thr Ile
        115                 120                 125

Ala Trp Ala Trp Trp Ile Ala Leu Arg Phe Ser Pro Gly Gly Asp Ile
    130                 135                 140

Tyr Phe Gly Ala Leu Leu Asn Ser Ile Ile His Val Leu Met Tyr Ser
145                 150                 155                 160

Tyr Tyr Ala Leu Ala Leu Leu Lys Val Ser Cys Pro Trp Lys Arg Tyr
                165                 170                 175

Leu Thr Gln Ala Gln Leu Leu Gln Phe Thr Ser Val Val Tyr Thr
            180                 185                 190

Gly Cys Thr Gly Tyr Thr His Tyr Tyr His Thr Lys His Gly Ala Asp
        195                 200                 205

Glu Thr Gln Pro Ser Leu Gly Thr Tyr Tyr Phe Cys Cys Gly Val Gln
```

```
                    210                 215                 220
Val Phe Glu Met Val Ser Leu Phe Val Leu Phe Ser Ile Phe Tyr Lys
225                 230                 235                 240

Arg Ser Tyr Ser Lys Lys Asn Lys Ser Gly Gly Lys Asp Ser Lys Lys
                245                 250                 255

Asn Asp Asp Gly Asn Asn Glu Asp Gln Cys His Lys Ala Met Lys Asp
                260                 265                 270

Ile Ser Glu Gly Ala Lys Glu Val Val Gly His Ala Ala Lys Asp Ala
            275                 280                 285

Gly Lys Leu Val Ala Thr Ala Ser Lys Ala Val Lys Arg Lys Gly Thr
        290                 295                 300

Arg Val Thr Gly Ala Met
305                 310

<210> SEQ ID NO 65
<211> LENGTH: 825
<212> TYPE: DNA
<213> ORGANISM: Thraustochytrium aureum
<220> FEATURE:
<221> NAME/KEY: CDS
<222> LOCATION: (1)..(825)
<223> OTHER INFORMATION: delta5-elongase

<400> SEQUENCE: 65 atg acg agc aac atg agc gcg tgg ggc gtc gcc gtc gac cag acg cag      48
Met Thr Ser Asn Met Ser Ala Trp Gly Val Ala Val Asp Gln Thr Gln
1               5                   10                  15 cag gtc gtc gac cag atc atg ggc ggc gcc gag ccg tac aag ctg aca      96
Gln Val Val Asp Gln Ile Met Gly Gly Ala Glu Pro Tyr Lys Leu Thr
            20                  25                  30 gaa ggg cgc atg acg aac gtc gag acg atg ctg gcg atc gag tgc ggc     144
Glu Gly Arg Met Thr Asn Val Glu Thr Met Leu Ala Ile Glu Cys Gly
        35                  40                  45 tac gcc gcc atg ctg ctg ttc ctg acc ccg atc atg aag cag gcc gag     192
Tyr Ala Ala Met Leu Leu Phe Leu Thr Pro Ile Met Lys Gln Ala Glu
    50                  55                  60 aag ccc ttc gag ctc aag tcc ttc aag ctc gcc cac aac ctg ttc ctg     240
Lys Pro Phe Glu Leu Lys Ser Phe Lys Leu Ala His Asn Leu Phe Leu
65                  70                  75                  80 ttc gtc ctg tcc gcc tac atg tgc ctc gag acc gtc cgc cag gcc tac     288
Phe Val Leu Ser Ala Tyr Met Cys Leu Glu Thr Val Arg Gln Ala Tyr
                85                  90                  95 ctt gcg ggc tac tcg gtg ttc ggc aac gac atg gag aag ggc agc gag     336
Leu Ala Gly Tyr Ser Val Phe Gly Asn Asp Met Glu Lys Gly Ser Glu
            100                 105                 110 ccg cac gcg cac ggc atg gcc caa atc gtg tgg atc ttt tac gtg tcc     384
Pro His Ala His Gly Met Ala Gln Ile Val Trp Ile Phe Tyr Val Ser
        115                 120                 125 aag gcg tac gag ttc gtg gac acg ctg atc atg atc ctg tgc aaa aag     432
Lys Ala Tyr Glu Phe Val Asp Thr Leu Ile Met Ile Leu Cys Lys Lys
    130                 135                 140 ttc aac cag gtc tcc gtc ctg cac gtg tac cac cac gcc acc atc ttt     480
Phe Asn Gln Val Ser Val Leu His Val Tyr His His Ala Thr Ile Phe
145                 150                 155                 160 gct atc tgg ttt atg atc gcc aag tac gcc ccg ggc ggc gac gca tac     528
Ala Ile Trp Phe Met Ile Ala Lys Tyr Ala Pro Gly Gly Asp Ala Tyr
                165                 170                 175 ttt agc gtc atc ctg aac tcg ttc gtg cac acc gtc atg tac gcg tac     576
Phe Ser Val Ile Leu Asn Ser Phe Val His Thr Val Met Tyr Ala Tyr
            180                 185                 190
```

| | | | | | | | | | | | | | | | | |
|---|---|---|---|---|---|---|---|---|---|---|---|---|---|---|---|---|
| tac | ttc | ttc | tcg | tcg | cag | ggc | ttc | ggg | ttc | gtc | aag | ccg | atc | aag | ccg | 624 |
| Tyr | Phe | Phe | Ser | Ser | Gln | Gly | Phe | Gly | Phe | Val | Lys | Pro | Ile | Lys | Pro | |
| | | | | 195 | | | | | 200 | | | | | 205 | | |
| tac | atc | acc | tcg | ctg | cag | atg | acg | cag | ttc | atg | gcg | atg | ctc | gtg | cag | 672 |
| Tyr | Ile | Thr | Ser | Leu | Gln | Met | Thr | Gln | Phe | Met | Ala | Met | Leu | Val | Gln | |
| 210 | | | | | 215 | | | | | 220 | | | | | | |
| tcg | ctg | tac | gac | tac | ctt | tac | ccg | tgc | gac | tac | ccg | cag | ggg | ctc | gtc | 720 |
| Ser | Leu | Tyr | Asp | Tyr | Leu | Tyr | Pro | Cys | Asp | Tyr | Pro | Gln | Gly | Leu | Val | |
| 225 | | | | | 230 | | | | | 235 | | | | | 240 | |
| aag | ctc | ctc | ggc | gtg | tac | atg | ctc | acc | ctg | ctt | gcg | ctc | ttc | ggc | aac | 768 |
| Lys | Leu | Leu | Gly | Val | Tyr | Met | Leu | Thr | Leu | Leu | Ala | Leu | Phe | Gly | Asn | |
| | | | | 245 | | | | | 250 | | | | | 255 | | |
| ttt | ttc | gtg | cag | agc | tac | ctc | aag | aag | tcg | aac | aag | ccc | aag | gcc | aag | 816 |
| Phe | Phe | Val | Gln | Ser | Tyr | Leu | Lys | Lys | Ser | Asn | Lys | Pro | Lys | Ala | Lys | |
| | | | 260 | | | | | 265 | | | | | 270 | | | |
| tcg | gcc | taa | | | | | | | | | | | | | | 825 |
| Ser | Ala | | | | | | | | | | | | | | | |

<210> SEQ ID NO 66
<211> LENGTH: 274
<212> TYPE: PRT
<213> ORGANISM: Thraustochytrium aureum

<400> SEQUENCE: 66

| | | | | | | | | | | | | | | |
|---|---|---|---|---|---|---|---|---|---|---|---|---|---|---|
| Met | Thr | Ser | Asn | Met | Ser | Ala | Trp | Gly | Val | Ala | Val | Asp | Gln | Thr | Gln |
| 1 | | | | 5 | | | | | 10 | | | | | 15 | |
| Gln | Val | Val | Asp | Gln | Ile | Met | Gly | Gly | Ala | Glu | Pro | Tyr | Lys | Leu | Thr |
| | | | 20 | | | | | 25 | | | | | 30 | | |
| Glu | Gly | Arg | Met | Thr | Asn | Val | Glu | Thr | Met | Leu | Ala | Ile | Glu | Cys | Gly |
| | | 35 | | | | | 40 | | | | | 45 | | | |
| Tyr | Ala | Ala | Met | Leu | Leu | Phe | Leu | Thr | Pro | Ile | Met | Lys | Gln | Ala | Glu |
| | 50 | | | | | 55 | | | | | 60 | | | | |
| Lys | Pro | Phe | Glu | Leu | Lys | Ser | Phe | Lys | Leu | Ala | His | Asn | Leu | Phe | Leu |
| 65 | | | | | 70 | | | | | 75 | | | | | 80 |
| Phe | Val | Leu | Ser | Ala | Tyr | Met | Cys | Leu | Glu | Thr | Val | Arg | Gln | Ala | Tyr |
| | | | | 85 | | | | | 90 | | | | | 95 | |
| Leu | Ala | Gly | Tyr | Ser | Val | Phe | Gly | Asn | Asp | Met | Glu | Lys | Gly | Ser | Glu |
| | | | 100 | | | | | 105 | | | | | 110 | | |
| Pro | His | Ala | His | Gly | Met | Ala | Gln | Ile | Val | Trp | Ile | Phe | Tyr | Val | Ser |
| | | 115 | | | | | 120 | | | | | 125 | | | |
| Lys | Ala | Tyr | Glu | Phe | Val | Asp | Thr | Leu | Ile | Met | Ile | Leu | Cys | Lys | Lys |
| | 130 | | | | | 135 | | | | | 140 | | | | |
| Phe | Asn | Gln | Val | Ser | Val | Leu | His | Val | Tyr | His | His | Ala | Thr | Ile | Phe |
| 145 | | | | | 150 | | | | | 155 | | | | | 160 |
| Ala | Ile | Trp | Phe | Met | Ile | Ala | Lys | Tyr | Ala | Pro | Gly | Gly | Asp | Ala | Tyr |
| | | | | 165 | | | | | 170 | | | | | 175 | |
| Phe | Ser | Val | Ile | Leu | Asn | Ser | Phe | Val | His | Thr | Val | Met | Tyr | Ala | Tyr |
| | | | 180 | | | | | 185 | | | | | 190 | | |
| Tyr | Phe | Phe | Ser | Ser | Gln | Gly | Phe | Gly | Phe | Val | Lys | Pro | Ile | Lys | Pro |
| | | | 195 | | | | | 200 | | | | | 205 | | |
| Tyr | Ile | Thr | Ser | Leu | Gln | Met | Thr | Gln | Phe | Met | Ala | Met | Leu | Val | Gln |
| | 210 | | | | | 215 | | | | | 220 | | | | |
| Ser | Leu | Tyr | Asp | Tyr | Leu | Tyr | Pro | Cys | Asp | Tyr | Pro | Gln | Gly | Leu | Val |
| 225 | | | | | 230 | | | | | 235 | | | | | 240 |
| Lys | Leu | Leu | Gly | Val | Tyr | Met | Leu | Thr | Leu | Leu | Ala | Leu | Phe | Gly | Asn |
| | | | | 245 | | | | | 250 | | | | | 255 | |

```
                Phe Val Gln Ser Tyr Leu Lys Lys Ser Asn Lys Pro Lys Ala Lys
                            260                 265                 270

Ser Ala

<210> SEQ ID NO 67
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta5-elongase

<400> SEQUENCE: 67 atg agc gcc tcc ggt gcg ctg ctg ccc gcg atc gcg ttc gcc gcg tac        48
Met Ser Ala Ser Gly Ala Leu Leu Pro Ala Ile Ala Phe Ala Ala Tyr
1               5                   10                  15 gcg tac gcg acg tac gcc tac gcc ttt gag tgg tcg cac gcg aat ggc        96
Ala Tyr Ala Thr Tyr Ala Tyr Ala Phe Glu Trp Ser His Ala Asn Gly
                20                  25                  30 atc gac aac gtc gac gcg cgc gag tgg atc ggt gcg ctg tcg ttg agg       144
Ile Asp Asn Val Asp Ala Arg Glu Trp Ile Gly Ala Leu Ser Leu Arg
            35                  40                  45 ctc ccg gcg atc gcg acg acg atg tac ctg ttg ttc tgc ctg gtc gga       192
Leu Pro Ala Ile Ala Thr Thr Met Tyr Leu Leu Phe Cys Leu Val Gly
        50                  55                  60 ccg agg ttg atg gcg aag cgc gag gcg ttc gac ccg aag ggg ttc atg       240
Pro Arg Leu Met Ala Lys Arg Glu Ala Phe Asp Pro Lys Gly Phe Met
65                  70                  75                  80 ctg gcg tac aat gcg tat cag acg gcg ttc aac gtc gtc gtg ctc ggg       288
Leu Ala Tyr Asn Ala Tyr Gln Thr Ala Phe Asn Val Val Val Leu Gly
                85                  90                  95 atg ttc gcg cga gag atc tcg ggg ctg ggg cag ccc gtg tgg ggg tca       336
Met Phe Ala Arg Glu Ile Ser Gly Leu Gly Gln Pro Val Trp Gly Ser
                100                 105                 110 acc atg ccg tgg agc gat aga aaa tcg ttt aag atc ctc ctc ggg gtg       384
Thr Met Pro Trp Ser Asp Arg Lys Ser Phe Lys Ile Leu Leu Gly Val
            115                 120                 125 tgg ttg cac tac aac aac caa tat ttg gag cta ttg gac act gtg ttc       432
Trp Leu His Tyr Asn Asn Gln Tyr Leu Glu Leu Leu Asp Thr Val Phe
        130                 135                 140 atg gtt gcg cgc aag aag acg aag cag ttg agc ttc ttg cac gtt tat       480
Met Val Ala Arg Lys Lys Thr Lys Gln Leu Ser Phe Leu His Val Tyr
145                 150                 155                 160 cat cac gcc ctg ttg atc tgg gcg tgg tgg ttg gtg tgt cac ttg atg       528
His His Ala Leu Leu Ile Trp Ala Trp Trp Leu Val Cys His Leu Met
                165                 170                 175 gcc acg aac gat tgt atc gat gcc tac ttc ggc gcg gcg tgc aac tcg       576
Ala Thr Asn Asp Cys Ile Asp Ala Tyr Phe Gly Ala Ala Cys Asn Ser
                180                 185                 190 ttc att cac atc gtg atg tac tcg tat tat ctc atg tcg gcg ctc ggc       624
Phe Ile His Ile Val Met Tyr Ser Tyr Tyr Leu Met Ser Ala Leu Gly
            195                 200                 205 att cga tgc ccg tgg aag cga tac atc acc cag gct caa atg ctc caa       672
Ile Arg Cys Pro Trp Lys Arg Tyr Ile Thr Gln Ala Gln Met Leu Gln
        210                 215                 220 ttc gtc att gtc ttc gcg cac gcc gtg ttc gtg ctg cgt cag aag cac       720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg       768
```

```
Cys Pro Val Thr Leu Pro Trp Ala Gln Met Phe Val Met Thr Asn Met
            245                 250                 255 ctc gtg ctc ttc ggg aac ttc tac ctc aag gcg tac tcg aac aag tcg      816
Leu Val Leu Phe Gly Asn Phe Tyr Leu Lys Ala Tyr Ser Asn Lys Ser
            260                 265                 270 cgc ggc gac ggc gcg agt tcc gtg aaa cca gcc gag acc acg cgc gcg      864
Arg Gly Asp Gly Ala Ser Ser Val Lys Pro Ala Glu Thr Thr Arg Ala
            275                 280                 285 ccc agc gtg cga cgc acg cga tct cga aaa att gac taa                  903
Pro Ser Val Arg Arg Thr Arg Ser Arg Lys Ile Asp
            290                 295                 300

<210> SEQ ID NO 68
<211> LENGTH: 300
<212> TYPE: PRT
<213> ORGANISM: Ostreococcus tauri

<400> SEQUENCE: 68

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
            85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
            115                 120                 125

Trp Leu His Tyr Asn Asn Gln Tyr Leu Glu Leu Leu Asp Thr Val Phe
        130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
            165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
210                 215                 220

Phe Val Ile Val Phe Ala His Ala Val Phe Leu Arg Gln Lys His
225                 230                 235                 240

Cys Pro Val Thr Leu Pro Trp Ala Gln Met Phe Val Met Thr Asn Met
            245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
            275                 280                 285

Pro Ser Val Arg Arg Thr Arg Ser Arg Lys Ile Asp
            290                 295                 300
```

<210> SEQ ID NO 69
<211> LENGTH: 879
<212> TYPE: DNA
<213> ORGANISM: Ostreococcus tauri
<220> FEATURE:
<221> NAME/KEY: CDS
<222> LOCATION: (1)..(879)
<223> OTHER INFORMATION: delta6-elongase

<400> SEQUENCE: 69

| | | | | | | | | | | | | | | | | |
|---|---|---|---|---|---|---|---|---|---|---|---|---|---|---|---|---|
| atg | agt | ggc | tta | cgt | gca | ccc | aac | ttt | tta | cac | aga | ttc | tgg | aca | aag | 48 |
| Met | Ser | Gly | Leu | Arg | Ala | Pro | Asn | Phe | Leu | His | Arg | Phe | Trp | Thr | Lys | |
| 1 | | | | 5 | | | | | 10 | | | | | 15 | | |
| tgg | gac | tac | gcg | att | tcc | aaa | gtc | gtc | ttc | acg | tgt | gcc | gac | agt | ttt | 96 |
| Trp | Asp | Tyr | Ala | Ile | Ser | Lys | Val | Val | Phe | Thr | Cys | Ala | Asp | Ser | Phe | |
| | | | 20 | | | | | 25 | | | | | 30 | | | |
| cag | tgg | gac | atc | ggg | cca | gtg | agt | tcg | agt | acg | gcg | cat | tta | ccc | gcc | 144 |
| Gln | Trp | Asp | Ile | Gly | Pro | Val | Ser | Ser | Ser | Thr | Ala | His | Leu | Pro | Ala | |
| | | 35 | | | | | 40 | | | | | 45 | | | | |
| att | gaa | tcc | cct | acc | cca | ctg | gtg | act | agc | ctc | ttg | ttc | tac | tta | gtc | 192 |
| Ile | Glu | Ser | Pro | Thr | Pro | Leu | Val | Thr | Ser | Leu | Leu | Phe | Tyr | Leu | Val | |
| | 50 | | | | | 55 | | | | | 60 | | | | | |
| aca | gtt | ttc | ttg | tgg | tat | ggt | cgt | tta | acc | agg | agt | tca | gac | aag | aaa | 240 |
| Thr | Val | Phe | Leu | Trp | Tyr | Gly | Arg | Leu | Thr | Arg | Ser | Ser | Asp | Lys | Lys | |
| 65 | | | | | 70 | | | | | 75 | | | | | 80 | |
| att | aga | gag | cct | acg | tgg | tta | aga | aga | ttc | ata | ata | tgt | cat | aat | gcg | 288 |
| Ile | Arg | Glu | Pro | Thr | Trp | Leu | Arg | Arg | Phe | Ile | Ile | Cys | His | Asn | Ala | |
| | | | | 85 | | | | | 90 | | | | | 95 | | |
| ttc | ttg | ata | gtc | ctc | agt | ctt | tac | atg | tgc | ctt | ggt | tgt | gtg | gcc | caa | 336 |
| Phe | Leu | Ile | Val | Leu | Ser | Leu | Tyr | Met | Cys | Leu | Gly | Cys | Val | Ala | Gln | |
| | | | 100 | | | | | 105 | | | | | 110 | | | |
| gcg | tat | cag | aat | gga | tat | act | tta | tgg | ggt | aat | gaa | ttc | aag | gcc | acg | 384 |
| Ala | Tyr | Gln | Asn | Gly | Tyr | Thr | Leu | Trp | Gly | Asn | Glu | Phe | Lys | Ala | Thr | |
| | | 115 | | | | | 120 | | | | | 125 | | | | |
| gaa | act | cag | ctt | gct | ctc | tac | att | tac | att | ttt | tac | gta | agt | aaa | ata | 432 |
| Glu | Thr | Gln | Leu | Ala | Leu | Tyr | Ile | Tyr | Ile | Phe | Tyr | Val | Ser | Lys | Ile | |
| | 130 | | | | | 135 | | | | | 140 | | | | | |
| tac | gag | ttt | gta | gat | act | tac | att | atg | ctt | ctc | aag | aat | aac | ttg | cgg | 480 |
| Tyr | Glu | Phe | Val | Asp | Thr | Tyr | Ile | Met | Leu | Leu | Lys | Asn | Asn | Leu | Arg | |
| 145 | | | | | 150 | | | | | 155 | | | | | 160 | |
| caa | gta | agt | ttc | cta | cac | att | tat | cac | cac | agc | acg | att | tcc | ttt | att | 528 |
| Gln | Val | Ser | Phe | Leu | His | Ile | Tyr | His | His | Ser | Thr | Ile | Ser | Phe | Ile | |
| | | | | 165 | | | | | 170 | | | | | 175 | | |
| tgg | tgg | atc | att | gct | cgg | agg | gct | ccg | ggt | ggt | gat | gct | tac | ttc | agc | 576 |
| Trp | Trp | Ile | Ile | Ala | Arg | Arg | Ala | Pro | Gly | Gly | Asp | Ala | Tyr | Phe | Ser | |
| | | | 180 | | | | | 185 | | | | | 190 | | | |
| gcg | gcc | ttg | aac | tca | tgg | gta | cac | gtg | tgc | atg | tac | acc | tat | tat | cta | 624 |
| Ala | Ala | Leu | Asn | Ser | Trp | Val | His | Val | Cys | Met | Tyr | Thr | Tyr | Tyr | Leu | |
| | | 195 | | | | | 200 | | | | | 205 | | | | |
| tta | tca | acc | ctt | att | gga | aaa | gaa | gat | cct | aag | cgt | tcc | aac | tac | ctt | 672 |
| Leu | Ser | Thr | Leu | Ile | Gly | Lys | Glu | Asp | Pro | Lys | Arg | Ser | Asn | Tyr | Leu | |
| | 210 | | | | | 215 | | | | | 220 | | | | | |
| tgg | tgg | ggt | cgc | cac | cta | acg | caa | atg | cag | atg | ctt | cag | ttt | ttc | ttc | 720 |
| Trp | Trp | Gly | Arg | His | Leu | Thr | Gln | Met | Gln | Met | Leu | Gln | Phe | Phe | Phe | |
| 225 | | | | | 230 | | | | | 235 | | | | | 240 | |
| aac | gta | ctt | caa | gcg | ttg | tac | tgc | gct | tcg | ttc | tct | acg | tat | ccc | aag | 768 |
| Asn | Val | Leu | Gln | Ala | Leu | Tyr | Cys | Ala | Ser | Phe | Ser | Thr | Tyr | Pro | Lys | |
| | | | | 245 | | | | | 250 | | | | | 255 | | |
| ttt | ttg | tcc | aaa | att | ctg | ctc | gtc | tat | atg | atg | agc | ctt | ctc | ggc | ttg | 816 |
| Phe | Leu | Ser | Lys | Ile | Leu | Leu | Val | Tyr | Met | Met | Ser | Leu | Leu | Gly | Leu | |

```
                              260                 265                 270
ttt  ggg  cat  ttc  tac  tat  tcc  aag  cac  ata  gca  gca  gct  aag  ctc  cag        864
Phe  Gly  His  Phe  Tyr  Tyr  Ser  Lys  His  Ile  Ala  Ala  Ala  Lys  Leu  Gln
          275                 280                 285 aaa  aaa  cag  cag  tga                                                                879
Lys  Lys  Gln  Gln
         290
```

<210> SEQ ID NO 70
<211> LENGTH: 292
<212> TYPE: PRT
<213> ORGANISM: Ostreococcus tauri

<400> SEQUENCE: 70

```
Met  Ser  Gly  Leu  Arg  Ala  Pro  Asn  Phe  Leu  His  Arg  Phe  Trp  Thr  Lys
1                   5                   10                  15

Trp  Asp  Tyr  Ala  Ile  Ser  Lys  Val  Val  Phe  Thr  Cys  Ala  Asp  Ser  Phe
                    20                  25                  30

Gln  Trp  Asp  Ile  Gly  Pro  Val  Ser  Ser  Thr  Ala  His  Leu  Pro  Ala
               35                   40                  45

Ile  Glu  Ser  Pro  Thr  Pro  Leu  Val  Thr  Ser  Leu  Leu  Phe  Tyr  Leu  Val
         50                  55                  60

Thr  Val  Phe  Leu  Trp  Tyr  Gly  Arg  Leu  Thr  Arg  Ser  Ser  Asp  Lys  Lys
65                  70                  75                  80

Ile  Arg  Glu  Pro  Thr  Trp  Leu  Arg  Arg  Phe  Ile  Ile  Cys  His  Asn  Ala
                    85                  90                  95

Phe  Leu  Ile  Val  Leu  Ser  Leu  Tyr  Met  Cys  Leu  Gly  Cys  Val  Ala  Gln
                100                 105                 110

Ala  Tyr  Gln  Asn  Gly  Tyr  Thr  Leu  Trp  Gly  Asn  Glu  Phe  Lys  Ala  Thr
               115                  120                 125

Glu  Thr  Gln  Leu  Ala  Leu  Tyr  Ile  Tyr  Ile  Phe  Tyr  Val  Ser  Lys  Ile
         130                 135                 140

Tyr  Glu  Phe  Val  Asp  Thr  Tyr  Ile  Met  Leu  Leu  Lys  Asn  Asn  Leu  Arg
145                 150                 155                 160

Gln  Val  Ser  Phe  Leu  His  Ile  Tyr  His  His  Ser  Thr  Ile  Ser  Phe  Ile
                    165                 170                 175

Trp  Trp  Ile  Ile  Ala  Arg  Arg  Ala  Pro  Gly  Gly  Asp  Ala  Tyr  Phe  Ser
               180                  185                 190

Ala  Ala  Leu  Asn  Ser  Trp  Val  His  Val  Cys  Met  Tyr  Thr  Tyr  Tyr  Leu
         195                 200                 205

Leu  Ser  Thr  Leu  Ile  Gly  Lys  Glu  Asp  Pro  Lys  Arg  Ser  Asn  Tyr  Leu
210                 215                 220

Trp  Trp  Gly  Arg  His  Leu  Thr  Gln  Met  Gln  Met  Leu  Gln  Phe  Phe  Phe
225                 230                 235                 240

Asn  Val  Leu  Gln  Ala  Leu  Tyr  Cys  Ala  Ser  Phe  Ser  Thr  Tyr  Pro  Lys
                    245                 250                 255

Phe  Leu  Ser  Lys  Ile  Leu  Leu  Val  Tyr  Met  Met  Ser  Leu  Leu  Gly  Leu
                260                 265                 270

Phe  Gly  His  Phe  Tyr  Tyr  Ser  Lys  His  Ile  Ala  Ala  Ala  Lys  Leu  Gln
               275                 280                 285

Lys  Lys  Gln  Gln
         290
```

<210> SEQ ID NO 71
<211> LENGTH: 1362
<212> TYPE: DNA

```
<213> ORGANISM: Primula farinosa
<220> FEATURE:
<221> NAME/KEY: CDS
<222> LOCATION: (1)..(1362)
<223> OTHER INFORMATION: delta6-desaturase

<400> SEQUENCE: 71 atg gct aac aaa tct cca cca aac ccc aaa aca ggt tac ata acc agc      48
Met Ala Asn Lys Ser Pro Pro Asn Pro Lys Thr Gly Tyr Ile Thr Ser
1               5                   10                  15 tca gac ctg aaa tcc cac aac aag gca ggt gac cta tgg ata tca atc      96
Ser Asp Leu Lys Ser His Asn Lys Ala Gly Asp Leu Trp Ile Ser Ile
            20                  25                  30 cac ggc caa gtc tac gac gtg tcc tct tgg gcc gcc ctt cat ccg ggg     144
His Gly Gln Val Tyr Asp Val Ser Ser Trp Ala Ala Leu His Pro Gly
        35                  40                  45 ggc act gcc cct ctc atg gcc ctt gca gga cac gac gtg acc gat gct     192
Gly Thr Ala Pro Leu Met Ala Leu Ala Gly His Asp Val Thr Asp Ala
    50                  55                  60 ttc ctc gcg tac cat ccc cct tcc act gcc cgt ctc ctc cct cct ctc     240
Phe Leu Ala Tyr His Pro Pro Ser Thr Ala Arg Leu Leu Pro Pro Leu
65                  70                  75                  80 tct acc aac ctc ctt ctt caa aac cac tcc gtc tcc ccc acc tcc tca     288
Ser Thr Asn Leu Leu Leu Gln Asn His Ser Val Ser Pro Thr Ser Ser
                85                  90                  95 gac tac cgc aaa ctc ctc gac aac ttc cat aaa cat ggc ctt ttc cgc     336
Asp Tyr Arg Lys Leu Leu Asp Asn Phe His Lys His Gly Leu Phe Arg
            100                 105                 110 gcc agg ggc cac act gct tac gcc acc ttc gtc ttc atg ata gcg atg     384
Ala Arg Gly His Thr Ala Tyr Ala Thr Phe Val Phe Met Ile Ala Met
        115                 120                 125 ttt cta atg agc gtg act gga gtc ctt tgc agc gac agt gcg tgg gtc     432
Phe Leu Met Ser Val Thr Gly Val Leu Cys Ser Asp Ser Ala Trp Val
    130                 135                 140 cat ttg gct agc ggc gga gca atg ggg ttc gcc tgg atc caa tgc gga     480
His Leu Ala Ser Gly Gly Ala Met Gly Phe Ala Trp Ile Gln Cys Gly
145                 150                 155                 160 tgg ata ggt cac gac tct ggg cat tac cgg att atg tct gac agg aaa     528
Trp Ile Gly His Asp Ser Gly His Tyr Arg Ile Met Ser Asp Arg Lys
                165                 170                 175 tgg aac tgg ttc gcg caa atc cta agc aca aac tgc ctc cag ggg att     576
Trp Asn Trp Phe Ala Gln Ile Leu Ser Thr Asn Cys Leu Gln Gly Ile
            180                 185                 190 agt atc ggg tgg tgg aag tgg aac cat aat gcg cac cac atc gct tgc     624
Ser Ile Gly Trp Trp Lys Trp Asn His Asn Ala His His Ile Ala Cys
        195                 200                 205 aat agc ctg gat tac gac ccc gac ctc cag tat atc cct ttg ctc gtc     672
Asn Ser Leu Asp Tyr Asp Pro Asp Leu Gln Tyr Ile Pro Leu Leu Val
    210                 215                 220 gtc tcc ccc aag ttc ttc aac tcc ctt act tct cgt ttc tac gac aag     720
Val Ser Pro Lys Phe Phe Asn Ser Leu Thr Ser Arg Phe Tyr Asp Lys
225                 230                 235                 240 aag ctg aac ttc gac ggc gtg tcg agg ttt ctg gtt tgc tac cag cac     768
Lys Leu Asn Phe Asp Gly Val Ser Arg Phe Leu Val Cys Tyr Gln His
                245                 250                 255 tgg acg ttt tat ccg gtc atg tgt gtc gct agg ctg aac atg ctc gcg     816
Trp Thr Phe Tyr Pro Val Met Cys Val Ala Arg Leu Asn Met Leu Ala
            260                 265                 270 cag tca ttt ata acg ctt ttc tcg agt agg gag gtg tgc cat agg gcg     864
Gln Ser Phe Ile Thr Leu Phe Ser Ser Arg Glu Val Cys His Arg Ala
        275                 280                 285
```

```
caa gag gtt ttc gga ctt gcc gtg ttt tgg gtt tgg ttt ccg ctt tta      912
Gln Glu Val Phe Gly Leu Ala Val Phe Trp Val Trp Phe Pro Leu Leu
    290                 295                 300 ctt tct tgt tta cct aat tgg ggc gag agg att atg ttt ttg ctt gcg      960
Leu Ser Cys Leu Pro Asn Trp Gly Glu Arg Ile Met Phe Leu Leu Ala
305                 310                 315                 320 agc tat tcc gtt acg ggg ata caa cac gtg cag ttc agc ttg aac cat     1008
Ser Tyr Ser Val Thr Gly Ile Gln His Val Gln Phe Ser Leu Asn His
                325                 330                 335 ttt tct tcg gac gtc tat gtg ggc ccg cca gta ggt aat gac tgg ttc     1056
Phe Ser Ser Asp Val Tyr Val Gly Pro Pro Val Gly Asn Asp Trp Phe
            340                 345                 350 aag aaa cag act gcc ggg aca ctt aac ata tcg tgc ccg gcg tgg atg     1104
Lys Lys Gln Thr Ala Gly Thr Leu Asn Ile Ser Cys Pro Ala Trp Met
355                 360                 365 gat tgg ttc cat ggc ggg tta cag ttt cag gtc gag cac cac ttg ttt     1152
Asp Trp Phe His Gly Gly Leu Gln Phe Gln Val Glu His His Leu Phe
    370                 375                 380 ccg cgg atg cct agg ggt cag ttt agg aag att tct cct ttt gtg agg     1200
Pro Arg Met Pro Arg Gly Gln Phe Arg Lys Ile Ser Pro Phe Val Arg
385                 390                 395                 400 gat ttg tgt aag aaa cac aac ttg cct tac aat atc gcg tct ttt act     1248
Asp Leu Cys Lys Lys His Asn Leu Pro Tyr Asn Ile Ala Ser Phe Thr
                405                 410                 415 aaa gcg aat gtg ttt acg ctt aag acg ctg aga aat acg gcc att gag     1296
Lys Ala Asn Val Phe Thr Leu Lys Thr Leu Arg Asn Thr Ala Ile Glu
            420                 425                 430 gct cgg gac ctc tct aat ccg ctc cca aag aat atg gtg tgg gaa gct     1344
Ala Arg Asp Leu Ser Asn Pro Leu Pro Lys Asn Met Val Trp Glu Ala
435                 440                 445 ctt aaa act ctc ggg tga                                              1362
Leu Lys Thr Leu Gly
    450

<210> SEQ ID NO 72
<211> LENGTH: 453
<212> TYPE: PRT
<213> ORGANISM: Primula farinosa

<400> SEQUENCE: 72

Met Ala Asn Lys Ser Pro Asn Pro Lys Thr Gly Tyr Ile Thr Ser
1               5                   10                  15

Ser Asp Leu Lys Ser His Asn Lys Ala Gly Asp Leu Trp Ile Ser Ile
            20                  25                  30

His Gly Gln Val Tyr Asp Val Ser Ser Trp Ala Ala Leu His Pro Gly
        35                  40                  45

Gly Thr Ala Pro Leu Met Ala Leu Ala Gly His Asp Val Thr Asp Ala
    50                  55                  60

Phe Leu Ala Tyr His Pro Pro Ser Thr Ala Arg Leu Leu Pro Pro Leu
65                  70                  75                  80

Ser Thr Asn Leu Leu Leu Gln Asn His Ser Val Ser Pro Thr Ser Ser
                85                  90                  95

Asp Tyr Arg Lys Leu Leu Asp Asn Phe His Lys His Gly Leu Phe Arg
            100                 105                 110

Ala Arg Gly His Thr Ala Tyr Ala Thr Phe Val Phe Met Ile Ala Met
        115                 120                 125

Phe Leu Met Ser Val Thr Gly Val Leu Cys Ser Asp Ser Ala Trp Val
    130                 135                 140
```

```
His Leu Ala Ser Gly Ala Met Gly Phe Ala Trp Ile Gln Cys Gly
145                 150                 155                 160

Trp Ile Gly His Asp Ser Gly His Tyr Arg Ile Met Ser Asp Arg Lys
                165                 170                 175

Trp Asn Trp Phe Ala Gln Ile Leu Ser Thr Asn Cys Leu Gln Gly Ile
            180                 185                 190

Ser Ile Gly Trp Trp Lys Trp Asn His Asn Ala His His Ile Ala Cys
        195                 200                 205

Asn Ser Leu Asp Tyr Asp Pro Asp Leu Gln Tyr Ile Pro Leu Leu Val
    210                 215                 220

Val Ser Pro Lys Phe Phe Asn Ser Leu Thr Ser Arg Phe Tyr Asp Lys
225                 230                 235                 240

Lys Leu Asn Phe Asp Gly Val Ser Arg Phe Leu Val Cys Tyr Gln His
                245                 250                 255

Trp Thr Phe Tyr Pro Val Met Cys Val Ala Arg Leu Asn Met Leu Ala
            260                 265                 270

Gln Ser Phe Ile Thr Leu Phe Ser Ser Arg Glu Val Cys His Arg Ala
        275                 280                 285

Gln Glu Val Phe Gly Leu Ala Val Phe Trp Val Trp Phe Pro Leu Leu
    290                 295                 300

Leu Ser Cys Leu Pro Asn Trp Gly Glu Arg Ile Met Phe Leu Leu Ala
305                 310                 315                 320

Ser Tyr Ser Val Thr Gly Ile Gln His Val Gln Phe Ser Leu Asn His
                325                 330                 335

Phe Ser Ser Asp Val Tyr Val Gly Pro Val Gly Asn Asp Trp Phe
            340                 345                 350

Lys Lys Gln Thr Ala Gly Thr Leu Asn Ile Ser Cys Pro Ala Trp Met
        355                 360                 365

Asp Trp Phe His Gly Gly Leu Gln Phe Gln Val Glu His His Leu Phe
    370                 375                 380

Pro Arg Met Pro Arg Gly Gln Phe Arg Lys Ile Ser Pro Phe Val Arg
385                 390                 395                 400

Asp Leu Cys Lys Lys His Asn Leu Pro Tyr Asn Ile Ala Ser Phe Thr
                405                 410                 415

Lys Ala Asn Val Phe Thr Leu Lys Thr Leu Arg Asn Thr Ala Ile Glu
            420                 425                 430

Ala Arg Asp Leu Ser Asn Pro Leu Pro Lys Asn Met Val Trp Glu Ala
        435                 440                 445

Leu Lys Thr Leu Gly
    450

<210> SEQ ID NO 73
<211> LENGTH: 1362
<212> TYPE: DNA
<213> ORGANISM: Primula vialii
<220> FEATURE:
<221> NAME/KEY: CDS
<222> LOCATION: (1)..(1362)
<223> OTHER INFORMATION: delta6-desaturase

<400> SEQUENCE: 73 atg gct aac aaa tct cca cca aac ccc aaa aca ggt tac att acc agc     48
Met Ala Asn Lys Ser Pro Pro Asn Pro Lys Thr Gly Tyr Ile Thr Ser
1               5                   10                  15 tca gac ctg aaa ggg cac aac aaa gca gga gac cta tgg ata tca atc     96
Ser Asp Leu Lys Gly His Asn Lys Ala Gly Asp Leu Trp Ile Ser Ile
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |

```
cac ggg gag gta tac gac gtg tcc tcg tgg gcc ggc ctt cac ccg ggg      144
His Gly Glu Val Tyr Asp Val Ser Ser Trp Ala Gly Leu His Pro Gly
         35                  40                  45 ggc agt gcc ccc ctc atg gcc ctc gca gga cac gac gta acc gac gct      192
Gly Ser Ala Pro Leu Met Ala Leu Ala Gly His Asp Val Thr Asp Ala
 50                  55                  60 ttt cta gcg tat cat cct cct tct acc gcc cgc ctc ctc cct ccc ctc      240
Phe Leu Ala Tyr His Pro Pro Ser Thr Ala Arg Leu Leu Pro Pro Leu
 65                  70                  75                  80 tcc acc aac ctc ctc ctt caa aac cac tcc gtc tcc ccc acc tcc tct      288
Ser Thr Asn Leu Leu Leu Gln Asn His Ser Val Ser Pro Thr Ser Ser
                 85                  90                  95 gac tac cgc aaa ctc ctc cac aac ttc cat aaa att ggt atg ttc cgc      336
Asp Tyr Arg Lys Leu Leu His Asn Phe His Lys Ile Gly Met Phe Arg
                100                 105                 110 gcc agg ggc cac act gct tac gcc acc ttc gtc atc atg ata gtg atg      384
Ala Arg Gly His Thr Ala Tyr Ala Thr Phe Val Ile Met Ile Val Met
            115                 120                 125 ttt cta acg agc gtg acc gga gtc ctt tgc agc gac agt gcg tgg gtc      432
Phe Leu Thr Ser Val Thr Gly Val Leu Cys Ser Asp Ser Ala Trp Val
130                 135                 140 cat ctg gct agc ggc gca gca atg ggg ttc gcc tgg atc cag tgc gga      480
His Leu Ala Ser Gly Ala Ala Met Gly Phe Ala Trp Ile Gln Cys Gly
145                 150                 155                 160 tgg ata ggt cac gac tct ggg cat tac cgg att atg tct gac agg aaa      528
Trp Ile Gly His Asp Ser Gly His Tyr Arg Ile Met Ser Asp Arg Lys
                165                 170                 175 tgg aac tgg ttc gcg cag gtc ctg agc aca aac tgc ctc cag ggg atc      576
Trp Asn Trp Phe Ala Gln Val Leu Ser Thr Asn Cys Leu Gln Gly Ile
            180                 185                 190 agt atc ggg tgg tgg aag tgg aac cat aac gcc cac cac att gct tgc      624
Ser Ile Gly Trp Trp Lys Trp Asn His Asn Ala His His Ile Ala Cys
        195                 200                 205 aat agc ctg gac tac gac ccc gac ctc cag tat atc cct ttg ctc gtg      672
Asn Ser Leu Asp Tyr Asp Pro Asp Leu Gln Tyr Ile Pro Leu Leu Val
210                 215                 220 gtc tcc ccc aag ttc ttc aac tcc ctt act tct cgt ttc tac gac aag      720
Val Ser Pro Lys Phe Phe Asn Ser Leu Thr Ser Arg Phe Tyr Asp Lys
225                 230                 235                 240 aag ctg aat ttc gac ggc gtg tca agg ttt ctg gtt tgc tac cag cac      768
Lys Leu Asn Phe Asp Gly Val Ser Arg Phe Leu Val Cys Tyr Gln His
                245                 250                 255 tgg acg ttt tat cca gtc atg tgt gtc gct agg cta aac atg atc gca      816
Trp Thr Phe Tyr Pro Val Met Cys Val Ala Arg Leu Asn Met Ile Ala
            260                 265                 270 cag tcg ttt ata acg ctt ttc tcg agc agg gag gtg ggt cat agg gcg      864
Gln Ser Phe Ile Thr Leu Phe Ser Ser Arg Glu Val Gly His Arg Ala
        275                 280                 285 caa gag att ttc gga ctt gct gtg ttt tgg gtt tgg ttt ccg ctc ctg      912
Gln Glu Ile Phe Gly Leu Ala Val Phe Trp Val Trp Phe Pro Leu Leu
290                 295                 300 ctc tct tgc tta cct aat tgg agc gag agg att atg ttt ctg cta gcg      960
Leu Ser Cys Leu Pro Asn Trp Ser Glu Arg Ile Met Phe Leu Leu Ala
305                 310                 315                 320 agc tat tcc gtt acg ggg ata cag cac gtg cag ttc agc ttg aac cat     1008
Ser Tyr Ser Val Thr Gly Ile Gln His Val Gln Phe Ser Leu Asn His
                325                 330                 335 ttt tct tcg gac gtc tac gtg ggc ccg cca gta gct aac gac tgg ttc     1056
```

```
Phe Ser Ser Asp Val Tyr Val Gly Pro Pro Val Ala Asn Asp Trp Phe
                 340                 345                 350 aag aaa cag act gct ggg aca ctt aac ata tcg tgc ccg gcg tgg atg    1104
Lys Lys Gln Thr Ala Gly Thr Leu Asn Ile Ser Cys Pro Ala Trp Met
            355                 360                 365 gac tgg ttc cat ggc ggg ttg cag ttt cag gtc gag cac cac ttg ttt    1152
Asp Trp Phe His Gly Gly Leu Gln Phe Gln Val Glu His His Leu Phe
    370                 375                 380 ccg cgg atg cct agg ggt cag ttt agg aag att tct cct ttt gtg agg    1200
Pro Arg Met Pro Arg Gly Gln Phe Arg Lys Ile Ser Pro Phe Val Arg
385                 390                 395                 400 gat ttg tgt aag aaa cac aac ttg cct tac aat atc gcg tct ttt act    1248
Asp Leu Cys Lys Lys His Asn Leu Pro Tyr Asn Ile Ala Ser Phe Thr
                405                 410                 415 aaa gca aac gtg ttg acg ctt aag acg ctg aga aat acg gcc att gag    1296
Lys Ala Asn Val Leu Thr Leu Lys Thr Leu Arg Asn Thr Ala Ile Glu
            420                 425                 430 gct cgg gac ctc tct aat ccg acc cca aag aat atg gtg tgg gaa gcc    1344
Ala Arg Asp Leu Ser Asn Pro Thr Pro Lys Asn Met Val Trp Glu Ala
    435                 440                 445 gtc cac aca cac ggc tag                                            1362
Val His Thr His Gly
    450

<210> SEQ ID NO 74
<211> LENGTH: 453
<212> TYPE: PRT
<213> ORGANISM: Primula vialii

<400> SEQUENCE: 74

Met Ala Asn Lys Ser Pro Pro Asn Pro Lys Thr Gly Tyr Ile Thr Ser
1               5                   10                  15

Ser Asp Leu Lys Gly His Asn Lys Ala Gly Asp Leu Trp Ile Ser Ile
            20                  25                  30

His Gly Glu Val Tyr Asp Val Ser Ser Trp Ala Gly Leu His Pro Gly
        35                  40                  45

Gly Ser Ala Pro Leu Met Ala Leu Ala Gly His Asp Val Thr Asp Ala
    50                  55                  60

Phe Leu Ala Tyr His Pro Pro Ser Thr Ala Arg Leu Leu Pro Pro Leu
65                  70                  75                  80

Ser Thr Asn Leu Leu Leu Gln Asn His Ser Val Ser Pro Thr Ser Ser
                85                  90                  95

Asp Tyr Arg Lys Leu Leu His Asn Phe His Lys Ile Gly Met Phe Arg
            100                 105                 110

Ala Arg Gly His Thr Ala Tyr Ala Thr Phe Val Ile Met Ile Val Met
        115                 120                 125

Phe Leu Thr Ser Val Thr Gly Val Leu Cys Ser Asp Ser Ala Trp Val
130                 135                 140

His Leu Ala Ser Gly Ala Ala Met Gly Phe Ala Trp Ile Gln Cys Gly
145                 150                 155                 160

Trp Ile Gly His Asp Ser Gly His Tyr Arg Ile Met Ser Asp Arg Lys
                165                 170                 175

Trp Asn Trp Phe Ala Gln Val Leu Ser Thr Asn Cys Leu Gln Gly Ile
            180                 185                 190

Ser Ile Gly Trp Trp Lys Trp Asn His Asn Ala His His Ile Ala Cys
        195                 200                 205

Asn Ser Leu Asp Tyr Asp Pro Asp Leu Gln Tyr Ile Pro Leu Leu Val
```

```
                     210                 215                 220
Val Ser Pro Lys Phe Phe Asn Ser Leu Thr Ser Arg Phe Tyr Asp Lys
225                 230                 235                 240

Lys Leu Asn Phe Asp Gly Val Ser Arg Phe Leu Val Cys Tyr Gln His
                245                 250                 255

Trp Thr Phe Tyr Pro Val Met Cys Val Ala Arg Leu Asn Met Ile Ala
            260                 265                 270

Gln Ser Phe Ile Thr Leu Phe Ser Ser Arg Glu Val Gly His Arg Ala
        275                 280                 285

Gln Glu Ile Phe Gly Leu Ala Val Phe Trp Val Trp Phe Pro Leu Leu
    290                 295                 300

Leu Ser Cys Leu Pro Asn Trp Ser Glu Arg Ile Met Phe Leu Leu Ala
305                 310                 315                 320

Ser Tyr Ser Val Thr Gly Ile Gln His Val Gln Phe Ser Leu Asn His
                325                 330                 335

Phe Ser Ser Asp Val Tyr Val Gly Pro Pro Val Ala Asn Asp Trp Phe
            340                 345                 350

Lys Lys Gln Thr Ala Gly Thr Leu Asn Ile Ser Cys Pro Ala Trp Met
        355                 360                 365

Asp Trp Phe His Gly Gly Leu Gln Phe Gln Val Glu His His Leu Phe
    370                 375                 380

Pro Arg Met Pro Arg Gly Gln Phe Arg Lys Ile Ser Pro Phe Val Arg
385                 390                 395                 400

Asp Leu Cys Lys Lys His Asn Leu Pro Tyr Asn Ile Ala Ser Phe Thr
                405                 410                 415

Lys Ala Asn Val Leu Thr Leu Lys Thr Leu Arg Asn Thr Ala Ile Glu
            420                 425                 430

Ala Arg Asp Leu Ser Asn Pro Thr Pro Lys Asn Met Val Trp Glu Ala
        435                 440                 445

Val His Thr His Gly
    450

<210> SEQ ID NO 75
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta5-elongase

<400> SEQUENCE: 75 atg agc gcc tcc ggt gcg ctg ctg ccc gcg atc gcg tcc gcc gcg tac      48
Met Ser Ala Ser Gly Ala Leu Leu Pro Ala Ile Ala Ser Ala Ala Tyr
1               5                  10                  15 gcg tac gcg acg tac gcc tac gcc ttt gag tgg tcg cac gcg aat ggc      96
Ala Tyr Ala Thr Tyr Ala Tyr Ala Phe Glu Trp Ser His Ala Asn Gly
            20                  25                  30 atc gac aac gtc gac gcg cgc gag tgg atc ggt gcg ctg tcg ttg agg     144
Ile Asp Asn Val Asp Ala Arg Glu Trp Ile Gly Ala Leu Ser Leu Arg
        35                  40                  45 ctc ccg gcg atc gcg acg acg atg tac ctg ttg ttc tgc ctg gtc gga     192
Leu Pro Ala Ile Ala Thr Thr Met Tyr Leu Leu Phe Cys Leu Val Gly
    50                  55                  60 ccg agg ttg atg gcg aag cgc gag gcg ttc gac ccg aag ggg ttc atg     240
Pro Arg Leu Met Ala Lys Arg Glu Ala Phe Asp Pro Lys Gly Phe Met
65                  70                  75                  80
```

-continued

```
ctg gcg tac aat gcg tat cag acg gcg ttc aac gtc gtc gtg ctc ggg       288
Leu Ala Tyr Asn Ala Tyr Gln Thr Ala Phe Asn Val Val Val Leu Gly
                 85                  90                  95 atg ttc gcg cga gag atc tcg ggg ctg ggg cag ccc gtg tgg ggg tca       336
Met Phe Ala Arg Glu Ile Ser Gly Leu Gly Gln Pro Val Trp Gly Ser
                100                 105                 110 acc atg ccg tgg agc gat aga aaa tcg ttt aag atc ctc ctc ggg gtg       384
Thr Met Pro Trp Ser Asp Arg Lys Ser Phe Lys Ile Leu Leu Gly Val
            115                 120                 125 tgg ttg cac tac aac aac aaa tat ttg gag cta ttg gac act gtg ttc       432
Trp Leu His Tyr Asn Asn Lys Tyr Leu Glu Leu Leu Asp Thr Val Phe
        130                 135                 140 atg gtt gcg cgc aag aag acg aag cag ttg agc ttc ttg cac gtt tat       480
Met Val Ala Arg Lys Lys Thr Lys Gln Leu Ser Phe Leu His Val Tyr
145                 150                 155                 160 cat cac gcc ctg ttg atc tgg gcg tgg tgg ttg gtg tgt cac ttg atg       528
His His Ala Leu Leu Ile Trp Ala Trp Trp Leu Val Cys His Leu Met
                165                 170                 175 gcc acg aac gat tgt atc gat gcc tac ttc ggc gcg gcg tgc aac tcg       576
Ala Thr Asn Asp Cys Ile Asp Ala Tyr Phe Gly Ala Ala Cys Asn Ser
                180                 185                 190 ttc att cac atc gtg atg tac tcg tat tat ctc atg tcg gcg ctc ggc       624
Phe Ile His Ile Val Met Tyr Ser Tyr Tyr Leu Met Ser Ala Leu Gly
            195                 200                 205 att cga tgc ccg tgg aag cga tac atc acc cag gct caa atg ctc caa       672
Ile Arg Cys Pro Trp Lys Arg Tyr Ile Thr Gln Ala Gln Met Leu Gln
        210                 215                 220 ttc gtc att gtc ttc gcg cac gcc gtg ttc gtg ctg cgt cag aag cac       720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg       768
Cys Pro Val Thr Leu Pro Trp Ala Gln Met Phe Val Met Thr Asn Met
                245                 250                 255 ctc gtg ctc ttc ggg aac ttc tac ctc aag gcg tac tcg aac aag tcg       816
Leu Val Leu Phe Gly Asn Phe Tyr Leu Lys Ala Tyr Ser Asn Lys Ser
                260                 265                 270 cgc ggc gac ggc gcg agt tcc gtg aaa cca gcc gag acc acg cgc gcg       864
Arg Gly Asp Gly Ala Ser Ser Val Lys Pro Ala Glu Thr Thr Arg Ala
            275                 280                 285 ccc agc gtg cga cgc acg cga tct cga aaa att gac taa                   903
Pro Ser Val Arg Arg Thr Arg Ser Arg Lys Ile Asp
        290                 295                 300

<210> SEQ ID NO 76
<211> LENGTH: 300
<212> TYPE: PRT
<213> ORGANISM: Ostreococcus tauri

<400> SEQUENCE: 76

Met Ser Ala Ser Gly Ala Leu Leu Pro Ala Ile Ala Ser Ala Ala Tyr
1               5                   10                  15

Ala Tyr Ala Thr Tyr Ala Tyr Ala Phe Glu Trp Ser His Ala Asn Gly
                20                  25                  30

Ile Asp Asn Val Asp Ala Arg Glu Trp Ile Gly Ala Leu Ser Leu Arg
            35                  40                  45

Leu Pro Ala Ile Ala Thr Thr Met Tyr Leu Leu Phe Cys Leu Val Gly
        50                  55                  60

Pro Arg Leu Met Ala Lys Arg Glu Ala Phe Asp Pro Lys Gly Phe Met
65                  70                  75                  80
```

```
Leu Ala Tyr Asn Ala Tyr Gln Thr Ala Phe Asn Val Val Leu Gly
                 85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
            115                 120                 125

Trp Leu His Tyr Asn Asn Lys Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
    195                 200                 205

Ile Arg Cys Pro Trp Lys Arg Tyr Ile Thr Gln Ala Gln Met Leu Gln
210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
    275                 280                 285

Pro Ser Val Arg Arg Thr Arg Ser Arg Lys Ile Asp
290                 295                 300

<210> SEQ ID NO 77
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta5-elongase

<400> SEQUENCE: 77 atg agc gcc tcc ggt gcg ctg ctg ccc gcg atc gcg ttc gcc gcg tac      48
Met Ser Ala Ser Gly Ala Leu Leu Pro Ala Ile Ala Phe Ala Ala Tyr
1               5                   10                  15 gcg tac gcg acg tac gcc tac gcc ttt gag tgg tcg cac gcg aat ggc      96
Ala Tyr Ala Thr Tyr Ala Tyr Ala Phe Glu Trp Ser His Ala Asn Gly
                20                  25                  30 atc gac aac gtc gac gcg cgc gag tgg atc ggt gcg ctg tcg ttg agg     144
Ile Asp Asn Val Asp Ala Arg Glu Trp Ile Gly Ala Leu Ser Leu Arg
            35                  40                  45 ctc ccg gcg atc gcg acg acg atg tac ctg ttg ttc tgc ctg gtc gga     192
Leu Pro Ala Ile Ala Thr Thr Met Tyr Leu Leu Phe Cys Leu Val Gly
        50                  55                  60 ccg agg ttg atg gcg aag cgc gag gcg ttc gac ccg aag ggg ttc atg     240
Pro Arg Leu Met Ala Lys Arg Glu Ala Phe Asp Pro Lys Gly Phe Met
65                  70                  75                  80 ctg gcg tac aat gcg tat cag acg gcg ttc aac gtc gtc gtg ctc ggg     288
Leu Ala Tyr Asn Ala Tyr Gln Thr Ala Phe Asn Val Val Val Leu Gly
                85                  90                  95 atg ttc gcg cga gag atc tcg ggg ctg ggg cag ccc gtg tgg ggg tca     336
```

```
Met Phe Ala Arg Glu Ile Ser Gly Leu Gly Gln Pro Val Trp Gly Ser
                100                 105                 110 acc atg ccg tgg agc gat aga aaa tcg ttt aag atc ctc ctc ggg gtg       384
Thr Met Pro Trp Ser Asp Arg Lys Ser Phe Lys Ile Leu Leu Gly Val
        115                 120                 125 tgg ttg cac tac aac aac aaa tat ttg gag cta ttg gac act gtg ttc       432
Trp Leu His Tyr Asn Asn Lys Tyr Leu Glu Leu Leu Asp Thr Val Phe
130                 135                 140 atg gtt gcg cgc aag aag acg aag cag ttg agc ttc ttg cac gtt tat       480
Met Val Ala Arg Lys Lys Thr Lys Gln Leu Ser Phe Leu His Val Tyr
145                 150                 155                 160 cat cac gcc ctg ttg atc tgg gcg tgg tgg ttg gtg tgt cac ttg atg       528
His His Ala Leu Leu Ile Trp Ala Trp Trp Leu Val Cys His Leu Met
                165                 170                 175 gcc acg aac gat tgt atc gat gcc tac ttc ggc gcg gcg tgc aac tcg       576
Ala Thr Asn Asp Cys Ile Asp Ala Tyr Phe Gly Ala Ala Cys Asn Ser
                180                 185                 190 ttc att cac atc gtg atg tac tcg tat tat ctc atg tcg gcg ctc ggc       624
Phe Ile His Ile Val Met Tyr Ser Tyr Tyr Leu Met Ser Ala Leu Gly
                195                 200                 205 att cga tgc ccg tgg aag cga tac atc acc cag gct caa atg ctc caa       672
Ile Arg Cys Pro Trp Lys Arg Tyr Ile Thr Gln Ala Gln Met Leu Gln
210                 215                 220 ttc gtc att gtc ttc gcg cac gcc gtg ttc gtg ctg cgt cag aag cac       720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg       768
Cys Pro Val Thr Leu Pro Trp Ala Gln Met Phe Val Met Thr Asn Met
                245                 250                 255 ctc gtg ctc ttc ggg aac ttc tac ctc aag gcg tac tcg aac aag tcg       816
Leu Val Leu Phe Gly Asn Phe Tyr Leu Lys Ala Tyr Ser Asn Lys Ser
                260                 265                 270 cgc ggc gac ggc gcg agt tcc gtg aaa cca gcc gag acc acg cgc gcg       864
Arg Gly Asp Gly Ala Ser Ser Val Lys Pro Ala Glu Thr Thr Arg Ala
                275                 280                 285 ccc agc gtg cga cgc acg cga tct cga aaa att gac taa                   903
Pro Ser Val Arg Arg Thr Arg Ser Arg Lys Ile Asp
290                 295                 300

<210> SEQ ID NO 78
<211> LENGTH: 300
<212> TYPE: PRT
<213> ORGANISM: Ostreococcus tauri

<400> SEQUENCE: 78

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
                20                  25                  30

Ile Asp Asn Val Asp Ala Arg Glu Trp Ile Gly Ala Leu Ser Leu Arg
            35                  40                  45

Leu Pro Ala Ile Ala Thr Thr Met Tyr Leu Leu Phe Cys Leu Val Gly
        50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
                100                 105                 110
```

```
Thr Met Pro Trp Ser Asp Arg Lys Ser Phe Lys Ile Leu Leu Gly Val
        115                 120                 125

Trp Leu His Tyr Asn Asn Lys Tyr Leu Glu Leu Leu Asp Thr Val Phe
        130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
                180                 185                 190

Phe Ile His Ile Val Met Tyr Ser Tyr Tyr Leu Met Ser Ala Leu Gly
            195                 200                 205

Ile Arg Cys Pro Trp Lys Arg Tyr Ile Thr Gln Ala Gln Met Leu Gln
        210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
                260                 265                 270

Arg Gly Asp Gly Ala Ser Ser Val Lys Pro Ala Glu Thr Thr Arg Ala
            275                 280                 285

Pro Ser Val Arg Arg Thr Arg Ser Arg Lys Ile Asp
        290                 295                 300

<210> SEQ ID NO 79
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta5-elongase

<400> SEQUENCE: 79 atg agc gcc tcc ggt gcg ctg ctg ccc gcg atc gcg tcc gcc gcg tac      48
Met Ser Ala Ser Gly Ala Leu Leu Pro Ala Ile Ala Ser Ala Ala Tyr
1               5                   10                  15 gcg tac gcg acg tac gcc tac gcc ttt gag tgg tcg cac gcg aat ggc      96
Ala Tyr Ala Thr Tyr Ala Tyr Ala Phe Glu Trp Ser His Ala Asn Gly
                20                  25                  30 atc gac aac gtc gac gcg cgc gag tgg atc ggt gcg ctg tcg ttg agg     144
Ile Asp Asn Val Asp Ala Arg Glu Trp Ile Gly Ala Leu Ser Leu Arg
            35                  40                  45 ctc ccg gcg atc gcg acg acg atg tac ctg ttg ttc tgc ctg gtc gga     192
Leu Pro Ala Ile Ala Thr Thr Met Tyr Leu Leu Phe Cys Leu Val Gly
        50                  55                  60 ccg agg ttg atg gcg aag cgc gag gcg ttc gac ccg aag ggg ttc atg     240
Pro Arg Leu Met Ala Lys Arg Glu Ala Phe Asp Pro Lys Gly Phe Met
65                  70                  75                  80 ctg gcg tac aat gcg tat cag acg gcg ttc aac gtc gtc gtg ctc ggg     288
Leu Ala Tyr Asn Ala Tyr Gln Thr Ala Phe Asn Val Val Val Leu Gly
                85                  90                  95 atg ttc gcg cga gag atc tcg ggg ctg ggg cag ccc gtg tgg ggg tca     336
Met Phe Ala Arg Glu Ile Ser Gly Leu Gly Gln Pro Val Trp Gly Ser
                100                 105                 110 acc atg ccg tgg agc gat aga aaa tcg ttt aag atc ctc ctc ggg gtg     384
Thr Met Pro Trp Ser Asp Arg Lys Ser Phe Lys Ile Leu Leu Gly Val
```

|   |   |   |   |   |   |   |   |   |   |   |   |   |   |   |   |     |
|---|---|---|---|---|---|---|---|---|---|---|---|---|---|---|---|-----|
|   | 115 |   |   |   | 120 |   |   |   | 125 |   |   |   |   |   |   |     |
| tgg | ttg | cac | tac | aac | aac | caa | tat | ttg | gag | cta | ttg | gac | act | gtg | ttc | 432 |
| Trp | Leu | His | Tyr | Asn | Asn | Gln | Tyr | Leu | Glu | Leu | Leu | Asp | Thr | Val | Phe |     |
|   | 130 |   |   |   | 135 |   |   |   | 140 |   |   |   |   |   |   |     |
| atg | gtt | gcg | cgc | aag | aag | acg | aag | cag | ttg | agc | ttc | ttg | cac | gtt | tat | 480 |
| Met | Val | Ala | Arg | Lys | Lys | Thr | Lys | Gln | Leu | Ser | Phe | Leu | His | Val | Tyr |     |
| 145 |   |   |   |   | 150 |   |   |   | 155 |   |   |   |   |   | 160 |     |
| cat | cac | gcc | ctg | ttg | atc | tgg | gcg | tgg | tgg | ttg | gtg | tgt | cac | ttg | atg | 528 |
| His | His | Ala | Leu | Leu | Ile | Trp | Ala | Trp | Trp | Leu | Val | Cys | His | Leu | Met |     |
|   |   |   | 165 |   |   |   |   | 170 |   |   |   |   | 175 |   |   |     |
| gcc | acg | aac | gat | tgt | atc | gat | gcc | tac | ttc | ggc | gcg | gcg | tgc | aac | tcg | 576 |
| Ala | Thr | Asn | Asp | Cys | Ile | Asp | Ala | Tyr | Phe | Gly | Ala | Ala | Cys | Asn | Ser |     |
|   |   | 180 |   |   |   |   | 185 |   |   |   |   | 190 |   |   |   |     |
| ttc | att | cac | atc | gtg | atg | tac | tcg | tat | tat | ctc | atg | tcg | gcg | ctc | ggc | 624 |
| Phe | Ile | His | Ile | Val | Met | Tyr | Ser | Tyr | Tyr | Leu | Met | Ser | Ala | Leu | Gly |     |
|   | 195 |   |   |   | 200 |   |   |   | 205 |   |   |   |   |   |   |     |
| att | cga | tgc | ccg | tgg | aag | cga | tac | atc | acc | cag | gct | caa | atg | ctc | caa | 672 |
| Ile | Arg | Cys | Pro | Trp | Lys | Arg | Tyr | Ile | Thr | Gln | Ala | Gln | Met | Leu | Gln |     |
|   | 210 |   |   |   | 215 |   |   |   | 220 |   |   |   |   |   |   |     |
| ttc | gtc | att | gtc | ttc | gcg | cac | gcc | gtg | ttc | gtg | ctg | cgt | cag | aag | cac | 720 |
| Phe | Val | Ile | Val | Phe | Ala | His | Ala | Val | Phe | Val | Leu | Arg | Gln | Lys | His |     |
| 225 |   |   |   |   | 230 |   |   |   | 235 |   |   |   |   |   | 240 |     |
| tgc | ccg | gtc | acc | ctt | cct | tgg | gcg | caa | atg | ttc | gtc | atg | acg | aac | atg | 768 |
| Cys | Pro | Val | Thr | Leu | Pro | Trp | Ala | Gln | Met | Phe | Val | Met | Thr | Asn | Met |     |
|   |   |   | 245 |   |   |   |   | 250 |   |   |   |   | 255 |   |   |     |
| ctc | gtg | ctc | ttc | ggg | aac | ttc | tac | ctc | aag | gcg | tac | tcg | aac | aag | tcg | 816 |
| Leu | Val | Leu | Phe | Gly | Asn | Phe | Tyr | Leu | Lys | Ala | Tyr | Ser | Asn | Lys | Ser |     |
|   |   | 260 |   |   |   |   | 265 |   |   |   |   | 270 |   |   |   |     |
| cgc | ggc | gac | ggc | gcg | agt | tcc | gtg | aaa | cca | gcc | gag | acc | acg | cgc | gcg | 864 |
| Arg | Gly | Asp | Gly | Ala | Ser | Ser | Val | Lys | Pro | Ala | Glu | Thr | Thr | Arg | Ala |     |
|   | 275 |   |   |   | 280 |   |   |   | 285 |   |   |   |   |   |   |     |
| ccc | agc | gtg | cga | cgc | acg | cga | tct | cga | aaa | att | gac | taa |   |   |   | 903 |
| Pro | Ser | Val | Arg | Arg | Thr | Arg | Ser | Arg | Lys | Ile | Asp |   |   |   |   |     |
|   | 290 |   |   |   | 295 |   |   |   | 300 |   |   |   |   |   |   |     |

<210> SEQ ID NO 80
<211> LENGTH: 300
<212> TYPE: PRT
<213> ORGANISM: Ostreococcus tauri

<400> SEQUENCE: 80

Met Ser Ala Ser Gly Ala Leu Leu Pro Ala Ile Ala Ser Ala Ala Tyr
1               5                   10                  15

Ala Tyr Ala Thr Tyr Ala Tyr Ala Phe Glu Trp Ser His Ala Asn Gly
                20                  25                  30

Ile Asp Asn Val Asp Ala Arg Glu Trp Ile Gly Ala Leu Ser Leu Arg
            35                  40                  45

Leu Pro Ala Ile Ala Thr Thr Met Tyr Leu Leu Phe Cys Leu Val Gly
        50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Leu Gly
                85                  90                  95

Met Phe Ala Arg Glu Ile Ser Gly Leu Gly Gln Pro Val Trp Gly Ser
                100                 105                 110

Thr Met Pro Trp Ser Asp Arg Lys Ser Phe Lys Ile Leu Leu Gly Val
            115                 120                 125

Trp Leu His Tyr Asn Asn Gln Tyr Leu Glu Leu Leu Asp Thr Val Phe

| | | | | | 130 | | | | | 135 | | | | | 140 | | |

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
            165                 170                 175

Ala Thr Asn Asp Cys Ile Asp Ala Tyr Phe Gly Ala Ala Cys Asn Ser
        180                 185                 190

Phe Ile His Ile Val Met Tyr Ser Tyr Leu Met Ser Ala Leu Gly
    195                 200                 205

Ile Arg Cys Pro Trp Lys Arg Tyr Ile Thr Gln Ala Gln Met Leu Gln
210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
            245                 250                 255

Leu Val Leu Phe Gly Asn Phe Tyr Leu Lys Ala Tyr Ser Asn Lys Ser
        260                 265                 270

Arg Gly Asp Gly Ala Ser Ser Val Lys Pro Ala Glu Thr Thr Arg Ala
    275                 280                 285

Pro Ser Val Arg Arg Thr Arg Ser Arg Lys Ile Asp
290                 295                 300

<210> SEQ ID NO 81
<211> LENGTH: 879
<212> TYPE: DNA
<213> ORGANISM: Ostreococcus tauri
<220> FEATURE:
<221> NAME/KEY: CDS
<222> LOCATION: (1)..(879)
<223> OTHER INFORMATION: delta6-elongase

<400> SEQUENCE: 81

```
atg agt ggc tta cgt gca ccc aac ttt tta cac aga ttc tgg aca aag      48
Met Ser Gly Leu Arg Ala Pro Asn Phe Leu His Arg Phe Trp Thr Lys
1               5                   10                  15 tgg gac tac gcg att tcc aaa gtc gtc ttc acg tgt gcc gac agt ttt      96
Trp Asp Tyr Ala Ile Ser Lys Val Val Phe Thr Cys Ala Asp Ser Phe
            20                  25                  30 cag tgg gac atc ggg cca gtg agt tcg agt acg gcg cat tta ccc gcc    144
Gln Trp Asp Ile Gly Pro Val Ser Ser Ser Thr Ala His Leu Pro Ala
        35                  40                  45 att gaa tcc cct acc cca ctg gtg act agc ctc ttg ttc tac tta gtc    192
Ile Glu Ser Pro Thr Pro Leu Val Thr Ser Leu Leu Phe Tyr Leu Val
    50                  55                  60 aca gtt ttc ttg tgg tat ggt cgt tta acc agg agt tca gac aag aaa    240
Thr Val Phe Leu Trp Tyr Gly Arg Leu Thr Arg Ser Ser Asp Lys Lys
65                  70                  75                  80 att aga gag cct acg tgg tta aga aga ttc ata ata tgt cat aat gcg    288
Ile Arg Glu Pro Thr Trp Leu Arg Arg Phe Ile Ile Cys His Asn Ala
                85                  90                  95 ttc ttg ata gtc ctc agt ctt tac atg tgc ctt ggt tgt gtg gcc caa    336
Phe Leu Ile Val Leu Ser Leu Tyr Met Cys Leu Gly Cys Val Ala Gln
            100                 105                 110 gcg tat cag aat gga tat act tta tgg ggt aat gaa ttc aag gcc acg    384
Ala Tyr Gln Asn Gly Tyr Thr Leu Trp Gly Asn Glu Phe Lys Ala Thr
        115                 120                 125 gaa act cag ctt gct ctc tac att tac att ttt tac gta agt aaa ata    432
Glu Thr Gln Leu Ala Leu Tyr Ile Tyr Ile Phe Tyr Val Ser Lys Ile
    130                 135                 140
```

| | | | | | | | | | | | | | | | | |
|---|---|---|---|---|---|---|---|---|---|---|---|---|---|---|---|---|
| tac | gag | ttt | gta | gat | act | tac | att | atg | ctt | ctc | aag | aat | aac | ttg | cgg | 480 |
| Tyr | Glu | Phe | Val | Asp | Thr | Tyr | Ile | Met | Leu | Leu | Lys | Asn | Asn | Leu | Arg | |
| 145 | | | | 150 | | | | | 155 | | | | | 160 | | |
| caa | gta | aga | ttc | cta | cac | act | tat | cac | cac | agc | acg | att | tcc | ttt | att | 528 |
| Gln | Val | Arg | Phe | Leu | His | Thr | Tyr | His | His | Ser | Thr | Ile | Ser | Phe | Ile | |
| | | | | 165 | | | | | 170 | | | | | 175 | | |
| tgg | tgg | atc | att | gct | cgg | agg | gct | ccg | ggt | ggt | gat | gct | tac | ttc | agc | 576 |
| Trp | Trp | Ile | Ile | Ala | Arg | Arg | Ala | Pro | Gly | Gly | Asp | Ala | Tyr | Phe | Ser | |
| | | | 180 | | | | | 185 | | | | | 190 | | | |
| gcg | gcc | ttg | aac | tca | tgg | gta | cac | gtg | tgc | atg | tac | acc | tat | tat | cta | 624 |
| Ala | Ala | Leu | Asn | Ser | Trp | Val | His | Val | Cys | Met | Tyr | Thr | Tyr | Tyr | Leu | |
| | | | | 195 | | | | | 200 | | | | | 205 | | |
| tta | tca | acc | ctt | att | gga | aaa | gaa | gat | cct | aag | cgt | tcc | aac | tac | ctt | 672 |
| Leu | Ser | Thr | Leu | Ile | Gly | Lys | Glu | Asp | Pro | Lys | Arg | Ser | Asn | Tyr | Leu | |
| | 210 | | | | | 215 | | | | | 220 | | | | | |
| tgg | tgg | ggt | cgc | cac | cta | acg | caa | atg | cag | atg | ctt | cag | ttt | ttc | ttc | 720 |
| Trp | Trp | Gly | Arg | His | Leu | Thr | Gln | Met | Gln | Met | Leu | Gln | Phe | Phe | Phe | |
| 225 | | | | | 230 | | | | | 235 | | | | | 240 | |
| aac | gta | ctt | caa | gcg | ttg | tac | tgc | gct | tcg | ttc | tct | acg | tat | ccc | aag | 768 |
| Asn | Val | Leu | Gln | Ala | Leu | Tyr | Cys | Ala | Ser | Phe | Ser | Thr | Tyr | Pro | Lys | |
| | | | | 245 | | | | | 250 | | | | | 255 | | |
| ttt | ttg | tcc | aaa | att | ctg | ctc | gtc | tat | atg | atg | agc | ctt | ctc | ggc | ttg | 816 |
| Phe | Leu | Ser | Lys | Ile | Leu | Leu | Val | Tyr | Met | Met | Ser | Leu | Leu | Gly | Leu | |
| | | | 260 | | | | | 265 | | | | | 270 | | | |
| ttt | ggg | cat | ttc | tac | tat | tcc | aag | cac | ata | gca | gca | gct | aag | ctc | cag | 864 |
| Phe | Gly | His | Phe | Tyr | Tyr | Ser | Lys | His | Ile | Ala | Ala | Ala | Lys | Leu | Gln | |
| | | 275 | | | | | 280 | | | | | 285 | | | | |
| aaa | aaa | cag | cag | tga | | | | | | | | | | | | 879 |
| Lys | Lys | Gln | Gln | | | | | | | | | | | | | |
| | 290 | | | | | | | | | | | | | | | |

<210> SEQ ID NO 82
<211> LENGTH: 292
<212> TYPE: PRT
<213> ORGANISM: Ostreococcus tauri

<400> SEQUENCE: 82

Met Ser Gly Leu Arg Ala Pro Asn Phe Leu His Arg Phe Trp Thr Lys
1               5                   10                  15

Trp Asp Tyr Ala Ile Ser Lys Val Val Phe Thr Cys Ala Asp Ser Phe
            20                  25                  30

Gln Trp Asp Ile Gly Pro Val Ser Ser Thr Ala His Leu Pro Ala
        35                  40                  45

Ile Glu Ser Pro Thr Pro Leu Val Thr Ser Leu Leu Phe Tyr Leu Val
    50                  55                  60

Thr Val Phe Leu Trp Tyr Gly Arg Leu Thr Arg Ser Ser Asp Lys Lys
65                  70                  75                  80

Ile Arg Glu Pro Thr Trp Leu Arg Arg Phe Ile Ile Cys His Asn Ala
                85                  90                  95

Phe Leu Ile Val Leu Ser Leu Tyr Met Cys Leu Gly Cys Val Ala Gln
            100                 105                 110

Ala Tyr Gln Asn Gly Tyr Thr Leu Trp Gly Asn Glu Phe Lys Ala Thr
        115                 120                 125

Glu Thr Gln Leu Ala Leu Tyr Ile Tyr Ile Phe Tyr Val Ser Lys Ile
    130                 135                 140

Tyr Glu Phe Val Asp Thr Tyr Ile Met Leu Leu Lys Asn Asn Leu Arg
145                 150                 155                 160

```
Gln Val Arg Phe Leu His Thr Tyr His His Ser Thr Ile Ser Phe Ile
                165                 170                 175

Trp Trp Ile Ile Ala Arg Arg Ala Pro Gly Gly Asp Ala Tyr Phe Ser
            180                 185                 190

Ala Ala Leu Asn Ser Trp Val His Val Cys Met Tyr Thr Tyr Tyr Leu
        195                 200                 205

Leu Ser Thr Leu Ile Gly Lys Glu Asp Pro Lys Arg Ser Asn Tyr Leu
    210                 215                 220

Trp Trp Gly Arg His Leu Thr Gln Met Gln Met Leu Gln Phe Phe Phe
225                 230                 235                 240

Asn Val Leu Gln Ala Leu Tyr Cys Ala Ser Phe Ser Thr Tyr Pro Lys
                245                 250                 255

Phe Leu Ser Lys Ile Leu Leu Val Tyr Met Met Ser Leu Leu Gly Leu
            260                 265                 270

Phe Gly His Phe Tyr Tyr Ser Lys His Ile Ala Ala Ala Lys Leu Gln
        275                 280                 285

Lys Lys Gln Gln
    290
```

<210> SEQ ID NO 83
<211> LENGTH: 831
<212> TYPE: DNA
<213> ORGANISM: Thraustochytrium sp.
<220> FEATURE:
<221> NAME/KEY: CDS
<222> LOCATION: (1)..(831)
<223> OTHER INFORMATION: delta5-elongase

<400> SEQUENCE: 83

```
atg gac gtc gtc gag cag caa tgg cgc cgc ttc gtg gac gcc gtg gac      48
Met Asp Val Val Glu Gln Gln Trp Arg Arg Phe Val Asp Ala Val Asp
1               5                   10                  15 aac gga atc gtg gag ttc atg gag cat gag aag ccc aac aag ctg aac      96
Asn Gly Ile Val Glu Phe Met Glu His Glu Lys Pro Asn Lys Leu Asn
                20                  25                  30 gag ggc aag ctc ttc acc tcg acc gag gag atg atg gcg ctt atc gtc     144
Glu Gly Lys Leu Phe Thr Ser Thr Glu Glu Met Met Ala Leu Ile Val
            35                  40                  45 ggc tac ctg gcg ttc gtg gtc ctc ggg tcc gcc ttc atg aag gcc ttt     192
Gly Tyr Leu Ala Phe Val Val Leu Gly Ser Ala Phe Met Lys Ala Phe
        50                  55                  60 gtc gat aag cct ttc gag ctc aag ttc ctc aag ctc gtg cac aac atc     240
Val Asp Lys Pro Phe Glu Leu Lys Phe Leu Lys Leu Val His Asn Ile
65                  70                  75                  80 ttc ctc acc ggt ctg tcc atg tac atg gcc acc gag tgc gcg cgc cag     288
Phe Leu Thr Gly Leu Ser Met Tyr Met Ala Thr Glu Cys Ala Arg Gln
                85                  90                  95 gca tac ctc ggc ggc tac aag ctc ttt ggc aac ccg atg gag aag ggc     336
Ala Tyr Leu Gly Gly Tyr Lys Leu Phe Gly Asn Pro Met Glu Lys Gly
            100                 105                 110 acc gag tcg cac gcc ccg ggc atg gcc aac atc atc tac atc ttc tac     384
Thr Glu Ser His Ala Pro Gly Met Ala Asn Ile Ile Tyr Ile Phe Tyr
        115                 120                 125 gtg agc aag ttc ctc gaa ttc ctc gac acc gtc ttc atg atc ctc ggc     432
Val Ser Lys Phe Leu Glu Phe Leu Asp Thr Val Phe Met Ile Leu Gly
    130                 135                 140 aag aag tgg aag cag ctc agc ttt ctc cac gtc tac cac cac gcg agc     480
Lys Lys Trp Lys Gln Leu Ser Phe Leu His Val Tyr His His Ala Ser
145                 150                 155                 160
```

```
atc agc ttc atc tgg ggc atc atc gcc cgc ttc gcg ccc ggt ggc gac        528
Ile Ser Phe Ile Trp Gly Ile Ile Ala Arg Phe Ala Pro Gly Gly Asp
        165                 170                 175 gcc tac ttc tct acc atc ctc aac agc agc gtg cat gtc gtg ctc tac        576
Ala Tyr Phe Ser Thr Ile Leu Asn Ser Ser Val His Val Val Leu Tyr
            180                 185                 190 ggc tac tac gcc tcg acc acc ctc ggc tac acc ttc atg cgc ccg ctg        624
Gly Tyr Tyr Ala Ser Thr Thr Leu Gly Tyr Thr Phe Met Arg Pro Leu
        195                 200                 205 cgc ccg tac att acc acc att cag ctc acg cag ttc atg gcc atg gtc        672
Arg Pro Tyr Ile Thr Thr Ile Gln Leu Thr Gln Phe Met Ala Met Val
    210                 215                 220 gtc cag tcc gtc tat gac tac tac aac ccc tgc gac tac ccg cag ccc        720
Val Gln Ser Val Tyr Asp Tyr Tyr Asn Pro Cys Asp Tyr Pro Gln Pro
225                 230                 235                 240 ctc gtc aag ctg ctc ttc tgg tac atg ctc acc atg ctc ggc ctc ttc        768
Leu Val Lys Leu Leu Phe Trp Tyr Met Leu Thr Met Leu Gly Leu Phe
                245                 250                 255 ggc aac ttc ttc gtg cag cag tac ctc aag ccc aag gcg ccc aag aag        816
Gly Asn Phe Phe Val Gln Gln Tyr Leu Lys Pro Lys Ala Pro Lys Lys
            260                 265                 270 cag aag acc atc taa                                                    831
Gln Lys Thr Ile
        275
```

<210> SEQ ID NO 84
<211> LENGTH: 276
<212> TYPE: PRT
<213> ORGANISM: Thraustochytrium sp.

<400> SEQUENCE: 84

```
Met Asp Val Val Glu Gln Gln Trp Arg Arg Phe Val Asp Ala Val Asp
1               5                   10                  15

Asn Gly Ile Val Glu Phe Met Glu His Glu Lys Pro Asn Lys Leu Asn
            20                  25                  30

Glu Gly Lys Leu Phe Thr Ser Thr Glu Glu Met Met Ala Leu Ile Val
        35                  40                  45

Gly Tyr Leu Ala Phe Val Val Leu Gly Ser Ala Phe Met Lys Ala Phe
    50                  55                  60

Val Asp Lys Pro Phe Glu Leu Lys Phe Lys Leu Val His Asn Ile
65                  70                  75                  80

Phe Leu Thr Gly Leu Ser Met Tyr Met Ala Thr Glu Cys Ala Arg Gln
                85                  90                  95

Ala Tyr Leu Gly Gly Tyr Lys Leu Phe Gly Asn Pro Met Glu Lys Gly
            100                 105                 110

Thr Glu Ser His Ala Pro Gly Met Ala Asn Ile Ile Tyr Ile Phe Tyr
        115                 120                 125

Val Ser Lys Phe Leu Glu Phe Leu Asp Thr Val Phe Met Ile Leu Gly
    130                 135                 140

Lys Lys Trp Lys Gln Leu Ser Phe Leu His Val Tyr His His Ala Ser
145                 150                 155                 160

Ile Ser Phe Ile Trp Gly Ile Ile Ala Arg Phe Ala Pro Gly Gly Asp
                165                 170                 175

Ala Tyr Phe Ser Thr Ile Leu Asn Ser Ser Val His Val Val Leu Tyr
            180                 185                 190

Gly Tyr Tyr Ala Ser Thr Thr Leu Gly Tyr Thr Phe Met Arg Pro Leu
        195                 200                 205
```

```
Arg Pro Tyr Ile Thr Thr Ile Gln Leu Thr Gln Phe Met Ala Met Val
    210                 215                 220
Val Gln Ser Val Tyr Asp Tyr Tyr Asn Pro Cys Asp Tyr Pro Gln Pro
225                 230                 235                 240
Leu Val Lys Leu Leu Phe Trp Tyr Met Leu Thr Met Leu Gly Leu Phe
                245                 250                 255
Gly Asn Phe Phe Val Gln Gln Tyr Leu Lys Pro Lys Ala Pro Lys Lys
                260                 265                 270
Gln Lys Thr Ile
        275

<210> SEQ ID NO 85
<211> LENGTH: 1077
<212> TYPE: DNA
<213> ORGANISM: Thalassiosira pseudonana
<220> FEATURE:
<221> NAME/KEY: CDS
<222> LOCATION: (1)..(1077)
<223> OTHER INFORMATION: delta5-elongase

<400> SEQUENCE: 85
```

| | | | | | | | | | | | | | | | | |
|---|---|---|---|---|---|---|---|---|---|---|---|---|---|---|---|---|
| atg | tgc | tca | cca | ccg | ccg | tca | caa | tcc | aaa | aca | aca | tcc | ctc | cta | gca | 48 |
| Met | Cys | Ser | Pro | Pro | Ser | Gln | Ser | Lys | Thr | Thr | Ser | Leu | Leu | Ala | | |
| 1 | | | | 5 | | | | | 10 | | | | | 15 | | |
| cgg | tac | acc | acc | gcc | gcc | ctc | ctc | ctc | acc | ctc | aca | acg | tgg | tgc | | 96 |
| Arg | Tyr | Thr | Thr | Ala | Ala | Leu | Leu | Leu | Thr | Leu | Thr | Thr | Trp | Cys | | |
| | | | 20 | | | | | 25 | | | | | 30 | | | |
| cac | ttc | gcc | ttc | cca | gcc | gcc | acc | gcc | aca | ccc | ggc | ctc | acc | gcc | gaa | 144 |
| His | Phe | Ala | Phe | Pro | Ala | Ala | Thr | Ala | Thr | Pro | Gly | Leu | Thr | Ala | Glu | |
| | | 35 | | | | | 40 | | | | | 45 | | | | |
| atg | cac | tcc | tac | aaa | gtc | cca | ctc | ggt | ctc | acc | gta | ttc | tac | ctg | ctg | 192 |
| Met | His | Ser | Tyr | Lys | Val | Pro | Leu | Gly | Leu | Thr | Val | Phe | Tyr | Leu | Leu | |
| | 50 | | | | | 55 | | | | | 60 | | | | | |
| agt | cta | ccg | tca | cta | aag | tac | gtt | acg | gac | aac | tac | ctt | gcc | aaa | aag | 240 |
| Ser | Leu | Pro | Ser | Leu | Lys | Tyr | Val | Thr | Asp | Asn | Tyr | Leu | Ala | Lys | Lys | |
| 65 | | | | | 70 | | | | | 75 | | | | | 80 | |
| tat | gat | atg | aag | tca | ctc | ctg | acg | gaa | tca | atg | gtg | ttg | tac | aat | gtg | 288 |
| Tyr | Asp | Met | Lys | Ser | Leu | Leu | Thr | Glu | Ser | Met | Val | Leu | Tyr | Asn | Val | |
| | | | | 85 | | | | | 90 | | | | | 95 | | |
| gcg | caa | gtg | ctg | ctc | aat | ggg | tgg | acg | gtg | tat | gcg | att | gtg | gat | gcg | 336 |
| Ala | Gln | Val | Leu | Leu | Asn | Gly | Trp | Thr | Val | Tyr | Ala | Ile | Val | Asp | Ala | |
| | | | 100 | | | | | 105 | | | | | 110 | | | |
| gtg | atg | aat | aga | gac | cat | cct | ttt | att | gga | agt | aga | agt | ttg | gtt | ggg | 384 |
| Val | Met | Asn | Arg | Asp | His | Pro | Phe | Ile | Gly | Ser | Arg | Ser | Leu | Val | Gly | |
| | | 115 | | | | | 120 | | | | | 125 | | | | |
| gcg | gcg | ttg | cat | agt | ggg | agc | tcg | tat | gcg | gtg | tgg | gtt | cat | tat | tgt | 432 |
| Ala | Ala | Leu | His | Ser | Gly | Ser | Ser | Tyr | Ala | Val | Trp | Val | His | Tyr | Cys | |
| | 130 | | | | | 135 | | | | | 140 | | | | | |
| gat | aag | tat | ttg | gag | ttc | ttt | gat | acg | tat | ttt | atg | gtg | ttg | agg | ggg | 480 |
| Asp | Lys | Tyr | Leu | Glu | Phe | Phe | Asp | Thr | Tyr | Phe | Met | Val | Leu | Arg | Gly | |
| 145 | | | | | 150 | | | | | 155 | | | | | 160 | |
| aaa | atg | gac | cag | gtc | tcc | ttc | ctc | cac | atc | tac | cac | cac | acg | acc | ata | 528 |
| Lys | Met | Asp | Gln | Val | Ser | Phe | Leu | His | Ile | Tyr | His | His | Thr | Thr | Ile | |
| | | | | 165 | | | | | 170 | | | | | 175 | | |
| gcg | tgg | gca | tgg | tgg | atc | gcc | ctc | cgc | ttc | tcc | ccc | ggc | gga | gac | att | 576 |
| Ala | Trp | Ala | Trp | Trp | Ile | Ala | Leu | Arg | Phe | Ser | Pro | Gly | Gly | Asp | Ile | |
| | | | 180 | | | | | 185 | | | | | 190 | | | |
| tac | ttc | ggg | gca | ctc | ctc | aac | tcc | atc | atc | cac | gtc | ctc | atg | tat | tcc | 624 |
| Tyr | Phe | Gly | Ala | Leu | Leu | Asn | Ser | Ile | Ile | His | Val | Leu | Met | Tyr | Ser | |
| | | 195 | | | | | 200 | | | | | 205 | | | | |

| | | | | | | | | | | | | | | | |
|---|---|---|---|---|---|---|---|---|---|---|---|---|---|---|---|
| tac | tac | gcc | ctt | gcc | cta | ctc | aag | gtc | agt | tgt | cca | tgg | aaa | cga | tac | 672 |
| Tyr | Tyr | Ala | Leu | Ala | Leu | Leu | Lys | Val | Ser | Cys | Pro | Trp | Lys | Arg | Tyr | |
| 210 | | | | 215 | | | | | 220 | | | | | | | |

| | | | | | | | | | | | | | | | |
|---|---|---|---|---|---|---|---|---|---|---|---|---|---|---|---|
| ttg | act | caa | gct | caa | tta | ttg | caa | ttc | aca | agt | gtg | gtg | gtt | tat | acg | 720 |
| Leu | Thr | Gln | Ala | Gln | Leu | Leu | Gln | Phe | Thr | Ser | Val | Val | Val | Tyr | Thr | |
| 225 | | | | 230 | | | | 235 | | | | | | 240 | | |

| | | | | | | | | | | | | | | | |
|---|---|---|---|---|---|---|---|---|---|---|---|---|---|---|---|
| ggg | tgt | acg | ggt | tat | act | cat | tac | tat | cat | acg | aag | cat | gga | gcg | gat | 768 |
| Gly | Cys | Thr | Gly | Tyr | Thr | His | Tyr | Tyr | His | Thr | Lys | His | Gly | Ala | Asp | |
| | | | | 245 | | | | 250 | | | | | 255 | | | |

| | | | | | | | | | | | | | | | |
|---|---|---|---|---|---|---|---|---|---|---|---|---|---|---|---|
| gag | aca | cag | cct | agt | tta | gga | acg | tat | tat | ttc | tgt | tgt | gga | gtg | cag | 816 |
| Glu | Thr | Gln | Pro | Ser | Leu | Gly | Thr | Tyr | Tyr | Phe | Cys | Cys | Gly | Val | Gln | |
| | | | 260 | | | | | 265 | | | | | 270 | | | |

| | | | | | | | | | | | | | | | |
|---|---|---|---|---|---|---|---|---|---|---|---|---|---|---|---|
| gtg | ttt | gag | atg | gtt | agt | ttg | ttt | gta | ctc | ttt | tcc | atc | ttt | tat | aaa | 864 |
| Val | Phe | Glu | Met | Val | Ser | Leu | Phe | Val | Leu | Phe | Ser | Ile | Phe | Tyr | Lys | |
| | | | 275 | | | | | 280 | | | | | 285 | | | |

| | | | | | | | | | | | | | | | |
|---|---|---|---|---|---|---|---|---|---|---|---|---|---|---|---|
| cga | tcc | tat | tcg | aag | aag | aac | aag | tca | gga | gga | aag | gat | agc | aag | aag | 912 |
| Arg | Ser | Tyr | Ser | Lys | Lys | Asn | Lys | Ser | Gly | Gly | Lys | Asp | Ser | Lys | Lys | |
| | 290 | | | | | 295 | | | | | 300 | | | | | |

| | | | | | | | | | | | | | | | |
|---|---|---|---|---|---|---|---|---|---|---|---|---|---|---|---|
| aat | gat | gat | ggg | aat | aat | gag | gat | caa | tgt | cac | aag | gct | atg | aag | gat | 960 |
| Asn | Asp | Asp | Gly | Asn | Asn | Glu | Asp | Gln | Cys | His | Lys | Ala | Met | Lys | Asp | |
| 305 | | | | 310 | | | | | 315 | | | | | 320 | | |

| | | | | | | | | | | | | | | | |
|---|---|---|---|---|---|---|---|---|---|---|---|---|---|---|---|
| ata | tcg | gag | ggt | gcg | aag | gag | gtt | gtg | ggg | cat | gca | gcg | aag | gat | gct | 1008 |
| Ile | Ser | Glu | Gly | Ala | Lys | Glu | Val | Val | Gly | His | Ala | Ala | Lys | Asp | Ala | |
| | | | | 325 | | | | | 330 | | | | | 335 | | |

| | | | | | | | | | | | | | | | |
|---|---|---|---|---|---|---|---|---|---|---|---|---|---|---|---|
| gga | aag | ttg | gtg | gct | acg | gcg | agt | aag | gct | gta | aag | agg | aag | gga | act | 1056 |
| Gly | Lys | Leu | Val | Ala | Thr | Ala | Ser | Lys | Ala | Val | Lys | Arg | Lys | Gly | Thr | |
| | | | 340 | | | | | 345 | | | | | 350 | | | |

| | | | | | | |
|---|---|---|---|---|---|---|
| cgt | gtt | act | ggt | gcc | atg | tag | 1077 |
| Arg | Val | Thr | Gly | Ala | Met | | |
| | | 355 | | | | | |

<210> SEQ ID NO 86
<211> LENGTH: 358
<212> TYPE: PRT
<213> ORGANISM: Thalassiosira pseudonana

<400> SEQUENCE: 86

Met Cys Ser Pro Pro Ser Gln Ser Lys Thr Thr Ser Leu Leu Ala
1               5                   10                  15

Arg Tyr Thr Thr Ala Ala Leu Leu Leu Thr Leu Thr Thr Trp Cys
                20                  25                  30

His Phe Ala Phe Pro Ala Ala Thr Ala Thr Pro Gly Leu Thr Ala Glu
            35                  40                  45

Met His Ser Tyr Lys Val Pro Leu Gly Leu Thr Val Phe Tyr Leu Leu
50                  55                  60

Ser Leu Pro Ser Leu Lys Tyr Val Thr Asp Asn Tyr Leu Ala Lys Lys
65                  70                  75                  80

Tyr Asp Met Lys Ser Leu Leu Thr Glu Ser Met Val Leu Tyr Asn Val
                85                  90                  95

Ala Gln Val Leu Leu Asn Gly Trp Thr Val Tyr Ala Ile Val Asp Ala
            100                 105                 110

Val Met Asn Arg Asp His Pro Phe Ile Gly Ser Arg Ser Leu Val Gly
        115                 120                 125

Ala Ala Leu His Ser Gly Ser Ser Tyr Ala Val Trp Val His Tyr Cys
    130                 135                 140

Asp Lys Tyr Leu Glu Phe Phe Asp Thr Tyr Phe Met Val Leu Arg Gly
145                 150                 155                 160

Lys Met Asp Gln Val Ser Phe Leu His Ile Tyr His His Thr Thr Ile

```
                        165                 170                 175
Ala Trp Ala Trp Trp Ile Ala Leu Arg Phe Ser Pro Gly Gly Asp Ile
            180                 185                 190

Tyr Phe Gly Ala Leu Leu Asn Ser Ile Ile His Val Leu Met Tyr Ser
            195                 200                 205

Tyr Tyr Ala Leu Ala Leu Leu Lys Val Ser Cys Pro Trp Lys Arg Tyr
            210                 215                 220

Leu Thr Gln Ala Gln Leu Leu Gln Phe Thr Ser Val Val Tyr Thr
225                 230                 235                 240

Gly Cys Thr Gly Tyr Thr His Tyr Tyr His Thr Lys His Gly Ala Asp
                245                 250                 255

Glu Thr Gln Pro Ser Leu Gly Thr Tyr Tyr Phe Cys Cys Gly Val Gln
            260                 265                 270

Val Phe Glu Met Val Ser Leu Phe Val Leu Phe Ser Ile Phe Tyr Lys
            275                 280                 285

Arg Ser Tyr Ser Lys Lys Asn Lys Ser Gly Gly Lys Asp Ser Lys Lys
            290                 295                 300

Asn Asp Asp Gly Asn Asn Glu Asp Gln Cys His Lys Ala Met Lys Asp
305                 310                 315                 320

Ile Ser Glu Gly Ala Lys Glu Val Val Gly His Ala Ala Lys Asp Ala
                325                 330                 335

Gly Lys Leu Val Ala Thr Ala Ser Lys Ala Val Lys Arg Lys Gly Thr
            340                 345                 350

Arg Val Thr Gly Ala Met
            355

<210> SEQ ID NO 87
<211> LENGTH: 1086
<212> TYPE: DNA
<213> ORGANISM: Phytophthora infestans
<220> FEATURE:
<221> NAME/KEY: CDS
<222> LOCATION: (1)..(1086)
<223> OTHER INFORMATION: omega3-desaturase

<400> SEQUENCE: 87 atg gcg acg aag gag gcg tat gtg ttc ccc act ctg acg gag atc aag        48
Met Ala Thr Lys Glu Ala Tyr Val Phe Pro Thr Leu Thr Glu Ile Lys
1               5                   10                  15 cgg tcg cta cct aaa gac tgt ttc gag gct tcg gtg cct ctg tcg ctc        96
Arg Ser Leu Pro Lys Asp Cys Phe Glu Ala Ser Val Pro Leu Ser Leu
            20                  25                  30 tac tac acc gtg cgt tgt ctg gtg atc gcg gtg gct cta acc ttc ggt       144
Tyr Tyr Thr Val Arg Cys Leu Val Ile Ala Val Ala Leu Thr Phe Gly
        35                  40                  45 ctc aac tac gct cgc gct ctg ccc gag gtc gag agc ttc tgg gct ctg       192
Leu Asn Tyr Ala Arg Ala Leu Pro Glu Val Glu Ser Phe Trp Ala Leu
    50                  55                  60 gac gcc gca ctc tgc acg ggc tac atc ttg ctg cag ggc atc gtg ttc       240
Asp Ala Ala Leu Cys Thr Gly Tyr Ile Leu Leu Gln Gly Ile Val Phe
65                  70                  75                  80 tgg ggc ttc ttc acg gtg ggc cac gat gcc ggc cac ggc gcc ttc tcg       288
Trp Gly Phe Phe Thr Val Gly His Asp Ala Gly His Gly Ala Phe Ser
                85                  90                  95 cgc tac cac ctg ctt aac ttc gtg gtg ggc act ttc atg cac tcg ctc       336
Arg Tyr His Leu Leu Asn Phe Val Val Gly Thr Phe Met His Ser Leu
            100                 105                 110 atc ctc acg ccc ttc gag tcg tgg aag ctc acg cac cgt cac cac cac       384
```

```
                                                    -continued

Ile Leu Thr Pro Phe Glu Ser Trp Lys Leu Thr His Arg His His His
        115                 120                 125 aag aac acg ggc aac att gac cgt gac gag gtc ttc tac ccg caa cgc      432
Lys Asn Thr Gly Asn Ile Asp Arg Asp Glu Val Phe Tyr Pro Gln Arg
130                 135                 140 aag gcc gac gac cac ccg ctg tct cgc aac ctg att ctg gcg ctc ggg      480
Lys Ala Asp Asp His Pro Leu Ser Arg Asn Leu Ile Leu Ala Leu Gly
145                 150                 155                 160 gca gcg tgg ctc gcc tat ttg gtc gag ggc ttc cct cct cgt aag gtc      528
Ala Ala Trp Leu Ala Tyr Leu Val Glu Gly Phe Pro Pro Arg Lys Val
                165                 170                 175 aac cac ttc aac ccg ttc gag cct ctg ttc gtg cgt cag gtg tca gct      576
Asn His Phe Asn Pro Phe Glu Pro Leu Phe Val Arg Gln Val Ser Ala
            180                 185                 190 gtg gta atc tct ctt ctc gcc cac ttc ttc gtg gcc gga ctc tcc atc      624
Val Val Ile Ser Leu Leu Ala His Phe Phe Val Ala Gly Leu Ser Ile
        195                 200                 205 tat ctg agc ctc cag ctg ggc ctt aag acg atg gca atc tac tac tat      672
Tyr Leu Ser Leu Gln Leu Gly Leu Lys Thr Met Ala Ile Tyr Tyr Tyr
210                 215                 220 gga cct gtt ttt gtg ttc ggc agc atg ctg gtc att acc acc ttc cta      720
Gly Pro Val Phe Val Phe Gly Ser Met Leu Val Ile Thr Thr Phe Leu
225                 230                 235                 240 cac cac aat gat gag gag acc cca tgg tac gcc gac tcg gag tgg acg      768
His His Asn Asp Glu Glu Thr Pro Trp Tyr Ala Asp Ser Glu Trp Thr
                245                 250                 255 tac gtc aag ggc aac ctc tcg tcc gtg gac cga tcg tac ggc gcg ctc      816
Tyr Val Lys Gly Asn Leu Ser Ser Val Asp Arg Ser Tyr Gly Ala Leu
            260                 265                 270 att gac aac ctg agc cac aac atc ggc acg cac cag atc cac cac ctt      864
Ile Asp Asn Leu Ser His Asn Ile Gly Thr His Gln Ile His His Leu
        275                 280                 285 ttc cct atc att ccg cac tac aaa ctc aag aaa gcc act gcg gcc ttc      912
Phe Pro Ile Ile Pro His Tyr Lys Leu Lys Lys Ala Thr Ala Ala Phe
290                 295                 300 cac cag gct ttc cct gag ctc gtg cgc aag agc gac gag cca att atc      960
His Gln Ala Phe Pro Glu Leu Val Arg Lys Ser Asp Glu Pro Ile Ile
305                 310                 315                 320 aag gct ttc ttc cgg gtt gga cgt ctc tac gca aac tac ggc gtt gtg     1008
Lys Ala Phe Phe Arg Val Gly Arg Leu Tyr Ala Asn Tyr Gly Val Val
                325                 330                 335 gac cag gag gcg aag ctc ttc acg cta aag gaa gcc aag gcg gcg acc     1056
Asp Gln Glu Ala Lys Leu Phe Thr Leu Lys Glu Ala Lys Ala Ala Thr
            340                 345                 350 gag gcg gcg gcc aag acc aag tcc acg taa                             1086
Glu Ala Ala Ala Lys Thr Lys Ser Thr
        355                 360

<210> SEQ ID NO 88
<211> LENGTH: 361
<212> TYPE: PRT
<213> ORGANISM: Phytophthora infestans

<400> SEQUENCE: 88

Met Ala Thr Lys Glu Ala Tyr Val Phe Pro Thr Leu Thr Glu Ile Lys
1               5                   10                  15

Arg Ser Le

```
        Leu Asn Tyr Ala Arg Ala Leu Pro Glu Val Glu Ser Phe Trp Ala Leu
            50                  55                  60

Asp Ala Ala Leu Cys Thr Gly Tyr Ile Leu Gln Gly Ile Val Phe
        65                  70                  75                  80

Trp Gly Phe Phe Thr Val Gly His Asp Ala Gly His Gly Ala Phe Ser
                        85                  90                  95

Arg Tyr His Leu Leu Asn Phe Val Val Gly Thr Phe Met His Ser Leu
                    100                 105                 110

Ile Leu Thr Pro Phe Glu Ser Trp Lys Leu Thr His Arg His His His
                    115                 120                 125

Lys Asn Thr Gly Asn Ile Asp Arg Asp Glu Val Phe Tyr Pro Gln Arg
            130                 135                 140

Lys Ala Asp Asp His Pro Leu Ser Arg Asn Leu Ile Leu Ala Leu Gly
        145                 150                 155                 160

Ala Ala Trp Leu Ala Tyr Leu Val Glu Gly Phe Pro Pro Arg Lys Val
                        165                 170                 175

Asn His Phe Asn Pro Phe Glu Pro Leu Phe Val Arg Gln Val Ser Ala
                    180                 185                 190

Val Val Ile Ser Leu Leu Ala His Phe Phe Val Ala Gly Leu Ser Ile
                    195                 200                 205

Tyr Leu Ser Leu Gln Leu Gly Leu Lys Thr Met Ala Ile Tyr Tyr Tyr
            210                 215                 220

Gly Pro Val Phe Val Phe Gly Ser Met Leu Val Ile Thr Thr Phe Leu
        225                 230                 235                 240

His His Asn Asp Glu Glu Thr Pro Trp Tyr Ala Asp Ser Glu Trp Thr
                        245                 250                 255

Tyr Val Lys Gly Asn Leu Ser Ser Val Asp Arg Ser Tyr Gly Ala Leu
                    260                 265                 270

Ile Asp Asn Leu Ser His Asn Ile Gly Thr His Gln Ile His His Leu
                    275                 280                 285

Phe Pro Ile Ile Pro His Tyr Lys Leu Lys Lys Ala Thr Ala Ala Phe
            290                 295                 300

His Gln Ala Phe Pro Glu Leu Val Arg Lys Ser Asp Glu Pro Ile Ile
        305                 310                 315                 320

Lys Ala Phe Phe Arg Val Gly Arg Leu Tyr Ala Asn Tyr Gly Val Val
                        325                 330                 335

Asp Gln Glu Ala Lys Leu Phe Thr Leu Lys Glu Ala Lys Ala Ala Thr
                    340                 345                 350

Glu Ala Ala Ala Lys Thr Lys Ser Thr
                    355                 360

<210> SEQ ID NO 89
<211> LENGTH: 1371
<212> TYPE: DNA
<213> ORGANISM: Ostreococcus tauri
<220> FEATURE:
<221> NAME/KEY: CDS
<222> LOCATION: (1)..(1371)
<223> OTHER INFORMATION: delta6-desaturase

<400> SEQUENCE: 89 atg tgc gtg gag acg gaa aat aac gat ggg atc ccc acg gtg gag atc         48
Met Cys Val Glu Thr Glu Asn Asn Asp Gly Ile Pro Thr Val Glu Ile
1               5                   10                  15 gcg ttc gac ggt gag cgc gag cgg gcg gag gca aac gtg aag ctg tcc         96
Ala Phe Asp Gly Glu Arg Glu Arg Ala Glu Ala Asn Val Lys Leu Ser
```

```
                    20                  25                  30
gcg gag aag atg gag ccg gcg gcg ctg gcg aag acg ttc gcg agg cgg      144
Ala Glu Lys Met Glu Pro Ala Ala Leu Ala Lys Thr Phe Ala Arg Arg
            35                  40                  45 tac gtc gtg atc gag ggg gtg gag tac gat gtg acg gat ttt aag cac      192
Tyr Val Val Ile Glu Gly Val Glu Tyr Asp Val Thr Asp Phe Lys His
 50                  55                  60 ccg gga gga acg gtt att ttc tat gcg ttg tca aac acc ggg gcg gac      240
Pro Gly Gly Thr Val Ile Phe Tyr Ala Leu Ser Asn Thr Gly Ala Asp
 65                  70                  75                  80 gcg acg gaa gcg ttc aag gag ttt cat cat cgg tcg aga aag gcg agg      288
Ala Thr Glu Ala Phe Lys Glu Phe His His Arg Ser Arg Lys Ala Arg
                85                  90                  95 aaa gcc ttg gcg gcg ctc ccg tct cga ccg gcc aag acg gcc aag gtg      336
Lys Ala Leu Ala Ala Leu Pro Ser Arg Pro Ala Lys Thr Ala Lys Val
            100                 105                 110 gac gac gcg gag atg ctc caa gat ttc gcc aag tgg cgg aaa gaa ttg      384
Asp Asp Ala Glu Met Leu Gln Asp Phe Ala Lys Trp Arg Lys Glu Leu
        115                 120                 125 gag aga gat gga ttc ttc aag ccc tct ccg gcg cac gtg gcg tat cgc      432
Glu Arg Asp Gly Phe Phe Lys Pro Ser Pro Ala His Val Ala Tyr Arg
130                 135                 140 ttc gcc gag ctc gcg gcg atg tac gct ctc ggg acg tac ctg atg tac      480
Phe Ala Glu Leu Ala Ala Met Tyr Ala Leu Gly Thr Tyr Leu Met Tyr
145                 150                 155                 160 gct cga tac gtc gtc tcc tcg gtg ctc gtg tac gct tgc ttt ttc ggc      528
Ala Arg Tyr Val Val Ser Ser Val Leu Val Tyr Ala Cys Phe Phe Gly
                165                 170                 175 gcc cga tgc ggt tgg gtg cag cac gag ggc gga cac agc tcg ctg acg      576
Ala Arg Cys Gly Trp Val Gln His Glu Gly Gly His Ser Ser Leu Thr
            180                 185                 190 ggc aac att tgg tgg gac aag cgc atc cag gcc ttc aca gcc ggg ttc      624
Gly Asn Ile Trp Trp Asp Lys Arg Ile Gln Ala Phe Thr Ala Gly Phe
        195                 200                 205 ggt ctc gcc ggt agc ggc gac atg tgg aac tcg atg cac aac aag cat      672
Gly Leu Ala Gly Ser Gly Asp Met Trp Asn Ser Met His Asn Lys His
210                 215                 220 cac gcg acg cct caa aag gtt cgt cac gac atg gat ctg gac acc acc      720
His Ala Thr Pro Gln Lys Val Arg His Asp Met Asp Leu Asp Thr Thr
225                 230                 235                 240 ccc gcg gtg gcg ttc ttc aac acc gcg gtg gaa gac aat cgt ccc cgt      768
Pro Ala Val Ala Phe Phe Asn Thr Ala Val Glu Asp Asn Arg Pro Arg
                245                 250                 255 ggc ttt agc aag tac tgg ttg cgc ctt cag gcg tgg acc ttc atc ccc      816
Gly Phe Ser Lys Tyr Trp Leu Arg Leu Gln Ala Trp Thr Phe Ile Pro
            260                 265                 270 gtg acg tcc ggc ttg gtg ctc ctt ttc tgg atg ttt ttc ctc cac ccc      864
Val Thr Ser Gly Leu Val Leu Leu Phe Trp Met Phe Phe Leu His Pro
        275                 280                 285 tcc aag gct ttg aag ggt ggc aag tac gaa gag ttg gtg tgg atg ctc      912
Ser Lys Ala Leu Lys Gly Gly Lys Tyr Glu Glu Leu Val Trp Met Leu
290                 295                 300 gcc gcg cac gtc atc cgc acg tgg acg atc aag gcg gtg acc gga ttc      960
Ala Ala His Val Ile Arg Thr Trp Thr Ile Lys Ala Val Thr Gly Phe
305                 310                 315                 320 acc gcg atg cag tcc tac ggc tta ttt ttg gcg acg agc tgg gtg agc      1008
Thr Ala Met Gln Ser Tyr Gly Leu Phe Leu Ala Thr Ser Trp Val Ser
                325                 330                 335 ggc tgc tat ctg ttt gca cac ttc tcc acg tcg cac acg cac ctg gat      1056
```

```
Gly Cys Tyr Leu Phe Ala His Phe Ser Thr Ser His Thr His Leu Asp
                340                 345                 350 gtg gtg ccc gcg gac gag cat ctc tcc tgg gtt cga tac gcc gtc gat    1104
Val Val Pro Ala Asp Glu His Leu Ser Trp Val Arg Tyr Ala Val Asp
            355                 360                 365 cac acg atc gac atc gat ccg agt caa ggt tgg gtg aac tgg ttg atg    1152
His Thr Ile Asp Ile Asp Pro Ser Gln Gly Trp Val Asn Trp Leu Met
370                 375                 380 ggc tac ctc aac tgc caa gtc atc cac cac ctc ttt ccg agc atg ccg    1200
Gly Tyr Leu Asn Cys Gln Val Ile His His Leu Phe Pro Ser Met Pro
385                 390                 395                 400 cag ttc cgc cag ccc gag gta tct cgc cgc ttc gtc gcc ttt gcg aaa    1248
Gln Phe Arg Gln Pro Glu Val Ser Arg Arg Phe Val Ala Phe Ala Lys
                405                 410                 415 aag tgg aac ctc aac tac aag gtc atg acc tac gcc ggt gcg tgg aag    1296
Lys Trp Asn Leu Asn Tyr Lys Val Met Thr Tyr Ala Gly Ala Trp Lys
            420                 425                 430 gca acg ctc gga aac ctc gac aac gtg ggt aag cac tac tac gtg cac    1344
Ala Thr Leu Gly Asn Leu Asp Asn Val Gly Lys His Tyr Tyr Val His
        435                 440                 445 ggc caa cac tcc gga aag acg gcg taa                                1371
Gly Gln His Ser Gly Lys Thr Ala
    450                 455

<210> SEQ ID NO 90
<211> LENGTH: 456
<212> TYPE: PRT
<213> ORGANISM: Ostreococcus tauri

<400> SEQUENCE: 90

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
```

```
             210                 215                 220
His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
            420                 425                 430

Ala Thr Leu Gly Asn Leu Asp Asn Val Gly Lys His Tyr Tyr Val His
        435                 440                 445

Gly Gln His Ser Gly Lys Thr Ala
    450                 455

<210> SEQ ID NO 91
<211> LENGTH: 606
<212> TYPE: DNA
<213> ORGANISM: Ostreococcus tauri
<220> FEATURE:
<221> NAME/KEY: CDS
<222> LOCATION: (1)..(606)
<223> OTHER INFORMATION: delta5-desaturase

<400> SEQUENCE: 91 atg tac ggt ttg cta tcg ctc aag tcg tgc ttc gtc gac gat ttc aac        48
Met Tyr Gly Leu Leu Ser Leu Lys Ser Cys Phe Val Asp Asp Phe Asn
1               5                   10                  15 gcc tac ttc tcc gga cgc atc ggc tgg gtc aag gtg atg aag ttc acc        96
Ala Tyr Phe Ser Gly Arg Ile Gly Trp Val Lys Val Met Lys Phe Thr
            20                  25                  30 cgc ggc gag gcg atc gca ttt tgg ggc acc aag ctc ttg tgg gcc gcg       144
Arg Gly Glu Ala Ile Ala Phe Trp Gly Thr Lys Leu Leu Trp Ala Ala
        35                  40                  45 tat tac ctc gcg ttg ccg cta aag atg tcg cat cgg ccg ctc gga gaa       192
Tyr Tyr Leu Ala Leu Pro Leu Lys Met Ser His Arg Pro Leu Gly Glu
    50                  55                  60 ctc ctc gca ctc tgg gcc gtc acc gag ttc gtc acc gga tgg ctg ttg       240
Leu Leu Ala Leu Trp Ala Val Thr Glu Phe Val Thr Gly Trp Leu Leu
65                  70                  75                  80
```

```
gcg ttc atg ttc caa gtc gcc cac gtc gtc ggc gag gtt cac ttc ttc     288
Ala Phe Met Phe Gln Val Ala His Val Val Gly Glu Val His Phe Phe
            85                  90                  95 acc ctc gac gcg aag aac cgc gtg aac ttg gga tgg gga gag gca cag     336
Thr Leu Asp Ala Lys Asn Arg Val Asn Leu Gly Trp Gly Glu Ala Gln
                100                 105                 110 ctc atg tcg agc gcg gat ttc gcc cac gga tcc aag ttt tgg acg cac     384
Leu Met Ser Ser Ala Asp Phe Ala His Gly Ser Lys Phe Trp Thr His
            115                 120                 125 ttc tcc gga ggc tta aac tac caa gtc gtc cac cat ctc ttc ccg ggc     432
Phe Ser Gly Gly Leu Asn Tyr Gln Val Val His His Leu Phe Pro Gly
        130                 135                 140 gtc tgc cac gtg cac tat ccc gcg ctc gcg cca att att aag gcg gca     480
Val Cys His Val His Tyr Pro Ala Leu Ala Pro Ile Ile Lys Ala Ala
145                 150                 155                 160 gct gag aag cac ggc ctc cac tac cag att tac ccc acg ttt tgg tcc     528
Ala Glu Lys His Gly Leu His Tyr Gln Ile Tyr Pro Thr Phe Trp Ser
            165                 170                 175 gcc ctg cgc gcg cac ttc cgg cac ctc gcc aac gtc ggc cgc gcc gcg     576
Ala Leu Arg Ala His Phe Arg His Leu Ala Asn Val Gly Arg Ala Ala
            180                 185                 190 tac gta ccg tcc ctc caa acc gtc gga tga                              606
Tyr Val Pro Ser Leu Gln Thr Val Gly
        195                 200

<210> SEQ ID NO 92
<211> LENGTH: 201
<212> TYPE: PRT
<213> ORGANISM: Ostreococcus tauri

<400> SEQUENCE: 92

Met Tyr Gly Leu Leu Ser Leu Lys Ser Cys Phe Val Asp Asp Phe Asn
1               5                   10                  15

Ala Tyr Phe Ser Gly Arg Ile Gly Trp Val Lys Val Met Lys Phe Thr
            20                  25                  30

Arg Gly Glu Ala Ile Ala Phe Trp Gly Thr Lys Leu Leu Trp Ala Ala
        35                  40                  45

Tyr Tyr Leu Ala Leu Pro Leu Lys Met Ser His Arg Pro Leu Gly Glu
    50                  55                  60

Leu Leu Ala Leu Trp Ala Val Thr Glu Phe Val Thr Gly Trp Leu Leu
65                  70                  75                  80

Ala Phe Met Phe Gln Val Ala His Val Val Gly Glu Val His Phe Phe
            85                  90                  95

Thr Leu Asp Ala Lys Asn Arg Val Asn Leu Gly Trp Gly Glu Ala Gln
                100                 105                 110

Leu Met Ser Ser Ala Asp Phe Ala His Gly Ser Lys Phe Trp Thr His
            115                 120                 125

Phe Ser Gly Gly Leu Asn Tyr Gln Val Val His His Leu Phe Pro Gly
        130                 135                 140

Val Cys His Val His Tyr Pro Ala Leu Ala Pro Ile Ile Lys Ala Ala
145                 150                 155                 160

Ala Glu Lys His Gly Leu His Tyr Gln Ile Tyr Pro Thr Phe Trp Ser
            165                 170                 175

Ala Leu Arg Ala His Phe Arg His Leu Ala Asn Val Gly Arg Ala Ala
            180                 185                 190

Tyr Val Pro Ser Leu Gln Thr Val Gly
        195                 200
```

<210> SEQ ID NO 93
<211> LENGTH: 714
<212> TYPE: DNA
<213> ORGANISM: Ostreococcus tauri
<220> FEATURE:
<221> NAME/KEY: CDS
<222> LOCATION: (1)..(714)
<223> OTHER INFORMATION: delta5-desaturase

<400> SEQUENCE: 93

```
atg gtg agc cat cac tcg tac tgt aac gac gcg gat ttg gat cag gat      48
Met Val Ser His His Ser Tyr Cys Asn Asp Ala Asp Leu Asp Gln Asp
1               5                   10                  15 gtg tac acc gca ctg ccg ctc ctg cgc ctg gac ccg tct cag gag ttg      96
Val Tyr Thr Ala Leu Pro Leu Leu Arg Leu Asp Pro Ser Gln Glu Leu
            20                  25                  30 aag tgg ttt cat cga tac cag gcg ttt tac gcc ccg ctc atg tgg ccg     144
Lys Trp Phe His Arg Tyr Gln Ala Phe Tyr Ala Pro Leu Met Trp Pro
        35                  40                  45 ttt ttg tgg ctc gcg gcg cag ttt ggc gac gcg cag aac atc ctg atc     192
Phe Leu Trp Leu Ala Ala Gln Phe Gly Asp Ala Gln Asn Ile Leu Ile
50                  55                  60 gac cga gcg tcg ccg ggc gtc gcg tac aag gga ttg atg gcg aac gag     240
Asp Arg Ala Ser Pro Gly Val Ala Tyr Lys Gly Leu Met Ala Asn Glu
65                  70                  75                  80 gtc gcg ctg tac gtt ctc ggt aag gtt tta cac ttt ggt ctt ctc ctc     288
Val Ala Leu Tyr Val Leu Gly Lys Val Leu His Phe Gly Leu Leu Leu
                85                  90                  95 ggc gtt cct gcg tac ttg cac gga ttg tcc aac gcg atc gtt cca ttc     336
Gly Val Pro Ala Tyr Leu His Gly Leu Ser Asn Ala Ile Val Pro Phe
            100                 105                 110 ttg gcg tac ggc gca ttc ggc tcc ttc gtc ctg tgc tgg ttc ttc atc     384
Leu Ala Tyr Gly Ala Phe Gly Ser Phe Val Leu Cys Trp Phe Phe Ile
        115                 120                 125 gtc agc cat aac ctc gaa gcg ctg aca ccc gtt aac ctt aac aag tcc     432
Val Ser His Asn Leu Glu Ala Leu Thr Pro Val Asn Leu Asn Lys Ser
    130                 135                 140 acg aag aac gac tgg ggg gcg tgg cag atc gag aca tcg gcg tct tgg     480
Thr Lys Asn Asp Trp Gly Ala Trp Gln Ile Glu Thr Ser Ala Ser Trp
145                 150                 155                 160 ggc aac gcg ttc tgg agc ttc ttc tct gga ggt ctg aac ctg caa atc     528
Gly Asn Ala Phe Trp Ser Phe Phe Ser Gly Gly Leu Asn Leu Gln Ile
                165                 170                 175 gag cac cac ctc ttc ccg ggc atg gcg cac aac ctg tac ccg aag atg     576
Glu His His Leu Phe Pro Gly Met Ala His Asn Leu Tyr Pro Lys Met
            180                 185                 190 gtg ccg atc atc aag gac gag tgt gcg aaa gcg ggc gtt cgc tac acc     624
Val Pro Ile Ile Lys Asp Glu Cys Ala Lys Ala Gly Val Arg Tyr Thr
        195                 200                 205 ggt tac ggt ggc tac acc ggc ctg ctc ccg atc acc cgc gac atg ttc     672
Gly Tyr Gly Gly Tyr Thr Gly Leu Leu Pro Ile Thr Arg Asp Met Phe
    210                 215                 220 tcc tac ctc cat aag tgt ggc cga acg gcg aaa cta gcc taa             714
Ser Tyr Leu His Lys Cys Gly Arg Thr Ala Lys Leu Ala
225                 230                 235
```

<210> SEQ ID NO 94
<211> LENGTH: 237
<212> TYPE: PRT
<213> ORGANISM: Ostreococcus tauri

<400> SEQUENCE: 94

```
Met Val Ser His His Ser Tyr Cys Asn Asp Ala Asp Leu Asp Gln Asp
1               5                   10                  15

Val Tyr Thr Ala Leu Pro Leu Leu Arg Leu Asp Pro Ser Gln Glu Leu
            20                  25                  30

Lys Trp Phe His Arg Tyr Gln Ala Phe Tyr Ala Pro Leu Met Trp Pro
            35                  40                  45

Phe Leu Trp Leu Ala Ala Gln Phe Gly Asp Ala Gln Asn Ile Leu Ile
        50                  55                  60

Asp Arg Ala Ser Pro Gly Val Ala Tyr Lys Gly Leu Met Ala Asn Glu
65                  70                  75                  80

Val Ala Leu Tyr Val Leu Gly Lys Val Leu His Phe Gly Leu Leu Leu
                85                  90                  95

Gly Val Pro Ala Tyr Leu His Gly Leu Ser Asn Ala Ile Val Pro Phe
            100                 105                 110

Leu Ala Tyr Gly Ala Phe Gly Ser Phe Val Leu Cys Trp Phe Phe Ile
        115                 120                 125

Val Ser His Asn Leu Glu Ala Leu Thr Pro Val Asn Leu Asn Lys Ser
130                 135                 140

Thr Lys Asn Asp Trp Gly Ala Trp Gln Ile Glu Thr Ser Ala Ser Trp
145                 150                 155                 160

Gly Asn Ala Phe Trp Ser Phe Phe Ser Gly Gly Leu Asn Leu Gln Ile
                165                 170                 175

Glu His His Leu Phe Pro Gly Met Ala His Asn Leu Tyr Pro Lys Met
            180                 185                 190

Val Pro Ile Ile Lys Asp Glu Cys Ala Lys Ala Gly Val Arg Tyr Thr
        195                 200                 205

Gly Tyr Gly Gly Tyr Thr Gly Leu Leu Pro Ile Thr Arg Asp Met Phe
210                 215                 220

Ser Tyr Leu His Lys Cys Gly Arg Thr Ala Lys Leu Ala
225                 230                 235

<210> SEQ ID NO 95
<211> LENGTH: 1611
<212> TYPE: DNA
<213> ORGANISM: Ostreococcus tauri
<220> FEATURE:
<221> NAME/KEY: CDS
<222> LOCATION: (1)..(1611)
<223> OTHER INFORMATION: delta4-desaturase

<400> SEQUENCE: 95 atg tac ctc gga cgc ggc cgt ctc gag agc ggg acg acg cga ggg atg        48
Met Tyr Leu Gly Arg Gly Arg Leu Glu Ser Gly Thr Thr Arg Gly Met
1               5                   10                  15 atg cgg acg cac gcg cgg cga ccg tcg acg acg tcg aat ccg tgc gcg        96
Met Arg Thr His Ala Arg Arg Pro Ser Thr Thr Ser Asn Pro Cys Ala
            20                  25                  30 cgg tca cgc gtg cgt aag acg acg gag cga tcg ctc gcg cga gtg cga       144
Arg Ser Arg Val Arg Lys Thr Thr Glu Arg Ser Leu Ala Arg Val Arg
        35                  40                  45 cga tcg acg agt gag aag gga agc gcg ctc gtg ctc gag cga gag agc       192
Arg Ser Thr Ser Glu Lys Gly Ser Ala Leu Val Leu Glu Arg Glu Ser
50                  55                  60 gaa cgg gag aag gag gag gga ggg aaa gcg cga gcg gag gga ttg cga       240
Glu Arg Glu Lys Glu Glu Gly Gly Lys Ala Arg Ala Glu Gly Leu Arg
65                  70                  75                  80 ttc caa cgc ccg gac gtc gcc gcg ccg ggg gga gcg gat cct tgg aac       288
```

```
                Phe Gln Arg Pro Asp Val Ala Ala Pro Gly Ala Asp Pro Trp Asn
                                85                  90                  95 gac gag aag tgg aca aag acc aag tgg acg gta ttc aga gac gtc gcg      336
Asp Glu Lys Trp Thr Lys Thr Lys Trp Thr Val Phe Arg Asp Val Ala
            100                 105                 110 tac gat ctc gat cct ttc ttc gct cga cac ccc gga gga gac tgg ctc      384
Tyr Asp Leu Asp Pro Phe Phe Ala Arg His Pro Gly Gly Asp Trp Leu
                115                 120                 125 ctg aac ttg gcc gtg gga cga gac tgc acc gcg ctc atc gaa tcc tat      432
Leu Asn Leu Ala Val Gly Arg Asp Cys Thr Ala Leu Ile Glu Ser Tyr
        130                 135                 140 cac ttg cga cca gag gtg gcg acg gct cgt ttc aga atg ctg ccc aaa      480
His Leu Arg Pro Glu Val Ala Thr Ala Arg Phe Arg Met Leu Pro Lys
145                 150                 155                 160 ctc gag gat ttt ccc gtc gag gcc gtg ccc aag tcc ccg aga ccg aac      528
Leu Glu Asp Phe Pro Val Glu Ala Val Pro Lys Ser Pro Arg Pro Asn
                165                 170                 175 gat tcg ccg tta tac aac aac att cgc aac cga gtc cgc gaa gag ctc      576
Asp Ser Pro Leu Tyr Asn Asn Ile Arg Asn Arg Val Arg Glu Glu Leu
            180                 185                 190 ttc cca gag gag gga aag aat atg cac aga cag ggc ggc gac cac ggc      624
Phe Pro Glu Glu Gly Lys Asn Met His Arg Gln Gly Gly Asp His Gly
        195                 200                 205 gac ggt gac gat tct ggg ttt cgc cgc ctt ttg ctt atg ccg tgt acc      672
Asp Gly Asp Asp Ser Gly Phe Arg Arg Leu Leu Leu Met Pro Cys Thr
210                 215                 220 tat tcc ctt ccg ggg gtt cct ttc cgg ctg cct cct cgg gtc tcg cgg      720
Tyr Ser Leu Pro Gly Val Pro Phe Arg Leu Pro Pro Arg Val Ser Arg
225                 230                 235                 240 ggg cgt gga ttg gtc tca cga ttc agg cac tgc gcc aac cac ggc gcg      768
Gly Arg Gly Leu Val Ser Arg Phe Arg His Cys Ala Asn His Gly Ala
                245                 250                 255 atg tct cct tcg ccg gcc gtt aac ggc gtc ctc ggt ttg acg aac gat      816
Met Ser Pro Ser Pro Ala Val Asn Gly Val Leu Gly Leu Thr Asn Asp
            260                 265                 270 ctc atc ggc ggc tcg tcc ttg atg tgg aga tat cac cac caa gtc agc      864
Leu Ile Gly Gly Ser Ser Leu Met Trp Arg Tyr His His Gln Val Ser
        275                 280                 285 cac cac att cat tgc aac gac aac gcc atg gat caa gac gtg tac acg      912
His His Ile His Cys Asn Asp Asn Ala Met Asp Gln Asp Val Tyr Thr
        290                 295                 300 gcg atg cca tta ttg cgt ttc gac gct cgc cgg ccc aag tcc tgg tac      960
Ala Met Pro Leu Leu Arg Phe Asp Ala Arg Arg Pro Lys Ser Trp Tyr
305                 310                 315                 320 cat cgc ttc cag cag tgg tac atg ttt tta gcg ttc ccg ttg ttg cag     1008
His Arg Phe Gln Gln Trp Tyr Met Phe Leu Ala Phe Pro Leu Leu Gln
                325                 330                 335 gtt gcc ttc caa gtc gga gac att gcc gca ctg ttc acg cgt gat acc     1056
Val Ala Phe Gln Val Gly Asp Ile Ala Ala Leu Phe Thr Arg Asp Thr
            340                 345                 350 gaa ggc gct aag ctt cac ggg gcg acg acg tgg gag ctt acc acg gtt     1104
Glu Gly Ala Lys Leu His Gly Ala Thr Thr Trp Glu Leu Thr Thr Val
        355                 360                 365 gtc ctc ggt aag att gtg cac ttc ggt ctt ttg ggg ccg ttg atg         1152
Val Leu Gly Lys Ile Val His Phe Gly Leu Leu Gly Pro Leu Met
370                 375                 380 aac cac gcg gtg agt tct gtt ttg ctg ggg atc gtc ggt ttc atg gcg     1200
Asn His Ala Val Ser Ser Val Leu Leu Gly Ile Val Gly Phe Met Ala
385                 390                 395                 400
```

```
tgc caa ggt ata gtt ctg gcg tgc acg ttt gct gtg agt cac aat gtc   1248
Cys Gln Gly Ile Val Leu Ala Cys Thr Phe Ala Val Ser His Asn Val
            405                 410                 415 gcg gag gcg aag ata cct gag gac acc gga gga gaa gcc tgg gag aga   1296
Ala Glu Ala Lys Ile Pro Glu Asp Thr Gly Gly Glu Ala Trp Glu Arg
        420                 425                 430 gat tgg ggt gtc cag cag ttg gtg act agc gcc gac tgg ggt gga aag   1344
Asp Trp Gly Val Gln Gln Leu Val Thr Ser Ala Asp Trp Gly Gly Lys
        435                 440                 445 ata ggt aac ttc ttc acg ggt ggc ctc aac ttg caa gtt gag cac cac   1392
Ile Gly Asn Phe Phe Thr Gly Gly Leu Asn Leu Gln Val Glu His His
        450                 455                 460 ttg ttt ccg gcg att tgc ttc gtc cac tac ccg gac atc gcg aag atc   1440
Leu Phe Pro Ala Ile Cys Phe Val His Tyr Pro Asp Ile Ala Lys Ile
465                 470                 475                 480 gtg aag gaa gaa gcg gcc aag ctc aac atc cct tac gcg tct tac agg   1488
Val Lys Glu Glu Ala Ala Lys Leu Asn Ile Pro Tyr Ala Ser Tyr Arg
                485                 490                 495 act ctt cct ggt att ttc gtc caa ttc tgg aga ttt atg aag gac atg   1536
Thr Leu Pro Gly Ile Phe Val Gln Phe Trp Arg Phe Met Lys Asp Met
            500                 505                 510 ggc acg gct gag caa att ggt gaa gtt cca ttg ccg aag att ccc aac   1584
Gly Thr Ala Glu Gln Ile Gly Glu Val Pro Leu Pro Lys Ile Pro Asn
        515                 520                 525 ccg cag ctc gcg ccg aag ctc gct tag                               1611
Pro Gln Leu Ala Pro Lys Leu Ala
        530                 535

<210> SEQ ID NO 96
<211> LENGTH: 536
<212> TYPE: PRT
<213> ORGANISM: Ostreococcus tauri

<400> SEQUENCE: 96

Met Tyr Leu Gly Arg Gly Arg Leu Glu Ser Gly Thr Thr Arg Gly Met
1               5                   10                  15

Met Arg Thr His Ala Arg Arg Pro Ser Thr Thr Ser Asn Pro Cys Ala
            20                  25                  30

Arg Ser Arg Val Arg Lys Thr Thr Glu Arg Ser Leu Ala Arg Val Arg
        35                  40                  45

Arg Ser Thr Ser Glu Lys Gly Ser Ala Leu Val Leu Glu Arg Glu Ser
    50                  55                  60

Glu Arg Glu Lys Glu Glu Gly Gly Lys Ala Arg Ala Glu Gly Leu Arg
65                  70                  75                  80

Phe Gln Arg Pro Asp Val Ala Ala Pro Gly Gly Ala Asp Pro Trp Asn
                85                  90                  95

Asp Glu Lys Trp Thr Lys Thr Lys Trp Thr Val Phe Arg Asp Val Ala
            100                 105                 110

Tyr Asp Leu Asp Pro Phe Phe Ala Arg His Pro Gly Gly Asp Trp Leu
        115                 120                 125

Leu Asn Leu Ala Val Gly Arg Asp Cys Thr Ala Leu Ile Glu Ser Tyr
    130                 135                 140

His Leu Arg Pro Glu Val Ala Thr Ala Arg Phe Arg Met Leu Pro Lys
145                 150                 155                 160

Leu Glu Asp Phe Pro Val Glu Ala Val Pro Lys Ser Pro Arg Pro Asn
                165                 170                 175

Asp Ser Pro Leu Tyr Asn Asn Ile Arg Asn Arg Val Arg Glu Glu Leu
            180                 185                 190
```

Phe Pro Glu Glu Gly Lys Asn Met His Arg Gln Gly Asp His Gly
                195                 200                 205

Asp Gly Asp Asp Ser Gly Phe Arg Arg Leu Leu Met Pro Cys Thr
    210                 215                 220

Tyr Ser Leu Pro Gly Val Pro Phe Arg Leu Pro Pro Arg Val Ser Arg
225                 230                 235                 240

Gly Arg Gly Leu Val Ser Arg Phe Arg His Cys Ala Asn His Gly Ala
                245                 250                 255

Met Ser Pro Ser Pro Ala Val Asn Gly Val Leu Gly Leu Thr Asn Asp
            260                 265                 270

Leu Ile Gly Gly Ser Ser Leu Met Trp Arg Tyr His His Gln Val Ser
        275                 280                 285

His His Ile His Cys Asn Asp Asn Ala Met Asp Gln Asp Val Tyr Thr
    290                 295                 300

Ala Met Pro Leu Leu Arg Phe Asp Ala Arg Arg Pro Lys Ser Trp Tyr
305                 310                 315                 320

His Arg Phe Gln Gln Trp Tyr Met Phe Leu Ala Phe Pro Leu Leu Gln
                325                 330                 335

Val Ala Phe Gln Val Gly Asp Ile Ala Ala Leu Phe Thr Arg Asp Thr
            340                 345                 350

Glu Gly Ala Lys Leu His Gly Ala Thr Thr Trp Glu Leu Thr Thr Val
        355                 360                 365

Val Leu Gly Lys Ile Val His Phe Gly Leu Leu Gly Pro Leu Met
    370                 375                 380

Asn His Ala Val Ser Ser Val Leu Leu Gly Ile Val Gly Phe Met Ala
385                 390                 395                 400

Cys Gln Gly Ile Val Leu Ala Cys Thr Phe Ala Val Ser His Asn Val
                405                 410                 415

Ala Glu Ala Lys Ile Pro Glu Asp Thr Gly Gly Glu Ala Trp Glu Arg
            420                 425                 430

Asp Trp Gly Val Gln Gln Leu Val Thr Ser Ala Asp Trp Gly Gly Lys
        435                 440                 445

Ile Gly Asn Phe Phe Thr Gly Gly Leu Asn Leu Gln Val Glu His His
    450                 455                 460

Leu Phe Pro Ala Ile Cys Phe Val His Tyr Pro Asp Ile Ala Lys Ile
465                 470                 475                 480

Val Lys Glu Glu Ala Ala Lys Leu Asn Ile Pro Tyr Ala Ser Tyr Arg
                485                 490                 495

Thr Leu Pro Gly Ile Phe Val Gln Phe Trp Arg Phe Met Lys Asp Met
            500                 505                 510

Gly Thr Ala Glu Gln Ile Gly Glu Val Pro Leu Pro Lys Ile Pro Asn
        515                 520                 525

Pro Gln Leu Ala Pro Lys Leu Ala
    530                 535

<210> SEQ ID NO 97
<211> LENGTH: 1455
<212> TYPE: DNA
<213> ORGANISM: Thalassiosira pseudonana
<220> FEATURE:
<221> NAME/KEY: CDS
<222> LOCATION: (1)..(1455)
<223> OTHER INFORMATION: delta6-desaturase

<400> SEQUENCE: 97

```
atg gga aaa gga gga gac gca gcc gca gct acc aag cgt agt gga gca        48
Met Gly Lys Gly Gly Asp Ala Ala Ala Ala Thr Lys Arg Ser Gly Ala
1               5                   10                  15 ttg aaa ttg gcg gag aag ccg cag aag tac act tgg cag gag gtg aag        96
Leu Lys Leu Ala Glu Lys Pro Gln Lys Tyr Thr Trp Gln Glu Val Lys
            20                  25                  30 aag cac atc acc ccc gac gat gcc tgg gta gtc cac caa aac aaa gtc       144
Lys His Ile Thr Pro Asp Asp Ala Trp Val Val His Gln Asn Lys Val
        35                  40                  45 tac gac gtc tcc aac tgg tac gac cac ccc ggt gga gcc gtg gtg ttc       192
Tyr Asp Val Ser Asn Trp Tyr Asp His Pro Gly Gly Ala Val Val Phe
    50                  55                  60 acc cac gcc gga gac gac atg acg gac atc ttc gcc gcc ttc cac gcc       240
Thr His Ala Gly Asp Asp Met Thr Asp Ile Phe Ala Ala Phe His Ala
65                  70                  75                  80 caa ggc tct cag gcc atg atg aag aag ttt tac att gga gat ttg att       288
Gln Gly Ser Gln Ala Met Met Lys Lys Phe Tyr Ile Gly Asp Leu Ile
                85                  90                  95 ccg gag agt gtg gag cat aag gat caa aga cag ttg gat ttc gag aag       336
Pro Glu Ser Val Glu His Lys Asp Gln Arg Gln Leu Asp Phe Glu Lys
            100                 105                 110 gga tat cgt gat tta cgg gcc aag ctt gtc atg atg ggg atg ttc aag       384
Gly Tyr Arg Asp Leu Arg Ala Lys Leu Val Met Met Gly Met Phe Lys
        115                 120                 125 tcg agt aag atg tat tat gca tac aag tgc tcg ttc aat atg tgc atg       432
Ser Ser Lys Met Tyr Tyr Ala Tyr Lys Cys Ser Phe Asn Met Cys Met
    130                 135                 140 tgg ttg gtg gcg gtg gcc atg gtg tac tac tcg gac agt ttg gca atg       480
Trp Leu Val Ala Val Ala Met Val Tyr Tyr Ser Asp Ser Leu Ala Met
145                 150                 155                 160 cac att gga tcg gct ctc ttg ttg gga ttg ttc tgg cag cag tgt gga       528
His Ile Gly Ser Ala Leu Leu Leu Gly Leu Phe Trp Gln Gln Cys Gly
                165                 170                 175 tgg ctt gcg cac gac ttt ctt cac cac caa gtc ttt aag caa cga aag       576
Trp Leu Ala His Asp Phe Leu His His Gln Val Phe Lys Gln Arg Lys
            180                 185                 190 tac gga gat ctc gtt ggc atc ttt tgg gga gat ctc atg cag ggg ttc       624
Tyr Gly Asp Leu Val Gly Ile Phe Trp Gly Asp Leu Met Gln Gly Phe
        195                 200                 205 tcg atg cag tgg tgg aag aac aag cac aat ggc cac cat gct gtt ccc       672
Ser Met Gln Trp Trp Lys Asn Lys His Asn Gly His His Ala Val Pro
    210                 215                 220 aac ttg cac aac tct tcc ttg gac agt cag gat ggt gat ccc gat att       720
Asn Leu His Asn Ser Ser Leu Asp Ser Gln Asp Gly Asp Pro Asp Ile
225                 230                 235                 240 gat acc atg cca ctc ctt gct tgg agt ctc aag cag gct cag agt ttc       768
Asp Thr Met Pro Leu Leu Ala Trp Ser Leu Lys Gln Ala Gln Ser Phe
                245                 250                 255 aga gag atc aat aag gga aag gac agt acc ttc gtc aag tac gct atc       816
Arg Glu Ile Asn Lys Gly Lys Asp Ser Thr Phe Val Lys Tyr Ala Ile
            260                 265                 270 aaa ttc cag gca ttc aca tac ttc ccc atc ctc ctc ttg gct cgc atc       864
Lys Phe Gln Ala Phe Thr Tyr Phe Pro Ile Leu Leu Leu Ala Arg Ile
        275                 280                 285 tct tgg ttg aat gaa tcc ttc aaa act gca ttc gga ctc gga gct gcc       912
Ser Trp Leu Asn Glu Ser Phe Lys Thr Ala Phe Gly Leu Gly Ala Ala
    290                 295                 300 tcg gag aat gcc aag ttg gag ttg gag aag cgt gga ctt cag tac cca       960
Ser Glu Asn Ala Lys Leu Glu Leu Glu Lys Arg Gly Leu Gln Tyr Pro
305                 310                 315                 320
```

```
ctt ttg gag aag ctt gga atc acc ctt cat tac act tgg atg ttc gtc    1008
Leu Leu Glu Lys Leu Gly Ile Thr Leu His Tyr Thr Trp Met Phe Val
            325                 330                 335 ctc tct tcc gga ttt gga agg tgg tct ctt cca tat tcc atc atg tat    1056
Leu Ser Ser Gly Phe Gly Arg Trp Ser Leu Pro Tyr Ser Ile Met Tyr
        340                 345                 350 ttc ttc act gcc aca tgc tcc tcg gga ctt ttc ctc gca ttg gtc ttt    1104
Phe Phe Thr Ala Thr Cys Ser Ser Gly Leu Phe Leu Ala Leu Val Phe
    355                 360                 365 gga ttg gga cac aac ggt atg tca gtg tac gat gcc acc acc cga cct    1152
Gly Leu Gly His Asn Gly Met Ser Val Tyr Asp Ala Thr Thr Arg Pro
370                 375                 380 gac ttc tgg caa ctc caa gtc acc act aca cgt aac atc att ggt gga    1200
Asp Phe Trp Gln Leu Gln Val Thr Thr Thr Arg Asn Ile Ile Gly Gly
385                 390                 395                 400 cac ggc att ccc caa ttc ttt gtg gat tgg ttc tgc ggt gga ttg caa    1248
His Gly Ile Pro Gln Phe Phe Val Asp Trp Phe Cys Gly Gly Leu Gln
            405                 410                 415 tac caa gtg gat cac cac ctc ttc ccc atg atg cct aga aac aat atc    1296
Tyr Gln Val Asp His His Leu Phe Pro Met Met Pro Arg Asn Asn Ile
        420                 425                 430 gcg aaa tgc cac aag ctt gtg gag tca ttc tgt aag gag tgg ggt gtg    1344
Ala Lys Cys His Lys Leu Val Glu Ser Phe Cys Lys Glu Trp Gly Val
    435                 440                 445 aag tac cat gag gcc gat atg tgg gat ggt acc gtg gaa gtg ttg caa    1392
Lys Tyr His Glu Ala Asp Met Trp Asp Gly Thr Val Glu Val Leu Gln
450                 455                 460 cat ctc tcc aag gtg tcg gat gat ttc ctt gtg gag atg gtg aag gat    1440
His Leu Ser Lys Val Ser Asp Asp Phe Leu Val Glu Met Val Lys Asp
465                 470                 475                 480 ttc cct gcc atg taa                                                1455
Phe Pro Ala Met <210> SEQ ID NO 98
<211> LENGTH: 484
<212> TYPE: PRT
<213> ORGANISM: Thalassiosira pseudonana

<400> SEQUENCE: 98

Met Gly Lys Gly Gly Asp Ala Ala Ala Thr Lys Arg Ser Gly Ala
1               5                   10                  15

Leu Lys Leu Ala Glu Lys Pro Gln Lys Tyr Thr Trp Gln Glu Val Lys
            20                  25                  30

Lys His Ile Thr Pro Asp Asp Ala Trp Val Val His Gln Asn Lys Val
        35                  40                  45

Tyr Asp Val Ser Asn Trp Tyr Asp His Pro Gly Gly Ala Val Val Phe
    50                  55                  60

Thr His Ala Gly Asp Asp Met Thr Asp Ile Phe Ala Ala Phe His Ala
65                  70                  75                  80

Gln Gly Ser Gln Ala Met Met Lys Lys Phe Tyr Ile Gly Asp Leu Ile
                85                  90                  95

Pro Glu Ser Val Glu His Lys Asp Gln Arg Gln Leu Asp Phe Glu Lys
            100                 105                 110

Gly Tyr Arg Asp Leu Arg Ala Lys Leu Val Met Met Gly Met Phe Lys
        115                 120                 125

Ser Ser Lys Met Tyr Tyr Ala Tyr Lys Cys Ser Phe Asn Met Cys Met
    130                 135                 140
```

```
Trp Leu Val Ala Val Ala Met Val Tyr Tyr Ser Asp Ser Leu Ala Met
145                 150                 155                 160

His Ile Gly Ser Ala Leu Leu Leu Gly Leu Phe Trp Gln Gln Cys Gly
            165                 170                 175

Trp Leu Ala His Asp Phe Leu His His Gln Val Phe Lys Gln Arg Lys
        180                 185                 190

Tyr Gly Asp Leu Val Gly Ile Phe Trp Gly Asp Leu Met Gln Gly Phe
    195                 200                 205

Ser Met Gln Trp Trp Lys Asn Lys His Asn Gly His His Ala Val Pro
210                 215                 220

Asn Leu His Asn Ser Ser Leu Asp Ser Gln Asp Gly Asp Pro Asp Ile
225                 230                 235                 240

Asp Thr Met Pro Leu Leu Ala Trp Ser Leu Lys Gln Ala Gln Ser Phe
            245                 250                 255

Arg Glu Ile Asn Lys Gly Lys Asp Ser Thr Phe Val Lys Tyr Ala Ile
        260                 265                 270

Lys Phe Gln Ala Phe Thr Tyr Phe Pro Ile Leu Leu Leu Ala Arg Ile
    275                 280                 285

Ser Trp Leu Asn Glu Ser Phe Lys Thr Ala Phe Gly Leu Gly Ala Ala
290                 295                 300

Ser Glu Asn Ala Lys Leu Glu Leu Glu Lys Arg Gly Leu Gln Tyr Pro
305                 310                 315                 320

Leu Leu Glu Lys Leu Gly Ile Thr Leu His Tyr Thr Trp Met Phe Val
            325                 330                 335

Leu Ser Ser Gly Phe Gly Arg Trp Ser Leu Pro Tyr Ser Ile Met Tyr
        340                 345                 350

Phe Phe Thr Ala Thr Cys Ser Ser Gly Leu Phe Leu Ala Leu Val Phe
    355                 360                 365

Gly Leu Gly His Asn Gly Met Ser Val Tyr Asp Ala Thr Thr Arg Pro
370                 375                 380

Asp Phe Trp Gln Leu Gln Val Thr Thr Thr Arg Asn Ile Ile Gly Gly
385                 390                 395                 400

His Gly Ile Pro Gln Phe Phe Val Asp Trp Phe Cys Gly Gly Leu Gln
            405                 410                 415

Tyr Gln Val Asp His His Leu Phe Pro Met Met Pro Arg Asn Asn Ile
        420                 425                 430

Ala Lys Cys His Lys Leu Val Glu Ser Phe Cys Lys Glu Trp Gly Val
    435                 440                 445

Lys Tyr His Glu Ala Asp Met Trp Asp Gly Thr Val Glu Val Leu Gln
450                 455                 460

His Leu Ser Lys Val Ser Asp Asp Phe Leu Val Glu Met Val Lys Asp
465                 470                 475                 480

Phe Pro Ala Met

<210> SEQ ID NO 99
<211> LENGTH: 1431
<212> TYPE: DNA
<213> ORGANISM: Thalassiosira pseudonana
<220> FEATURE:
<221> NAME/KEY: CDS
<222> LOCATION: (1)..(1431)
<223> OTHER INFORMATION: delta5-desaturase

<400> SEQUENCE: 99 atg ccc ccc aac gcc gat atc tcc cgc atc cgc aac cgc atc ccc acc      48
Met Pro Pro Asn Ala Asp Ile Ser Arg Ile Arg Asn Arg Ile Pro Thr
```

-continued

```
1               5                   10                  15
aaa aca ggt acc gtt gcc tct gcc gac aac aac gac ccc gcc acc caa      96
Lys Thr Gly Thr Val Ala Ser Ala Asp Asn Asn Asp Pro Ala Thr Gln
             20                  25                  30 tcc gtc cga acc ctc aaa tct ctc aag ggc aac gag gtc gtc atc aac     144
Ser Val Arg Thr Leu Lys Ser Leu Lys Gly Asn Glu Val Val Ile Asn
         35                  40                  45 ggc aca att tat gac att gct gac ttt gtc cat cct gga gga gag gtt    192
Gly Thr Ile Tyr Asp Ile Ala Asp Phe Val His Pro Gly Gly Glu Val
     50                  55                  60 gtc aag ttc ttt ggt ggg aat gat gtt act att cag tat aat atg att    240
Val Lys Phe Phe Gly Gly Asn Asp Val Thr Ile Gln Tyr Asn Met Ile
65                  70                  75                  80 cat ccg tat cat acg ggg aaa cat ctg gag aag atg aag gct gtt gga    288
His Pro Tyr His Thr Gly Lys His Leu Glu Lys Met Lys Ala Val Gly
                 85                  90                  95 aag gtt gta gat tgg cag tcg gac tac aag ttc gac acc ccc ttt gaa    336
Lys Val Val Asp Trp Gln Ser Asp Tyr Lys Phe Asp Thr Pro Phe Glu
             100                 105                 110 cga gag atc aaa tca gaa gtg ttc aag atc gta cgt cgc ggg cgt gag    384
Arg Glu Ile Lys Ser Glu Val Phe Lys Ile Val Arg Arg Gly Arg Glu
         115                 120                 125 ttc ggc aca aca ggc tac ttc ctc cgt gcc ttt ttc tac atc gct ctc    432
Phe Gly Thr Thr Gly Tyr Phe Leu Arg Ala Phe Phe Tyr Ile Ala Leu
     130                 135                 140 ttc ttc acc atg caa tac act ttc gcc aca tgc acc acc ttc acc acc    480
Phe Phe Thr Met Gln Tyr Thr Phe Ala Thr Cys Thr Thr Phe Thr Thr
145                 150                 155                 160 tac gat cac tgg tat cag agt ggt gta ttc atc gca att gtg ttt ggt    528
Tyr Asp His Trp Tyr Gln Ser Gly Val Phe Ile Ala Ile Val Phe Gly
                 165                 170                 175 att tca cag gca ttc att ggg ttg aat gtc cag cac gat gcc aat cac    576
Ile Ser Gln Ala Phe Ile Gly Leu Asn Val Gln His Asp Ala Asn His
             180                 185                 190 gga gct gcc agt aag cgt ccc tgg gtg aat gac ttg ttg gga ttt gga    624
Gly Ala Ala Ser Lys Arg Pro Trp Val Asn Asp Leu Leu Gly Phe Gly
         195                 200                 205 acg gat ttg att gga tct aac aaa tgg aat tgg atg gca cag cat tgg    672
Thr Asp Leu Ile Gly Ser Asn Lys Trp Asn Trp Met Ala Gln His Trp
     210                 215                 220 act cat cac gct tac act aac cat agt gag aag gat ccc gat agc ttc    720
Thr His His Ala Tyr Thr Asn His Ser Glu Lys Asp Pro Asp Ser Phe
225                 230                 235                 240 agc tcg gaa cct atg ttt gca ttc aat gac tat ccc att gga cac ccg    768
Ser Ser Glu Pro Met Phe Ala Phe Asn Asp Tyr Pro Ile Gly His Pro
                 245                 250                 255 aag aga aag tgg tgg cat agg ttc cag gga ggg tac ttc ctc ttc atg    816
Lys Arg Lys Trp Trp His Arg Phe Gln Gly Gly Tyr Phe Leu Phe Met
             260                 265                 270 ctt gga ctt tac tgg ctc tcg act gta ttc aat ccg caa ttc att gat    864
Leu Gly Leu Tyr Trp Leu Ser Thr Val Phe Asn Pro Gln Phe Ile Asp
         275                 280                 285 ctt cgt caa cgt ggg gct cag tac gtc gga att caa atg gag aat gat    912
Leu Arg Gln Arg Gly Ala Gln Tyr Val Gly Ile Gln Met Glu Asn Asp
     290                 295                 300 ttc att gtc aag agg agg aag tac gcc gtt gca ttg agg atg atg tac    960
Phe Ile Val Lys Arg Arg Lys Tyr Ala Val Ala Leu Arg Met Met Tyr
305                 310                 315                 320 att tac ttg aac att gtc agc ccc ttc atg aac aat ggt ttg agc tgg   1008
```

```
Ile Tyr Leu Asn Ile Val Ser Pro Phe Met Asn Asn Gly Leu Ser Trp
            325                 330                 335 tct acc ttt gga atc atc atg ttg atg gga atc agc gag agt ctc act      1056
Ser Thr Phe Gly Ile Ile Met Leu Met Gly Ile Ser Glu Ser Leu Thr
            340                 345                 350 ctc agt gtg ctc ttc tcg ttg tct cac aac ttc atc aat tcg gat cgt      1104
Leu Ser Val Leu Phe Ser Leu Ser His Asn Phe Ile Asn Ser Asp Arg
            355                 360                 365 gat cct acg gct gac ttc aaa aag acc gga gaa caa gtg tgc tgg ttc      1152
Asp Pro Thr Ala Asp Phe Lys Lys Thr Gly Glu Gln Val Cys Trp Phe
370                 375                 380 aag tcg cag gtg gag act tcg tct acc tat ggg ggt ttt att tcc gga      1200
Lys Ser Gln Val Glu Thr Ser Ser Thr Tyr Gly Gly Phe Ile Ser Gly
385                 390                 395                 400 tgt ctt acg gga gga ctc aac ttt cag gtg gaa cat cat ctc ttt ccc      1248
Cys Leu Thr Gly Gly Leu Asn Phe Gln Val Glu His His Leu Phe Pro
            405                 410                 415 cgt atg agc agt gct tgg tat cct tac att gca cct acg gtt cgt gag      1296
Arg Met Ser Ser Ala Trp Tyr Pro Tyr Ile Ala Pro Thr Val Arg Glu
            420                 425                 430 gtt tgc aag aag cac ggg gtg aac tac gct tat tat cct tgg att ggg      1344
Val Cys Lys Lys His Gly Val Asn Tyr Ala Tyr Tyr Pro Trp Ile Gly
            435                 440                 445 cag aat ttg gta tca aca ttc aaa tac atg cat cgc gct ggt agt gga      1392
Gln Asn Leu Val Ser Thr Phe Lys Tyr Met His Arg Ala Gly Ser Gly
450                 455                 460 gcc aac tgg gag ctc aag ccg ttg tct gga agt gcc taa                  1431
Ala Asn Trp Glu Leu Lys Pro Leu Ser Gly Ser Ala
465                 470                 475

<210> SEQ ID NO 100
<211> LENGTH: 476
<212> TYPE: PRT
<213> ORGANISM: Thalassiosira pseudonana

<400> SEQUENCE: 100

Met Pro Pro Asn Ala Asp Ile Ser Arg Ile Arg Asn Arg Ile Pro Thr
1               5                   10                  15

Lys Thr Gly Thr Val Ala Ser Ala Asp Asn Asn Asp Pro Ala Thr Gln
            20                  25                  30

Ser Val Arg Thr Leu Lys Ser Leu Lys Gly Asn Glu Val Val Ile Asn
        35                  40                  45

Gly Thr Ile Tyr Asp Ile Ala Asp Phe Val His Pro Gly Gly Glu Val
    50                  55                  60

Val Lys Phe Phe Gly Gly Asn Asp Val Thr Ile Gln Tyr Asn Met Ile
65                  70                  75                  80

His Pro Tyr His Thr Gly Lys His Leu Glu Lys Met Lys Ala Val Gly
                85                  90                  95

Lys Val Val Asp Trp Gln Ser Asp Tyr Lys Phe Asp Thr Pro Phe Glu
            100                 105                 110

Arg Glu Ile Lys Ser Glu Val Phe Lys Ile Val Arg Arg Gly Arg Glu
        115                 120                 125

Phe Gly Thr Thr Gly Tyr Phe Leu Arg Ala Phe Tyr Ile Ala Leu
    130                 135                 140

Phe Phe Thr Met Gln Tyr Thr Phe Ala Thr Cys Thr Thr Phe Thr Thr
145                 150                 155                 160

Tyr Asp His Trp Tyr Gln Ser Gly Val Phe Ile Ala Ile Val Phe Gly
                165                 170                 175
```

```
Ile Ser Gln Ala Phe Ile Gly Leu Asn Val Gln His Asp Ala Asn His
            180                 185                 190

Gly Ala Ala Ser Lys Arg Pro Trp Val Asn Asp Leu Leu Gly Phe Gly
            195                 200                 205

Thr Asp Leu Ile Gly Ser Asn Lys Trp Asn Trp Met Ala Gln His Trp
    210                 215                 220

Thr His His Ala Tyr Thr Asn His Ser Glu Lys Asp Pro Asp Ser Phe
225                 230                 235                 240

Ser Ser Glu Pro Met Phe Ala Phe Asn Asp Tyr Pro Ile Gly His Pro
                245                 250                 255

Lys Arg Lys Trp Trp His Arg Phe Gln Gly Gly Tyr Phe Leu Phe Met
                260                 265                 270

Leu Gly Leu Tyr Trp Leu Ser Thr Val Phe Asn Pro Gln Phe Ile Asp
            275                 280                 285

Leu Arg Gln Arg Gly Ala Gln Tyr Val Gly Ile Gln Met Glu Asn Asp
    290                 295                 300

Phe Ile Val Lys Arg Lys Tyr Ala Val Ala Leu Arg Met Met Tyr
305                 310                 315                 320

Ile Tyr Leu Asn Ile Val Ser Pro Phe Met Asn Asn Gly Leu Ser Trp
                325                 330                 335

Ser Thr Phe Gly Ile Ile Met Leu Met Gly Ile Ser Glu Ser Leu Thr
            340                 345                 350

Leu Ser Val Leu Phe Ser Leu Ser His Asn Phe Ile Asn Ser Asp Arg
    355                 360                 365

Asp Pro Thr Ala Asp Phe Lys Lys Thr Gly Glu Gln Val Cys Trp Phe
370                 375                 380

Lys Ser Gln Val Glu Thr Ser Ser Thr Tyr Gly Gly Phe Ile Ser Gly
385                 390                 395                 400

Cys Leu Thr Gly Gly Leu Asn Phe Gln Val Glu His His Leu Phe Pro
                405                 410                 415

Arg Met Ser Ser Ala Trp Tyr Pro Tyr Ile Ala Pro Thr Val Arg Glu
                420                 425                 430

Val Cys Lys Lys His Gly Val Asn Tyr Ala Tyr Tyr Pro Trp Ile Gly
            435                 440                 445

Gln Asn Leu Val Ser Thr Phe Lys Tyr Met His Arg Ala Gly Ser Gly
    450                 455                 460

Ala Asn Trp Glu Leu Lys Pro Leu Ser Gly Ser Ala
465                 470                 475

<210> SEQ ID NO 101
<211> LENGTH: 1449
<212> TYPE: DNA
<213> ORGANISM: Thalassiosira pseudonana
<220> FEATURE:
<221> NAME/KEY: CDS
<222> LOCATION: (1)..(1449)
<223> OTHER INFORMATION: delta5-desaturase

<400> SEQUENCE: 101 atg cca ccc aac gcc gag gtc aaa aac ctc cgt tca cgt tcc atc cca    48
Met Pro Pro Asn Ala Glu Val Lys Asn Leu Arg Ser Arg Ser Ile Pro
1               5                   10                  15 acg aag aag tcc agt tca tcg tca tcc acc gcg aac gac gat ccg gct    96
Thr Lys Lys Ser Ser Ser Ser Ser Thr Ala Asn Asp Asp Pro Ala
            20                  25                  30 acc caa tcc acc tca cct gtg aac cga acc ctc aag tct ttg aat gga   144
```

|     |     |     |     |     |     |     |     |     |     |     |     |     |     |     |
|-----|-----|-----|-----|-----|-----|-----|-----|-----|-----|-----|-----|-----|-----|-----|
| Thr | Gln | Ser | Thr | Ser | Pro | Val | Asn | Arg | Thr | Leu | Lys | Ser | Leu | Asn | Gly |
|     |     | 35  |     |     |     | 40  |     |     |     | 45  |     |     |     |     |

```
aac gaa ata gct att gac ggt gtc atc tat gat att gat ggc ttt gtc      192
Asn Glu Ile Ala Ile Asp Gly Val Ile Tyr Asp Ile Asp Gly Phe Val
         50                  55                  60 cat cct gga gga gag gtt att agc ttc ttt gga ggc aac gat gtg act      240
His Pro Gly Gly Glu Val Ile Ser Phe Phe Gly Gly Asn Asp Val Thr
 65                  70                  75                  80 gta cag tac aaa atg att cat ccg tat cat aat agt aag cat ctc gag      288
Val Gln Tyr Lys Met Ile His Pro Tyr His Asn Ser Lys His Leu Glu
                     85                  90                  95 aag atg aga gcc gtt gga aag att gca gac tac tcc aca gag tac aag      336
Lys Met Arg Ala Val Gly Lys Ile Ala Asp Tyr Ser Thr Glu Tyr Lys
                 100                 105                 110 ttc gac aca ccc ttt gaa cga gag atc aaa tcc gaa gtg ttc aaa atc      384
Phe Asp Thr Pro Phe Glu Arg Glu Ile Lys Ser Glu Val Phe Lys Ile
             115                 120                 125 gtc cgt cga gga cgt gaa ttc ggt aca aca gga tat ttc ctc cgt gcc      432
Val Arg Arg Gly Arg Glu Phe Gly Thr Thr Gly Tyr Phe Leu Arg Ala
 130                 135                 140 ttc ttc tac att gct ctc ttc ttc acc atg caa tac acc ttc gcc aca      480
Phe Phe Tyr Ile Ala Leu Phe Phe Thr Met Gln Tyr Thr Phe Ala Thr
145                 150                 155                 160 tgc act acc ttc acc acc tac gat cat tgg tat caa agt ggt gta ttc      528
Cys Thr Thr Phe Thr Thr Tyr Asp His Trp Tyr Gln Ser Gly Val Phe
                     165                 170                 175 atc gcc att gtg ttt ggt atc tca caa gct ttc att ggg ttg aat gta      576
Ile Ala Ile Val Phe Gly Ile Ser Gln Ala Phe Ile Gly Leu Asn Val
                 180                 185                 190 caa cat gat gcc aat cac gga gct gct agc aaa cga cct tgg gtg aat      624
Gln His Asp Ala Asn His Gly Ala Ala Ser Lys Arg Pro Trp Val Asn
             195                 200                 205 gat ctc ctt gga tct gga gct gat ctc atc ggt gga tgc aaa tgg aac      672
Asp Leu Leu Gly Ser Gly Ala Asp Leu Ile Gly Gly Cys Lys Trp Asn
 210                 215                 220 tgg ttg gct cag cat tgg act cat cat gcg tat acc aat cac gct gat      720
Trp Leu Ala Gln His Trp Thr His His Ala Tyr Thr Asn His Ala Asp
225                 230                 235                 240 aaa gat cct gat agc ttt agt tcc gag ccg gtc ttc aac ttt aac gat      768
Lys Asp Pro Asp Ser Phe Ser Ser Glu Pro Val Phe Asn Phe Asn Asp
                     245                 250                 255 tat ccc att ggt cac ccc aaa aga aag tgg tgg cat agg ttc caa ggg      816
Tyr Pro Ile Gly His Pro Lys Arg Lys Trp Trp His Arg Phe Gln Gly
                 260                 265                 270 ctc tac ttc cta atc atg ctg agt ttc tat tgg gta tcg atg gta ttc      864
Leu Tyr Phe Leu Ile Met Leu Ser Phe Tyr Trp Val Ser Met Val Phe
             275                 280                 285 aac cca caa gtt atc gac ctc cgt cat gct gga gct gcc tac gtt gga      912
Asn Pro Gln Val Ile Asp Leu Arg His Ala Gly Ala Ala Tyr Val Gly
 290                 295                 300 ttt cag atg gag aac gac ttt atc gtc aaa cgg aga aag tat gca atg      960
Phe Gln Met Glu Asn Asp Phe Ile Val Lys Arg Arg Lys Tyr Ala Met
305                 310                 315                 320 gca ctt cgt gca atg tac ttc tat ttc aac atc tat tgt ccg att gtc     1008
Ala Leu Arg Ala Met Tyr Phe Tyr Phe Asn Ile Tyr Cys Pro Ile Val
                     325                 330                 335 aac aat gga ttg act tgg tcg aca gtt gga atc atc ctc tta atg gga     1056
Asn Asn Gly Leu Thr Trp Ser Thr Val Gly Ile Ile Leu Leu Met Gly
                 340                 345                 350
```

| | | | | | | | | | | | | | | | | |
|---|---|---|---|---|---|---|---|---|---|---|---|---|---|---|---|---|
| gtt | agc | gaa | agc | ttc | atg | ctc | tcc | ggt | cta | ttc | gta | ctc | tca | cac | aac | 1104 |
| Val | Ser | Glu | Ser | Phe | Met | Leu | Ser | Gly | Leu | Phe | Val | Leu | Ser | His | Asn | |
| | | 355 | | | | 360 | | | | | 365 | | | | | |
| ttt | gaa | aat | tcc | gaa | cgt | gat | cct | acc | tct | gag | tat | cgc | aag | act | ggt | 1152 |
| Phe | Glu | Asn | Ser | Glu | Arg | Asp | Pro | Thr | Ser | Glu | Tyr | Arg | Lys | Thr | Gly | |
| | 370 | | | | 375 | | | | 380 | | | | | | | |
| gag | caa | gta | tgt | tgg | ttc | aag | tct | caa | gtg | gag | act | tct | tct | acc | tac | 1200 |
| Glu | Gln | Val | Cys | Trp | Phe | Lys | Ser | Gln | Val | Glu | Thr | Ser | Ser | Thr | Tyr | |
| 385 | | | | 390 | | | | | 395 | | | | | 400 | | |
| gga | ggt | atc | gtt | gct | ggg | tgt | ctc | act | ggt | gga | ctc | aac | ttt | caa | gtg | 1248 |
| Gly | Gly | Ile | Val | Ala | Gly | Cys | Leu | Thr | Gly | Gly | Leu | Asn | Phe | Gln | Val | |
| | | | 405 | | | | 410 | | | | 415 | | | | | |
| gag | cat | cat | ttg | ttc | ccg | agg | atg | agc | agt | gct | tgg | tat | cct | ttc | atc | 1296 |
| Glu | His | His | Leu | Phe | Pro | Arg | Met | Ser | Ser | Ala | Trp | Tyr | Pro | Phe | Ile | |
| | | 420 | | | | 425 | | | | | 430 | | | | | |
| gcg | ccg | aag | gtt | aga | gag | att | tgt | aag | aag | cat | gga | gtt | aga | tac | gct | 1344 |
| Ala | Pro | Lys | Val | Arg | Glu | Ile | Cys | Lys | Lys | His | Gly | Val | Arg | Tyr | Ala | |
| | 435 | | | | 440 | | | | | 445 | | | | | | |
| tac | tat | ccg | tac | atc | tgg | cag | aac | ttg | cat | tct | acc | gtg | agt | tac | atg | 1392 |
| Tyr | Tyr | Pro | Tyr | Ile | Trp | Gln | Asn | Leu | His | Ser | Thr | Val | Ser | Tyr | Met | |
| 450 | | | | 455 | | | | | 460 | | | | | | | |
| cat | ggg | acg | gga | acg | gga | gct | aga | tgg | gag | ctt | cag | ccg | ttg | tct | gga | 1440 |
| His | Gly | Thr | Gly | Thr | Gly | Ala | Arg | Trp | Glu | Leu | Gln | Pro | Leu | Ser | Gly | |
| 465 | | | | 470 | | | | 475 | | | | | 480 | | | |
| agg | gcg | tag | | | | | | | | | | | | | | 1449 |
| Arg | Ala | | | | | | | | | | | | | | | |

<210> SEQ ID NO 102
<211> LENGTH: 482
<212> TYPE: PRT
<213> ORGANISM: Thalassiosira pseudonana

<400> SEQUENCE: 102

Met Pro Pro Asn Ala Glu Val Lys Asn Leu Arg Ser Arg Ser Ile Pro
1               5                   10                  15

Thr Lys Lys Ser Ser Ser Ser Ser Thr Ala Asn Asp Asp Pro Ala
            20                  25                  30

Thr Gln Ser Thr Ser Pro Val Asn Arg Thr Leu Lys Ser Leu Asn Gly
        35                  40                  45

Asn Glu Ile Ala Ile Asp Gly Val Ile Tyr Asp Ile Asp Gly Phe Val
50                  55                  60

His Pro Gly Gly Glu Val Ile Ser Phe Phe Gly Gly Asn Asp Val Thr
65                  70                  75                  80

Val Gln Tyr Lys Met Ile His Pro Tyr His Asn Ser Lys His Leu Glu
                85                  90                  95

Lys Met Arg Ala Val Gly Lys Ile Ala Asp Tyr Ser Thr Glu Tyr Lys
            100                 105                 110

Phe Asp Thr Pro Phe Glu Arg Glu Ile Lys Ser Glu Val Phe Lys Ile
        115                 120                 125

Val Arg Arg Gly Arg Glu Phe Gly Thr Thr Gly Tyr Phe Leu Arg Ala
    130                 135                 140

Phe Phe Tyr Ile Ala Leu Phe Phe Thr Met Gln Tyr Thr Phe Ala Thr
145                 150                 155                 160

Cys Thr Thr Phe Thr Thr Tyr Asp His Trp Tyr Gln Ser Gly Val Phe
                165                 170                 175

Ile Ala Ile Val Phe Gly Ile Ser Gln Ala Phe Ile Gly Leu Asn Val
            180                 185                 190

```
Gln His Asp Ala Asn His Gly Ala Ala Ser Lys Arg Pro Trp Val Asn
        195                 200                 205

Asp Leu Leu Gly Ser Gly Ala Asp Leu Ile Gly Gly Cys Lys Trp Asn
210                 215                 220

Trp Leu Ala Gln His Trp Thr His His Ala Tyr Thr Asn His Ala Asp
225                 230                 235                 240

Lys Asp Pro Asp Ser Phe Ser Ser Glu Pro Val Phe Asn Phe Asn Asp
                245                 250                 255

Tyr Pro Ile Gly His Pro Lys Arg Lys Trp Trp His Arg Phe Gln Gly
            260                 265                 270

Leu Tyr Phe Leu Ile Met Leu Ser Phe Tyr Trp Val Ser Met Val Phe
        275                 280                 285

Asn Pro Gln Val Ile Asp Leu Arg His Ala Gly Ala Ala Tyr Val Gly
290                 295                 300

Phe Gln Met Glu Asn Asp Phe Ile Val Lys Arg Arg Lys Tyr Ala Met
305                 310                 315                 320

Ala Leu Arg Ala Met Tyr Phe Tyr Phe Asn Ile Tyr Cys Pro Ile Val
                325                 330                 335

Asn Asn Gly Leu Thr Trp Ser Thr Val Gly Ile Ile Leu Leu Met Gly
            340                 345                 350

Val Ser Glu Ser Phe Met Leu Ser Gly Leu Phe Val Leu Ser His Asn
        355                 360                 365

Phe Glu Asn Ser Glu Arg Asp Pro Thr Ser Glu Tyr Arg Lys Thr Gly
        370                 375                 380

Glu Gln Val Cys Trp Phe Lys Ser Gln Val Glu Thr Ser Ser Thr Tyr
385                 390                 395                 400

Gly Gly Ile Val Ala Gly Cys Leu Thr Gly Gly Leu Asn Phe Gln Val
                405                 410                 415

Glu His His Leu Phe Pro Arg Met Ser Ser Ala Trp Tyr Pro Phe Ile
            420                 425                 430

Ala Pro Lys Val Arg Glu Ile Cys Lys Lys His Gly Val Arg Tyr Ala
        435                 440                 445

Tyr Tyr Pro Tyr Ile Trp Gln Asn Leu His Ser Thr Val Ser Tyr Met
450                 455                 460

His Gly Thr Gly Thr Gly Ala Arg Trp Glu Leu Gln Pro Leu Ser Gly
465                 470                 475                 480

Arg Ala

<210> SEQ ID NO 103
<211> LENGTH: 1512
<212> TYPE: DNA
<213> ORGANISM: Thalassiosira pseudonana
<220> FEATURE:
<221> NAME/KEY: CDS
<222> LOCATION: (1)..(1512)
<223> OTHER INFORMATION: delta4-desaturase

<400> SEQUENCE: 103 atg tgc aac ggc aac ctc cca gca tcc acc gca cag ctc aag tcc acc      48
Met Cys Asn Gly Asn Leu Pro Ala Ser Thr Ala Gln Leu Lys Ser Thr
1               5                   10                  15 tcg aag ccc cag cag caa cat gag cat cgc acc atc tcc aag tcc gag      96
Ser Lys Pro Gln Gln Gln His Glu His Arg Thr Ile Ser Lys Ser Glu
                20                  25                  30 ctc gcc caa cac aac acg ccc aaa tca gca tgg tgt gcc gtc cac tcc     144
Leu Ala Gln His Asn Thr Pro Lys Ser Ala Trp Cys Ala Val His Ser
            35                  40                  45
```

```
act ccc gcc acc gac cca tcc cac tcc aac aac aaa caa cac gca cac      192
Thr Pro Ala Thr Asp Pro Ser His Ser Asn Asn Lys Gln His Ala His
 50                  55                  60 cta gtc ctc gac att acc gac ttt gcg tcc cgc cat cca ggg gga gac      240
Leu Val Leu Asp Ile Thr Asp Phe Ala Ser Arg His Pro Gly Gly Asp
65                  70                  75                  80 ctc atc ctc ctc gct tcc ggc aaa gac gcc tcg gtg ctg ttt gaa aca      288
Leu Ile Leu Leu Ala Ser Gly Lys Asp Ala Ser Val Leu Phe Glu Thr
             85                  90                  95 tac cat cca cgt gga gtt ccg acg tct ctc att caa aag ctg cag att      336
Tyr His Pro Arg Gly Val Pro Thr Ser Leu Ile Gln Lys Leu Gln Ile
                100                 105                 110 gga gtg atg gag gag gag gcg ttt cgg gat tcg ttt tac agt tgg act      384
Gly Val Met Glu Glu Glu Ala Phe Arg Asp Ser Phe Tyr Ser Trp Thr
            115                 120                 125 gat tct gac ttt tat act gtg ttg aag agg agg gtt gtg gag cgg ttg      432
Asp Ser Asp Phe Tyr Thr Val Leu Lys Arg Arg Val Val Glu Arg Leu
130                 135                 140 gag gag agg ggg ttg gac agg agg gga tcg aaa gag att tgg atc aag      480
Glu Glu Arg Gly Leu Asp Arg Arg Gly Ser Lys Glu Ile Trp Ile Lys
145                 150                 155                 160 gct ttg ttc ttg ttg gtt gga ttt tgg tac tgt ttg tac aag atg tat      528
Ala Leu Phe Leu Leu Val Gly Phe Trp Tyr Cys Leu Tyr Lys Met Tyr
                165                 170                 175 act acg tcg gat atc gat cag tac ggt att gcc att gcc tat tct att      576
Thr Thr Ser Asp Ile Asp Gln Tyr Gly Ile Ala Ile Ala Tyr Ser Ile
                180                 185                 190 gga atg gga acc ttt gcg gca ttc atc ggc acg tgt att caa cac gat      624
Gly Met Gly Thr Phe Ala Ala Phe Ile Gly Thr Cys Ile Gln His Asp
            195                 200                 205 gga aat cac ggt gca ttc gct cag aac aag tta ctc aac aag ttg gct      672
Gly Asn His Gly Ala Phe Ala Gln Asn Lys Leu Leu Asn Lys Leu Ala
210                 215                 220 ggg tgg acg ttg gat atg att ggt gcg agt gcg ttt acg tgg gag ctt      720
Gly Trp Thr Leu Asp Met Ile Gly Ala Ser Ala Phe Thr Trp Glu Leu
225                 230                 235                 240 cag cac atg ctg ggg cat cat cca tat acg aat gtg ttg gat ggg gtg      768
Gln His Met Leu Gly His His Pro Tyr Thr Asn Val Leu Asp Gly Val
                245                 250                 255 gag gag gag agg aag gag agg ggg gag gat gtt gct ttg gaa gaa aag      816
Glu Glu Glu Arg Lys Glu Arg Gly Glu Asp Val Ala Leu Glu Glu Lys
                260                 265                 270 gat cag gat ttt gaa gtt gcc aca tcc gga cga tta tat cat att gat      864
Asp Gln Asp Phe Glu Val Ala Thr Ser Gly Arg Leu Tyr His Ile Asp
            275                 280                 285 gcc aat gta cgt tat ggt tcg gta tgg aat gtc atg agg ttt tgg gct      912
Ala Asn Val Arg Tyr Gly Ser Val Trp Asn Val Met Arg Phe Trp Ala
290                 295                 300 atg aag gtc att acg atg gga tat atg atg gga tta cca atc tac ttt      960
Met Lys Val Ile Thr Met Gly Tyr Met Met Gly Leu Pro Ile Tyr Phe
305                 310                 315                 320 cat gga gta ctg agg gga gtt gga ttg ttt gtt att ggg cat ttg gcg     1008
His Gly Val Leu Arg Gly Val Gly Leu Phe Val Ile Gly His Leu Ala
                325                 330                 335 tgt gga gag ttg ttg gcg acg atg ttt att gtg aat cac gtc att gag     1056
Cys Gly Glu Leu Leu Ala Thr Met Phe Ile Val Asn His Val Ile Glu
            340                 345                 350 ggt gtg agt tat gga acg aag gat ttg gtt ggt ggt gcg agt cat gta     1104
Gly Val Ser Tyr Gly Thr Lys Asp Leu Val Gly Gly Ala Ser His Val
```

```
gat gag aag aag att gtc aag cca acg act gta ttg gga gat aca cca    1152
Asp Glu Lys Lys Ile Val Lys Pro Thr Thr Val Leu Gly Asp Thr Pro
    370                 375                 380 atg gta aag act cgc gag gag gca ttg aaa agc aac agc aat aac aac    1200
Met Val Lys Thr Arg Glu Glu Ala Leu Lys Ser Asn Ser Asn Asn Asn
385                 390                 395                 400 aag aag aag gga gag aag aac tcg gta cca tcc gtt cca ttc aac gac    1248
Lys Lys Lys Gly Glu Lys Asn Ser Val Pro Ser Val Pro Phe Asn Asp
                405                 410                 415 tgg gca gca gtc caa tgc cag acc tcc gtg aat tgg tct cca ggc tca    1296
Trp Ala Ala Val Gln Cys Gln Thr Ser Val Asn Trp Ser Pro Gly Ser
            420                 425                 430 tgg ttc tgg aat cac ttt tct ggg gga ctc tct cat cag att gag cat    1344
Trp Phe Trp Asn His Phe Ser Gly Gly Leu Ser His Gln Ile Glu His
        435                 440                 445 cac ttg ttc ccc agc att tgt cat aca aac tac tgt cat atc cag gat    1392
His Leu Phe Pro Ser Ile Cys His Thr Asn Tyr Cys His Ile Gln Asp
    450                 455                 460 gtt gtg gag agt acg tgt gct gag tac gga gtt ccg tat cag agt gag    1440
Val Val Glu Ser Thr Cys Ala Glu Tyr Gly Val Pro Tyr Gln Ser Glu
465                 470                 475                 480 agt aat ttg ttt gtt gct tat gga aag atg att agt cat ttg aag ttt    1488
Ser Asn Leu Phe Val Ala Tyr Gly Lys Met Ile Ser His Leu Lys Phe
                485                 490                 495 ttg ggt aaa gcc aag tgt gag tag                                    1512
Leu Gly Lys Ala Lys Cys Glu
            500

<210> SEQ ID NO 104
<211> LENGTH: 503
<212> TYPE: PRT
<213> ORGANISM: Thalassiosira pseudonana

<400> SEQUENCE: 104

Met Cys Asn Gly Asn Leu Pro Ala Ser Thr Ala Gln Leu Lys Ser Thr
1               5                   10                  15

Ser Lys Pro Gln Gln Gln His Glu His Arg Thr Ile Ser Lys Ser Glu
            20                  25                  30

Leu Ala Gln His Asn Thr Pro Lys Ser Ala Trp Cys Ala Val His Ser
        35                  40                  45

Thr Pro Ala Thr Asp Pro Ser His Ser Asn Asn Lys Gln His Ala His
    50                  55                  60

Leu Val Leu Asp Ile Thr Asp Phe Ala Ser Arg His Pro Gly Gly Asp
65                  70                  75                  80

Leu Ile Leu Leu Ala Ser Gly Lys Asp Ala Ser Val Leu Phe Glu Thr
                85                  90                  95

Tyr His Pro Arg Gly Val Pro Thr Ser Leu Ile Gln Lys Leu Gln Ile
            100                 105                 110

Gly Val Met Glu Glu Glu Ala Phe Arg Asp Ser Phe Tyr Ser Trp Thr
        115                 120                 125

Asp Ser Asp Phe Tyr Thr Val Leu Lys Arg Arg Val Val Glu Arg Leu
    130                 135                 140

Glu Glu Arg Gly Leu Asp Arg Arg Gly Ser Lys Glu Ile Trp Ile Lys
145                 150                 155                 160

Ala Leu Phe Leu Leu Val Gly Phe Pro Trp Tyr Cys Leu Tyr Lys Met Tyr
                165                 170                 175
```

```
Thr Thr Ser Asp Ile Asp Gln Tyr Gly Ile Ala Ile Ala Tyr Ser Ile
            180                 185                 190
Gly Met Gly Thr Phe Ala Ala Phe Ile Gly Thr Cys Ile Gln His Asp
        195                 200                 205
Gly Asn His Gly Ala Phe Ala Gln Asn Lys Leu Leu Asn Lys Leu Ala
    210                 215                 220
Gly Trp Thr Leu Asp Met Ile Gly Ala Ser Ala Phe Thr Trp Glu Leu
225                 230                 235                 240
Gln His Met Leu Gly His His Pro Tyr Thr Asn Val Leu Asp Gly Val
                245                 250                 255
Glu Glu Glu Arg Lys Glu Arg Gly Glu Asp Val Ala Leu Glu Glu Lys
            260                 265                 270
Asp Gln Asp Phe Glu Val Ala Thr Ser Gly Arg Leu Tyr His Ile Asp
        275                 280                 285
Ala Asn Val Arg Tyr Gly Ser Val Trp Asn Val Met Arg Phe Trp Ala
    290                 295                 300
Met Lys Val Ile Thr Met Gly Tyr Met Met Gly Leu Pro Ile Tyr Phe
305                 310                 315                 320
His Gly Val Leu Arg Gly Val Gly Leu Phe Val Ile Gly His Leu Ala
                325                 330                 335
Cys Gly Glu Leu Leu Ala Thr Met Phe Ile Val Asn His Val Ile Glu
            340                 345                 350
Gly Val Ser Tyr Gly Thr Lys Asp Leu Val Gly Gly Ala Ser His Val
        355                 360                 365
Asp Glu Lys Lys Ile Val Lys Pro Thr Thr Val Leu Gly Asp Thr Pro
    370                 375                 380
Met Val Lys Thr Arg Glu Glu Ala Leu Lys Ser Asn Ser Asn Asn
385                 390                 395                 400
Lys Lys Lys Gly Glu Lys Asn Ser Val Pro Ser Val Pro Phe Asn Asp
                405                 410                 415
Trp Ala Ala Val Gln Cys Gln Thr Ser Val Asn Trp Ser Pro Gly Ser
            420                 425                 430
Trp Phe Trp Asn His Phe Ser Gly Gly Leu Ser His Gln Ile Glu His
        435                 440                 445
His Leu Phe Pro Ser Ile Cys His Thr Asn Tyr Cys His Ile Gln Asp
    450                 455                 460
Val Val Glu Ser Thr Cys Ala Glu Tyr Gly Val Pro Tyr Gln Ser Glu
465                 470                 475                 480
Ser Asn Leu Phe Val Ala Tyr Gly Lys Met Ile Ser His Leu Lys Phe
                485                 490                 495
Leu Gly Lys Ala Lys Cys Glu
            500
```

<210> SEQ ID NO 105
<211> LENGTH: 1257
<212> TYPE: DNA
<213> ORGANISM: Thalassiosira pseudonana
<220> FEATURE:
<221> NAME/KEY: CDS
<222> LOCATION: (1)..(1257)
<223> OTHER INFORMATION: omega3-desaturase

<400> SEQUENCE: 105

```
atg tac aga tta aca tcc acc ttc ctc atc gca ttg gca ttc tcc tcc        48
Met Tyr Arg Leu Thr Ser Thr Phe Leu Ile Ala Leu Ala Phe Ser Ser
1               5                   10                  15
```

| | |
|---|---|
| tcc atc aat gcc ttc tct cca caa cgg cca cca cgt act atc acc aaa<br>Ser Ile Asn Ala Phe Ser Pro Gln Arg Pro Pro Arg Thr Ile Thr Lys<br>20              25              30 | 96 |
| agt aaa gtc caa agc acc gtg cta ccc ata ccg acc aag gat gat ctg<br>Ser Lys Val Gln Ser Thr Val Leu Pro Ile Pro Thr Lys Asp Asp Leu<br>35              40              45 | 144 |
| aac ttt ctc caa cca caa ctc gat gag aat gat ctc tac ctc gac gat<br>Asn Phe Leu Gln Pro Gln Leu Asp Glu Asn Asp Leu Tyr Leu Asp Asp<br>50              55              60 | 192 |
| gtc aac act cca cca aga gca ggt acc atc atg aag atg ttg ccg aag<br>Val Asn Thr Pro Pro Arg Ala Gly Thr Ile Met Lys Met Leu Pro Lys<br>65              70              75              80 | 240 |
| gaa acg ttc aac att gat aca gca act tca ttg ggt tac ttt ggt atg<br>Glu Thr Phe Asn Ile Asp Thr Ala Thr Ser Leu Gly Tyr Phe Gly Met<br>85              90              95 | 288 |
| gat atg gca gcg gtt gta tcg tcc atg acg ttg cta aat gct att gta<br>Asp Met Ala Ala Val Val Ser Ser Met Thr Leu Leu Asn Ala Ile Val<br>100              105              110 | 336 |
| act tcg gat cag tac cat gct ctt cca ctt cct ctc caa gca gca aca<br>Thr Ser Asp Gln Tyr His Ala Leu Pro Leu Pro Leu Gln Ala Ala Thr<br>115              120              125 | 384 |
| gtg att ccc ttt cag cta ttg gct ggg ttc gcc atg tgg tgt atg tgg<br>Val Ile Pro Phe Gln Leu Leu Ala Gly Phe Ala Met Trp Cys Met Trp<br>130              135              140 | 432 |
| tgc att gga cac gat gct gga cat tct act gtt tcg aag aca aag tgg<br>Cys Ile Gly His Asp Ala Gly His Ser Thr Val Ser Lys Thr Lys Trp<br>145              150              155              160 | 480 |
| atc aac cga gtc gtt ggt gaa gtg gct cat tct gtt gtt tgt ctc acg<br>Ile Asn Arg Val Val Gly Glu Val Ala His Ser Val Val Cys Leu Thr<br>165              170              175 | 528 |
| ccg ttc gtg cct tgg cag atg tcg cat agg aaa cac cat ttg aat cac<br>Pro Phe Val Pro Trp Gln Met Ser His Arg Lys His His Leu Asn His<br>180              185              190 | 576 |
| aat cat att gaa aag gac tac tct cat aag tgg tac agt cgc gac gag<br>Asn His Ile Glu Lys Asp Tyr Ser His Lys Trp Tyr Ser Arg Asp Glu<br>195              200              205 | 624 |
| ttt gat gat atc cca caa ctc tat aag aca ttt ggc tac aac cca aga<br>Phe Asp Asp Ile Pro Gln Leu Tyr Lys Thr Phe Gly Tyr Asn Pro Arg<br>210              215              220 | 672 |
| atg atg caa ctt cca ttc ctc tac ttc atg tat ctt gca ttg gga att<br>Met Met Gln Leu Pro Phe Leu Tyr Phe Met Tyr Leu Ala Leu Gly Ile<br>225              230              235              240 | 720 |
| cca gat ggt ggg cat gtt gtg ttc tac gga aga atg tgg gaa gga gtg<br>Pro Asp Gly Gly His Val Val Phe Tyr Gly Arg Met Trp Glu Gly Val<br>245              250              255 | 768 |
| tca ttg cag aag aag ttt gat gct gct att tct gtg gcc gta tca tgt<br>Ser Leu Gln Lys Lys Phe Asp Ala Ala Ile Ser Val Ala Val Ser Cys<br>260              265              270 | 816 |
| gca act gct gga tcg ctt tgg atg aat atg ggt aca gca gac ttc acg<br>Ala Thr Ala Gly Ser Leu Trp Met Asn Met Gly Thr Ala Asp Phe Thr<br>275              280              285 | 864 |
| gtg gta tgc atg gtt cct tgg cta gtt cta tcg tgg tgg ctc ttc atg<br>Val Val Cys Met Val Pro Trp Leu Val Leu Ser Trp Trp Leu Phe Met<br>290              295              300 | 912 |
| gta aca tac ctt cag cat cat tca gaa gac gga aag cta tac act gat<br>Val Thr Tyr Leu Gln His His Ser Glu Asp Gly Lys Leu Tyr Thr Asp<br>305              310              315              320 | 960 |
| gaa acg ttt aca ttt gaa aag gga gcc ttc gag acc gtg gat cgt tcg<br>Glu Thr Phe Thr Phe Glu Lys Gly Ala Phe Glu Thr Val Asp Arg Ser<br>325              330              335 | 1008 |

```
tac ggc aag ttg atc aac cga atg tcg cat cac atg atg gac ggt cac    1056
Tyr Gly Lys Leu Ile Asn Arg Met Ser His His Met Met Asp Gly His
            340                 345                 350 gtg gtg cac cac ttg ttc ttt gaa cgt gta cct cac tac aga tta gag    1104
Val Val His His Leu Phe Phe Glu Arg Val Pro His Tyr Arg Leu Glu
355                 360                 365 gca gct acc gaa gct ctt gtg aaa gga atg gat gaa acg gga cag aaa    1152
Ala Ala Thr Glu Ala Leu Val Lys Gly Met Asp Glu Thr Gly Gln Lys
    370                 375                 380 cat ttg tac aaa tac att gat act cct gat ttc aat gcc gag att gtc    1200
His Leu Tyr Lys Tyr Ile Asp Thr Pro Asp Phe Asn Ala Glu Ile Val
385                 390                 395                 400 aac gga ttt cgc gac aat tgg ttc ctt gtt gaa gag gag aac atc aaa    1248
Asn Gly Phe Arg Asp Asn Trp Phe Leu Val Glu Glu Glu Asn Ile Lys
                405                 410                 415 agg gag tag                                                        1257
Arg Glu

<210> SEQ ID NO 106
<211> LENGTH: 418
<212> TYPE: PRT
<213> ORGANISM: Thalassiosira pseudonana

<400> SEQUENCE: 106

Met Tyr Arg Leu Thr Ser Thr Phe Leu Ile Ala Leu Ala Phe Ser Ser
1               5                   10                  15

Ser Ile Asn Ala Phe Ser Pro Gln Arg Pro Arg Thr Ile Thr Lys
            20                  25                  30

Ser Lys Val Gln Ser Thr Val Leu Pro Ile Pro Thr Lys Asp Asp Leu
        35                  40                  45

Asn Phe Leu Gln Pro Gln Leu Asp Glu Asn Asp Leu Tyr Leu Asp Asp
    50                  55                  60

Val Asn Thr Pro Pro Arg Ala Gly Thr Ile Met Lys Met Leu Pro Lys
65                  70                  75                  80

Glu Thr Phe Asn Ile Asp Thr Ala Thr Ser Leu Gly Tyr Phe Gly Met
                85                  90                  95

Asp Met Ala Ala Val Val Ser Ser Met Thr Leu Leu Asn Ala Ile Val
            100                 105                 110

Thr Ser Asp Gln Tyr His Ala Leu Pro Leu Pro Leu Gln Ala Ala Thr
        115                 120                 125

Val Ile Pro Phe Gln Leu Leu Ala Gly Phe Ala Met Trp Cys Met Trp
    130                 135                 140

Cys Ile Gly His Asp Ala Gly His Ser Thr Val Ser Lys Thr Lys Trp
145                 150                 155                 160

Ile Asn Arg Val Val Gly Glu Val Ala His Ser Val Val Cys Leu Thr
                165                 170                 175

Pro Phe Val Pro Trp Gln Met Ser His Arg Lys His His Leu Asn His
            180                 185                 190

Asn His Ile Glu Lys Asp Tyr Ser His Lys Trp Tyr Ser Arg Asp Glu
        195                 200                 205

Phe Asp Asp Ile Pro Gln Leu Tyr Lys Thr Phe Gly Tyr Asn Pro Arg
    210                 215                 220

Met Met Gln Leu Pro Phe Leu Tyr Phe Met Tyr Leu Ala Leu Gly Ile
225                 230                 235                 240

Pro Asp Gly Gly His Val Val Phe Tyr Gly Arg Met Trp Glu Gly Val
                245                 250                 255
```

```
Ser Leu Gln Lys Lys Phe Asp Ala Ala Ile Ser Val Ala Val Ser Cys
            260                 265                 270

Ala Thr Ala Gly Ser Leu Trp Met Asn Met Gly Thr Ala Asp Phe Thr
            275                 280                 285

Val Val Cys Met Val Pro Trp Leu Val Leu Ser Trp Trp Leu Phe Met
290                 295                 300

Val Thr Tyr Leu Gln His His Ser Glu Asp Gly Lys Leu Tyr Thr Asp
305                 310                 315                 320

Glu Thr Phe Thr Phe Glu Lys Gly Ala Phe Glu Thr Val Asp Arg Ser
                325                 330                 335

Tyr Gly Lys Leu Ile Asn Arg Met Ser His His Met Met Asp Gly His
            340                 345                 350

Val Val His His Leu Phe Phe Glu Arg Val Pro His Tyr Arg Leu Glu
            355                 360                 365

Ala Ala Thr Glu Ala Leu Val Lys Gly Met Asp Glu Thr Gly Gln Lys
            370                 375                 380

His Leu Tyr Lys Tyr Ile Asp Thr Pro Asp Phe Asn Ala Glu Ile Val
385                 390                 395                 400

Asn Gly Phe Arg Asp Asn Trp Phe Leu Val Glu Glu Asn Ile Lys
            405                 410                 415

Arg Glu

<210> SEQ ID NO 107
<211> LENGTH: 1086
<212> TYPE: DNA
<213> ORGANISM: Ostreococcus tauri
<220> FEATURE:
<221> NAME/KEY: CDS
<222> LOCATION: (1)..(1086)
<223> OTHER INFORMATION: delta12-desaturase

<400> SEQUENCE: 107 atg cag gag ggg gtg cga aac att ccg aac gag tgc ttt gag acg gga      48
Met Gln Glu Gly Val Arg Asn Ile Pro Asn Glu Cys Phe Glu Thr Gly
1               5                   10                  15 cat ctt gaa aga ccc tgg cgt tcc ggc cgg tgt ggg cgc gat ccc ggt      96
His Leu Glu Arg Pro Trp Arg Ser Gly Arg Cys Gly Arg Asp Pro Gly
                20                  25                  30 tcg aat tgg ggc gct ggc ttc cgc ttt ttt tcg ctc aag ggg ttt tgg     144
Ser Asn Trp Gly Ala Gly Phe Arg Phe Phe Ser Leu Lys Gly Phe Trp
            35                  40                  45 tgg ccg gcg tgg tgg gcg tac gcg ttc gtg acg ggg acg gcg gcc act     192
Trp Pro Ala Trp Trp Ala Tyr Ala Phe Val Thr Gly Thr Ala Ala Thr
        50                  55                  60 ggg tgt tgg gtc gcc gcg cac gag tgc ggg cac ggc gcg ttc agc gat     240
Gly Cys Trp Val Ala Ala His Glu Cys Gly His Gly Ala Phe Ser Asp
65                  70                  75                  80 aac aag acg ttg caa gat gcg gtt gga tac gtg ttg cac tcg ttg ctc     288
Asn Lys Thr Leu Gln Asp Ala Val Gly Tyr Val Leu His Ser Leu Leu
                85                  90                  95 ttg gtg ccg tac ttt tct tgg cag cga tca cac gcg gtg cat cac tcg     336
Leu Val Pro Tyr Phe Ser Trp Gln Arg Ser His Ala Val His His Ser
            100                 105                 110 agg acg aat cac gtt ctt gag ggc gag acg cac gtg ccg gcg cgc ttg     384
Arg Thr Asn His Val Leu Glu Gly Glu Thr His Val Pro Ala Arg Leu
        115                 120                 125 ggg acg gaa gac gcc aac gtc gtg ttc aag ctt cgc gaa ttg atc ggt     432
Gly Thr Glu Asp Ala Asn Val Val Phe Lys Leu Arg Glu Leu Ile Gly
```

```
                  130                 135                 140
gaa ggg ccg ttc acg ttt ttc aac ctc gtc ggc gtc ttc gcg ctc gga        480
Glu Gly Pro Phe Thr Phe Phe Asn Leu Val Gly Val Phe Ala Leu Gly
145                 150                 155                 160 tgg ccg att tac ttg ctc acc ggc gcg agc ggc gga ccg gtg cgc ggt        528
Trp Pro Ile Tyr Leu Leu Thr Gly Ala Ser Gly Gly Pro Val Arg Gly
                165                 170                 175 aac acg aac cac ttc tta ccc ttc atg ggc gag aaa ggt aag cac gcg        576
Asn Thr Asn His Phe Leu Pro Phe Met Gly Glu Lys Gly Lys His Ala
            180                 185                 190 ctg ttc ccg ggt aag tgg gcg aag aag gtg tgg cag tct gac atc ggc        624
Leu Phe Pro Gly Lys Trp Ala Lys Lys Val Trp Gln Ser Asp Ile Gly
        195                 200                 205 gtt gtt gcc gtc ctg ggc gcg ctc gcg gct tgg gcg gcg cac agc ggg        672
Val Val Ala Val Leu Gly Ala Leu Ala Ala Trp Ala Ala His Ser Gly
    210                 215                 220 att gcc aca gtg atg gca ctc tac gtc ggc ccg tac atg gtg acc aac        720
Ile Ala Thr Val Met Ala Leu Tyr Val Gly Pro Tyr Met Val Thr Asn
225                 230                 235                 240 ttt tgg ctc gtc ttg tac acg tgg tta cag cac acc gac gtt gac gtg        768
Phe Trp Leu Val Leu Tyr Thr Trp Leu Gln His Thr Asp Val Asp Val
                245                 250                 255 ccg cac ttc gag ggc gac gat tgg aac ttg gtc aag ggg gca ttc atg        816
Pro His Phe Glu Gly Asp Asp Trp Asn Leu Val Lys Gly Ala Phe Met
            260                 265                 270 acg atc gat cgc ccg tac ggc cca gtt ttt gat ttc ttg cac cac cgc        864
Thr Ile Asp Arg Pro Tyr Gly Pro Val Phe Asp Phe Leu His His Arg
        275                 280                 285 atc ggc agc acg cac gtc gcg cac cac atc aac aca cca ttc ccg cat        912
Ile Gly Ser Thr His Val Ala His His Ile Asn Thr Pro Phe Pro His
    290                 295                 300 tac aag gct caa atg gcg acg gat gcg cta aag gag gcg tat ccc gac        960
Tyr Lys Ala Gln Met Ala Thr Asp Ala Leu Lys Glu Ala Tyr Pro Asp
305                 310                 315                 320 ctc tac ctt tac gat cca act ccg atc gcg acc gct acg tgg cgc gtg       1008
Leu Tyr Leu Tyr Asp Pro Thr Pro Ile Ala Thr Ala Thr Trp Arg Val
                325                 330                 335 ggg agc aag tgc atc gcc gtc gtg aag aag gga gac gaa tgg gtg ttc       1056
Gly Ser Lys Cys Ile Ala Val Val Lys Lys Gly Asp Glu Trp Val Phe
            340                 345                 350 acg gat aag caa ctc ccg gtc gcg gcg tga                               1086
Thr Asp Lys Gln Leu Pro Val Ala Ala
        355                 360

<210> SEQ ID NO 108
<211> LENGTH: 361
<212> TYPE: PRT
<213> ORGANISM: Ostreococcus tauri

<400> SEQUENCE: 108

Met Gln Glu Gly Val Arg Asn Ile Pro Asn Glu Cys Phe Glu Thr Gly
1               5                   10                  15

His Leu Glu Arg Pro Trp Arg Ser Gly Arg Cys Gly Arg Asp Pro Gly
            20                  25                  30

Ser Asn Trp Gly Ala Gly Phe Arg Phe Ser Leu Lys Gly Phe Trp
        35                  40                  45

Trp Pro Ala Trp Trp Ala Tyr Ala Phe Val Thr Gly Thr Ala Ala Thr
    50                  55                  60

Gly Cys Trp Val Ala Ala His Glu Cys Gly His Gly Ala Phe Ser Asp
```

```
                65                  70                  75                  80
            Asn Lys Thr Leu Gln Asp Ala Val Gly Tyr Val Leu His Ser Leu Leu
                            85                  90                  95
            Leu Val Pro Tyr Phe Ser Trp Gln Arg Ser His Ala Val His His Ser
                            100                 105                 110
            Arg Thr Asn His Val Leu Glu Gly Glu Thr His Val Pro Ala Arg Leu
                            115                 120                 125
            Gly Thr Glu Asp Ala Asn Val Val Phe Lys Leu Arg Glu Leu Ile Gly
                130                 135                 140
            Glu Gly Pro Phe Thr Phe Phe Asn Leu Val Gly Val Phe Ala Leu Gly
            145                 150                 155                 160
            Trp Pro Ile Tyr Leu Leu Thr Gly Ala Ser Gly Pro Val Arg Gly
                            165                 170                 175
            Asn Thr Asn His Phe Leu Pro Phe Met Gly Glu Lys Gly Lys His Ala
                            180                 185                 190
            Leu Phe Pro Gly Lys Trp Ala Lys Lys Val Trp Gln Ser Asp Ile Gly
                            195                 200                 205
            Val Val Ala Val Leu Gly Ala Leu Ala Ala Trp Ala Ala His Ser Gly
                210                 215                 220
            Ile Ala Thr Val Met Ala Leu Tyr Val Gly Pro Tyr Met Val Thr Asn
            225                 230                 235                 240
            Phe Trp Leu Val Leu Tyr Thr Trp Leu Gln His Thr Asp Val Asp Val
                            245                 250                 255
            Pro His Phe Glu Gly Asp Asp Trp Asn Leu Val Lys Gly Ala Phe Met
                            260                 265                 270
            Thr Ile Asp Arg Pro Tyr Gly Pro Val Phe Asp Phe Leu His His Arg
                            275                 280                 285
            Ile Gly Ser Thr His Val Ala His His Ile Asn Thr Pro Phe Pro His
                290                 295                 300
            Tyr Lys Ala Gln Met Ala Thr Asp Ala Leu Lys Glu Ala Tyr Pro Asp
            305                 310                 315                 320
            Leu Tyr Leu Tyr Asp Pro Thr Pro Ile Ala Thr Ala Thr Trp Arg Val
                            325                 330                 335
            Gly Ser Lys Cys Ile Ala Val Val Lys Lys Gly Asp Glu Trp Val Phe
                            340                 345                 350
            Thr Asp Lys Gln Leu Pro Val Ala Ala
                            355                 360

<210> SEQ ID NO 109
<211> LENGTH: 1305
<212> TYPE: DNA
<213> ORGANISM: Thalassiosira pseudonana
<220> FEATURE:
<221> NAME/KEY: CDS
<222> LOCATION: (1)..(1305)
<223> OTHER INFORMATION: delta12-desaturase

<400> SEQUENCE: 109 atg gga aag gga gga aga tca gta acc cgc gct caa aca gca gaa aag      48
Met Gly Lys Gly Gly Arg Ser Val Thr Arg Ala Gln Thr Ala Glu Lys
1               5                   10                  15 tca gca cac acc atc caa acc ttc acc gac ggc cga tgg gtc tcc ccc      96
Ser Ala His Thr Ile Gln Thr Phe Thr Asp Gly Arg Trp Val Ser Pro
            20                  25                  30 tac aac ccc ctc gca aaa gat gca cct gaa ctc ccc tcc aag ggt gaa     144
Tyr Asn Pro Leu Ala Lys Asp Ala Pro Glu Leu Pro Ser Lys Gly Glu
        35                  40                  45
```

-continued

| | | |
|---|---|---|
| atc aag gcg gtc atc ccc aaa gag tgc ttc gaa cga agc tac ctc cac<br>Ile Lys Ala Val Ile Pro Lys Glu Cys Phe Glu Arg Ser Tyr Leu His<br>50                      55                      60 | 192 |
| tcc atg tac ttc gtc ctc cgt gac acc gtc atg gcg gtg gcc tgc gcc<br>Ser Met Tyr Phe Val Leu Arg Asp Thr Val Met Ala Val Ala Cys Ala<br>65                     70                   75                   80 | 240 |
| tac atc gcc cac tca acg ctc tcc acc gat att ccc tcc gag tta ctg<br>Tyr Ile Ala His Ser Thr Leu Ser Thr Asp Ile Pro Ser Glu Leu Leu<br>                     85                   90                   95 | 288 |
| agc gtg gac gca ctc aaa tgg ttc ctc gga tgg aac acc tac gcc ttt<br>Ser Val Asp Ala Leu Lys Trp Phe Leu Gly Trp Asn Thr Tyr Ala Phe<br>          100                 105                 110 | 336 |
| tgg atg ggg tgc att ctc acc gga cac tgg gtc cta gcc cat gaa tgt<br>Trp Met Gly Cys Ile Leu Thr Gly His Trp Val Leu Ala His Glu Cys<br>          115                 120                 125 | 384 |
| gga cat ggt gca ttc tct ccc tct cag acg ttt aat gac ttt tgg ggg<br>Gly His Gly Ala Phe Ser Pro Ser Gln Thr Phe Asn Asp Phe Trp Gly<br>          130                 135                 140 | 432 |
| ttc att atg cat cag gcg gtg ttg gtt ccg tat ttc gcc tgg cag tac<br>Phe Ile Met His Gln Ala Val Leu Val Pro Tyr Phe Ala Trp Gln Tyr<br>145                     150                 155                 160 | 480 |
| tct cat gcg aag cat cat cga cgt acc aac aac att atg gat ggg gag<br>Ser His Ala Lys His His Arg Arg Thr Asn Asn Ile Met Asp Gly Glu<br>                    165                 170                 175 | 528 |
| agc cat gtg ccc aat atc gcc aag gaa atg gga ttg aac gag aag aat<br>Ser His Val Pro Asn Ile Ala Lys Glu Met Gly Leu Asn Glu Lys Asn<br>          180                 185                 190 | 576 |
| gag cgc agt gga gga tat gcc gcc att cat gag gct att gga gat gga<br>Glu Arg Ser Gly Gly Tyr Ala Ala Ile His Glu Ala Ile Gly Asp Gly<br>          195                 200                 205 | 624 |
| ccc ttt gcg atg ttt caa atc ttt gct cac ttg gtg atc ggg tgg cct<br>Pro Phe Ala Met Phe Gln Ile Phe Ala His Leu Val Ile Gly Trp Pro<br>          210                 215                 220 | 672 |
| att tac ttg atg gga ttt gct tcc act gga cgt ctc ggt cag gat ggg<br>Ile Tyr Leu Met Gly Phe Ala Ser Thr Gly Arg Leu Gly Gln Asp Gly<br>225                     230                 235                 240 | 720 |
| aag gaa ctt cag gct gga gag atc atc gac cat tac cgt cct tgg agt<br>Lys Glu Leu Gln Ala Gly Glu Ile Ile Asp His Tyr Arg Pro Trp Ser<br>          245                 250                 255 | 768 |
| aag atg ttc ccc acc aag ttg cga ttc aaa att gct ctt tcg aca ctt<br>Lys Met Phe Pro Thr Lys Leu Arg Phe Lys Ile Ala Leu Ser Thr Leu<br>          260                 265                 270 | 816 |
| gga gtg att gcc gcc tgg gtt ggg ttg tac ttt gct gca caa gag tat<br>Gly Val Ile Ala Ala Trp Val Gly Leu Tyr Phe Ala Ala Gln Glu Tyr<br>          275                 280                 285 | 864 |
| gga gtc ttg ccc gtg gtt ctt tgg tac att ggc cca ctc atg tgg aat<br>Gly Val Leu Pro Val Val Leu Trp Tyr Ile Gly Pro Leu Met Trp Asn<br>          290                 295                 300 | 912 |
| cag gcg tgg ctt gtg ctc tac act tgg ctt cag cac aat gat ccc tcc<br>Gln Ala Trp Leu Val Leu Tyr Thr Trp Leu Gln His Asn Asp Pro Ser<br>305                     310                 315                 320 | 960 |
| gtg cct caa tat gga agt gac gaa tgg aca tgg gtc aag gga gct ttg<br>Val Pro Gln Tyr Gly Ser Asp Glu Trp Thr Trp Val Lys Gly Ala Leu<br>          325                 330                 335 | 1008 |
| tcg acg att gat cgc ccg tat ggt atc ttt gac ttc ttc cat cac aag<br>Ser Thr Ile Asp Arg Pro Tyr Gly Ile Phe Asp Phe Phe His His Lys<br>          340                 345                 350 | 1056 |
| att gga agc act cac gta gct cat cat ttg ttc cac gag atg cca ttt<br>Ile Gly Ser Thr His Val Ala His His Leu Phe His Glu Met Pro Phe | 1104 |

```
                355                 360                 365
tac aag gcg gat gtg gct act gcg tcg atc aag ggt ttc ttg gag ccg    1152
Tyr Lys Ala Asp Val Ala Thr Ala Ser Ile Lys Gly Phe Leu Glu Pro
        370                 375                 380 aag gga ctt tac aac tat gat cca acg cct tgg tat gtg gcc atg tgg    1200
Lys Gly Leu Tyr Asn Tyr Asp Pro Thr Pro Trp Tyr Val Ala Met Trp
385                 390                 395                 400 agg gtg gcc aag act tgt cat tat att gag gat gtg gat gga gtt cag    1248
Arg Val Ala Lys Thr Cys His Tyr Ile Glu Asp Val Asp Gly Val Gln
                405                 410                 415 tat tat aag agt ttg gag gat gtg cct ttg aag aag gat gcc aag aag    1296
Tyr Tyr Lys Ser Leu Glu Asp Val Pro Leu Lys Lys Asp Ala Lys Lys
            420                 425                 430 tct gat tag                                                        1305
Ser Asp

<210> SEQ ID NO 110
<211> LENGTH: 434
<212> TYPE: PRT
<213> ORGANISM: Thalassiosira pseudonana

<400> SEQUENCE: 110

Met Gly Lys Gly Gly Arg Ser Val Thr Arg Ala Gln Thr Ala Glu Lys
1               5                   10                  15

Ser Ala His Thr Ile Gln Thr Phe Thr Asp Gly Arg Trp Val Ser Pro
            20                  25                  30

Tyr Asn Pro Leu Ala Lys Asp Ala Pro Glu Leu Pro Ser Lys Gly Glu
        35                  40                  45

Ile Lys Ala Val Ile Pro Lys Glu Cys Phe Glu Arg Ser Tyr Leu His
    50                  55                  60

Ser Met Tyr Phe Val Leu Arg Asp Thr Val Met Ala Val Ala Cys Ala
65                  70                  75                  80

Tyr Ile Ala His Ser Thr Leu Ser Thr Asp Ile Pro Ser Glu Leu Leu
                85                  90                  95

Ser Val Asp Ala Leu Lys Trp Phe Leu Gly Trp Asn Thr Tyr Ala Phe
            100                 105                 110

Trp Met Gly Cys Ile Leu Thr Gly His Trp Val Leu Ala His Glu Cys
        115                 120                 125

Gly His Gly Ala Phe Ser Pro Ser Gln Thr Phe Asn Asp Phe Trp Gly
    130                 135                 140

Phe Ile Met His Gln Ala Val Leu Val Pro Tyr Phe Ala Trp Gln Tyr
145                 150                 155                 160

Ser His Ala Lys His His Arg Arg Thr Asn Asn Ile Met Asp Gly Glu
                165                 170                 175

Ser His Val Pro Asn Ile Ala Lys Glu Met Gly Leu Asn Glu Lys Asn
            180                 185                 190

Glu Arg Ser Gly Gly Tyr Ala Ala Ile His Glu Ala Ile Gly Asp Gly
        195                 200                 205

Pro Phe Ala Met Phe Gln Ile Phe Ala His Leu Val Ile Gly Trp Pro
    210                 215                 220

Ile Tyr Leu Met Gly Phe Ala Ser Thr Gly Arg Leu Gly Gln Asp Gly
225                 230                 235                 240

Lys Glu Leu Gln Ala Gly Glu Ile Ile Asp His Tyr Arg Pro Trp Ser
                245                 250                 255

Lys Met Phe Pro Thr Lys Leu Arg Phe Lys Ile Ala Leu Ser Thr Leu
            260                 265                 270
```

```
Gly Val Ile Ala Ala Trp Val Gly Leu Tyr Phe Ala Ala Gln Glu Tyr
            275                 280                 285

Gly Val Leu Pro Val Val Leu Trp Tyr Ile Gly Pro Leu Met Trp Asn
290                 295                 300

Gln Ala Trp Leu Val Leu Tyr Thr Trp Leu Gln His Asn Asp Pro Ser
305                 310                 315                 320

Val Pro Gln Tyr Gly Ser Asp Glu Trp Thr Trp Val Lys Gly Ala Leu
                325                 330                 335

Ser Thr Ile Asp Arg Pro Tyr Gly Ile Phe Asp Phe His His Lys
            340                 345                 350

Ile Gly Ser Thr His Val Ala His His Leu Phe His Glu Met Pro Phe
            355                 360                 365

Tyr Lys Ala Asp Val Ala Thr Ala Ser Ile Lys Gly Phe Leu Glu Pro
    370                 375                 380

Lys Gly Leu Tyr Asn Tyr Asp Pro Thr Pro Trp Tyr Val Ala Met Trp
385                 390                 395                 400

Arg Val Ala Lys Thr Cys His Tyr Ile Glu Asp Val Asp Gly Val Gln
                405                 410                 415

Tyr Tyr Lys Ser Leu Glu Asp Val Pro Leu Lys Lys Asp Ala Lys Lys
            420                 425                 430

Ser Asp

<210> SEQ ID NO 111
<211> LENGTH: 879
<212> TYPE: DNA
<213> ORGANISM: Ostreococcus tauri
<220> FEATURE:
<221> NAME/KEY: CDS
<222> LOCATION: (1)..(879)
<223> OTHER INFORMATION: delta6-elongase

<400> SEQUENCE: 111 atg agt ggc tta cgt gca ccc aac ttt tta cac aga ttc tgg aca aag      48
Met Ser Gly Leu Arg Ala Pro Asn Phe Leu His Arg Phe Trp Thr Lys
1               5                   10                  15 tgg gac tac gcg att tcc aaa gtc gtc ttc acg tgt gcc gac agt ttt      96
Trp Asp Tyr Ala Ile Ser Lys Val Val Phe Thr Cys Ala Asp Ser Phe
            20                  25                  30 cag tgg gac atc ggg cca gtg agt tcg agt acg gcg cat tta ccc gcc     144
Gln Trp Asp Ile Gly Pro Val Ser Ser Ser Thr Ala His Leu Pro Ala
        35                  40                  45 att gaa tcc cct acc cca ctg gtg act agc ctc ttg ttc tac tta gtc     192
Ile Glu Ser Pro Thr Pro Leu Val Thr Ser Leu Leu Phe Tyr Leu Val
    50                  55                  60 aca gtt ttc ttg tgg tat ggt cgt tta acc agg agt tca gac aag aaa     240
Thr Val Phe Leu Trp Tyr Gly Arg Leu Thr Arg Ser Ser Asp Lys Lys
65                  70                  75                  80 att aga gag cct acg tgg tta aga aga ttc ata ata tgt cat aat gcg     288
Ile Arg Glu Pro Thr Trp Leu Arg Arg Phe Ile Ile Cys His Asn Ala
                85                  90                  95 ttc ttg ata gtc ctc agt ctt tac atg tgc ctt ggt tgt gtg gcc caa     336
Phe Leu Ile Val Leu Ser Leu Tyr Met Cys Leu Gly Cys Val Ala Gln
            100                 105                 110 gcg tat cag aat gga tat act tta tgg ggt aat gaa ttc aag gcc acg     384
Ala Tyr Gln Asn Gly Tyr Thr Leu Trp Gly Asn Glu Phe Lys Ala Thr
        115                 120                 125 gaa act cag ctt gct ctc tac att tac att ttt tac gta agt aaa ata     432
Glu Thr Gln Leu Ala Leu Tyr Ile Tyr Ile Phe Tyr Val Ser Lys Ile
```

```
            130                 135                 140
tac gag ttt gta gat act tac att atg ctt ctc aag aat aac ttg cgg      480
Tyr Glu Phe Val Asp Thr Tyr Ile Met Leu Leu Lys Asn Asn Leu Arg
145                 150                 155                 160 caa gta agt ttc cta cac att tat cac cac agc acg att tcc ttt att      528
Gln Val Ser Phe Leu His Ile Tyr His His Ser Thr Ile Ser Phe Ile
                165                 170                 175 tgg tgg atc att gct cgg agg gct ccg ggt ggt gat gct tac ttc agc      576
Trp Trp Ile Ile Ala Arg Arg Ala Pro Gly Gly Asp Ala Tyr Phe Ser
            180                 185                 190 gcg gcc ttg aac tca tgg gta cac gtg tgc atg tac acc tat tat cta      624
Ala Ala Leu Asn Ser Trp Val His Val Cys Met Tyr Thr Tyr Tyr Leu
        195                 200                 205 tta tca acc ctt att gga aaa gaa gat cct aag cgt tcc aac tac ctt      672
Leu Ser Thr Leu Ile Gly Lys Glu Asp Pro Lys Arg Ser Asn Tyr Leu
    210                 215                 220 tgg tgg ggt cgc cac cta acg caa atg cag atg ctt cag ttt ttc ttc      720
Trp Trp Gly Arg His Leu Thr Gln Met Gln Met Leu Gln Phe Phe Phe
225                 230                 235                 240 aac gta ctt caa gcg ttg tac tgc gct tcg ttc tct acg tat ccc aag      768
Asn Val Leu Gln Ala Leu Tyr Cys Ala Ser Phe Ser Thr Tyr Pro Lys
                245                 250                 255 ttt ttg tcc aaa att ctg ctc gtc tat atg atg agc ctt ctc ggc ttg      816
Phe Leu Ser Lys Ile Leu Leu Val Tyr Met Met Ser Leu Leu Gly Leu
            260                 265                 270 ttt ggg cat ttc tac tat tcc aag cac ata gca gca gct aag ctc cag      864
Phe Gly His Phe Tyr Tyr Ser Lys His Ile Ala Ala Ala Lys Leu Gln
        275                 280                 285 aaa aaa cag cag tga                                                   879
Lys Lys Gln Gln
    290

<210> SEQ ID NO 112
<211> LENGTH: 292
<212> TYPE: PRT
<213> ORGANISM: Ostreococcus tauri

<400> SEQUENCE: 112

Met Ser Gly Leu Arg Ala Pro Asn Phe Leu His Arg Phe Trp Thr Lys
1               5                   10                  15

Trp Asp Tyr Ala Ile Ser Lys Val Val Phe Thr Cys Ala Asp Ser Phe
            20                  25                  30

Gln Trp Asp Ile Gly Pro Val Ser Ser Thr Ala His Leu Pro Ala
        35                  40                  45

Ile Glu Ser Pro Thr Pro Leu Val Thr Ser Leu Leu Phe Tyr Leu Val
    50                  55                  60

Thr Val Phe Leu Trp Tyr Gly Arg Leu Thr Arg Ser Ser Asp Lys Lys
65                  70                  75                  80

Ile Arg Glu Pro Thr Trp Leu Arg Arg Phe Ile Ile Cys His Asn Ala
                85                  90                  95

Phe Leu Ile Val Leu Ser Leu Tyr Met Cys Leu Gly Cys Val Ala Gln
            100                 105                 110

Ala Tyr Gln Asn Gly Tyr Thr Leu Trp Gly Asn Glu Phe Lys Ala Thr
        115                 120                 125

Glu Thr Gln Leu Ala Leu Tyr Ile Tyr Ile Phe Tyr Val Ser Lys Ile
    130                 135                 140

Tyr Glu Phe Val Asp Thr Tyr Ile Met Leu Leu Lys Asn Asn Leu Arg
145                 150                 155                 160
```

```
Gln Val Ser Phe Leu His Ile Tyr His His Ser Thr Ile Ser Phe Ile
                165                 170                 175

Trp Trp Ile Ile Ala Arg Arg Ala Pro Gly Gly Asp Ala Tyr Phe Ser
            180                 185                 190

Ala Ala Leu Asn Ser Trp Val His Val Cys Met Tyr Thr Tyr Tyr Leu
        195                 200                 205

Leu Ser Thr Leu Ile Gly Lys Glu Asp Pro Lys Arg Ser Asn Tyr Leu
    210                 215                 220

Trp Trp Gly Arg His Leu Thr Gln Met Gln Met Leu Gln Phe Phe Phe
225                 230                 235                 240

Asn Val Leu Gln Ala Leu Tyr Cys Ala Ser Phe Ser Thr Tyr Pro Lys
                245                 250                 255

Phe Leu Ser Lys Ile Leu Leu Val Tyr Met Met Ser Leu Leu Gly Leu
            260                 265                 270

Phe Gly His Phe Tyr Tyr Ser Lys His Ile Ala Ala Ala Lys Leu Gln
        275                 280                 285

Lys Lys Gln Gln
    290

<210> SEQ ID NO 113
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta5-elongase

<400> SEQUENCE: 113 atg agc gcc tcc ggt gcg ctg ctg ccc gcg atc gcg ttc gcc gcg tac      48
Met Ser Ala Ser Gly Ala Leu Leu Pro Ala Ile Ala Phe Ala Ala Tyr
1               5                   10                  15 gcg tac gcg acg tac gcc tac gcc ttt gag tgg tcg cac gcg aat ggc      96
Ala Tyr Ala Thr Tyr Ala Tyr Ala Phe Glu Trp Ser His Ala Asn Gly
                20                  25                  30 atc gac aac gtc gac gcg cgc gag tgg atc ggt gcg ctg tcg ttg agg     144
Ile Asp Asn Val Asp Ala Arg Glu Trp Ile Gly Ala Leu Ser Leu Arg
            35                  40                  45 ctc ccg gcg atc gcg acg acg atg tac ctg ttg ttc tgc ctg gtc gga     192
Leu Pro Ala Ile Ala Thr Thr Met Tyr Leu Leu Phe Cys Leu Val Gly
        50                  55                  60 ccg agg ttg atg gcg aag cgc gag gcg ttc gac ccg aag ggg ttc atg     240
Pro Arg Leu Met Ala Lys Arg Glu Ala Phe Asp Pro Lys Gly Phe Met
65                  70                  75                  80 ctg gcg tac aat gcg tat cag acg gcg ttc aac gtc gtc gtg ctc ggg     288
Leu Ala Tyr Asn Ala Tyr Gln Thr Ala Phe Asn Val Val Val Leu Gly
                85                  90                  95 atg ttc gcg cga gag atc tcg ggg ctg ggg cag ccc gtg tgg ggg tca     336
Met Phe Ala Arg Glu Ile Ser Gly Leu Gly Gln Pro Val Trp Gly Ser
                100                 105                 110 acc atg ccg tgg agc gat aga aaa tcg ttt aag atc ctc ctc ggg gtg     384
Thr Met Pro Trp Ser Asp Arg Lys Ser Phe Lys Ile Leu Leu Gly Val
            115                 120                 125 tgg ttg cac tac aac aac aaa tat ttg gag cta ttg gac act gtg ttc     432
Trp Leu His Tyr Asn Asn Lys Tyr Leu Glu Leu Leu Asp Thr Val Phe
        130                 135                 140 atg gtt gcg cgc aag aag acg aag cag ttg agc ttc ttg cac gtt tat     480
Met Val Ala Arg Lys Lys Thr Lys Gln Leu Ser Phe Leu His Val Tyr
145                 150                 155                 160
```

```
cat cac gcc ctg ttg atc tgg gcg tgg tgg ttg gtg tgt cac ttg atg       528
His His Ala Leu Leu Ile Trp Ala Trp Trp Leu Val Cys His Leu Met
                165                 170                 175 gcc acg aac gat tgt atc gat gcc tac ttc ggc gcg gcg tgc aac tcg       576
Ala Thr Asn Asp Cys Ile Asp Ala Tyr Phe Gly Ala Ala Cys Asn Ser
            180                 185                 190 ttc att cac atc gtg atg tac tcg tat tat ctc atg tcg gcg ctc ggc       624
Phe Ile His Ile Val Met Tyr Ser Tyr Tyr Leu Met Ser Ala Leu Gly
        195                 200                 205 att cga tgc ccg tgg aag cga tac atc acc cag gct caa atg ctc caa       672
Ile Arg Cys Pro Trp Lys Arg Tyr Ile Thr Gln Ala Gln Met Leu Gln
    210                 215                 220 ttc gtc att gtc ttc gcg cac gcc gtg ttc gtg ctg cgt cag aag cac       720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg       768
Cys Pro Val Thr Leu Pro Trp Ala Gln Met Phe Val Met Thr Asn Met
                245                 250                 255 ctc gtg ctc ttc ggg aac ttc tac ctc aag gcg tac tcg aac aag tcg       816
Leu Val Leu Phe Gly Asn Phe Tyr Leu Lys Ala Tyr Ser Asn Lys Ser
            260                 265                 270 cgc ggc gac ggc gcg agt tcc gtg aaa cca gcc gag acc acg cgc gcg       864
Arg Gly Asp Gly Ala Ser Ser Val Lys Pro Ala Glu Thr Thr Arg Ala
        275                 280                 285 ccc agc gtg cga cgc acg cga tct cga aaa att gac taa                   903
Pro Ser Val Arg Arg Thr Arg Ser Arg Lys Ile Asp
    290                 295                 300

<210> SEQ ID NO 114
<211> LENGTH: 300
<212> TYPE: PRT
<213> ORGANISM: Ostreococcus tauri

<400> SEQUENCE: 114

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
        115                 120                 125

Trp Leu His Tyr Asn Asn Lys Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
```

```
                    180                 185                 190
Phe Ile His Ile Val Met Tyr Ser Tyr Tyr Leu Met Ser Ala Leu Gly
            195                 200                 205
Ile Arg Cys Pro Trp Lys Arg Tyr Ile Thr Gln Ala Gln Met Leu Gln
        210                 215                 220
Phe Val Ile Val Phe Ala His Ala Val Phe Val Leu Arg Gln Lys His
225                 230                 235                 240
Cys Pro Val Thr Leu Pro Trp Ala Gln Met Phe Val Met Thr Asn Met
                245                 250                 255
Leu Val Leu Phe Gly Asn Phe Tyr Leu Lys Ala Tyr Ser Asn Lys Ser
            260                 265                 270
Arg Gly Asp Gly Ala Ser Ser Val Lys Pro Ala Glu Thr Thr Arg Ala
        275                 280                 285
Pro Ser Val Arg Arg Thr Arg Ser Arg Lys Ile Asp
    290                 295                 300

<210> SEQ ID NO 115
<211> LENGTH: 13
<212> TYPE: PRT
<213> ORGANISM: Unknown
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is Ser, Cys, Leu or Gly, preferably is Cys
      or Leu
<220> FEATURE:
<221> NAME/KEY: MISC_FEATURE
<222> LOCATION: (3)..(3)
<223> OTHER INFORMATION: Xaa is Thr, Phe, Ile, Ser, Val, Trp or Gly,
      preferably is Phe or Trp
<220> FEATURE:
<221> NAME/KEY: MISC_FEATURE
<222> LOCATION: (4)..(4)
<223> OTHER INFORMATION: Xaa is Val or Ile
<220> FEATURE:
<221> NAME/KEY: MISC_FEATURE
<222> LOCATION: (6)..(6)
<223> OTHER INFORMATION: Xaa is Val, Ile or Thr, preferably is Val or
      Ile
<220> FEATURE:
<221> NAME/KEY: MISC_FEATURE
<222> LOCATION: (7)..(7)
<223> OTHER INFORMATION: Xaa is Ile, Phe, Val, Leu or Cys, preferably
      is Cys or Val
<220> FEATURE:
<221> NAME/KEY: MISC_FEATURE
<222> LOCATION: (10)..(10)
<223> OTHER INFORMATION: Xaa is Ser, Gly, Tyr, Thr or Ala, preferably
      is Thr or Ser
<220> FEATURE:
<221> NAME/KEY: MISC_FEATURE
<222> LOCATION: (13)..(13)
<223> OTHER INFORMATION: Xaa is Phe, Met, Thr, Leu, Ala or Gly,
      preferably is Leu

<400> SEQUENCE: 115

Asn Xaa Xaa Xaa His Xaa Xaa Met Tyr Xaa Tyr Tyr Xaa
1               5                   10

<210> SEQ ID NO 116
<211> LENGTH: 10
<212> TYPE: PRT
<213> ORGANISM: Unknown
<220> FEATURE:
<223> OTHER INFORMATION: Consensus sequence
<220> FEATURE:
<221> NAME/KEY: MISC_FEATURE
```

```
<222> LOCATION: (3)..(3)
<223> OTHER INFORMATION: Xaa is Ala, Ser or Thr, preferably is Ala or
      Ser, especially preferably is Ala
<220> FEATURE:
<221> NAME/KEY: MISC_FEATURE
<222> LOCATION: (4)..(4)
<223> OTHER INFORMATION: Xaa is Thr, Met, Val, Leu, Ile or Ser,
      preferably is Leu or Thr, especially preferably is Leu
<220> FEATURE:
<221> NAME/KEY: MISC_FEATURE
<222> LOCATION: (5)..(5)
<223> OTHER INFORMATION: Xaa is Val, Thr, Met, Leu or Ile, preferably is
      Ile or Ser, especially preferably is Ile
<220> FEATURE:
<221> NAME/KEY: MISC_FEATURE
<222> LOCATION: (6)..(6)
<223> OTHER INFORMATION: Xaa is Val, Met, Leu, Ile, Ala, Pro, Ser or
      Phe, preferably is Ile or Ser, especially preferably is Ile

<400> SEQUENCE: 116

His His Xaa Xaa Xaa Xaa Trp Ala Trp Trp
1               5                   10

<210> SEQ ID NO 117
<211> LENGTH: 909
<212> TYPE: DNA
<213> ORGANISM: Xenopus laevis
<220> FEATURE:
<221> NAME/KEY: CDS
<222> LOCATION: (1)..(909)
<223> OTHER INFORMATION: delta5-elongase

<400> SEQUENCE: 117 atg gcc ttc aag gag ctc aca tca agg gca gtg ctc ctg tat gat gaa        48
Met Ala Phe Lys Glu Leu Thr Ser Arg Ala Val Leu Leu Tyr Asp Glu
1               5                   10                  15 tgg att aaa gat gct gat cct agg gtt gaa gac tgg cca ctc atg tcc        96
Trp Ile Lys Asp Ala Asp Pro Arg Val Glu Asp Trp Pro Leu Met Ser
            20                  25                  30 tct cct atc cta caa acc atc atc atc ggc gct tac atc tac ttt gtc       144
Ser Pro Ile Leu Gln Thr Ile Ile Ile Gly Ala Tyr Ile Tyr Phe Val
        35                  40                  45 aca tca ttg ggc cca agg atc atg gag aac agg aag ccg ttt gct ctg       192
Thr Ser Leu Gly Pro Arg Ile Met Glu Asn Arg Lys Pro Phe Ala Leu
    50                  55                  60 aag gag atc atg gca tgt tac aac tta ttc atg gtt ctg ttt tct gtg       240
Lys Glu Ile Met Ala Cys Tyr Asn Leu Phe Met Val Leu Phe Ser Val
65                  70                  75                  80 tac atg tgc tat gag ttt ctc atg tcg ggc tgg gct act gga tat tcc       288
Tyr Met Cys Tyr Glu Phe Leu Met Ser Gly Trp Ala Thr Gly Tyr Ser
                85                  90                  95 ttt aga tgt gac att gtt gac tac tct cag tca cct cag gcg tta cgg       336
Phe Arg Cys Asp Ile Val Asp Tyr Ser Gln Ser Pro Gln Ala Leu Arg
            100                 105                 110 atg gcc tgg acc tgc tgg ctc ttc tat ttt tca aag ttc att gaa tta       384
Met Ala Trp Thr Cys Trp Leu Phe Tyr Phe Ser Lys Phe Ile Glu Leu
        115                 120                 125 tta gac act gtt ttc ttt gtg ctg cgt aag aag aac agc cag att aca       432
Leu Asp Thr Val Phe Phe Val Leu Arg Lys Lys Asn Ser Gln Ile Thr
    130                 135                 140 ttc ctg cac gtc tat cac cac tcc att atg cct tgg acg tgg tgg ttt       480
Phe Leu His Val Tyr His His Ser Ile Met Pro Trp Thr Trp Trp Phe
145                 150                 155                 160 gga gtc aaa ttt gct cca ggt ggt ttg ggc aca ttc cat gca ctg gtg       528
Gly Val Lys Phe Ala Pro Gly Gly Leu Gly Thr Phe His Ala Leu Val
                165                 170                 175
```

```
aac tgt gtg gtc cat gtt atc atg tac agc tac tac ggc ctg tca gcc      576
Asn Cys Val Val His Val Ile Met Tyr Ser Tyr Tyr Gly Leu Ser Ala
        180                 185                 190 ttg ggg cct gcc tac cag aag tac ctg tgg tgg aaa aag tac atg acg      624
Leu Gly Pro Ala Tyr Gln Lys Tyr Leu Trp Trp Lys Lys Tyr Met Thr
        195                 200                 205 tct atc caa ctg acc cag ttc ttg atg gtt act ttt cac atc ggc cag      672
Ser Ile Gln Leu Thr Gln Phe Leu Met Val Thr Phe His Ile Gly Gln
210                 215                 220 ttc ttc ttc atg gag aat tgc ccg tac cag tat ccc gtc ttc ttg tat      720
Phe Phe Phe Met Glu Asn Cys Pro Tyr Gln Tyr Pro Val Phe Leu Tyr
225                 230                 235                 240 gtc att tgg ctg tac ggg ttc gtt ttc tta atc ttg ttc ctc aac ttc      768
Val Ile Trp Leu Tyr Gly Phe Val Phe Leu Ile Leu Phe Leu Asn Phe
                245                 250                 255 tgg ttc cac gct tac atc aaa gga cag agg ctg ccg aaa gcc gtc caa      816
Trp Phe His Ala Tyr Ile Lys Gly Gln Arg Leu Pro Lys Ala Val Gln
            260                 265                 270 aat ggc cac tgc aag aac aac aac aac caa gaa aac act tgg tgc aag      864
Asn Gly His Cys Lys Asn Asn Asn Asn Gln Glu Asn Thr Trp Cys Lys
        275                 280                 285 aac aaa aac cag aaa aac ggt gca ttg aaa agc aaa aac cat tga          909
Asn Lys Asn Gln Lys Asn Gly Ala Leu Lys Ser Lys Asn His
290                 295                 300

<210> SEQ ID NO 118
<211> LENGTH: 302
<212> TYPE: PRT
<213> ORGANISM: Xenopus laevis

<400> SEQUENCE: 118

Met Ala Phe Lys Glu Leu Thr Ser Arg Ala Val Leu Leu Tyr Asp Glu
1               5                   10                  15

Trp Ile Lys Asp Ala Asp Pro Arg Val Glu Asp Trp Pro Leu Met Ser
            20                  25                  30

Ser Pro Ile Leu Gln Thr Ile Ile Gly Ala Tyr Ile Tyr Phe Val
        35                  40                  45

Thr Ser Leu Gly Pro Arg Ile Met Glu Asn Arg Lys Pro Phe Ala Leu
    50                  55                  60

Lys Glu Ile Met Ala Cys Tyr Asn Leu Phe Met Val Leu Phe Ser Val
65                  70                  75                  80

Tyr Met Cys Tyr Glu Phe Leu Met Ser Gly Trp Ala Thr Gly Tyr Ser
                85                  90                  95

Phe Arg Cys Asp Ile Val Asp Tyr Ser Gln Ser Pro Gln Ala Leu Arg
            100                 105                 110

Met Ala Trp Thr Cys Trp Leu Phe Tyr Phe Ser Lys Phe Ile Glu Leu
        115                 120                 125

Leu Asp Thr Val Phe Phe Val Leu Arg Lys Lys Asn Ser Gln Ile Thr
    130                 135                 140

Phe Leu His Val Tyr His His Ser Ile Met Pro Trp Thr Trp Trp Phe
145                 150                 155                 160

Gly Val Lys Phe Ala Pro Gly Gly Leu Gly Thr Phe His Ala Leu Val
                165                 170                 175

Asn Cys Val Val His Val Ile Met Tyr Ser Tyr Tyr Gly Leu Ser Ala
            180                 185                 190

Leu Gly Pro Ala Tyr Gln Lys Tyr Leu Trp Trp Lys Lys Tyr Met Thr
        195                 200                 205
```

```
Ser Ile Gln Leu Thr Gln Phe Leu Met Val Thr Phe His Ile Gly Gln
    210                 215                 220

Phe Phe Phe Met Glu Asn Cys Pro Tyr Gln Tyr Pro Val Phe Leu Tyr
225                 230                 235                 240

Val Ile Trp Leu Tyr Gly Phe Val Phe Leu Ile Leu Phe Leu Asn Phe
                245                 250                 255

Trp Phe His Ala Tyr Ile Lys Gly Gln Arg Leu Pro Lys Ala Val Gln
            260                 265                 270

Asn Gly His Cys Lys Asn Asn Asn Gln Glu Asn Thr Trp Cys Lys
        275                 280                 285

Asn Lys Asn Gln Lys Asn Gly Ala Leu Lys Ser Lys Asn His
    290                 295                 300

<210> SEQ ID NO 119
<211> LENGTH: 870
<212> TYPE: DNA
<213> ORGANISM: Ciona intestinalis
<220> FEATURE:
<221> NAME/KEY: CDS
<222> LOCATION: (1)..(870)
<223> OTHER INFORMATION: delta5-elongase

<400> SEQUENCE: 119 atg gac gta ctt cat cgt ttc tta gga ttc tac gaa tgg acg ctg act      48
Met Asp Val Leu His Arg Phe Leu Gly Phe Tyr Glu Trp Thr Leu Thr
1               5                   10                  15 ttc gcg gac ccc cga gtg gca aaa tgg cct tta ata gaa aac ccc ctt      96
Phe Ala Asp Pro Arg Val Ala Lys Trp Pro Leu Ile Glu Asn Pro Leu
                20                  25                  30 cct aca att gct att gtg ttg ctg tac ctg gcg ttt gtt ctg tat att     144
Pro Thr Ile Ala Ile Val Leu Leu Tyr Leu Ala Phe Val Leu Tyr Ile
            35                  40                  45 ggg ccg cgt ttt atg cga aaa aga gca cca gtt gac ttt ggt tta ttc     192
Gly Pro Arg Phe Met Arg Lys Arg Ala Pro Val Asp Phe Gly Leu Phe
        50                  55                  60 ctc cct gga tat aac ttt gct ttg gtt gca tta aat tat tat atc ctg     240
Leu Pro Gly Tyr Asn Phe Ala Leu Val Ala Leu Asn Tyr Tyr Ile Leu
65                  70                  75                  80 caa gaa gtg gtc act ggg agt tat ggg gct ggg tat gat ttg gtt tgc     288
Gln Glu Val Val Thr Gly Ser Tyr Gly Ala Gly Tyr Asp Leu Val Cys
                85                  90                  95 aca cca ctt cga agt gat tcc tac gat ccc aat gaa atg aag gtt gca     336
Thr Pro Leu Arg Ser Asp Ser Tyr Asp Pro Asn Glu Met Lys Val Ala
            100                 105                 110 aac gct gta tgg tgg tat tat gta tcc aag ata ata gag ttg ttt gat     384
Asn Ala Val Trp Trp Tyr Tyr Val Ser Lys Ile Ile Glu Leu Phe Asp
        115                 120                 125 act gtg ttg ttc act cta cgc aaa cga gac cga caa gta act ttc ctt     432
Thr Val Leu Phe Thr Leu Arg Lys Arg Asp Arg Gln Val Thr Phe Leu
    130                 135                 140 cat gtt tat cac cat tct acc atg ccc ctg ttg tgg tgg att ggg gca     480
His Val Tyr His His Ser Thr Met Pro Leu Leu Trp Trp Ile Gly Ala
145                 150                 155                 160 aag tgg gtg cct ggt ggg caa tca ttt gtt ggc atc ata ctg aac tcc     528
Lys Trp Val Pro Gly Gly Gln Ser Phe Val Gly Ile Ile Leu Asn Ser
                165                 170                 175 agt gtt cat gtt atc atg tat acg tac tat gga ttg tca gcc ttg ggg     576
Ser Val His Val Ile Met Tyr Thr Tyr Tyr Gly Leu Ser Ala Leu Gly
            180                 185                 190
```

| | | |
|---|---|---|
| cct cac atg cag aag ttt cta tgg tgg aag aaa tat atc aca atg ttg<br>Pro His Met Gln Lys Phe Leu Trp Trp Lys Lys Tyr Ile Thr Met Leu<br>        195                    200                  205 | | 624 |
| caa ctg gtt caa ttt gtt ctt gcc atc tac cat act gct cga tca ttg<br>Gln Leu Val Gln Phe Val Leu Ala Ile Tyr His Thr Ala Arg Ser Leu<br>210                    215                    220 | | 672 |
| tac gtt aaa tgt ccc tcg cct gtt tgg atg cac tgg gca ctt atc ttg<br>Tyr Val Lys Cys Pro Ser Pro Val Trp Met His Trp Ala Leu Ile Leu<br>225                    230                    235                  240 | | 720 |
| tac gct ttc tca ttc att ttg ctt ttc tca aac ttc tac atg cat gcc<br>Tyr Ala Phe Ser Phe Ile Leu Leu Phe Ser Asn Phe Tyr Met His Ala<br>                245                    250                  255 | | 768 |
| tat atc aag aaa tca aga aaa ggg aaa gag aat ggc agt cga gga aaa<br>Tyr Ile Lys Lys Ser Arg Lys Gly Lys Glu Asn Gly Ser Arg Gly Lys<br>        260                    265                    270 | | 816 |
| ggt ggt gta agt aat gga aag gaa aag ctg cac gct aat ggt aaa acc<br>Gly Gly Val Ser Asn Gly Lys Glu Lys Leu His Ala Asn Gly Lys Thr<br>                275                    280                  285 | | 864 |
| gat taa<br>Asp | | 870 |

<210> SEQ ID NO 120
<211> LENGTH: 289
<212> TYPE: PRT
<213> ORGANISM: Ciona intestinalis

<400> SEQUENCE: 120

Met Asp Val Leu His Arg Phe Leu Gly Phe Tyr Glu Trp Thr Leu Thr
1               5                   10                  15

Phe Ala Asp Pro Arg Val Ala Lys Trp Pro Leu Ile Glu Asn Pro Leu
            20                  25                  30

Pro Thr Ile Ala Ile Val Leu Leu Tyr Leu Ala Phe Val Leu Tyr Ile
        35                  40                  45

Gly Pro Arg Phe Met Arg Lys Arg Ala Pro Val Asp Phe Gly Leu Phe
    50                  55                  60

Leu Pro Gly Tyr Asn Phe Ala Leu Val Ala Leu Asn Tyr Tyr Ile Leu
65                  70                  75                  80

Gln Glu Val Val Thr Gly Ser Tyr Gly Ala Gly Tyr Asp Leu Val Cys
                85                  90                  95

Thr Pro Leu Arg Ser Asp Ser Tyr Asp Pro Asn Glu Met Lys Val Ala
            100                 105                 110

Asn Ala Val Trp Trp Tyr Tyr Val Ser Lys Ile Ile Glu Leu Phe Asp
        115                 120                 125

Thr Val Leu Phe Thr Leu Arg Lys Arg Asp Arg Gln Val Thr Phe Leu
    130                 135                 140

His Val Tyr His His Ser Thr Met Pro Leu Leu Trp Trp Ile Gly Ala
145                 150                 155                 160

Lys Trp Val Pro Gly Gly Gln Ser Phe Val Gly Ile Ile Leu Asn Ser
                165                 170                 175

Ser Val His Val Ile Met Tyr Thr Tyr Tyr Gly Leu Ser Ala Leu Gly
            180                 185                 190

Pro His Met Gln Lys Phe Leu Trp Trp Lys Lys Tyr Ile Thr Met Leu
        195                 200                 205

Gln Leu Val Gln Phe Val Leu Ala Ile Tyr His Thr Ala Arg Ser Leu
    210                 215                 220

Tyr Val Lys Cys Pro Ser Pro Val Trp Met His Trp Ala Leu Ile Leu
225                 230                 235                 240

-continued

```
            Tyr Ala Phe Ser Phe Ile Leu Leu Phe Ser Asn Phe Tyr Met His Ala
                            245                 250                 255

Tyr Ile Lys Lys Ser Arg Lys Gly Lys Glu Asn Gly Ser Arg Gly Lys
                        260                 265                 270

Gly Gly Val Ser Asn Gly Lys Glu Lys Leu His Ala Asn Gly Lys Thr
                    275                 280                 285

Asp

<210> SEQ ID NO 121
<211> LENGTH: 30
<212> TYPE: DNA
<213> ORGANISM: Unknown
<220> FEATURE:
<221> NAME/KEY: misc_feature
<222> LOCATION: (1)..(30)
<223> OTHER INFORMATION: Primer

<400> SEQUENCE: 121
aggatccatg gccttcaagg agctcacatc                                        30

<210> SEQ ID NO 122
<211> LENGTH: 35
<212> TYPE: DNA
<213> ORGANISM: Unknown
<220> FEATURE:
<221> NAME/KEY: misc_feature
<222> LOCATION: (1)..(35)
<223> OTHER INFORMATION: Primer

<400> SEQUENCE: 122
cctcgagtca atggttttg cttttcaatg caccg                                   35

<210> SEQ ID NO 123
<211> LENGTH: 25
<212> TYPE: DNA
<213> ORGANISM: Unknown
<220> FEATURE:
<221> NAME/KEY: misc_feature
<222> LOCATION: (1)..(25)
<223> OTHER INFORMATION: Primer

<400> SEQUENCE: 123
taagcttatg gacgtacttc atcgt                                             25

<210> SEQ ID NO 124
<211> LENGTH: 26
<212> TYPE: DNA
<213> ORGANISM: Unknown
<220> FEATURE:
<221> NAME/KEY: misc_feature
<222> LOCATION: (1)..(26)
<223> OTHER INFORMATION: Primer

<400> SEQUENCE: 124
tcagatcttt aatcggtttt accatt                                            26

<210> SEQ ID NO 125
<211> LENGTH: 34
<212> TYPE: DNA
<213> ORGANISM: Unknown
<220> FEATURE:
<221> NAME/KEY: misc_feature
<222> LOCATION: (1)..(34)
<223> OTHER INFORMATION: Primer

<400> SEQUENCE: 125
```
gcggccgcac catggccttc aaggagctca catc                    34

<210> SEQ ID NO 126
<211> LENGTH: 38
<212> TYPE: DNA
<213> ORGANISM: Unknown
<220> FEATURE:
<221> NAME/KEY: misc_feature
<222> LOCATION: (1)..(38)
<223> OTHER INFORMATION: Primer

<400> SEQUENCE: 126
gcggccgcct tcaatggttt ttgcttttca atgcaccg                38

<210> SEQ ID NO 127
<211> LENGTH: 29
<212> TYPE: DNA
<213> ORGANISM: Unknown
<220> FEATURE:
<221> NAME/KEY: misc_feature
<222> LOCATION: (1)..(29)
<223> OTHER INFORMATION: Primer

<400> SEQUENCE: 127
gcggccgcac catggacgta cttcatcgt                          29

<210> SEQ ID NO 128
<211> LENGTH: 27
<212> TYPE: DNA
<213> ORGANISM: Unknown
<220> FEATURE:
<221> NAME/KEY: misc_feature
<222> LOCATION: (1)..(27)
<223> OTHER INFORMATION: Primer

<400> SEQUENCE: 128
gcggccgctt taatcggttt taccatt                            27

<210> SEQ ID NO 129
<211> LENGTH: 60
<212> TYPE: DNA
<213> ORGANISM: Unknown
<220> FEATURE:
<221> NAME/KEY: misc_feature
<222> LOCATION: (1)..(60)
<223> OTHER INFORMATION: Primer

<400> SEQUENCE: 129
gtcgacccgc ggactagtgg gccctctaga cccgggggat ccggatctgc tggctatgaa    60

<210> SEQ ID NO 130
<211> LENGTH: 60
<212> TYPE: DNA
<213> ORGANISM: Unknown
<220> FEATURE:
<221> NAME/KEY: misc_feature
<222> LOCATION: (1)..(60)
<223> OTHER INFORMATION: Primer

<400> SEQUENCE: 130
gtcgacccgc ggactagtgg gccctctaga cccgggggat ccggatctgc tggctatgaa    60

<210> SEQ ID NO 131
<211> LENGTH: 789
<212> TYPE: DNA
<213> ORGANISM: Euglena gracilis
<220> FEATURE:

```
<221> NAME/KEY: CDS
<222> LOCATION: (1)..(789)
<223> OTHER INFORMATION: delta5-elongase

<400> SEQUENCE: 131
```

| | | | | | | | | | | | | | | | |
|---|---|---|---|---|---|---|---|---|---|---|---|---|---|---|---|
| atg | ctg | ggg | gcc | atc | gcg | gac | gtc | gtg | ctc | cgg | ggg | ccc | gcc | gca | ttc | 48 |
| Met | Leu | Gly | Ala | Ile | Ala | Asp | Val | Val | Leu | Arg | Gly | Pro | Ala | Ala | Phe | |
| 1 | | | | 5 | | | | | 10 | | | | | 15 | | |

| cac | tgg | gac | cct | gcc | acc | acc | ccg | ctc | gca | tcg | atc | gtc | agc | ccc | tgt | 96 |
| His | Trp | Asp | Pro | Ala | Thr | Thr | Pro | Leu | Ala | Ser | Ile | Val | Ser | Pro | Cys | |
| | | | 20 | | | | | 25 | | | | | 30 | | | |

| gtg | gcc | tcc | gtg | gcg | tac | ctg | ggg | gcc | atc | ggg | ctg | ctg | aag | cgc | cgc | 144 |
| Val | Ala | Ser | Val | Ala | Tyr | Leu | Gly | Ala | Ile | Gly | Leu | Leu | Lys | Arg | Arg | |
| | | 35 | | | | | 40 | | | | | 45 | | | | |

| act | gga | ccg | gag | gtc | cgc | tcc | aag | ccc | ttc | gag | ctg | cta | cac | aac | ggg | 192 |
| Thr | Gly | Pro | Glu | Val | Arg | Ser | Lys | Pro | Phe | Glu | Leu | Leu | His | Asn | Gly | |
| | 50 | | | | | 55 | | | | | 60 | | | | | |

| ctg | ctg | gtg | ggc | tgg | tcc | ctg | gtg | gtg | ctg | ctc | ggg | acg | ctg | tac | ggc | 240 |
| Leu | Leu | Val | Gly | Trp | Ser | Leu | Val | Val | Leu | Leu | Gly | Thr | Leu | Tyr | Gly | |
| 65 | | | | | 70 | | | | | 75 | | | | | 80 | |

| gcg | ttc | cag | cgc | gtg | cag | gag | gac | ggc | cgg | ggg | gtg | cag | gcc | ctc | ctg | 288 |
| Ala | Phe | Gln | Arg | Val | Gln | Glu | Asp | Gly | Arg | Gly | Val | Gln | Ala | Leu | Leu | |
| | | | | 85 | | | | | 90 | | | | | 95 | | |

| tgc | acc | cag | cgg | cca | cca | tct | cag | atc | tgg | gac | ggc | ccg | gtg | ggg | tac | 336 |
| Cys | Thr | Gln | Arg | Pro | Pro | Ser | Gln | Ile | Trp | Asp | Gly | Pro | Val | Gly | Tyr | |
| | | | 100 | | | | | 105 | | | | | 110 | | | |

| ttc | acg | tac | ctc | ttc | tac | ctc | gcg | aag | tac | tgg | gag | ctg | gcg | gac | act | 384 |
| Phe | Thr | Tyr | Leu | Phe | Tyr | Leu | Ala | Lys | Tyr | Trp | Glu | Leu | Ala | Asp | Thr | |
| | | 115 | | | | | 120 | | | | | 125 | | | | |

| gtc | atc | ctc | gcc | ctc | cgc | cag | aag | ccc | acc | atc | ccc | ctc | cac | gtc | tac | 432 |
| Val | Ile | Leu | Ala | Leu | Arg | Gln | Lys | Pro | Thr | Ile | Pro | Leu | His | Val | Tyr | |
| | 130 | | | | | 135 | | | | | 140 | | | | | |

| cat | cac | gcc | gtc | atg | ctg | ttc | atc | gtg | tgg | tcg | tgg | ttc | gcg | cac | ccc | 480 |
| His | His | Ala | Val | Met | Leu | Phe | Ile | Val | Trp | Ser | Trp | Phe | Ala | His | Pro | |
| 145 | | | | | 150 | | | | | 155 | | | | | 160 | |

| tgg | ctc | gag | ggg | agc | tgg | tgg | tgc | tcc | ctg | gtc | aac | tct | ttc | atc | cac | 528 |
| Trp | Leu | Glu | Gly | Ser | Trp | Trp | Cys | Ser | Leu | Val | Asn | Ser | Phe | Ile | His | |
| | | | | 165 | | | | | 170 | | | | | 175 | | |

| acg | gtg | atg | tac | tcg | tac | tac | acc | ctg | acg | gtg | gtt | ggc | atc | aac | cct | 576 |
| Thr | Val | Met | Tyr | Ser | Tyr | Tyr | Thr | Leu | Thr | Val | Val | Gly | Ile | Asn | Pro | |
| | | | 180 | | | | | 185 | | | | | 190 | | | |

| tgg | tgg | aag | aag | tgg | atg | acc | acc | atg | cag | atc | atc | cag | ttc | atc | acg | 624 |
| Trp | Trp | Lys | Lys | Trp | Met | Thr | Thr | Met | Gln | Ile | Ile | Gln | Phe | Ile | Thr | |
| | | 195 | | | | | 200 | | | | | 205 | | | | |

| ggc | tgc | gtg | tac | gtc | atg | gcg | ttc | ttc | ggc | cta | tat | tat | gcc | ggg | gcg | 672 |
| Gly | Cys | Val | Tyr | Val | Met | Ala | Phe | Phe | Gly | Leu | Tyr | Tyr | Ala | Gly | Ala | |
| | 210 | | | | | 215 | | | | | 220 | | | | | |

| ggc | tgc | acc | tcc | aac | gtg | tac | act | gcc | tgg | ttc | tcg | atg | ggg | gtc | aac | 720 |
| Gly | Cys | Thr | Ser | Asn | Val | Tyr | Thr | Ala | Trp | Phe | Ser | Met | Gly | Val | Asn | |
| 225 | | | | | 230 | | | | | 235 | | | | | 240 | |

| ctc | agc | ttt | ctg | tgg | ctc | ttc | gct | ctt | ttc | ttc | cgc | cgg | tca | tac | agc | 768 |
| Leu | Ser | Phe | Leu | Trp | Leu | Phe | Ala | Leu | Phe | Phe | Arg | Arg | Ser | Tyr | Ser | |
| | | | | 245 | | | | | 250 | | | | | 255 | | |

| aaa | cct | agc | cgg | aag | gag | tag | | | | | | | | | | 789 |
| Lys | Pro | Ser | Arg | Lys | Glu | | | | | | | | | | | |
| | | | 260 | | | | | | | | | | | | | |

```
<210> SEQ ID NO 132
<211> LENGTH: 262
<212> TYPE: PRT
<213> ORGANISM: Euglena gracilis
```

-continued

<400> SEQUENCE: 132

| Met | Leu | Gly | Ala | Ile | Ala | Asp | Val | Val | Leu | Arg | Gly | Pro | Ala | Ala | Phe |
|---|---|---|---|---|---|---|---|---|---|---|---|---|---|---|---|
| 1 | | | | 5 | | | | | 10 | | | | | 15 | |

| His | Trp | Asp | Pro | Ala | Thr | Thr | Pro | Leu | Ala | Ser | Ile | Val | Ser | Pro | Cys |
|---|---|---|---|---|---|---|---|---|---|---|---|---|---|---|---|
| | | | 20 | | | | | 25 | | | | | 30 | | |

| Val | Ala | Ser | Val | Ala | Tyr | Leu | Gly | Ala | Ile | Gly | Leu | Leu | Lys | Arg | Arg |
|---|---|---|---|---|---|---|---|---|---|---|---|---|---|---|---|
| | | 35 | | | | | 40 | | | | | 45 | | | |

| Thr | Gly | Pro | Glu | Val | Arg | Ser | Lys | Pro | Phe | Glu | Leu | Leu | His | Asn | Gly |
|---|---|---|---|---|---|---|---|---|---|---|---|---|---|---|---|
| | 50 | | | | | 55 | | | | | 60 | | | | |

| Leu | Leu | Val | Gly | Trp | Ser | Leu | Val | Val | Leu | Leu | Gly | Thr | Leu | Tyr | Gly |
|---|---|---|---|---|---|---|---|---|---|---|---|---|---|---|---|
| 65 | | | | | 70 | | | | | 75 | | | | | 80 |

| Ala | Phe | Gln | Arg | Val | Gln | Glu | Asp | Gly | Arg | Gly | Val | Gln | Ala | Leu | Leu |
|---|---|---|---|---|---|---|---|---|---|---|---|---|---|---|---|
| | | | | 85 | | | | | 90 | | | | | 95 | |

| Cys | Thr | Gln | Arg | Pro | Pro | Ser | Gln | Ile | Trp | Asp | Gly | Pro | Val | Gly | Tyr |
|---|---|---|---|---|---|---|---|---|---|---|---|---|---|---|---|
| | | | 100 | | | | | 105 | | | | | 110 | | |

| Phe | Thr | Tyr | Leu | Phe | Tyr | Leu | Ala | Lys | Tyr | Trp | Glu | Leu | Ala | Asp | Thr |
|---|---|---|---|---|---|---|---|---|---|---|---|---|---|---|---|
| | | 115 | | | | | 120 | | | | | 125 | | | |

| Val | Ile | Leu | Ala | Leu | Arg | Gln | Lys | Pro | Thr | Ile | Pro | Leu | His | Val | Tyr |
|---|---|---|---|---|---|---|---|---|---|---|---|---|---|---|---|
| | 130 | | | | | 135 | | | | | 140 | | | | |

| His | His | Ala | Val | Met | Leu | Phe | Ile | Val | Trp | Ser | Trp | Phe | Ala | His | Pro |
|---|---|---|---|---|---|---|---|---|---|---|---|---|---|---|---|
| 145 | | | | | 150 | | | | | 155 | | | | | 160 |

| Trp | Leu | Glu | Gly | Ser | Trp | Trp | Cys | Ser | Leu | Val | Asn | Ser | Phe | Ile | His |
|---|---|---|---|---|---|---|---|---|---|---|---|---|---|---|---|
| | | | | 165 | | | | | 170 | | | | | 175 | |

| Thr | Val | Met | Tyr | Ser | Tyr | Tyr | Thr | Leu | Thr | Val | Gly | Ile | Asn | Pro |
|---|---|---|---|---|---|---|---|---|---|---|---|---|---|---|
| | | | 180 | | | | | 185 | | | | | 190 | |

| Trp | Trp | Lys | Lys | Trp | Met | Thr | Thr | Met | Gln | Ile | Ile | Gln | Phe | Ile | Thr |
|---|---|---|---|---|---|---|---|---|---|---|---|---|---|---|---|
| | | 195 | | | | | 200 | | | | | 205 | | | |

| Gly | Cys | Val | Tyr | Val | Met | Ala | Phe | Phe | Gly | Leu | Tyr | Tyr | Ala | Gly | Ala |
|---|---|---|---|---|---|---|---|---|---|---|---|---|---|---|---|
| | 210 | | | | | 215 | | | | | 220 | | | | |

| Gly | Cys | Thr | Ser | Asn | Val | Tyr | Thr | Ala | Trp | Phe | Ser | Met | Gly | Val | Asn |
|---|---|---|---|---|---|---|---|---|---|---|---|---|---|---|---|
| 225 | | | | | 230 | | | | | 235 | | | | | 240 |

| Leu | Ser | Phe | Leu | Trp | Leu | Phe | Ala | Leu | Phe | Phe | Arg | Arg | Ser | Tyr | Ser |
|---|---|---|---|---|---|---|---|---|---|---|---|---|---|---|---|
| | | | | 245 | | | | | 250 | | | | | 255 | |

| Lys | Pro | Ser | Arg | Lys | Glu |
|---|---|---|---|---|---|
| | | | 260 | | |

<210> SEQ ID NO 133
<211> LENGTH: 789
<212> TYPE: DNA
<213> ORGANISM: Euglena gracilis
<220> FEATURE:
<221> NAME/KEY: CDS
<222> LOCATION: (1)..(789)
<223> OTHER INFORMATION: delta5-elongase

<400> SEQUENCE: 133

| atg | ctg | ggg | gcc | atc | gcg | gac | gtc | gtg | ctc | cgg | ggg | ccc | gcc | gca | ttc | 48 |
|---|---|---|---|---|---|---|---|---|---|---|---|---|---|---|---|---|
| Met | Leu | Gly | Ala | Ile | Ala | Asp | Val | Val | Leu | Arg | Gly | Pro | Ala | Ala | Phe | |
| 1 | | | | 5 | | | | | 10 | | | | | 15 | | |

| cac | tgg | gac | cct | gcc | acc | acc | ccg | ctc | gca | tcg | atc | gtc | agc | ccc | tgt | 96 |
|---|---|---|---|---|---|---|---|---|---|---|---|---|---|---|---|---|
| His | Trp | Asp | Pro | Ala | Thr | Thr | Pro | Leu | Ala | Ser | Ile | Val | Ser | Pro | Cys | |
| | | | 20 | | | | | 25 | | | | | 30 | | | |

| gtg | gcc | tcc | gtg | gcg | tac | ctg | ggg | gcc | atc | ggg | ctg | ctg | aag | cgc | cgc | 144 |
|---|---|---|---|---|---|---|---|---|---|---|---|---|---|---|---|---|
| Val | Ala | Ser | Val | Ala | Tyr | Leu | Gly | Ala | Ile | Gly | Leu | Leu | Lys | Arg | Arg | |
| | | 35 | | | | | 40 | | | | | 45 | | | | |

| act | gga | ccg | gag | gtc | cgc | tcc | aag | ccc | ttc | gag | ctg | cta | cac | aac | ggg | 192 |
|---|---|---|---|---|---|---|---|---|---|---|---|---|---|---|---|---|

```
Thr Gly Pro Glu Val Arg Ser Lys Pro Phe Glu Leu Leu His Asn Gly
     50                  55                  60 ctg ctg gtg ggc tgg tcc ctc gtg gtg ctg ctc ggg acg ctg tac ggc     240
Leu Leu Val Gly Trp Ser Leu Val Val Leu Leu Gly Thr Leu Tyr Gly
 65                  70                  75                  80 gcg tac cag cgc gtg cag gag gac ggc cgg ggg gtg cag gcc ctg ctg     288
Ala Tyr Gln Arg Val Gln Glu Asp Gly Arg Gly Val Gln Ala Leu Leu
                     85                  90                  95 tgc acc cag cgg cca cca tct cag atc tgg gac ggc ccg gtg ggg tac     336
Cys Thr Gln Arg Pro Pro Ser Gln Ile Trp Asp Gly Pro Val Gly Tyr
                100                 105                 110 ttc acg tac ctt ttc tac ctc gcg aag tac tgg gag ctg gtg gac act     384
Phe Thr Tyr Leu Phe Tyr Leu Ala Lys Tyr Trp Glu Leu Val Asp Thr
            115                 120                 125 gtc atc ctc gcc ctc cgc cag aag ccc acc atc ccc ctc cac gtc tac     432
Val Ile Leu Ala Leu Arg Gln Lys Pro Thr Ile Pro Leu His Val Tyr
        130                 135                 140 cat cac gcc gtc atg ctg ttc att gtg tgg tcg tgg ttc gcg cac ccc     480
His His Ala Val Met Leu Phe Ile Val Trp Ser Trp Phe Ala His Pro
145                 150                 155                 160 tgg ctc gag ggg agc tgg tgg tgc tcc ctg gtc aac tct ttc atc cac     528
Trp Leu Glu Gly Ser Trp Trp Cys Ser Leu Val Asn Ser Phe Ile His
                    165                 170                 175 acg gtg atg tac tcg tat tac acc ctg acg gtg gtt ggc atc aac cct     576
Thr Val Met Tyr Ser Tyr Tyr Thr Leu Thr Val Val Gly Ile Asn Pro
                180                 185                 190 tgg tgg aag aag tgg atg acc acc atg cag atc atc cag ttc atc acg     624
Trp Trp Lys Lys Trp Met Thr Thr Met Gln Ile Ile Gln Phe Ile Thr
            195                 200                 205 ggc tgc gtg tac gtc acg gcg ttc ttc ggc cta tac tat gcc ggg gcg     672
Gly Cys Val Tyr Val Thr Ala Phe Phe Gly Leu Tyr Tyr Ala Gly Ala
        210                 215                 220 ggc tgc acc tcc aac gtg tac act gcc tgg ttc tcg atg ggg gtc aac     720
Gly Cys Thr Ser Asn Val Tyr Thr Ala Trp Phe Ser Met Gly Val Asn
225                 230                 235                 240 ctc agc ttt ctg tgg ctc ttc gct ctt ttc ttc cgc cgg tcg tac agc     768
Leu Ser Phe Leu Trp Leu Phe Ala Leu Phe Phe Arg Arg Ser Tyr Ser
                    245                 250                 255 aaa cct agc cgg aag gag tag                                         789
Lys Pro Ser Arg Lys Glu
                260

<210> SEQ ID NO 134
<211> LENGTH: 262
<212> TYPE: PRT
<213> ORGANISM: Euglena gracilis

<400> SEQUENCE: 134

Met Leu Gly Ala Ile Ala Asp Val Val Leu Arg Gly Pro Ala Ala Phe
 1               5                  10                  15

His Trp Asp Pro Ala Thr Thr Pro Leu Ala Ser Ile Val Ser Pro Cys
                20                  25                  30

Val Ala Ser Val Ala Tyr Leu Gly Ala Ile Gly Leu Leu Lys Arg Arg
            35                  40                  45

Thr Gly Pro Glu Val Arg Ser Lys Pro Phe Glu Leu Leu His Asn Gly
        50                  55                  60

Leu Leu Val Gly Trp Ser Leu Val Val Leu Leu Gly Thr Leu Tyr Gly
 65                  70                  75                  80

Ala Tyr Gln Arg Val Gln Glu Asp Gly Arg Gly Val Gln Ala Leu Leu
```

```
                    85                  90                  95
Cys Thr Gln Arg Pro Ser Gln Ile Trp Asp Gly Pro Val Gly Tyr
                100                 105                 110

Phe Thr Tyr Leu Phe Tyr Leu Ala Lys Tyr Trp Glu Leu Val Asp Thr
            115                 120                 125

Val Ile Leu Ala Leu Arg Gln Lys Pro Thr Ile Pro Leu His Val Tyr
130                 135                 140

His His Ala Val Met Leu Phe Ile Val Trp Ser Trp Phe Ala His Pro
145                 150                 155                 160

Trp Leu Glu Gly Ser Trp Trp Cys Ser Leu Val Asn Ser Phe Ile His
                165                 170                 175

Thr Val Met Tyr Ser Tyr Tyr Thr Leu Thr Val Val Gly Ile Asn Pro
            180                 185                 190

Trp Trp Lys Lys Trp Met Thr Thr Met Gln Ile Ile Gln Phe Ile Thr
        195                 200                 205

Gly Cys Val Tyr Val Thr Ala Phe Phe Gly Leu Tyr Tyr Ala Gly Ala
    210                 215                 220

Gly Cys Thr Ser Asn Val Tyr Thr Ala Trp Phe Ser Met Gly Val Asn
225                 230                 235                 240

Leu Ser Phe Leu Trp Leu Phe Ala Leu Phe Phe Arg Arg Ser Tyr Ser
                245                 250                 255

Lys Pro Ser Arg Lys Glu
            260

<210> SEQ ID NO 135
<211> LENGTH: 897
<212> TYPE: DNA
<213> ORGANISM: Arabidopsis thaliana
<220> FEATURE:
<221> NAME/KEY: CDS
<222> LOCATION: (1)..(897)
<223> OTHER INFORMATION: delta5-elongase

<400> SEQUENCE: 135 atg gca tct gtt tac tcc acc cta acc tac tgg ctc gtc cac cac ccc     48
Met Ala Ser Val Tyr Ser Thr Leu Thr Tyr Trp Leu Val His His Pro
1               5                   10                  15 tac att gcc aac ttc acg tgg acc gaa ggt gaa aca cta ggc tcc acc     96
Tyr Ile Ala Asn Phe Thr Trp Thr Glu Gly Glu Thr Leu Gly Ser Thr
            20                  25                  30 gtt ttc ttt gtc ttt gtc gtc gtc tcc ctt tac ctc tcc gcc aca ttc    144
Val Phe Phe Val Phe Val Val Val Ser Leu Tyr Leu Ser Ala Thr Phe
        35                  40                  45 ctc ctc cga tac acc gtc gat tca ctc ccc aca ctc ggt ccc cgc att    192
Leu Leu Arg Tyr Thr Val Asp Ser Leu Pro Thr Leu Gly Pro Arg Ile
50                  55                  60 ctc aaa cca atc aca gcc gtt cac agc ctc att ctc ttc ctc ctc tcc    240
Leu Lys Pro Ile Thr Ala Val His Ser Leu Ile Leu Phe Leu Leu Ser
65                  70                  75                  80 tta acc atg gcc gtt ggt tgc act ctc tcc cta atc tct tcc tcg gac    288
Leu Thr Met Ala Val Gly Cys Thr Leu Ser Leu Ile Ser Ser Ser Asp
                85                  90                  95 ccg aag gcg cgt ctc ttc gac gcc gtt tgt ttc ccc ctc gac gtg aaa    336
Pro Lys Ala Arg Leu Phe Asp Ala Val Cys Phe Pro Leu Asp Val Lys
            100                 105                 110 cct aag gga ccg ctt ttc ttt tgg gct caa gtc ttt tac ctc tcg aag    384
Pro Lys Gly Pro Leu Phe Phe Trp Ala Gln Val Phe Tyr Leu Ser Lys
        115                 120                 125
```

| | | | | | | | | | | | | | | | | |
|---|---|---|---|---|---|---|---|---|---|---|---|---|---|---|---|---|
| atc | ctt | gag | ttc | gta | gac | aca | ctt | ctc | atc | ata | ctc | aac | aaa | tca | atc | 432 |
| Ile | Leu | Glu | Phe | Val | Asp | Thr | Leu | Leu | Ile | Ile | Leu | Asn | Lys | Ser | Ile | |
| | 130 | | | | | 135 | | | | | 140 | | | | | |
| caa | cgg | ctc | tcg | ttc | ctc | cac | gtc | tac | cac | cac | gca | acg | gtt | gtg | att | 480 |
| Gln | Arg | Leu | Ser | Phe | Leu | His | Val | Tyr | His | His | Ala | Thr | Val | Val | Ile | |
| 145 | | | | | 150 | | | | | 155 | | | | | 160 | |
| ttg | tgc | tac | ctc | tgg | tta | cga | aca | cgt | caa | tcg | atg | ttt | cct | gtt | ggg | 528 |
| Leu | Cys | Tyr | Leu | Trp | Leu | Arg | Thr | Arg | Gln | Ser | Met | Phe | Pro | Val | Gly | |
| | | | | 165 | | | | | 170 | | | | | 175 | | |
| ctc | gtg | ttg | aac | tcg | acg | gtc | cat | gtg | att | atg | tac | ggg | tac | tat | ttc | 576 |
| Leu | Val | Leu | Asn | Ser | Thr | Val | His | Val | Ile | Met | Tyr | Gly | Tyr | Tyr | Phe | |
| | | | 180 | | | | | 185 | | | | | 190 | | | |
| ctc | tgc | gct | atc | gga | tcg | agg | ccc | aag | tgg | aag | aag | ttg | gtg | acg | aat | 624 |
| Leu | Cys | Ala | Ile | Gly | Ser | Arg | Pro | Lys | Trp | Lys | Lys | Leu | Val | Thr | Asn | |
| | | 195 | | | | | 200 | | | | | 205 | | | | |
| ttt | caa | atg | gtt | cag | ttt | gct | ttc | ggc | atg | ggg | tta | gga | gcc | gct | tgg | 672 |
| Phe | Gln | Met | Val | Gln | Phe | Ala | Phe | Gly | Met | Gly | Leu | Gly | Ala | Ala | Trp | |
| 210 | | | | | 215 | | | | | 220 | | | | | | |
| atg | ctc | cca | gag | cat | tat | ttc | ggg | tcg | ggt | tgc | gcc | ggg | att | tgg | aca | 720 |
| Met | Leu | Pro | Glu | His | Tyr | Phe | Gly | Ser | Gly | Cys | Ala | Gly | Ile | Trp | Thr | |
| 225 | | | | | 230 | | | | | 235 | | | | | 240 | |
| gtt | tat | ttc | aat | ggt | gtg | ttt | act | gct | tct | cta | ttg | gct | ctc | ttc | tac | 768 |
| Val | Tyr | Phe | Asn | Gly | Val | Phe | Thr | Ala | Ser | Leu | Leu | Ala | Leu | Phe | Tyr | |
| | | | | 245 | | | | | 250 | | | | | 255 | | |
| aac | ttc | cac | tcc | aag | aac | tat | gag | aag | act | aca | acg | tcg | cct | ttg | tat | 816 |
| Asn | Phe | His | Ser | Lys | Asn | Tyr | Glu | Lys | Thr | Thr | Thr | Ser | Pro | Leu | Tyr | |
| | | | 260 | | | | | 265 | | | | | 270 | | | |
| aag | atc | gaa | tcc | ttt | ata | ttt | att | cac | gga | gag | agg | tgg | gca | aat | aaa | 864 |
| Lys | Ile | Glu | Ser | Phe | Ile | Phe | Ile | His | Gly | Glu | Arg | Trp | Ala | Asn | Lys | |
| | | 275 | | | | | 280 | | | | | 285 | | | | |
| gcg | att | aca | tta | ttt | tcc | aag | aaa | aac | gat | taa | | | | | | 897 |
| Ala | Ile | Thr | Leu | Phe | Ser | Lys | Lys | Asn | Asp | | | | | | | |
| | 290 | | | | | 295 | | | | | | | | | | |

<210> SEQ ID NO 136
<211> LENGTH: 298
<212> TYPE: PRT
<213> ORGANISM: Arabidopsis thaliana

<400> SEQUENCE: 136

Met Ala Ser Val Tyr Ser Thr Leu Thr Tyr Trp Leu Val His His Pro
1               5                   10                  15

Tyr Ile Ala Asn Phe Thr Trp Thr Glu Gly Glu Thr Leu Gly Ser Thr
            20                  25                  30

Val Phe Phe Val Phe Val Val Ser Leu Tyr Leu Ser Ala Thr Phe
        35                  40                  45

Leu Leu Arg Tyr Thr Val Asp Ser Leu Pro Thr Leu Gly Pro Arg Ile
    50                  55                  60

Leu Lys Pro Ile Thr Ala Val His Ser Leu Ile Leu Phe Leu Leu Ser
65                  70                  75                  80

Leu Thr Met Ala Val Gly Cys Thr Leu Ser Leu Ile Ser Ser Ser Asp
                85                  90                  95

Pro Lys Ala Arg Leu Phe Asp Ala Val Cys Phe Pro Leu Asp Val Lys
            100                 105                 110

Pro Lys Gly Pro Leu Phe Phe Trp Ala Gln Val Phe Tyr Leu Ser Lys
        115                 120                 125

Ile Leu Glu Phe Val Asp Thr Leu Leu Ile Ile Leu Asn Lys Ser Ile
    130                 135                 140

```
Gln Arg Leu Ser Phe Leu His Val Tyr His Ala Thr Val Val Ile
145                 150                 155                 160

Leu Cys Tyr Leu Trp Leu Arg Thr Arg Gln Ser Met Phe Pro Val Gly
                165                 170                 175

Leu Val Leu Asn Ser Thr Val His Val Ile Met Tyr Gly Tyr Tyr Phe
            180                 185                 190

Leu Cys Ala Ile Gly Ser Arg Pro Lys Trp Lys Leu Val Thr Asn
        195                 200                 205

Phe Gln Met Val Gln Phe Ala Phe Gly Met Gly Leu Gly Ala Ala Trp
210                 215                 220

Met Leu Pro Glu His Tyr Phe Gly Ser Gly Cys Ala Gly Ile Trp Thr
225                 230                 235                 240

Val Tyr Phe Asn Gly Val Phe Thr Ala Ser Leu Leu Ala Leu Phe Tyr
                245                 250                 255

Asn Phe His Ser Lys Asn Tyr Glu Lys Thr Thr Thr Ser Pro Leu Tyr
            260                 265                 270

Lys Ile Glu Ser Phe Ile Phe Ile His Gly Glu Arg Trp Ala Asn Lys
        275                 280                 285

Ala Ile Thr Leu Phe Ser Lys Lys Asn Asp
    290                 295

<210> SEQ ID NO 137
<211> LENGTH: 837
<212> TYPE: DNA
<213> ORGANISM: Arabidopsis thaliana
<220> FEATURE:
<221> NAME/KEY: CDS
<222> LOCATION: (1)..(837)
<223> OTHER INFORMATION: delta5-elongase

<400> SEQUENCE: 137 atg gca tca att tac tcc tct tta acc tac tgg ctc gtt aac cac ccc     48
Met Ala Ser Ile Tyr Ser Ser Leu Thr Tyr Trp Leu Val Asn His Pro
1               5                   10                  15 tac atc tcc aat ttt act tgg atc gaa ggt gaa acc cta ggc tcc acc     96
Tyr Ile Ser Asn Phe Thr Trp Ile Glu Gly Glu Thr Leu Gly Ser Thr
            20                  25                  30 gtc ttt ttc gta tcc gtc gta gtc tcc gtt tac ctc tcc gcc acg ttc    144
Val Phe Phe Val Ser Val Val Val Ser Val Tyr Leu Ser Ala Thr Phe
        35                  40                  45 ctc ctc cga tcc gcc atc gat tca ctc cca tca ctc agt cca cgt atc    192
Leu Leu Arg Ser Ala Ile Asp Ser Leu Pro Ser Leu Ser Pro Arg Ile
    50                  55                  60 ctc aaa ccg atc aca gcc gtc cac agc cta atc ctc tgt ctc ctc tcc    240
Leu Lys Pro Ile Thr Ala Val His Ser Leu Ile Leu Cys Leu Leu Ser
65                  70                  75                  80 tta gtc atg gcc gtc ggt tgc act ctc tca ata acc tca tct cac gcg    288
Leu Val Met Ala Val Gly Cys Thr Leu Ser Ile Thr Ser Ser His Ala
                85                  90                  95 tct tca gat ccg atg gcg cgt ttc ctt cac gcg att tgc ttt ccc gtc    336
Ser Ser Asp Pro Met Ala Arg Phe Leu His Ala Ile Cys Phe Pro Val
            100                 105                 110 gac gtt aaa cct aac gga ccg ctt ttc ttc tgg gct caa gtc ttc tac    384
Asp Val Lys Pro Asn Gly Pro Leu Phe Phe Trp Ala Gln Val Phe Tyr
        115                 120                 125 ctc tcg aag atc ctc gag ttc gga gac acg atc ctc atc ata ctc ggc    432
Leu Ser Lys Ile Leu Glu Phe Gly Asp Thr Ile Leu Ile Ile Leu Gly
    130                 135                 140 aaa tca atc caa cgg cta tcc ttc ctc cac gtg tac cac cac gcg acg    480
```

| | | | | | | | | | | | | | |
|---|---|---|---|---|---|---|---|---|---|---|---|---|---|
| Lys | Ser | Ile | Gln | Arg | Leu | Ser | Phe | Leu | His | Val | Tyr | His | His | Ala | Thr |
| 145 | | | | 150 | | | | | 155 | | | | | 160 | |

```
gtt gtg gtc atg tgt tat ctc tgg ctc cga act cgc caa tcg atg ttt       528
Val Val Val Met Cys Tyr Leu Trp Leu Arg Thr Arg Gln Ser Met Phe
                165                 170                 175 ccg att gcg ctc gtg acg aat tcg acg gta cac gtc atc atg tac ggt       576
Pro Ile Ala Leu Val Thr Asn Ser Thr Val His Val Ile Met Tyr Gly
            180                 185                 190 tac tac ttc ctc tgc gcc gtt gga tcg agg ccc aag tgg aag aga ttg       624
Tyr Tyr Phe Leu Cys Ala Val Gly Ser Arg Pro Lys Trp Lys Arg Leu
        195                 200                 205 gtg acg gat tgt cag att gtt cag ttt gtt ttc agt ttc ggg tta tcc       672
Val Thr Asp Cys Gln Ile Val Gln Phe Val Phe Ser Phe Gly Leu Ser
    210                 215                 220 ggt tgg atg ctc cga gag cac tta ttc ggg tcg ggt tgc acc ggg att       720
Gly Trp Met Leu Arg Glu His Leu Phe Gly Ser Gly Cys Thr Gly Ile
225                 230                 235                 240 tgg gga tgg tgt ttc aac gct gca ttt aat gct tct ctt ttg gct ctc       768
Trp Gly Trp Cys Phe Asn Ala Ala Phe Asn Ala Ser Leu Leu Ala Leu
                245                 250                 255 ttt tcc aac ttc cat tca aag aat tat gtc aag aag cca acg aga gag       816
Phe Ser Asn Phe His Ser Lys Asn Tyr Val Lys Lys Pro Thr Arg Glu
            260                 265                 270 gat ggc aaa aaa agc gat tag                                           837
Asp Gly Lys Lys Ser Asp
        275

<210> SEQ ID NO 138
<211> LENGTH: 278
<212> TYPE: PRT
<213> ORGANISM: Arabidopsis thaliana

<400> SEQUENCE: 138

Met Ala Ser Ile Tyr Ser Ser Leu Thr Tyr Trp Leu Val Asn His Pro
1               5                   10                  15

Tyr Ile Ser Asn Phe Thr Trp Ile Glu Gly Glu Thr Leu Gly Ser Thr
            20                  25                  30

Val Phe Phe Val Ser Val Val Ser Val Tyr Leu Ser Ala Thr Phe
        35                  40                  45

Leu Leu Arg Ser Ala Ile Asp Ser Leu Pro Ser Leu Ser Pro Arg Ile
    50                  55                  60

Leu Lys Pro Ile Thr Ala Val His Ser Leu Ile Leu Cys Leu Leu Ser
65                  70                  75                  80

Leu Val Met Ala Val Gly Cys Thr Leu Ser Ile Thr Ser Ser His Ala
                85                  90                  95

Ser Ser Asp Pro Met Ala Arg Phe Leu His Ala Ile Cys Phe Pro Val
            100                 105                 110

Asp Val Lys Pro Asn Gly Pro Leu Phe Phe Trp Ala Gln Val Phe Tyr
        115                 120                 125

Leu Ser Lys Ile Leu Glu Phe Gly Asp Thr Ile Leu Ile Leu Gly
    130                 135                 140

Lys Ser Ile Gln Arg Leu Ser Phe Leu His Val Tyr His His Ala Thr
145                 150                 155                 160

Val Val Val Met Cys Tyr Leu Trp Leu Arg Thr Arg Gln Ser Met Phe
                165                 170                 175

Pro Ile Ala Leu Val Thr Asn Ser Thr Val His Val Ile Met Tyr Gly
            180                 185                 190
```

```
Tyr Tyr Phe Leu Cys Ala Val Gly Ser Arg Pro Lys Trp Lys Arg Leu
            195                 200                 205

Val Thr Asp Cys Gln Ile Val Gln Phe Val Phe Ser Phe Gly Leu Ser
    210                 215                 220

Gly Trp Met Leu Arg Glu His Leu Phe Gly Ser Gly Cys Thr Gly Ile
225                 230                 235                 240

Trp Gly Trp Cys Phe Asn Ala Ala Phe Asn Ala Ser Leu Leu Ala Leu
                245                 250                 255

Phe Ser Asn Phe His Ser Lys Asn Tyr Val Lys Pro Thr Arg Glu
                260                 265                 270

Asp Gly Lys Lys Ser Asp
        275

<210> SEQ ID NO 139
<211> LENGTH: 6
<212> TYPE: PRT
<213> ORGANISM: Unknown
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Xaa is Val, Tyr or Ile, preferably is Val or
      Thr
<220> FEATURE:
<221> NAME/KEY: MISC_FEATURE
<222> LOCATION: (4)..(4)
<223> OTHER INFORMATION: Xaa is Tyr or Phe, preferably is Tyr

<400> SEQUENCE: 139

Leu His Xaa Xaa His His
1               5

<210> SEQ ID NO 140
<211> LENGTH: 8
<212> TYPE: PRT
<213> ORGANISM: Unknown
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is Asn, Asp, Thr, Gln, Met, Ser or Ala,
      preferably is Gln
<220> FEATURE:
<221> NAME/KEY: MISC_FEATURE
<222> LOCATION: (3)..(3)
<223> OTHER INFORMATION: Xaa is Thr, Cys, Leu, Met, Ala, Ile, Val or
      Phe, preferably is Ala or Met
<220> FEATURE:
<221> NAME/KEY: MISC_FEATURE
<222> LOCATION: (5)..(5)
<223> OTHER INFORMATION: Xaa is Met, Ile or Leu, preferably is Met
<220> FEATURE:
<221> NAME/KEY: MISC_FEATURE
<222> LOCATION: (6)..(6)
<223> OTHER INFORMATION: Xaa is Val, Ile, Leu, Thr or Phe, preferably
      is Leu

<400> SEQUENCE: 140

Thr Xaa Xaa Gln Xaa Xaa Gln Phe
1               5

<210> SEQ ID NO 141
<211> LENGTH: 6
<212> TYPE: PRT
<213> ORGANISM: Unknown
<220> FEATURE:
<223> OTHER INFORMATION: Consensus sequence
```

```
<220> FEATURE:
<221> NAME/KEY: MISC_FEATURE
<222> LOCATION: (3)..(3)
<223> OTHER INFORMATION: Xaa is Leu, Ile, Val, Tyr, Phe or Ala,
      preferably is Phe

<400> SEQUENCE: 141

Asp Thr Xaa Phe Met Val
1               5

<210> SEQ ID NO 142
<211> LENGTH: 8
<212> TYPE: PRT
<213> ORGANISM: Unknown
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: Xaa is Met, Ile or Leu, preferably is Met or
      Leu, especially preferably is Met
<220> FEATURE:
<221> NAME/KEY: MISC_FEATURE
<222> LOCATION: (6)..(6)
<223> OTHER INFORMATION: Xaa is Val, Ile, Leu, Thr or Phe, preferably
      is Leu

<400> SEQUENCE: 142

Thr Gln Ala Gln Xaa Xaa Gln Phe
1               5

<210> SEQ ID NO 143
<211> LENGTH: 60
<212> TYPE: DNA
<213> ORGANISM: Unknown
<220> FEATURE:
<221> NAME/KEY: misc_feature
<222> LOCATION: (1)..(60)
<223> OTHER INFORMATION: Primer

<400> SEQUENCE: 143
gtcgacccgc ggactagtgg gccctctaga cccgggggat ccggatctgc tggctatgaa    60

<210> SEQ ID NO 144
<211> LENGTH: 60
<212> TYPE: DNA
<213> ORGANISM: Unknown
<220> FEATURE:
<221> NAME/KEY: misc_feature
<222> LOCATION: (1)..(60)
<223> OTHER INFORMATION: Primer

<400> SEQUENCE: 144
gtcgacccgc ggactagtgg gccctctaga cccgggggat ccggatctgc tggctatgaa    60

<210> SEQ ID NO 145
<211> LENGTH: 36
<212> TYPE: DNA
<213> ORGANISM: Unknown
<220> FEATURE:
<221> NAME/KEY: misc_feature
<222> LOCATION: (1)..(36)
<223> OTHER INFORMATION: Primer

<400> SEQUENCE: 145
ggtaccacat aatgtgcgtg gagacggaaa ataacg                              36

<210> SEQ ID NO 146
<211> LENGTH: 33
```

```
<212> TYPE: DNA
<213> ORGANISM: Unknown
<220> FEATURE:
<221> NAME/KEY: misc_feature
<222> LOCATION: (1)..(33)
<223> OTHER INFORMATION: Primer

<400> SEQUENCE: 146
ctcgagttac gccgtctttc cggagtgttg gcc                          33

<210> SEQ ID NO 147
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: Primer

<400> SEQUENCE: 147
gcggccgctt acgtggactt ggtc                                    24

<210> SEQ ID NO 148
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: Primer

<400> SEQUENCE: 148
gcggccgcat ggcgacgaag gagg                                    24

<210> SEQ ID NO 149
<211> LENGTH: 25
<212> TYPE: DNA
<213> ORGANISM: Unknown
<220> FEATURE:
<221> NAME/KEY: misc_feature
<222> LOCATION: (1)..(25)
<223> OTHER INFORMATION: Primer

<400> SEQUENCE: 149
taagcttaca tggcgacgaa ggagg                                   25

<210> SEQ ID NO 150
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: Primer

<400> SEQUENCE: 150
tggatccact tacgtggact tggt                                    24

<210> SEQ ID NO 151
<211> LENGTH: 60
<212> TYPE: DNA
<213> ORGANISM: Unknown
<220> FEATURE:
<221> NAME/KEY: misc_feature
<222> LOCATION: (1)..(60)
<223> OTHER INFORMATION: Primer

<400> SEQUENCE: 151
```
gtcgacccgc ggactagtgg gccctctaga cccgggggat ccggatctgc tggctatgaa       60

<210> SEQ ID NO 152
<211> LENGTH: 31
<212> TYPE: DNA
<213> ORGANISM: Unknown
<220> FEATURE:
<221> NAME/KEY: misc_feature
<222> LOCATION: (1)..(31)
<223> OTHER INFORMATION: Primer

<400> SEQUENCE: 152
gcggccgcac catgtgctca ccaccgccgt c                                      31

<210> SEQ ID NO 153
<211> LENGTH: 26
<212> TYPE: DNA
<213> ORGANISM: Unknown
<220> FEATURE:
<221> NAME/KEY: misc_feature
<222> LOCATION: (1)..(26)
<223> OTHER INFORMATION: Primer

<400> SEQUENCE: 153
gcggccgcct acatggcacc agtaac                                            26

<210> SEQ ID NO 154
<211> LENGTH: 31
<212> TYPE: DNA
<213> ORGANISM: Unknown
<220> FEATURE:
<221> NAME/KEY: misc_feature
<222> LOCATION: (1)..(31)
<223> OTHER INFORMATION: Primer

<400> SEQUENCE: 154
gcggccgcac catgtgctca tcaccgccgt c                                      31

<210> SEQ ID NO 155
<211> LENGTH: 26
<212> TYPE: DNA
<213> ORGANISM: Unknown
<220> FEATURE:
<221> NAME/KEY: misc_feature
<222> LOCATION: (1)..(26)
<223> OTHER INFORMATION: Primer

<400> SEQUENCE: 155
gcggccgcct acatggcacc agtaac                                            26

<210> SEQ ID NO 156
<211> LENGTH: 31
<212> TYPE: DNA
<213> ORGANISM: Unknown
<220> FEATURE:
<221> NAME/KEY: misc_feature
<222> LOCATION: (1)..(31)
<223> OTHER INFORMATION: Primer

<400> SEQUENCE: 156
gcggccgcac catggacgcc tacaacgctg c                                      31

<210> SEQ ID NO 157
<211> LENGTH: 27
<212> TYPE: DNA
<213> ORGANISM: Unknown
<220> FEATURE:
<221> NAME/KEY: misc_feature

```
<222> LOCATION: (1)..(27)
<223> OTHER INFORMATION: Primer

<400> SEQUENCE: 157
gcggccgcct aagcactctt cttcttt                                          27

<210> SEQ ID NO 158
<211> LENGTH: 23
<212> TYPE: DNA
<213> ORGANISM: Unknown
<220> FEATURE:
<221> NAME/KEY: misc_feature
<222> LOCATION: (1)..(23)
<223> OTHER INFORMATION: Primer

<400> SEQUENCE: 158
accatgtgct caccaccgcc gtc                                              23

<210> SEQ ID NO 159
<211> LENGTH: 18
<212> TYPE: DNA
<213> ORGANISM: Unknown
<220> FEATURE:
<221> NAME/KEY: misc_feature
<222> LOCATION: (1)..(18)
<223> OTHER INFORMATION: Primer

<400> SEQUENCE: 159
ctacatggca ccagtaac                                                    18

<210> SEQ ID NO 160
<211> LENGTH: 23
<212> TYPE: DNA
<213> ORGANISM: Unknown
<220> FEATURE:
<221> NAME/KEY: misc_feature
<222> LOCATION: (1)..(23)
<223> OTHER INFORMATION: Primer

<400> SEQUENCE: 160
accatgtgct catcaccgcc gtc                                              23

<210> SEQ ID NO 161
<211> LENGTH: 18
<212> TYPE: DNA
<213> ORGANISM: Unknown
<220> FEATURE:
<221> NAME/KEY: misc_feature
<222> LOCATION: (1)..(18)
<223> OTHER INFORMATION: Primer

<400> SEQUENCE: 161
ctacatggca ccagtaac                                                    18

<210> SEQ ID NO 162
<211> LENGTH: 23
<212> TYPE: DNA
<213> ORGANISM: Unknown
<220> FEATURE:
<221> NAME/KEY: misc_feature
<222> LOCATION: (1)..(23)
<223> OTHER INFORMATION: Primer

<400> SEQUENCE: 162
accatggacg cctacaacgc tgc                                              23

<210> SEQ ID NO 163
```

```
<211> LENGTH: 19
<212> TYPE: DNA
<213> ORGANISM: Unknown
<220> FEATURE:
<221> NAME/KEY: misc_feature
<222> LOCATION: (1)..(19)
<223> OTHER INFORMATION: Primer

<400> SEQUENCE: 163
ctaagcactc ttcttcttt                                              19

<210> SEQ ID NO 164
<211> LENGTH: 60
<212> TYPE: DNA
<213> ORGANISM: Unknown
<220> FEATURE:
<221> NAME/KEY: misc_feature
<222> LOCATION: (1)..(60)
<223> OTHER INFORMATION: Primer

<400> SEQUENCE: 164
gtcgacccgc ggactagtgg gccctctaga cccggsggat ccggatctgc tggctatgaa    60

<210> SEQ ID NO 165
<211> LENGTH: 60
<212> TYPE: DNA
<213> ORGANISM: Unknown
<220> FEATURE:
<221> NAME/KEY: misc_feature
<222> LOCATION: (1)..(60)
<223> OTHER INFORMATION: Primer

<400> SEQUENCE: 165
gtcgacccgc ggactagtgg gccctctaga cccggsggat ccggatctgc tggctatgaa    60

<210> SEQ ID NO 166
<211> LENGTH: 29
<212> TYPE: DNA
<213> ORGANISM: Unknown
<220> FEATURE:
<221> NAME/KEY: misc_feature
<222> LOCATION: (1)..(29)
<223> OTHER INFORMATION: Primer

<400> SEQUENCE: 166
gcggccgcat aatgacgagc aacatgagc                                   29

<210> SEQ ID NO 167
<211> LENGTH: 29
<212> TYPE: DNA
<213> ORGANISM: Unknown
<220> FEATURE:
<221> NAME/KEY: misc_feature
<222> LOCATION: (1)..(29)
<223> OTHER INFORMATION: Primer

<400> SEQUENCE: 167
gcggccgctt aggccgactt ggccttggg                                   29

<210> SEQ ID NO 168
<211> LENGTH: 34
<212> TYPE: DNA
<213> ORGANISM: Unknown
<220> FEATURE:
<221> NAME/KEY: misc_feature
<222> LOCATION: (1)..(34)
<223> OTHER INFORMATION: Primer

<400> SEQUENCE: 168
```
gcggccgcac catggacgtc gtcgagcagc aatg 34

<210> SEQ ID NO 169
<211> LENGTH: 36
<212> TYPE: DNA
<213> ORGANISM: Unknown
<220> FEATURE:
<221> NAME/KEY: misc_feature
<222> LOCATION: (1)..(36)
<223> OTHER INFORMATION: Primer

<400> SEQUENCE: 169
gcggccgctt agatggtctt ctgcttcttg ggcgcc 36

<210> SEQ ID NO 170
<211> LENGTH: 23
<212> TYPE: DNA
<213> ORGANISM: Unknown
<220> FEATURE:
<221> NAME/KEY: misc_feature
<222> LOCATION: (1)..(23)
<223> OTHER INFORMATION: Primer

<400> SEQUENCE: 170
gacataatga cgagcaacat gag 23

<210> SEQ ID NO 171
<211> LENGTH: 25
<212> TYPE: DNA
<213> ORGANISM: Unknown
<220> FEATURE:
<221> NAME/KEY: misc_feature
<222> LOCATION: (1)..(25)
<223> OTHER INFORMATION: Primer

<400> SEQUENCE: 171
cggcttaggc cgacttggcc ttggg 25

<210> SEQ ID NO 172
<211> LENGTH: 30
<212> TYPE: DNA
<213> ORGANISM: Unknown
<220> FEATURE:
<221> NAME/KEY: misc_feature
<222> LOCATION: (1)..(30)
<223> OTHER INFORMATION: Primer

<400> SEQUENCE: 172
agacataatg gacgtcgtcg agcagcaatg 30

<210> SEQ ID NO 173
<211> LENGTH: 28
<212> TYPE: DNA
<213> ORGANISM: Unknown
<220> FEATURE:
<221> NAME/KEY: misc_feature
<222> LOCATION: (1)..(28)
<223> OTHER INFORMATION: Primer

<400> SEQUENCE: 173
ttagatggtc ttctgcttct tgggcgcc 28

<210> SEQ ID NO 174
<211> LENGTH: 60
<212> TYPE: DNA
<213> ORGANISM: Unknown
<220> FEATURE:

```
<221> NAME/KEY: misc_feature
<222> LOCATION: (1)..(60)
<223> OTHER INFORMATION: Primer

<400> SEQUENCE: 174
gtcgacccgc ggactagtgg gccctctaga cccgggggat ccggatctgc tggctatgaa      60

<210> SEQ ID NO 175
<211> LENGTH: 29
<212> TYPE: DNA
<213> ORGANISM: Unknown
<220> FEATURE:
<221> NAME/KEY: misc_feature
<222> LOCATION: (1)..(29)
<223> OTHER INFORMATION: Primer

<400> SEQUENCE: 175
gcggccgcat aatggcttca acatggcaa                                       29

<210> SEQ ID NO 176
<211> LENGTH: 32
<212> TYPE: DNA
<213> ORGANISM: Unknown
<220> FEATURE:
<221> NAME/KEY: misc_feature
<222> LOCATION: (1)..(32)
<223> OTHER INFORMATION: Primer

<400> SEQUENCE: 176
gcggccgctt atgtcttctt gctcttcctg tt                                   32

<210> SEQ ID NO 177
<211> LENGTH: 26
<212> TYPE: DNA
<213> ORGANISM: Unknown
<220> FEATURE:
<221> NAME/KEY: misc_feature
<222> LOCATION: (1)..(26)
<223> OTHER INFORMATION: Primer

<400> SEQUENCE: 177
gcggccgcat aatggagact tttaat                                          26

<210> SEQ ID NO 178
<211> LENGTH: 28
<212> TYPE: DNA
<213> ORGANISM: Unknown
<220> FEATURE:
<221> NAME/KEY: misc_feature
<222> LOCATION: (1)..(28)
<223> OTHER INFORMATION: Primer

<400> SEQUENCE: 178
gcggccgctc agtccccct cactttcc                                         28

<210> SEQ ID NO 179
<211> LENGTH: 29
<212> TYPE: DNA
<213> ORGANISM: Unknown
<220> FEATURE:
<221> NAME/KEY: misc_feature
<222> LOCATION: (1)..(29)
<223> OTHER INFORMATION: Primer

<400> SEQUENCE: 179
aagcttacat aatggcttca acatggcaa                                       29
```

<210> SEQ ID NO 180
<211> LENGTH: 30
<212> TYPE: DNA
<213> ORGANISM: Unknown
<220> FEATURE:
<221> NAME/KEY: misc_feature
<222> LOCATION: (1)..(30)
<223> OTHER INFORMATION: Primer

<400> SEQUENCE: 180
ggatccttat gtcttcttgc tcttcctgtt                                    30

<210> SEQ ID NO 181
<211> LENGTH: 26
<212> TYPE: DNA
<213> ORGANISM: Unknown
<220> FEATURE:
<221> NAME/KEY: misc_feature
<222> LOCATION: (1)..(26)
<223> OTHER INFORMATION: Primer

<400> SEQUENCE: 181
aagcttacat aatggagact tttaat                                        26

<210> SEQ ID NO 182
<211> LENGTH: 27
<212> TYPE: DNA
<213> ORGANISM: Unknown
<220> FEATURE:
<221> NAME/KEY: misc_feature
<222> LOCATION: (1)..(27)
<223> OTHER INFORMATION: Primer

<400> SEQUENCE: 182
ggatccttca gtccccctc actttcc                                        27

<210> SEQ ID NO 183
<211> LENGTH: 993
<212> TYPE: DNA
<213> ORGANISM: Phaeodactylum tricornutum
<220> FEATURE:
<221> NAME/KEY: CDS
<222> LOCATION: (103)..(939)
<223> OTHER INFORMATION: delta6-elongase

<400> SEQUENCE: 183
ggtcttttgt ggtagctatc gtcatcacac gcaggtcgtt gctcactatc gtgatccgta   60
tattgaccgt gcacttgtgt aaaacagaga tatttcaaga gt atg atg gta cct      114
                                              Met Met Val Pro
                                               1 tca agt tat gac gag tat atc gtc atg gtc aac gac ctt ggc gac tct    162
Ser Ser Tyr Asp Glu Tyr Ile Val Met Val Asn Asp Leu Gly Asp Ser
 5                  10                  15                  20 att ctg agc tgg gcc gac cct gat cac tat cgt gga cat acc gag gga    210
Ile Leu Ser Trp Ala Asp Pro Asp His Tyr Arg Gly His Thr Glu Gly
                 25                  30                  35 tgg gag ttc act gac ttt tct gct gct ttt agc att gcc gtc gcg tac    258
Trp Glu Phe Thr Asp Phe Ser Ala Ala Phe Ser Ile Ala Val Ala Tyr
             40                  45                  50 ctc ctg ttt gtc ttt gtt gga tct ctc att atg agt atg gga gtc ccc    306
Leu Leu Phe Val Phe Val Gly Ser Leu Ile Met Ser Met Gly Val Pro
         55                  60                  65 gca att gac cct tat ccg ctc aag ttt gtc tac aat gtt tca cag att    354
Ala Ile Asp Pro Tyr Pro Leu Lys Phe Val Tyr Asn Val Ser Gln Ile
     70                  75                  80

```
atg ctt tgt gct tac atg acc att gaa gcc agt ctt cta gct tat cgt        402
Met Leu Cys Ala Tyr Met Thr Ile Glu Ala Ser Leu Leu Ala Tyr Arg
 85                  90                  95                 100 aac ggc tac aca ttc tgg cct tgc aac gat tgg gac ttt gaa aag ccg        450
Asn Gly Tyr Thr Phe Trp Pro Cys Asn Asp Trp Asp Phe Glu Lys Pro
                    105                 110                 115 cct atc gct aag ctc ctc tgg ctc ttt tac gtt tcc aaa att tgg gat        498
Pro Ile Ala Lys Leu Leu Trp Leu Phe Tyr Val Ser Lys Ile Trp Asp
                120                 125                 130 ttt tgg gac acc atc ttt att gtt ctc ggg aag aag tgg cgt caa ctt        546
Phe Trp Asp Thr Ile Phe Ile Val Leu Gly Lys Lys Trp Arg Gln Leu
            135                 140                 145 tcc ttc ctg cac gtc tac cat cac acc acc atc ttt ctc ttc tac tgg        594
Ser Phe Leu His Val Tyr His His Thr Thr Ile Phe Leu Phe Tyr Trp
        150                 155                 160 ttg aat gca cat gta aac ttt gat ggt gat att ttc ctc acc atc gtc        642
Leu Asn Ala His Val Asn Phe Asp Gly Asp Ile Phe Leu Thr Ile Val
165                 170                 175                 180 ttg aac ggt ttc atc cac acc gtc atg tac acg tac tac ttc att tgc        690
Leu Asn Gly Phe Ile His Thr Val Met Tyr Thr Tyr Tyr Phe Ile Cys
                    185                 190                 195 atg cac acc aag gtc cca gag acc ggc aaa tcc ttg ccc att tgg tgg        738
Met His Thr Lys Val Pro Glu Thr Gly Lys Ser Leu Pro Ile Trp Trp
                200                 205                 210 aaa tct agt ttg aca agc atg cag ctg gtg cag ttc atc acg atg atg        786
Lys Ser Ser Leu Thr Ser Met Gln Leu Val Gln Phe Ile Thr Met Met
            215                 220                 225 acg cag gct atc atg atc ttg tac aag ggc tgt gct gct ccc cat agc        834
Thr Gln Ala Ile Met Ile Leu Tyr Lys Gly Cys Ala Ala Pro His Ser
        230                 235                 240 cgg gtg gtg aca tcg tac ttg gtt tac att ttg tcg ctc ttt att ttg        882
Arg Val Val Thr Ser Tyr Leu Val Tyr Ile Leu Ser Leu Phe Ile Leu
245                 250                 255                 260 ttc gcc cag ttc ttt gtc agc tca tac ctc aag ccg aag aag aag aag        930
Phe Ala Gln Phe Phe Val Ser Ser Tyr Leu Lys Pro Lys Lys Lys Lys
                    265                 270                 275 aca gct taa gcgaaatttg ggtctacgtt aaaacaatta cgttacaaaa                979
Thr Ala aaaaaaaaaa aaaa                                                        993

<210> SEQ ID NO 184
<211> LENGTH: 278
<212> TYPE: PRT
<213> ORGANISM: Phaeodactylum tricornutum

<400> SEQUENCE: 184

Met Met Val Pro Ser Ser Tyr Asp Glu Tyr Ile Val Met Val Asn Asp
 1               5                  10                  15

Leu Gly Asp Ser Ile Leu Ser Trp Ala Asp Pro Asp His Tyr Arg Gly
             20                  25                  30

His Thr Glu Gly Trp Glu Phe Thr Asp Phe Ser Ala Ala Phe Ser Ile
         35                  40                  45

Ala Val Ala Tyr Leu Leu Phe Val Phe Val Gly Ser Leu Ile Met Ser
     50                  55                  60

Met Gly Val Pro Ala Ile Asp Pro Tyr Pro Leu Lys Phe Val Tyr Asn
 65                  70                  75                  80

Val Ser Gln Ile Met Leu Cys Ala Tyr Met Thr Ile Glu Ala Ser Leu
                 85                  90                  95
```

```
Leu Ala Tyr Arg Asn Gly Tyr Thr Phe Trp Pro Cys Asn Asp Trp Asp
            100                 105                 110

Phe Glu Lys Pro Pro Ile Ala Lys Leu Leu Trp Leu Phe Tyr Val Ser
        115                 120                 125

Lys Ile Trp Asp Phe Trp Asp Thr Ile Phe Ile Val Leu Gly Lys Lys
    130                 135                 140

Trp Arg Gln Leu Ser Phe Leu His Val Tyr His His Thr Thr Ile Phe
145                 150                 155                 160

Leu Phe Tyr Trp Leu Asn Ala His Val Asn Phe Asp Gly Asp Ile Phe
                165                 170                 175

Leu Thr Ile Val Leu Asn Gly Phe Ile His Thr Val Met Tyr Thr Tyr
            180                 185                 190

Tyr Phe Ile Cys Met His Thr Lys Val Pro Glu Thr Gly Lys Ser Leu
        195                 200                 205

Pro Ile Trp Trp Lys Ser Ser Leu Thr Ser Met Gln Leu Val Gln Phe
    210                 215                 220

Ile Thr Met Met Thr Gln Ala Ile Met Ile Leu Tyr Lys Gly Cys Ala
225                 230                 235                 240

Ala Pro His Ser Arg Val Val Thr Ser Tyr Leu Val Tyr Ile Leu Ser
                245                 250                 255

Leu Phe Ile Leu Phe Ala Gln Phe Phe Val Ser Ser Tyr Leu Lys Pro
            260                 265                 270

Lys Lys Lys Lys Thr Ala
        275
```

```
<210> SEQ ID NO 185
<211> LENGTH: 20
<212> TYPE: DNA
<213> ORGANISM: Unknown
<220> FEATURE:
<221> NAME/KEY: misc_feature
<222> LOCATION: (1)..(20)
<223> OTHER INFORMATION: N at positions 3 and 18 is C or T.
<220> FEATURE:
<221> NAME/KEY: misc_feature
<222> LOCATION: (1)..(20)
<223> OTHER INFORMATION: Primer

<400> SEQUENCE: 185
aanctuctut ggctuttnta                                                 20

<210> SEQ ID NO 186
<211> LENGTH: 23
<212> TYPE: DNA
<213> ORGANISM: Unknown
<220> FEATURE:
<221> NAME/KEY: misc_feature
<222> LOCATION: (1)..(23)
<223> OTHER INFORMATION: N at positions 3 and 15 is C or T. N at
      position 9, 12 and 21 is A or G.
<220> FEATURE:
<221> NAME/KEY: misc_feature
<222> LOCATION: (1)..(23)
<223> OTHER INFORMATION: Primer

<400> SEQUENCE: 186
gantguacna anaantgugc naa                                             23

<210> SEQ ID NO 187
<211> LENGTH: 446
<212> TYPE: DNA
<213> ORGANISM: Unknown
<220> FEATURE:
```

```
<221> NAME/KEY: misc_feature
<222> LOCATION: (1)..(446)
<223> OTHER INFORMATION: PCR-Fragment

<400> SEQUENCE: 187
aagctcctct ggctctttta cgtttccaaa atttgggatt tttgggacac catctttatt      60
gttctcggga agaagtggcg tcaactttcc ttcctgcacg tctaccatca caccaccatc     120
tttctcttct actggttgaa tgcacatgta aactttgatg gtgatatttt cctcaccatc     180
gtcttgaacg gtttcatcca caccgtcatg tacacgtact acttcatttg catgcacacc     240
aaggtcccag agaccggcaa atccttgccc atttggtgga atctagtttt gacaagcatg     300
cagctggtgc agttcatcac gatgatgacg caggctatca tgatcttgta caagggctgt     360
gctgctcccc atagccgggt ggtgacatcg tacttggttt acattttgtc gctctttatt     420
ttgttcgccc agttctttgt cagctc                                          446

<210> SEQ ID NO 188
<211> LENGTH: 30
<212> TYPE: DNA
<213> ORGANISM: Unknown
<220> FEATURE:
<221> NAME/KEY: misc_feature
<222> LOCATION: (1)..(30)
<223> OTHER INFORMATION: Primer

<400> SEQUENCE: 188
gcggccgcac ataatgatgg taccttcaag                                       30

<210> SEQ ID NO 189
<211> LENGTH: 22
<212> TYPE: DNA
<213> ORGANISM: Unknown
<220> FEATURE:
<221> NAME/KEY: misc_feature
<222> LOCATION: (1)..(22)
<223> OTHER INFORMATION: Primer

<400> SEQUENCE: 189
gaagacagct taatagacta gt                                               22

<210> SEQ ID NO 190
<211> LENGTH: 31
<212> TYPE: DNA
<213> ORGANISM: Unknown
<220> FEATURE:
<221> NAME/KEY: misc_feature
<222> LOCATION: (1)..(31)
<223> OTHER INFORMATION: Primer

<400> SEQUENCE: 190
gcggccgcac catgatggta ccttcaagtt a                                     31

<210> SEQ ID NO 191
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: Primer

<400> SEQUENCE: 191
gaagacagct taataggcgg ccgc                                             24
```

-continued

```
<210> SEQ ID NO 192
<211> LENGTH: 859
<212> TYPE: DNA
<213> ORGANISM: Unknown
<220> FEATURE:
<221> NAME/KEY: misc_feature
<222> LOCATION: (1)..(859)
<223> OTHER INFORMATION: PCR product

<400> SEQUENCE: 192
gcggccgcac ataatgatgg taccttcaag ttatgacgag tatatcgtca tggtcaacga      60
ccttggcgac tctattctga gctgggccga ccctgatcac tatcgtggac ataccgaggg     120
atgggagttc actgactttt ctgctgcttt tagcattgcc gtcgcgtacc tcctgtttgt     180
ctttgttgga tctctcatta tgagtatggg agtccccgca attgacccct atccgctcaa     240
gtttgtctac aatgtttcac agattatgct ttgtgcttac atgaccattg aagccagtct     300
tctagcttat cgtaacggct acacattctg gccttgcaac gattgggact ttgaaaagcc     360
gcctatcgct aagctcctct ggctctttta cgtttccaaa atttgggatt tttgggacac     420
catctttatt gttctcggga agaagtggcg tcaactttcc ttcctgcacg tctaccatca     480
caccaccatc tttctcttct actggttgaa tgcacatgta aactttgatg gtgatatttt     540
cctcaccatc gtcttgaacg gtttcatcca caccgtcatg tacacgtact acttcatttg     600
catgcacacc aaggtcccag agaccggcaa atccttgccc atttggtgga aatctagttt     660
gacaagcatg cagctggtgc agttcatcac gatgatgacg caggctatca tgatcttgta     720
caagggctgt gctgctcccc atagccgggt ggtgacatcg tacttggttt acattttgtc     780
gctctttatt ttgttcgccc agttctttgt cagctcatac ctcaagccga agaagaagaa     840
gacagcttaa tagactagt                                                   859
```

METHOD FOR THE PRODUCTION OF MULTIPLE-UNSATURATED FATTY ACIDS IN TRANSGENIC ORGANISMS

RELATED APPLICATIONS

This application is a national stage application (under 35 U.S.C. 371) of PCT/EP2004/007957 filed Jul. 16, 2004 which claims benefit to German application 103 35 992.3 filed Aug. 1, 2003, German application 103 44 557.9 filed Sep. 24, 2003, German application 103 47 869.8 filed Oct. 10, 2003, German application 103 59 593.7 filed Dec. 18, 2003, German application 10 2004 009 457.8 filed Feb. 27, 2004, German application 10 2004 012 370.5 filed Mar. 13, 2004, and German application 10 2004 024 014.0 filed May 14, 2004.

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: "Sequence Listing-12810-00193-US", date recorded: Jul. 16, 2007, size: 561 KB.

FIELD OF THE INVENTION

The present invention relates to a process for the production of polyunsaturated fatty acids in an organism by introducing, into the organism, nucleic acids which encode polypeptides with Δ5-elongase activity. These nucleic acid sequences, if appropriate together with further nucleic acid sequences which encode polypeptides of the biosynthesis of the fatty acid or lipid metabolism, can advantageously be expressed in the organism. Especially advantageous are nucleic acid sequences which encode a Δ6-desaturase, a Δ5-desaturase, Δ4-desaturase, Δ12-desaturase and/or Δ6-elongase activity. These desaturases and elongases are advantageously derived from *Thalassiosira*, *Euglena* or *Ostreococcus*. The invention furthermore relates to a process for the production of oils and/or triacylglycerides with an elevated content of long-chain polyunsaturated fatty acids.

In a preferred embodiment, the present invention furthermore relates to a method for the production of unsaturated ω3-fatty acids and to a method for the production of triglycerides with an elevated content of unsaturated fatty acids, especially ω3-fatty acids with more than three double bonds. The invention relates to the generation of a transgenic organism, preferably a transgenic plant or a transgenic microorganism, with an elevated content of unsaturated ω3-fatty acids, oils or lipids with ω3-double bonds as the result of the expression of the elongases and desaturases used in the method according to the invention, advantageously in conjunction with ω3-desaturases, for example an ω3-desaturase from fungi of the family Pythiaceae such as the genus *Phytophthora*, for example the genus and species *Phytophthora infestans*, or an ω3-desaturase from algae such as the family of the Prasinophyceae, for example the genus *Ostreococcus*, specifically the genus and species *Ostreococcus tauri*, or diatoms such as the genus *Thalassiosira*, specifically the genus and species *Thalassiosira pseudonana*.

The invention furthermore relates to the nucleic acid sequences, nucleic acid constructs, vectors and organisms comprising the nucleic acid sequences according to the invention, vectors comprising the nucleic acid sequences and/or the nucleic acid constructs and to transgenic organisms comprising the abovementioned nucleic acid sequences, nucleic acid constructs and/or vectors.

A further part of the invention relates to oils, lipids and/or fatty acids produced by the process according to the invention and to their use. Moreover, the invention relates to unsaturated fatty acids and to triglycerides with an elevated content of unsaturated fatty acids and to their use.

DESCRIPTION OF RELATED ART

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter. Polyunsaturated ω3-fatty acids and ω6-fatty acids are therefore an important constituent in animal and human nutrition.

Polyunsaturated long-chain ω3-fatty acids such as eicosapentaenoic acid (=EPA, $C20:5^{\Delta 5,8,11,14,17}$) or docosahexaenoic acid (=DHA, $C22:6^{\Delta 4,7,10,13,16,19}$) are important components in human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids.

Owing to the present-day composition of human food, an addition of polyunsaturated ω3-fatty acids, which are preferentially found in fish oils, to the food is particularly important. Thus, for example, polyunsaturated fatty acids such as docosahexaenoic acid (=DHA, $C22:6^{\Delta 4,7,10,13,16,19}$) or eicosapentaenoic acid (=EPA, $C20:5^{\Delta 5,8,11,14,17}$) are added to infant formula to improve the nutritional value. The unsaturated fatty acid DHA is said to have a positive effect on the development and maintenance of brain functions.

Hereinbelow, polyunsaturated fatty acids are referred to as PUFA, PUFAs, LCPUFA or LCPUFAs (poly unsaturated fatty acids, PUFA, long chain holy unsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as DHA, EPA, arachidonic acid (=ARA, $C20:4^{\Delta 5,8,11,14}$), dihomo-γ-linolenic acid ($C20:3^{\Delta 8,11,14}$) or docosapentaenoic acid (DPA, $C22:5^{\Delta 7,10,13,16,19}$) are not synthesized in oil crops such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω3-fatty acids are said to have a positive effect on the cholesterol level in the blood and thus on the possibility of preventing heart disease. The risk of heart disease, stroke or hypertension can be reduced markedly by adding these ω3-fatty acids to the food. Also, ω3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids (known as the $PG_2$ series) which are formed from ω6-fatty acids generally promote inflammatory reactions, while eicosanoids (known as the $PG_3$ series) from ω3-fatty acids have little or no proinflammatory effect.

Owing to the positive characteristics of the polyunsaturated fatty acids, there has been no lack of attempts in the past to make available genes which are involved in the synthesis of these fatty acids or triglycerides for the production of oils in various organisms with a modified content of unsaturated fatty acids. Thus, WO 91/13972 and its US equivalent describes a Δ9-desaturase. WO 93/11245 claims a Δ15-desaturase and WO 94/11516 a Δ12-desaturase. Further-desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, U.S. Pat. No. 5,614,393, WO 96/21022, WO 00/21557 and WO 99/27111 and the application for the production of fatty acids in transgenic organisms is described in WO 98/46763, WO 98/46764 and WO 98/46765. In this context, the expression of various desaturases and the formation of polyunsaturated fatty acids is also described and claimed in WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are microalgae such as *Phaeodactylum tricornutum*, *Porphiridium* species, *Thraustochytrium* species, *Schizochytrium* species or *Cryptheocodinium* species, ciliates such as *Stylonychia* or *Colpidium*, fungae such as *Mortierella*, *Entomophthora* or *Mucor* and/or mosses such as *Physcomitrella*, *Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible.

However, only limited amounts of the desired polyunsaturated fatty acids such as DPA, EPA or ARA can be produced with the aid of the abovementioned microorganisms, and, depending on the microorganism used, these are generally obtained as fatty acid mixtures of, for example, EPA, DPA and ARA.

A variety of synthetic pathways is being discussed for the synthesis of arachidonic acid, eicosapentaenoic acid (EPA) and docosahexaenoic acid (DHA) (FIG. 1). Thus, EPA or DHA are produced in marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of the above-described pathway by Δ6-desaturase, Δ6-elongase, Δ5-desaturase, Δ5-elongase and Δ4-desaturase is the Sprecher pathway (Sprecher 2000, Biochim. Biophys. Acta 1486:219-231) in mammals. Instead of the Δ4-desaturation, a further elongation step is effected here to give $C_{24}$, followed by a further Δ6-desaturation and finally β-oxidation to give the $C_{22}$ chain length. Thus what is known as Sprecher pathway (see FIG. 1) is, however, not suitable for the production in plants and microorganisms since the regulatory mechanisms are not known.

Depending on their desaturation pattern, the polyunsaturated fatty acids can be divided into two large classes, viz. ω6- or ω3-fatty acids, which differ with regard to their metabolic and functional activities (FIG. 1).

The starting material for the ω6-metabolic pathway is the fatty acid linoleic acid ($18:2^{\Delta 9,12}$) while the ω3-pathway proceeds via linolenic acid ($18:3^{\Delta 9,12,15}$). Linolenic acid is formed by the activity of an ω3-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and ω3-desaturase) and must take up these fatty acids (essential fatty acids) via the food. Starting with these precursors, the physiologically important polyunsaturated fatty acids arachidonic acid (=ARA, $20:4^{\Delta 5,8,11,14}$), an ω6-fatty acid and the two ω3-fatty acids eicosapentaenoic acid (=EPA, $20:5^{\Delta 5,8,11,14,17}$) and docosahexaenoic acid (DHA, $22:6^{\Delta 4,7,10,13,17,19}$) are synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), Entzundungen (Calder 2002, Proc. Nutr. Soc. 61, 345-358) and Arthritis (Cleland and James 2000, J. Rheumatol. 27, 2305-2307).

As regards the physiology of nutrition, it is therefore important, when synthesizing polyunsaturated fatty acids, to achieve a shift between the ω6-synthetic pathway and the ω3-synthetic pathway (see FIG. 1) so that more ω3-fatty acids are produced. The enzymatic activities of a variety of ω3-desaturases which desaturate $C_{18:2}$-, $C_{22:4}$- or $C_{22:5}$-fatty acids have been described in the literature (see FIG. 1). However, none of the desaturases which have been described in terms of biochemistry converts a broad substrate spectrum of the ω6-synthetic pathway into the corresponding fatty acids of the ω3-synthetic pathway.

There is therefore a continuing high demand for an ω3-desaturase which is suitable for the production of ω3-polyunsaturated fatty acids. All known plant and cyanobacterial ω3-desaturases desaturate $C_{18}$-fatty acids with linoleic acid as substrate, but cannot desaturate any $C_{20}$- or $C_{22}$-fatty acids.

The fungus *Saprolegnia dicilina* is known to have an ω3-desaturase [Pereira et al. 2004, Biochem. J. 378(Pt 2):665-71] which can desaturate $C_{20}$-polyunsaturated fatty acids. However, the disadvantage is that this ω3-desaturase cannot desaturate any $C_{18}$- or $C_{22}$-PUFAs such as the important fatty acids $C_{18:2}$-, $C_{22:4}$- or $C_{22:5}$-fatty acids of the ω6-synthetic pathway. A further disadvantage of this enzyme is that it cannot desaturate any fatty acids which are bound to phospholipids. Only the CoA-fatty acid esters are converted.

The elongation of fatty acids, by elongases, by 2 or 4 C atoms is of crucial importance for the production of $C_{20}$- and $C_{22}$-PUFAs, respectively. This process proceeds via 4 steps. The first step is the condensation of malonyl-CoA with the fatty-acid-acyl-CoA by ketoacyl-CoA synthase (KCS, hereinbelow referred to as elongase). This is followed by a reduction step (ketoacyl-CoA reductase, KCR), a dehydration step (dehydratase) and a final reduction step (enoyl-CoA reductase). It has been postulated that the elongase activity affects the specificity and rate of the entire process (Millar and Kunst, 1997 Plant Journal 12:121-131).

There have been a large number of attempts in the past to obtain elongase genes. Millar and Kunst, 1997 (Plant Journal 12:121-131) and Millar et al. 1999, (Plant Cell 11:825-838) describe the characterization of plant elongases for the synthesis of monounsaturated long-chain fatty acids (C22:1) and for the synthesis of very long-chain fatty acids for the formation of waxes in plants ($C_{28}$-$C_{32}$). Descriptions regarding the synthesis of arachidonic acid and EPA are found, for example, in WO0159128, WO0012720, WO02077213 and WO0208401. The synthesis of polyunsaturated $C_{24}$-fatty acids is described, for example, in Tvrdik et al. 2000, JCB 149:707-717 or WO0244320.

No specific elongase has been described to date for the production of DHA (C22:6 n-3) in organisms which do not naturally produce this fatty acid. Only elongases which provide $C_{20}$- or $C_{24}$-fatty acids have been described to date. A Δ5-elongase activity has not been described to date.

Higher plants comprise polyunsaturated fatty acids such as linoleic acid (C18:2) and linolenic acid (C18:3). ARA, EPA and DHA are found not at all in the seed oil of higher plants, or only in miniscule amounts (E. Ucciani: Nouveau Dictionnaire des Huiles Végétales [New Dictionary of Vegetable Oils]. Technique & Documentation—Lavoisier, 1995. ISBN: 2-7430-0009-0). However, the production of LCPUFAs in higher plants, preferably in oil crops such as oilseed rape, linseed, sunflower and soybeans, would be advantageous since large amounts of high-quality LCPUFAs for the food industry, animal nutrition and pharmaceutical purposes might be obtained economically. To this end, it is advantageous to introduce, into oil crops, genes which encode enzymes of the LCPUFA biosynthesis via recombinant methods and to express them therein. These genes encode for example Δ6-desaturases, Δ6-elongases, Δ5-desaturases or Δ4-desaturases. These genes can advantageously be isolated from microorganisms and lower plants which produce LCPUFAs and incorporate them in the membranes or triacylglycerides. Thus, it has already been possible to isolate Δ6-desaturase genes from the moss *Physcomitrella patens* and Δ6-elongase genes from *P. patens* and from the nematode *C. elegans*.

The first transgenic plants which comprise and express genes encoding LCPUFA biosynthesis enzymes and which, as a consequence, produce LCPUFAs were described for the first time, for example, in DE-A-102 19 203 (process for the production of polyunsaturated fatty acids in plants). However, these plants produce LCPUFAs in amounts which require further optimization for processing the oils which are present in the plants.

To make possible the fortification of food and/or of feed with these polyunsaturated fatty acids, there is therefore a great need for a simple, inexpensive process for the production of these polyunsaturated fatty acids, specifically in eukaryotic systems.

BRIEF DESCRIPTION OF THE DRAWINGS

FIG. 1 shows various synthetic pathways for the biosynthesis of DHA (docosahexaenoic acid).

FIG. 2 shows substrate specificity of the Δ5-elongase (SEQ ID NO: 53 for various fatty acids.

FIG. 3 shows reconstitution of DHA biosynthesis in yeast starting from 20:5ω3.

FIG. 4 shows reconstitution of DHA biosynthesis in yeast starting from 18:4ω3.

FIG. 5 shows fatty acid composition (in mol %) of transgenic yeasts which had been transformed with the vectors pYes3-OmELO3 (SEQ ID NO: 53)/pYes2-EgD4 (SEQ ID NO: 39) or pYes3-OmELO3 (SEQ ID NO: 53)/pYes2-EgD4 (SEQ ID NO: 39)+pESCLeu-PtD5 (SEQ ID NO: 5).

FIG. 6 shows feeding experiment for determining the functionality and substrate specificity with yeast strains.

FIG. 7 shows elongation of eicosapentaenoic acid by OtElo1 (SEQ ID NO: 67).

FIG. 8 shows elongation of arachidonic acid by OtElo1 (SEQ ID NO: 67).

FIG. 9 shows expression of TpELO1 (SEQ ID NO: 67) in yeast.

FIG. 10 shows expression of TpELO3 (SEQ ID NO: 45) in yeast.

FIG. 11 shows expression of *Thraustochytrium* Δ5-elongase TL16/pYES2.1 in yeast.

FIG. 12 shows desaturation of linoleic acid (18:2ω6-fatty acid) to give α-linolenic acid (18:3 ω3-fatty acid) by Pi-omega3Des (SEQ ID NO: 87).

FIG. 13 shows desaturation of γ-linolenic acid (18:3 ω6-fatty acid) to give stearidonic acid (18:4 ω3-fatty acid) by Pi-omega3Des (SEQ ID NO: 87).

FIG. 14 shows desaturation of C20:2 ω6-fatty acid to give C20:3 ω3-fatty acid by Pi-omega3Des (SEQ ID NO: 87).

FIG. 15 shows desaturation of C20:3 ω6-fatty acid to give C20:4 ω3-fatty acid by Pi-omega3Des (SEQ ID NO: 87).

FIG. 16 shows desaturation of arachidonic acid (C20:4 ω6-fatty acid) to give eicosapentaenoic acid (C20:5 ω3-fatty acid) by Pi-omega3Des (SEQ ID NO: 87).

FIG. 17 shows desaturation of docosatetraenoic acid (C22:4 ω6-fatty acid) to give docosapentaenoic acid (C22:5 ω3-fatty acid) by Pi-omega3Des (SEQ ID NO: 87).

FIG. 18 shows substrate specificity of Pi-omega3Des (SEQ ID NO: 87) for various fatty acids.

FIG. 19 shows desaturation of phospholipid-bound arachidonic acid to EPA by Pi-Omega3Des (SEQ ID NO: 87).

FIG. 20 shows conversion by OtDes6.1 (SEQ ID NO: 89) of linoleic acid (arrow) into γ-linolenic acid (γ-18:3).

FIG. 21 shows conversion of linoleic acid and α-linolenic acid (A and C) and reconstitution of the ARA and EPA synthetic pathways, respectively, in yeast (B and D) in the presence of OtD6.1 (SEQ ID NO: 89).

FIG. 22 shows expression of ELO(XI) (SEQ ID NO: 117) in yeast.

FIG. 24 shows elongation of eicosapentaenoic acid by OtElo1 (SEQ ID NO: 67) (B) and OtElo1.2 (SEQ ID NO: 113) (D), respectively. The controls (A, C) do not show the elongation product (22:5ω3).

FIG. 25 shows elongation of arachidonic acid by OtElo1 (SEQ ID NO: 67) (B) and OtElo1.2 (SEQ ID NO: 113) (D), respectively. The controls (A, C) do not show the elongation product (22:4ω6).

FIG. 26 shows elongation of 20:5n-3 by the elongase At3g06470 (SEQ ID NO:137).

FIG. 27 shows substrate specificity of the *Xenopus* Elongase (A), the *Ciona* Elongase (B) and the *Oncorhynchus* Elongase (C).

FIG. 28 shows substrate specificity of the *Ostreococcus* Δ5-elongase (A), the *Ostreococcus* Δ6-elongase (B), the *Thalassiosira* Δ5-elongase (C) and *Thalassiosira* Ostreococcus Δ6-elongase (D).

FIG. 29 shows expression of the *Phaeodactylum tricornutum* Δ6-elongase (PtELO6; SEQ ID NO: 183) in yeast. A) shows the elongation of the C18:3$^{Δ6,9,12}$-fatty acid and B) the elongation of the C18:4$^{Δ6,9,12,15}$-fatty acid.

FIG. 30 shows the substrate specificity of PtELO6 (SEQ ID NO: 183) with regard to the substrates fed.

DETAILED DESCRIPTION OF THE INVENTION

Figure 23:
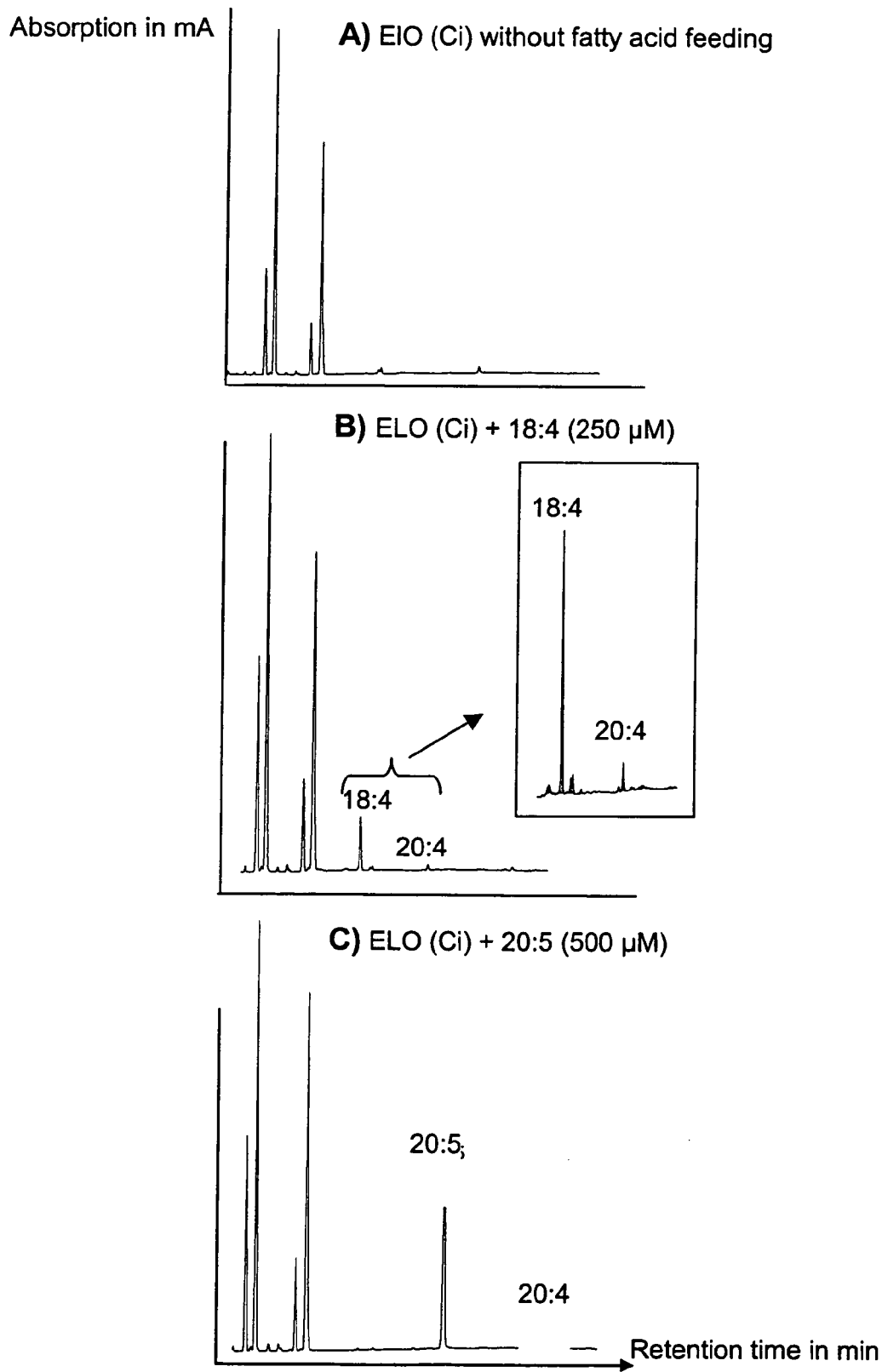
FIG. 23 shows the substrate specificity of ELO (Ci) (SEQ ID NO: 119) after expression and after feeding various fatty acids.

It was therefore an object to provide further genes or enzymes which are suitable for the synthesis of LCPUFAs, specifically genes with Δ5-elongase, Δ5-desaturase, Δ4-desaturase, Δ12-desaturase or Δ6-desaturase activity, for the production of polyunsaturated fatty acids. A further object of the present invention was the provision of genes or enzymes which make possible a shift from the ω6-fatty acids to the ω3-fatty acids. Another object was to develop a process for the production of polyunsaturated fatty acids in an organism, advantageously in a eukaryotic organism, preferably in a plant or a microorganism. This object was achieved by the process according to the invention for the production of compounds of the formula I

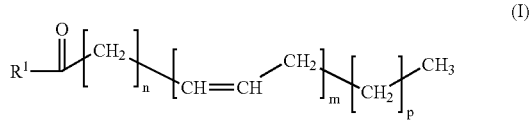

(I)

in transgenic organisms with a content of at least 1% by weight of these compounds based on the total lipid content of the transgenic organism, which comprises the following process steps:

a) introducing, into the organism, at least one nucleic acid sequence which encodes a Δ9-elongase and/or a Δ6-desaturase activity, and
b) introducing, into the organism, at least one nucleic acid sequence which encodes a Δ8-desaturase and/or a Δ6-elongase activity, and
c) introducing, into the organism, at least one nucleic acid sequence which encodes a Δ5-desaturase activity, and
d) introducing, into the organism, at least one nucleic acid sequence which encodes a Δ5-elongase activity, and
e) introducing, into the organism, at least one nucleic acid sequence which encodes a Δ4-desaturase activity, and
where the variables and substituents in formula I have the following meanings:
R$^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

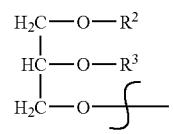

(II)

in which
R$^2$=hydrogen, lysophosphatidyl choline, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl,
R$^3$=hydrogen, saturated or unsaturated $C_2$-$C_{24}$-alkylcarbonyl, or R$^2$ and R$^3$ independently of one another are a radical of the formula Ia:

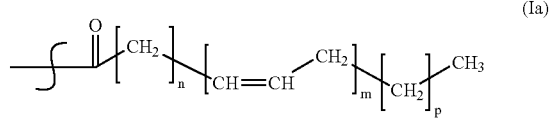

(Ia)

in which
n=2, 3, 4, 5, 6, 7 or 9, m=2, 3, 4, 5 or 6 and p=0 or 3.
R$^1$ in the formula I is hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

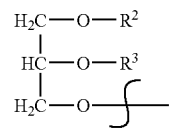

(II)

The abovementioned radicals of R$^1$ are always bonded to the compounds of the formula I in the form of their thioesters.

R$^2$ in the formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially preferred radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

$R^3$ in the formula II is hydrogen, saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl-, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially preferred radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The polyunsaturated fatty acids produced in the process according to the invention advantageously comprise at least two, advantageously three, four, five or six, double bonds. The fatty acids especially advantageously comprise four, five or six double bonds. Fatty acids produced in the process advantageously have 18, 20 or 22 C atoms in the fatty acid chain; the fatty acids preferably comprise 20 or 22 carbon atoms in the fatty acid chain. Saturated fatty acids are advantageously reacted to a minor degree, or not at all, by the nucleic acids used in the process. To a minor degree is to be understood as meaning that the saturated fatty acids are reacted with less than 5% of the activity, advantageously less than 3%, especially advantageously with less than 2%, very especially preferably with less than 1, 0.5, 0.25 or 0.125% of the activity in comparison with polyunsaturated fatty acids. These fatty acids which have been produced can be produced in the process as a single product or be present in a fatty acid mixture.

The nucleic acid sequences used in the process according to the invention are isolated nucleic acid sequences which encode polypeptides with Δ9-elongase, Δ6-desaturase, Δ8-desaturase, Δ6-elongase, Δ5-desaturase, Δ5-elongase and/or Δ4-desaturase activity.

Nucleic acid sequences which are advantageously used in the process according to the invention are those which encode polypeptides with Δ9-elongase, Δ6-desaturase, Δ8-desaturase, Δ6-elongase, Δ5-desaturase, Δ5-elongase or Δ4-desaturase activity, selected from the group consisting of:

a) a nucleic acid sequence with the sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183, or b) nucleic acid sequences which, as the result of the degeneracy of the genetic code, can be derived from the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, SEQ ID NO: 114, SEQ ID NO: 118, SEQ ID NO: 120, SEQ ID NO: 132 or SEQ ID NO: 134, SEQ ID NO: 136, SEQ ID NO: 138 or SEQ ID NO: 184, or c) derivatives of the nucleic acid sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183, which encode polypeptides with at least 40% identity at the amino acid level with SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, SEQ ID NO: 114, SEQ ID NO: 118, SEQ ID NO: 120, SEQ ID NO: 132 or SEQ ID NO: 134, SEQ ID NO: 136, SEQ ID NO: 138 or SEQ ID NO: 184 or and which have Δ9-elongase, Δ6-desaturase, Δ8-desaturase, Δ6-elongase, Δ5-desaturase, Δ5-elongase or Δ4-desaturase activity.

The substituents $R^2$ or $R^3$ in the formulae I and II are advantageously and independently of one another saturated or unsaturated $C_{18}$-$C_{22}$-alkylcarbonyl, especially advantageously they are, independently of one another, unsaturated $C_{18}$-, $C_{20}$- or $C_{22}$-alkylcarbonyl with at least two double bonds.

A preferred embodiment of the method is characterized in that a nucleic acid sequence which encodes polypeptides with ω3-desaturase activity, selected from the group consisting of:
a) a nucleic acid sequence with the sequence shown in SEQ ID NO: 87 or SEQ ID NO: 105, or b) nucleic acid sequences which, as the result of the degeneracy of the genetic code, can be derived from the amino acid sequence shown in SEQ ID NO: 88 or SEQ ID NO: 106, or c) derivatives of the nucleic acid sequence shown in SEQ ID NO: 87 or SEQ ID NO: 105 which encode polypeptides with at least 60% identity at the amino acid level with SEQ ID NO: 88 or SEQ ID NO: 106 and which have ω3-desaturase activity.

is additionally introduced into the organism.

In a further preferred embodiment, the process comprises the additional introduction, into the organism, of a nucleic acid sequence which encodes polypeptides with Δ12-desaturase activity, selected from the group consisting of:
a) a nucleic acid sequence with the sequence shown in SEQ ID NO: 107 or SEQ ID NO: 109 or
b) nucleic acid sequences which, as the result of the degeneracy of the genetic code, can be derived from the amino acid sequence shown in SEQ ID NO: 108 or SEQ ID NO: 110, or
c) derivatives of the nucleic acid sequence shown in SEQ ID NO: 107 or SEQ ID NO: 109 which encode polypeptides with at least 60% identity at the amino acid level with SEQ ID NO: 108 or SEQ ID NO: 110 and which have Δ12-desaturase activity.

These abovementioned Δ12-desaturase sequences can be used together with the nucleic acid sequences used in the process and which encode Δ9-elongases, Δ6-desaturases, Δ8-desaturases, Δ6-elongases, Δ5-desaturases, Δ5-elongases and/or Δ4-desaturases, alone or in combination with the ω3-desaturase sequences.

Table 1 shows the nucleic acid sequences, the organism of origin and the sequence ID number.

| No. | Organism | Activity | Sequence number |
|---|---|---|---|
| 1. | Euglena gracilis | Δ8-desaturase | SEQ ID NO: 1 |
| 2. | Isochrysis galbana | Δ9-elongase | SEQ ID NO: 3 |
| 3. | VPhaedodactylum tricornutum | Δ5-desaturase | SEQ ID NO: 5 |
| 4. | VCeratodon pupureus | Δ5-desaturase | SEQ ID NO: 7 |
| 5. | Physcomitrella patens | Δ5-desaturase | SEQ ID NO: 9 |
| 6. | Thraustrochytrium sp. | Δ5-desaturase | SEQ ID NO: 11 |
| 7. | Mortierella alpina | Δ5-desaturase | SEQ ID NO: 13 |
| 8. | Caenorhabditis elegans | Δ5-desaturase | SEQ ID NO: 15 |
| 9. | Borago officinalis | Δ6-desaturase | SEQ ID NO: 17 |
| 10. | VCeratodon purpureus | Δ6-desaturase | SEQ ID NO: 19 |
| 11. | Phaeodactylum tricornutum | Δ6-desaturase | SEQ ID NO: 21 |
| 12. | Physcomitrella patens | Δ6-desaturase | SEQ ID NO: 23 |
| 13. | Caenorhabditis elegans | Δ6-desaturase | SEQ ID NO: 25 |
| 14. | Physcomitrella patens | Δ6-elongase | SEQ ID NO: 27 |
| 15. | Thraustrochytrium sp. | Δ6-elongase | SEQ ID NO: 29 |
| 16. | Phytopthera infestans | Δ6-elongase | SEQ ID NO: 31 |
| 17. | Mortierella alpina | Δ6-elongase | SEQ ID NO: 33 |
| 18. | Mortierella alpina | Δ6-elongase | SEQ ID NO: 35 |
| 19. | Caenorhabditis elegans | Δ6-elongase | SEQ ID NO: 37 |
| 20. | Euglena gracilis | Δ4-desaturase | SEQ ID NO: 39 |
| 21. | Thraustrochytrium sp. | Δ4-desaturase | SEQ ID NO: 41 |
| 22. | Thalassiosira pseudonana | Δ5-elongase | SEQ ID NO: 43 |
| 23. | Thalassiosira pseudonana | Δ6-elongase | SEQ ID NO: 45 |
| 24. | Crypthecodinium cohnii | Δ5-elongase | SEQ ID NO: 47 |
| 25. | Crypthecodinium cohnii | Δ5-elongase | SEQ ID NO: 49 |
| 26. | Oncorhynchus mykiss | Δ5-elongase | SEQ ID NO: 51 |
| 27. | Oncorhynchus mykiss | Δ5-elongase | SEQ ID NO: 53 |
| 28. | Thalassiosira pseudonana | Δ5-elongase | SEQ ID NO: 59 |
| 29. | Thalassiosira pseudonana | Δ5-elongase | SEQ ID NO: 61 |
| 30. | Thalassiosira pseudonana | Δ5-elongase | SEQ ID NO: 63 |
| 31. | Thraustrochytrium aureum | Δ5-elongase | SEQ ID NO: 65 |
| 32. | Ostreococcus tauri | Δ5-elongase | SEQ ID NO: 67 |
| 33. | Ostreococcus tauri | Δ6-elongase | SEQ ID NO: 69 |
| 34. | Primula farinosa | Δ6-desaturase | SEQ ID NO: 71 |
| 35. | Primula vialii | Δ6-desaturase | SEQ ID NO: 73 |
| 36. | Ostreococcus tauri | Δ5-elongase | SEQ ID NO: 75 |

-continued

| No. | Organism | Activity | Sequence number |
|---|---|---|---|
| 37. | Ostreococcus tauri | Δ5-elongase | SEQ ID NO: 77 |
| 38. | Ostreococcus tauri | Δ5-elongase | SEQ ID NO: 79 |
| 39. | Ostreococcus tauri | Δ6-elongase | SEQ ID NO: 81 |
| 40. | Thraustrochytrium sp. | Δ5-elongase | SEQ ID NO: 83 |
| 41. | Thalassiosira pseudonana | Δ5-elongase | SEQ ID NO: 85 |
| 42. | Phytopthora infestans | ω3-desaturase | SEQ ID NO: 87 |
| 43. | Ostreococcus tauri | Δ6-desaturase | SEQ ID NO: 89 |
| 44. | Ostreococcus tauri | Δ5-desaturase | SEQ ID NO: 91 |
| 45. | Ostreococcus tauri | Δ5-desaturase | SEQ ID NO: 93 |
| 46. | Ostreococcus tauri | Δ4-desaturase | SEQ ID NO: 95 |
| 47. | Thalassiosira pseudonana | Δ6-desaturase | SEQ ID NO: 97 |
| 48. | Thalassiosira pseudonana | Δ5-desaturase | SEQ ID NO: 99 |
| 49. | Thalassiosira pseudonana | Δ5-desaturase | SEQ ID NO: 101 |
| 50. | Thalassiosira pseudonana | Δ4-desaturase | SEQ ID NO: 103 |
| 51. | Thalassiosira pseudonana | ω3-desaturase | SEQ ID NO: 105 |
| 52. | Ostreococcus tauri | Δ12-desaturase | SEQ ID NO: 107 |
| 53. | Thalassiosira pseudonana | Δ12-desaturase | SEQ ID NO: 109 |
| 54. | Ostreococcus tauri | Δ6-elongase | SEQ ID NO: 111 |
| 55. | Ostreococcus tauri | Δ5-elongase | SEQ ID NO: 113 |
| 56. | Xenopus laevis (BC044967) | Δ5-elongase | SEQ ID NO: 117 |
| 57. | Ciona intestinalis (AK112719) | Δ5-elongase | SEQ ID NO: 119 |
| 58. | Euglena gracilis | Δ5-elongase | SEQ ID NO: 131 |
| 59. | Euglena gracilis | Δ5-elongase | SEQ ID NO: 133 |
| 60. | Arabidopsis thaliana | Δ5-elongase | SEQ ID NO: 135 |
| 61. | Arabidopsis thaliana | Δ5-elongase | SEQ ID NO: 137 |
| 62. | Phaeodactylum tricornutum | Δ6-elongase | SEQ ID NO: 183 |

The polyunsaturated fatty acids produced in the process are advantageously bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms, preferred are long-chain fatty acids more preferably long-chain polyunsaturated fatty acids with 18, 20 and/or 22 C atoms.

The process according to the invention advantageously yields fatty acid esters with polyunsaturated $C_{18}$-, $C_{20}$- and/or $C_{22}$-fatty acid molecules with at least two double bonds in the fatty acid ester, advantageously with at least three, four, five or six double bonds in the fatty acid ester, especially advantageously with at least five or six double bonds in the fatty acid ester and advantageously leads to the synthesis of linoleic acid (=LA, $C18:2^{\Delta9,12}$), γ-linolenic acid (=GLA, $C18:3^{\Delta6,9,12}$), stearidonic acid (=SDA, $C18:4^{\Delta6,9,12,15}$), dihomo-γ-linolenic acid (=DGLA, $20:3^{\Delta8,11,14}$), ω3-eicosatetraenoic acid (=ETA, $C20:4^{\Delta5,8,11,14}$), arachidonic acid (ARA, $C20:4^{\Delta5,8,11,14}$), eicosapentaenoic acid (EPA, $C20:5^{\Delta5,8,11,14,17}$), ω6-docosapentaenoic acid ($C22:5^{\Delta4,7,10,13,16}$), ω6-docosatetraenoic acid ($C22:4^{\Delta7,10,13,16}$), ω3-docosapentaenoic acid (=DPA, $C22:5^{\Delta7,10,13,16,19}$), docosahexaenoic acid (=DHA, $C22:6^{\Delta4,7,10,13,16,19}$) or mixtures of these, preferably ARA, EPA and/or DHA. ω3-Fatty acids such as EPA and/or DHA are very especially preferably produced.

The fatty acid esters with polyunsaturated $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters which comprise the polyunsaturated fatty acids with at least two, three, four, five or six, preferably five or six double bonds, from the organisms which have been used for the preparation of the fatty acid esters; preferably, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPU-FAs produced in a content of at least 3% by weight, advantageously at least 5% by weight, preferably at least 8% by weight, especially preferably at least 10% by weight, most preferably at least 15% by weight, based on the total fatty acids in the transgenic organisms, preferably in a transgenic plant. In this context, it is advantageous to convert $C_{18}$- and/or $C_{20}$-fatty acids which are present in the host organisms to at least 10%, preferably to at least 20%, especially preferably to at least 30%, most preferably to at least 40% to give the corresponding products such as DPA or DHA, to mention just two examples. The fatty acids are advantageously produced in bound form. These unsaturated fatty acids can, with the aid of the nucleic acids used in the process according to the invention, be positioned at the sn1, sn2 and/or sn3 position of the advantageously produced triglycerides. Since a plurality of reaction steps are performed by the starting compounds linoleic acid (C18:2) and linolenic acid (C18:3) in the process according to the invention, the end products of the process such as, for example, arachidonic acid (ARA), eicosapentaenoic acid (EPA) ω6-docosapentaenoic acid or DHA are not obtained as absolutely pure products; minor traces of the precursors are always present in the end product. If, for example, both linoleic acid and linolenic acid are present in the starting organism and the starting plant, the end products such as ARA, EPA or DHA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA, EPA or only DHA, bound or as free acids, are produced as end products in a transgenic plant owing to the process according to the invention. If the compounds ARA, EPA and DHA are produced simultaneously, they are advantageously produced in a ratio of at least 1:1:2 (EPA:ARA:DHA), advantageously of at least 1:1:3, preferably 1:1:4, especially preferably 1:1:5.

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c, 11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. In a further preferred form of the invention, these abovementioned fatty acids occur to less than 0.9%, 0.8%, 0.7%, 0.6% or 0.5%, especially preferably to less than 0.4%, 0.3%, 0.2%, 0.1%, based on the total fatty acids. The fatty acid esters or fatty acid mixtures produced by the process according to the invention advantageously comprise less than 0.1%, based on the total fatty acids, and/or no butyric acid, no cholesterol, no clupanodonic acid (=docosapentaenoic acid, $C22:5^{\Delta 4,8,12,15,21}$) and no nisinic acid (tetracosahexaenoic acid, $C23:6^{\Delta 3,8,12,15,18,21}$).

Owing to the nucleic acid sequences, or the nucleic acid sequences used in the process according to the invention, an increase in the yield of polyunsaturated fatty acids of at least 50%, advantageously of at least 80%, especially advantageously of at least 100%, very especially advantageously of at least 150%, in comparison with the nontransgenic starting organism, for example a yeast, an alga, a fungus or a plant such as *arabidopsis* or linseed can be obtained when the fatty acids are detected by GC analysis (see examples).

Chemically pure polyunsaturated fatty acids or fatty acid compositions can also be synthesized by the processes described above. To this end, the fatty acids or the fatty acid compositions are isolated from the organisms, such as the microorganisms or the plants or the culture medium in or on which the organisms have been grown, or from the organism and the culture medium, in the known manner, for example via extraction, distillation, crystallization, chromatography or a combination of these methods. These chemically pure fatty acids or fatty acid compositions are advantageous for applications in the food industry sector, the cosmetic sector and especially the pharmacological industry sector.

Suitable organisms for the production in the process according to the invention are, in principle, any organisms such as microorganisms, nonhuman animals or plants.

Plants which are suitable are, in principle, all those plants which are capable of synthesizing fatty acids, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Euglenaceae, Prasinophyceae or vegetable plants or ornamentals such as *Tagetes*.

Examples which may be mentioned are the following plants selected from the group consisting of: Adelotheciaceae such as the genera *Physcomitrella*, for example the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus columa* [hazelnut], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae, such as the genera *Amphora, Cymbella, Okedenia, Phaeodactylum, Reimeria*, for example the genus and species *Phaeodactylum tricomutum*, Ditrichaceae, such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium altemifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euglenaceae, such as the genera *Ascoglena, Astasia, Colacium, Cyclidiopsis, Euglena, Euglenopsis, Hyalaphacus, Khawkinea, Lepocinclis, Phacus, Strombomonas, Trachelomonas*, for example the genus and species *Euglena gracilis*; Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae, such as the genera *Pisum, Albizia, Cathormion, Feuillea, Inga, Pithecolobium, Acacia, Mimosa, Medicajo, Glycine, Dolichos, Phaseolus*, soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbeck, Feuilleea lebbeck, Mimosa lebbeck, Mimosa speciosa, Medicago sativa, Medicago falcata, Medicago varia* [alfalfa] *Glycine max Dolichos soja, Glycine gracilis, Glycine hispida, Phaseolus max, Soja hispida* or *Soja max* [soybean], Funariaceae, such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygromretrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *senratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elaeis*, for example the genus and species *Elaeis guineensis* [oil palm], Papaveraceae, such as, for example, the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata*

[cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondi, Holcus bicolor, Holcus sorghum, Sorghum aethiopicum, Sorghum arundinaceum, Sorghum caffrorum, Sorghum cemuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize] *Triticum aestivum, Triticum durum, Triticum turgidum, Triticum hybemum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*: for example the genus and species *Porphyridium cruentum*, Proteaceae, such as the genus *Macadamia*, for example the genus and species *Macadamia intergrifolia* [macadamia], Prasinophyceae, such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae, such as the genus *Coffea*, for example the genera and species *Coffea* spp., *Coffea arabica, Coffea canephora* or *Coffea liberica* [coffee], Scrophulariaceae, such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [verbascum], Solanaceae, such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffi, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant] *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Advantageous microorganisms are, for example, fungi selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Sacharomycetaceae, Saprolegniaceae, Schizosacharomycetaceae, Sodariaceae or Tuberculariaceae.

Examples of microorganisms which may be mentioned are those from the groups Choanephoraceae, such as the genera *Blakeslea, Choanephora*, for example the genera and species *Blakeslea trispora, Choanephora cucurbitarum, Choanephora infundibulifera* var. *cucurbitarum*, Mortierellaceae, such as the genus *Mortierella*, for example the genera and species *Mortierella isabellina, Mortierella polycephala, Mortierella ramanniana, Mortierella vinacea, Mortierella zonata*, Pythiaceae, such as the genera *Phytium, Phytophthora*, for example the genera and species *Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae* var. *parasitica, Phytophthora palmivora, Phytophthora parasitica, Phytophthora syringae*, Saccharomycetaceae, such as the genera *Hansenula, Pichia, Saccharomyces, Saccharomycodes, Yarrowia*, for example the genera and species *Hansenula anomala, Hansenula californica, Hansenula canadensis, Hansenula capsulata, Hansenula ciferrii, Hansenula glucozyma, Hansenula henricii, Hansenula holstii, Hansenula minuta, Hansenula nonfermentans, Hansenula philodendri, Hansenula polymorpha, Hansenula saturnus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia cifemmi, Pichia farinosa, Pichia fermentans, Pichia finlandica, Pichia glucozyma, Pichia guilliermondii, Pichia haplophila, Pichia henricii, Pichia holstii, Pichiajadinii, Pichia lindnerii, Pichia membranaefaciens, Pichia methanolica, Pichia minuta* var. *minuta, Pichia minuta* var. *nonfermentans, Pichia norvegensis, Pichia ohmeri, Pichia pastoris, Pichia philodendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceti, Saccharomyces bailii, Saccharomyces bayanus, Saccharomyces bisporus, Saccharomyces capensis, Saccharomyces carlsbergensis, Saccharomyces cerevisiae, Saccharomyces cerevisiae* var. *ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii, Yarrowia lipolytica*, Schizosacharomycetaceae such as the genera *Schizosaccharomyces* e.g. the species *Schizosaccharomyces japonicus* var. *japonicus, Schizosaccharomyces japonicus* var. *versatilis, Schizosaccharomyces malidevorans, Schizosaccharomyces octosporus, Schizosaccharomyces pombe* var. *malidevorans, Schizosaccharomyces pombe* var. *pombe*, Thraustochytriaceae such as the genera *Althornia, Aplanochytrium, Japonochytrium, Schizochytrium, Thraustochytrium* e.g. the species *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium

*aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense*.

Further advantageous microorganisms are, for example, bacteria selected from the group of the families Bacillaceae, Enterobacteriacae or Rhizobiaceae.

Examples which may be mentioned are the following microorganisms selected from the group consisting of: Bacillaceae, such as the genus *Bacillus*, for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia*, for example the genera and species *Citrobacter amalonaticus, Citrobacter diversus, Citrobacter freundii, Citrobacter genomo* species, *Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia colimutabile, Escherichia fergusonii, Escherichia hermannii, Escherichia* sp., *Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizobiaceae, such as the genera *Agrobacterium, Carbophilus, Chelatobacter, Ensifer, Rhizobium, Sinorhizobium*, for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense*.

Further examples of advantageous microorganisms for the process according to the invention are protists or diatoms selected from the group of the families Dinophyceae, Turaniellidae or Oxytrichidae, such as the genera and species: *Crypthecodinium cohnii, Phaeodactylum tricornutum, Stylonychia mytilus, Stylonychia pustulata, Stylonychia putrina, Stylonychia notophora, Stylonychia* sp., *Colpidium campylum* or *Colpidium* sp.

Those which are advantageously applied in the process according to the invention are transgenic organisms such as fungi, such as *mortierella* or *thraustrochytrium*, yeasts such as *Saccharomyces* or *Schizosaccharomyces*, mosses such as *Physcomitrella* or *Ceratodon*, nonhuman animals such as *Caenorhabditis*, algae such as *Nephroselmis, Pseudoscourfielda, Prasinococcus, Scherffelia, Tetraselmis, Mantoniella, Ostreococcus, Crypthecodinium* or *Phaeodactylum* or plants such as dicotyledonous or monocotyledonous plants. Organisms which are especially advantageously used in the process according to the invention are organisms which belong to the oil-producing organisms, that is to say which are used for the production of oil, such as fungi, such as *Mortierelia* or *Thraustochytrium*, algae such as *Nephroselmis, Pseudoscourfielda, Prasinococcus, Scherffelia, Tetraselmis, Mantoniella, Ostreococcus, Crypthecodinium, Phaeodactylum*, or plants, in particular plants, preferably oilseed or oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, *verbascum*, thistle, wild roses, hazelnut, almond, macadamia, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula*, *Punica*, evening primrose, pumpkin/squash, linseed, soybean, borage, trees (oil palm, coconut). Especially preferred are plants which are high in C18:2- and/or C18:3-fatty acids, such as sunflower, safflower, tobacco, *verbascum*, sesame, cotton, pumpkin/squash, poppy, evening primrose, walnut, linseed, hemp or thistle. Very especially preferred plants are plants such as safflower, sunflower, poppy, evening primrose, walnut, linseed or hemp.

It is therefore advantageous for the above-described method according to the invention additionally to introduce, into the organism, further nucleic acids which encode enzymes of the fatty acid or lipid metabolism, in addition to the nucleic acids introduced in process step (a) to (d) and to the optionally introduced nucleic acid sequences which encode the ω3-desaturases.

In principle, all genes of the fatty acid or lipid metabolism can be used in the process for the production of polyunsaturated fatty acids, advantageously in combination with the Δ5-elongase(s), Δ6-elongase(s) and/or ω3-desaturases [for the purposes of the present invention, the plural is understood as comprising the singular and vice versa]. Genes of the fatty acid or lipid metabolism selected from the group consisting of acyl-CoA dehydrogenase(s), acyl-ACP [=acyl carrier protein] desaturase(s), acyl-ACP thioesterase(s), fatty acid acyl transferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) are advantageously used in combination with the Δ5-elongase, Δ6-elongase and/or ω3-desaturase. Genes selected from the group of the Δ4-desaturases, Δ5-desaturases, Δ6-desaturases, Δ8-desaturases, Δ9-desaturases, Δ12-desaturases, Δ6-elongases or Δ9-elongases are especially preferably used in combination with the above genes for the Δ5-elongase, Δ6-elongase and/or ω3-desaturase, it being possible to use individual genes or a plurality of genes in combination.

In comparison with the human elongases or elongases from nonhuman animals such as those from *Oncorhynchus*, *Xenopus* or *Ciona*, the Δ5-elongases according to the invention have the advantageous property that they do not elongate $C_{22}$-fatty acids to the corresponding $C_{24}$-fatty acids. Furthermore, they advantageously do not convert fatty acids with a double bond in Δ6-position, as are converted by the human elongases or the elongases from nonhuman animals. Especially advantageous Δ5-elongases preferentially only convert unsaturated $C_{20}$-fatty acids. These advantageous Δ5-elongases have some putative transmembrane helices (5-7). Advantageously, only $C_{20}$-fatty acids with one double bond in Δ5-position are converted, with ω3-$C_{20}$-fatty acids being preferred (EPA). In a preferred embodiment of the invention, they furthermore have the property that they advantageously have no, or only relatively little, Δ6-elongase activity, in addition to the Δ5-elongase activity. In contrast, the human elongases or elongases from nonhuman animals have approximately the same activity on fatty acids with a Δ6- or Δ5-double bond. These advantageous elongases are referred to as what are known as monofunctional elongases. The human elongases or the elongases from nonhuman animals, in contrast, are referred to as multifunctional elongases which, in addition to the abovementioned substrates, also convert monounsaturated $C_{16}$- and $C_{18}$-fatty acids, for example with a Δ9- or Δ11-double bond. In a yeast feeding test in which EPA had been added to the yeasts to act as substrate, the monofunctional elongases advantageously convert at least 15% of the added EPAs into docosapentaenoic acid (DPA, $C22:5^{\Delta 7,10,13,16,19}$), advantageously at least 20% by weight, especially advantageously at least 25% by weight. If γ-linolenic acid (=GLA, $C18:3^{\Delta 6,9,12}$) is added as substrate, this substance is advantageously not elongated at all. $C18:3^{\Delta 5,9,12}$ is likewise not elongated. In another advantageous embodiment, less than 60% by weight, advantageously less than 55% by weight, especially preferably less than 50% by weight, especially advantageously less than 45% by weight, very especially advantageously less than 40% by weight, of the added GLA are converted into dihomo-γ-linolenic acid (=$C20:3^{\Delta 8,11,14}$). In a further, very especially preferred embodiment of the Δ5-elongase activity according to the invention, GLA is not converted.

FIGS. 27 and 28 show the measured substrate specificities of the different elongases. FIG. 27 shows the specifities of the multifunctional elongases of *Xenopus laevis* (FIG. 27 A), *Ciona intestinalis* (FIG. 27 B) and *Oncorhynchus mykiss* (FIG. 27 C). All of these elongases convert a broad spectrum of substrates. In the method according to the invention, this can give rise to by-products which must be converted by further enzymatic activities. This is why these enzymes are less preferred in the method according to the invention. The preferred monofunctional elongases and their substrate specificity are shown in FIG. 28. FIG. 28 A shows the specificity of the *Ostreococcus tauri* Δ5-elongase. This enzyme only converts fatty acids with a double bond in the Δ5-position. Advantageously, only C20-fatty acids are converted. A similarly high substrate specificity is shown by the *Thalassiosira pseudonana* Δ5-elongase (FIG. 28 C). Both the *Ostreococcus tauri* Δ6-elongase (FIG. 28 B) and that of *Thalassiosira pseudonana* (FIG. 28 D) advantageously only convert fatty acids with a double bond in the Δ6-position. Advantageously, only C18-fatty acids are converted. The Δ5-elongases from *Arabidopsis thaliana* and *Euglena gracilis* are also distinguished by their specificity.

Advantageous Δ6-elongases according to the invention are likewise distinguished by high specificity, that is to say that $C_{18}$-fatty acids are elongated by preference. Advantageously, they convert fatty acids with a double bond in the Δ6-position. Especially advantageous Δ6-elongases advantageously convert $C_{18}$-fatty acids with three or four double bonds in the molecule, which fatty acids must comprise one double bond in the Δ6-position. In a preferred embodiment of the invention, they furthermore have the characteristic that they advantageously have no, or only relatively little, Δ5-elongase activity, besides the Δ6-elongase activity. In contrast, the human elongases or elongases from nonhuman animals have approximately the same activity on fatty acids with a Δ6- or Δ5-double bond. These advantageous elongases are referred to as what are known as monofunctional elongases. As described above, the human elongases or the elongases from nonhuman animals are referred to, in contrast, as multifunctional elongases which, besides the abovementioned substrates, also convert monounsaturated $C_{16}$- and $C_{18}$-fatty acids, for example with Δ9- or Δ11-double bond. In a yeast feeding test in which EPA had been added to the yeast to act as substrate, the monofunctional elongases advantageously convert at least 10% by weight of the added α-linolenic acid (=ALA, $C18:3^{\Delta 9,12,15}$) or at least 40% by weight of the added γ-linolenic acid (=GLA, $C18:3^{\Delta 6,9,12}$), advantageously at least 20% by weight or 50% by weight, especially advantageously at least 25% by weight or 60% by weight. It is especially advantageous that $C18:4^{\Delta 6,9,12,15}$ (stearidonic acid) is also elongated. In this context, SDA is converted to at least 40% by weight, advantageously to at least 50% by weight, especially advantageously to at least 60% by weight, very especially advantageously to at least 70% by weight. Especially advantageous Δ6-elongases show no or only very little activity (conversion rate less than 0.1% by weight) toward the following substrates: $C18:1^{\Delta 6}$, $C18:1^{\Delta 9}$, $C18:1^{\Delta}$, $C20:2^{\Delta 14}$, $C20:3^{\Delta 11,14,17}$, $C20:3^{\Delta 8,11,14}$, $C20:4^{\Delta 5,8,11,14}$, $C20:5^{\Delta 5,8,11,14,17}$ or $C22:4^{\Delta 7,10,13,16}$.

FIGS. 29 and 30 and table 18 show the measured substrate specificities of the various elongases.

In contrast with the known ω3-desaturase, the ω3-desaturase according to the invention has the advantageous characteristic that it is capable of desaturating a broad spectrum of ω6-fatty acids; $C_{20}$- and $C_{22}$-fatty acids such as $C_{20:2}$-, $C_{20:3}$-, $C_{20:4}$-, $C_{22:4}$- or $C_{22:5}$-fatty acids are desaturated by preference. However, the shorter $C_{18}$-fatty acids such as $C_{18:2}$- or $C_{18:3}$-fatty acids are also advantageously desaturated. Owing to these characteristics of the ω3-desaturase, it is advantageously possible to shift the fatty acid spectrum within an organism, advantageously within a plant or a fungus, from the ω6-fatty acids toward the ω3-fatty acids. Preferably, the ω3-desaturase according to the invention desaturates $C_{20}$-fatty acids. Within the organism, these fatty acids from the existing fatty acid pool are converted to at least 10%, 15%, 20%, 25% or 30% into the corresponding ω3-fatty acids. The activity of the enzyme ω3-desaturase toward the $C_{18}$-fatty acids is lower by a factor of 10, i.e. only approximately 1.5 to 3% of the fatty acids present in the fatty acid pool are converted into the corresponding ω3-fatty acids. Preferred substrate of the ω3-desaturase according to the invention are the ω6-fatty acids which are bound in phospholipids. FIG. 19 demonstrates clearly with reference to the desaturation of dihomo-γ-linolenic acid [$C_{20:4}^{\Delta 8,11,14}$], that, during the desaturation process, the ω3-desaturase advantageously does not distinguish between fatty acids which are bound at the sn1 position or at the sn2 position. Both fatty acids bound at the sn1 position and fatty acids bound at the sn2 position in the phospholipids are desaturated. Furthermore, it is advantageous that the ω3-desaturase converts a broad range of phospholipids such as phosphatidylcholine (=PC), phosphatidylinositol (=PIS) or phosphatidylethanolamine (=PE). Finally, desaturation products can also be found in the neutral lipids (=NL), that is to say in the triglycerides.

In comparison with the known Δ4-desaturases, Δ5-desaturases and Δ6-desaturases, the advantage of the Δ4-desaturases, Δ5-desaturases and Δ6-desaturases according to the invention is that they can convert fatty acids which are bound to phospholipids or CoA-fatty acid esters, advantageously CoA-fatty acid esters.

The Δ12-desaturases used in the process according to the invention advantageously convert oleic acid ($C18:1^{\Delta 9}$) into linoleic acid ($C18:2^{\Delta 9,12}$) or $C18:2^{\Delta 6,9}$ into $C18:3^{\Delta 6,9,12}$ (=GLA). The Δ12-desaturases used advantageously convert fatty acids which are bound to phospholipids or CoA-fatty acid esters, advantageously those which are bound to CoA-fatty acid esters.

Owing to the enzymatic activity of the nucleic acids used in the process according to the invention which encode polypeptides with Δ5-elongase, Δ6-elongase and/or ω3-desaturase activity, advantageously in combination with nucleic acid sequences which encode polypeptides of the fatty acid or lipid metabolism, such as additional polypeptides with Δ4-, Δ5-, Δ6-, Δ8-, Δ12-desaturase or Δ5-, Δ6- or Δ9-elongase activity, a wide range of polyunsaturated fatty acids can be produced in the process according to the invention. Depending on the choice of the organisms, such as the advantageous plants, used for the process according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, $C18:2^{\Delta 9,12}$) is present as unsaturated fatty acid in the plant used for the process, the process can only afford GLA, DGLA and ARA as products, all of which can be present as free fatty acids or in bound form. If only α-linolenic acid (=ALA, $C18:3^{\Delta 9,12,15}$) is present as unsaturated fatty acid in the plant used for the process, as is the case, for example, in linseed, the process can only afford SDA, ETA or EPA and/or DHA as products, all of which can be present as free fatty acids or in bound form, as described above. Owing to the modification of the activity of the enzyme Δ5-elongase advantageously in combination with Δ4-, Δ5-, Δ6-, Δ12-desaturase, and/or Δ6-elongase, or Δ4-, Δ5-, Δ8-, Δ12-desaturase, and/or Δ9-elongase which play a role in the synthesis, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferably formed. If Δ5-desaturase, Δ5-elongase and Δ4-desaturase are additionally introduced into the organisms, advantageously into the plant, ARA, EPA and/or DHA are additionally formed. This also applies to organisms into which the Δ8-desaturase and Δ9-elongase had previously been introduced. Advantageously, only ARA, EPA or DHA or mixtures of these are synthesized, depending on the fatty acid present in the organism, or in the plant, which acts as starting substance for the synthesis. Since biosynthetic cascades are involved, the end products in question are not present in pure form in the organisms. Small amounts of the precursor compounds are always additionally present in the end product. These small amounts amount to less than 20% by weight, advantageously less than 15% by weight, especially advantageously less than 10% by weight, most advantageously less than 5, 4, 3, 2 or 1% by weight, based on the end products DGLA, ETA or their mixtures, or ARA, EPA, DHA or their mixtures, advantageously EPA or DHA or their mixtures.

The protein encoded by the nucleic acid according to the invention demonstrates high specificity for the two precursors $C18:4^{\Delta 6,9,12,15}$- and $C20:5^{\Delta 5,8,11,14,17}$-fatty-acids for the synthesis of DHA (precursors and synthesis of DHA, see FIG. 1). Thus, the protein encoded by SEQ NO: 53 has specificity for Δ6- and Δ5-fatty acids with additionally one ω3-double bond (FIG. 2). Δ5-elongase has ketoacyl-CoA synthase activity which advantageously elongates fatty acid residues of acyl-CoA esters by 2 carbon atoms.

With the aid of the Δ5-elongase genes, the *Phaeodacylum* Δ5-desaturase and the *Euglena* Δ4-desaturase, it was possible to demonstrate the synthesis of DHA in yeast (*Saccharomyces cerevisiae*) (FIG. 3).

In addition to the production directly in the organism, of the starting fatty acids for the Δ5-elongase, Δ6-elongase and/or ω3-desaturase of the invention, the fatty acids can also be fed externally. The production in the organism is preferred for reasons of economy. Preferred substrates of ω3-desaturase are linoleic acid ($C18:2^{\Delta 9,12}$), γ-linolenic acid ($C18:3^{\Delta 6,9,12}$), eicosadienoic acid ($C20:2^{\Delta 11,14}$), dihomo-γ-linolenic acid ($C20:3^{\Delta 8,11,14}$), arachidonic acid (C20:4$^{\Delta5,8,11,14}$), docosatetraenoic acid (C22:4$^{\Delta7,10,13,16}$) and docosapentaenoic acid (C22:5$^{\Delta4,7,10,13,15}$).

To increase the yield in the above-described process for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which encodes a polypeptide with Δ12-desaturase. This is particularly advantageous in oil-producing organisms such as those from the family of the Brassicaceae, such as the genus *Brassica*, for example oilseed rape; the family of the Elaeagnaceae, such as the genus *Elaeagnus*, for example the genus and species *Olea europaea*, or the family Fabaceae, such as the genus *Glycine*, for example the genus and species *Glycine max*, which are high in oleic acid. Since these organisms are only low in linoleic acid (Mikoklajczak et al., Journal of the American Oil Chemical Society, 38, 1961, 678-681), the use of the abovementioned Δ12-desaturases for producing the starting material linoleic acid is advantageous.

Nucleic acids used in the process according to the invention are advantageously derived from plants such as algae, for example algae of the family of the Prasinophyceae such as the genera *Heteromastix, Mammella, Mantoniella, Micromonas, Nephroselmis, Ostreococcus, Prasinocladus, Prasinococcus, Pseudoscourfielda, Pycnococcus, Pyramimonas, Scherffelia* or *Tetraselmis* such as the genera and species *Heteromastix longifillis, Mamiella gilva, Mantoniella squamata, Micromonas pusilla, Nephroselmis olivacea, Nephroselmis pyriformis, Nephroselmis rotunda, Ostreococcus tauri, Ostreococcus* sp. *Prasinocladus ascus, Prasinocladus lubricus, Pycnococcus provasoii, Pyramimonas amylifera, Pyramimonas disomata, Pyramimonas obovata, Pyramimonas orientalis, Pyramimonas parkeae, Pyramimonas spinifera, Pyramimonas* sp., *Tetraselmis apiculata, Tetraselmis carteriaformis, Tetraselmis chui, Tetraselmis convolutae, Tetraselmis desikacharyl, Tetraselmis gracilis, Tetraselmis hazeni, Tetraselmis impellucida, Tetraselmis inconspicua, Tetraselmis levis, Tetraselmis maculata, Tetraselmis marina, Tetraselmis striata, Tetraselmis subcordiformis, Tetraselmis suecica, Tetraselmis tetrabrachia, Tetraselmis tetrathele, Tetraselmis verrucosa, Tetraselmis verrucosa fo. rubens* or *Tetraselmis* sp. or from algae of the family Euglenaceae such as the genera *Ascoglena, Astasia, Colacium, Cyclidiopsis, Euglena, Euglenopsis, Hyalophacus, Khawkinea, Lepocinclis, Phacus, Strombomonas* or *Trachelomonas*, such as the genera and species *Euglena acus, Euglena geniculata, Euglena gracilis, Euglena mixocylindracea, Euglena rostrifera, Euglena viridis, Colacium stentorium, Trachelomonas cylindrica* or *Trachelomonas volvocina*. The nucleic acids used are advantageously derived from algae of the genera *Euglena, Mantoniella* or *Ostreococcus*.

Further advantageous plants are algae such as *Isochrysis* or *Crypthecodinium*, algae/diatoms such as *Thalassiosira* or *Phaeodactylum*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, bacteria such as *Shewanella*, yeasts or animals such as nematodes such as *Caenorhabditis*, insects, frogs, abalone, or fish. The isolated nucleic acid sequences according to the invention are advantageously derived from an animal of the order of the vertebrates. Preferably, the nucleic acid sequences are derived from the classes of the *Vertebrata; Euteleostomi, Actinopterygii; Neopterygii; Teleostei; Euteleostei, Protacanthopterygii, Salmoniformes; Salmonidae* or *Oncorhynchus* or *Vertebrata, Amphibia, Anura, Pipidae, Xenopus* or *Evertebrata* such as *Protochordata, Tunicata, Holothuroidea, Cionidae* such as *Amaroucium constellatum, Botryllus schlosseri, Ciona intestinalis, Molgula citrina, Molgula manhattensis, Perophora viridis* or *Styela partita*. The nucleic acids are especially advantageously derived from fungi, animals, or from plants such as algae or mosses, preferably from the order of the Salmoniformes, such as the family of the Salmonidae, such as the genus *Salmo*, for example from the genera and species *Oncorhynchus mykiss, Trutta trutta* or *Salmo trutta fario*, from algae, such as the genera *Mantoniella* or *Ostreococcus*, or from the diatoms such as the genera *Thalassiosira* or *Phaeodactylum* or from algae such as *Crypthecodinium*.

The process according to the invention advantageously the abovementioned nucleic acid sequences or their derivatives or homologues which encode polypeptides which retain the enzymatic activity of the proteins encoded by nucleic acid sequences. These sequences, individually or in combination with the nucleic acid sequences which encode Δ12-desaturase, Δ4-desaturase, Δ5-desaturase, Δ6-desaturase, Δ5-elongase, Δ6-elongase and/or ω3-desaturase, are cloned into expression constructs and used for the introduction into, and expression in, organisms. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with a nucleic acid sequence according to the invention which encodes the Δ12-desaturase, Δ4-desaturase, Δ5-desaturase, Δ6-desaturase, Δ5-elongase, Δ6-elongase and/or ω3-desaturase, a gene construct or a vector as described above, alone or in combination with further nucleic acid sequences which encode proteins of the fatty acid or lipid metabolism. In a further preferred embodiment, this process furthermore comprises the step of obtaining the oils, lipids or free fatty acids from the organism or from the culture. The culture can, for example, take the form of a fermentation culture, for example in the case of the cultivation of microorganisms, such as, for example, *Mortierella, Thalassiosira, Mantoniella, Ostreococcus, Saccharomyces* or *Thraustochytrium*, or a greenhouse- or field-grown culture of a plant. The cell or the organism produced thus is advantageously a cell of an oil-producing organism, such as an oil crop, such as, for example, peanut, oilseed rape, canola, linseed, hemp, peanut, soybean, safflower, hemp, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

For the purposes of the invention, "transgenic" or "recombinant" means with regard to, for example, a nucleic acid sequence, an expression cassette (=gene construct) or a vector comprising the nucleic acid sequence or an organism transformed with the nucleic acid sequences, expression cassettes or vectors according to the invention, all those constructions brought about by recombinant methods in which either a) the nucleic acid sequence according to the invention, or
b) a genetic control sequence which is operably linked with the nucleic acid sequence according to the invention, for example a promoter, or
c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original organism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding Δ12-desaturase, Δ4-desaturase, Δ5-desaturase, Δ6-desaturase, Δ8-desaturase, ω3-desaturase, Δ9-elongase, Δ6-elongase and/or Δ5-elongase genes—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic organism or transgenic plant for the purposes of the invention is therefore understood as meaning, as above, that the nucleic acids used in the process are not at their natural locus in the genome of an organism, it being possible for the nucleic acids to be expressed homologously or heterologously. However, as mentioned, transgenic also means that, while the nucleic acids according to the invention are at their natural position in the genome of an organism, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic organisms are fungi such as *Mortierella* or *Phytophtora*, mosses such as *Physcomitrella*, algae such as *Mantoniella, Euglena, Crypthecodinium* or *Ostreococcus*, diatoms such as *Thalassiosira* or *Phaeodactylum*, or plants such as the oil crops.

Organisms or host organisms for the nucleic acids, the expression cassette or the vector used in the process according to the invention are, in principle, advantageously all organisms which are capable of synthesizing fatty acids, specifically unsaturated fatty acids, and/or which are suitable for the expression of recombinant genes. Examples which may be mentioned are plants such as *Arabidopsis*, Asteraceae such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Thraustochytrium, Saprolegnia, Phytophtora* or *Pythium*, bacteria, such as the genus *Escherichia* or *Shewanella*, yeasts, such as the genus *Saccharomyces*, cyanobacteria, ciliates, algae such as *Mantoniella, Euglena, Thalassiosira* or *Ostreococcus*, or protozoans such as dinoflagellates, such as *Crypthecodinium*. Preferred organisms are those which are naturally capable of synthesizing substantial amounts of oil, such as fungi, such as *Mortierella alpina, Pythium insidiosum, Phytophtora infestans*, or plants such as soybean, oilseed rape, coconut, oil palm, safflower, flax, hemp, castor-oil plant, *Calendula*, peanut, cacao bean or sunflower, or yeasts such as *Saccharomyces cerevisiae* with soybean, flax, oilseed rape, safflower, sunflower, *Calendula, Mortierella* or *Saccharomyces cerevisiae* being especially preferred. In principle, host organisms are, in addition to the abovementioned transgenic organisms, also transgenic animals, advantageously nonhuman animals, for example *C. elegans, Ciona intestinalis* or *Xenopus laevis*.

Further utilizable host cells are detailed in: Goeddel, Gene Expression Technology: Methods in Enzymology 185, Academic Press, San Diego, Calif. (1990).

Expression strains which can be used, for example those with a lower protease activity, are described in: Gottesman, S., Gene Expression Technology: Methods in Enzymology 185, Academic Press, San Diego, Calif. (1990) 119-128.

These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids. Polyunsaturated fatty acids produced by this process can be obtained by harvesting the organisms, either from the crop in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvents such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigment remaining in the product, the products are subjected to bleaching, for example using fillers earth or active charcoal. At the end, the product is deodorized, for example using steam.

The PUFAs or LCPUFAs produced by this process are advantageously $C_{18}$-, $D_{20}$- or $C_{22}$-fatty acid molecules, advantageously $C_{20}$- or $C_{22}$-fatty acid molecules, with at least two double bonds in the fatty acid molecule, preferably three, four, five or six double bonds. These $C_{18}$-, $C_{20}$- or $C_{22}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the above-described process, especially preferably oil, lipid or a fatty acid composition comprising PUFAs and being derived from transgenic plants.

As described above, these oils, lipids or fatty acids advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t2c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. In a further preferred form of the invention, these abovementioned fatty acids occur to less than 0.9%, 0.8%, 0.7%, 0.6% or 0.5%, especially preferably to less than 0.4%, 0.3%, 0.2%, 0.1%, based on the total fatty acids. The fatty acid esters or fatty acid mixtures produced by the process according to the invention advantageously comprise less than 0.1%, based on the total fatty acids, and/or no butyric acid, no cholesterol, no clupanodonic acid (=docosapentaenoic acid, $C22:5^{\Delta4,8,12,15,21}$) and no nisinic acid (tetracosahexaenoic acid, $C23:6^{\Delta3,8,12,15,18,21}$).

The oils, lipids or fatty acids according to the invention advantageously comprise at least 0.5%, 1%, 2%, 3%, 4% or 5%, advantageously at least 6%, 7%, 8%, 9% or 10%, especially advantageously at least 11%, 12%, 13%, 14% or 15% of ARA or at least 0.5%, 1%, 2%, 3%, 4% or 5%, advantageously at least 6% or 7%, especially advantageously at least 8%, 9% or 10% of EPA and/or DHA, based on the total fatty acid content of the production organism, advantageously of a plant, especially preferably of an oil crop plant such as soybean, oilseed rape, coconut, oil palm, safflower, flax, hemp, castor-oil plant, *Calendula*, peanut, cacao bean, sunflower, or the abovementioned further mono- or dicotyledonous oil crop plants.

A further embodiment according to the invention is the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. These oils, lipids, fatty acids or fatty acid mixtures, which are composed of vegetable and animal constituents, may also be used for the preparation of feedstuffs, foodstuffs, cosmetics or pharmacologicals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid.

The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds which are produced in the process are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least five or six double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains which also accumulate PUFAs in the triacylglycerol fraction are particularly advantageous for the process according to the invention and thus for the modification of the lipid and PUFA production system in a host, in particular plants such as oil crops, for example oilseed rape, canola, linseed, hemp, soybeans, sunflowers and borage. They can therefore be used advantageously in the process according to the invention.

Substrates which are advantageously suitable for the nucleic acids which are used in the process according to the invention and which encode polypeptides with $\Delta 12$-desaturase, $\Delta 5$-desaturase, $\Delta 4$-desaturase, $\Delta 6$-desaturase, $\Delta 8$-desaturase, $\Delta 9$-elongase, $\Delta 5$-elongase, $\Delta 6$-elongase and/or $\omega 3$-desaturase activity and/or the further nucleic acids used, such as the nucleic acids which encode polypeptides of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) are advantageously $C_{16}$-, $C_{18}$- or $C_{20}$-fatty acids. The fatty acids converted as substrates in the process are preferably converted in the form of their acyl-CoA esters and/or their phospholipid esters.

To produce the long-chain PUFAs according to the invention, the polyunsaturated $C_{18}$-fatty acids must first be desaturated by the enzymatic activity of a desaturase and subsequently be elongated by at least two carbon atoms via an elongase. After one elongation cycle, this enzyme activity gives $C_{20}$-fatty acids and after two elongation cycles $C_{22}$-fatty acids. The activity of the desaturases and elongases used in the process according to the invention preferably leads to $C_{18}$-, $C_{20}$- and/or $C_{22}$-fatty acids, advantageously with at least two double bonds in the fatty acid molecule, preferably with three, four, five or six double bonds, especially preferably to give $C_{20}$- and/or $C_{22}$-fatty acids with at least two double bonds in the fatty acid molecule, preferably with three, four, five or six double bonds, very specially preferably with five or six double bonds in the molecule.

After a first desaturation and the elongation have taken place, further desaturation and elongation steps such as, for example, such a desaturation in the $\Delta 5$ and $\Delta 4$ position may take place. Products of the process according to the invention which are especially preferred are dihomo-γ-linolenic acid, arachidonic acid, eicosapentaenoic acid, docosapentaenoic acid and/or docosahexaenoic acid. The $C_{20}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of the fatty acids, oils, lipids or fats in the plants which are advantageously used is, for example, in general the seed or cell strata of the seed, so that seed-specific expression of the nucleic acids used in the process makes sense. However, it is obvious that the biosynthesis of fatty acids, oils or lipids need not be limited to the seed tissue, but can also take place in a tissue-specific manner in all the other parts of the plant, for example in epidermal cells or in the tubers.

If microorganisms such as yeasts, such as *Saccharomyces* or *Schizosaccharomyces*, fungi such as *Mortierella*, *Aspergillus*, *Phytophtora*, *Entomophthora*, *Mucor* or *Thraustochytrium*, algae such as *Isochrysis*, *Mantoniella*, *Euglena*, *Ostreococcus*, *Phaeodactylum* or *Crypthecodinium* are used as organisms in the process according to the invention, these organisms are advantageously grown in fermentation cultures.

Owing to the use of the nucleic acids according to the invention which encode a $\Delta 5$-elongase, the polyunsaturated fatty acids produced in the process can be increased by at least 5%, preferably by at least 10%, especially preferably by at least 20%, very especially preferably by at least 50% in comparison with the wild types of the organisms which do not comprise the nucleic acids recombinantly.

In principle, the polyunsaturated fatty acids produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic organisms is enlarged by the process according to the invention.

If microorganisms are used as organisms in the process according to the invention, they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while passing in oxygen. The pH of the liquid medium can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview over known cultivation methods can be found in the textbook by Chmiel (Bioprozeβtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium to be used must suitably meet the requirements of the strains in question. Descriptions of culture media for various microorganisms can be found in the textbook "Manual of Methods für General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents include dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° to 40° C. and preferably 25° C. to 40° C. The culture is continued until formation of the desired product is at a maximum. This aim is normally achieved within 10 to 160 hours.

The fermentation broths obtained in this way, in particular those containing polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The fatty acids obtained in the process are also suitable as starting material for the chemical synthesis of further products of interest. For example, they can be used in combination with one another or alone for the preparation of pharmaceuticals, foodstuffs, animal feeds or cosmetics.

The invention furthermore relates to isolated nucleic acid sequences encoding polypeptides with Δ5-elongase, where the Δ5-elongases encoded by the nucleic acid sequences convert $C_{20}$-fatty acids with at least four double bonds in the fatty acid molecule, which are advantageously eventually incorporated into diacylglycerides and/or triacylglycerides.

Advantageous isolated nucleic acid sequences are nucleic acid sequences which encode polypeptides with Δ5-elongase activity and which comprise an amino acid sequence selected from the group of an amino acid sequence with the sequence shown in SEQ ID NO: 115, SEQ ID NO: 116, SEQ ID NO: 139, SEQ ID NO: 140, SEQ ID NO: 141 or SEQ ID NO: 142.

Further advantageous isolated nucleic acid sequences are nucleic acid sequences which encode polypeptides with Δ5-elongase activity and which comprise a combination of the amino acid sequences selected from the group consisting of:
a) SEQ ID NO: 115 and SEQ ID NO: 139, SEQ ID NO: 115 and SEQ ID NO: 140 or SEQ ID NO: 139 and SEQ ID NO: 140; or
b) SEQ ID NO: 116 and SEQ ID NO: 141, SEQ ID NO: 116 and SEQ ID NO: 142 or SEQ ID NO: 141 and SEQ ID NO: 142; or
c) SEQ ID NO: 115, SEQ ID NO: 139 and SEQ ID NO: 140 or SEQ ID NO: 116, SEQ ID NO: 141 and SEQ ID NO: 142.

The sequences shown in the sequences SEQ ID NO: 115 (NXXXHXXMYXYYX), SEQ ID NO: 116 (HHXXXX-WAWW), SEQ ID NO: 139 (LHXXHH), SEQ ID NO: 140 (TXXQXXQF), SEQ ID NO: 141 (DTXFMV) and SEQ ID NO: 142 (TQAQXXQF) constitute conserved regions of the various elongases. Table 2 shows the meaning of the amino acids marked with X, which are present in the abovementioned nucleic acid sequences (column 3). The preferred amino acids in the various positions can also be found in the table (column 3). Column 1 indicates the SEQ ID NO, column 2 the position in the sequence.

TABLE 2

Meaning of the amino acid marked X in the consensus sequences.

| SEQ ID NO: | Position of the X in the sequence | Amino acid | Preferred amino acid |
|---|---|---|---|
| 115 (NXXXHXXMYXYYX) | 2 | Ser, Cys, Leu, Gly | Cys, Leu |
| 115 | 3 | Thr, Phe, Ile, Ser, Val, Trp, Gly | Phe, Trp |
| 115 | 4 | Val, Ile | Val, Ile |
| 115 | 6 | Val, Ile, Thr | Val, Ile |
| 115 | 7 | Ile, Phe, Val, Leu, Cys | Cys, Val |
| 115 | 10 | Ser, Gly, Tyr, Thr, Ala | Thr, Ser |
| 115 | 13 | Phe, Met, Thr, Leu, Ala, Gly | Leu |
| 116 (HHXXXXWAWW) | 3 | Ala, Ser, Thr | Ala, Ser especially preferably Ala |
| 116 | 4 | Thr, Met, Val, Leu, Ile, Ser | Leu, Thr especially preferably Leu |
| 116 | 5 | Val, Thr, Met, Leu, Ile | Ile, Ser especially preferably Ile |
| 116 | 6 | Val, Met, Leu, Ile, Ala, Pro, Ser, Phe | Ile, Ser especially preferably Ile |
| 139 LHXXHH | 3 | Val, Tyr, Ile | Val, Thr |
| 139 | 4 | Tyr, Phe | Tyr |
| 140 TXXQXXQF | 2 | Asn, Asp, Thr, Gln, Met, Ser, Ala | Gln |
| 140 | 3 | Thr, Cys, Leu, Met, Ala, Ile, Val, Phe | Ala, Met |
| 140 | 5 | Met, Ile, Leu | Met |

TABLE 2-continued

Meaning of the amino acid marked X in the consensus sequences.

| SEQ ID NO: | Position of the X in the sequence | Amino acid | Preferred amino acid |
|---|---|---|---|
| 140 | 6 | Val, Ile, Leu, Thr, Phe | Leu |
| 141 DTXFMV | 3 | Leu, Ile, Val, Tyr, Phe, Ala | Phe |
| 142 TQAQXXQF | 5 | Met, Ile, Leu | Met, Leu especially preferably Met |
| 142 | 6 | Val, Ile, Leu, Thr, Phe | Leu |

Especially advantageous Δ5-elongases comprise at least one of the sequences SEQ ID NO: 116, SEQ ID NO: 141 and/or SEQ ID NO: 142.

Especially advantageous isolated nucleic acid sequences are sequences selected from the group consisting of:
a) a nucleic acid sequence with the sequence shown in SEQ ID NO: 43, SEQ ID NO: 45, SEQ ID NO: 47, SEQ ID NO: 49, SEQ ID NO: 59, SEQ ID NO: 61, SEQ ID NO: 63; SEQ ID NO: 65, SEQ ID NO: 67, SEQ ID NO: 75, SEQ ID NO: 77, SEQ ID NO: 79, SEQ ID NO: 83, SEQ ID NO: 85, SEQ ID NO: 113, SEQ ID NO: 131 or SEQ ID NO: 133,
b) nucleic acid sequences which, as the result of the degeneracy of the genetic code, can be derived from the amino sequence shown in SEQ ID NO: 44, SEQ ID NO: 46, SEQ ID NO: 48, SEQ ID NO: 50, SEQ ID NO: 60, SEQ ID NO: 62, SEQ ID NO: 64, SEQ ID NO: 66, SEQ ID NO: 68, SEQ ID NO: 76, SEQ ID NO: 78, SEQ ID NO: 80, SEQ ID NO: 84, SEQ ID NO: 86, SEQ ID NO: 114, SEQ ID NO: 132 or SEQ ID NO: 134, or
c) derivatives of the nucleic acid sequence shown in SEQ ID NO: 43, SEQ ID NO: 45, SEQ ID NO: 47, SEQ ID NO: 49, SEQ ID NO: 59, SEQ ID NO: 61, SEQ ID NO: 63; SEQ ID NO: 65, SEQ ID NO: 67, SEQ ID NO: 75, SEQ ID NO: 77, SEQ ID NO: 79, SEQ ID NO: 83, SEQ ID NO: 85, SEQ-ID NO: 113, SEQ ID NO: 131 or SEQ ID NO: 133, which encode polypeptides with at least 40% homology at the amino acid level with SEQ ID NO: 44, SEQ ID NO: 46, SEQ ID NO: 48, SEQ ID NO: 50, SEQ ID NO: 60, SEQ ID NO: 62, SEQ ID NO: 64, SEQ ID NO: 66, SEQ ID NO: 68, SEQ ID NO: 76, SEQ ID NO: 78, SEQ ID NO: 80, SEQ ID NO: 84, SEQ ID NO: 85, SEQ ID NO: 113, SEQ ID NO: 131 or SEQ ID NO: 133 and which have Δ5-elongase activity.

The invention furthermore relates to isolated nucleic acid sequences which encode polypeptides with Δ6-elongase activity, selected from the group consisting of:
a) a nucleic acid sequence with the sequence shown in SEQ ID NO: 69, SEQ ID NO: 81, SEQ ID NO: 111 or SEQ ID NO: 183,
b) nucleic acid sequences which, as the result of the degeneracy of the genetic code, can be derived from the amino acid sequence shown in SEQ ID NO: 70, SEQ ID NO: 82, SEQ ID NO: 112 or SEQ ID NO: 184, or
c) derivatives of the nucleic acid sequence shown in SEQ ID NO: 69, SEQ ID NO: 81, SEQ ID NO: 111 or SEQ ID NO: 183 which encode polypeptides with at least 40% homology at the amino acid level with SEQ ID NO: 70, SEQ ID NO: 82, SEQ ID NO: 112 or SEQ ID NO: 184 and which have Δ6-elongase activity.

The invention furthermore relates to isolated nucleic acid sequences which encode polypeptides with ω3-desaturase activity, selected from the group consisting of:
a) a nucleic acid sequence with the sequence shown in SEQ ID NO: 87 or SEQ ID NO: 105,
b) nucleic acid sequences which, as the result of the degeneracy of the genetic code, can be derived from the amino acid sequence shown in SEQ ID NO: 88 or SEQ ID NO: 106, or
c) derivatives of the nucleic acid sequence shown in SEQ ID NO: 87 or SEQ ID NO: 105 which have polypeptides with at least 60% identity at the amino acid level with SEQ ID NO: 88 or SEQ ID NO: 106 and which have ω3-desaturase activity.

The invention furthermore relates to isolated nucleic acid sequences encoding a polypeptide with Δ6-desaturase activity, selected from the group consisting of:
a) a nucleic acid sequence with the sequence shown in SEQ ID NO: 89 or in SEQ ID NO: 97, or
b) nucleic acid sequences which, as the result of the degeneracy of the genetic code, can be derived from the amino acid sequence shown in SEQ ID NO: 90 or SEQ ID NO: 98, or
c) derivatives of the nucleic acid sequence shown in SEQ ID NO: 89 or SEQ ID NO: 97 which encode polypeptides with at least 40% homology at the amino acid level with SEQ ID NO: 90 or SEQ ID NO: 98 and which have Δ6-desaturase activity.

The invention furthermore relates to isolated nucleic acid sequences encoding a polypeptide with Δ5-desaturase activity, selected from the group consisting of:
a) a nucleic acid sequence with the sequence shown in SEQ ID NO: 91, SEQ ID NO: 93, SEQ ID NO: 99 or in SEQ ID NO: 101,
b) nucleic acid sequences which, as the result of the degeneracy of the genetic code, can be derived from the amino acid sequence shown in SEQ ID NO: 92, SEQ ID NO: 94, SEQ ID NO: 100 or in SEQ ID NO: 102, or
c) derivatives of the nucleic acid sequence shown in SEQ ID NO: 91, SEQ ID NO: 93, SEQ ID NO: 99 or in SEQ ID NO: 101 which encode polypeptides with at least 40% homology at the amino acid level with SEQ ID NO: 92, SEQ ID NO: 94, SEQ ID NO: 100 or in SEQ ID NO: 102 and which have Δ5-desaturase activity.

The invention furthermore relates to isolated nucleic acid sequences encoding a polypeptide with Δ4-desaturase activity, selected from the group consisting of:

a) a nucleic acid sequence with the sequence shown in SEQ ID NO: 95 or in SEQ ID NO: 103,
b) nucleic acid sequences which, as the result of the degeneracy of the genetic code, can be derived from the amino acid sequence shown in SEQ ID NO: 96 or SEQ ID NO: 104, or
c) derivatives of the nucleic acid sequence shown in SEQ ID NO: 95 or SEQ ID NO: 103 which encode polypeptides with at least 40% homology at the amino acid level with SEQ ID NO: 96 or SEQ ID NO: 104 and which have Δ4-desaturase activity.

The invention furthermore relates to isolated nucleic acid sequences encoding a polypeptide with Δ12-desaturase activity, selected from the group consisting of:
a) a nucleic acid sequence with the sequence shown in SEQ ID NO: 107 or in SEQ ID NO: 109,
b) nucleic acid sequences which, as the result of the degeneracy of the genetic code, can be derived from the amino acid sequence shown in SEQ ID NO: 108 or SEQ ID NO: 110, or
c) derivatives of the nucleic acid sequence shown in SEQ ID NO: 107 or SEQ ID NO: 109 which encode polypeptides with at least 50% homology at the amino acid level with SEQ ID NO: 108 or SEQ ID NO: 110 and which have Δ12-desaturase activity.

The invention furthermore relates to gene constructs which comprise the nucleic acid sequences SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183, according to the invention, wherein the nucleic acid is linked operably with one or more regulatory signals. In addition, additional biosynthesis genes of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) may be present in the gene construct. Advantageously, biosynthesis genes of the fatty acid or lipid metabolism selected from the group Δ4-desaturase, Δ5-desaturase, Δ6-desaturase, Δ8-desaturase, Δ9-desaturase, Δ12-desaturase, Δ6-elongase, Δ9-elongase or ω3-desaturase are additionally present.

All of the nucleic acid sequences used in the process according to the invention are advantageously derived from a eukaryotic organism such as a plant, a microorganism or an animal. The nucleic acid sequences are preferably derived from the order Salmoniformes, algae such as *Mantoniella, Crypthecodinium, Euglena* or *Ostreococcus*, fungi such as the genus *Phytophthora* or from diatoms such as the genera *Thalassiosira* or *Phaeodactylum*.

The nucleic acid sequences used in the process which encode proteins with ω3-desaturase, Δ4-desaturase, Δ5-desaturase, Δ6-desaturase, Δ8-desaturase, Δ9-desaturase, Δ12-desaturase, Δ5-elongase, Δ6-elongase or Δ9-elongase activity are advantageously introduced alone or, preferably, in combination with an expression cassette (=nucleic acid construct) which makes possible the expression of the nucleic acids in an organism, advantageously a plant or a microorganism. The nucleic acid construct can comprise more than one nucleic acid sequence with an enzymatic activity, such as, for example, of a Δ12-desaturase, Δ4-desaturase, Δ5-desaturase, Δ6-desaturase, Δ5-elongase, Δ6-elongase and/or ω3-desaturase.

To introduce the nucleic acids used in the process, the latter are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step. Suitable cloning vectors are generally known to the skilled worker. These include, in particular, vectors which are capable of replication in microbial systems, that is to say mainly vectors which ensure efficient cloning in yeasts or fungi and which make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the *Agrobacterium*-mediated transformation and the T-DNA-delimiting sequences (T-DNA border). These vector systems advantageously also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E. coli* and in *Agrobacterium*. These binary vectors include vectors from the series pBIB-HYG, pPZP, pBecks, pGreen. In accordance with the invention, Bin19, pBI101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned with vector fragments which have been prepared in a similar manner, using ligase. In this context, a particular nucleic acid construct, or vector or plasmid construct, can have one or else more than one codogenic gene segment. The codogenic gene segments in these constructs are preferably linked operably with regulatory sequences. The regulatory sequences include, in particular, plant sequences such as the above-described promoters and terminator sequences. The constructs can advantageously be stably propagated in microorganisms, in particular in *E. coli* and *Agrobacterium tumefaciens*, under selective conditions and make possible the transfer of heterologous DNA into plants or microorganisms.

The nucleic acids used in the process, the inventive nucleic acids and nucleic acid constructs, can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient PUFA producers.

A series of mechanisms by which a modification of the $\Delta 12$-desaturase, $\Delta 5$-elongase, $\Delta 6$-elongase, $\Delta 5$-desaturase, $\Delta 4$-desaturase, $\Delta 6$-desaturase and/or $\omega 3$-desaturase protein and of the further proteins used in the process, such as $\Delta 12$-desaturase, $\Delta 9$-elongase, $\Delta 6$-desaturase, $\Delta 8$-desaturase, $\Delta 6$-elongase, $\Delta 5$-desaturase or $\Delta 4$-desaturase protein, is possible exist, so that the yield, production and/or production efficiency of the advantageous polyunsaturated fatty acids in a plant, preferably in an oil crop plant or a microorganism, can be influenced directly owing to this modified protein. The number or activity of the $\Delta 12$-desaturase, $\omega 3$-desaturase, $\Delta 9$-elongase, $\Delta 6$-desaturase, $\Delta 8$-desaturase, $\Delta 6$-elongase, $\Delta 5$-desaturase, $\Delta 5$-elongase or $\Delta 4$-desaturase proteins or genes can be increased, so that greater amounts of the gene products and, ultimately, greater amounts of the compounds of the general formula I are produced. A de novo synthesis in an organism which has lacked the activity and ability to biosynthesize the compounds prior to introduction of the corresponding gene(s) is also possible. This applies analogously to the combination with further desaturases or elongases or further enzymes of the fatty acid and lipid metabolism. The use of various divergent sequences, i.e. sequences which differ at the DNA sequence level, may also be advantageous in this context, or else the use of promoters for gene expression which make possible a different gene expression in the course of time, for example as a function of the degree of maturity of a seed or an oil-storing tissue.

Owing to the introduction of a $\Delta 12$-desaturase, $\omega 3$-desaturase, $\Delta 9$-elongase, $\Delta 6$-desaturase, $\Delta 8$-desaturase, $\Delta 6$-elongase, $\Delta 5$-desaturase, $\Delta 5$-elongase and/or $\Delta 4$-desaturase gene into an organism, alone or in combination with other genes in a cell, it is not only possible to increase biosynthesis flux towards the end product, but also to increase, or to create de novo the corresponding triacylglycerol composition. Likewise, the number or activity of other genes which are involved in the import of nutrients which are required for the biosynthesis of one or more fatty acids, oils, polar and/or neutral lipids, can be increased, so that the concentration of these precursors, cofactors or intermediates within the cells or within the storage compartment is increased, whereby the ability of the cells to produce PUFAs as described below is enhanced further. By optimizing the activity or increasing the number of one or more $\Delta 12$-desaturase, $\omega 3$-desaturase, $\Delta 9$-elongase, $\Delta 6$-desaturase, $\Delta 8$-desaturase, $\Delta 6$-elongase, $\Delta 5$-desaturase, $\Delta 5$-elongase or $\Delta 4$-desaturase genes which are involved in the biosynthesis of these compounds, or by destroying the activity of one or more genes which are involved in the degradation of these compounds, an enhanced yield, production and/or efficiency of production of fatty acid and lipid molecules in organisms, advantageously in plants, is made possible.

The isolated nucleic acid molecules used in the process according to the invention encode proteins or parts of these, where the proteins or the individual protein or parts thereof comprise(s) an amino acid sequence with sufficient homology to an amino acid sequence which is shown in the sequences SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 118, SEQ ID NO: 120, SEQ ID NO: 132, SEQ ID NO: 134, SEQ ID NO: 136, SEQ ID NO: 138 or SEQ ID NO: 184 so that the proteins or parts thereof retain a $\Delta 12$-desaturase, $\omega 3$-desaturase, $\Delta 9$-elongase, $\Delta 6$-desaturase, $\Delta 8$-desaturase, $\Delta 6$-elongase, $\Delta 5$-desaturase, $\Delta 5$-elongase or $\Delta 4$-desaturase activity. The proteins or parts thereof which is/are encoded by the nucleic acid molecule(s) preferably retains their essential enzymatic activity and the ability of participating in the metabolism of compounds required for the synthesis of cell membranes or lipid bodies in organisms, advantageously in plants, or in the transport of molecules across these membranes. Advantageously, the proteins encoded by the nucleic acid molecules have at least approximately 50%, preferably at least approximately 60% and more preferably at least approximately 70%, 80% or 90% and most preferably at least approximately 85%, 86%, 87%, 88%, 89%, 90%, 91%, 92%, 93%, 94%, 95%, 96%, 97%, 98%, 99% or more identity with the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ-ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 118, SEQ ID NO: 120, SEQ ID NO: 132, SEQ ID NO: 134, SEQ ID NO: 136, SEQ ID NO: 138 or SEQ ID NO: 184. For the purposes of the invention, homology or homologous is understood as meaning identity or identical, respectively.

The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

Essential enzymatic activity of the Δ12-desaturase, ω3-desaturase, Δ9-elongase, Δ6-desaturase, Δ8-desaturase, Δ6-elongase, Δ5-desaturase, Δ5-elongase or Δ4-desaturase used in the process according to the invention is understood as meaning that they retain at least an enzymatic activity of at least 10%, preferably 20%, especially preferably 30% and very especially 40% in comparison with the proteins/enzymes encoded by the sequence SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 and their derivatives and can thus participate in the metabolism of compounds required for the synthesis of fatty acids, fatty acid esters such as diacylglycerides and/or triacylglycerides in an organism, advantageously a plant or a plant cell, or in the transport of molecules across membranes, meaning $C_{18}$-, $C_{20}$- or $C_{22}$-carbon chains in the fatty acid molecule with double bonds at least two, advantageously three, four, five or six positions.

Nucleic acids which can advantageously be used in the process are derived from bacteria, fungi, diatoms, animals such as *Caenorhabditis* or *Oncorhynchus* or plants such as algae or mosses, such as the genera *Shewanella, Physcomitrella, Thraustochytrium, Fusarium, Phytophthora, Ceratodon, Mantoniella, Ostreococcus, Isochrysis, Aleurita, Muscarioides, Mortierella, Borago, Phaeodactylum, Crypthecodinium*, specifically from the genera and species *Oncorhynchus mykiss, Xenopus laevis, Ciona intestinalis, Thalassiosira pseudonona, Mantoniella squamata, Ostreococcus* sp., *Ostreococcus tauri, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Borago officinalis, Phaeodactylum tricornutum, Caenorhabditis elegans* or especially advantageously from *Oncorhynchus mykiss, Euglena gracilis, Thalassiosira pseudonona* or *Crypthecodinium cohnii*.

Alternatively, nucleic acid sequences which encode a Δ12-desaturase, ω3-desaturase, Δ9-elongase, Δ6-desaturase, Δ8-desaturase, Δ6-elongase, Δ5-desaturase, Δ5-elongase or Δ4-desaturase and which advantageously hybridize under stringent conditions with a nucleic acid sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 can be used in the process according to the invention.

The nucleic acid sequences used in the process are advantageously introduced into an expression cassette which makes possible the expression of the nucleic acids in organisms such as microorganisms or plants.

In doing so, the nucleic acid sequences which encode Δ12-desaturase, ω3-desaturase, Δ9-elongase, Δ6-desaturase, Δ8-desaturase, Δ6-elongase, Δ5-desaturase, Δ5-elongase or Δ4-desaturase are linked operably with one or more regulatory signals, advantageously for enhancing gene expression. These regulatory sequences are intended to make possible the specific expression of the genes and proteins. Depending on the host organism, this may mean, for example, that the gene is expressed and/or overexpressed only after induction has taken place, or else that it is expressed and/or overexpressed immediately. For example, these regulatory sequences take the form of sequences to which inductors or repressors bind, thus controlling the expression of the nucleic acid. In addition to these novel regulatory sequences, or instead of these sequences, the natural regulatory elements of these sequences may still be present before the actual structural genes and, if appropriate, may have been genetically modified in such a way that their natural regulation is eliminated and the expression of the genes is enhanced. However, the expression cassette (=expression construct=gene construct) can also be simpler in construction, that is to say no additional regulatory signals have been inserted before the nucleic acid sequence or its derivatives, and the natural promoter together with its regulation was not removed. Instead, the natural regulatory sequence has been mutated in such a way that regulation no longer takes place and/or gene expression is enhanced. These modified promoters can also be positioned on their own before the natural gene in the form of part-sequences (=promoter with parts of the nucleic acid sequences used in accordance with the invention) in order to enhance the activity. Moreover, the gene construct may advantageously also comprise one or more what are known as enhancer sequences in operable linkage with the promoter, which make possible an enhanced expression of the nucleic acid sequence. Additional advantageous sequences, such as further regulatory elements or terminator sequences, may also be inserted at the 3' end of the DNA sequences. The Δ12-desaturase, ω3-desaturase, Δ4-desaturase, Δ5-desaturase, Δ6-desaturase, Δ8-desaturase, Δ5-elongase, Δ6-elongase and/or Δ9-elongase genes may be present in one or more copies of the expression cassette (=gene construct). Preferably, only one copy of the genes is present in each expression cassette. This gene construct or the gene constructs can be expressed together in the host organism. In this context, the gene construct(s) can be inserted in one or more vectors and be present in the cell in free form, or else be inserted in the genome. It is advantageous for the insertion of further genes in the genome when the genes to be expressed are present together in one gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

A further embodiment of the invention is one or more gene constructs which comprise one or more sequences which are defined by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 or its derivatives and which encode polypeptides as shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 118, SEQ ID NO: 120, SEQ ID NO: 132, SEQ ID NO: 134, SEQ ID NO: 136, SEQ ID NO: 138 or SEQ ID NO: 184. The abovementioned Δ112-desaturase, ω3-desaturase, Δ9-elongase, Δ6-desaturase, Δ8-desaturase, Δ6-elongase, Δ5-desaturase, Δ5-elongase or Δ4-desaturase proteins lead advantageously to a desaturation or elongation of fatty acids, the substrate advantageously having one, two, three, four, five or six double bonds and advantageously 18, 20 or 22 carbon atoms in the fatty acid molecule. The same applies to their homologs, derivatives or analogs, which are linked operably with one or more regulatory signals, advantageously for enhancing gene expression.

Advantageous regulatory sequences for the novel process are present for example in promoters such as the cos, tac, trp, tet, trp-tet, lpp, lac, lpp-lac, lacIq, T7, T5, T3, gal, trc, ara, SP6, λ-PR or λ-PL promoter and are advantageously employed in Gram-negative bacteria. Further advantageous regulator sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscissic acid-inducible) or WO 93/21334 (ethanol- or cyclohexenol-inducible) promoters. Further suitable plant promoters are the cytosolic FBPase promoter or the ST-LSI promoter of potato (Stockhaus et al., EMBO J. 8, 1989, 2445), the *glycine max* phosphoribosylpyrophosphate amidotransferase promoter (Genbank Accession No. U87999) or the node-specific promoter described in EP-A-0 249 676.

Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arabidopsis* oleosin promoter), U.S. Pat. No. 5,504,200 (*Phaseolus vulgaris* phaseolin promoter), WO 91/13980 (*Brassica* Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890.

In principle, it is possible to use all natural promoters together with their regulatory sequences, such as those mentioned above, for the novel process. It is also possible and advantageous to use synthetic promoters, either in addition or alone, in particular when they mediate seed-specific expression, such as those described in WO 99/16890.

In order to achieve a particularly high PUFA content, especially in transgenic plants, the PUFA biosynthesis genes should advantageously be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Preferred promoters are listed hereinbelow: USP (=unknown seed protein) and vicilin (*Vicia faba*) [Bäumlein et al., Mol. Gen. Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Baumlein et al., Plant J., 2, 2, 1992], Lpt2 and lpt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracycline-inducible promoter (Gatz et al. (1992) Plant J. 2, 397-404) and an ethanol-inducible promoter.

To ensure the stable integration of the biosynthesis genes into the transgenic plant over a plurality of generations, each of the nucleic acids which encode Δ12-desaturase, ω3-desaturase, Δ9-elongase, Δ6-desaturase, Δ8-desaturase, Δ6-elongase, Δ5-desaturase, Δ5-elongase and/or Δ4-desaturase and which are used in the process should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator sequence. Such advantageous constructs are disclosed, for example, in DE 101 02 337 or DE 101 02 338. However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator sequences can be used in the expression cassette. However, it is also possible to use only one type of promoter in the cassette. This, however, may lead to undesired recombination events.

As described above, the transcription of the genes which have been introduced should advantageously be terminated by suitable terminator sequences at the 3' end of the biosynthesis genes which have been introduced (behind the stop codon). An example of a sequence which can be used in this context is the OCS1 terminator sequence. As is the case with the promoters, different terminator sequences should be used for each gene.

As described above, the gene construct can also comprise further genes to be introduced into the organisms. It is possible and advantageous to introduce into the host organisms, and to express therein, regulatory genes such as genes for inductors, repressors or enzymes which, owing to their enzyme activity, engage in the regulation of one or more genes of a biosynthesis pathway. These genes can be of heterologous or of homologous origin. Moreover, further biosynthesis genes of the fatty acid or lipid metabolism can advantageously be present in a nucleic acid construct, or gene construct; however, these genes can also be positioned on one or more further nucleic acid constructs. Biosynthesis genes of the fatty acid or lipid metabolism which are preferably used is a gene selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allenoxide synthase(s), hydroperoxide lyase(s) or fatty acid elongase(s) or combinations thereof. Especially advantageous nucleic acid sequences are biosynthesis genes of the fatty acid or lipid metabolism selected from the group of the acyl-CoA:lysophospholipid acyltransferase, ω3-desaturase, Δ4-desaturase, Δ5-desaturase, Δ6-desaturase, Δ8-desaturase, Δ9-desaturase, Δ12-desaturase, Δ5-elongase, Δ6-elongase and/or Δ9-elongase.

In this context, the abovementioned nucleic acids or genes can be cloned into expression cassettes, like those mentioned above, in combination with other elongases and desaturases and used for transforming plants with the aid of *Agrobacterium*.

Here, the regulatory sequences or factors can, as described above, preferably have a positive effect on, and thus enhance, the expression genes which have been introduced. Thus, enhancement of the regulatory elements can advantageously take place at the transcriptional level by using strong transcription signals such as promoters and/or enhancers. However, an enhanced translation is also possible, for example by improving the stability of the mRNA. In principle, the expression cassettes can be used directly for introduction into the plants or else be introduced into a vector.

These advantageous vectors, preferably expression vectors, comprise the nucleic acids which encode the Δ12-desaturases, ω3-desaturases, Δ9-elongases, Δ6-desaturases, Δ8-desaturases, Δ6-elongases, Δ5-desaturases, Δ5-elongases or Δ4-desaturases and which are used in the process, or else a nucleic acid construct which the nucleic acid used either alone or in combination with further biosynthesis genes of the fatty acid or lipid metabolism such as the acyl-CoA:lysophospholipid acyltransferases, ω3-desaturases, Δ4-desaturases, Δ5-desaturases, Δ6-desaturases, Δ8-desaturases, Δ9-desaturases, Δ12-desaturases, ω3-desaturases, Δ5-elongases, Δ6-elongases and/or Δ9-elongases. As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome.

Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is also intended to cover other forms of expression vectors, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA.

The recombinant expression vectors advantageously used in the process comprise the nucleic acids described below or the above-described gene construct in a form which is suitable for expressing the nucleic acids used in a host cell, which means that the recombinant expression vectors comprise one or more regulatory sequences, selected on the basis of the host cells used for the expression, which regulatory sequence(s) is/are linked operably with the nucleic acid sequence to be expressed. In a recombinant expression vector, "linked operably" means that the nucleotide sequence of interest is bound to the regulatory sequence(s) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the desired expression level of the protein and the like.

The recombinant expression vectors used can be designed for the expression of Δ12-desaturases, ω3-desaturases, Δ9-elongases, Δ6-desaturases, Δ8-desaturases, Δ6-elongases, Δ5-desaturases, Δ5-elongases and/or Δ4-desaturases in prokaryotic or eukaryotic cells. This is advantageous since intermediate steps of the vector construction are frequently carried out in microorganisms for the sake of simplicity. For example, the Δ12-desaturase, ω3-desaturases, Δ9-elongases, Δ6-desaturase, Δ8-desaturases, Δ6-elongase, Δ5-desaturase, Δ5-elongase and/or Δ4-desaturase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) und pRIT5 (Pharmacia, Piscataway, N.J.), where glutathione S-transferase (GST), maltose-E binding protein and protein A, respectively, is fused with the recombinant target protein.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example in *E. coli* pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples for vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396428: Academic Press: San Diego]. Further suitable yeast vectors are, for example, pAG-1, YEp6, YEp13 or pEMBLYe23.

As an alternative, Δ12-desaturases, ω3-desaturases, Δ9-elongases, Δ6-desaturases, Δ8-desaturases, Δ6-elongases, Δ5-desaturases, Δ5-elongases and/or Δ4-desaturases can be expressed in insect cells using Baculovirus vectors. Baculovirus expression vectors which are available for the expression of proteins in cultured insect cells (for example Sf9 cells) comprise the pAc series (Smith et al. (198.3) Mol. Cell. Biol. 3:2156-2165) and the pVL series (Lucklow and Summers (1989) Virology 170:31-39).

The abovementioned vectors are only a small overview over suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018). For further suitable expression systems for prokaryotic and eukaryotic cells, see the Chapters 16 and 17 in Sambrook, J., Fritsch, E. F., and Maniatis, T., Molecular Cloning: A Laboratory Manual, 2. edition, Cold Spring Harbor Laboratory, Cold Spring Harbor Laboratory Press, Cold Spring Harbor, N.Y., 1989.

In a further embodiment of the process, the Δ12-desaturases, ω3-desaturases, Δ9-elongases, Δ6-desaturases, Δ8-desaturases, Δ6-elongases, Δ5-desaturases, Δ5-elongases and/or Δ4-desaturases can be expressed in single-celled plant cells (such as algae), see Falciatore et al., 1999, Marine Biotechnology 1 (3):239-251 and references cited therein, and in plant cells from higher plants (for example spermatophytes such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38.

A plant expression cassette preferably comprises regulatory sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminator sequences which are functionally active in plants are also suitable.

Since plant gene expression is very often not limited to the transcriptional level, a plant expression cassette preferably comprises other sequences which are linked operably, such as translation enhancers, for example the overdrive sequence, which enhances the tobacco mosaic virus 5'-untranslated leader sequence, which increases the protein/RNA ratio (Gallie et al., 1987, Nucl. Acids Research 15:8693-8711).

As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CaMV (Franck et al., Cell 21 (1980) 285-294),19S CaMV (see also U.S. Pat. No. 5,352,605 and WO 84/02913), or plant promoters, such as the promoter of the Rubisco subunit, which is described in U.S. Pat. No. 4,962,028.

Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmid reticulum, elaioplasts, peroxisomes and other compartments of plant cells.

As described above, plant gene expression can also be achieved via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the *sorghum* kasirin gene or the rye secalin gene, which are described in WO 99/16890.

In particular, it may be desired to bring about the multi-parallel expression of the Δ12-desaturases, ω3-desaturases, Δ9-elongases, Δ6-desaturases, Δ8-desaturases, Δ6-elongases, Δ5-desaturases, Δ5-elongases and/or Δ4-desaturases used in the process. Such expression cassettes can be introduced via the simultaneous transformation of a plurality of individual expression constructs or, preferably, by combining a plurality of expression cassettes on one construct. Also, a plurality of vectors can be transformed with in each case a plurality of expression cassettes and then transferred into the host cell.

Other promoters which are likewise especially suitable are those which bring about a plastid-specific expression, since plastids constitute the compartment in which the precursors and some end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

Vector DNA can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual, 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Host cells which are suitable in principle for taking up the nucleic acid according to the invention, the gene product according to the invention or the vector according to the invention are all prokaryotic or eukaryotic organisms. The host organisms which are advantageously used are microorganisms such as fungi or yeasts, or plant cells, preferably plants or parts thereof. Fungi, yeasts or plants are preferably used, especially preferably plants, very especially preferably plants such as oil crops, which are high in lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassava, pepper, *Tagetes*, Solanacea plants such as potato, tobacco, eggplant and tomato, *Vicia* species, pea, alfalfa, bushy plants (coffee, cacao, tea), *Salix* species, trees (oil palm, coconut), and perennial grasses and fodder crops. Especially preferred plants according to the invention are oil crops such as soybean, peanut, oilseed rape, canola, linseed, hemp, evening primrose, sunflower, safflower, trees (oil palm, coconut).

The invention furthermore relates to above-described isolated nucleic acid sequence which encode polypeptides with Δ5-elongase activity, where the elongase encoded by the nucleic acid sequences converts $C_{16}$- and $C_{18}$-fatty acids with one double bond and advantageously polyunsaturated $C_{18}$-fatty acids with one Δ6 double bond and polyunsaturated $C_{20}$-fatty acids with one Δ5 double bond. $C_{22}$-fatty acids are not elongated.

Advantageous isolated nucleic acid sequences are nucleic acid sequences which encode polypeptides with Δ5-elongase activity and which comprise an amino acid sequence selected from the group of an amino acid sequence with the sequence shown in SEQ ID NO: 115, SEQ ID NO: 116, SEQ ID NO: 139, SEQ ID NO: 140, SEQ ID NO: 141 or SEQ ID NO: 142.

Further advantageous isolated nucleic acid sequences are nucleic acid sequences which encode polypeptides with Δ5-elongase activity and which comprise a combination of the amino acid sequences selected from the group consisting of:
a) SEQ ID NO: 115 and SEQ ID NO: 139, SEQ ID NO: 115 and SEQ ID NO: 140 or SEQ ID NO: 139 and SEQ ID NO: 140; or
b) SEQ ID NO: 116 and SEQ ID NO: 141, SEQ ID NO: 116 and SEQ ID NO: 142 or SEQ ID NO: 141 and SEQ ID NO: 142; or
c) SEQ ID NO: 115, SEQ ID NO: 139 and SEQ ID NO: 140 or SEQ ID NO: 116, SEQ ID NO: 141 and SEQ ID NO: 142.

Preferred nucleic acid sequences which encode polypeptides with Δ5-elongase activity advantageously comprise the abovementioned amino acid sequences. The latter are described in greater detail in table 2.

Especially advantageous isolated nucleic acid sequences are sequences selected from the group consisting of:
a) a nucleic acid sequence with the sequence shown in SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 75, SEQ ID NO: 77, SEQ ID NO: 79, SEQ ID NO: 83, SEQ ID NO: 85, SEQ ID NO: 113, SEQ ID NO: 131 or SEQ ID NO: 133,
b) nucleic acid sequences which, as the result of the degeneracy of the genetic code, can be derived from the amino acid sequence shown in SEQ ID NO: 44, SEQ ID NO: 46, SEQ ID NO: 48, SEQ ID NO: 50, SEQ ID NO: 60, SEQ ID NO: 62, SEQ ID NO: 64, SEQ ID NO: 66, SEQ ID NO: 68, SEQ ID NO: 76, SEQ ID NO: 78, SEQ ID NO: 80, SEQ ID NO: 84, SEQ ID NO: 86, SEQ ID NO: 114, SEQ ID NO: 132 or SEQ ID NO: 134, or
c) derivatives of the nucleic acid sequence shown in SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 75, SEQ ID NO: 77, SEQ ID NO: 79, SEQ ID NO: 83, SEQ ID NO: 85, SEQ ID NO: 113, SEQ ID NO: 131 or SEQ ID NO: 133 which have polypeptides with at least 40% homology at the amino acid level with SEQ ID NO: 44, SEQ ID NO: 46, SEQ ID NO: 48, SEQ ID NO: 50, SEQ ID NO: 60, SEQ ID NO: 62, SEQ ID NO: 64, SEQ ID NO: 66, SEQ ID NO: 68, SEQ ID NO: 76, SEQ ID NO: 78, SEQ ID NO: 80, SEQ ID NO: 84, SEQ ID NO: 86, SEQ ID NO: 114, SEQ ID NO: 132 or SEQ ID NO: 134 and which have Δ5-elongase activity.

The invention furthermore relates to the nucleic acid sequences which are enumerated hereinbelow and which encode Δ6-elongases, ω3-desaturases, Δ6-desaturases, Δ5-desaturases, Δ4-desaturases or Δ12-desaturases.

Further advantageous isolated nucleic acid sequences are sequences selected from the group consisting of:
a) a nucleic acid sequence with the sequence shown in SEQ ID NO: 69, SEQ ID NO: 81, SEQ ID NO: 111 or SEQ ID NO: 183,
b) nucleic acid sequences which, as the result of the degeneracy of the genetic code, can be derived from the amino acid sequence shown in SEQ ID NO: 70, SEQ ID NO: 82, SEQ ID NO: 112 or SEQ ID NO: 184, or
c) derivatives of the nucleic acid sequence shown in SEQ ID NO: 69, SEQ ID NO: 81, SEQ ID NO: 111 or SEQ ID NO: 183 which encode polypeptides with at least 40% homology at the amino acid level with SEQ ID NO: 70, SEQ ID NO: 82, SEQ ID NO: 112 or SEQ ID NO: 184 and which have Δ6-elongase activity.

Isolated nucleic acid sequences encoding polypeptides with ω3-desaturase activity, selected from the group consisting of:
a) a nucleic acid sequence with the sequence shown in SEQ ID NO: 87 or SEQ ID NO: 105,
b) nucleic acid sequences which, as the result of the degeneracy of the genetic code, can be derived from the amino acid sequence shown in SEQ ID NO: 88 or SEQ ID NO: 106, or
c) derivatives of the nucleic acid sequence shown in SEQ ID NO: 87 or SEQ ID NO: 105 which have polypeptides with at least 60% identity at the amino acid level with SEQ ID NO: 88 or SEQ ID NO: 106 and which have ω3-desaturase activity.

Isolated nucleic acid sequences encoding polypeptides with Δ6-desaturase activity, selected from the group consisting of:
a) a nucleic acid sequence with the sequence shown in SEQ ID NO: 89 or in SEQ ID NO: 97,
b) nucleic acid sequences which, as the result of the degeneracy of the genetic code, can be derived from the amino acid sequence shown in SEQ ID NO: 90 or SEQ ID NO: 98, or
c) derivatives of the nucleic acid sequence shown in SEQ ID NO: 89 or SEQ ID NO: 97 which encode polypeptides with at least 40% homology at the amino acid level with SEQ ID NO: 90 or SEQ ID NO: 98 and which have Δ6-desaturase activity.

Isolated nucleic acid sequences encoding polypeptides with Δ5-desaturase activity, selected from the group consisting of:
a) a nucleic acid sequence with the sequence shown in SEQ ID NO: 91, SEQ ID NO: 93, SEQ ID NO: 99 or in SEQ ID NO: 101,
b) nucleic acid sequences which, as the result of the degeneracy of the genetic code, can be derived from the amino acid sequence shown in SEQ ID NO: 92, SEQ ID NO: 94, SEQ ID NO: 100 or in SEQ ID NO: 102, or
c) derivatives of the nucleic acid sequence shown in SEQ ID NO: 91, SEQ ID NO: 93, SEQ ID NO: 99 or in SEQ ID NO: 101 which encode polypeptides with at least 40% homology at the amino acid level with SEQ ID NO: 92, SEQ ID NO: 92, SEQ ID NO: 94, SEQ ID NO: 100 or in SEQ ID NO: 102 and which have Δ5-desaturase activity.

Isolated nucleic acid sequences encoding polypeptides with Δ12-desaturase activity, selected from the group consisting of:
a) a nucleic acid sequence with the sequence shown in SEQ ID NO: 95 or in SEQ ID NO: 103,
b) nucleic acid sequences which, as the result of the degeneracy of the genetic code, can be derived from the amino acid sequence shown in SEQ ID NO: 96 or in SEQ ID NO: 104, or
c) derivatives of the nucleic acid sequence shown in SEQ ID NO: 95 or in SEQ ID NO: 103 which encode polypeptides with at least 40% homology at the amino acid level with SEQ ID NO: 96 or in SEQ ID NO: 104 and which have Δ6-desaturase activity.

Isolated nucleic acid sequences encoding polypeptides with Δ12-desaturase activity, selected from the group consisting of:
a) a nucleic acid sequence with the sequence shown in SEQ ID NO: 107 or SEQ ID NO: 109,
b) nucleic acid sequences which, as the result of the degeneracy of the genetic code, can be derived from the amino acid sequence shown in SEQ ID NO: 108 or SEQ ID NO: 110, or
c) derivatives of the nucleic acid sequence shown in SEQ ID NO: 107 or SEQ ID NO: 109 which encode polypeptides with at least 50% homology at the amino acid level with SEQ ID NO: 108 or SEQ ID NO: 110 and which have Δ12-desaturase activity.

The abovementioned nucleic acids according to the invention are derived from organisms such as nonhuman animals, ciliates, fungi, plants such as algae or dinoflagellates which are capable of synthesizing PUFAs.

The isolated abovementioned nucleic acid sequences are advantageously derived from the order Salmoniformes, *Xenopus* or *Ciona*, the diatom genera *Thalassiosira* or *Crythecodinium*, or from the family of the Prasinophyceae, such as the genus *Ostreococcus* or the family Euglenaceae, such as the genus *Euglena*, or Pythiaceae, such as the genus *Phytophthora*.

The invention furthermore relates to isolated nucleic acid sequences as described above which encode polypeptides with ω3-desaturase activity, where the ω3-desaturases encoded by the nucleic acid sequences convert $C_{18}$-, $C_{20}$- and $C_{22}$-fatty acids with two, three, four or five double bonds and advantageously polyunsaturated $C_{18}$-fatty acids with two or three double bonds and polyunsaturated $C_{20}$-fatty acids with two, three or four double bonds. $C_{22}$-Fatty acids with four or five double bonds are also desaturated.

As described above, the invention furthermore relates to isolated nucleic acid sequence which encode polypeptides with Δ12-desaturases, Δ4-desaturases, Δ5-desaturases and Δ6-desaturases, where the Δ12-desaturases, Δ4-desaturases, Δ5-desaturases or Δ6-desaturases encoded by these nucleic acid sequences convert $C_{18}$-, $C_{20}$- and $C_{22}$-fatty acids with one, two, three, four or five double bonds and advantageously polyunsaturated $C_{18}$-fatty acids with one, two or three double bonds such as $C18:1^{\Delta 9}$, $C18:2^{\Delta 9,12}$, $C18:3^{\Delta 9,12,15}$, polyunsaturated $C_{20}$-fatty acids with three or four double bonds such as $C20:3^{\Delta 8,11,14}$ or $C20:4^{\Delta 8,11,14,17}$ or polyunsaturated $C_{22}$-fatty acids with four or five double bonds such as $C22:4^{\Delta 7,10,13,16}$ or $C22:5^{\Delta 7,10,13,16,19}$. The fatty acids are advantageously desaturated in the phospholipids or CoA-fatty acid esters, advantageously in the CoA-fatty acid esters.

In an advantageous embodiment, the term "nucleic acid (molecule)" as used in the present context additionally comprises the untranslated sequence at the 3' and at the 5' end of the coding gene region: at least 500, preferably 200, especially preferably 100 nucleotides of the sequence upstream of the 5' end of the coding region and at least 100, preferably 50, especially preferably 20 nucleotides of the sequence downstream of the 3' end of the coding gene region. An "isolated" nucleic acid molecule is separate from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' ends of the nucleic acid). In various embodiments, the isolated Δ12-desaturase, ω3-desaturase, Δ9-elongase, Δ6-desaturase, Δ8-desaturase, Δ6-elongase, Δ5-desaturase, Δ5-elongase or Δ4-desaturase molecule can comprise for example fewer than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived.

The nucleic acid molecules used in the process, for example a nucleic acid molecule with a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 or of a part thereof can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe and standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for isolating further nucleic acid sequences which can be used in the process. Moreover, a nucleic acid molecule comprising a complete sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 or a part thereof can be isolated by polymerase chain reaction, where oligonucleotide primers which are used on the basis of this sequence or parts thereof (for example a nucleic acid molecule comprising the complete sequence or part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for the amplification by means of polymerase chain reaction can be generated based on one of the sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 or with the aid of the amino acid sequences detailed in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 118, SEQ ID NO: 120, SEQ ID NO: 132, SEQ ID NO: 134, SEQ ID NO: 136, SEQ ID NO: 138 or SEQ ID NO: 184. A nucleic acid according to the invention can be amplified by standard PCR amplification techniques using cDNA or, alternatively, genomic DNA as template and suitable oligonucleotide primers. The nucleic acid amplified thus can be cloned into a suitable vector and characterized by means of DNA sequence analysis. Oligonucleotides which correspond to a desaturase nucleotide sequence can be generated by standard synthetic methods, for example using an automatic DNA synthesizer.

Homologs of the Δ12-desaturase, ω3-desaturase, Δ9-elongase, Δ6-desaturase, Δ8-desaturase, Δ6-elongase, Δ5-desaturase, Δ5-elongase or Δ4-desaturase nucleic acid sequences with the sequence SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO:

105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 means, for example, allelic variants with at least approximately 50 or 60%, preferably at least approximately 60 or 70%, more preferably at least approximately 70 or 80%, 90% or 95% and even more preferably at least approximately 85%, 86%, 87%, 88%, 89%, 90%, 91%, 92%, 93%, 94%, 95%, 96%, 97%, 98%, 99% or more identity or homology with a nucleotide sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 or its homologs, derivatives or analogs or parts thereof. Furthermore, isolated nucleic acid molecules of a nucleotide sequence which hybridize with one of the nucleotide sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 or with a part thereof, for example hybridized under stringent conditions. A part thereof is understood as meaning, in accordance with the invention, that at least 25 base pairs (=bp), 50 bp, 75 bp, 100 bp, 125 bp or 150 bp, preferably at least 175 bp, 200 bp, 225 bp, 250 bp, 275 bp or 300 bp, especially preferably 350 bp, 400 bp, 450 bp, 500 bp or more base pairs are used for the hybridization. It is also possible and advantageous to use the full sequence. Allelic variants comprise in particular functional variants which can be obtained by deletion, insertion or substitution of nucleotides from/into the sequence detailed in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183, it being intended, however, that the enzyme activity of the resulting proteins which are synthesized is advantageously retained for the insertion of one or more genes. Proteins which retain the enzymatic activity of Δ12-desaturase, ω3-desaturase, Δ9-elongase, Δ6-desaturase, Δ8-desaturase, Δ6-elongase, Δ5-desaturase, Δ5-elongase or Δ4-desaturase, i.e. whose activity is essentially not reduced, means proteins with at least 10%, preferably 20%, especially preferably 30%, very especially preferably 40% of the original enzyme activity in comparison with the protein encoded by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183. The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

Homologs of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 means for example also bacterial, fungal and plant homologs, truncated sequences, single-stranded DNA or RNA of the coding and noncoding DNA sequence.

Homologs of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 117, SEQ ID NO: 119, SEQ ID NO: 131, SEQ ID NO: 133, SEQ ID NO: 135, SEQ ID NO: 137 or SEQ ID NO: 183 also means derivatives such as, for example, promoter variants. The promoters upstream of the nucleotide sequences detailed can be modified by one or more nucleotide exchanges, by insertion(s) and/or deletion(s) without the functionality or activity of the promoters being adversely affected, however. It is furthermore possible that the modification of the promoter sequence enhances their activity or that they are replaced entirely by more active promoters, including those from heterologous organisms.

The abovementioned nucleic acids and protein molecules with Δ12-desaturase, ω3-desaturase, Δ9-elongase, Δ6-desaturase, Δ8-desaturase, Δ6-elongase, Δ5-desaturase, Δ5-elongase and/or Δ4-desaturase activity which are involved in the metabolism of lipids and fatty acids, PUFA cofactors and enzymes or in the transport of lipophilic compounds across membranes are used in the process according to the invention for the modulation of the production of PUFAs in transgenic organisms, advantageously in plants, such as maize, wheat, rye, oats, triticale, rice, barley, soybean, peanut, cotton, Linum species such as linseed or flax, Brassica species such as oilseed rape, canola and turnip rape, pepper, sunflower, borage, evening primrose and Tagetes, Solanaceae plants such as potato, tobacco, eggplant and tomato, Vicia species, pea, cassava, alfalfa, bushy plants (coffee, cacao, tea), Salix species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes lead to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only incorporated into triacylglycerol but also into membrane lipids.

Brassicaceae, Boraginaceae, Primulaceae, or Linaceae are particularly suitable for the production of PUFAs, for example stearidonic acid, eicosapentaenoic acid and docosahexaenoic acid. Linseed (Linum usitatissimum) is especially advantageously suitable for the production of PUFAs with the nucleic acid sequences according to the invention, advantageously, as described, in combination with further desaturases and elongases.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After condensation reaction, these two product molecules together form acetoacetyl-ACP, which is converted via a series of condensation, reduction and dehydratization reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) E. coli and Salmonella. ASM Press: Washington, D.C., pp. 612-636 and references cited therein; Lengeler et al. (Ed.) (1999) Biology of Procaryotes. Thieme: Stuttgart, New York, and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool. This is made possible by acyl-CoA:lysophospholipid acyltransferases. Moreover, these enzymes are capable of transferring the elongated fatty acids from the CoA esters back to the phospholipids. If appropriate, this reaction sequence can be followed repeatedly.

Examples of precursors for the biosynthesis of PUFAs are oleic acid, linoleic acid and linolenic acid. The C18-carbon fatty acids must be elongated to C20 and C22 in order to obtain fatty acids of the eicosa and docosa chain type. With the aid of the desaturases used in the process, such as the Δ12-, ω3-, Δ4-, Δ5-, Δ6- and Δ8-desaturases and/or Δ5-, Δ6-, Δ9-elongases, arachidonic acid, eicosapentaenoic acid, docosapentaenoic acid or docosahexaenoic acid, advantageously eicosapentaenoic acid and/or docosahexaenoic acid, can be produced and subsequently employed in various applications regarding foodstuffs, feedstuffs, cosmetics or pharmaceuticals. $C_{20}$- and/or $C_{22}$-fatty acids with at least two, advantageously at least three, four, five or six, double bonds in the fatty acid molecule, preferably $C_{20}$- or $C_{22}$-fatty acids with advantageously four, five or six double bonds in the fatty acid molecule, can be prepared using the abovementioned enzymes. Desaturation may take place before or after elongation of the fatty acid in question. This is why the products of the desaturase activities and the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the desaturases and elongases used in the process according to the invention are $C_{16}$-, $C_{18}$- or $C_{20}$-fatty acids such as, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid, arachidonic acid, eicosatetraenoic acid or eicosapentaenoic acid. The synthesized $C_{20}$- or $C_{22}$-fatty acids with at least two, three, four, five or six double bonds in the fatty acids are obtained in the process according to the invention in the form of the free fatty acid or in the form of their esters, for example in the form of their glycerides.

The term "glyceride" is understood as meaning glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engeneering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engeneering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantity and must therefore take up additional quantities, although they can be synthesized readily by other organisms such as bacteria; for example, cats are no longer capable of synthesizing arachidonic acid.

Phospholipids for the purposes of the invention are understood as meaning phosphatidylcholine, phosphatidylethanolamine, phosphatidylserine, phosphatidylglycerol and/or phosphatidylinositol, advantageously phosphatidylcholine.

The terms production or productivity are known in the art and comprise the concentration of the fermentation product (compounds of the formula I) which is formed within a specific period of time and in a specific fermentation volume (for example kg of product per hour per liter). It also comprises the productivity within a plant cell or a plant, that is to say the content of the desired fatty acids produced in the process relative to the content of all fatty acids in this cell or plant. The term production efficiency comprises the time required for obtaining a specific production quantity (for example the time required by the cell to establish a certain throughput rate of a fine chemical). The term yield or product/carbon yield is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained in a specific culture quantity over a specified period of time is increased. The terms biosynthesis or biosynthetic pathway are known in the art and comprise the synthesis of a compound, preferably an organic compound, by a cell from intermediates, for example in a multi-step and strongly regulated process. The terms catabolism or catabolic pathway are known in the art and comprise the cleavage of a compound, preferably of an organic compound, by a cell to give catabolites (in more general terms, smaller or less complex molecules), for example in a multi-step and strongly regulated process. The term metabolism is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

In a further embodiment, derivatives of the nucleic acid molecule according to the invention represented in SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 131, SEQ ID NO: 133 or SEQ ID NO: 183 encode proteins with at least 40%, advantageously approximately 50 or 60%, advantageously at least approximately 60 or 70% and more preferably at least approximately 70 or 80%, 80 to 90%, 90 to 95% and most preferably at least approximately 96%, 97%, 98%, 99% or more homology (=identity) with a complete amino acid sequence of SEQ ID NO: 44, SEQ ID NO: 46, SEQ ID NO: 48, SEQ ID NO: 50, SEQ ID NO: 60, SEQ ID NO: 62, SEQ ID NO: 64, SEQ ID NO: 66, SEQ ID NO: 68, SEQ ID NO: 70, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 132, SEQ ID NO: 134 or SEQ ID NO: 184. The homology was calculated over the entire amino acid or nucleic acid sequence region. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program BestFit and the following settings: Gap Weight: 50, Length Weight: 3, Average Match: 10.000 and Average Mismatch: 0.000. Unless otherwise specified, these settings were always used as standard settings for the sequence alignments.

Moreover, the invention comprises nucleic acid molecules which differ from one of the nucleotide sequences shown in SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 131, SEQ ID NO: 133 or SEQ ID NO: 183 (and parts thereof) owing to the degeneracy of the genetic code and which thus encode the same $\Delta 112$-desaturase, $\omega 3$-desaturase, $\Delta 6$-desaturase, $\Delta 5$-desaturase, $\Delta 4$-desaturase, $\Delta 6$-elongase or $\Delta 5$-elongase as those encoded by the nucleotide sequences shown in SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 113, SEQ ID NO: 131, SEQ ID NO: 133 or SEQ ID NO: 183.

In addition to the $\Delta 12$-desaturases, $\omega 3$-desaturases, $\Delta 5$-elongases, $\Delta 6$-desaturases, $\Delta 5$-desaturases, $\Delta 4$-desaturases or $\Delta 6$-elongases shown in SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79; SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 113, SEQ ID NO: 131, SEQ ID NO: 133 or SEQ ID NO: 183, the skilled worker will recognize that DNA sequence polymorphisms which lead to changes in the amino acid sequences of the $\Delta 12$-desaturase, $\omega 3$-desaturase, $\Delta 5$-elongase, $\Delta 6$-desaturase, $\Delta 5$-desaturase, $\Delta 4$-desaturase and/or $\Delta 6$-elongase may exist within a population. These genetic polymorphisms in the $\Delta 12$-desaturase, $\omega 3$-desaturase, $\Delta 5$-elongase, $\Delta 6$-desaturase, $\Delta 5$-desaturase, $\Delta 4$-desaturase and/or $\Delta 6$-elongase gene may exist between individuals within a population owing to natural variation. These natural variants usually bring about a variance of 1 to 5% in the nucleotide sequence of the $\Delta 12$-desaturase, $\omega 3$-desaturase, $\Delta 5$-elongase, $\Delta 6$-desaturase, $\Delta 5$-desaturase, $\Delta 4$-desaturase and/or $\Delta 6$-elongase gene. Each and every one of these nucleotide variations and resulting amino acid polymorphisms in the $\Delta 12$-desaturase, $\omega 3$-desaturase, $\Delta 5$-elongase, $\Delta 6$-desaturase, $\Delta 5$-desaturase, $\Delta 4$-desaturase and/or $\Delta 6$-elongase which are the result of natural variation and do not modify the functional activity are to be encompassed by the invention.

Owing to their homology to the $\Delta 12$-desaturase, $\omega 3$-desaturase, $\Delta 5$-elongase, $\Delta 6$-desaturase, $\Delta 5$-desaturase, $\Delta 4$-desaturase and/or $\Delta 6$-elongase nucleic acids disclosed here, nucleic acid molecules which are advantageous for the process according to the invention can be isolated following standard hybridization techniques under stringent hybridization conditions, using the sequences or part thereof as hybridization probe. In this context it is possible, for example, to use isolated nucleic acid molecules which are least 15 nucleotides in length and which hybridize under stringent conditions with the nucleic acid molecules which comprise a nucleotide sequence of SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 113, SEQ ID NO: 131, SEQ ID NO: 133 or SEQ ID NO: 183. Nucleic acids with at least 25, 50, 100, 200 or more nucleotides can also be used. The "hybridizes under stringent conditions" as used in the present context is intended to describe hybridization and washing conditions under which nucleotide sequences with at least 60% homology to one another usually remain hybridized with one another. Conditions are preferably such that sequences with at least approximately 65%, preferably at least approximately 70% and especially preferably at least 75% or more homology to one another usually remain hybridized to one another. These stringent conditions are known to the skilled worker and described, for example, in Current Protocols in Molecular Biology, John Wiley & Sons, N.Y. (1989), 6.3.1-6.3.6. A preferred nonlimiting example of stringent hybridization conditions is hybridizations in 6× sodium chloride/sodium citrate (=O—SSC) at approximately 45° C., followed by one or more washing steps in 0.2×SSC, 0.1% SDS at 50 to 65° C. The skilled worker knows that these hybridization conditions differ depending on the type of nucleic acid and, for example when organic solvents are present, regarding temperature and buffer concentration. Under "standard hybridization conditions", for example, the hybridization temperature is, depending on the type of nucleic acid, between 42° C. and 58° C. in aqueous buffer with a concentration of 0.1 to 5×SSC (pH 7.2). If organic solvents, for example 50% formamide, are present in the abovementioned buffer, the temperature under standard conditions is approximately 42° C. The hybridization conditions for DNA:DNA hybrids, for example, are 0.1×SSC and 20° C. to 45° C., preferably 30° C. to 45° C. The hybridization conditions for DNA:RNA hybrids are, for example, 0.1× SSC and 30° C. to 55° C., preferably 45° C. to 55° C. The abovementioned hybridization conditions are determined by way of example for a nucleic acid with approximately 100 bp (=base pairs) in length and with a G+C content of 50% in the absence of formamide. The skilled worker knows how to determine the required hybridization conditions on the basis of the abovementioned textbooks or textbooks such as Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

In order to determine the percentage of homology (=identity) of two amino acid sequences (for example one of the sequences of SEQ ID NO: 44, SEQ ID NO: 46, SEQ ID NO: 48, SEQ ID NO: 50, SEQ ID NO: 60, SEQ ID NO: 62, SEQ ID NO: 64, SEQ ID NO: 66, SEQ ID NO: 68, SEQ ID NO: 70, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 114, SEQ ID NO: 132, SEQ ID NO: 134 or SEQ ID NO: 184) or of two nucleic acids (for example SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 113, SEQ ID NO: 131, SEQ ID NO: 133 or SEQ ID NO: 183) the sequences are written one under the other for an optimal comparison (for example, gaps may be introduced into the sequence of a protein or of a nucleic acid in order to generate an optimal alignment with the other protein or the other nucleic acid). Then, the amino acid residue or nucleotides at the corresponding amino acid positions or nucleotide positions are compared. If a position in a sequence is occupied by the same amino acid residue or the same nucleotide as the corresponding position in the other sequence, then the molecules are homologous at this position (i.e. amino acid or nucleic acid "homology" as used in the present context corresponds to amino acid or nucleic acid "identity"). The percentage of homology between the two sequences is a function of the number of positions which the sequences share (i.e. % homology=number of identical positions/total number of positions×100). The terms homology and identity are therefore to be considered as synonymous.

An isolated nucleic acid molecule which encodes a Δ12-desaturase, ω3-desaturase, Δ6-desaturase, Δ5-desaturase, Δ4-desaturase, Δ5-elongase and/or Δ6-elongase which is homologous to a protein sequence of SEQ ID NO: 44, SEQ ID NO: 46, SEQ ID NO: 48, SEQ ID NO: 50, SEQ ID NO: 60, SEQ ID NO: 62, SEQ ID NO: 64, SEQ ID NO: 66, SEQ ID NO: 68, SEQ ID NO: 70, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 114, SEQ ID NO: 132, SEQ ID NO: 134 or SEQ ID NO: 184 can be generated by introducing one or more nucleotide substitutions, additions or deletions in/into a nucleotide sequence of SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 113, SEQ ID NO: 131, SEQ ID NO: 133 or SEQ ID NO: 183 so that one or more amino acid substitutions, additions or deletions are introduced in/into the protein which is encoded. Mutations in one of the sequences of SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 113, SEQ ID NO: 131, SEQ ID NO: 133 or SEQ ID NO: 183 can be introduced by standard techniques such as site-specific mutagenesis and PCR-mediated mutagenesis. It is preferred to generate conservative amino acid substitutions in one or more of the predicted nonessential amino acid residues. In a "conservative amino acid substitution", the amino acid residue is replaced by an amino acid residue with a similar side chain. Families of amino acid residues with similar side chains have been defined in the art. These families comprise amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in a Δ12-desaturase, ω3-desaturase, Δ6-desaturase, Δ5-desaturase, Δ4-desaturase, Δ5-elongase or Δ6-elongase is thus preferably replaced by another amino acid residue from the same family of side chains. In another embodiment, the mutations can, alternatively, be introduced randomly over all or part of the sequence encoding the Δ12-desaturase, ω3-desaturase, Δ6-desaturase, Δ5-desaturase, Δ4-desaturase, Δ5-elongase or Δ6-elongase, for example by saturation mutagenesis, and the resulting mutants can be screened by recombinant expression for the herein described Δ12-desaturase, ω3-desaturase, Δ6-desaturase, Δ5-desaturase, Δ4-desaturase, Δ5-elongase or Δ6-elongase activity in order to identify mutants which have retained the Δ12-desaturase, ω3-desaturase, Δ6-desaturase, Δ5-desaturase, Δ4-desaturase, Δ5-elongase or Δ6-elongase activity. Following the mutagenesis of one of the sequences SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 113, SEQ ID NO: 131, SEQ ID NO: 133 or SEQ ID NO: 183, the protein which is encoded can be expressed recombinantly, and the activity of the protein can be determined, for example using the tests described in the present text.

The invention furthermore relates to transgenic nonhuman organisms which comprise the nucleic acids SEQ ID NO: 43, SEQ ID NO: 45, SEQ ID NO: 47, SEQ ID NO: 49, SEQ ID NO: 59, SEQ ID NO: 61, SEQ ID NO: 63, SEQ ID NO: 65, SEQ ID NO: 67, SEQ ID NO: 69, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 113, SEQ ID NO: 131, SEQ ID NO: 133 or SEQ ID NO: 183 according to the invention or a gene construct or a vector which comprise these nucleic acid sequences according to the invention. The nonhuman organism is advantageously a microorganism, a nonhuman animal or a plant, especially preferably a plant.

The present invention is illustrated in greater detail by the examples which follow, which are not to be construed as limiting. The content of all of the references, patent applications, patents and published patent applications cited in the present patent application is herewith incorporated by reference.

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of E. coli cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the method of Sanger (Sanger et al. (1977) Proc. Natl. Acad. Sci. USA 74, 5463-5467). Fragments obtained by polymerase chain reaction were sequenced and verified to avoid polymerase errors in constructs to be expressed.

Example 3

Cloning of Oncorhynchus mykiss Genes

The search for conserved regions in the protein sequences corresponding to the elongase genes detailed in the application identified two sequences with corresponding motifs in the Genbank sequence database.

| Name of gene | Genbank No. | Amino acids |
|---|---|---|
| OmELO2 | CA385234, CA364848, CA366480 | 264 |
| OmELO3 | CA360014, CA350786 | 295 |

Oncoryhnchus mykiss total RNA was isolated with the aid of the RNAeasy kit from Qiagen (Valencia, Calif., US). Poly-A+ RNA (mRNA) was isolated from the total RNA with the aid of oligo-dT-cellulose (Sambrook et al., 1989). The RNA was subjected to reverse transcription using the Reverse Transcription System kit from Promega, and the cDNA synthesized was cloned into the vector lambda ZAP (lambda ZAP Gold, Stratagene). The cDNA was then unpackaged in accordance with the manufacturer's instructions to give the plasmid DNA. The cDNA plasmid library was then used for the PCR for cloning expression plasmids.

Example 4

Cloning of Expression Plasmids for the Purposes of Heterologous Expression in Yeasts The following oligonucleotides were used for the PCR reaction for cloning the two sequences for the heterologous expression in yeasts:

| Primer | Nucleotide sequence |
|---|---|
| 5' f* OmELO2 | 5'aagcttacataatggcttcaacatggcaa (SEQ ID NO: 179) |
| 3' r* OmELO2 | 5'ggatccttatgtcttcttgctcttcctgtt (SEQ ID NO: 180) |
| 5' f OmELO3 | 5'aagcttacataatggagacttttaat (SEQ ID NO: 181) |
| 3' r OmELO3 | 5'ggatccttcagtccccctcactttcc (SEQ ID NO: 182) |

*f: forward, r: reverse

Composition of the PCR Mix (50 µl):
5.00 µl template cDNA
5.00 µl 10× buffer (Advantage polymerase)+25 mM MgCl₂
5.00 µl 2 mM dNTP
1.25 µl of each primer (10 pmol/µl)
0.50 µl Advantage polymerase
The Advantage polymerase from Clontech was employed.
PCR Reaction Conditions:
Annealing temperature: 1 minute at 55° C.
Denaturation temperature: 1 minute at 94° C.
Elongation temperature: 2 minutes at 72° C.
Number of cycles: 35

The PCR product was incubated for 2 hours at 37° C. with the restriction enzymes HindIII and BamHI. The yeast expression vector pYES3 (Invitrogen) was incubated in the same manner. Thereafter, the 812 bp PCR product, the 905 bp PCR product and the vector were separated by agarose gel electrophoresis and the corresponding DNA fragments were excised. The DNA was purified by means of Qiagen gel purification kit following the manufacturer's instructions. Thereafter, vector and elongase cDNA were ligated. The Rapid Ligation kit from Roche was used for this purpose. The resulting plasmids pYES3-OmELO2 and pYES3-OmELO3 were verified by sequencing and transformed into the Saccharomyces strain INVSc1 (Invitrogen) by electroporation (1500 V). As a control, pYES3 was transformed in parallel. Thereafter, the yeasts were plated onto minimal dropout tryptophan medium supplemented with 2% glucose. Cells which were capable of growth without tryptophan in the medium thus comprised the corresponding plasmids pYES3, pYES3-OmELO2 (SEQ ID NO: 51) and pYES3-OmELO3 (SEQ ID NO: 53). After the selection, in each case two transformants were chosen for the further functional expression.

Example 5

Cloning Expression Plasmids for the Purposes of Seed-Specific Expression in Plants To transform plants, a further transformation vector based on pSUN-USP was generated. To this end, NotI cleavage sites were introduced at the 5' and 3' ends of the coding sequence, using the following primer pair:

PSUN-OmELO2

(SEQ ID NO: 175)
Forward: 5'-GCGGCCGCATAATGGCTTCAACATGGCAA (SEQ ID NO: 176)
Reverse: 3'-GCGGCCGCTTATGTCTTCTTGCTCTTCCTGTT

PSUN-OMELO3

(SEQ ID NO: 177)
Forward: 5'-GCGGCCGCataatggagactttaat (SEQ ID NO: 178)
Reverse: 3'-GCGGCCGCtcagtccccctcactttcc Composition of the PCR Mix (50 µl):
5.00 µl template cDNA
5.00 µl 10× buffer (Advantage polymerase)+25 mM MgCl$_2$
5.00 µl 2 mM dNTP
1.25 µl of each primer (10 pmol/µl)
0.50 µl Advantage polymerase
The Advantage polymerase from Clontech was employed.
PCR Reaction Conditions:
Annealing temperature: 1 minute at 55° C.
Denaturation temperature: 1 minute at 94° C.
Elongation temperature: 2 minutes at 72° C.
Number of cycles: 35

The PCR products were incubated for 16 hours at 37° C. with the restriction enzyme NotI. The plant expression vector pSUN300-USP was incubated in the same manner. Thereafter, the PCR products and the 7624 bp vector were separated by agarose gel electrophoresis and the corresponding DNA fragments were excised. The DNA was purified by means of Qiagen gel purification kit following the manufacturer's instructions. Thereafter, vector and PCR products were ligated. The Rapid Ligation kit from Roche was used for this purpose. The resulting plasmids pSUN-OmELO2 and pSUN-OmELO3 were verified by sequencing.

pSUN300 is a derivative of plasmid pPZP (Hajdukiewicz, P, Svab, Z, Maliga, P., (1994) The small versatile pPZP family of *Agrobacterium* binary vectors for plant transformation. Plant Mol Biol 25:989-994). pSUN-USP originated from pSUN300, by inserting a USP promoter as EcoRI fragment into pSUN300. The polyadenylation signal is that of the octopine synthase gene from the *A. tumefaciens* Ti plasmid (ocs terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982). The USP promoter corresponds to the nucleotides 1-684 (Genbank Accession X56240), where part of the noncoding region of the USP gene is present in the promoter. The promoter fragment which is 684 base pairs in size was amplified by means of commercially available T7 standard primers (Stratagene) and with the aid of a synthesized primer via a PCR reaction following standard methods (primer sequence: 5'-GTCGACCCGCGGACTAGTGGGC-CCTCT-AGACCCGGGGGATCCGGATCTGCTGGCTAT-GAA-3', SEQ ID NO: 174). The PCR fragment was cut again with EcoRI/SalI and introduced into the vector pSUN300 with OCS terminator. This gave rise to the plasmid with the name pSUN-USP. The construct was used for the transformation of *Arabidopsis thaliana*, oilseed rape, tobacco and linseed.

Example 6

Lipid Extraction from Yeasts and Seeds

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of desired product (i.e. of the lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research, Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for the production of the desired compound, such as intermediates and by-products, in order to determine the overall production efficiency of the compound. The analytical methods comprise measuring the amount of nutrients in the medium (for example sugars, hydrocarbons, nitrogen sources, phosphate and other ions), measuring the biomass composition and the growth, analyzing the production of conventional metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas liquid chromatography/mass spectrometry; TAG, triacylglycerol; TLC, thin-layer chromatography).

The unambiguous detection for the presence of fatty acid products can be obtained by analyzing recombinant organisms using analytical standard methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometric methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 μm, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Plant material is initially homogenized mechanically by comminuting in a pestle and mortar to make it more amenable to extraction.

This is followed by heating at 10° C. for 10 minutes and, after cooling on ice, by resedimentation. The cell sediment is hydrolyzed for one hour at 90° C. with 1 M methanolic sulfuric acid and 2% dimethoxypropane, and the lipids are transmethylated. The resulting fatty acid methyl esters (FAMEs) are extracted in petroleum ether. The extracted FAMEs are analyzed by gas liquid chromatography using a capillary column (Chrompack, WCOT Fused Silica, CP-Wax-52 CB, 25 m, 0.32 mm) and a temperature gradient of from 170° C. to 240° C. in 20 minutes and 5 minutes at 240° C. The identity of the fatty acid methyl esters is confirmed by comparison with corresponding FAME standards (Sigma). The identity and position of the double bond can be analyzed further by suitable chemical derivatization of the FAME mixtures, for example to give 4,4-dimethoxyoxazoline derivatives (Christie, 1998) by means of GC-MS.

Yeasts which had been transformed as described in Example 4 with the plasmids pYES3, pYES3-OmELO2 and pYES3-OmELO3 were analyzed as follows:

The yeast cells from the main cultures were harvested by centrifugation (100×g, 10 min, 20° C.) and washed with 100 mM NaHCO$_3$, pH 8.0 to remove residual medium and fatty acids. Fatty acid methyl esters (FAMEs) were prepared from the yeast cell sediments by acid methananolysis. To this end, the cell sediments were incubated with 2 ml of 1 N methanolic sulfuric acid and 2% (v/v) dimethoxypropane for 1 hour at 80° C. The FAMEs were extracted by extracting twice with petroleum ether (PE). To remove underivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 μl of PE. The samples were separated on a DB-23 capillary column (30 m, 0.25 mm, 0.25 μm, Agilent) in a Hewlett-Packard 6850 gas chromatograph flame ionization detector. The conditions for the GLC analysis were as follows: the oven temperature was programmed from 50° C. to 250° C. with a rate of 5° C./min and finally 10 minutes at 250° C. (holding).

The signals were identified by comparing the retention times with corresponding fatty acid standards (Sigma).

The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 7

Functional Characterization of OmELO2 and OmELO3

While OmELO2 shows no elongase activity, OmELO3 was shown to have a pronounced activity with different substrates. The substrate specificity of OmElo3 was determined after expression and feeding a variety of fatty acids (FIG. 2). The substrates fed can be detected in large amounts in all transgenic yeasts. All transgenic yeasts show the synthesis of novel fatty acids, the products of the OmElo3 reaction. This means that functional expression of the gene OmElo3 has been possible.

FIG. 2 shows that OmElo3 has a substrate specificity which leads with high specificity to the elongation of Δ5- and Δ6-fatty acids with one ω3-double bond. Moreover, ω6-fatty acids (C18 and C20) were furthermore also elongated with less specificity. The best substrates for OmElo3 (up to 66% elongation) were stearidonic acid (C18:4 ω3) and eicosapentaenoic acid (C20:5 ω3).

Example 8

Reconstitution of the Synthesis of DHA in Yeast

The reconstitution of the biosynthesis of DHA (22:6 ω3) was carried out starting from EPA (20:5 ω3) or stearidonic acid (18:4 ω3) by coexpressing OmElo3 together with the *Euglena gracilis* Δ4-desaturase or the *Phaeodactylum tricornutum* Δ5-desaturase and the *Euglena gracilis* Δ4-desaturase. To this end, the expression vectors pYes2-EgD4 and pESCLeu-PtD5 were additionally constructed. The above-mentioned yeast strain which is already transformed with pYes3-OtElo3 (SEQ ID NO: 55), was transformed further with pYes2-EgD4, or simultaneously with pYes2-EgD4 and pESCLeu-PtD5. The transformed yeasts were selected on complete minimal dropout tryptophan and uracil medium agar plates supplemented with 2% glucose in the case of the pYes3-OmELO/pYes2-EgD4 strain and complete minimal dropout tryptophan, uracil and leucine medium in the case of the pYes3-OmELO/pYes2-EgD4+pESCLeu-PtD5 strain. Expression was induced by addition of 2% (w/v) galactose as indicated above. The cultures were incubated for a further 120 hours at 15° C.

FIG. 3 shows the fatty acid profiles of transgenic yeasts which had been fed with 20:5 ω3. In the control yeast (A), which had been transformed with the vector pYes3-OmElo3 (SEQ ID NO: 53) and the Hank vector pYes2, 20:5 ω3 was elongated very efficiently to give 22:5 ω3 (65% elongation), The additional introduction of EgΔ-4-desaturase resulted in the conversion of 22:5 ω3 into 22:6 ω3 (DHA). The fatty acid composition of the transgenic yeasts is shown in FIG. 5. After coexpression of OmElo3 and EgD4, up to 3% of DHA was detected in yeasts.

In a further coexpression experiment, OmElo3, EgD4 and a *P. tricornutum* Δ5-desaturase (PtD5) were expressed together. The transgenic yeasts were fed stearidonic acid (18:4 ω3) and they were analyzed (FIG. 4). The fatty acid composition of these yeasts is shown in FIG. 5. The fatty acid fed, 18:4 ω3, was elongated by OmElo3 to give 20:4 ω3 (60% elongation). The latter was desaturated by PtD5 to give 20:5 ω3. The PtD5 activity was 15%. Moreover, it was possible to elongate 20:5 ω3 by OmElo3 to give 22:5 ω3. Thereafter, the newly synthesized 22:5 ω3 was desaturated to 22:6 ω3 (DHA). Up to 0.7% of DHA was obtained in these experiments.

It can be seen from these experiments that the sequences OmElo3, EgD4 and PtD5 which are used in the present invention are suitable for the production of DHA in eukaryotic cells.

Example 9

Generation of Transgenic Plants a) Generation of Transgenic Oilseed Rape Plants (Modified Method of Moloney et al., 1992, Plant Cell Reports, 8:238-242)

Binary vectors in *Agrobacterium tumefaciens* C58C1: pGV2260 or *Escherichia coli* (Deblaere et al, 1984, Nucl. Acids. Res. 13, 4777-4788) can be used for generating transgenic oilseed rape plants. To transform oilseed rape plants (Var. Drakkar, NPZ Nordeutsche Pflanzenzucht, Hohenlieth, Germany), a 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) is used. Petiols or hypocotyls of freshly germinated sterile oilseed rape plants (in each case approx. 1 cm$^2$) are incubated with a 1:50 agrobacterial dilution for 5-10 minutes in a Petri dish. This is followed by 3 days of coincubation in the dark at 25° C. on 3MS medium supplemented with 0.8% Bacto agar. The cultures are then grown for 3 days at 16 hours light/8 hours dark and the cultivation is continued in a weekly rhythm on MS medium supplemented with 500 mg/l Claforan (cefotaxim sodium), 50 mg/l kanamycin, 20 µM benzylaminopurine (BAP), now supplemented with 1.6 g/l of glucose. Growing shoots are transferred to MS medium supplemented with 2% sucrose, 250 mg/l Claforan and 0.8% Bacto agar. If no roots develop after three weeks, 2-indolebutyric acid was added to the medium as growth hormone for rooting.

Regenerated shoots were obtained on 2MS medium supplemented with kanamycin and Claforan; after rooting, they were transferred to compost and, after growing on for two weeks in a controlled-environment cabinet or in the greenhouse, allowed to flower, and mature seeds were harvested and analyzed by lipid analysis for elongase expression, such as Δ5-elongase or Δ6-elongase activity or ω3-desaturase activity. In this manner, lines with elevated contents of polyunsaturated C$_{20}$- and C22-fatty acids can be identified.

b) Generation of Transgenic Linseed Plants

Transgenic linseed plants can be generated for example by the method of Bell et al., 1999, In Vitro Cell. Dev. Biol. Plant. 35(6):456-465 by means of particle bombardment. In general, linseed was transformed by an *agrobacteria*-mediated transformation, for example by the method of Mlynarova et al. (1994), Plant Cell Report 13: 282-285.

Example 10

Cloning Δ5-Elongase Genes from *Thraustochytrium aureum* ATCC34304 and *Thraustochytrium* ssp By comparing the various elongase protein sequences found in the present application, it was possible to define conserved nucleic acid regions (histidine box: His-Val-X-His-His, tyrosine box: Met-Tyr-X-Tyr-Tyr). An EST database of *T. aureum* ATCC34304 and *Thraustochytrium* ssp. was screened for further Δ5-elongases with the aid of these sequences. The following new sequences were found:

| Name of gene | Nucleotides | Amino acids |
| --- | --- | --- |
| BioTaurELO1 | 828 bp | 275 |
| TL16y2 | 831 | 276 |

*T. aureum* ATCC34304 and *Thraustochytrium* ssp. total RNA was isolated with the aid of the RNAeasy kit from Qiagen (Valencia, Calif., US). mRNA was isolated from the total RNA with the aid of the PolyATract isolation system (Promega). The mRNA was subjected to reverse transcription using the Marathon cDNA amplification kit (BD Biosciences) and adaptors were ligated in accordance with the manufacturer's instructions. The cDNA library was then used for the PCR for cloning expression plasmids by means of 5'- and 3'-RACE (rapid amplification of cDNA ends).

Example 11

Cloning of Expression Plasmids for the Heterologous Expression in Yeasts

The following oligonucleotides were used for the PCR reaction for cloning the sequence for the heterologous expression in yeasts:

| Primer | Nucleotide sequence |
| --- | --- |
| 5' f* BioTaurELO1 | 5'gacataatgacgagcaacatgag (SEQ ID NO: 170) |
| 3' r* BioTaurELO1 | 5'cggcttaggccgacttggccttggg (SEQ ID NO: 171) |
| 5' f*TL16y2 | 5'agacataatggacgtcgtcgagcagcaatg (SEQ ID NO: 172) |
| 3' r*TL16y2 | 5'ttagatggtcttctgcttcttgggcgcc (SEQ ID NO: 173) |

*f: forward, r: reverse

Composition of the PCR Mix (50 µl):
5.00 µl template cDNA
5.00 µl 10× buffer (Advantage polymerase)+25 mM MgCl$_2$
5.00 µl 2 mM dNTP
1.25 µl of each primer (10 pmol/µl)
0.50 µl Advantage polymerase
The Advantage polymerase from Clontech was employed.
PCR Reaction Conditions:
Annealing temperature: 1 minute at 55° C.
Denaturation temperature: 1 minute at 94° C.
Elongation temperature: 2 minutes at 72° C.
Number of cycles: 35

The PCR products BioTaurELO1 (see SEQ ID NO: 65) and TL16y2 (see SEQ ID NO: 83) were incubated for 30 minutes at 21° C. together with the yeast expression vector pYES2.1-TOPO (Invitrogen) in accordance with the manufacturer's instructions. Here, the PCR product was ligated into the vector by means of a T-overhang and the activity of a topoisomerase (Invitrogen). After the incubation, *E. coli* DH5 (cells were transformed. Suitable clones were identified by PCR, the plasmid DNA was isolated by means of the Qiagen DNAeasy kit and verified by sequencing. The correct sequence was then transformed into the *Saccharomyces* strain INVSc1 (Invitrogen) by electroporation (1500 V). As a control, the blank vector pYES2.1 was transformed in parallel. Thereafter, the yeasts were plated out on minimal dropout uracil medium supplemented with 2% glucose.

Cells which were capable of growing in the medium without uracil thus comprise the corresponding plasmids pYES2.1, pYES2.1-BioTaurELO1 and pYES2.1-TL16y2. After the selection, in each case two transformants were chosen for the further functional expression.

Example 12

Cloning Expression Plasmids for the Purposes of Seed-Specific Expression in Plants To transform plants, a further transformation vector based on pSUN-USP was generated. To this end, NotI cleavage sites were introduced at the 5' and 3' ends of the coding sequence, using the following primer pair:

```
PSUN-BioTaurELO1
                                  (SEQ ID NO: 166)
Forward: 5'-GCGGCCGCATAATGACGAGCAACATGAGC (SEQ ID NO: 167)
Reverse: 3'-GCGGCCGCTTAGGCCGACTTGGCCTTGGG PSUN-TL16y2
                                  (SEQ ID NO: 168)
Forward: 5'-GCGGCCGCACCATGGACGTCGTCGAGCAGCAATG (SEQ ID NO: 169)
Reverse: 5'-GCGGCCGCTTAGATGGTCTTCTGCTTCTTGGGCGCC
```

Composition of the PCR Mix (50 µl):
5.00 µl template cDNA
5.00 µl 10× buffer (Advantage polymerase)+25 mM $MgCl_2$
5.00 µl 2 mM dNTP
1.25 µl of each primer (10 pmol/µl)
0.50 µl Advantage polymerase
The Advantage polymerase from Clontech was employed.
PCR Reaction Conditions:
Annealing temperature: 1 minute at 55° C.
Denaturation temperature: 1 minute at 94° C.
Elongation temperature: 2 minutes at 72° C.
Number of cycles: 35

The PCR products were incubated for 16 hours at 37° C. with the restriction enzyme NotI. The plant expression vector pSUN300-USP was incubated in the same manner. Thereafter, the PCR products and the 7624 bp vector were separated by agarose gel electrophoresis and the corresponding DNA fragments were excised. The DNA was purified by means of Qiagen gel purification kit following the manufacturer's instructions. Thereafter, vector and PCR products were ligated. The Rapid Ligation kit from Roche was used for this purpose. The resulting plasmids pSUN-BioTaurELO1 and pSUN-TL16y2 were verified by sequencing.

pSUN300 is a derivative of plasmid pPZP (Hajdukiewicz, P, Svab, Z, Maliga, P., (1994) The small versatile pPZP family of *Agrobacterium* binary vectors for plant transformation. Plant Mol Biol 25:989-994). pSUN-USP originated from pSUN300, by inserting a USP promoter as EcoRI fragment into pSUN300. The polyadenylation signal is that of the octopine synthase gene from the *A. tumefaciens* Ti plasmid (ocs terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982). Der USP promoter corresponds to the nucleotides 1-684 (Genbank Accession X56240), where part of the noncoding region of the USP gene is present in the promoter. The promoter fragment which is 684 base pairs in size was amplified by means of commercially available T7 standard primers (Stratagene) and with the aid of a synthesized primer via a PCR reaction following standard methods (primer sequence: 5'-GTCGACCCGCGGACTAGTGGGC-CCTCT-AGACCCGGGGGATCCGGATCTGCTGGCTAT-GAA-3', SEQ ID NO: 165). The PCR fragment was cut again with EcoRI/SalI and introduced into the vector pSUN300 with OCS terminator. This gave rise to the plasmid with the name pSUN-USP. The construct was used for the transformation of *Arabidopsis thaliana*, oilseed rape, tobacco and linseed.

The lipid extraction from yeasts and seeds was carried out as described in Example 6

Example 13

Functional Characterization of BioTaurELO1 and TL16y2

The substrate specificity of BioTaurELO1 was determined after expression and feeding of various fatty acids (FIG. 6). FIG. 6 shows the feeding experiments for determining the functionality and substrate specificity with yeast strains which comprise either the vector pYes2.1 (control) or the vector pYes2.1-BioTaurELO1 (=BioTaur) with the Δ5-elongase. In both batches, 200 µM of γ-linolenic acid and eicosapentaenoic acid were added to the yeast incubation medium, and incubation was carried out for 24 hours. After the fatty acids had been extracted from the yeasts, they were transmethylated and separated by gas chromatography. The elongation products obtained from the two fatty acids which had been fed are identified by arrows.

The substrates fed can be detected in large amounts in all transgenic yeasts. All transgenic yeasts show the synthesis of novel fatty acids, the products of the BioTaurELO1 reaction. This means that functional expression of the gene BioTaurELO1 has been possible.

FIG. 6 shows that BioTaurELO1 shows a substrate specificity which leads with high specificity to the elongation of Δ5- and Δ6-fatty acids with one ω3-double bond. ω6-Fatty acids (C18 and C20) were furthermore also elongated. γ-Linolenic acid (C18:3 ω6) is converted at a rate of 65.28%, stearidonic acid (C18:4 ω3) at a rate of 65.66% and eicosapentaenoic acid (C20:5 ω3) at a rate of 22.01%. The substrate specificities of the various feeding experiments are shown in table 3 (see end of description).

The conversion rate of GLA when GLA and EPA were fed was 65.28%. The conversion rate of EPA when the same amounts of GLA and EPA were fed was 9.99%. If only EPA was fed, the EPA conversion rate was 22.01%. Arachidonic acid (=ARA) was also converted when fed. The conversion rate was 14.47%. Stearidonic acid (=SDA) was also converted. In this case, the conversion rate was 65.66%.

The functionality and substrate specificity of TL16y2 was determined after expression and feeding of various fatty acids. Table 4 shows the feeding experiments. The feeding experiments were carried-out in the same manner as described for BioTaurELO1. The substrates fed can be detected in large amounts in all transgenic yeasts. All transgenic yeasts showed the synthesis of novel fatty acids, the products of the TL16y2 reaction (FIG. 11). This means that functional expression of the gene TL16y2 has been possible.

TABLE 4

Expression of TL16y2 in yeast.
Areas of the gas chromatographic analysis in %

| Plasmid | Fatty acid | C18:3 (n-6) | C18:4 (n-3) | C20:3 (n-6) | C20:4 (n-6) | C20:4 (n-3) | C20:5 (n-3) | C22:4 (n-6) | C22:5 (n-3) |
|---|---|---|---|---|---|---|---|---|---|
| pYES | 250 uM EPA | | | | | | 13.79 | | |
| TL16y2 | 250 uM EPA | | | | | | 25.81 | | 2.25 |
| pYES | 50 uM EPA | | | | | | 5.07 | | |
| TL16y2 | 50 uM EPA | | | | | | 2.48 | | 1.73 |
| pYES | 250 uM GLA | 8.31 | | | | | | | |
| TL16y2 | 250 uM GLA | 3.59 | | 10.71 | | | | | |
| pYES | 250 uM ARA | | | | 16.03 | | | | |
| TL16y2 | 250 uM ARA | | | | 15.2 | | 3.87 | | |
| pYES | 250 uM SDA | | 26.79 | | | 0.35 | | | |
| TL16y2 | 250 uM SDA | | 7.74 | | | 29.17 | | | |

The results for TL16y2 in comparison with the control, which are shown in Table 4, show the following conversion rates in percent: a) % conversion rate EPA (250 μM): 8%, b) % conversion rate EPA (50 μM): 41%, c) % conversion rate ARA: 20.3%, d) % conversion rate SDA: 79.4% and e) % conversion rate GLA: 74.9%.

Thus, TL16y2 shows Δ5-, Δ6- and Δ8-elongase activity. Among these, the activity for C18-fatty acids with Δ6-double bond is the highest. Depending on the concentration of fatty acids fed, this is followed by the elongation of C20-fatty acids with one Δ5- or Δ8-double bond.

Example 14

Cloning Genes from Ostreococcus tauri

By searching for conserved regions in the protein sequences with the aid of the elongase genes listed in the application with Δ5-elongase activity or Δ6-elongase activity, it was possible to identify two sequences with corresponding motifs in an Ostreococcus tauri sequence database (genomic sequences). The sequences are the following

| Name of gene | SEQ ID | Amino acids |
|---|---|---|
| OtELO1 (Δ5-elongase) | SEQ ID NO: 67 | 300 |
| OtELO2 (Δ6-elongase) | SEQ ID NO: 81 | 292 |

OtElo1 (SEQ ID NO: 67) has the highest similarity With a Dania rerio elongase (GenBank AAN77156; approx. 26% identity), while OtElo2 (SEQ ID NO: 81) has the greatest similarity with the Physcomitrella Elo (PSE) [approx. 36% identity] (alignments were carried out using the tBLASTn algorithm (Altschul et al., J. Mol. Biol. 1990, 215: 403-410).

The cloning procedure was carried out as follows:
40 ml of an Ostreococcus tauri culture in the stationary phase were spun down and the pellet was resuspended in 100 μl of double-distilled water and stored at −20° C. The relevant genomic DNAs were amplified based on the PCR method. The corresponding primer pairs were selected in such a way that they contained the yeast consensus sequence for highly efficient translation (Kozak, Cell 1986, 44:283-292) next to the start codon. The amplification of the OtElo-DNAs was carried out using in each case 1 μl of defrosted cells, 200 μM dNTPs, 2.5 U Taq polymerase and 100 pmol of each primer in a total volume of 50 μl. The conditions for the PCR were as follows: first denaturation at 95° C. for 5 minutes, followed by 30 cycles at 94° C. for 30 seconds, 55° C. for 1 minute and 72° C. for 2 minutes, and a final elongation step at 72° C. for 10 minutes.

Example 15

Cloning of Expression Plasmids for Heterologous Expression in Yeasts

To characterize the function of the Ostreococcus tauri elongases, the open reading frames of the DNAs in question were cloned downstream of the galactose-inducible GAL1 promoter of pYES2.1/V5-His-TOPO (Invitrogen), giving rise to pOTE1 and pOTE2.

The Saccharomyces cerevisiae strain 334 was transformed with the vector pOTE1 or pOTE2, respectively, by electroporation (1500 V). A yeast which was transformed with the blank vector pYES2 was used as control. The transformed yeasts were selected on complete minimal dropout uracil medium (CMdum) agar plates supplemented with 2% glucose. After the selection, in each case three transformants were selected for the further functional expression.

To express the Ot elongases, precultures consisting of in each case 5 ml of CMdum dropout uracil liquid medium supplemented with 2% (w/v) raffinose were initially inoculated with the selected transformants and incubated for 2 days at 30° C. and 200 rpm. Then, 5 ml of CMdum (dropout uracil) liquid medium supplemented with 2% of raffinose and 300 μM various fatty acids were inoculated with the precultures to an $OD_{600}$ of 0.05. Expression was induced by the addition of 2% (w/v) of galactose. The cultures were incubated for a further 96 hours at 20° C.

Example 16

Cloning of Expression Plasmids for the Seed-Specific Expression in Plants

To transform plants, a further transformation vector based on pSUN-USP was generated. To this end, NotI cleavage sites were inserted at the 5' and 3' end of the coding sequences, using PCR. The corresponding primer sequences were derived from the 5' and 3' regions of OtElo1 (SEQ ID NO: 67) and OtElo2 (SEQ ID NO: 81).

Composition of the PCR Mix (50 μl):
5.00 μl template cDNA
5.00 μl 10× buffer (Advantage polymerase)+25 mM $MgCl_2$
5.00 μl 2 mM dNTP
1.25 μl of each primer (10 pmol/μl)
0.50 μl Advantage polymerase The Advantage polymerase from Clontech was employed.
PCR Reaction Conditions:
Annealing temperature: 1 min 55° C.
Denaturation temperature: 1 min 94° C.
Elongation temperature: 2 min 72° C.
Number of cycles: 35

The PCR products were incubated with the restriction enzyme NotI for 16 hours at 37° C. The plant expression vector pSUN300-USP was incubated in the same manner. Thereafter, the PCR product and the vector were separated by agarose gel electrophoresis and the corresponding DNA fragments were excised. The DNA was purified by means of the Qiagen Gel Purification Kit following the manufacturer's instructions. Thereafter, vector and PCR products were ligated. The Rapid Ligation Kit from Roche was used for this purpose. The resulting plasmids pSUN-OtELO1 and pSUN-OtELO2 were verified by sequencing.

pSUN300 is a derivative of plasmid pPZP (Hajdukiewicz, P, Svab, Z, Maliga, P., (1994). The small versatile pPZP family of *Agrobacterium* binary vectors for plant transformation. Plant Mol Biol 25:989-994). pSUN-USP originated from pSUN300, by inserting a USP promoter into pSUN300 in the form of an EcoRI fragment. The polyadenylation signal is that of the *Ostreococcus* gene from the *A. tumefaciens* Ti plasmid (ocs-Terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982). The USP promoter corresponds to nucleotides 1 to 684 (Genbank Accession X56240), where part of the noncoding region of the USP gene is present in the promoter. The promoter fragment which is 684 base pairs in size was amplified by a PCR reaction and standard methods with the aid of a synthesized primer and by means of a commercially available T7 standard primer (Stratagene). Primer sequence: 5'-GTCGAC-CCGCGGACTAGTGGG-CCCTCTAGAC-CCGGGGGATCCGGATCTGCTGGCTATGAA-3', SEQ ID NO: 164). The PCR fragment was recut with EcoRI/SalI and inserted into the vector pSUN300 with OCS terminator. This gave rise to the plasmid with the name pSUN-USP. The construct was used for the transformation of *Arabidopsis thaliana*, oilseed rape, tobacco and linseed.

Example 17

Expression of OtELO1 (SEQ ID NO: 67) and OtELO2 (SEQ ID NO: 81) in Yeasts

Yeasts which had been transformed with the plasmids pYES3, pYES3-OtELO1 and pYES3-OtELO2 as described in Example 15 were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove non-derivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 25° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 18

Functional Characterization of OtELO1 (SEQ ID NO: 6) and OtELO2 (SEQ ID NO: 81)

The substrate specificity of OtElo1 (SEQ ID NO: 67) was determined after expression and after feeding various fatty acids (Tab. 5). The substrates fed can be detected in large amounts in all of the transgenic yeasts. The transgenic yeasts revealed the synthesis of novel fatty acids, the products of the OtElo1 reaction. This means that the gene OtElo1 was expressed. functionally.

Table 4 shows that OtElo1 (SEQ ID NO: 67) has a narrow degree of substrate specificity. OtElo1 (SEQ ID NO: 67) was only capable of elongating the C$_{20}$-fatty acids eicosapentaenoic acid (FIG. 7) and arachidonic acid (FIG. 8), hut preferentially ω3-desaturated eicosapentaenoic acid.

TABLE 5

| Fatty acid substrate | Conversion rate (in %) |
|---|---|
| 16:0 | — |
| 16:1$^{\Delta 9}$ | — |
| 18:0 | — |
| 18:1$^{\Delta 9}$ | — |
| 18:1$^{\Delta 11}$ | — |
| 18:2$^{\Delta 9,12}$ | — |
| 18:3$^{\Delta 6,9,12}$ | — |
| 18:3$^{\Delta 5,9,12}$ | — |
| 20:3$^{\Delta 8,11,14}$ | — |
| 20:4$^{\Delta 5,8,11,14}$ | 10.8 ± 0.6 |
| 20:5$^{\Delta 5,8,11,14,17}$ | 46.8 ± 3.6 |
| 22:4$^{\Delta 7,10,13,16}$ | — |
| 22:6$^{\Delta 4,7,10,13,16,19}$ | — |

Table 5 shows the substrate specificity of the elongase OtElo1 (SEQ ID NO: 67) for C$_{20}$-polyunsaturated fatty acids with a double bond in the Δ5 position in comparison with various fatty acids.

The yeasts which had been transformed with the vector pOTE1 were grown in minimal medium in the presence of the fatty acids stated. The fatty acid methyl esters were synthesized by subjecting intact cells to acid methanolysis. Thereafter, the FAMEs were analyzed by GLC. Each value represents the mean (n=3)±standard deviation.

The substrate specificity of OtElo2 (SEQ ID NO: 81) was determined after expression and after feeding various fatty acids (Tab. 6). The substrates fed can be detected in large amounts in all of the transgenic yeasts. The transgenic yeasts revealed the synthesis of novel fatty acids, the products of the OtElo2 reaction. This means that the gene OtElo2 was expressed functionally.

TABLE 6

| Fatty acid substrate | Conversion rate (in %) |
|---|---|
| 16:0 | — |
| 16:1$^{\Delta 9}$ | — |
| 16:3$^{\Delta 7,10,13}$ | — |
| 18:0 | — |
| 18:1$^{\Delta 6}$ | — |
| 18:1$^{\Delta 9}$ | — |
| 18:1$^{\Delta 11}$ | — |
| 18:2$^{\Delta 9,12}$ | — |
| 18:3$^{\Delta 6,9,12}$ | 15.3± |
| 18:3$^{\Delta 5,9,12}$ | — |
| 18:4$^{\Delta 6,9,12,15}$ | 21.1± |
| 20:2$^{\Delta 11,14}$ | — |
| 20:3$^{\Delta 8,11,14}$ | — |
| 20:4$^{\Delta 5,8,11,14}$ | — |
| 20:5$^{\Delta 5,8,11,14,17}$ | — |
| 22:4$^{\Delta 7,10,13,16}$ | — |
| 22:5$^{\Delta 7,10,13,16,19}$ | — |
| 22:6$^{\Delta 4,7,10,13,16,19}$ | — |

Table 6 shows the substrate specificity of the elongase OtElo2 (SEQ ID NO: 81) with regard to various fatty acids.

The yeasts which had been transformed with the vector pOTE2 were grown in minimal medium in the presence of the fatty acids stated. The fatty acid methyl esters were synthesized by subjecting inact cells to acid methanolysis. Thereafter, the FAMEs were analyzed by GLC. Each value represents the mean (n=3)±standard deviation.

The enzymatic activity shown in Table 3 clearly demonstrates that OtElo2 (SEQ ID NO: 81) is a Δ6-elongase.

Example 19

Cloning of Genes from *Thalassiosira pseudonana*

By searching for conserved regions in the protein sequences with the aid of the elongase genes with Δ5-elongase activity or Δ6-elongase activity, which are detailed in the application, it is possible to identify two sequences with corresponding motifs in a *Thalassiosira pseudonana* sequence database (genomic sequences). The sequences were the following:

| Name of gene | SEQ ID | Amino acids |
|---|---|---|
| TpELO1 (Δ5-elongase) | 85 | 358 |
| TpELO2 (Δ5-elongase) | 59 | 358 |
| TpELO3 (Δ6-elongase) | 45 | 272 |

A 2 l culture of *T. pseudonana* was grown in f/2 medium (Guillard, R. R. L. 1975. Culture of phytoplankton for feeding marine invertebrates. In *Culture of Marine Invertebrate Animals* (Eds. Smith, W. L. and Chanley, M. H.), Plenum Press, New York, pp 29-60) for 14 days at a light intensity of 80 E/cm$^2$. After centrifugation of the cells, RNA was isolated with the aid of the RNAeasy kits from Qiagen (Valencia, Calif., US) following the manufacturer's instructions. The mRNA was subjected to reverse transcription with the Marathon cDNA amplification kit (BD Biosciences), and adaptors were ligated in accordance with the manufacturer's instructions. The cDNA library was then used for the PCR for cloning expression plasmids by means of 5'- and 3'-RACE (rapid amplification of cDNA ends).

Example 20

Cloning of Expression Plasmids for the Purposes of Heterologous Expression in Yeasts The primer pairs in question were selected in such a way that they bore the yeast consensus sequence for highly efficient translation (Kozak, Cell 1986, 44:283-292) next to the start codon. The amplification of the TpElo DNAs was carried out in each case with 1 μl cDNA, 200 μM dNTPs, 2.5 U Advantage polymerase and 100 pmol of each primer in a total volume of 50 μl. The PCR conditions were as follows: first denaturation at 95° C. for 5 minutes, followed by 30 cycles at 94° C. for 30 seconds, 55° C. for 1 minute and 72° C. for 2 minutes, and a last elongation step at 72° C. for 10 minutes.

The following oligonucleotides for the PCR reaction were used for cloning the sequence for the heterologous expression in yeasts:

| Name of gene, and SEQ ID NO: | Primer sequence |
|---|---|
| TpELO1 (Δ5-elongase), SEQ ID NO: 85 | F:5'-accatgtgctcaccaccgccgtc (SEQ ID NO: 158) R:5'-ctacatggcaccagtaac (SEQ ID NO: 159) |
| TpELO2 (Δ5-elongase), SEQ ID NO: 59 | F:5'-accatgtgctcatcaccgccgtc (SEQ ID NO: 160) R:5'-ctacatggcaccagtaac (SEQ ID NO: 161) |
| TpELO3 (Δ6-elongase), SEQ ID NO: 45 | F:5'-accatggacgcctacaacgctgc (SEQ ID NO: 162) R:5'-ctaagcactcttcttcttt (SEQ ID NO: 163) |

*F = forward primer, R = reverse primer

The PCR products were incubated for 30 minutes at −21° C. with the yeast expression vector pYES2.1-TOPO (Invitrogen) following the manufacturer's instructions. The PCR product was ligated into the vector by means of a T-overhang and the activity of a topoisomerase (Invitrogen). After the incubation, *E. coli* DH5α cells were transformed. Suitable clones were identified by PCR, the plasmid DNA was isolated by means of the Qiagen DNAeasy kit and verified by sequencing. The correct sequence was then transformed into the *Saccharomyces* strain INVSc1 (Invitrogen) by electroporation (1500 V). As a control, the blank vector pYES2.1 was transformed in parallel. Thereafter, the yeasts were plated out on minimal dropout uracil medium supplemented with 2% glucose. Cells which were capable of growing in the medium without uracil thus comprise the corresponding plasmids pYES2.1, pYES2.1-TpELO1, pYES2.1-ELO2 and pYES2.1-TpELO3. After the selection, in each case two transformants were chosen for the further functional expression.

Example 21

Cloning Expression Plasmids for the Purposes of Seed-Specific Expression in Plants To transform plants, a further transformation vector based on pSUN-USP is generated. To this end, NotI cleavage sites are introduced at the 5' and 3' ends of the coding sequence, using the following primer pair:

PSUN-TPELO1

(SEQ ID NO: 152)
Forward: 5'-GCGGCCGCACCATGTGCTCACCACCGCCGTC (SEQ ID NO: 153)
Reverse: 3'-GCGGCCGCCTACATGGCACCAGTAAC

PSUN-TPELO2

(SEQ ID NO: 154)
Forward: 5'-GCGGCCGCACCATGTGCTCATCACCGCCGTC (SEQ ID NO: 155)
Reverse: 3'-GCGGCCGCCTACATGGCACCAGTAAC

PSUN-TPELO3

(SEQ ID NO: 156)
Forward: 5'-GCGGCCGCaccatggacgcctacaacgctgc (SEQ ID NO: 157)
Reverse: 3'-GCGGCCGCCTAAGCACTCTTCTTCTTT Composition of the PCR Mix (50 µl):

5.00 µl template cDNA 5.00 µl 10× buffer (Advantage polymerase)+25 mM $MgCl_2$ 5.00 µl 2 mM dNTP 1.25 µl of each primer (10 pmol/µl)

0.50 µl Advantage polymerase

The Advantage polymerase from Clontech was employed.

PCR Reaction Conditions:

Annealing temperature: 1 minute at 55° C.

Denaturation temperature: 1 minute at 94° C.

Elongation temperature: 2 minutes at 72° C.

Number of cycles: 35

The PCR products were incubated for 16 hours at 37° C. with the restriction enzyme NotI. The plant expression vector pSUN300-USP was incubated in the same manner. Thereafter, the PCR products and the 7624 bp vector were separated by agarose gel electrophoresis and the corresponding DNA fragments were excised. The DNA was purified by means of Qiagen gel purification kit following the manufacturer's instructions. Thereafter, vector and PCR products were ligated. The Rapid Ligation kit from Roche was used for this purpose. The resulting plasmids pSUN-TPELO1, pSUN-TPELO2 and pSUN-TPELO3 were verified by sequencing.

pSUN300 is a derivative of plasmid pPZP (Hajdukiewicz, P, Svab, Z, Maliga, P., (1994) The small versatile pPZP family of Agrobacterium binary vectors for plant transformation. Plant Mol Biol 25:989-994). pSUN-USP originated from pSUN300, by inserting a USP promoter as EcoRI fragment into pSUN300. The polyadenylation signal is that of the octopine synthase gene from the A. tumefaciens Ti plasmid (ocs terminator, Genbank Accession V00088) (De Greve, H., Dhaese, P., Seurinck, J., Lemmers, M., Van Montagu, M. and Schell, J. Nucleotide sequence and transcript map of the Agrobacterium tumefaciens Ti plasmid-encoded octopine synthase gene J. Mol. Appl. Genet. 1 (6), 499-511 (1982). The USP promoter corresponds to the nucleotides 1-684 (Genbank Accession X56240), where part of the noncoding region of the USP gene is present in the promoter. The promoter fragment which is 684 base pairs in size was amplified by means of commercially available T7 standard primers (Stratagene) and with the aid of a synthesized primer via a PCR reaction following standard methods.

(Primer sequence: 5'-GTCGACCCGCGGACTAGTGGGCCCTCTAG

ACCCGGGGGA-TCCGGATCTGCTGGCTATGAA-3';

SEQ ID NO: 151).

The PCR fragment was cut again with EcoRI/SalI and introduced into the vector pSUN300 with OCS terminator. This gave rise to the plasmid with the name pSUN-USP. The construct was used for the transformation of *Arabidopsis thaliana*, oilseed rape, tobacco and linseed.

The lipid extraction from yeasts and seeds was carried out as described in Example 6

Example 22

Expression of TpELO1 (SEQ ID NO: 85), TpELO2 (SEQ ID NO: 59) and TpELO3 (SEQ ID NO:45) in Yeasts Yeasts which had been transformed with the plasmids pYES2, pYES2-TpELO1, pYES2-TpELO2 and pYES2-TpELO3 as described in Example 4 were analyzed as follows:

The yeast cells from the main cultures were harvested by centrifugation (100×g, 5 min, 20° C.) and washed with 100 mM $NaHCO_3$, pH 8.0 to remove residual medium and fatty acids. Starting with the yeast cell sediments, fatty acid methyl esters (FAMEs) were prepared by acid methanolysis. To this end, the cell sediments were incubated for 1 hour at 80° C. together with 2 ml of 1 N methanolic sulfuric acid and 2% (v/v) of dimethoxypropane. The FAMEs were extracted twice with petroleum ether (PE). To remove nonderivatized fatty acids, the organic phases were washed in each case once with 2 ml of 100 mM $NaHCO_3$, pH 8.0 and 2 ml of distilled water. Thereafter, the PE phases were dried with $Na_2SO_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 23

Functional characterization of TpELO1 (SEQ ID NO: 85) and TPELO3 (SEQ ID NO: 45)

The substrate specificity of TpElo1 (SEQ ID NO: 85) was determined after expression and after feeding various fatty acids (FIG. 9). The substrates fed can be detected in large amounts in all of the transgenic yeasts. The transgenic yeasts revealed the synthesis of novel fatty acids, the products of the TpElo1 reaction. This means that the gene TpElo1 was expressed functionally.

Table 7 Shows that TpElo1 (SEQ ID NO: 85) has a narrow degree of substrate specificity. TpElo1 (SEQ ID NO: 85)

was only capable of elongating the C20-fatty acids eicosapentaenoic acid and arachidonic acid, but preferentially ω3-desaturated eicosapentaenoic acid.

The yeasts which had been transformed with the vector pYES2-TpELO1 were grown in minimal medium in the presence of the fatty acids stated. Then, the fatty acid methyl esters were synthesized by subjecting intact cells to acid methanolysis. Thereafter the FAMEs were analyzed by GLC.

TABLE 7

Expression of TpELO1 (SEQ ID NO: 85) in yeast. Columns 1 and 3 show the control reactions for columns 2 (fed 250 μM 20:4 Δ5, 8, 11, 14) and 4 (fed 250 μM 20:5 Δ5, 8, 11, 14, 17).

| Fatty acids | Expression 1 | Expression 2 | Expression 3 | Expression 4 |
|---|---|---|---|---|
| 16:0 | 18.8 | 17.8 | 25.4 | 25.2 |
| 16:1$^{\Delta 9}$ | 28.0 | 29.8 | 36.6 | 36.6 |
| 18:0 | 5.2 | 5.0 | 6.8 | 6.9 |
| 18:1$^{\Delta 9}$ | 25.5 | 23.6 | 24.6 | 23.9 |
| 20:4$^{\Delta 5,8,11,14}$ | 22.5 | 23.4 | — | — |
| 22:4$^{\Delta 7,10,13,16}$ | — | 0.4 | — | — |
| 20:5$^{\Delta 5,8,11,14,17}$ | — | — | 6.6 | 6.5 |
| 22:5$^{\Delta 7,10,13,16,19}$ | — | — | — | 0.9 |
| % conversion rate | 0 | 1.7 | 0 | 12.2 |

The substrate specificity of TpElo3 (SEQ ID NO: 45) was determined after expression and after feeding various fatty acids (FIG. 10). The substrates fed can be detected in large amounts in all of the transgenic yeasts. The transgenic yeasts revealed the synthesis of novel fatty acids, the products of the TpElo3 reaction. This means that the gene TpElo3 was expressed functionally.

Table 8 shows that TpElo3 (SEQ ID NO: 45) has narrow substrate specificity. TpElo3 (SEQ ID NO: 45) was only capable of elongating the C18-fatty acids γ-linolenic acid and stearidonic acid, but preferred ω3-desaturated stearidonic acid.

The yeasts which had been transformed with the vector pYES2-TpELO3 were grown in minimal medium in the presence of the fatty acids stated. Then, the fatty acid methyl esters were synthesized by subjecting intact cells to acid methanolysis. Thereafter the FAMEs were analyzed by GLC.

TABLE 8

Expression von TpELO3 in yeast. Column 1 shows the fatty acid profile of yeast without feeding. Column 2 shows the control reaction. In columns 3 to 6, γ-linolenic acid, stearidonic acid, arachidonic acid and eicosapentaenoic acid were fed (250 μM of each fatty acid).

| Fatty acids | 1 | 2 | 3 | 4 | 5 | 6 |
|---|---|---|---|---|---|---|
| 16:0 | 17.9 | 20.6 | 17.8 | 16.7 | 18.8 | 18.8 |
| 16:1$^{\Delta 9}$ | 41.7 | 18.7 | 27.0 | 33.2 | 24.0 | 31.3 |
| 18:0 | 7.0 | 7.7 | 6.4 | 6.6 | 5.2 | 6.0 |
| 18:1$^{\Delta 9}$ | 33.3 | 16.8 | 24.2 | 31.8 | 25.5 | 26.4 |
| 18:2$^{\Delta 9,12}$ | — | 36.1 | — | — | — | — |
| 18:3$^{\Delta 6,9,12}$ | — | — | 6.1 | — | — | — |
| 18:4$^{\Delta 6,9,12,15}$ | — | — | — | 1.7 | — | — |
| 20:2$^{\Delta 11,14}$ | — | 0 | — | — | — | — |
| 20:3$^{\Delta 8,11,14}$ | — | — | 18.5 | — | — | — |
| 20:4$^{\Delta 8,11,14,17}$ | — | — | — | 10.0 | — | — |
| 20:4$^{\Delta 5,8,11,14}$ | — | — | — | — | 22.5 | — |
| 22:4$^{\Delta 7,10,13,16}$ | — | — | — | — | 0 | — |
| 20:5$^{\Delta 5,8,11,14,17}$ | — | — | — | — | — | 17.4 |
| 22:5$^{\Delta 7,10,13,16,19}$ | — | — | — | — | — | 0 |
| % conversion rate | 0 | 0 | 75 | 85 | 0 | 0 |

Example 24

Cloning an Expression Plasmid for Heterologous Expression of Pi-omega3Des (SEQ ID NO: 87) in Yeasts For heterologous expression in yeasts, the Pi-omega3Des clone (SEQ ID NO: 87) was cloned into the yeast expression vector pYES3 via PCR with suitable Pi-omega3Des-specific primers. Only the open reading frame, of the gene, which encoded the Pi-omega3Des protein was amplified; it was provided with two cleavage sites for cloning into the expression vector pYES3:

```
                                        (SEQ ID NO: 149)
Forward Primer: 5'-TAAGCTTACATGGCGACGAAGGAGG (SEQ ID NO: 150)
Reverse Primer: 5'-TGGATCCACTTACGTGGACTTGGT.
```

Composition of the PCR Mix (50 μl):
5.00 μl template cDNA
5.00 μl 10× buffer (Advantage polymerase)+25 mM MgCl$_2$
5.00 μl 2 mM dNTP
1.25 μl of each primer (10 pmol/μl of the 5'-ATG and of the 3'-stop primer)
0.50 μl Advantage polymerase
The Advantage polymerase from Clontech was employed.
PCR Reaction Conditions:
Annealing temperature: 1 minute at 55° C.
Denaturation temperature: 1 minute at 94° C.
Elongation temperature: 2 minutes at 72° C.
Number of cycles: 35

The PCR product was incubated for 2 hours at 37° C. with the restriction enzymes HindIII and BamHI. The yeast expression vector pYES3 (Invitrogen) was incubated in the same manner. Thereafter, the 1104 bp PCR product and the vector were separated by agarose gel electrophoresis and the corresponding DNA fragments were excised. The DNA was purified by means of Qiagen gel purification kit following the manufacturer's instructions. Thereafter, vector and desaturase cDNA were ligated. The Rapid Ligation kit from Roche was used for this purpose. The resulting plasmid pYES3-Pi-omega3Des were verified by sequencing and transformed into the *Saccharomyces* strain INVSc1 (Invitrogen) by electroporation (1500 V). As a control, pYES3 was transformed in parallel. Thereafter, the yeasts were plated onto minimal dropout tryptophan medium supplemented with 2% glucose. Cells which were capable of growth without tryptophan in the medium thus comprised the corresponding plasmids pYES3, pYES3-Pi-omega3Des. After the selection, in each case two transformants were chosen for the further functional expression.

Example 25

Cloning Expression Plasmids for the Purposes of Seed-Specific Expression in Plants To transform plants, a further transformation vector based on pSUN-USP was generated. To this end, NotI cleavage sites were introduced at the 5' and 3' ends of the coding sequence, using the following primer pair:
PSUN-Pi-omega3Des

```
                                        (SEQ ID NO: 147)
Reverse: 3'-GCGGCCGCTTACGTGGACTTGGTC (SEQ ID NO: 148)
Forward: 5'-GCGGCCGCatGGCGACGAAGGAGG
```

Composition of the PCR Mix (50 µl):
5.00 µl template cDNA
5.00 µl 10× buffer (Advantage polymerase)+25 mM $MgCl_2$
5.00 µl 2 mM dNTP
1.25 µl of each primer (10 pmol/µl)
0.50 µl Advantage polymerase
The Advantage polymerase from Clontech was employed.
PCR Reaction Conditions:
Annealing temperature: 1 minute at 55° C.
Denaturation temperature: 1 minute at 94° C.
Elongation temperature: 2 minutes at 72° C.
Number of cycles: 35

The PCR products were incubated for 4 hours at 37° C. with the restriction enzyme NotI.

The plant expression vector pSUN300-USP was incubated in the same manner. Thereafter, the PCR products and the 7624 bp vector were separated by agarose gel electrophoresis and the corresponding DNA fragments were excised. The DNA was purified by means of Qiagen gel purification kit following the manufacturer's instructions. Thereafter, vector and PCR products were ligated. The Rapid Ligation kit from Roche was used for this purpose. The resulting plasmid pSUN-Piomega3Des was verified by sequencing.

Example 26

Expression of Pi-omega3Des (SEQ ID NO: 87) in Yeasts

Yeasts which had been transformed with the plasmid pYES3 or pYES3-Pi-omega3Des as described in Example 24 were analyzed as follows:

The yeast cells from the main cultures were harvested by centrifugation (100×g, 5 min, 20° C.) and washed with 100 mM $NaHCO_3$, pH 8.0 to remove residual medium and fatty acids. Fatty acid methyl esters (FAMEs) were prepared from the yeast cell sediments by acid methanolysis. To this end, the cell sediments were incubated with 2 ml of 1 N methanolic sulfuric acid and 2% (v/v) dimethoxypropane for 1 hour at 80° C. The FAMEs were extracted by extracting twice with petroleum ether (PE). To remove underivatized fatty acids, the organic phases were washed in each case once with 2 ml of 100 mM $NaHCO_3$, pH 8.0 and 2 ml of distilled water. Thereafter, the PE phases were dried with $Na_2SO_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 minutes at 250° C. (holding).

The signals were identified by comparing the retention times with corresponding fatty acid standards (Sigma). The methodology is described for example in Napier and Michaelson, 2001, Lipids. 36(8):761-766; Sayanova et al., 20011 Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 27

Functional Characterization of Pi-omega3Des (SEQ ID NO: 87)

The substrate specificity of Pi-omega3Des (SEQ ID NO: 87) was determined after expression and after feeding various fatty acids (FIGS. 12 to 18). The substrates fed can be detected in large amounts in all of the transgenic yeasts, proving the uptake of these fatty acids into the yeasts. The transgenic yeasts revealed the synthesis of novel fatty acids, the products of the Pi-omega3Des reaction. This means that the gene Pi-omega3Des was expressed functionally.

FIG. 12 shows the desaturation of linoleic acid (18:2 ω-6-fatty acid) to α-linolenic acid (18:3 ω-3-fatty acid) by Pi-omega3Des (SEQ ID NO: 87). The fatty acid methyl esters were synthesized by subjecting intact cells which had been transformed with the blank vector pYES2 (FIG. 12 A) or the vector pYes3-Pi-omega3Des (FIG. 12 B) to acid methanolysis. The yeasts were grown in minimal medium in the presence of $C18:2^{\Delta 9,12}$ fatty acid (300 µM). Thereafter, the FAMEs were analyzed via GLC.

FIG. 13 shows the desaturation of γ-linolenic acid (18:3 ω-6-fatty acid) to stearidonic acid (18:4 ω-3-fatty acid) by Pi-omega3Des (SEQ ID NO: 87).

FIG. 14 shows the desaturation of C20:2-ω-6-fatty acid to C20:3-ω-3-fatty acid by Pi-omega3Des (SEQ ID NO: 87). The fatty acid methyl esters were synthesized by subjecting intact cells which had been transformed with the blank vector pYES2 (FIG. 14 A) or the vector pYes3-Pi-omega3Des (FIG. 14 B) to acid methanolysis. The yeasts were grown in minimal medium in the presence of $C20:2^{\Delta 11,14}$-fatty acid (300 µM). Thereafter, the FAMEs were analyzed via GLC.

FIG. 15 shows the desaturation C20:3-ω-6-fatty acid to C20:4-ω-3-fatty acid by Pi-omega3Des (SEQ ID NO: 87). The fatty acid methyl esters were synthesized by subjecting intact cells which had been transformed with the blank vector pYES2 (FIG. 15 A) or the vector pYes3-Pi-omega3Des (FIG. 15 B) to acid methanolysis. The yeasts were grown in minimal medium in the presence of $C20:3^{\Delta 5,8,11,14}$-fatty acid (300 µM). Thereafter, the FAMEs were analyzed via GLC.

FIG. 16 shows the desaturation of arachidonic acid (C20:4-ω-6-fatty acid) to eicosapentaenoic acid (C20:5-ω-3-fatty acid) by Pi-omega3Des (SEQ ID NO: 87).

The fatty acid methyl esters were synthesized by subjecting intact cells which had been transformed with the blank vector pYES2 (FIG. 16 A) or the vector pYes3-Pi-omega3Des (FIG. 16 B) to acid methanolysis. The yeasts were grown in minimal medium in the presence of $C20:4^{\Delta 5,8,11,14}$-fatty acid (300 µM), Thereafter, the FAMEs were analyzed via GLC.

FIG. 17 shows the desaturation of docosatetraenoic acid (C22:4-ω-6-fatty acid) to docosapentaenoic acid (C22:5-ω-

3-fatty acid) by Pi-omega3Des (SEQ ID NO: 87). The fatty acid methyl esters were synthesized by subjecting intact cells which had been transformed with the blank vector pYES2 (FIG. 17 A) or the vector pYes3-Pi-omega3Des (FIG. 17 B) to acid methanolysis. The yeasts were grown in minimal medium in the presence of $C22:4^{\Delta7,10,13,16}$-fatty acid (300 µM), Thereafter, the FAMEs were analyzed via GLC.

The substrate specificity of Pi-omega3Des (SEQ ID NO: 87) toward various fatty acids can be seen from FIG. 18. The yeasts which had been transformed with the vector pYes3-Pi-omega3Des were grown in minimal medium in the presence of the fatty acids stated. The fatty acid methyl esters were synthesized by subjecting intact cells to acid methanolysis. Thereafter, the FAMEs were analyzed via GLC. Each value represents a mean of three measurements. The conversion rates (% desaturation) were calculated using the formula:

[product]/[product]+[substrate]*100.

As described in Example 9, Pi-omega3Des (SEQ ID NO: 87) can also be used for generating transgenic plants. The lipids can then be extracted from the seeds of these plants as described in Example 6.

Example 28

Cloning Desaturase Genes from *Ostreococcus tauri*

The search for conserved regions in the protein sequences with the aid of conserved motifs (His boxes, Domergue et al. 2002, Eur. J. Biochem. 269, 4105-4113) allowed the identification of five sequences with corresponding motifs in an *Ostreococcus tauri* sequence database (genomic sequences). The sequences are the following:

| Name of gene | SEQ ID | Amino acids | Homology |
| --- | --- | --- | --- |
| OtD4 | SEQ ID NO: 95 | 536 | Δ4-desaturase |
| OtD5.1 | SEQ ID NO: 91 | 201 | Δ5-desaturase |
| OtD5.2 | SEQ ID NO: 93 | 237 | Δ5-desaturase |
| OtD6.1 | SEQ ID NO: 89 | 457 | Δ6-desaturase |
| OtFad2 | SEQ ID NO: 107 | 361 | Δ12-desaturase |

The alignments for finding homologies of the individual genes were carried out using the tBLASTn algorithm (Altschul et al., J. Mol. Biol. 1990, 215: 403-410).

Cloning was carried out as follows:

40 ml of an *Ostreococcus tauri* culture in the stationary phase were spun down and the pellet was resuspended in 100 µl of double-distilled water and stored at −20° C. The relevant genomic DNAs were amplified based on the PCR method. The corresponding primer pairs were selected in such a way that they contained the yeast consensus sequence for highly efficient translation (Kozak, Cell 1986, 44:283-292) next to the start codon. The amplification of the OtDes-DNAs was carried out using in each case 1 µl of defrosted cells, 200 µM dNTPs, 2.5 U Taq polymerase and 100 pmol of each primer in a total volume of 50 µl. The conditions for the PCR were as follows: first denaturation at 95° C. for 5 minutes, followed by 30 cycles at 94° C. for 30 seconds, 55° C. for 1 minute and 72° C. for 2 minutes, and a final elongation step at 72° C. for 10 minutes.

The following primers were employed for the PCR:

OtDes6.1 Forward:
(SEQ ID NO: 145)
5'ggtaccacataatgtgcgtggagacggaaaataacg3'

OtDes6.1 Reverse:
(SEQ ID NO: 146)
5'ctcgagttacgccgtctttccggagtgttggcc3'

Example 29

Cloning of Expression Plasmids for Heterologous Expression in Yeasts

To characterize the function of the desaturase OtDes6.1 (=Δ6-desaturase; SEQ ID NO: 89) from *Ostreococcus tauri*, the open reading frame of the DNA upstream of the galactose-inducible GAL1 promoter of pYES2.1/V5-His-TOPO (Invitrogen) was cloned, giving rise to the corresponding pYES2.1-OtDes6.1 clone. In a similar manner, further *Ostreococcus* desaturase genes can be cloned.

The *Saccharomyces cerevisiae* strain 334 was transformed with the vector pYES2.1-OtDes6.1 by electroporation (1500 V). A yeast which was transformed with the blank vector pYES2 was used as control. The transformed yeasts were selected on complete minimal dropout uracil medium (CMdum) agar plates supplemented with 2% glucose. After the selection, in each case three transformants were selected for the further functional expression.

To express the OtDes6.1 desaturase (SEQ ID NO: 89), precultures consisting of in each case 5 ml of CMdum dropout uracil liquid medium supplemented with 2% (w/v) raffinose were initially inoculated with the selected transformants and incubated for 2 days at 30° C. and 200 rpm. Then, 5 ml of CMdum (dropout uracil) liquid medium supplemented with 2% of raffinose and 300 µM various fatty acids were inoculated with the precultures to an $OD_{600}$ of 0.05. Expression was induced by the addition of 2% (w/v) of galactose. The cultures were incubated for a further 96 hours at 20° C.

Example 30

Cloning of Expression Plasmids for the Seed-Specific Expression in Plants

A further transformation vector based on pSUN-USP is generated for the transformation of plants. To this end, NotI cleavage sites are introduced at the 5' and 3' ends of the coding sequences, using PCR. The corresponding primer sequences are derived from the 5' and 3 regions of the desaturases.
Composition of the PCR Mix (50 µl):
5.00 µl template cDNA
5.00 µl 10× buffer (Advantage polymerase)+25 mM $MgCl_2$
5.00 µl 2 mM dNTP
1.25 µl of each primer (10 pmol/µl)
0.50 µl Advantage polymerase
The Advantage polymerase from Clontech was employed.
PCR Reaction Conditions:
Annealing temperature: 1 min 55° C.
Denaturation temperature: 1 min 94° C.
Elongation temperature: 2 min 72° C.
Number of cycles: 35
The PCR products were incubated with the restriction enzyme NotI for 16 hours at 37° C. The plant expression vector pSUN300-USP was incubated in the same manner.

Thereafter, the PCR products and the vector were separated by agarose gel electrophoresis and the corresponding DNA fragments were excised. The DNA was purified by means of the Qiagen Gel Purification Kit following the manufacturer's instructions. Thereafter, vector and PCR products were ligated. The Rapid Ligation Kit from Roche was used for this purpose. The resulting plasmids were verified by sequencing.

pSUN300 is a derivative of plasmid pPZP (Hajdukiewicz, P, Svab, Z, Maliga, P., (1994) The small versatile pPZP family of *Agrobacterium* binary vectors for plant transformation. Plant Mol Biol 25:989-994). pSUN-USP originated from pSUN300, by inserting a USP promoter into pSUN300 in the form of an EcoRI fragment. The polyadenylation signal is that of the *Ostreococcus* gene from the *A. tumefaciens* Ti plasmid (ocs-Terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982)). The USP promoter corresponds to nucleotides 1 to 684 (Genbank Accession X56240), where part of the noncoding region of the USP gene is present in the promoter. The promoter fragment which is 684 base pairs in size was amplified by a PCR reaction and standard methods with the aid of a synthesized primer and by means of a commercially available T7 standard primer (Stratagene). (Primer sequence: 5'-GTCGAC-CCGCGGACTAGTGGGCCCTCTAGAC-CCGGGGGATCC GGATCTGCTGGCTATGAA-3', SEQ ID NO: 144).

The PCR fragment was recut with EcoRI/SalI and inserted into the vector pSUN300 with OCS terminator. This gave rise to the plasmid with the name pSUN-USP. The construct was used for the transformation of *Arabidopsis thaliana*, oilseed rape, tobacco and linseed.

Example 31

Expression of OtDes6.1 (SEQ ID NO: 89) in Yeasts

Yeasts which had been transformed with the plasmids pYES2 and pYES2-OtDes6.1 as described in Example 4 were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove non-derivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 32

Functional Characterization of *Ostreococcus* Desaturases

The substrate specificity of desaturases can be determined after expression in yeast (see Examples cloning of desaturase genes, yeast expression) by feeding, using various yeasts. Descriptions for the determination of the individual activities can be found in WO 93/11245 for Δ15-desaturases, WO 94/11516 for Δ12-desaturases, WO 93/06712, U.S. Pat. No. 5,614,393, U.S. Pat. No. 5,614,393, WO 96/21022, WO 0021557 and WO 99/27111 for Δ6-desaturases, Qiu et al. 2001, J. Biol. Chem. 276, 31561-31566 for Δ4-desaturases, Hong et-al. 2002, Lipids 37, 863-868 for Δ5-desaturases.

Table 9 shows the substrate specificity of the desaturase OtDes6.1 (SEQ ID NO: 89) with regard to various fatty acids. The substrate specificity of OtDes6.1 (SEQ ID NO: 89) was determined after expression and after feeding various fatty acids. The substrates fed can be detected in large amounts in all of the transgenic yeasts. The transgenic yeasts revealed the synthesis of novel fatty acids, the products of the OtDes6.1 reaction (FIG. 20). This means that the gene OtDes6.1 was expressed functionally.

The yeasts which had been transformed with the vector pYES2-OtDes6.1 were grown in minimal medium in the presence of the stated fatty acids. The fatty acid methyl esters were synthesized by subjecting intact cells to acid methanolysis. Thereafter, the FAMEs were analyzed via GLC. Each value represents the mean (n=3)±standard deviation. The activity corresponds to the conversion rate calculated using the formula [substrate/(substrate+product)*100].

Table 9 shows that OtDes6.1 (SEQ ID NO: 89) has substrate specificity for linoleic and linolenic acid (18:2 and 18:3), since these fatty acids result in the highest activities. In contrast, the activity for oleic acid (18:1) and palmitoleic acid (16:1) is markedly less pronounced. The preferred conversion. of linoleic and linolenic acid demonstrates the suitability of this desaturase for the production of polyunsaturated fatty acids.

| Substrates | Activity in % |
| --- | --- |
| 16:1$^{\Delta 9}$ | 5.6 |
| 18:1$^{\Delta 9}$ | 13.1 |
| 18:2$^{\Delta 9,12}$ | 68.7 |
| 18:3$^{\Delta 9,12,15}$ | 64.6 |

FIG. 20 shows the conversion of linoleic acid b OtDes6.1 (SEQ ID NO: 89). The FAMEs were analyzed via gas chromatography. The substrate fed (C18:2) is converted into γ-C18:3. Both starting material and product formed are indicated by arrows.

FIG. 21 shows the conversion of linoleic acid (=LA) and α-linolenic acid (=ALA) in the presence of OtDes6.1 (SEQ ID NO: 89) to give γ-linolenic acid (=GLA) and stearidonic acid (=STA). respectively (FIGS. 21 A and C). Furthermore, FIG. 21 shows the conversion of linoleic acid (=LA) and α-linolenic acid (=ALA) in the presence of the Δ6-desaturase OtDes6.1 (SEQ ID NO: 89) together with the Δ6-elongase PSE1 from *Physcomitrella patens* (Zank et al. 2002, Plant J. 31:255-268) and the Δ5-desaturase PtD5 from *Phaeodactylum tricornutum* (Domergue et al. 2002, Eur. J. Biochem, 269, 4105-4113) to give dihomo-γ-linolenic acid (=DHGLA) and arachidonic acid (=ARA, FIG. 21 B) and to give dihomostearidonic acid (=DHSTA) and eicosapentaenoic acid (=EPA, FIG. 21 D), respectively. FIG. 21 shows clearly that the reaction products GLA and STA of the Δ6-desaturase OtDes6.1 (SEQ ID NO: 89) in the presence of the Δ6-elongase PSE1 are elongated almost quantitatively to give DHGLA and DHSTA, respectively. The subsequent desaturation by the Δ5-desaturase PtD5 to give ARA and EPA, respectively, is also problem-free. Approximately 25-30% of the elongase product is desaturated (FIGS. 21 B and D).

Table 10 hereinbelow gives an overview of *Ostreococcus* desaturases which have been cloned:

| Name | bp | aa | Homology | Cyt. B5 | His box1 | His box2 | His box3 |
|---|---|---|---|---|---|---|---|
| OtD4 | 1611 | 536 | Δ4-desaturase | HPGG | HCANH | WRYHHQVSHH | QVEHHLFP |
| OtD5.1 | 606 | 201 | Δ5-desaturase | — | — | — | QVVHHLFP |
| OtD5.2 | 714 | 237 | Δ5-desaturase | — | — | WRYHHMVSHH | QIEHHLFP |
| OtD6.1 | 1443 | 480 | Δ6-desaturase | HPGG | HEGGH | WNSMHNKHH | QVIHHLFP |
| OtFAD2 | 1086 | 361 | Δ12-desaturase | — | HECGH | WQRSHAVHH | HVAHH |

Example: 33

Cloning of Desaturase Genes from *Thalassiosira pseudonana*

The search for conserved regions in the protein sequences with the aid of conserved motifs (His boxes, see motifs) allowed the identification of six sequences with corresponding motifs in a *Thalassiosira pseudonana* sequence database (genomic sequences). The sequences are the following:

| Name of gene | SEQ ID | Amino acids | Homology |
|---|---|---|---|
| TpD4 | SEQ ID NO: 103 | 503 | Δ-4-desaturase |
| TpD5-1 | SEQ ID NO: 99 | 476 | Δ-5-desaturase |
| TpD5-2 | SEQ ID NO: 101 | 482 | Δ-5-desaturase |
| TpD6 | SEQ ID NO: 97 | 484 | Δ-6-desaturase |
| TpFAD2 | SEQ ID NO: 109 | 434 | Δ-12-desaturase |
| TpO3 | SEQ ID NO: 105 | 418 | ω-3-desaturase |

Cloning was carried out as follows:

40 ml of a *Thalassiosira pseudonana* culture in the stationary phase were spun down and the pellet was resuspended in 100 μl of double-distilled water and stored at −20° C. The relevant genomic DNAs were amplified based on the PCR method. The corresponding primer pairs were selected in such a way that they contained the yeast consensus sequence for highly efficient translation (Kozak, Cell 1986, 44:283-292) next to the start codon. The amplification of the TpDes-DNAs was carried out using in each case 1 μl of defrosted cells, 200 μM dNTPs, 2.5 U Taq polymerase and 100 pmol of each primer in a total volume of 50 μl. The conditions for the PCR were as follows: first denaturation at 95° C. for 5 minutes, followed by 30 cycles at 94° C. for 30 seconds, 55° C. for 1 minute and 72° C. for 2 minutes, and a final elongation step at 72° C. for 10 minutes.

Example: 34

Cloning of Expression Plasmids for the Heterologous Expression in Yeasts

To characterize the function of the *Thalassiosira pseudonana* desaturases, the open reading frame of the DNA in question is cloned downstream of the galactose-inducible GALL promoter of pYES2.1/V5-His-TOPO (Invitrogen), giving rise to the corresponding pYES2.1 clones.

The *Saccharomyces cerevisiae* strain 334 is transformed with the vectors pYES2.1-TpDesaturasen by electroporation (1500 V). A yeast which is transformed with the blank vector pYES2 is used for control purposes. The transformed yeasts are selected on complete minimal medium (CMdum) agar plates supplemented with 2% glucose, but lacking uracil. After the selection, in each case three transformants are chosen for the further functional expression.

To express the Tp desaturases, precultures of in each case 5 ml CMdum liquid medium supplemented with 2% (w/v) raffinose, but lacking uracil, are first inoculated with the transformants chosen and incubated for 2 days at 30° C., 200 rpm.

Then, 5 ml of CMdum liquid medium (without uracil) supplemented with 2% of raffinose and 300 μM of various fatty acids are inoculated with the precultures $OD_{600}$ of 0.05. Expression is induced by addition of 2% (w/v) galactose. The cultures are incubated for a further 96 h at 20° C.

Example 35

Cloning of Expression Plasmids for the Seed-Specific Expression in Plants

A further transformation vector based on pSUN-USP is generated for the transformation of plants. To this end, NotI cleavage sites are introduced at the 5' and 3' ends of the coding sequences, using PCR. The corresponding primer sequences are derived from the 5' and 3 regions of the desaturases.

Composition of the PCR Mix (50 μl):

5.00 μl template cDNA 5.00 μl 10× buffer (Advantage polymerase)+25 mM $MgCl_2$ 5.00 μl 2 mM dNTP 1.25 μl of each primer (10 pmol/μl)

0.50 μl Advantage polymerase

The Advantage polymerase from Clontech was employed.
PCR Reaction Conditions:
Annealing temperature: 1 min 55° C.
Denaturation temperature: 1 min 94° C.
Elongation temperature: 2 min 72° C.
Number of cycles: 35

The PCR products were incubated with the restriction enzyme NotI for 16 hours at 37° C. The plant expression vector pSUN300-USP was incubated in the same manner. Thereafter, the PCR products and the vector were separated by agarose gel electrophoresis and the corresponding DNA fragments were excised. The DNA was purified by means of the Qiagen Gel-Purification Kit following the manufacturer's instructions. Thereafter, vector and PCR products were ligated. The Rapid Ligation Kit from Roche was used for this purpose. The resulting plasmids were verified by sequencing.

pSUN300 is a derivative of plasmid pPZP (Hajdukiewicz, P, Svab, Z, Maliga, P., (1994) The small versatile pPZP family of Agrobacterium binary vectors for plant transformation. Plant Mol Biol 25:989-994). pSUN-USP originated from pSUN300, by inserting a USP promoter into pSUN300 in the form of an EcoRI fragment. The polyadenylation signal is the OCS gene from the A. tumefaciens Ti plasmid (ocs-Terminator, Genbank Accession V00088) (De Greve, H., Dhaese, P., Seurinck, J., Lemmers, M., Van Montagu, M. and Schell, J. Nucleotide sequence and transcript map of the Agrobacterium tumefaciens Ti plasmid-encoded octopine synthase gene J. Mol. Appl. Genet. 1 (6), 499-511 (1982)). The USP promoter corresponds to nucleotides 1 to 684 (Genbank Accession X56240), where part of the noncoding region of the USP gene is present in the promoter. The promoter fragment which is 684 base pairs in size was amplified by a PCR reaction and standard methods with the aid of a synthesized primer and by means of a commercially available T7 standard primer (Stratagene).

(Primer sequence:
5'-GTCGACCCGCGGACTAGTGGGCCCTCTAGACCCGGGGGATCCGGATC

TGCTGGCTATGAAA3'; SEQ ID NO: 143).

The PCR fragment was recut with EcoRI/SalI and inserted into the vector pSUN300 with OCS terminator. This gave rise to the plasmid with the name pSUN-USP. The construct was used for the transformation of Arabidopsis thaliana, oilseed rape, tobacco and linseed.

Example 36

Expression of Tp Desaturases in Yeasts

Yeasts which had been transformed with the plasmids pYES2 and pYES2-Tp desaturases as described in Example 4 were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove non-derivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 μl of PE. The samples were separated on a DB-23 capillary column (30 m, 0.25 mm, 0.25 μm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 37

Functional Characterization of Thalassiosira pseudonana Desaturases

The substrate specificity of desaturases can be determined after expression in yeast (see Examples cloning of desaturase genes, yeast expression) by feeding, using various yeasts. Descriptions for the determination of the individual activities can be found in WO 93/11245 for Δ15-desaturases, WO 94/11516 for Δ12-desaturases, WO 93/06712, U.S. Pat. No. 5,614,393, U.S. Pat. No. 5,614,393, WO 96/21022, WO 0021557 and WO 99/27111 for Δ6-desaturases, Qiu et al. 2001, J. Biol. Chem. 276, 31561-31566 for Δ4-desaturases, Hong et al. 2002, Lipids 37, 863-868 for Δ5-desaturases.

The activity of the individual desaturases is calculated from the conversion rate using the formula [substrate/(substrate+product)*100].

Tables 11 and 12 which follow give an overview over the cloned Thalassiosira pseudonana desaturases

TABLE 11

Length and characteristics of the cloned Thalassiosira desaturases.

| Desaturase | cDNA (bp) | Protein (aa) | Cyt. B5 | His box1 | His box2 | His box3 |
|---|---|---|---|---|---|---|
| TpD4 | 1512 | 503 | HPGG | HDGNH | WELQHMLGHH | QIEHHLFP |
| TpD5-1 | 1431 | 476 | HPGG | HDANH | WMAQHWTHH | QVEHHLFP |
| TpD5-2 | 1443 | 482 | HPGG | HDANH | WLAQHWTHH | QVEHHLFP |
| TpD6 | 1449 | 484 | HPGG | HDFLH | WKNKHNGHH | QVDHHLFP |

TABLE 11-continued

Length and characteristics of the cloned *Thalassiosira* desaturases.

| Desaturase | cDNA (bp) | Protein (aa) | Cyt. B5 | His box1 | His box2 | His box3 |
|---|---|---|---|---|---|---|
| TpFAD2 (d12) | 1305 | 434 | — | HECGH | HAKHH | HVAHHLFH |
| TpO3 | 1257 | 419 | — | HDAGH | WLFMVTYLQHH | HVVHHLF |

TABLE 12

Length, exons, homology and identities of the cloned desaturases.

| Des. | GDN A (bp) | Exon 1 | Exon 2 | First Blast Hit | Hom./Iden. |
|---|---|---|---|---|---|
| TpD4 | 2633 | 496-1314 | 1571-2260 | Thrautochitrium D4-des | 56%/43% |
| TpD5-1 | 2630 | 490-800 | 900-2019 | Phaeodactylum D5-des | 74%/62% |
| TpD5-2 | 2643 | 532-765 | 854-2068 | Phaeodactylum D5-des | 72%/61% |
| TpD6 | 2371 | 379-480 | 630-1982 | Phaeodactylum D6-des | 83%/69% |
| TpFAD2 | 2667 | 728-2032 | — | Phaeodactylum FAD2 | 76%/61% |
| TpO3 | 2402 | 403-988 | 1073-1743 | Chaenorhabdidis Fad2 | 49%/28% |

The Δ12-desaturase genes from *Ostreococcus* and *Thalassiosira* can also be cloned in analogy to the abovementioned examples.

Example 38

Cloning of Elongase Genes from *Xenopus laevis* and *Ciona intestinalis*

By searching for conserved regions (see consensus sequences, SEQ ID NO: 115 and SEQ ID NO: 116) in the protein sequences of the gene databases (Genbank) with the aid of the elongase genes with Δ5-elongase activity or Δ6-elongase activity which are detailed in the present application, it was possible to identify and isolate further elongase sequences from other organisms. Using suitable motifs, it was possible to identify further sequences from in each case *X. laevis* and *C. intestinalis*, respectively. The sequences were the following:

| Name of gene | Organism | Genbank No. | SEQ ID NO: | Amino acids |
|---|---|---|---|---|
| ELO(Xl) | *Xenopus laevis* | BC044967 | 117 | 303 |
| ELO(Ci) | *Ciona intestinalis* | AK112719 | 119 | 290 |

The *X. laevis* cDNA clone was obtained from the NIH (National Institute of Health) [Genetic and genomic tools for Xenopus research: The NIH *Xenopus* initiative, Dev. Dyn. 225 (4), 384-391 (2002)].

The *C. intestinalis* cDNA clone was obtained from the University of Kyoto [Satou, Y., Yamada, L., Mochizuki, Y., Takatori, N., Kawashima, T., Sasaki, A., Hamaguchi, M., Awazu, S., Yagi, K., Sasakura, Y., Nakayama, A., Ishikawa, H., Inaba, K. and Satoh, N. "A cDNA resource from the basal chordate *Ciona intestinalis*" JOURNAL Genesis 33 (4), 153-154 (2002)].

Example 39

Cloning of Expression Plasmids for the Heterologous Expression in Yeasts

The elongase DNAs were amplified with in each case 1 µl cDNA, 200 µM dNTPs, 2.5 U Advantage polymerase and 100 pmol of each primer in a total volume of 50 µl. The PCR conditions were as follows: first denaturation at 95° C. for 5 minutes, followed by 30 cycles at 94° C. for 30 seconds, 55° C. for 1 minute and 72° C. for 2 minutes, and a last elongation step at 72° C. for 10 minutes.

The following oligonucleotides were used for the PCR reaction for cloning the sequence for the heterologous expression in yeasts:

```
Name of gene,
and SEQ ID NO: Primer sequence

ELO(Xl)
SEQ ID NO: 121 F:5'-AGGATCCATGGCCTTCAAGGAGCTCACATC
SEQ ID NO: 122 R:5'-CCTCGAGTCAATGGTTTTTGCTTTTCAATGC
                 ACCG

ELO(Ci),
SEQ ID NO: 123 F:5'-TAAGCTTATGGACGTACTTCATCGT
SEQ ID NO: 124 R:5'-TCAGATCTTTAATCGGTTTTACCATT
```

*F = forward primer, R = reverse primer

The PCR products were incubated for 30 minutes at 21° C. with the yeast expression vector pYES2.1-TOPO (Invitrogen) following the manufacturer's instructions. The PCR product was ligated into the vector by means of a T-overhang and the activity of a topoisomerase (Invitrogen). After the incubation, E. coli DH5α cells are transformed. Suitable clones were identified by PCR, the plasmid DNA was isolated by means of the Qiagen DNAeasy kit and verified by sequencing. The correct sequence was then transformed into the Saccharomyces strain INVSc1 (Invitrogen) by electroporation (1500 V). As a control, the blank vector pYES2.1 was transformed in parallel. Thereafter, the yeasts were plated of minimal dropout uracil medium supplemented with 2% glucose. Cells which were capable of growing in the medium without uracil thus comprise the corresponding plasmids pYES2.1, pYES2.1-ELO(XI) und pYES2.1-ELO(Ci). After the selection, in each case two transformants were chosen for the further functional expression.

Example 40

Cloning Expression Plasmids for the Purposes of Seed-Specific Expression in Plants To transform plants, a further transformation vector based on pSUN-USP was generated. To this end, NotI cleavage sites were introduced at the 5' and 3' ends of the coding sequence, using the following primer pair:

```
pSUN-ELO(XI)
                                         (SEQ ID NO: 125)
Forward: 5'-GCGGCCGCACCATGGCCTTCAAGGAGCTCACATC (SEQ ID NO: 126)
Reverse: 3'-GCGGCCGCCTTCAATGGTTTTTGCTTTTCAATGCACCG pSUN-ELO(Ci)
                                         (SEQ ID NO: 127)
Forward: 5'-GCGGCCGCACCATGGACGTACTTCATCGT (SEQ ID NO: 128)
Reverse: 3'-GCGGCCGCTTTAATCGGTTTTACCATT
```

Composition of the PCR Mix (50 µl):
5.00 µl template cDNA
5.00 µl 10× buffer (Advantage polymerase)+25 mM MgCl$_2$
5.00 µl 2 mM dNTP
1.25 µl per primer (10 pmol/µl)
0.50 µl Advantage polymerase
The Advantage polymerase from Clontech was employed.
PCR Reaction Conditions:
Annealing temperature: 1 minute at 55° C.
Denaturation temperature: 1 minute at 94° C.
Elongation temperature: 2 minutes at 72° C.
Number of cycles: 35

The PCR products were incubated for 16 hours at 37° C. with the restriction enzyme NotI. The plant expression vector pSUN300-USP was incubated in the same manner. Thereafter, the PCR products and the 7624 bp vector were separated by agarose gel electrophoresis and the corresponding, DNA fragments were excised. The DNA was purified by means of Qiagen gel purification kit following the manufacturer's instructions. Thereafter, vector and PCR products were ligated. The Rapid Ligation kit from Roche was used for this purpose. The resulting plasmids pSUN-ELO(XI) und pSUN-ELO(Ci) were verified by sequencing.

pSUN300 is a derivative of plasmid pPZP (Hajdukiewicz, P, Svab, Z, Maliga, P., (1994) The small versatile pPZP family of Agrobacterium binary vectors for plant transformation. Plant Mol Biol 25:989-994). pSUN-USP originated from pSUN300, by inserting a USP promoter as EcoRI fragment into pSUN300. The polyadenylation signal is that of the octopine synthase gene from the A. tumefaciens Ti plasmid (ocs terminator, Genbank Accession V00088) (De Greve, H., Dhaese, P., Seurinck, J., Lemmers, M., Van Montagu, M. and Schell, J. Nucleotide sequence and transcript map of the Agrobacterium tumefaciens Ti plasmid-encoded octopine synthase gene J. Mol. Appl. Genet. 1 (6), 499-511 (1982). Der USP promoter corresponds to the nucleotides 1-684 (Genbank Accession X56240), where part of the noncoding region of the USP gene is present in the promoter. The promoter fragment which is 684 base pairs in size was amplified by means of commercially available T7 standard primers (Stratagene) and with the aid of a synthesized primer via a PCR reaction following standard methods

```
Primer sequence:
                                         (SEQ ID NO: 129)
5'-GTCGACCCGCGGACTAGTGGGCCCTCTAGACCCGGGGGATCCGGATC
TGCTGGCTATGAA-3'.
```

The PCR fragment was cut again with EcoRI/SalI and introduced into the vector pSUN300 with OCS terminator. This gave rise to the plasmid with the name pSUN-USP. The construct was used for the transformation of Arabidopsis thaliana, oilseed rape, tobacco and linseed.

The lipid extraction from yeasts and seeds was as described in Example 6.

Example 41

Expression of ELO(XI) (SEQ ID NO: 117) and ELO(Ci) (SEQ ID NO: 119) in Yeasts Yeasts which had been transformed with the plasmids pYES2, pYES2-ELO(XI) and pYES2-ELO(Ci) as described in Example 4 were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove non-derivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature as programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 42

Functional Characterization of ELO(XI) (SEQ ID NO: 117) and ELO(Ci) (SEQ ID NO: 119)

The substrate specificity of ELO(XI) was determined after expression and after feeding various fatty acids (FIG. 22).

The substrates fed can be detected in large amounts in all of the transgenic yeasts. The transgenic yeasts revealed the synthesis of novel fatty acids, the products of the ELO(XI) reaction. This means that the gene ELO(XI) was expressed functionally.

Table 13 shows that ELO(XI) has a broad substrate specificity. Both C18- and C20-fatty acids are elongated, a preference of Δ5- and Δ6-desaturated fatty acids being observed.

The yeasts which had been transformed with the vector pYES2-ELO(XI) were grown in minimal medium in the presence of the fatty acids stated. The fatty acid methyl esters were synthesized by subjecting intact cells to acid methanolysis. Thereafter, the FAMEs were analyzed via GLC.

TABLE 13

Expression of ELO(XI) in yeast. The conversion rate of various starting materials (fed at in each case 250 µM) is shown.

| Starting materials | Conversion of the starting materials by ELO(XI) in % |
|---|---|
| 16:0 | 3 |
| 16:1$^{\Delta 9}$ | 0 |
| 18:0 | 2 |
| 18:1$^{\Delta 9}$ | 0 |
| 18:2$^{\Delta 9,12}$ | 3 |
| 18:3$^{\Delta 6,9,12}$ | 12 |
| 18:3$^{\Delta 5,9,12}$ | 13 |
| 18:3$^{\Delta 9,12,15}$ | 3 |
| 18:4$^{\Delta 6,9,12,15}$ | 20 |
| 20:3$^{\Delta 8,11,14}$ | 5 |
| 20:3$^{\Delta 11,14,17}$ | 13 |
| 20:4$^{\Delta 5,8,11,14}$ | 15 |
| 20:5$^{\Delta 5,8,11,14,17}$ | 10 |
| 22:4$^{\Delta 7,10,13,16}$ | 0 |
| 22:6$^{\Delta 4,7,10,13,16,19}$ | 0 |

The substrate specificity of ELO(Ci) was determined after expression and after feeding various fatty acids (FIG. 23). The substrates fed can be detected in large amounts in all of the transgenic yeasts. The transgenic yeasts revealed the synthesis of novel fatty acids, the products of the ELO(Ci) reaction. This means that the gene ELO(Ci) was expressed functionally

TABLE 14

Expression of ELO(Ci) in yeast. The conversion rate of various starting materials (fed at in each case 250 µM) is shown.

| Starting materials | Conversion of the starting materials by ELO(Ci) in % |
|---|---|
| 16:0 | 0 |
| 16:1$^{\Delta 9}$ | 0 |
| 18:0 | 0 |
| 18:1$^{\Delta 9}$ | 0 |
| 18:2$^{\Delta 9,12}$ | 23 |
| 18:3$^{\Delta 6,9,12}$ | 10 |
| 18:3$^{\Delta 5,9,12}$ | 38 |
| 18:3$^{\Delta 9,12,15}$ | 25 |
| 18:4$^{\Delta 6,9,12,15}$ | 3 |
| 20:3$^{\Delta 8,11,14}$ | 10 |
| 20:3$^{\Delta 11,14,17}$ | 8 |
| 20:4Δ5, 8, 11, 14 | 10 |
| 20:5Δ5, 8, 11, 14, 17 | 15 |
| 22:4Δ7, 10, 13, 16 | 0 |
| 22:6Δ4, 7, 10, 13, 16, 19 | 0 |

Table 14 shows that ELO(Ci) has a broad substrate specificity. Both C18- and C20-fatty acids are elongated, a preference of Δ5- and Δ6-desaturated fatty acids being observed.

The yeasts which had been transformed with the vector pYES2-ELO(Ci) were grown in minimal medium in the presence of the fatty acids stated. The fatty acid methyl esters were synthesized by subjecting intact cells to acid methanolysis. Thereafter, the FAMEs were analyzed via GLC.

Example 43

Cloning of Genes from *Ostreococcus tauri*

By searching for conserved regions in the protein sequences with the aid of the elongase genes with Δ5-elongase activity or Δ6-elongase activity, which are described herein, it was possible to identify in each case two sequences with corresponding motifs in an *Ostreococcus tauri* sequence database (genomic sequences). The sequences were the following:

| Name of gene | SEQ ID | Amino acids |
|---|---|---|
| OtELO1 (Δ5-elongase) | SEQ ID NO: 67 | 300 |
| OtELO1.2 (Δ5-elongase) | SEQ ID NO: 113 | 300 |
| OtELO2 (Δ6-elongase) | SEQ ID NO: 81 | 292 |
| OtELO2.1 (Δ6-elongase) | SEQ ID NO: 111 | 292 |

OtElo1 (SEQ ID NO: 67) and OtElo1.2 (SEQ ID NO: 113) show the highest degree of similarity to an elongate from *Danio rerio* (GenBank AAN77156; approx. 26% identity), while OtElo2 (SEQ ID NO: 81) and OtElo2.1 (SEQ ID NO: 111) show the highest similarity with the *Physcomitrella* Elo (PSE) [approx. 36% identity] (alignments were carried out using the tBLASTn algorithm (Altschul et A, T. Mol. Biol. 1990, 215: 403-410).

The elongases were cloned as follows:

40 ml of an *Ostreococcus tauri* culture in the stationary phase were spun down, resuspended in 100 µl of double-distilled water and stored at −20° C. Based on the PCR method, the respective genomic DNAs were amplified. The respective primer pairs were chosen in such a way that they bore the yeast consensus sequence for highly efficient translation (Kozak, Cell 1986, 44:283-292) adjacent to the start codon. The OtElo DNAs were amplified in each case using 1 µl of defrosted cells, 200 µM dNTPs, 2.5 U Taq polymerase and 100 pmol of each primer in a total volume of 50 µl. The PCR conditions were as follows: first denaturation at 95° C. for 5 minutes, followed by 30 cycles at 94° C. for 30 seconds, 55° C. for 1 minute and 72° C. for 2 minutes, and a last elongation step at 72° C. for 10 minutes.

Example 44

Cloning of Expression Plasmids for the Heterologous Expression Yeasts

To characterize the function of the *Ostreococcus tauri* elongases, the open reading frame of the DNA in question is cloned downstream of the galactose-inducible GALL promoter of pYES2.1/V5-His-TOPO (Invitrogen), giving rise to the corresponding pOTE1, pOTE1.2, pOTE2 and pOTE2.1 clones.

The *Saccharomyces cerevisiae* strain 334 is transformed with the vectors pOTE1, pOTE1.2, pOT22 and pOTE2.1, respectively by electroporation (1500 V). A yeast which is transformed with the blank vector pYES2 is used for control purposes. The transformed yeasts are selected on complete minimal medium (CMdum) agar plates supplemented with 2% glucose, but lacking uracil. After the selection, in each case three transformants are chosen for the further functional expression.

To express the Ot elongases, precultures of in each case 5 ml CMdum liquid medium supplemented with 2% (w/v) raffinose, but lacking uracil, are first inoculated with the transformants chosen and incubated for 2 days at 30° C., 200 rpm.

Then, 5 ml of CMdum liquid medium (without uracil) supplemented with 2% of raffinose and 300 µM of various fatty acids are inoculated with the precultures $OD_{600}$ of 0.05. Expression is induced by addition of 2% (w/v) galactose. The cultures are incubated for a further 96 h at 20° C.

Example 45

Cloning of Expression Plasmids for the Seed-Specific Expression in Plants

A further transformation vector based on pSUN-USP is generated for the transformation of plants. To this end, NotI cleavage sites are introduced at the 5' and 3' ends of the coding sequences, using PCR. The corresponding primer sequences are derived from the 5' and 3 regions of OtElo1 (SEQ ID NO: 67), OtElo1.2 (SEQ ID NO: 113), OtElo2 (SEQ ID NO: 69) and OtElo2.1 (SEQ ID NO: 111).
Composition of the PCR Mix (50 µl):
5.00 µl template cDNA
5.00 µl 10× buffer (Advantage polymerase)+25 mM $MgCl_2$
5.00 µl 2 mM dNTP
1.25 µl of each primer (10 pmol/µl)
0.50 µl Advantage polymerase
The Advantage polymerase from. Clontech was employed.
PCR Reaction Conditions:
Annealing temperature: 1 min 55° C.
Denaturation temperature: 1 min 94° C.
Elongation temperature: 2 min 72° C.
Number of cycles: 35

The PCR products were incubated with the restriction enzyme NotI for 16 hours at 37° C. The plant expression vector pSUN300-USP was incubated in the same manner. Thereafter, the PCR products and the vector were separated by agarose gel electrophoresis and the corresponding DNA fragments were excised. The DNA was purified by means of the Qiagen Gel Purification Kit following the manufacturer's instructions. Thereafter, vector and PCR products were ligated. The Rapid Ligation Kit from Roche was used for this purpose. The resulting plasmids were verified by pSUN-OtEllO1, pSUN-OtELO1.2, pSUN-OtELO2 and pSUN-OtELO2.2 sequencing.

pSUN300 is a derivative of plasmid pPZP (Hajdukiewicz, P, Svab, Z, Maliga, P., (1994) The small versatile pPZP family of *Agrobacterium* binary vectors for plant transformation. Plant Mol Biol 25:989-994). pSUN-USP originated from pSUN300, by inserting a USP promoter into pSUN300 in the form of an EcoRI fragment. The polyadenylation signal is that of the *Ostreococcus* gene from the *A. tumefaciens* Ti plasmid (ocs-Terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982). The USP promoter corresponds to nucleotides 1 to 684 (Genbank Accession X56240), where part of the noncoding region of the USP gene is present in the promoter. The promoter fragment which is 684 base pairs in size was amplified by a PCR reaction and standard methods with the aid of a synthesized primer and by means of a commercially available T7 standard primer (Stratagene).

```
(Primer sequence:
                                      (SEQ ID NO: 130)
5'-GTCGACCCGCGGACTAGTGGGCCCTCTAGACCCGGGGGATCCGGATC
TGCTGGCTATGAA-3').
```

The PCR fragment was recut with EcoRI/SalI and inserted into the vector pSUN300 with OCS terminator. This gave rise to the plasmid with the name pSUN-USP. The construct was used for the transformation of *Arabidopsis thaliana*, oilseed rape, tobacco and linseed.

Example 46

Expression of OtElo1 (SEQ ID NO: 67), OtElo1.2 (SEQ ID NO: 113), OtElo2 (SEQ ID NO: 69) and OtELO2.1 (SEQ ID NO: 111) in Yeasts Yeasts which had been transformed with the plasmids pYES3, pYES3-OtELO1, pYES3-OtELO1.2, pYES3-OtELO2 and pYES3-OtELO2.2 as described in Example 15 were analyzed as follows:

The yeast cells from the main cultures were harvested by centrifugation (100×g, 5 min, 20° C.) and washed with 100 mM $NaHCO_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove non-derivatized fatty acids, the organic phases were washed in each case once with 2 ml of 100 mM $NaHCO_3$, pH 8.0 and 2 ml of distilled water. Thereafter, the PE phases were dried with $Na_2SO_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 47

Functional Characterization of OtElo1 (SEQ ID NO: 67), OtElo1.2 (SEQ ID NO: 113), OtElo2 (SEQ ID NO: 69) and OtElo2.1 (SEQ ID NO: 111)

The substrate specificity of OtElo1 (SEQ ID NO: 67) was determined after expression and after feeding various fatty acids (Tab. 15). The substrates fed can be detected in large amounts in all of the transgenic yeasts. The transgenic yeasts revealed the synthesis of novel fatty acids, the products of the OtElo1 reaction. This means that the gene OtElo1 was expressed functionally.

Table 15 shows that OtElo1 (SEQ ID NO: 67) and OtElo1.2 (SEQ ID NO: 113) have a narrow substrate specificity. OtElo1 (SEQ ID NO: 67) and OtElo1.2 (SEQ ID NO: 113) were only capable of elongating the C20-fatty acids eicosapentaenoic acid (FIG. 24A, 24B) and arachidonic acid (FIG. 25A, 25B), but preferred eicosapentaenoic acid, which is ω-3-desaturated.

Table 15 shows the substrate specificity of the elongase OtElo1 (SEQ ID NO: 67) and OtElo1.2 (SEQ ID NO: 113) for C20-polyunsaturated fatty acids with a double bond in the Δ5 position in comparison with various fatty acids.

The yeasts which had been transformed with the vector pOTE1 and pOTE1.2, respectively, were grown in minimal medium in the presence of the fatty acids stated. The fatty acid methyl esters were synthesized by subjecting intact cells to acid methanolysis. Thereafter, the FAMEs were analyzed via GLC.

The substrate specificity of OtElo1 (SEQ ID NO: 67) and OtElo2.1 (SEQ ID NO: 111) was determined after expression and after feeding various fatty acids (Tab. 16). The substrates fed can be detected in large amounts in all of the transgenic yeasts. The transgenic yeasts revealed the synthesis of novel fatty acids, the products of the OtElo2 reaction. This means that the genes OtElo2 and OtElo2.1 were expressed functionally.

TABLE 15

| Fatty acid substrate | Conversion rate (in %) OtElo1 | Conversion rate (in %) OtElo1.2 |
|---|---|---|
| 16:0 | — | — |
| 16:1$^{\Delta 9}$ | — | — |
| 18:0 | — | — |
| 18:1$^{\Delta 9}$ | — | — |
| 18:1$^{\Delta 11}$ | — | — |
| 18:2$^{\Delta 9,12}$ | — | — |
| 18:3$^{\Delta 6,9,12}$ | — | — |
| 18:3$^{\Delta 5,9,12}$ | — | — |
| 20:3$^{\Delta 8,11,14}$ | — | — |
| 20:4$^{\Delta 5,8,11,14}$ | 10.8 ± 0.6 | 38.0 |
| 20:5$^{\Delta 5,8,11,14,17}$ | 46.8 ± 3.6 | 68.6 |
| 22:4$^{\Delta 7,10,13,16}$ | — | — |
| 22:6$^{\Delta 4,7,10,13,16,19}$ | — | — |

Table 16 shows the substrate specificity of the elongase OtElo2 (SEQ ID NO: 81) and OtElo2.1 (SEQ ID NO: 111) for various fatty acids. The activity of OtElo2.1 (SEQ ID NO: 111) is markedly higher.

The yeasts which had been transformed with the vector pOTE2 and pOTE2.1, respectively, were grown in minimal medium in the presence of the fatty acids stated. The fatty acid methyl esters were synthesized by subjecting intact cells to acid methanolysis. Thereafter, the FAMEs were analyzed via GLC.

The enzymatic activity which is shown in Table 16 demonstrates clearly that OtElo2 (SEQ ID NO: 81), or OtElo2.1 (SEQ ID NO: 111), is a Δ6-elongase.

TABLE 16

| Fatty acid substrate | Conversion rate (in %) OtElo2 | Conversion rate (in %) OtELO2.1 |
|---|---|---|
| 16:0 | — | — |
| 16:1$^{\Delta 9}$ | — | — |
| 16:3$^{\Delta 7,10,13}$ | — | — |

TABLE 16-continued

| Fatty acid substrate | Conversion rate (in %) OtElo2 | Conversion rate (in %) OtELO2.1 |
|---|---|---|
| 18:0 | — | — |
| 18:1$^{\Delta 6}$ | — | — |
| 18:1$^{\Delta 9}$ | — | — |
| 18:1$^{\Delta 11}$ | — | — |
| 18:2$^{\Delta 9,12}$ | — | — |
| 18:3$^{\Delta 6,9,12}$ | 15.3 | 55.7 |
| 18:3$^{\Delta 5,9,12}$ | — | — |
| 18:4$^{\Delta 6,9,12,15}$ | 21.1 | 70.4 |
| 20:2$^{\Delta 11,14}$ | — | — |
| 20:3$^{\Delta 8,11,14}$ | — | — |
| 20:4$^{\Delta 5,8,11,14}$ | — | — |
| 20:5$^{\Delta 5,8,11,14,17}$ | — | — |
| 22:4$^{\Delta 7,10,13,16}$ | — | — |
| 22:5$^{\Delta 7,10,13,16,19}$ | — | — |
| 22:6$^{\Delta 4,7,10,13,16,19}$ | — | — |

FIG. 24 A-D shows the elongation of eicosapentaenoic acid by OtElo1 (B; SEQ ID NO: 67) and OtElo1.2 (D; SEQ ID NO: 11.3), respectively. The controls (A, C) do not show the elongation product (22:5ω3).

FIG. 25 A-D shows the elongation of arachidonic acid by OtElo1 (B; SEQ ID NO: 67) and OtElo1.2 (D; SEQ ID NO: 113), respectively. The controls (A, C) do not show the elongation product (22:4ω6).

Example 48

Cloning of Elongase Genes from *Euglena gracilis* and *Arabidopsis thaliana*

By searching for conserved regions in the protein sequences with the aid of the elongase genes with Δ5-elongase activity or Δ6-elongase activity, which are detailed in the application, it was possible to identify sequences from *Arabidopsis thaliana* and *Euglena gracilis*, respectively, with corresponding motifs in sequence databases (Genbank, *Euglena* EST library). The sequences are the following:

| Name of gene | SEQ ID | Amino acids |
|---|---|---|
| EGY1019 (*E. gracilis*) | SEQ ID NO: 131 | 262 |
| EGY2019 (*E. gracilis*) | SEQ ID NO: 133 | 262 |
| At3g06460 (*A. thaliana*) | SEQ ID NO: 135 | 298 |
| At3g06470 (*A. thaliana*) | SEQ ID NO: 137 | 278 |

The *Euglena gracilis* elongases were cloned as follows:
The *Euglena gracilis* strain 1224-5/25 was obtained from the Sammiung für Algenkulturen Göttingen [Göttingen collection of algal cultures] (SAG). For the isolation, the strain was grown in medium 11 (Calvayrac R and Douce R, FEBS Letters 7:259-262, 1970) for 4 days at 23° C. with a light/dark interval of 8 h/16 h (light intensity 35 mol s-1 m-2).

Total RNA of a four-day-old *Euglena* culture was isolated with the aid of the RNAeasy kit from Qiagen (Valencia, Calif., US). Poly-A+ RNA (mRNA) was isolated from the total RNA with the aid of oligo-dt-cellulose (Sambrook et al., 1989). The RNA was subjected to reverse transcription using the Reverse Transcription System kit from Promega, and the cDNA synthesized was cloned into the vector lambda ZAP (lambda ZAP Gold, Stratagene). The cDNA was depackaged in accordance with the manufacturer's instructions to give plasmid DNA, and clones were part-sequenced for random sequencing. mRNA was isolated from the total RNA with the aid of the PolyATract isolation system (Promega). The mRNA was subjected to reverse transcription using the Marathon cDNA amplification kit (BD Biosciences), and the adapters were ligated in accordance with the manufacturer's instructions. The cDNA library was then used for the PCR for cloning expression plasmids by means of 5' and 3'-RACE (rapid amplification of cDNA ends).

The *Arabidopsis thaliana* elongases were cloned as follows:

Starting from the genomic DNA, primers for the two genes were derived in each case at the 5' and 3' end of the open reading frame.

The method of Chrigwin et al., (1979) was used for isolating total RNA from *A. Thaliana*. Leaves of 21-day-old plants were comminuted with a pestle and mortar in liquid nitrogen, treated with disruption buffer and incubated for 15 minutes at 37° C. After centrifugation (10 min, 4° C., 12 000×g), the RNA in the supernatant was precipitated with 0.02 volume of 3 M sodium acetate pH 5.0 and 0.75 volume of ethanol at −20° C. for 5 hours. Then, after a further centrifugation step, the RNA was taken up in 1 ml of TES per g of starting material, extracted once with one volume of phenol/chloroform and once with one volume of chloroform, and the RNA was precipitated with 2.5 M LiCl. After the subsequent centrifugation and washing with 80% ethanol, the RNA was resuspended in water. The cDNA was synthesized as described by Sambrook et al. 1989, and RT-PCR was carried out with the derived primers. The PCR products were cloned into the vector pYES2.1-TOPO (Invitrogen) following the manufacturer's instructions.

Example 49

Cloning of Expression Plasmids for the Heterologous Expression in Yeasts

To characterize the function of the *A. thaliana* desaturases, the open reading frame of the DNA in question is cloned downstream of the galactose-inducible GALL promoter of pYES2.1/V5-His-TOPO (Invitrogen), giving rise to the corresponding pAt60 and pAt70 clones.

The *Saccharomyces cerevisiae* strain 334 is transformed with the vectors pAt60 and pAt70, respectively by electroporation (1500 V). A yeast which is transformed with the blank vector pYES2.1 is used for control purposes. The transformed yeasts are selected on complete minimal medium (CMdum) agar plates supplemented with 2% glucose, but lacking uracil. After the selection, in each case three transformants are chosen for the further functional expression.

To express the At elongases, precultures of in each case 5 ml of CMdum liquid medium supplemented with 2% (w/v) raffinose, but without uracil, were inoculated with the selected transformants and incubated for 2 hours at 30° C., 200 rpm.

5 ml of CMdum liquid medium (without uracil) supplemented with 2% of raffinose and 300 µM various fatty acids were then inoculated with the precultures to an OD$_{600}$ of 0.05. Expression was induced by the addition of 2% (w/v) galactose. The cultures were incubated for a further 96 hours at 20° C.

Example 50

Expression of pAt60 and pAt70 in Yeasts

Yeasts which had been transformed with the plasmids pYES2.1, pAt60 and pAt70, respectively, as described in Example 5 were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove non-derivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 51

Functional Characterization of pAt60 and pAt70

The substrate specificity of the elongases At3g06460 (SEQ ID NO: 135) and At3g06470 (SEQ ID NO: 137), respectively, was determined followed expression and feeding of various fatty acids (Tab. 17, FIG. 26). The substrates fed can be detected in all of the transgenic yeasts. The transgenic yeasts showed the synthesis of new fatty acids, the products of the genes At3g06460 and At3g06470, respectively. This means that these genes were expressed functionally.

TABLE 17

Elongation of EPA by the elongasen At3g06460 and At3g06470, respectively. Analysis of the yeast extracts after feeding with 250 uM EPA.

| Gene | Fatty acid fed | C20:5n-3 content | C22:5n-3 content |
|---|---|---|---|
| At3g06460 | EPA (C20:5n-3) | 20.8 | 0.6 |
| At3g06460 | EPA (C20:5n-3) | 25.4 | 1.1 |
| Conversion rate of EPA | At3g06460: 3.0% | | At3g06470: 4.1% |

FIG. 26 shows the elongation of 20:5n-3 by the elongases At3g06470.

Example 52

Cloning of an Elongase from *Phaeodactylum tricomutum*

Starting from conserved regions in the protein sequences with the aid of the elongase genes with Δ6-elongase activity detailed in the application, degenerate primers were generated and these primers were used for screening a *Phaeodactylum* cDNA library by means of PCR. The following primer sequences were employed:

| Name of primer | Sequence 5'-3' orientation | Corresponding amino acids |
|---|---|---|
| Phaelo forward 1 | AA(C/T)CTUCTUTGGCTUTT(C/T)TA (SEQ-ID NO. 185) | NLLWLFY |
| Phaelo reverse 1 | GA(C/T)TGUAC(A/G)AA(A/G)AA (C/T)TGUGC(A/G)AA (SEQ ID NO. 186) | FAQFFVQS |

Nucleotide bases in brackets mean that a mixture of oligonucleotides with in each case one or the other nucleotide base is present.

Preparation of the *Phaeodactylum* cDNA Library:

A 2 l culture of *P. tricornutum* UTEX 646 was grown in f/2 medium (Guillard, R. R. L. 1975. Culture of phytoplankton for feeding marine invertebrates. In *Culture of Marine Invertebrate Animals* (Eds. Smith, W. L. and Chanley, M. H.), Plenum Press, New York, pp 29-60) for 14 days at a light intensity of 35 E/cm². After centrifugation, frozen cells were ground to a fine powder in the presence of liquid nitrogen and resuspended in 2 ml of homogenization buffer (0.33 M sorbitol 0.3 M, NaCl, 10 mM EDTA, 10 mM EGTA, 2% SDS, 2% mercaptoethanol in 0.2 M Tris-Cl pH 8.5). After addition of 4 ml of phenol and 2 ml of chloroform, the mixture was shaken vigorously for 15 minutes at 45-50° C. It was subsequently centrifuged (10 min×10 000 g), and the aqueous phase was extracted stepwise using chloroform. Nucleic acids were then precipitated by addition of 1/20 volume of 4 M sodium hydrogencarbonate solution and centrifuged. The pellet was taken up in 80 mM Tris-borate pH 7.0 and 1 mM EDTA, and the RNA was precipitated with 8 M lithium chloride. After centrifugation and washing with 70% ethanol, the RNA pellet was taken up in RNase-free water. Poly(A)-RNA was isolated with Dynabeads (Dynal, Oslo, Norway) following the manufacturer's instructions, and the first-strain cDNA synthesis was carried out using MLV-Rtase from Roche (Mannheim). The second-strand synthesis was then carried out by means of DNA polymerase I and Klenow fragment, followed by RNase H digestion. The cDNA was treated with T4 DNA polymerase, and EcoRI/XhoI adaptors (Pharmacia, Freiburg) were subsequently attached by means of T4 ligase. After XhoI digestion, phosphorylation and gel separation, fragments greater than 300 bp were ligated into the phage lambda ZAP Express following the manufacturer's instructions (Stratagene, Amsterdam, The Netherlands). After mass excision of the cDNA library and plasmid recovery, the plasmid library was transformed into *E. coli* DH10B cells and employed for PCR screening.

Using the abovementioned degenerate primers, it was possible to generate the PCR fragment with the SEQ ID NO: 187.

This fragment was labeled with digoxigenin (Roche, Mannheim) and used as probe for screening the phage library.

Using the sequence SEQ ID NO: 187, it was possible to obtain the gene sequence SEQ ID NO: 183, which constitutes the full-length RNA molecule of the *Phaeodactylum* Δ6-elongase:

Example 53

Cloning of Expression Plasmids for the Heterologous Expression in Yeasts

The primer pairs in question were chosen in such a way that they bore the yeast consensus sequence for highly efficient translation (Kozak, Cell 1986, 44:283-292) next to the start codon. The PtELO6 DNA was amplified with in each case 1 µl of cDNA, 200 µM dNTPs, 2.5 U of Advantage polymerase and 100 pmol of each primer in a total volume of 50 µl. The PCR conditions were as follows: first denaturation of 95° C. for 5 minutes, followed by 30 cycles at 94° C. for 30 seconds, 55° C. for 1 minute and 72° C. for 2 minutes, and a last elongation step at 72° C. for 10 minutes.

The following oligonucleotides were used for the PCR reaction for cloning the sequence for the heterologous expression in yeasts:

| Name of gene, and SEQ ID NO: | Primer sequence |
|---|---|
| PtELO6 (SEQ ID NO: 183) | F: 5'-GCGGCCGCACATAATGATGGTACCTTCAAG (SEQ ID NO: 188) R: 3'-GAAGACAGCTTAATAGACTAGT (SEQ ID NO: 189) |

*F = forward primer, R = reverse primer

The PCR products were incubated for 30 minutes at 21° C. with the yeast expression vector pYES2.1-TOPO (Invitrogen) following the manufacturer's instructions. The PCR product (see SEQ ID NO: 192) was ligated into the vector by means of a T-overhang and the activity of a topoisomerase (Invitrogen). After the incubation, *E. coli* DH5α cells were transformed. Suitable clones were identified by PCR, the plasmid DNA was isolated by means of the Qiagen DNAeasy kit and verified by sequencing. The correct sequence was then transformed into the *Saccharomyces* strain INVSc1 (Invitrogen) by electroporation (1500 V). As a control, the blank vector pYES2.1 was transformed in parallel. Thereafter, the yeasts were plated of minimal dropout uracil medium supplemented with 2% glucose. Cells which were capable of growing in the medium without uracil thus comprise the corresponding plasmids pYES2.1 and pYES2.1-PtELO6. After the selection, in each case two transformants were chosen for the further functional expression.

Example 54

Cloning Expression Plasmids for the Purposes of Seed-Specific Expression in Plants To transform plants, a further transformation vector based on pSUN-USP was generated. To this end, NotI cleavage sites were introduced at the 5' and 3' ends of the coding sequence, using the following primer pair:

```
PSUN-PtELO6
                                         (SEQ ID NO: 190)
Forward: 5'-GCGGCCGCACCATGATGGTACCTTCAAGTTA (SEQ ID NO: 191)
Reverse: 3'-GAAGACAGCTTAATAGGCGGCCGC
```

Composition of the PCR Mix (50 µl):
5.00 µl template cDNA
5.00 µl 10× buffer (Advantage polymerase)+25 mM MgCl2
5.00 µl 2 mM dNTP
1.25 µl per primer (10 pmol/µl)
0.50 µl Advantage polymerase The Advantage polymerase from Clontech was employed.
PCR Reaction Conditions:
Annealing temperature: 1 minute at 55° C.
Denaturation temperature: 1 minute at 94° C.
Elongation temperature: 2 minutes at 72° C.
Number of cycles: 35

The PCR products were incubated for 16 hours at 37° C. with the restriction enzyme NotI. The plant expression vector pSUN300-USP was incubated in the same manner. Thereafter, the PCR products and the 7624 bp vector were separated by agarose gel electrophoresis and the corresponding, DNA fragments were excised. The DNA was purified by means of Qiagen gel purification kit following the manufacturer's instructions. Thereafter, vector and PCR products were ligated. The Rapid Ligation kit from Roche was used for this purpose. The resulting plasmid pSUN-PtELO was verified by sequencing.

pSUN300 is a derivative of plasmid pPZP (Hajdukiewicz, P, Svab, Z, Maliga, P., (1994) The small versatile pPZP family of *Agrobacterium* binary vectors for plant transformation. Plant Mol Biol 25:989-994). pSUN-USP originated from pSUN300, by inserting a USP promoter as EcoRI fragment into pSUN300. The polyadenylation signal is that of the octopine synthase gene from the *A. tumefaciens* Ti plasmid (ocs terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982). Der USP promoter corresponds to the nucleotides 1-684 (Genbank Accession X56240), where part of the noncoding region of the USP gene is present in the promoter. The promoter fragment which is 684 base pairs in size was amplified by means of commercially available T7 standard primers (Stratagene) and with the aid of a synthesized primer via a PCR reaction following standard methods.

(Primer sequence:
5'-GTCGACCCGCGGACTAGTGGGCCCTCTAGACCCGGGGGATCCGGATC

TGCTGGCTATGAA-3'; SEQ ID NO: 151).

The PCR fragment was cut again with EcoRI/SalI and introduced into the vector pSUN300 with OCS terminator. This gave rise to the plasmid with the name pSUN-USP. The construct was used for the transformation of *Arabidopsis thaliana*, oilseed rape, tobacco and linseed.

The lipid extraction from yeasts and seeds was as described in Example 6.

Example 55

Expression of PtElo in Yeasts

Yeasts which had been transformed with the plasmids pYES2 and pYES2-PtELO6 as described in Example 4 were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove non-derivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 56

Functional Characterization of PtELO6 (SEQ ID NO: 183)

FIG. 29 shows the conversion of C18:3$^{\Delta 6,9,12}$ and C18:4$^{\Delta 6,9,12,15}$. The substrates are elongated by in each case two carbon atoms; the fatty acids C20:3$^{\Delta 8,11,14}$ and C20:4$^{\Delta 8,11,14,17}$ are formed, respectively. The substrate specificity of PtELO6 was determined after expression and feeding various fatty acids (FIG. 30). Large amounts of the substrates fed can be detected in all of the transgenic yeasts. The transgenic yeasts show the synthesis of new fatty acids, the products of the PtElo6 reaction. This means that the gene PtELO6 has been expressed functionally.

Table 18 shows that PtElo6 has a narrow substrate specificity. PtELO6 was only able to elongate the C18-fatty acids linoleic acid, linolenic acid, γ-linolenic acid and stearidonic acid, but preferred stearidonic acid, which is ω3-desaturated (see also FIG. 30).

Feeding experiment: fatty acids (in bold) were added at in each case 250 µm. The formation of the underlying fatty acids is new.

TABLE 18

| Substrate specificity of PtElo6 (SEQ ID NO: 183) | | | | |
| --- | --- | --- | --- | --- |
| Fatty acid fed: | +18:2 | +18:3 | +18:3 | +18:4 |
| 16:0 | 16.2 | 18.2 | 15.2 | 20 | 04:48 |
| 16:1 | 50.6 | 20.5 | 22.8 | 33.5 | 34.2 |
| 18:0 | 5.4 | 6.3 | 6.2 | 5.2 | 12.4 |
| 18:1 | 27.7 | 14.6 | 19.6 | 19.3 | 16.7 |
| 18:2 | | 40 | | | |
| 18:3 | | | 32.9 | | |
| 18:3 | | | | 12.3 | |
| 18:4 | | | | | 4.5 |
| 20:2 | | 0.4 | | | |

TABLE 18-continued

Substrate specificity of PtEIo6 (SEQ ID NO: 183)

| Fatty acid fed: | +18:2 | +18:3 | +18:3 | +18:4 |
|---|---|---|---|---|
| 20:3 | | 3.4 | | |
| 20:3 | | | 9.7 | |
| 20:4 | | | | 14.5 |
| % Elongation | 0.0 | 0.99 | 9.37 | 44.09 | 76.32 |

The following fatty acids were fed, but not converted:
$18:1^{\Delta 6}$, $18:1^{\Delta 9}$, $18:1^{\Delta 11}$
$20:2^{\Delta 11,14}$, $20:3^{\Delta 11,14,17}$, $20:3^{\Delta 8,11,14}$, $20:4^{\Delta 5,8,11,14,17}$,
$20:5^{\Delta 5,8,11,14,17}$
$22:4^{\Delta 7,10,13,16}$ The yeasts which had been transformed with the vector pYES2-PtELO6 were grown in minimal medium in the presence of the fatty acids stated. The fatty acid methyl esters were synthesized by subjecting intact cells to acid methanolysis. Thereafter, the FAMEs were analyzed via GLC. In this way, the results which were shown in FIGS. 29 and 30 and in Table 16 were obtained.

EQUIVALENTS

Many equivalents of the specific embodiments according to the invention described herein can be identified or found by the skilled worker resorting simply to routine experiments. These equivalents are intended to be within the scope of the patent claims.

TABLE 3

Conversion rates of the fatty acids fed. The conversion rates were calculated using the formula:
[conversion rate] = [product]/[substrate] + [product] * 100.
BioTaur clones area in % of the GC analysis

| Clone | Fatty acid | C16:0 | C16:1 (n-7) | C18:0 | C18:1 (n-9) | C18:3 (n-6) | C18:4 (n-3) | C20:3 (n-6) | C20:4 (n-6) | C20:4 (n-3) | C20:5 (n-3) | C22:4 (n-6) | C22:4 (n-3) | C22:5 (n-3) |
|---|---|---|---|---|---|---|---|---|---|---|---|---|---|---|
| Vector | none | 21.261 | 41.576 | 4.670 | 25.330 | | | | | | | | | |
| BioTaur | none | 20.831 | 37.374 | 4.215 | 26.475 | | | | | | | | | |
| Vector | GLA + EPA | 22.053 | 23.632 | 5.487 | 17.289 | 11.574 | | | | | 13.792 | | | |
| BioTaur | GLA + EPA | 20.439 | 25.554 | 6.129 | 19.587 | 3.521 | | 6.620 | | | 10.149 | | | 1.127 |
| Vector | EPA | 20.669 | 28.985 | 6.292 | 21.712 | | | | | | 16.225 | | | |
| BioTaur | EPA | 20.472 | 26.913 | 6.570 | 23.131 | | | | | | 11.519 | | | 3.251 |
| Vector | ARA | 23.169 | 23.332 | 6.587 | 12.735 | | | | 27.069 | | | | | |
| BioTaur | ARA | 20.969 | 31.281 | 5.367 | 21.351 | | | | 9.648 | | | | 1.632 | |
| Vector | SDA | 18.519 | 12.626 | 6.642 | 6.344 | | 47.911 | | | | | | | |
| BioTaur | SDA | 19.683 | 15.878 | 7.246 | 8.403 | | 13.569 | | | 25.946 | | | 0.876 | |

We claim:

1. A process for the production of a transgenic organism having a content of at least 1% by weight of docosahexaenoic acid and/or eicosapentaenoic acid based on the total lipid content of the transgenic organism, said process comprises the following process steps:
   a) introducing, into the organism, at least one nucleic acid sequence which encodes a polypeptide with Δ6-desaturase activity,
   b) introducing, into the organism, at least one nucleic acid sequence which encodes a polypeptide with Δ6-elongase activity,
   c) introducing, into the organism, at least one nucleic acid sequence which encodes a polypeptide with Δ5-desaturase activity,
   d) introducing, into the organism, at least one nucleic acid sequence which encodes a polypeptide with Δ5-elongase activity that elongates unsaturated $C_{20}$-fatty acids, wherein said nucleic acid sequence is selected from the group consisting of:
      (i) the nucleic acid sequence of SEQ ID NO: 43, SEQ ID NO: 47, SEQ ID NO: 49, SEQ ID NO: 51, SEQ ID NO: 53, SEQ ID NO: 59, SEQ ID NO: 61, SEQ ID NO: 63, SEQ ID NO: 65, SEQ ID NO: 67, SEQ ID NO: 75, SEQ ID NO: 77, SEQ ID NO: 79, SEQ ID NO: 83, SEQ ID NO: 85, SEQ ID NO: 113, SEQ ID NO: 117, SEQ ID NO: 119, SEQ ID NO: 131, SEQ ID NO: 133, SEQ ID NO: 135, or SEQ ID NO: 137;
      (ii) a nucleic acid sequence encoding a polypeptide comprising the amino acid sequence of SEQ ID NO: 44, SEQ ID NO: 48, SEQ ID NO: 50, SEQ ID NO: 52, SEQ ID NO: 54, SEQ ID NO: 60, SEQ ID NO: 62, SEQ ID NO: 64, SEQ ID NO: 66, SEQ ID NO: 68, SEQ ID NO: 76, SEQ ID NO: 78, SEQ ID NO: 80, SEQ ID NO: 84, SEQ ID NO: 86, SEQ ID NO: 114, SEQ ID NO: 118, SEQ ID NO: 120, SEQ ID NO: 132, SEQ ID NO: 134, SEQ ID NO: 136, or SEQ ID NO: 138; and
      (iii) a nucleic acid sequence encoding a polypeptide having at least 70% sequence identity with the amino acid sequence of SEQ ID NO: 44, SEQ ID NO: 48, SEQ ID NO: 50, SEQ ID NO: 52, SEQ ID NO: 54, SEQ ID NO: 60, SEQ ID NO: 62, SEQ ID NO: 64, SEQ ID NO: 66, SEQ ID NO: 68, SEQ ID NO: 76, SEQ ID NO: 78, SEQ ID NO: 80, SEQ ID NO: 84, SEQ ID NO: 86, SEQ ID NO: 114, SEQ ID NO: 118, SEQ ID NO: 120, SEQ ID NO: 132, SEQ ID NO: 134, SEQ ID NO: 136, or SEQ ID NO: 138; and
   e) introducing, into the organism, at least one nucleic acid sequence which encodes a polypeptide with Δ4-desaturase activity.

2. The process according to claim 1, wherein the at least one nucleic acid sequence which encodes a polypeptide with Δ6-desaturase, Δ6-elongase, Δ5-desaturase, or Δ4-desaturase activity is selected from the group consisting of:
   a) the nucleic acid sequence of SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 45, SEQ ID NO: 69, SEQ ID NO: 71, SEQ ID NO: 73, SEQ ID NO: 81, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 111, or SEQ ID NO: 183, b) a nucleic acid sequence encoding a polypeptide comprising the amino acid sequence of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 46, SEQ ID NO: 70, SEQ ID NO: 72, SEQ ID NO: 74, SEQ ID NO: 82, SEQ ID NO: 84, SEQ ID NO: 86, SEQ ID NO: 88, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, or SEQ ID NO: 184, and c) a nucleic acid sequence encoding a polypeptide having at least 70% sequence identity to the amino acid sequence of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 46, SEQ ID NO: 70, SEQ ID NO: 72, SEQ ID NO: 74, SEQ ID NO: 82, SEQ ID NO: 88, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, or SEQ ID NO: 184 and having Δ6-desaturase, Δ6-elongase, Δ5-desaturase, or Δ4-desaturase activity.

3. The process according to claim 1, wherein a nucleic acid sequence which encodes a polypeptide with ω3-desaturase activity is additionally introduced into the organism, wherein said nucleic acid sequence is selected from the group consisting of:

a) a nucleic acid sequence with the sequence shown in SEQ ID NO: 87 or SEQ ID NO: 105, b) a nucleic acid sequence which, as the result of the degeneracy of the genetic code, can be derived from the amino acid sequence shown in SEQ ID NO: 88 or SEQ ID NO: 106, and c) a derivative of the nucleic acid sequence shown in SEQ ID NO: 87 or SEQ ID NO: 105 which encodes a polypeptide with at least 70% identity at the amino acid level with SEQ ID NO: 88 or SEQ ID NO: 106 and having ω3-desaturase activity.

4. The process according to claim 1, wherein a nucleic acid sequence which encodes a polypeptide with Δ12-desaturase activity is additionally introduced into the organism, wherein said nucleic acid sequence is selected from the group consisting of:

a) a nucleic acid sequence with the sequence shown in SEQ ID NO: 107 or SEQ ID NO: 109, b) a nucleic acid sequence which, as the result of the degeneracy of the genetic code, can be derived from the amino acid sequence shown in SEQ ID NO: 108 or SEQ ID NO: 110, and c) a derivative of the nucleic acid sequence shown in SEQ ID NO: 107 or SEQ ID NO: 109 which encodes a polypeptide with at least 70% identity at the amino acid level with SEQ ID NO: 108 or SEQ ID NO: 110 and having Δ12-desaturase activity.

5. The process according to claim 1, wherein the transgenic organism is a transgenic microorganism or a transgenic plant.

6. The process according to claim 1, wherein the transgenic organism is an oil-producing plant, a vegetable plant or an ornamental.

7. The process according to claim 1, wherein the transgenic organism is a transgenic plant selected from the group consisting of the plant families: Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae and Prasinophyceae.

8. The process according to claim 1, wherein the docosahexaenoic acid and/or eicosapentaenoic acid is isolated from the organism in the form of oils, lipids or free fatty acids.

9. The process according to claim 1, wherein the docosahexaenoic acid or eicosapentaenoic acid is isolated in a concentration of at least 5% by weight based on the total lipid content of the transgenic organism.

10. The process of claim 1, wherein the polypeptide with Δ5-elongase activity elongates only unsaturated $C_{20}$-fatty acids.

11. A process for the production of a transgenic organism having a content of at least 1% by weight of docosahexaenoic acid and/or eicosapentaenoic acid based on the total lipid content of the transgenic organism, said process comprises the following process steps:

a) introducing, into the organism, at least one nucleic acid sequence which encodes a polypeptide with Δ6-desaturase activity, b) introducing, into the organism, at least one nucleic acid sequence which encodes a polypeptide with Δ6-elongase activity, c) introducing, into the organism, at least one nucleic acid sequence which encodes a polypeptide with Δ5-desaturase activity, d) introducing, into the organism, at least one nucleic acid sequence which encodes a polypeptide with Δ5-elongase activity that elongates unsaturated $C_{20}$-fatty acids, and e) introducing, into the organism, at least one nucleic acid sequence which encodes a polypeptide with Δ4-desaturase activity, wherein the at least one nucleic acid sequence which encodes a polypeptide with Δ5-elongase activity comprises:

i) the nucleic acid sequence of SEQ ID NO: 113, ii) a nucleic acid sequence encoding the amino acid sequence of SEQ ID NO: 114, iii) a nucleic acid sequence having at least 70% sequence identity to the nucleic acid sequence of SEQ ID NO: 113, or iv) a nucleic acid sequence encoding a polypeptide having at least 70% sequence identity to the amino acid sequence of SEQ ID NO: 114.

12. The process of claim 11, wherein the at least one nucleic acid sequence which encodes a polypeptide with Δ5-elongase activity comprises a nucleic acid sequence having at least 80% sequence identity to the nucleic acid sequence of SEQ ID NO: 113 or a nucleic acid sequence encoding a polypeptide having at least 80% sequence identity to the amino acid sequence of SEQ ID NO: 114.

13. The process of claim 11, wherein the at least one nucleic acid sequence which encodes a polypeptide with Δ5-elongase activity comprises a nucleic acid sequence having at least 90% sequence identity to the nucleic acid sequence of SEQ ID NO: 113 or a nucleic acid sequence encoding a polypeptide having at least 90% sequence identity to the amino acid sequence of SEQ ID NO: 114.

14. The process of claim 11, wherein the at least one nucleic acid sequence which encodes a polypeptide with Δ5-elongase activity comprises a nucleic acid sequence having at least 95% sequence identity to the nucleic acid sequence of SEQ ID NO: 113 or a nucleic acid sequence encoding a polypeptide having at least 95% sequence identity to the amino acid sequence of SEQ ID NO: 114.

15. A transgenic plant obtained by the process of claim 5, or a plant part or seed thereof, wherein said transgenic plant, or said plant part or seed thereof, comprises:
   a) the at least one nucleic acid sequence which encodes a polypeptide with Δ6-desaturase activity;
   b) the at least one nucleic acid sequence which encodes a polypeptide with Δ6-elongase activity;
   c) the at least one nucleic acid sequence which encodes a polypeptide with Δ5-desaturase activity;
   d) the at least one nucleic acid sequence which encodes a polypeptide with Δ5-elongase activity that elongates unsaturated $C_{20}$-fatty acids; and
   e) the at least one nucleic acid sequence which encodes a polypeptide with Δ4-desaturase activity,
   and wherein said transgenic plant, or said plant part or seed thereof, has a content of at least 1% by weight of docosahexaenoic acid and/or eicosapentaenoic acid based on the total lipid content of said transgenic plant, or said plant part or seed thereof.

16. A process for the production of oils, lipids, or fatty acids, said process comprises:
   a) obtaining the transgenic plant of claim 15; and
   b) isolating oils, lipids, or fatty acids from said transgenic plant or seeds thereof.

17. The process of claim 16, wherein the oils, lipids, or fatty acids are isolated from the seeds of said transgenic plant.

18. A process for the production of feedstuffs, foodstuffs, cosmetics or pharmaceuticals, said process comprises:
   a) obtaining oils, lipids, or fatty acids produced by the process of claim 16; and
   b) processing said oils, lipids, or fatty acids to produce feedstuffs, foodstuffs, cosmetics or pharmaceuticals.

19. The process of claim 11, wherein the transgenic organism is a transgenic microorganism or a transgenic plant.

20. A transgenic plant obtained by the process of claim 19, or a plant part or seed thereof, wherein said transgenic plant, or said plant part or seed thereof, comprises:
   a) the at least one nucleic acid sequence which encodes a polypeptide with Δ6-desaturase activity;
   b) the at least one nucleic acid sequence which encodes a polypeptide with Δ6-elongase activity;
   c) the at least one nucleic acid sequence which encodes a polypeptide with Δ5-desaturase activity;
   d) the at least one nucleic acid sequence which encodes a polypeptide with Δ5-elongase activity that elongates unsaturated $C_{20}$-fatty acids; and
   e) the at least one nucleic acid sequence which encodes a polypeptide with Δ4-desaturase activity,
   and wherein said transgenic plant, or said plant part or seed thereof, has a content of at least 1% by weight of docosahexaenoic acid and/or eicosapentaenoic acid based on the total lipid content of said transgenic plant, or said plant part or seed thereof.

21. A process for the production of oils, lipids, or fatty acids, said process comprises:
   a) obtaining the transgenic plant of claim 20; and
   b) isolating oils, lipids, or fatty acids from said transgenic plant or seeds thereof.

22. The process of claim 21, wherein the oils, lipids, or fatty acids are isolated from the seeds of said transgenic plant.

23. A process for the production of feedstuffs, foodstuffs, cosmetics or pharmaceuticals, said process comprises:
   a) obtaining oils, lipids, or fatty acids produced by the process of claim 21; and
   b) processing said oils, lipids, or fatty acids to produce feedstuffs, foodstuffs, cosmetics or pharmaceuticals.

24. The process of claim 11, wherein the transgenic organism is an oil-producing plant, a vegetable plant or an ornamental.

25. The process of claim 11, wherein the transgenic organism is a transgenic plant selected from the group consisting of the plant families: Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae and Prasinophyceae.

26. The process of claim 11, wherein the docosahexaenoic acid and/or eicosapentaenoic acid is isolated from the organism in the form of oils, lipids or free fatty acids.

27. The process of claim 11, wherein the docosahexaenoic acid or eicosapentaenoic acid is isolated in a concentration of at least 5% by weight based on the total lipid content of the transgenic organism.

* * * * *